(12) United States Patent
Mainolfi et al.

(10) Patent No.: US 12,187,728 B2
(45) Date of Patent: *Jan. 7, 2025

(54) CAFFEINE INHIBITORS OF MTHFD2 AND USES THEREOF

(71) Applicant: Raze Therapeutics, Inc., Cambridge, MA (US)

(72) Inventors: Nello Mainolfi, Belmont, MA (US); Mikel P. Moyer, Brookline, MA (US); Eddine Saiah, Brookline, MA (US); Cristina Lecci, Oxfordshire (GB); Robert David Matthew Pace, Oxfordshire (GB); Heather Tye, Oxfordshire (GB); Julia Vile, Oxfordshire (GB)

(73) Assignee: Raze Therapeutics, Inc., Charlestown, MA (US)

( * ) Notice: Subject to any disclaimer, the term of this patent is extended or adjusted under 35 U.S.C. 154(b) by 46 days.

This patent is subject to a terminal disclaimer.

(21) Appl. No.: 17/579,443

(22) Filed: Jan. 19, 2022

(65) Prior Publication Data

US 2023/0067237 A1   Mar. 2, 2023

Related U.S. Application Data

(63) Continuation of application No. 16/061,683, filed as application No. PCT/US2016/066666 on Dec. 14, 2016, now Pat. No. 11,370,792.

(60) Provisional application No. 62/266,802, filed on Dec. 14, 2015.

(51) Int. Cl.
| | |
|---|---|
| C07D 473/30 | (2006.01) |
| A61K 45/06 | (2006.01) |
| A61P 35/00 | (2006.01) |
| C07D 473/18 | (2006.01) |
| A61P 3/04 | (2006.01) |
| A61P 17/06 | (2006.01) |
| A61P 19/02 | (2006.01) |

(52) U.S. Cl.
CPC .......... C07D 473/30 (2013.01); A61K 45/06 (2013.01); A61P 35/00 (2018.01); C07D 473/18 (2013.01); A61P 3/04 (2018.01); A61P 17/06 (2018.01); A61P 19/02 (2018.01)

(58) Field of Classification Search
CPC .................................................. C07D 473/30
See application file for complete search history.

(56) References Cited

U.S. PATENT DOCUMENTS

| | | |
|---|---|---|
| 3,094,529 A | 6/1963 | Klosa et al. |
| 5,639,600 A | 6/1997 | McGrath et al. |
| 6,020,337 A | 2/2000 | Leigh et al. |
| 7,071,189 B2 | 7/2006 | Kawashima et al. |
| 7,087,648 B1 | 8/2006 | McGrath |
| 7,253,176 B1 | 8/2007 | Waer et al. |
| 7,390,799 B2 | 6/2008 | Bruncko et al. |
| 8,029,770 B2 | 10/2011 | Lu et al. |
| 8,138,347 B2 | 3/2012 | Knight et al. |
| 8,207,175 B2 | 6/2012 | Van Aalten et al. |
| 9,029,567 B2 | 5/2015 | Khamar et al. |
| 11,370,792 B2* | 6/2022 | Mainolfi .............. C07D 473/18 |
| 2007/0197563 A1 | 8/2007 | Schoenafinger et al. |
| 2009/0023704 A1 | 1/2009 | Cheng et al. |
| 2009/0105282 A1 | 4/2009 | Pickett et al. |
| 2010/0168425 A1 | 7/2010 | Glushkov et al. |
| 2014/0296263 A1 | 10/2014 | Aslanian et al. |

FOREIGN PATENT DOCUMENTS

| | | |
|---|---|---|
| CN | 102993203 B | 11/2015 |
| DE | 19 38 016 A1 | 1/1971 |
| WO | WO-200116134 A1 | 3/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2004106337 A1 | 12/2004 |
| WO | WO-2005007623 A2 | 1/2005 |
| WO | WO-2005021548 A2 | 3/2005 |
| WO | WO-2005113554 A2 | 12/2005 |
| WO | WO-2006078846 A1 | 7/2006 |
| WO | WO-2006091897 A2 | 8/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009024542 A2 | 2/2009 |
| WO | WO-2009114512 A1 | 9/2009 |

(Continued)

OTHER PUBLICATIONS

Berge, S. M. et al. Pharmaceutical Salts. J. Pharmaceutical Sciences, vol. 66, No. 1, Jan. 1977, pp. 1-19.
Cottam, H.B., et al. Substituted Xanthines, Pteridinediones, and Related Compounds as Potential Antiinflammatory Agents. Synthesis and Biological Evaluation of Inhibitors of Tumor Necrosis Factor ?. J. Med. Chem., vol. 39, No. 1, Jan. 1996, pp. 2-9.
De Nunzio, C. et al. The Controversial Relationship Between Benign Prostatic Hyperplasia and Prostate Cancer: The Role of Inflammation. European Urology, vol. 60, No. 1, Jul. 2011, pp. 106-117; abstract.
Fingert, HJ et al. Cytotoxic, Cell Cycle, and Chromosomal Effects of Methylxanthines in Human Tumor Cells Treated With Alkylating Agents. Cancer Research vol. 46, May 1986, pp. 2463-2467.
International Search Report and Written Opinion issued by the United States Patent and Trademark Office as International Searching Authority for International Patent Application PCT/US2016/666666.

(Continued)

*Primary Examiner* — Paul V Ward
(74) *Attorney, Agent, or Firm* — Dechert LLP; Andrea L. C. Reid; Todd K. Macklin

(57) ABSTRACT

The present invention provides compounds, compositions thereof, and methods of using the same.

16 Claims, No Drawings

(56) References Cited

FOREIGN PATENT DOCUMENTS

| WO | WO-2011005871 A1 | 1/2011 |
|---|---|---|
| WO | WO-2011090760 A1 | 7/2011 |
| WO | WO-2014150688 A1 | 9/2014 |

OTHER PUBLICATIONS

Jain et al., "Metabolite Profiling Identifies a Key Role for Glycine in Rapid Cancer Cell Proliferation," Science, 2012, 336:1040-1044.
Muller, C.E. et al. Synthesis and Structure?Activity Relationships of 3,7-Dimethyl-1-propargylxanthine Derivatives, A2A-Selective Adenosine Receptor Antagonists. J. Med. Chem., vol. 40, No. 26, Dec. 1997, pp. 4396-4405.
Nilsson, et al., "Metabolic enzyme expression highlights a key role for MTHFD2 and the mitochondral folate pathway in cancer," Nature Communications, 2013, 5(3128): 1-10.
Pubchem. NCGC00100306-01. Mar. 27, 2007, pp. 1-6 [online], [retrieved on Jan. 26, 2017]. Retrieved from the Internet, <https://pubchem.ncbi.nlm.nih.gov/substance/24274004#section=Top>; pp. 3 and 6-7.
Pubchem. SID 110205319.28 Feb. 28, 2011, pp. 1-7 [online], [retrieved on Jan. 26, 2017]. Retrieved from the Internet, <https://pubchem.ncbi.nlm.nih.gov/substance/110205319#section=Top>; pp. 1, 3, 7.
Rybár, A., et al. 3,7-Dialkyl-8-alkyl-or-aryl-3,7-dihydropurine-2,6-diones. Collect. Czech. Chem. Commun., vol. 55, No. 9, pp. 2257-2269.
Supplementary Partial European Search Report from European Patent App. No. 16876595.6 dated Sep. 6, 2019.
Weinberg, SE. et al. Targeting mitochondria metabolism for cancer therapy. Nature Chemical Biology, vol. 11, No. 1, Jan. 2015, pp. 9-15; p. 3, paragraph 3; figure 3.

\* cited by examiner

CAFFEINE INHIBITORS OF MTHFD2 AND USES THEREOF

TECHNICAL FIELD OF THE INVENTION

The present invention relates to compounds and methods useful for inhibiting methylenetetrahydrofolate dehydrogenase. The invention also provides pharmaceutically acceptable compositions comprising compounds of the present invention and methods of using said compositions in the treatment of various disorders.

BACKGROUND OF THE INVENTION

Mitochondrial glycine (and one-carbon, or 1-C, metabolism) is important in cancer cell metabolism. Glycine consumption is altered in some cancers, and is a unique predictor of antifolate sensitivity as well as of cancer cell proliferation. Glycine starvation can reduce the proliferation of sensitive cancers.

MTHFD2 is a bifunctional enzyme, localized to the mitochondria, that catalyzes two reactions in the mitochondrial 1-C pathway: the dehydrogenase and cyclohydrolase reactions. MTHFD2 is highly upregulated across many cancers relative to normal tissues. Genetic silencing of MTHFD2 and inhibition with small molecules slows proliferation across a number of cancer cell lines. Targeting MTHFD2 by small molecule inhibitors could be a therapeutic strategy to reduce cancer cell growth and survival. Accordingly, there remains a need to find MTHFD2 inhibitors useful as therapeutic agents.

SUMMARY OF THE INVENTION

It has now been found that compounds of this invention, and pharmaceutically acceptable compositions thereof, are effective as MTHFD2 inhibitors. Such compounds have the general formula I:

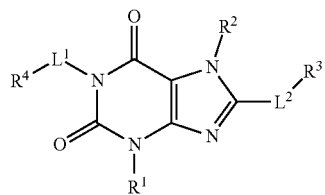

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with MTHFD2. Such diseases, disorders, or conditions include cellular proliferative disorders (e.g., cancer) such as those described herein.

DETAILED DESCRIPTION OF CERTAIN EMBODIMENTS

1. General Description of Certain Embodiments of the Invention

Compounds of the present invention, and compositions thereof, are useful as inhibitors of MTHFD2. In certain embodiments, the present invention provides a compound of formula I:

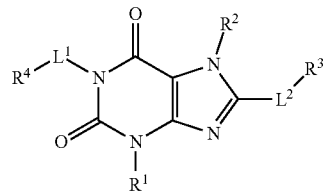

I or a pharmaceutically acceptable salt thereof, wherein:
each of $R^1$ and $R^2$ is hydrogen or optionally substituted $C_{1-6}$ aliphatic;
$L^1$ is a covalent bond or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—;
each R is independently hydrogen, or an optionally substituted group selected from $C_{1-6}$ aliphatic, phenyl, a 4-7 membered saturated or partially unsaturated monocyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur; or:
two R groups on the same nitrogen are taken together with their intervening atoms to form a 4-7 membered monocyclic saturated, partially unsaturated, or heteroaryl ring having 0-3 heteroatoms, in addition to the nitrogen, independently selected from nitrogen, oxygen, or sulfur;
$L^2$ is a covalent bond, or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—, or:
$R^2$ and $L^2$ are taken together with their intervening atoms to form a 5-7 membered partially unsaturated heterocyclic ring having 1-2 nitrogens;
$R^3$ is hydrogen, optionally substituted $C_{1-6}$ aliphatic, or Ring B optionally substituted with 0-4 independently selected $R^y$ groups;
each $R^y$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R;
$R^4$ is hydrogen, optionally substituted $C_{1-6}$ aliphatic, or Ring A optionally substituted with 0-4 independently selected $R^x$ groups;
each $R^x$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R;
Ring A is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur; and Ring B is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺(C₁₋₄alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a ¹³C- or ¹⁴C-enriched carbon are within the scope of this invention. Such compounds are useful, for example, as analytical tools, as probes in biological assays, or as therapeutic agents in accordance with the present invention.

As used herein, the term "inhibitor" is defined as a compound that binds to and/or inhibits MTHFD2 with measurable affinity. In certain embodiments, an inhibitor has an IC₅₀ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change in MTHFD2 activity between a sample comprising a compound of the present invention, or composition thereof, and MTHFD2, and an equivalent sample comprising MTHFD2, in the absence of said compound, or composition thereof.

3. Description of Exemplary Embodiments

In certain embodiments, the present invention provides a compound of formula I:

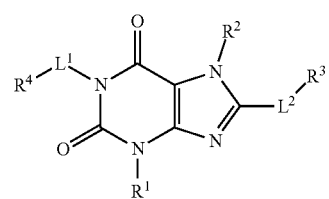

or a pharmaceutically acceptable salt thereof, wherein:
each of R¹ and R² is independently hydrogen or optionally substituted C₁₋₆ aliphatic;
L¹ is a covalent bond or a bivalent C₁₋₄ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO₂—, —SO₂N(R)—, —C(O)—, —OC(O)—, —C(O)O—, —O—, —S—, —SO—, or —SO₂—;

each R is independently hydrogen, or an optionally substituted group selected from $C_{1-6}$ aliphatic, phenyl, a 4-7 membered saturated or partially unsaturated monocyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur; or:

two R groups on the same nitrogen are taken together with their intervening atoms to form a 4-7 membered monocyclic saturated, partially unsaturated, or heteroaryl ring having 0-3 heteroatoms, in addition to the nitrogen, independently selected from nitrogen, oxygen, or sulfur;

$L^2$ is a covalent bond, or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—, or:

$R^2$ and $L^2$ are taken together with their intervening atoms to form a 5-7 membered partially unsaturated heterocyclic ring having 1-2 nitrogens;

$R^3$ is hydrogen, optionally substituted $C_{1-6}$ aliphatic, or Ring B optionally substituted with 0-4 independently selected $R^y$ groups;

each $R^y$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R;

$R^4$ is hydrogen, optionally substituted $C_{1-6}$ aliphatic, or Ring A optionally substituted with 0-4 independently selected $R^x$ groups;

each $R^x$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R;

Ring A is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur; and Ring B is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur.

As defined generally above, $R^1$ is hydrogen or optionally substituted $C_{1-6}$ aliphatic.

In some embodiments, $R^1$ is hydrogen.

In some embodiments, $R^1$ is optionally substituted $C_{1-6}$ aliphatic. In some embodiments, $R^1$ is methyl.

In some embodiments, $R^1$ is selected from those recited in Table A, below

As defined generally above, $R^2$ is hydrogen or optionally substituted $C_{1-6}$ aliphatic.

In some embodiments, $R^2$ is hydrogen.

In some embodiments, $R^2$ is optionally substituted $C_{1-6}$ aliphatic. In some embodiments, $R^2$ is methyl.

In some embodiments, $R^2$ is selected from those recited in Table A, below

As defined generally above, $L^1$ is a covalent bond or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—.

In some embodiments, $L^1$ is a covalent bond. In some embodiments, $L^1$ is a bivalent $C_{1-4}$ saturated or unsaturated, straight or branched, hydrocarbon chain. In some embodiments, $L^1$ is —CH$_2$—

In some embodiments, $L^1$ is selected from those recited in Table A, below.

As defined generally above, $L^2$ is a covalent bond or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—.

In some embodiments, $L^2$ is a covalent bond.

In other embodiments $L^2$ is a bivalent $C_{1-4}$ saturated or unsaturated, straight or branched, hydrocarbon chain. In some embodiments, $L^2$ is $C_1$. In other embodiments $L^2$ is $C_2$.

In some embodiments, $L^2$ is a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—. In some embodiments, $L^2$ is —NR—.

In some embodiments, $L^2$ is selected from those recited in Table A, below.

As generally defined above, $R^3$ is hydrogen, optionally substituted $C_{1-6}$ aliphatic, or Ring B optionally substituted with 0-4 independently selected $R^y$ groups.

In some embodiments, $R^3$ is hydrogen.

In some embodiments, $R^3$ is Ring B optionally substituted with 0-4 independently selected $R^y$ groups wherein Ring B is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur.

In some embodiments, Ring B is a 4-7 membered monocyclic saturated or partially unsaturated carbocyclic ring. In some embodiments, Ring B is cyclobutyl. In some embodiments, Ring B is cyclopentyl. In some embodiments, Ring B is cyclohexyl.

In some embodiments, Ring B is a 4-7 membered monocyclic saturated or partially unsaturated heterocyclic ring having 1-2 heteroatoms independently selected from nitrogen, oxygen, or sulfur. In some embodiments, Ring B is piperidonyl. In some embodiments, Ring B is morpholinyl. In some embodiments, Ring B is pyrrolidinonyl. In some embodiments, Ring B is piperidinyl. In some embodiments, Ring B is tetrahydropyranyl.

In some embodiments, Ring B is a 5-6 membered heteroaryl ring having 1-3 heteroatoms independently selected from nitrogen, oxygen, or sulfur. In some embodiments, Ring B is pyridinyl. In some embodiments, Ring B is 2-pyrimidonyl. In some embodiments, Ring B is pyrimidinyl. In some embodiments, Ring B is pyrazinyl.

In some embodiments, $R^3$ is selected from those recited in Table A, below.

As generally defined above, $R^y$ is independently halogen, R, —OR, —SR, —N(R)$_2$, —C(O)R, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R.

In some embodiments, $R^y$ is —OR. In some embodiments, $R^y$ is —OH.

In some embodiments, $R^y$ is —C(O)OR. In some embodiments, $R^y$ is —C(O)OH.

In some embodiments, $R^y$ is selected from those recited in Table A, below.

As generally defined above, $R^4$ is hydrogen, optionally substituted $C_{1-6}$ aliphatic, or Ring A optionally substituted with 0-4 independently selected $R^x$ groups.

In some embodiments, $R^4$ is Ring A wherein Ring A is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur.

In some embodiments, Ring A is phenyl. In some embodiments, Ring A is dichlorophenyl.

In some embodiments, Ring A is an 8-11 membered bicyclic saturated, partially saturated or aromatic ring having 0-3 heteroatoms independently selected from nitrogen, oxygen, or sulfur. In some embodiments, Ring A is indolyl. In some embodiments, Ring A is naphthyl. In some embodiments, Ring A is benzothiophenyl. In some embodiments, Ring A is benzimidazolyl.

In some embodiments, Ring A is selected from those recited in Table A, below.

As generally defined above, $R^x$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH)R.

In some embodiments, $R^x$ is R. In some embodiments, $R^x$ is —CF$_3$. In some embodiments, $R^x$ is methyl. In some embodiments, $R^x$ is ethyl. In some embodiments, $R^x$ is cyclopropyl. In some embodiments, $R^x$ is —CH$_2$OH. In some embodiments, $R^x$ is —CH$_2$NH$_2$. In some embodiments, $R^x$ is —CH$_2$NHC(O)CH$_3$.

In some embodiments, $R^x$ is halogen. In some embodiments, $R^x$ is chloro. In some embodiments, $R^x$ is fluoro.

In some embodiments, $R^x$ is —OR. In some embodiments, $R^x$ is —OCH$_3$. In some embodiments, $R^x$ is —OCHF$_2$.

In some embodiments, $R^x$ is —C(O)N(R)$_2$. In some embodiments, $R^x$ is —C(O)NH$_2$.

In some embodiments, $R^x$ is selected from those recited in Table A, below.

Exemplary compounds of the invention are set forth in Table A, below.

Table A:

Example 112: 1-(3,4-dichlorobenzyl)-8-(3,3-difluorocyclobutylamino)-3,7-dimethyl-1H-purine-2,6(3H,7H)-dione.

Example 49: 1-[(3,4-dichlorophenyl)methyl]-3,7-dimethyl-8-{[(3S)-oxolan-3-yl]amino}-2,3,6,7-tetrahydro-1H-purine-2,6-dione.

Example 109: 1-(3,4-chlorobenzyl)-3,7-dimethyl-8-(2-oxo-2,3,4,5-tetrahydro-1H-benzo[b]azepin-8-ylamino)-1H-purine-2,6(3H,7H)-dione.

Example 365: 3,7-dimethyl-1-[(7-methyl-1H-indol-2-yl)methyl]-8-(4-pyridylamino)purine-2,6-dione.

Example 1: 1-(3,4-dichlorobenzyl)-8-((2-hydroxyethyl)amino)-3,7-dimethyl-1H-purine-2,6(3H,7H)-dione.

Example 8: 1-[(3,4-dichlorophenyl)methyl]-8-{[(2S)-2-hydroxypropyl]amino}-3,7-dimethyl-2,3,6,7-tetrahydro-1H-purine-2,6-dione.

Example 9: 1-[(3,4-dichlorophenyl)methyl]-8-{[(2R)-2-hydroxypropyl]amino}-3,7-dimethyl-2,3,6,7-tetrahydro-1H-purine-2,6-dione.

Example 13: 1-[(3,4-dichlorophenyl)methyl]-8-{[(2R)-2,3-dihydroxypropyl]amino}-3,7-dimethyl-2,3,6,7-tetrahydro-1H-purine-2,6-dione.

Example 14: 1-[(3,4-dichlorophenyl)methyl]-8-{[(2S)-2,3-dihydroxypropyl]amino}-3,7-dimethyl-2,3,6,7-tetrahydro-1H-purine-2,6-dione.

Example 15: 1-[(4-chlorophenyl)methyl]-8-{[(2R)-2,3-dihydroxypropyl]amino}-3,7-dimethyl-2,3,6,7-tetrahydro-1H-purine-2,6-dione.

Example 16: 1-[(4-chlorophenyl)methyl]-8-{[(2S)-2,3-dihydroxypropyl]amino}-3,7-dimethyl-2,3,6,7-tetrahydro-1H-purine-2,6-dione.

Example 17: 1-[(4-chlorophenyl)methyl]-8-{[(2R)-2-hydroxypropyl]amino}-3,7-dimethyl-2,3,6,7-tetrahydro-1H-purine-2,6-dione.

Example 18: 1-[(4-chlorophenyl)methyl]-8-{[(2S)-2-hydroxypropyl]amino}-3,7-dimethyl-2,3,6,7-tetrahydro-1H-purine-2,6-dione.

Example 21: 1-[(3,4-dichlorophenyl)methyl]-3,7-dimethyl-8-(methylamino)-2,3,6,7-tetrahydro-1H-purine-2,6-dione.

Example 22: N-[2-({1-[(3,4-dichlorophenyl)methyl]-3,7-dimethyl-2,6-dioxo-2,3,6,7-tetrahydro-1H-purin-8-yl}amino)ethyl]acetamide.

Example 23: 1-[(4-chloro-3-fluorophenyl)methyl]-8-[(3-hydroxypropyl)amino]-3,7-dimethyl-2,3,6,7-tetrahydro-1H-purine-2,6-dione.

Example 24: 1-[(4-chloro-3-fluorophenyl)methyl]-8-{[(2R)-2-hydroxypropyl]amino}-3,7-dimethyl-2,3,6,7-tetrahydro-1H-purine-2,6-dione.

Example 25: 1-[(4-chloro-3-fluorophenyl)methyl]-8-{[(2S)-2-hydroxypropyl]amino}-3,7-dimethyl-2,3,6,7-tetrahydro-1H-purine-2,6-dione.

Example 26: 1-[(4-chlorophenyl)methyl]-8-{[(2R)-4-hydroxybutan-2-yl]amino}-3,7-dimethyl-2,3,6,7-tetrahydro-1H-purine-2,6-dione.

Example 27: 1-[(3,4-dichlorophenyl)methyl]-8-{[(2R)-4-hydroxybutan-2-yl]amino}-3,7-dimethyl-2,3,6,7-tetrahydro-1H-purine-2,6-dione.

Example 28: 1-[(3,4-dichlorophenyl)methyl]-8-[(4-hydroxybutyl)amino]-3,7-dimethyl-2,3,6,7-tetrahydro-1H-purine-2,6-dione.

Example 29: 1-[(3,4-difluorophenyl)methyl]-8-[(3-hydroxypropyl)amino]-3,7-dimethyl-2,3,6,7-tetrahydro-1H-purine-2,6-dione.

Example 30: 1-[(3,4-difluorophenyl)methyl]-8-{[(2S)-2-hydroxypropyl]amino}-3,7-dimethyl-2,3,6,7-tetrahydro-1H-purine-2,6-dione.

Example 31: 1-[(4-chlorophenyl)methyl]-8-{[(2S)-4-hydroxybutan-2-yl]amino}-3,7-dimethyl-2,3,6,7-tetrahydro-1H-purine-2,6-dione.

Example 32: 1-[(3,4-dichlorophenyl)methyl]-8-{[(2S)-4-hydroxybutan-2-yl]amino}-3,7-dimethyl-2,3,6,7-tetrahydro-1H-purine-2,6-dione.

Example 33: 1-[(3,4-dichlorophenyl)methyl]-8-[(3-hydroxycyclohexyl)amino]-3,7-dimethyl-2,3,6,7-tetrahydro-1H-purine-2,6-dione.

Example 34: 8-{[(2S)-2-hydroxypropyl]amino}-1-[(4-methoxyphenyl)methyl]-3,7-dimethyl-2,3,6,7-tetrahydro-1H-purine-2,6-dione.

Example 35: 1-[(3,4-dichlorophenyl)methyl]-3,7-dimethyl-8-[(piperidin-4-yl)amino]-2,3,6,7-tetrahydro-1H-purine-2,6-dione.

Example 36: 8-{[(2S)-2-hydroxypropyl]amino}-3,7-dimethyl-1-{[4-(trifluoromethyl)phenyl]methyl}-2,3,6,7-tetrahydro-1H-purine-2,6-dione.

Example 37: 3-({1-[(3,4-dichlorophenyl)methyl]-3,7-dimethyl-2,6-dioxo-2,3,6,7-tetrahydro-1H-purin-8-yl}amino)propanoic acid.

Example 38: (±)-1-[(3,4-dichlorophenyl)methyl]-3,7-dimethyl-8-{[(trans)-4-aminocyclohexyl]amino}-2,3,6,7-tetrahydro-1H-purine-2,6-dione.

Example 39: (±)-1-[(3,4-dichlorophenyl)methyl]-3,7-dimethyl-8-{[(cis)-4-aminocyclohexyl]amino}-2,3,6,7-tetrahydro-1H-purine-2,6-dione.

Example 40: 1-[(3,4-dichlorophenyl)methyl]-8-{[2-(dimethylamino)ethyl]amino}-3,7-dimethyl-2,3,6,7-tetrahydro-1H-purine-2,6-dione.

Example 41: (±)-1-[(3,4-dichlorophenyl)methyl]-3,7-dimethyl-8-{[(cis)-4-hydroxycyclohexyl]amino}-2,3,6,7-tetrahydro-1H-purine-2,6-dione.

Example 42: 1-[(3,4-dichlorophenyl)methyl]-3,7-dimethyl-8-[(1H-pyrazol-4-ylmethyl)amino]-1H-purine-2,6-dione.

Examples 43 and 71: 1-(3,4-dichlorobenzyl)-8-((1S,3R)-3-hydroxycyclopentylamino)-3,7-dimethyl-1H-purine-2,6(3H,7H)-dione and dichlorobenzyl)-8-((1R,3S)-3-hydroxycyclopentylamino)-3,7-dimethyl-1H-purine-2,6(3H,7H)-dione Examples 44 and 70: 1-(3,4-dichlorobenzyl)-8-((1R,3R)-3-hydroxycyclopentylamino)-3,7-dimethyl-1H-purine-2,6(3H,7H)-dione 1-(3,4-dichlorobenzyl)-8-((1S,3S)-3-hydroxycyclopentylamino)-3,7-dimethyl-1H-purine-2,6(3H,7H)-dione.

Example 45: 1-[(3,4-dichlorophenyl)methyl]-8-[(3-hydroxy-3-methylbutyl)amino]-3,7-dimethyl-2,3,6,7-tetrahydro-1H-purine-2,6-dione.

Example 46: 1-[(3,4-dichlorophenyl)methyl]-3,7-dimethyl-8-{[(3S)-oxan-3-yl]amino}-2,3,6,7-tetrahydro-1H-purine-2,6-dione.

Example 47: 1-[(3,4-dichlorophenyl)methyl]-3,7-dimethyl-8-{[(3R)-oxan-3-yl]amino}-2,3,6,7-tetrahydro-1H-purine-2,6-dione.

Example 48: 1-[(3,4-dichlorophenyl)methyl]-3,7-dimethyl-8-[(oxan-4-yl)amino]-2,3,6,7-tetrahydro-1H-purine-2,6-dione.

Example 50: (1S,3R)-3-({1-[(3,4-dichlorophenyl)methyl]-3,7-dimethyl-2,6-dioxo-2,3,6,7-tetrahydro-1H-purin-8-yl}amino)cyclopentane-1-carboxylic acid.

Example 51: 1-(1-benzothiophen-5-ylmethyl)-8-{[(2S)-4-hydroxybutan-2-yl]amino}-3,7-dimethyl-2,3,6,7-tetrahydro-1H-purine-2,6-dione.

Example 52: 1-(1-benzothiophen-5-ylmethyl)-8-[(3-hydroxypropyl)amino]-3,7-dimethyl-2,3,6,7-tetrahydro-1H-purine-2,6-dione.

Example 53: 1-[(3,4-dichlorophenyl)methyl]-8-[(1,3-dihydroxypropan-2-yl)amino]-3,7-dimethyl-2,3,6,7-tetrahydro-1H-purine-2,6-dione.

Example 54: 1-[(3,4-dichlorophenyl)methyl]-8-{[2-(2-hydroxyethoxy)ethyl]amino}-3,7-dimethyl-2,3,6,7-tetrahydro-1H-purine-2,6-dione.

Example 55: 1-(3,4-dichlorobenzyl)-8-(((trans)-4-hydroxycyclohexyl)amino)-3,7-dimethyl-3,7-dihydro-1H-purine-2,6-dione Example 56: 8-[(3-hydroxypropyl)amino]-3,7-dimethyl-1-{[4-(trifluoromethyl)phenyl]methyl}-2,3,6,7-tetrahydro-1H-purine-2,6-dione.

Example 57: 8-{[(2R)-2-hydroxypropyl]amino}-3,7-dimethyl-1-{[4-(trifluoromethyl)phenyl]methyl}-2,3,6,7-tetrahydro-1H-purine-2,6-dione.

Example 59: 8-(cyclohexylamino)-1-[(3,4-dichlorophenyl)methyl]-3,7-dimethyl-2,3,6,7-tetrahydro-1H-purine-2,6-dione.

Example 60: 1-[(3,4-dichlorophenyl)methyl]-3,7-dimethyl-8-{[(3R)-pyrrolidin-3-yl]amino}-2,3,6,7-tetrahydro-1H-purine-2,6-dione.

Example 61: 1-[(3,4-dichlorophenyl)methyl]-3,7-dimethyl-8-{[(3S)-pyrrolidin-3-yl]amino}-2,3,6,7-tetrahydro-1H-purine-2,6-dione.

Example 62: 1-(3,4-dichlorophenyl)-8-[(3-hydroxypropyl)amino]-3,7-dimethyl-2,3,6,7-tetrahydro-1H-purine-2,6-dione.

Example 63: 1-[(3,4-dichlorophenyl)methyl]-3,7-dimethyl-8-{[(3R)-oxolan-3-yl]amino}-2,3,6,7-tetrahydro-1H-purine-2,6-dione.

Example 64: (1R,3S)-3-(1-(3,4-dichlorobenzyl)-3,7-dimethyl-2,6-dioxo-2,3,6,7-tetrahydro-1H-purin-8-ylamino)cyclopentanecarboxylic acid.

Example 65: 8-[(azetidin-3-yl)amino]-1-[(3,4-dichlorophenyl)methyl]-3,7-dimethyl-2,3,6,7-tetrahydro-1H-purine-2,6-dione.

Example 66: 1-[(3,4-dichlorophenyl)methyl]-3,7-dimethyl-8-{[(cis)-3-hydroxycyclobutyl]amino}-2,3,6,7-tetrahydro-1H-purine-2,6-dione.

Example 67: 1-{[4-chloro-3-(trifluoromethyl)phenyl]methyl}-8-[(3-hydroxypropyl)amino]-3,7-dimethyl-2,3,6,7-tetrahydro-1H-purine-2,6-dione.

Example 68: 1-[(3,4-dichlorophenyl)methyl]-3,7-dimethyl-8-{[(3S)-piperidin-3-yl]amino}-2,3,6,7-tetrahydro-1H-purine-2,6-dione.

Example 69: 1-[(3,4-dichlorophenyl)methyl]-3,7-dimethyl-8-{[(3R)-piperidin-3-yl]amino}-2,3,6,7-tetrahydro-1H-purine-2,6-dione.

Example 72: 1-[1-(3,4-dichlorophenyl)ethyl]-8-[(3-hydroxypropyl)amino]-3,7-dimethyl-2,3,6,7-tetrahydro-1H-purine-2,6-dione.

Example 73: 1-{[3-chloro-4-(trifluoromethyl)phenyl]methyl}-8-[(3-hydroxypropyl)amino]-3,7-dimethyl-2,3,6,7-tetrahydro-1H-purine-2,6-dione.

Examples 74 and 75: (±)-1-(1-benzothiophen-5-ylmethyl)-8-{[(cis)-3-hydroxycyclopentyl]amino}-3,7-dimethyl-2,3,6,7-tetrahydro-1H-purine-2,6-dione and (±)-1-(1-benzothiophen-5-ylmethyl)-8-{[(trans)-3-hydroxycyclopentyl]amino}-3,7-dimethyl-2,3,6,7-tetrahydro-1H-purine-2,6-dione.

Examples 76 and 144: 8-((1R,3R)-3-hydroxycyclopentylamino)-3,7-dimethyl-1-(4-(trifluoromethyl)benzyl)-1H-purine-2,6(3H,7H)-dione and 8-((1S,3S)-3-hydroxycyclopentylamino)-3,7-dimethyl-1-(4-(trifluoromethyl)benzyl)-1H-purine-2,6(3H,7H)-dione.

Example 77: (1S,3R)-3-[(3,7-dimethyl-2,6-dioxo-1-{[4-(trifluoromethyl)phenyl]methyl}-2,3,6,7-tetrahydro-1H-purin-8-yl)amino]cyclopentane-1-carboxylic acid.

Example 173: (±)-1-(3,4-dichlorobenzyl)-8-((cis)-3-hydroxycyclohexylamino)-3,7-dimethyl-1H-purine-2,6(3H,7H)-dione.

Examples 78 and 79: 1-(3,4-dichlorobenzyl)-8-((1S,3R)-3-hydroxycyclohexylamino)-3,7-dimethyl-1H-purine-2,6(3H,7H)-dione and 1-(3,4-dichlorobenzyl)-8-((1R,3S)-3-hydroxycyclohexylamino)-3,7-dimethyl-1H-purine-2,6(3H,7H)-dione.

Example 172: (±)-1-(3,4-dichlorobenzyl)-8-((trans)-3-hydroxycyclohexylamino)-3,7-dimethyl-1H-purine-2,6(3H,7H)-dione.

Example 80 and 81: 1-(3,4-dichlorobenzyl)-8-((1S,3S)-3-hydroxycyclohexylamino)-3,7-dimethyl-1H-purine-2,6(3H,7H)-dione and 1-(3,4-dichlorobenzyl)-8-((1R,3R)-3-hydroxycyclohexylamino)-3,7-dimethyl-1H-purine-2,6(3H,7H)-dione.

Examples 82 and 83: (S)-1-(3,4-dichlorobenzyl)-3,7-dimethyl-8-(6-oxopiperidin-3-ylamino)-1H-purine-2,6(3H,7H)-dione and (R)-1-(3,4-dichlorobenzyl)-3,7-dimethyl-8-(6-oxopiperidin-3-ylamino)-1H-purine-2,6(3H,7H)-dione.

Example 84: (±)-1-(3,4-dichlorobenzyl)-8-(((cis)-3-(dimethylamino)cyclohexyl)amino)-3,7-dimethyl-3,7-dihydro-1H-purine-2,6-dione or (±)-1-(3,4-dichlorobenzyl)-8-(((trans)-3-(dimethylamino)cyclohexyl)amino)-3,7-dimethyl-3,7-dihydro-1H-purine-2,6-dione.

Example 85: 8-((3-aminocyclohexyl)amino)-1-(3,4-dichlorobenzyl)-3,7-dimethyl-3,7-dihydro-1H-purine-2,6-dione.

Example 86: 1-[(3,4-dichlorophenyl)methyl]-3,7-dimethyl-8-[(2-oxopyrrolidin-3-yl)amino]-2,3,6,7-tetrahydro-1H-purine-2,6-dione.

Example 87: (1R,3S)-3-{[1-(1-benzothiophen-5-ylmethyl)-3,7-dimethyl-2,6-dioxo-2,3,6,7-tetrahydro-1H-purin-8-yl]amino}cyclopentane-1-carboxylic acid.

Example 88: (±)-1-[(3,4-dichlorophenyl)methyl]-3,7-dimethyl-8-[(5-oxopyrrolidin-3-yl)amino]-2,3,6,7-tetrahydro-1H-purine-2,6-dione.

Example 89: (±)-1-[(3,4-dichlorophenyl)methyl]-3,7-dimethyl-8-[(2-oxopiperidin-3-yl)amino]-2,3,6,7-tetrahydro-1H-purine-2,6-dione.

Example 90: 1-[(3,4-dichlorophenyl)methyl]-8-[(3-hydroxypropyl)amino]-3-methyl-2,3,6,7-tetrahydro-1H-purine-2,6-dione.

Example 91: (±)-1-[(3,4-dichlorophenyl)methyl]-8-{[(trans)-2-hydroxycyclohexyl]amino}-3,7-dimethyl-2,3,6,7-tetrahydro-1H-purine-2,6-dione±.

Example 92: 1-[(3,4-dichlorophenyl)methyl]-8-{[(1S,2S)-2-hydroxycyclopentyl]amino}-3,7-dimethyl-2,3,6,7-tetrahydro-1H-purine-2,6-dione.

Example 93: 1-[(3,4-dichlorophenyl)methyl]-8-{[(1R,2R)-2-hydroxycyclopentyl]amino}-3,7-dimethyl-2,3,6,7-tetrahydro-1H-purine-2,6-dione.

Example 94: 1-[(3,4-dichlorophenyl)methyl]-8-{[(1S,2R)-2-hydroxycyclopentyl]amino}-3,7-dimethyl-2,3,6,7-tetrahydro-1H-purine-2,6-dione.

Example 95: (±)-1-[(3,4-dichlorophenyl)methyl]-8-{[(cis)-2-hydroxycyclohexyl]amino}-3,7-dimethyl-2,3,6,7-tetrahydro-1H-purine-2,6-dione.

Example 96: 1-[(4-chloro-3-methoxyphenyl)methyl]-8-[(3-hydroxypropyl)amino]-3,7-dimethyl-2,3,6,7-tetrahydro-1H-purine-2,6-dione.

Example 97: 1-[(3,4-dichlorophenyl)methyl]-8-[(3-hydroxypropyl)amino]-7-methyl-2,3,6,7-tetrahydro-1H-purine-2,6-dione.

Example 98: Ethyl 2-(1-(3,4-dichlorobenzyl)-8-((3-hydroxypropyl)amino)-7-methyl-2,6-dioxo-1,2,6,7-tetrahydro-3H-purin-3-yl)acetate.

Example 99: 1-((1H-benzo[d]imidazol-2-yl)methyl)-8-((1S,3R)-3-hydroxycyclopentylamino)-3,7-dimethyl-1H-purine-2,6(3H,7H)-dione.

Example 161: Methyl 1-(3,4-dichlorobenzyl)-3,7-dimethyl-2,6-dioxo-2,3,6,7-tetrahydro-1H-purine-8-carboxylate.

Example 100: 1-(3,4-dichlorobenzyl)-8-(hydroxymethyl)-3,7-dimethyl-1H-purine-2,6(3H,7H)-dione.

Example 162: ethyl 2-(1-(3,4-dichlorobenzyl)-3,7-dimethyl-2,6-dioxo-2,3,6,7-tetrahydro-1H-purin-8-yl)acetate.

Example 101: 2-(1-(3,4-dichlorobenzyl)-3,7-dimethyl-2,6-dioxo-2,3,6,7-tetrahydro-1H-purin-8-yl)acetic acid.

Example 102: 2-(1-(3,4-dichlorobenzyl)-3,7-dimethyl-2,6-dioxo-2,3,6,7-tetrahydro-1H-purin-8-ylamino)ethanesulfonamide.

Example 103: 1-[(4-chloro-3-methoxyphenyl)methyl]-8-{[(1R,2R)-2-hydroxycyclopentyl]amino}-3,7-dimethyl-2,3,6,7-tetrahydro-1H-purine-2,6-dione.

Example 104: (S)-1-(3,4-dichlorobenzyl)-3,7-dimethyl-8-((tetrahydrofuran-2-yl)methylamino)-1H-purine-2,6(3H,7H)-dione.

Example 105: (S)-3,7-dimethyl-8-((tetrahydrofuran-2-yl)methylamino)-1-(4-(trifluoromethyl)benzyl)-1H-purine-2,6(3H,7H)-dione.

Example 106: 1-(3,4-dichlorobenzyl)-8-((1-hydroxycyclohexyl)methylamino)-3,7-dimethyl-1H-purine-2,6(3H,7H)-dione.

Example 107: 8-((1-hydroxycyclohexyl)methylamino)-3,7-dimethyl-1-(4-(trifluoromethyl)benzyl)-1H-purine-2,6(3H,7H)-dione.

Example 108: 1-(3,4-dichlorobenzyl)-8-((1R,2R)-2-hydroxycyclohexylamino)-3,7-dimethyl-1H-purine-2,6(3H,7H)-dione.

Example 110: (1S,2R)-2-(3,7-dimethyl-2,6-dioxo-1-(4-(trifluoromethyl)benzyl)-2,3,6,7-tetrahydro-1H-purin-8-ylamino)cyclopentanecarboxylic acid.

Example 111: (1S,2R)-2-(1-(3,4-dichlorobenzyl)-3,7-dimethyl-2,6-dioxo-2,3,6,7-tetrahydro-1H-purin-8-ylamino)cyclopentanecarboxylic acid.

Example 113: 8-((1R,2R)-2-hydroxycyclohexylamino)-3,7-dimethyl-1-(4-(trifluoromethyl)benzyl)-1H-purine-2,6(3H,7H)-dione.

Example 114: (±)-3-(1-(3,4-dichlorobenzyl)-3,7-dimethyl-2,6-dioxo-2,3,6,7-tetrahydro-1H-purin-8-ylamino) cyclohexanecarboxylic acid.

Example 115: (±)-3-(3,7-dimethyl-2,6-dioxo-1-(4-(trifluoromethyl)benzyl)-2,3,6,7-tetrahydro-1H-purin-8-ylamino)cyclohexanecarboxylic acid.

Example 116: 1-(3,4-dichlorobenzyl)-3,7-dimethyl-8-(pyrazin-2-ylmethylamino)-1H-purine-2,6(3H,7H)-dione.

Example 117: 1-(3,4-dichlorobenzyl)-3,7-dimethyl-8-(pyridin-3-ylmethylamino)-1H-purine-2,6(3H,7H)-dione.

Example 118: 1-(3,4-dichlorobenzyl)-3,7-dimethyl-8-(pyridin-4-ylmethylamino)-1H-purine-2,6(3H,7H)-dione.
Example 119: 8-(3-amino-1H-pyrazol-1-yl)-1-(3,4-dichlorobenzyl)-3,7-dimethyl-1H-purine-2,6(3H,7H)-dione.
Example 120: (S)-8-(1-cyclohexyl-3-hydroxypropan-2-ylamino)-3,7-dimethyl-1-(4-(trifluoromethyl)benzyl)-1H-purine-2,6(3H,7H)-dione.
Example 121: (S)-8-(1-cyclohexyl-3-hydroxypropan-2-ylamino)-1-(3,4-dichlorobenzyl)-3,7-dimethyl-1H-purine-2,6(3H,7H)-dione.
Example 122: 1-(3,4-dichlorobenzyl)-3,7-dimethyl-8-(pyridazin-3-ylamino)-1H-purine-2,6(3H,7H)-dione.
Example 123: 1-(3,4-dichlorobenzyl)-3,7-dimethyl-8-(oxazol-2-ylamino)-1H-purine-2,6(3H,7H)-dione.
Example 124: 1-(3,4-dichlorobenzyl)-8-(1-(hydroxymethyl)cyclopentylamino)-3,7-dimethyl-1H-purine-2,6(3H,7H)-dione.
Example 125: 1-(3,4-dichlorobenzyl)-3,7-dimethyl-8-(pyridin-4-ylamino)-1H-purine-2,6(3H,7H)-dione.
Example 126: 1-(3,4-dichlorobenzyl)-3,7-dimethyl-8-(pyrazin-2-ylamino)-1H-purine-2,6(3H,7H)-dione.
Example 127: 1-(3,4-dichlorobenzyl)-3,7-dimethyl-8-(phenylamino)-1H-purine-2,6(3H,7H)-dione.
Example 128: 8-(1-(hydroxymethyl)cyclopentylamino)-3,7-dimethyl-1-(4-(trifluoromethyl)benzyl)-1H-purine-2,6(3H,7H)-dione.
Example 129: (R)-2-(1-(3,4-dichlorobenzyl)-3,7-dimethyl-2,6-dioxo-2,3,6,7-tetrahydro-1H-purin-8-ylamino)propanoic acid.
Example: 130: 3-(1-(3,4-dichlorobenzyl)-3,7-dimethyl-2,6-dioxo-2,3,6,7-tetrahydro-1H-purin-8-ylamino)benzonitrile.
Example 131: 3-(1-(3,4-dichlorobenzyl)-3,7-dimethyl-2,6-dioxo-2,3,6,7-tetrahydro-1H-purin-8-ylamino)propanenitrile.
Example 132 and 143: 8-(3H-1,2,4-triazol-3-ylamino)-1-(3,4-dichlorobenzyl)-3,7-dimethyl-1H-purine-2,6(3H,7H)-dione and 8-(5-amino-1H-1,2,4-triazol-1-yl)-1-(3,4-dichlorobenzyl)-3,7-dimethyl-1H-purine-2,6(3H,7H)-dione.
Example 171: (±)-8-((cis)-3-hydroxycyclopentylamino)-3,7-dimethyl-1-(4-(trifluoromethyl)benzyl)-1H-purine-2,6(3H,7H)-dione.
Examples 133 and 156: 8-((1S,3R)-3-hydroxycyclopentylamino)-3,7-dimethyl-1-(4-(trifluoromethyl)benzyl)-1H-purine-2,6(3H,7H)-dione and 8-((1R,3S)-3-hydroxycyclopentylamino)-3,7-dimethyl-1-(4-(trifluoromethyl)benzyl)-1H-purine-2,6(3H,7H)-dione.
Example 134: 2-(1-(3,4-dichlorobenzyl)-3,7-dimethyl-2,6-dioxo-2,3,6,7-tetrahydro-1H-purin-8-yl amino)acetic acid.
Example 135 and 136: 8-(4-amino-1H-pyrazol-1-yl)-1-(3,4-dichlorobenzyl)-3,7-dimethyl-6,7-dihydro-1H-purin-2(3H)-one and 8-(4-amino-1H-pyrazol-1-yl)-1-(3,4-dichlorobenzyl)-3,7-dimethyl-6,7-dihydro-1H-purin-2(3H)-one.
Example 137: 8-(benzylamino)-1-(3,4-dichlorobenzyl)-3,7-dimethyl-1H-purine-2,6(3H,7H)-dione.
Example 138: 1-(3,4-dichlorobenzyl)-8-(4-hydroxypyrimidin-2-ylamino)-3,7-dimethyl-1H-purine-2,6(3H,7H)-dione.
Example 139: 1-(3,4-dichlorobenzyl)-3,7-dimethyl-8-(pyridin-2-ylmethylamino)-1H-purine-2,6(3H,7H)-dione.
Example 140: 1-(3,4-dichlorobenzyl)-3,7-dimethyl-8-(2-oxo-1,2-dihydropyrimidin-4-ylamino)-1H-purine-2,6(3H,7H)-dione.
Example 141: 8-(1H-pyrazol-3-ylamino)-1-(3,4-dichlorobenzyl)-3,7-dimethyl-1H-purine-2,6(3H,7H)-dione.
Example 142: 2-(1-(3,4-dichlorobenzyl)-3,7-dimethyl-2,6-dioxo-2,3,6,7-tetrahydro-1H-purin-8-ylamino)benzonitrile.
Example 145: 8-(3,3-difluorocyclobutylamino)-3,7-dimethyl-1-(4-(trifluoromethyl)benzyl)-1H-purine-2,6(3H,7H)-dione.
Example 146: 1-(3,4-dichlorobenzyl)-3,7-dimethyl-8-(pyridin-2-ylamino)-1H-purine-2,6(3H,7H)-dione.
Example 147: 1-(1-(3,4-dichlorobenzyl)-3,7-dimethyl-2,6-dioxo-2,3,6,7-tetrahydro-1H-purin-8-ylamino)cyclopropanecarboxylic acid.
Example 148: 1-(1-(3,4-dichlorobenzyl)-3,7-dimethyl-2,6-dioxo-2,3,6,7-tetrahydro-1H-purin-8-ylamino)cyclopentanecarboxylic acid.
Example 149: 1-(3,7-dimethyl-2,6-dioxo-1-(4-(trifluoromethyl)benzyl)-2,3,6,7-tetrahydro-1H-purin-8-ylamino)cyclopentanecarboxylic acid.
Example 150: 8-(6-aminopyridin-2-ylamino)-1-(3,4-dichlorobenzyl)-3,7-dimethyl-1H-purine-2,6(3H,7H)-dione.
Example 151: 2-cyclohexyl-2-((3,7-dimethyl-2,6-dioxo-1-(4-(trifluoromethyl)benzyl)-2,3,6,7-tetrahydro-1H-purin-8-yl)amino)acetic acid
Example 152: 1-(3,4-dichlorobenzyl)-3,7-dimethyl-1H-purine-2,6(3H,7H)-dione.
Example 153: 8-amino-1-(3,4-dichlorobenzyl)-3,7-dimethyl-1H-purine-2,6(3H,7H)-dione.
Example 154: Methyl 4-(1-(3,4-dichlorobenzyl)-3,7-dimethyl-2,6-dioxo-2,3,6,7-tetrahydro-1H-purin-8-ylamino)benzoate.
Example 155: (±)-1-((1H-indol-2-yl)methyl)-8-((cis)-3-hydroxycyclopentylamino)-3,7-dimethyl-1H-purine-2,6(3H,7H)-dione.
Example 158: 1-(3,4-dichlorobenzyl)-8-(2-hydroxyethyl)-3,7-dimethyl-1H-purine-2,6(3H,7H)-dione.
Example 157: 1-(3,4-dichlorobenzyl)-8-(2-(dimethylamino)ethyl)-3,7-dimethyl-1H-purine-2,6(3H,7H)-dione.
Example 159 and 160: 1-(3,4-dichlorobenzyl)-3,7-dimethyl-8-(2-morpholinoethyl)-1H-purine-2,6(3H,7H)-dione (159) and 1-(3,4-dichlorobenzyl)-3,7-dimethyl-8-vinyl-1H-purine-2,6(3H,7H)-dione (160).
Example 163: (±)-1-((1H-indol-6-yl)methyl)-8-((cis)-3-hydroxycyclopentylamino)-3,7-dimethyl-1H-purine-2,6(3H,7H)-dione.
Example 164: 1-[(3,4-dichlorophenyl)methyl]-8-[(3-hydroxy-3-methylcyclopentyl)amino]-3,7-dimethyl-2,3,6,7-tetrahydro-1H-purine-2,6-dione.
Example 165: Methyl 2-chloro-5-({8-[(3-hydroxypropyl)amino]-3,7-dimethyl-2,6-dioxo-2,3,6,7-tetrahydro-1H-purin-1-yl}methyl)benzoate.
Example 166: 1-{[4-chloro-3-(hydroxymethyl)phenyl]methyl}-8-[(3-hydroxypropyl)amino]-3,7-dimethyl-2,3,6,7-tetrahydro-1H-purine-2,6-dione.
Example 167: 1-[(3,4-dichlorophenyl)methyl]-8-[(3-hydroxypropyl)amino]-7-methyl-6,7-dihydro-1H-purin-6-one.
Example 168: (S)-3,7-dimethyl-8-((tetrahydrofuran-2-yl)methylamino)-1-(4-(trifluoromethyl)benzyl)-1H-purine-2,6(3H,7H)-dione.
Example 169: (R)-2-(1-(3,4-dichlorobenzyl)-3,7-dimethyl-2,6-dioxo-2,3,6,7-tetrahydro-1H-purin-8-ylamino)propanoic acid.
Example 170: (S)-1-(3,4-dichlorobenzyl)-3,7-dimethyl-8-((tetrahydrofuran-2-yl)methylamino)-1H-purine-2,6(3H,7H)-dione.

Example 174: 1-((1H-indol-2-yl)methyl)-3,7-dimethyl-8-(pyridin-4-ylamino)-1H-purine-2,6(3H,7H)-dione.

Example 175: (±)-1-((5-chloro-1H-indol-2-yl)methyl)-8-((cis)-3-hydroxycyclopentylamino)-3,7-dimethyl-1H-purine-2,6(3H,7H)-dione.

Example 176: 1-((5-chloro-1H-indol-2-yl)methyl)-3,7-dimethyl-8-(pyridin-4-ylamino)-1H-purine-2,6(3H,7H)-dione.

Example 177: (±)-8-((cis)-3-hydroxycyclopentylamino)-3,7-dimethyl-1-((5-methyl-1H-indol-2-yl)methyl)-1H-purine-2,6(3H,7H)-dione.

Example 178: (±)-1-((5-chloro-1-methyl-1H-indol-2-yl)methyl)-8-((cis)-3-hydroxycyclopentylamino)-3,7-dimethyl-1H-purine-2,6(3H,7H)-dione.

Example 179: (±)-8-((cis)-3-hydroxycyclopentylamino)-3,7-dimethyl-1-((1-methyl-1H-indol-2-yl)methyl)-1H-purine-2,6(3H,7H)-dione.

Example 180: (±)-8-((cis)-3-hydroxycyclopentylamino)-3,7-dimethyl-1-((3-phenyl-1H-pyrazol-5-yl)methyl)-1H-purine-2,6(3H,7H)-dione.

Example 181: 3,7-dimethyl-1-((5-methyl-1H-indol-2-yl)methyl)-8-(pyridin-4-ylamino)-1H-purine-2,6(3H,7H)-dione.

Example 182: (±)-8-((cis)-3-hydroxycyclopentylamino)-1-((5-methoxy-1H-indol-2-yl)methyl)-3,7-dimethyl-1H-purine-2,6(3H,7H)-dione.

Example 183: 1-((5-methoxy-1H-indol-2-yl)methyl)-3,7-dimethyl-8-(pyridin-4-ylamino)-1H-purine-2,6(3H,7H)-dione.

Examples 184 and 187: (1S,3R)-3-(1-(3,4-dichlorobenzyl)-3,7-dimethyl-2,6-dioxo-2,3,6,7-tetrahydro-1H-purin-8-ylamino)cyclohexanecarboxylic acid and (1R,3S)-3-(1-(3,4-dichlorobenzyl)-3,7-dimethyl-2,6-dioxo-2,3,6,7-tetrahydro-1H-purin-8-ylamino)cyclohexanecarboxylic acid.

Examples 186 and 209 (1S,3S)-3-(1-(3,4-dichlorobenzyl)-3,7-dimethyl-2,6-dioxo-2,3,6,7-tetrahydro-1H-purin-8-ylamino)cyclohexanecarboxylic acid and (1R,3R)-3-(1-(3,4-dichlorobenzyl)-3,7-dimethyl-2,6-dioxo-2,3,6,7-tetrahydro-1H-purin-8-ylamino)cyclohexanecarboxylic acid.

Example 185: 1-((1,5-dimethyl-1H-indol-2-yl)methyl)-8-((1S,3R)-3-hydroxycyclopentylamino)-3,7-dimethyl-1H-purine-2,6(3H,7H)-dione.

Example 188: (±)-8-((cis)-3-hydroxycyclopentylamino)-1-((5-methoxy-1-methyl-1H-indol-2-yl)methyl)-3,7-dimethyl-1H-purine-2,6(3H,7H)-dione.

Example 189: 1-((1H-indol-2-yl)methyl)-3,7-dimethyl-8-(2-oxo-1,2-dihydropyrimidin-4-ylamino)-1H-purine-2,6(3H,7H)-dione.

Example 190: 3,7-dimethyl-1-((5-methyl-1H-indol-2-yl)methyl)-8-(2-oxo-1,2-dihydropyrimidin-4-ylamino)-1H-purine-2,6(3H,7H)-dione.

Example 191: 1-((1H-indol-2-yl)methyl)-8-(4-hydroxypiperidin-1-yl)-3,7-dimethyl-1H-purine-2,6(3H,7H)-dione.

Example 192: 1-((1H-indol-2-yl)methyl)-8-(3-hydroxyazetidin-1-yl)-3,7-dimethyl-1H-purine-2,6(3H,7H)-dione.

Example 193: 8-(4-hydroxypiperidin-1-yl)-3,7-dimethyl-1-((5-methyl-1H-indol-2-yl)methyl)-1H-purine-2,6(3H,7H)-dione.

Example 194: 8-(3-hydroxyazetidin-1-yl)-3,7-dimethyl-1-((5-methyl-1H-indol-2-yl)methyl)-1H-purine-2,6(3H,7H)-dione.

Example 195: 1-((1H-indol-2-yl)methyl)-8-(2H-1,2,4-triazol-3-ylamino)-3,7-dimethyl-1H-purine-2,6(3H,7H)-dione.

Example 196: 1-((5-chloro-1-methyl-1H-indol-2-yl)methyl)-8-(4-hydroxypiperidin-1-yl)-3,7-dimethyl-1H-purine-2,6(3H,7H)-dione.

Example 197: 1-((5-chloro-1-methyl-1H-indol-2-yl)methyl)-8-(3-hydroxyazetidin-1-yl)-3,7-dimethyl-1H-purine-2,6(3H,7H)-dione.

Example 198: 1-((5-chloro-1H-indol-2-yl)methyl)-8-(4-hydroxypiperidin-1-yl)-3,7-dimethyl-1H-purine-2,6(3H,7H)-dione.

Example 199: 1-((5-chloro-1H-indol-2-yl)methyl)-8-(3-hydroxyazetidin-1-yl)-3,7-dimethyl-1H-purine-2,6(3H,7H)-dione.

Example 200: 1-((5-chloro-1H-indol-2-yl)methyl)-3,7-dimethyl-8-(pyridazin-3-ylamino)-1H-purine-2,6(3H,7H)-dione.

Example 201: 1-((1H-indol-2-yl)methyl)-3,7-dimethyl-8-(pyridazin-3-ylamino)-1H-purine-2,6(3H,7H)-dione.

Example 202: 8-(1H-1,2,4-triazol-5-ylamino)-3,7-dimethyl-1-((5-methyl-1H-indol-2-yl)methyl)-1H-purine-2,6(3H,7H)-dione.

Example 203: 1-((5-chloro-1-methyl-1H-indol-2-yl)methyl)-3,7-dimethyl-8-(pyridazin-3-ylamino)-1H-purine-2,6(3H,7H)-dione.

Example 204: 1-((5-chloro-1-methyl-1H-indol-2-yl)methyl)-3,7-dimethyl-8-(pyrimidin-4-ylamino)-1H-purine-2,6(3H,7H)-dione.

Example 205: 3,7-dimethyl-1-((5-methyl-1H-indol-2-yl)methyl)-8-(pyrimidin-4-ylamino)-1H-purine-2,6(3H,7H)-dione.

Example 206: 1-((5-chloro-1H-indol-2-yl)methyl)-3,7-dimethyl-8-(2-oxo-1,2-dihydropyrimidin-4-ylamino)-1H-purine-2,6(3H,7H)-dione.

Example 207: 8-(1H-1,2,4-triazol-5-ylamino)-1-((5-chloro-1H-indol-2-yl)methyl)-3,7-dimethyl-1H-purine-2,6(3H,7H)-dione.

Example 208: 1-((5-chloro-1H-indol-2-yl)methyl)-3,7-dimethyl-8-(pyrimidin-4-ylamino)-1H-purine-2,6(3H,7H)-dione.

Example 210: 8-(2-hydroxyethyl)-3,7-dimethyl-1-((5-methyl-1H-indol-2-yl)methyl)-1H-purine-2,6(3H,7H)-dione.

Example 211: (±)-1-(3,4-dichlorobenzyl)-3,7-dimethyl-8-(2-oxopiperidin-4-ylamino)-1H-purine-2,6(3H,7H)-dione.

Example 212: 1-((1H-indol-2-yl)methyl)-8-(2-hydroxyethyl)-3,7-dimethyl-1H-purine-2,6(3H,7H)-dione.

Example 213: (S)-1-((1H-indol-2-yl)methyl)-3,7-dimethyl-8-(2-oxopiperidin-3-ylamino)-1H-purine-2,6(3H,7H)-dione.

Example 214: (±)-1-((1H-indol-2-yl)methyl)-3,7-dimethyl-8-(5-oxopyrrolidin-3-ylamino)-1H-purine-2,6(3H,7H)-dione.

Example 215: (±)-1-((1H-indol-2-yl)methyl)-3,7-dimethyl-8-(2-oxopiperidin-4-ylamino)-1H-purine-2,6(3H,7H)-dione.

Example 216: 1-((1H-indol-2-yl)methyl)-3,7-dimethyl-8-(pyrimidin-4-ylamino)-1H-purine-2,6(3H,7H)-dione.

Example 217: 1-((1H-indol-2-yl)methyl)-8-(5-amino-1H-pyrazol-1-yl)-3,7-dimethyl-1H-purine-2,6(3H,7H)-dione.

Example 218: 8-(5-amino-1H-pyrazol-1-yl)-3,7-dimethyl-1-((5-methyl-1H-indol-2-yl)methyl)-1H-purine-2,6(3H,7H)-dione.

Example 219: 8-(3-amino-1H-pyrazol-1-yl)-1-((5-chloro-1H-indol-2-yl)methyl)-3,7-dimethyl-1H-purine-2,6(3H,7H)-dione.

Example 220: 8-(3-amino-1H-pyrazol-1-yl)-1-((5-chloro-1-methyl-1H-indol-2-yl)methyl)-3,7-dimethyl-1H-purine-2,6(3H,7H)-dione.

Example 221: (R)-1-((1H-indol-2-yl)methyl)-3,7-dimethyl-8-(2-oxopiperidin-3-ylamino)-1H-purine-2,6(3H,7H)-dione.

Example 222: 1-((1H-indol-2-yl)methyl)-3,7-dimethyl-8-(2-oxopyrrolidin-3-ylamino)-1H-purine-2,6(3H,7H)-dione.

Example 223: 1-((5-chloro-1H-indol-2-yl)methyl)-8-(2-hydroxyethyl)-3,7-dimethyl-1H-purine-2,6(3H,7H)-dione.

Example 224: 1-((5-chloro-1-methyl-1H-indol-2-yl)methyl)-3,7-dimethyl-8-(2-oxo-1,2-dihydropyrimidin-4-ylamino)-1H-purine-2,6(3H,7H)-dione.

Example 225: 1-((5-chloro-1-methyl-1H-indol-2-yl)methyl)-3,7-dimethyl-8-(2-morpholinoethyl)-1H-purine-2,6(3H,7H)-dione.

Example 226: 1-((1H-indol-2-yl)methyl)-3,7-dimethyl-8-(2-morpholinoethyl)-1H-purine-2,6(3H,7H)-dione.

Example 227: 3,7-dimethyl-1-((5-methyl-1H-indol-2-yl)methyl)-8-(2-morpholinoethyl)-1H-purine-2,6(3H,7H)-dione.

Example 228: (S)-1-((1H-indol-2-yl)methyl)-3,7-dimethyl-8-(6-oxopiperidin-3-ylamino)-1H-purine-2,6(3H,7H)-dione or (R)-1-((1H-indol-2-yl)methyl)-3,7-dimethyl-8-(6-oxopiperidin-3-ylamino)-1H-purine-2,6(3H,7H)-dione.

Example 229: 1-((5-chloro-1H-indol-2-yl)methyl)-3,7-dimethyl-8-(2-morpholinoethyl)-1H-purine-2,6(3H,7H)-dione.

Example 230: 8-(5-amino-1H-1,2,4-triazol-1-yl)-1-((5-chloro-1-methyl-1H-indol-2-yl)methyl)-3,7-dimethyl-1H-purine-2,6(3H,7H)-dione.

Example 231: 1-((1H-indol-2-yl)methyl)-8-amino-3,7-dimethyl-1H-purine-2,6(3H,7H)-dione.

Example 232: 8-amino-3,7-dimethyl-1-((5-methyl-1H-indol-2-yl)methyl)-1H-purine-2,6(3H,7H)-dione Example 233: 1-((1,5-dimethyl-1H-indol-2-yl)methyl)-3,7-dimethyl-1H-purine-2,6(3H,7H)-dione.

Example 234: 1-((1H-indol-2-yl)methyl)-3,7-dimethyl-1H-purine-2,6(3H,7H)-dione.

Example 235: 3,7-dimethyl-1-((1-methyl-1H-indol-2-yl)methyl)-1H-purine-2,6(3H,7H)-dione.

Example 236: 3,7-dimethyl-1-((5-methyl-1H-indol-2-yl)methyl)-1H-purine-2,6(3H,7H)-dione.

Example 237: 8-amino-1-((5-chloro-1-methyl-1H-indol-2-yl)methyl)-3,7-dimethyl-1H-purine-2,6(3H,7H)-dione.

Example 239: 1-((5-methoxy-1H-indol-2-yl)methyl)-3,7-dimethyl-1H-purine-2,6(3H,7H)-dione.

Example 238: 1-((5-methoxy-1-methyl-1H-indol-2-yl)methyl)-3,7-dimethyl-1H-purine-2,6(3H,7H)-dione.

Example 240: 1-((5-chloro-1H-indol-2-yl)methyl)-3,7-dimethyl-1H-purine-2,6(3H,7H)-dione.

Example 241: 8-amino-1-((5-chloro-1H-indol-2-yl)methyl)-3,7-dimethyl-1H-purine-2,6(3H,7H)-dione.

Example 242: 1-((5-chloro-1-methyl-1H-indol-2-yl)methyl)-3,7-dimethyl-1H-purine-2,6(3H,7H)-dione.

Example 243: 8-amino-1-((5-methoxy-1H-indol-2-yl)methyl)-3,7-dimethyl-1H-purine-2,6(3H,7H)-dione.

Example 244: 1-(3,4-dichlorobenzyl)-3,7-dimethyl-2,6-dioxo-2,3,6,7-tetrahydro-1H-purine-8-carboxamide.

Example 245: 1-(3,4-dichlorobenzyl)-3,7-dimethyl-8-(oxetan-3-ylamino)-1H-purine-2,6(3H,7H)-dione.

Example 246: 2-(1-(3,4-dichlorobenzyl)-3-methyl-2,6-dioxo-2,3-dihydro-1H-purin-7(6H)-yl)acetamide.

Example 247: (±)-2-chloro-4-((8-((trans)-3-hydroxycyclopentylamino)-3,7-dimethyl-2,6-dioxo-2,3,6,7-tetrahydro-1H-purin-1-yl)methyl)benzonitrile.

Example 248: 1-(3,4-dichlorobenzyl)-7-(2-hydroxyethyl)-3-methyl-1H-purine-2,6(3H,7H)-dione.

Example 249: 1-(4-chloro-3-methoxybenzyl)-3,7-dimethyl-1H-purine-2,6(3H,7H)-dione.

Example 250: 1-(3,4-dichlorobenzyl)-3-ethyl-7-methyl-1H-purine-2,6(3H,7H)-dione.

Example 251: 1-(3,4-dichlorobenzyl)-3-methyl-1H-purine-2,6(3H,7H)-dione.

Example 252: 1-(4-chloro-3-(methoxymethyl)benzyl)-3,7-dimethyl-1H-purine-2,6(3H,7H)-dione.

Example 253: 1-(3,4-dichlorobenzyl)-9-methyl-1H-purine-2,6(3H,9H)-dione.

Example 254: 1-(3,4-dichlorobenzyl)-8-(3-(hydroxymethyl)cyclohexylamino)-3,7-dimethyl-1H-purine-2,6(3H,7H)-dione.

Example 255: 1-(3,4-dichlorobenzyl)-8-(3-(hydroxymethyl)cyclopentylamino)-3,7-dimethyl-1H-purine-2,6(3H,7H)-dione.

Example 256: 2-chloro-5-((3,7-dimethyl-2,6-dioxo-2,3,6,7-tetrahydro-1H-purin-1-yl)methyl)benzonitrile.

Example 257: 2-((3,7-dimethyl-2,6-dioxo-2,3,6,7-tetrahydro-1H-purin-1-yl)methyl)-1H-indole-5-carbonitrile.

Example 258: (±)-(cis)-ethyl 3-(1-(3,4-dichlorobenzyl)-3,7-dimethyl-2,6-dioxo-2,3,6,7-tetrahydro-1H-purin-8-ylamino)cyclobutanecarboxylate.

Example 259: (±)-(cis)-3-(1-(3,4-dichlorobenzyl)-3,7-dimethyl-2,6-dioxo-2,3,6,7-tetrahydro-1H-purin-8-ylamino)cyclobutanecarboxylic acid.

Example 260: 3-(1-((1H-indol-6-yl)methyl)-3,7-dimethyl-2,6-dioxo-2,3,6,7-tetrahydro-1H-purin-8-ylamino)cyclohexanecarboxylic acid.

Example 261: (±)-1-(3,4-dichlorobenzyl)-8-((cis)-3-(hydroxymethyl)cyclobutylamino)-3,7-dimethyl-1H-purine-2,6(3H,7H)-dione.

Example 262: 1-(3,4-dichlorobenzyl)-8-((1R,3R)-3-hydroxycyclopentylamino)-3,9-dimethyl-1H-purine-2,6(3H,9H)-dione.

Example 263: 1-((1H-indol-6-yl)methyl)-3,7-dimethyl-1H-purine-2,6(3H,7H)-dione.

Example 264: (±)-(cis)-4-((1-(3,4-dichlorobenzyl)-3,7-dimethyl-2,6-dioxo-2,3,6,7-tetrahydro-1H-purin-8-yl)amino)cyclohexanecarboxylic acid.

Example 265: 1-(3,4-dichlorobenzyl)-8-(3-(1-hydroxyethyl)cyclopentylamino)-3,7-dimethyl-1H-purine-2,6(3H,7H)-dione.

Example 266: (1R,3R)-ethyl 3-(1-(3,4-dichlorobenzyl)-3,7-dimethyl-2,6-dioxo-2,3,6,7-tetrahydro-1H-purin-8-yl)cyclobutanecarboxylate.

Example 267: 1-(3,4-dichlorobenzyl)-8-(3-(methoxymethyl)cyclopentylamino)-3,7-dimethyl-1H-purine-2,6(3H,7H)-dione.

Example 268: 1-(3,4-dichlorobenzyl)-8-((1R,3R)-3-(hydroxymethyl)cyclobutyl)-3,7-dimethyl-3,7-dihydro-1H-purine-2,6-dione.

Example 269: 4-[[1-[(3,4-dichlorophenyl)methyl]-3,7-dimethyl-2,6-dioxo-purin-8-yl]amino]benzoic acid.

Example 313: 4-[[1-[(3,4-dichlorophenyl)methyl]-3,7-dimethyl-2,6-dioxo-purin-8-yl]amino]benzamide.

Example 270: 4-((1-(3,4-dichlorobenzyl)-3,7-dimethyl-2,6-dioxo-2,3,6,7-tetrahydro-1H-purin-8-yl)(hydroxy)methyl)cyclohexanecarboxylic acid.

Example 271: 8-(cyclopropylamino)-1-[(3,4-dichlorophenyl)methyl]-3,7-dimethyl-purine-2,6-dione.

Example 272: (±)-trans-4-[[1-[(3,4-dichlorophenyl)methyl]-3,7-dimethyl-2,6-dioxo-purin-8-yl]amino]cyclohexanecarboxylic acid.

Example 273: 1-[(3,4-dichlorophenyl)methyl]-8-(2-methoxyethylamino)-3,7-dimethyl-purine-2,6-dione.

Example 274: N-[1-[(3,4-dichlorophenyl)methyl]-3,7-dimethyl-2,6-dioxo-purin-8-yl]acetamide Example 275: 1-(3,4-dichlorobenzyl)-8-((1R,3S)-3-(hydroxymethyl)cyclopentylamino)-3,7-dimethyl-1H-purine-2,6(3H,7H)-dione.

Example 276: (1S,3R)-ethyl 3-(1-(3,4-dichlorobenzyl)-3,7-dimethyl-2,6-dioxo-2,3,6,7-tetrahydro-1H-purin-8-ylamino)cyclopentanecarboxylate.

Example 277: 3-(4-(1-(3,4-dichlorobenzyl)-3,7-dimethyl-2,6-dioxo-2,3,6,7-tetrahydro-1H-purin-8-ylamino)pyridin-2-yl)propanoic acid.

Example 278: 1-[(3,4-dichlorophenyl)methyl]-3,7-dimethyl-8-(2,2,2-trifluoroethylamino)purine-2,6-dione.

Example 279: (±)-trans-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid.

Example 281: 3-(2-(1-(3,4-dichlorobenzyl)-3,7-dimethyl-2,6-dioxo-2,3,6,7-tetrahydro-1H-purin-8-yl amino)pyridin-4-yl)propanoic acid.

Example 282: 3-(6-(1-(3,4-dichlorobenzyl)-3,7-dimethyl-2,6-dioxo-2,3,6,7-tetrahydro-1H-purin-8-ylamino)pyridin-2-yl)propanoic acid.

Example 283: 3-(4-(1-(3,4-dichlorobenzyl)-3,7-dimethyl-2,6-dioxo-2,3,6,7-tetrahydro-1H-purin-8-ylamino)pyridin-2-yl)propanamide.

Example 284: (±)-trans-1-(3,4-dichlorobenzyl)-8-((2-(2-(hydroxymethyl)cyclopropyl)pyridin-4-yl)amino)-3,7-dimethyl-1H-purine-2,6(3H,7H)-dione.

Examples 337 and 338: 1-(3,4-dichlorobenzyl)-8-((2-((1R,2R)-2-(hydroxymethyl)cyclopropyl)pyridin-4-yl)amino)-3,7-dimethyl-1H-purine-2,6(3H,7H)-dione and 1-(3,4-dichlorobenzyl)-8-((2-((1S, 2S)-2-(hydroxymethyl)cyclopropyl)pyridin-4-yl)amino)-3,7-dimethyl-1H-purine-2,6(3H,7H)-dione.

Example 285: 1-((4-chloro-1H-indol-2-yl)methyl)-3,7-dimethyl-8-(pyridin-4-ylamino)-1H-purine-2,6(3H,7H)-dione.

Example 286: 3-((1-(3,4-dichlorobenzyl)-3,7-dimethyl-2,6-dioxo-2,3,6,7-tetrahydro-1H-purin-8-yl)amino)benzoic acid.

Example 287: 2-(3-((1-(3,4-dichlorobenzyl)-3,7-dimethyl-2,6-dioxo-2,3,6,7-tetrahydro-1H-purin-8-yl)amino)phenyl)acetic acid.

Example 288: 2-(4-((1-(3,4-dichlorobenzyl)-3,7-dimethyl-2,6-dioxo-2,3,6,7-tetrahydro-1H-purin-8-yl)amino)phenyl)acetic acid.

Example 289: (1R,3R)-3-(1-(1H-indol-2-yl)methyl)-3,7-dimethyl-2,6-dioxo-2,3,6,7-tetrahydro-1H-purin-8-ylamino)cyclobutanecarboxylic acid.

Example 290: 1((1H-pyrrolo[2,3-b]pyridin-2-yl)methyl)-3,7-dimethyl-1H-purine-2,6(3H,7H)-dione.

Example 291: 3-(3-(1-(3,4-dichlorobenzyl)-3,7-dimethyl-2,6-dioxo-2,3,6,7-tetrahydro-1H-purin-8-ylamino)phenyl)propanoic acid.

Example 292: 3-(6-(1-(3,4-dichlorobenzyl)-3,7-dimethyl-2,6-dioxo-2,3,6,7-tetrahydro-1H-purin-8-ylamino)pyridin-2-yl)propanamide.

Example 293: 1-(3,4-dichlorobenzyl)-8-(6-(3-hydroxypropyl)pyridin-2-ylamino)-3,7-dimethyl-1H-purine-2,6(3H,7H)-dione.

Example 294: 3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid.

Example 295: 1-((1H-indol-2-yl)methyl)-8-((1R,3R)-3-(hydroxymethyl)cyclobutylamino)-3,7-dimethyl-1H-purine-2,6(3H,7H)-dione.

Example 296: (±)-trans-2-(4-((1-(3,4-Dichlorobenzyl)-3,7-dimethyl-2,6-dioxo-2,3,6,7-tetrahydro-1H-purin-8-yl)amino)pyridin-2-yl)cyclopropanecarboxamide.

Example 297: 4-[[1-(1H-indol-2-ylmethyl)-3,7-dimethyl-2,6-dioxo-purin-8-yl]amino]benzoic acid.

Example 298: 1-(3,4-dichlorobenzyl)-8-((4-(hydroxymethyl)phenyl)amino)-3,7-dimethyl-3,7-dihydro-1H-purine-2,6-dione.

Example 299: (±)-trans-2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid.

Examples 300 and 301: (1R,2R)-2-(4-((1-(3,4-dichloro benzyl)-3,7-dimethyl-2,6-dioxo-2,3,6,7-tetrahydro-1H-purin-8-yl)amino)pyridin-2-yl)cyclopropanecarboxylic acid and (1S,2S)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid.

Example 302: 1-((4-chloro-1H-indol-2-yl)methyl)-3,7-dimethyl-8-(pyridin-2-ylamino)-1H-purine-2,6(3H,7H)-dione.

Example 303: 4-(1-(3,4-dichlorobenzyl)-3,7-dimethyl-2,6-dioxo-2,3,6,7-tetrahydro-1H-purin-8-ylamino)picolinic acid.

Example 304: 3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanamide.

Example 305: 1-((4-chloro-1H-indol-2-yl)methyl)-8-((1r,3r)-3-(hydroxymethyl)cyclobutylamino)-3,7-dimethyl-1H-purine-2,6(3H,7H)-dione.

Example 306: 3-(7-(2-amino-2-oxoethyl)-1-(3,4-dichlorobenzyl)-3-methyl-2,6-dioxo-2,3,6,7-tetrahydro-1H-purin-8-ylamino)cyclohexanecarboxylic acid.

Example 307: 3-(7-(carboxymethyl)-1-(3,4-dichlorobenzyl)-3-methyl-2,6-dioxo-2,3,6,7-tetrahydro-1H-purin-8-ylamino)cyclohexanecarboxylic acid.

Example 308: 3-(1-((4-chloro-1H-indol-2-yl)methyl)-3,7-dimethyl-2,6-dioxo-2,3,6,7-tetrahydro-1H-purin-8-ylamino)cyclohexanecarboxylic acid.

Example 309: 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylic acid.

Example 310: 1-((4-fluoro-1H-indol-2-yl)methyl)-3,7-dimethyl-8-(pyridin-4-ylamino)-1H-purine-2,6(3H,7H)-dione.

Example 311: 1-((3-chloro-1H-indol-2-yl)methyl)-3,7-dimethyl-8-(pyridin-4-ylamino)-1H-purine-2,6(3H,7H)-dione.

Example 312: 1-((6-chloro-1H-indol-2-yl)methyl)-3,7-dimethyl-8-(pyridin-4-ylamino)-1H-purine-2,6(3H,7H)-dione.

Example 314: 2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetic acid Example 315: (±)-trans-2-[6-[[1-[(4-chloro-1H-indol-2-yl)methyl]-3,7-dimethyl-2,6-dioxo-purin-8-yl] amino]-2-pyridyl]cyclopropanecarboxylic acid.

Example 398: (1R,2R)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid and (1S,2S)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid.

Example 316: 3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylic acid.

Example 317: 1-((1H-indol-2-yl)methyl)-8-((1S,3R)-3-(hydroxymethyl)cyclopentylamino)-3,7-dimethyl-1H-purine-2,6(3H,7H)-dione.

Example 318: 3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylic acid.

Example 319: 3-(4-(1-(3,4-dichlorobenzyl)-3,7-dimethyl-2,6-dioxo-2,3,6,7-tetrahydro-1H-purin-8-yl amino)pyridin-2-yl)cyclobutanecarboxamide.

Example 320: 1-(3,4-dichlorobenzyl)-8-(2-(3-(hydroxymethyl)cyclobutyl)pyridin-4-ylamino)-3,7-dimethyl-1H-purine-2,6(3H,7H)-dione.

Example 321: (±)-trans-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid.

Example 322 and 363: (1R,2R)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic and (1S,2S)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid.

Example 323: 1-(3,4-dichlorobenzyl)-8-((3-(2-hydroxyethyl)-2,3-dihydro-1H-inden-5-yl)amino)-3,7-dimethyl-1H-purine-2,6(3H,7H)-dione.

Example 324: 1-(3,4-dichlorobenzyl)-8-((2-(hydroxymethyl)-2,3-dihydro-1H-inden-5-yl)amino)-3,7-dimethyl-1H-purine-2,6(3H,7H)-dione.

Example 325: (±)-1-(3,4-dichlorobenzyl)-8-((trans)-3-(hydroxymethyl)cyclopentylamino)-3,7-dimethyl-1H-purine-2,6(3H,7H)-dione.

Example 326: 3,7-dimethyl-1-((6-methyl-1H-indol-2-yl)methyl)-8-(pyridin-4-ylamino)-1H-purine-2,6(3H,7H)-dione.

Example 327: 8-((1R,3R)-3-(hydroxymethyl)cyclobutylamino)-3,7-dimethyl-1-((4-methyl-1H-indol-2-yl)methyl)-1H-purine-2,6(3H,7H)-dione.

Example 328: 1-((4-methyl-1H-indol-2-yl)methyl)-3,7-dimethyl-8-(pyridin-4-ylamino)-1H-purine-2,6(3H,7H)-dione.

Example 329: 3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N,N-dimethylpropanamide.

Example 330: 3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N-methylpropanamide.

Example 331: 4-[[1-[(4-chloro-1H-indol-2-yl)methyl]-3,7-dimethyl-2,6-dioxo-purin-8-yl]amino]benzoic acid.

Example 332: (±)-cis-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid.

Example 333: 1-[(4-chloro-1H-indol-2-yl)methyl]-8-[(2-methoxy-4-pyridyl)amino]-3,7-dimethyl-purine-2,6-dione.

Example 334: 1-[(4-chloro-1H-indol-2-yl)methyl]-8-[(2-trifluoromethyl-4-pyridyl)amino]-3,7-dimethyl-purine-2,6-dione.

Example 335: (±)-trans-1-((4-chloro-1H-indol-2-yl)methyl)-8-((6-(-2-(hydroxymethyl)cyclopropyl)pyridin-2-yl)amino)-3,7-dimethyl-1H-purine-2,6(3H,7H)-dione.

Example 336: N-[1-[(4-chloro-1H-indol-2-yl)methyl]-3,7-dimethyl-2,6-dioxo-purin-8-yl]methanesulfonamide.

Example 339: 2-(3-((1-((4-chloro-1H-indol-2-yl)methyl)-3,7-dimethyl-2,6-dioxo-2,3,6,7-tetrahydro-1H-purin-8-yl)amino)phenyl)acetic acid.

Example 340: 3,7-dimethyl-1-((3-methyl-1H-indol-2-yl)methyl)-8-(pyridin-4-ylamino)-1H-purine-2,6(3H,7H)-dione.

Example 341: 3-(7-(2-carboxyethyl)-1-(3,4-dichlorobenzyl)-3-methyl-2,6-dioxo-2,3,6,7-tetrahydro-1H-purin-8-ylamino)cyclohexanecarboxylic acid.

Example 342: 3-(3,7-dimethyl-1-((4-methyl-1H-indol-2-yl)methyl)-2,6-dioxo-2,3,6,7-tetrahydro-1H-purin-8-ylamino)cyclohexanecarboxylic acid.

Example 343: 1-((4-chloro-1H-indol-2-yl)methyl)-3,7-dimethyl-8-(pyridin-3-ylamino)-1H-purine-2,6(3H,7H)-dione.

Example 344: 1-(3, 4-diclorobenzyl)-8-(2-(3-hydroxylcyclobutyl) pyridine-4-ylamino)-3,7-dimethyl-1-H-purine-2,6(3H,7H)-dione.

Example 345: 2-[4-[[1-[(4-chloro-1H-indol-2-yl)methyl]-3,7-dimethyl-2,6-dioxo-purin-8-yl]amino]phenyl]acetic acid.

Example 346: 3-[[1-[(4-chloro-1H-indol-2-yl)methyl]-3,7-dimethyl-2,6-dioxo-purin-8-yl]amino]benzoic acid.

Example 347: 1-((4-chloro-1H-indol-2-yl)methyl)-8-((1S, 2R)-2-hydroxycyclopentylamino)-3,7-dimethyl-1H-purine-2,6(3H,7H)-dione.

Example 348: 1-((4-bromo-1H-indol-2-yl) methyl)-3,7-dimethyl-8-(pyridin-4-ylamino)-1H-purine-2,6(3H,7H)-dione.

Example 349: 3,7-dimethyl-1-(naphthalen-2-ylmethyl)-8-(pyridin-4-ylamino)-1H-purine-2,6(3H,7H)-dione.

Example 350: 2-((3,7-dimethyl-2,6-dioxo-8-(pyridin-4-ylamino)-2,3,6,7-tetrahydro-1H-purin-1-yl)methyl)-1H-indole-4-carbonitrile.

Example 351: 1-((4-chloro-1H-indol-2-yl)methyl)-8-(6-(3-hydroxycyclopentyl) pyridin-2-ylamino)-3,7-dimethyl-1H-purine 2,6(3H,7H)-dione.

Example 352: 1-(3,4-diclorobenzyl)-8-(6-(3-hydroxycyclobutyl)pyridine-2-ylamino)-3,7-dimethyl-1H-purine-2,6(3H,7H)-dione.

Example 353: 8-(2-amino-1H-benzo[d]imidazol-1-yl)-1-((4-chloro-1H-indol-2-yl)methyl)-3,7-dimethyl-1H-purine-2,6(3H,7H)-dione.

Example 354: 1-((4-chloro-1H-indol-2-yl)methyl)-3,7-dimethyl-8-(pyrazin-2-ylamino)-1H-purine-2,6(3H,7H)-dione.

Example 355: 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid.

Example 356: 1-[(4-chloro-1H-indol-2-yl)methyl]-8-(1H-imidazol-2-ylamino)-3,7-dimethyl-purine-2,6-dione.

Example 357: (±)-cis-2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid.

Example 358: 8-(aminomethyl)-1-[(4-chloro-1H-indol-2-yl)methyl]-3,7-dimethyl-purine-2,6-dione Example 359: 4-chloro-2-((8-(((1R,2S)-2-hydroxycyclopentyl)amino)-3,7-dimethyl-2,6-dioxo-2,3,6,7-tetrahydro-1H-purin-1-yl)methyl)-1H-indole-1-carboxylic acid.

Example 360: 2-(1-((4-chloro-1H-indol-2-yl)methyl)-3,7-dimethyl-2,6-dioxo-2,3,6,7-tetrahydro-1H-purin-8-ylamino)acetamide.

Example 361: 1-((4-chloro-1H-indol-2-yl)methyl)-3-ethyl-7-methyl-8-(pyridin-4-ylamino)-1H-purine-2,6(3H,7H)-dione.

Example 362: 1-((4-chloro-1H-indol-2-yl)methyl)-3,7-dimethyl-8-(pyrimidin-4-ylamino)-3,7-dihydro-1H-purine-2,6-dione.

Example 364: (±)-trans-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxamide.

Example 366: 1-[(7-fluoro-1H-indol-2-yl)methyl]-3,7-dimethyl-8-(4-pyridylamino)purine-2,6-dione.

Example 367: 1-[(4-chloro-1H-indol-2-yl)methyl]-3,7-dimethyl-8-(4-methylsulfonylanilino)purine-2,6-dione.

Example 368: (±)-cis-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid.

Example 369: 3-(7-(2-aminoethyl)-1-(3,4-dichlorobenzyl)-3-methyl-2,6-dioxo-2,3,6,7-tetrahydro-1H—

Example 370: 1-((4-methoxy-1H-indol-2-yl)methyl)-3,7-dimethyl-8-(pyridin-4-ylamino)-1H-purine-2,6(3H,7H)-dione.

Example 371: 8-(3-aminopiperidin-1-yl)-1-((4-chloro-1H-indol-2-yl)methyl)-3,7-dimethyl-1H-purine-2,6(3H,7H)-dione.

Example 372: (±)-cis-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropane-1-carboxylic acid.

Example 373: 1-[(7-chloro-1H-indol-2-yl)methyl]-3,7-dimethyl-8-(4-pyridylamino)purine-2,6-dione.

Example 374: 3,7-dimethyl-1-((4-phenyl-1H-indol-2-yl)methyl)-8-(pyridin-4-ylamino)-1H-purine-2,6(3H,7H)-dione.

Example 375: 1-((1-chloronaphthalen-2-yl)methyl)-3,7-dimethyl-8-(pyridin-4-ylamino)-1H-purine-2,6(3H,7H)-dione.

Example 376: 8-(3-aminopyrrolidin-1-yl)-1-((4-chloro-1H-indol-2-yl)methyl)-7-methyl-1H-purine-2,6(3H,7H)-dione.

Example 377: 3-(6-(1-((4-chloro-1H-indol-2-yl)methyl)-3,7-dimethyl-2,6-dioxo-2,3,6,7-tetrahydro-1H-purin-8-ylamino)-3-methylpyridin-2-yl)propanoic acid.

Example 378: 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanamide.

Example 379: 2-((8-(2-aminoacetamido)-3,7-dimethyl-2,6-dioxo-2,3,6,7-tetrahydro-1H-purin-1-yl)methyl)-4-chloro-1H-indole-1-carboxylic acid.

Example 380: 1-((4-chloro-1H-indol-2-yl)methyl)-8-(6-methoxypyridin-3-ylamino)-3,7-dimethyl-1H-purine-2,6(3H,7H)-dione.

Example 381: 1-((4-chloro-1H-indol-2-yl)methyl)-8-(6-chloropyridin-3-ylamino)-3,7-dimethyl-1H-purine-2,6(3H,7H)-dione.

Example 382: 1-((4-chloro-1H-indol-2-yl)methyl)-3,7-dimethyl-8-(6-(trifluoromethyl)pyridin-3-yl amino)-1H-purine-2,6(3H,7H)-dione.

Example 383: 1-((4-chloro-1H-indol-2-yl)methyl)-3,7-dimethyl-8-(6-methylpyridin-3-ylamino)-1H-purine-2,6(3H,7H)-dione.

Example 384: 1-((4-chloro-1H-indol-2-yl)methyl)-8-(6-fluoropyridin-3-ylamino)-3,7-dimethyl-1H-purine-2,6(3H,7H)-dione.

Example 386: 8-(2-aminoethyl)-1-((4-chloro-1H-indol-2-yl)methyl)-3,7-dimethyl-1H-purine-2,6(3H,7H)-dione.

Example 387: 1-((4-ethyl-1H-indol-2-yl)methyl)-3,7-dimethyl-8-(pyridin-4-ylamino)-1H-purine-2,6(3H,7H)-dione.

Example 388: 1-((4-chloro-1H-indol-2-yl)methyl)-8-(hydroxy(phenyl)methyl)-3,7-dimethyl-1H-purine-2,6(3H,7H)-dione.

Example 389: 8-(1-aminoethyl)-1-[(4-chloro-1H-indol-2-yl)methyl]-3,7-dimethyl-purine-2,6-dione.

Examples 435 and 436: (S)-8-(1-aminoethyl)-1-((4-chloro-1H-indol-2-yl)methyl)-3,7-dimethyl-1H-purine-2,6(3H,7H)-dione and (R)-8-(1-aminoethyl)-1-((4-chloro-1H-indol-2-yl)methyl)-3,7-dimethyl-1H-purine-2,6(3H,7H)-dione.

Example 456: 8-(1-aminoethyl)-1-[(3,4-dichloro-1H-indol-2-yl)methyl]-3,7-dimethyl-purine-2,6-dione.

Example 457: 1-[(4-chloro-1H-indol-2-yl)methyl]-8-[1-(dimethylamino)ethyl]-3,7-dimethyl-purine-2,6-dione.

Example 390: N-((4-((1-((4-chloro-1H-indol-2-yl)methyl)-3,7-dimethyl-2,6-dioxo-2,3,6,7-tetrahydro-1H-purin-8-yl)amino)phenyl)sulfonyl)acetamide.

Example 391: 1-[(4-chloro-1H-indol-2-yl)methyl]-3,7-dimethyl-8-(3-piperidyl)purine-2,6-dione.

Example 392: 1-[(4-chloro-1H-indol-2-yl)methyl]-3,7-dimethyl-8-[(5-piperazin-1-yl-2-pyridyl)amino]purine-2,6-dione.

Example 393: 1-((1H-pyrrolo[2,3-c]pyridin-2-yl)methyl)-3,7-dimethyl-8-(pyridin-4-ylamino)-1H-purine-2,6(3H,7H)-dione.

Example 394: 8-(2-aminoethyl)-1,3,7-trimethyl-1H-purine-2,6(3H,7H)-dione.

Example 395: 8-((1R,2S)-2-aminocyclopentylamino)-1-((4-chloro-1H-indol-2-yl)methyl)-3,7-dimethyl-1H-purine-2,6(3H,7H)-dione.

Example 396: 3-(3-chloro-6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid.

Example 397: 8-((4-(1H-tetrazol-5-yl)phenyl)amino)-1-((4-chloro-1H-indol-2-yl)methyl)-3,7-dimethyl-1H-purine-2,6(3H,7H)-dione.

Example 399: 1-[(4-chloro-1H-indol-2-yl)methyl]-3,7-dimethyl-8-[(6-phenyl-2-pyridyl)amino]purine-2,6-dione.

Example 400: 1-[(4-chloro-1H-indol-2-yl)methyl]-3,7-dimethyl-8-[(5-phenyl-2-pyridyl)amino]purine-2,6-dione.

Example 401: 1-((4-cyclopropyl-1H-indol-2-yl)methyl)-3,7-dimethyl-8-(pyridin-4-yl amino)-1H-purine-2,6(3H,7H)-dione.

Example 402: 1-((5-chloronaphthalen-2-yl)methyl)-3,7-dimethyl-8-(pyridin-4-ylamino)-1H-purine-2,6(3H,7H)-dione.

Example 403: 1-((4-chloro-1H-indol-2-yl)methyl)-8-((1S,2S)-2-hydroxycyclopentylamino)-3,7-dimethyl-1H-purine-2,6(3H,7H)-dione.

Example 404: 3,7-dimethyl-8-(pyridin-4-ylamino)-1-((4-(trifluoromethyl)-1H-indol-2-yl)methyl)-1H-purine-2,6(3H,7H)-dione.

Example 405: 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-dimethylpropanamide.

Example 406: 1-((4-chloro-1H-indol-2-yl)methyl)-3,7-dimethyl-8-(2-(3-oxo-3-(piperidin-1-yl)propyl)pyrimidin-4-ylamino)-1H-purine-2,6(3H,7H)-dione.

Example 407: 1-((4-chloro-1H-indol-2-yl)methyl)-8-(6-(hydroxymethyl)pyridin-3-yl amino)-3,7-dimethyl-1H-purine-2,6(3H,7H)-dione.

Example 408: Methyl 5-(1-((4-chloro-1H-indol-2-yl)methyl)-3,7-dimethyl-2,6-dioxo-2,3,6,7-tetrahydro-1H-purin-8-ylamino)picolinate.

Example 409: 5-(1-((4-chloro-1H-indol-2-yl)methyl)-3,7-dimethyl-2,6-dioxo-2,3,6,7-tetrahydro-1H-purin-8-ylamino)picolinamide.

Example 410: 3,7-dimethyl-1-((5-methylnaphthalen-2-yl)methyl)-8-(pyridin-4-ylamino)-1H-purine-2,6(3H,7H)-dione.
Example 411: 8-(amino(phenyl)methyl)-1-((4-chloro-1H-indol-2-yl)methyl)-3,7-dimethyl-1H-purine-2,6(3H,7H)-dione.
Example 412: 3-(4-(3,7-dimethyl-1-((4-methyl-1H-indol-2-yl)methyl)-2,6-dioxo-2,3,6,7-tetrahydro-1H-purin-8-ylamino)pyrimidin-2-yl)propanoic acid.
Example 413: 8-(2-(3-(azetidin-1-yl)-3-oxopropyl)pyrimidin-4-ylamino)-1-((4-chloro-1H-indol-2-yl)methyl)-3,7-dimethyl-1H-purine-2,6(3H,7H)-dione.
Example 414: 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N-cyclopropyl-N-methylpropanamide.
Example 415: 3-(4-(1-((4-chloro-1H-indol-2-yl)methyl)-3,7-dimethyl-2,6-dioxo-2,3,6,7-tetrahydro-1H-purin-8-yl amino)pyrimidin-2-yl)-N-methylpropanamide.
Example 416: 1-((4-chloro-1H-indol-2-yl)methyl)-3,7-dimethyl-8-((2-(3-morpholino-3-oxopropyl)pyrimidin-4-yl)amino)-3,7-dihydro-1H-purine-2,6-dione.
Example 417: 1-((4-chloro-1H-indol-2-yl)methyl)-3,7-dimethyl-8-(2-(3-oxo-3-(pyrrolidin-1-yl)propyl)pyrimidin-4-ylamino)-1H-purine-2,6(3H,7H)-dione.
Example 418: 3-(7-(2-aminoethyl)-1-((4-chloro-1H-indol-2-yl)methyl)-3-methyl-2,6-dioxo-2,3,6,7-tetrahydro-1H-purin-8-ylamino)cyclohexanecarboxylic acid.
Example 419: 1-((3,4-dimethyl-1H-indol-2-yl)methyl)-3,7-dimethyl-8-(pyridin-4-ylamino)-1H-purine-2,6(3H,7H)-dione.
Example 420: 4-[[1-[(4-chloro-1H-indol-2-yl)methyl]-3,7-dimethyl-2,6-dioxo-purin-8-yl]amino]benzamide.
Example 421: 1-[(7-chloro-1H-indol-2-yl)methyl]-8-methoxy-3,7-dimethyl-purine-2,6-dione.
Example 422: N-[1-[(4-chloro-1H-indol-2-yl)methyl]-3,7-dimethyl-2,6-dioxo-purin-8-yl]-2,2,2-trifluoro-acetamide.
Example 423: 1-((3,4-dichloro-1H-indol-2-yl)methyl)-3,7-dimethyl-8-(pyrrolidin-3-yl)-1H-purine-2,6(3H,7H)-dione.
Example 424: 1-[(4-chloro-1H-indol-2-yl)methyl]-3,7-dimethyl-8-pyrrolidin-2-yl-purine-2,6-dione
Example 425: 1-[(4-chloro-1H-indol-2-yl)methyl]-3,7-dimethyl-8-pyrrolidin-3-yl-purine-2,6-dione
Example 426: 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-diethylpropanamide
Example 427: 5-(1-((4-chloro-1H-indol-2-yl)methyl)-3,7-dimethyl-2,6-dioxo-2,3,6,7-tetrahydro-1H-purin-8-ylamino)picolinonitrile.
Example 428: 1-((4-chloro-1H-indol-2-yl)methyl)-3,7-dimethyl-8-(2-(3-oxo-3-(piperazin-1-yl)propyl)pyrimidin-4-ylamino)-1H-purine-2,6(3H,7H)-dione.
Example 429: 8-(6-(aminomethyl)pyridin-3-ylamino)-1-((4-chloro-1H-indol-2-yl)methyl)-3,7-dimethyl-1H-purine-2,6(3H,7H)-dione.
Example 431: 2-[4-[[1-[(4-chloro-1H-indol-2-yl)methyl]-3,7-dimethyl-2,6-dioxo-purin-8-yl]amino]phenyl]acetamide.
Example 432: 1-((4-chloro-1H-indol-2-yl)methyl)-8-(4-(hydroxymethyl)phenylamino)-3,7-dimethyl-1H-purine-2,6(3H,7H)-dione.
Example 433: 1-[(7-chloro-1-methyl-indol-2-yl)methyl]-8-methoxy-3,7-dimethyl-purine-2,6-dione.
Example 430: 1-((4-chloro-1H-indol-2-yl)methyl)-3,7-dimethyl-8-(piperidin-2-yl)-3,7-dihydro-1H-purine-2,6-dione.
Example 434: 8-(1-aminopropyl)-1-[(4-chloro-1H-indol-2-yl)methyl]-3,7-dimethyl-purine-2,6-dione.
Example 437: 8-(1-amino-2-methyl-propyl)-1-[(4-chloro-1H-indol-2-yl)methyl]-3,7-dimethyl-purine-2,6-dione.
Example 442: 8-(1-amino-2-cyclopropyl-ethyl)-1-[(4-chloro-1H-indol-2-yl)methyl-3,7-dimethyl-purine-2,6-dione.
Example 443: 8-[amino(cyclobutyl)methyl]-1-[(4-chloro-1H-indol-2-yl)methyl]-3,7-dimethyl-purine-2,6-dione.
Example 444: 8-[amino(cyclopropyl)methyl]-1-[(4-chloro-1H-indol-2-yl)methyl]-3,7-dimethyl-purine-2,6-dione.
Example 445: 8-[amino(3-pyridyl)methyl]-1-[(4-chloro-1H-indol-2-yl)methyl]-3,7-dimethyl-purine-2,6-dione.
Example 446: 8-[amino(cyclohexyl)methyl]-1-[(4-chloro-1H-indol-2-yl)methyl]-3,7-dimethyl-purine-2,6-dione.
Example 453: 1-[(4-chloro-1H-indol-2-yl)methyl]-3,7-dimethyl-8-morpholin-2-yl-purine-2,6-dione.
Example 464: 8-(amino(cyclopentyl)methyl)-1-((4-chloro-1H-indol-2-yl)methyl)-3,7-dimethyl-3,7-dihydro-1H-purine-2,6-dione.
Example 438: 1-[(4-chloro-1H-indol-2-yl)methyl]-3,7-dimethyl-8-[1-(methylamino)ethyl]purine-2,6-dione.
Examples 454 and 455: 8-[amino(tetrahydropyran-4-yl)methyl]-1-[(4-chloro-1H-indol-2-yl)methyl]-3,7-dimethyl-purine-2,6-dione (Example 453) and 8-[amino(tetrahydropyran-4-yl)methyl]-1-[(3,4-dichloro-1H-indol-2-yl)methyl]-3,7-dimethyl-purine-2,6-dione (Example 454).
Example 467: 8-[amino(oxetan-3-yl)methyl]-1-[(4-chloro-1H-indol-2-yl)methyl]-3,7-dimethyl-purine-2,6-dione.
Example 458: 8-(1-amino-2-hydroxy-ethyl)-1-[(4-chloro-1H-indol-2-yl)methyl]-3,7-dimethyl-purine-2,6-dione.
Example 439: 8-((1S,2R)-2-aminocyclopentylamino)-1-((4-chloro-1H-indol-2-yl)methyl)-3,7-dimethyl-1H-purine-2,6(3H,7H)-dione.
Example 440: 2-amino-N-((4-(1((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide.
Example 441: 8-(1-aminoethyl)-1-((4-chloro-1H-indol-2-yl)methyl)-3-ethyl-7-methyl-1H-purine-2,6(3H,7H)-dione.
Example 447: (R)-8-(1-amino-2-(pyridin-4-yl)ethyl)-1-((4-chloro-1H-indol-2-yl)methyl)-3,7-dimethyl-1H-purine-2,6(3H,7H)-dione.
Example 448: 8-(1-aminoethyl)-3,7-dimethyl-1-((5-methylnaphthalen-2-yl)methyl)-1H-purine-2,6(3H,7H)-dione.
Example 449: (S)-8-(1-amino-2-(pyridin-4-yl)ethyl)-1-((4-chloro-1H-indol-2-yl)methyl)-3,7-dimethyl-1H-purine-2,6(3H,7H)-dione.
Example 450: 8-(1-amino-2-phenylethyl)-1-((4-chloro-1H-indol-2-yl)methyl)-3,7-dimethyl-1H-purine-2,6(3H,7H)-dione.
Example 469: 8-(2-(aminomethyl)pyrimidin-4-ylamino)-1-((4-chloro-1H-indol-2-yl)methyl)-3,7-dimethyl-1H-purine-2,6(3H,7H)-dione.
Example 451: N-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide.
Example 452: 8-(1-aminoethyl)-1-((5-cyclopropylnaphthalen-2-yl)methyl)-3,7-dimethyl-1H-purine-2,6(3H,7H)-dione.
Example 459: 8-(1-aminoethyl)-3-ethyl-7-methyl-1-((5-methylnaphthalen-2-yl)methyl)-1H-purine-2,6(3H,7H)-dione.

Example 460: 1-((1H-pyrrolo[3,2-c]pyridin-2-yl)methyl)-3,7-dimethyl-8-(pyridin-4-ylamino)-1H-purine-2,6(3H,7H)-dione.

Example 461: 8-(amino(pyridin-4-yl)methyl)-1-((4-chloro-1H-indol-2-yl)methyl)-3,7-dimethyl-1H-purine-2,6(3H,7H)-dione.

Example 462: 1-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)urea.

Example 463: 8-(1-aminoethyl)-1-((5-ethylnaphthalen-2-yl)methyl)-3,7-dimethyl-1H-purine-2,6(3H,7H)-dione.

Example 465: 8-[1-amino-3-hydroxy-2-(hydroxymethyl)propyl]-1-[(4-chloro-1H-indol-2-yl)methyl]-3,7-dimethyl-purine-2,6-dione.

Example 466: 1-[(4-chloro-1H-indol-2-yl)methyl]-3-cyclopropyl-7-methyl-8-(4-pyridylamino)purine-2,6-dione.

Example 468 and 471: (E)-1-((4-chloro-1H-indol-2-yl)methyl)-8-((hydroxyimino)(pyridin-4-yl)methyl)-3,7-dimethyl-1H-purine-2,6(3H,7H)-dione and (Z)-1-((4-chloro-1H-indol-2-yl)methyl)-8-((hydroxyimino)(pyridin-4-yl)methyl)-3,7-dimethyl-1H-purine-2,6(3H,7H)-dione.

Example 470: (R)-8-(1-amino-2-(pyridin-3-yl)ethyl)-1-((4-chloro-1H-indol-2-yl)methyl)-3,7-dimethyl-1H-purine-2,6(3H,7H)-dione Example 472: (R)-8-(1-amino-2-(pyridin-2-yl)ethyl)-1-((4-chloro-1H-indol-2-yl)methyl)-3,7-dimethyl-1H-purine-2,6(3H,7H)-dione.

Example 473: 8-(amino(pyridin-2-yl)methyl)-1-((4-chloro-1H-indol-2-yl)methyl)-3,7-dimethyl-1H-purine-2,6(3H,7H)-dione.

Example 474: 1-((4-chloro-7-fluoro-1H-indol-2-yl)methyl)-3,7-dimethyl-8-(pyridin-4-ylamino)-1H-purine-2,6(3H,7H)-dione.

Example 475: 3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanamide.

Example 476: 3-((4-chloro-1H-indol-2-yl)methyl)-1-methyl-6,7,8,9-tetrahydropyrazino[1,2-f]purine-2,4(1H,3H)-dione.

Example 477: 1-((4,7-dichloro-1H-indol-2-yl)methyl)-3,7-dimethyl-8-(pyridin-4-ylamino)-1H-purine-2,6(3H,7H)-dione.

Example 478 and 481: (E)-1-((4-chloro-1H-indol-2-yl)methyl)-8-(1-(hydroxyimino)ethyl)-3,7-dimethyl-1H-purine-2,6(3H,7H)-dione and (Z)-1-((4-chloro-1H-indol-2-yl)methyl)-8-(1-(hydroxyimino)ethyl)-3,7-dimethyl-1H-purine-2,6(3H,7H)-dione.

Example 479: Methyl 2-(1-((4-chloro-1H-indol-2-yl)methyl)-3,7-dimethyl-2,6-dioxo-2,3,6,7-tetrahydro-1H-purin-8-yl)-2-methylpropanoate.

Example 483: 1-((4-chloro-1-methyl-1H-indol-5-yl)methyl)-3,7-dimethyl-8-(pyridin-4-ylamino)-1H-purine-2,6(3H,7H)-dione.

Example 484: 1-((4-chloro-1H-indol-5-yl)methyl)-3,7-dimethyl-8-(pyridin-4-ylamino)-1H-purine-2,6(3H,7H)-dione.

Example 480: 2-(1-((4-chloro-1H-indol-2-yl)methyl)-3,7-dimethyl-2,6-dioxo-2,3,6,7-tetrahydro-1H-purin-8-yl)-2-(pyridin-4-yl)acetamide.

Example 485: 8-(1-aminopropan-2-yl)-1-((4-chloro-1H-indol-2-yl)methyl)-3,7-dimethyl-1H-purine-2,6(3H,7H)-dione.

In some embodiments, the present invention provides a compound set forth in Table 1, above, or a pharmaceutically acceptable salt thereof.

In some embodiments, the present invention provides a compound of formula I, wherein the command is not any of commands depicted in Table A-1, below.

TABLE A-1

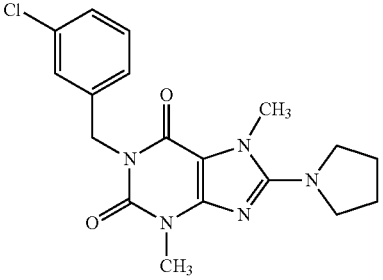 [SMILES: Cn1c(N2CCCC2)nc2c1c(=O)n(Cc1cccc(Cl)c1)c(=O)n2C]
I-2

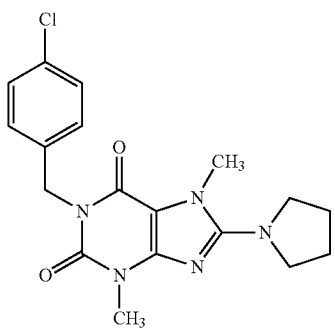 [SMILES: Cn1c(N2CCCC2)nc2c1c(=O)n(Cc1ccc(Cl)cc1)c(=O)n2C]
I-3

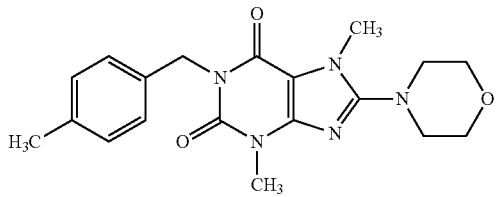 [SMILES: Cc1ccc(Cn2c(=O)c3c(nc(N4CCOCC4)n3C)n(C)c2=O)cc1]
I-4

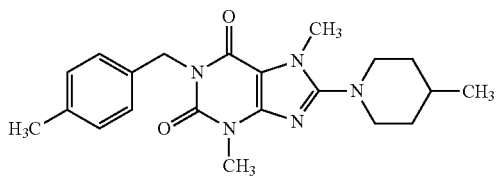
I-5

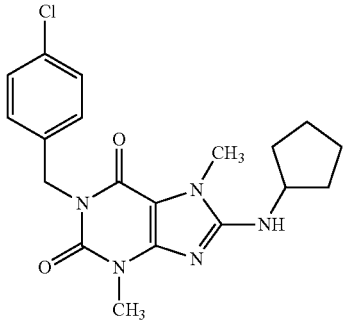 [SMILES: Cn1c(NC2CCCC2)nc2c1c(=O)n(Cc1ccc(Cl)cc1)c(=O)n2C]
I-6

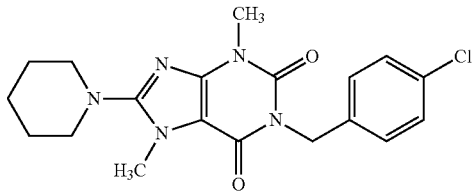 [SMILES: Cn1c(N2CCCCC2)nc2c1c(=O)n(Cc1ccc(Cl)cc1)c(=O)n2C]
I-7

TABLE A-1-continued

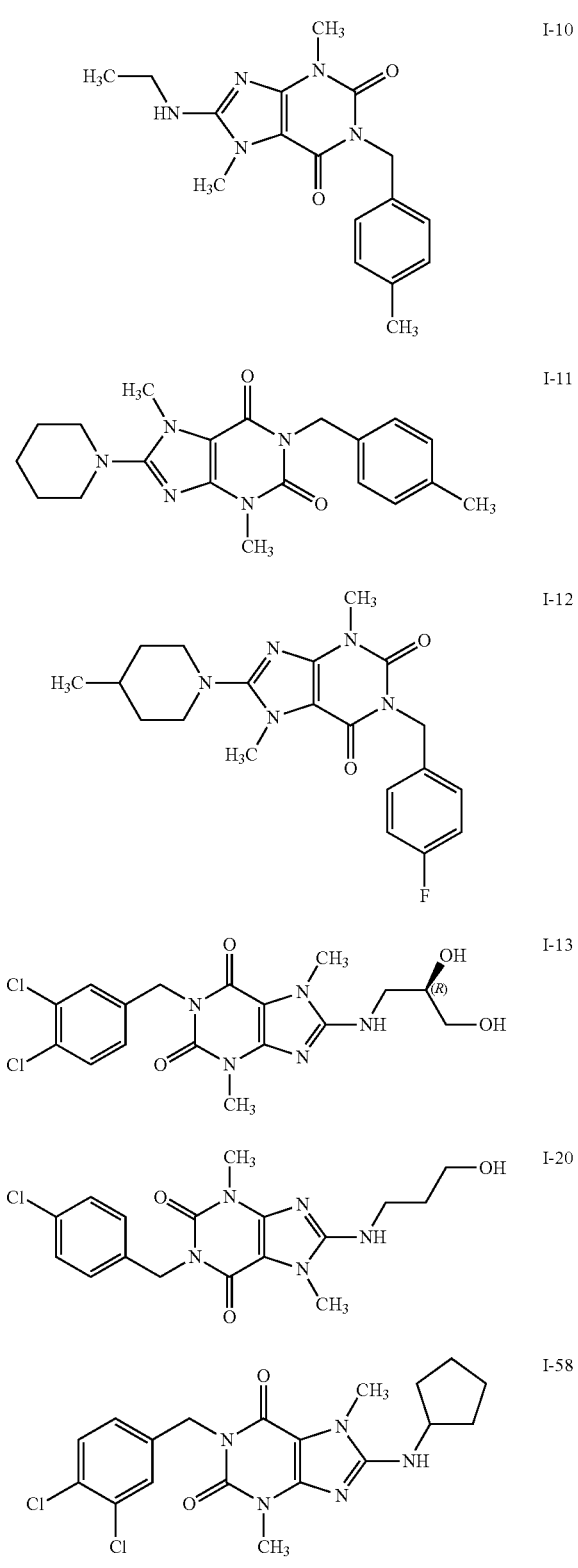

In some embodiments, the present invention provides a compound of formula I, wherein the compound is not any of the compounds of Examples 26, 31, 62, 117, 137, 152, or 273.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit MTHFD2, in a biological sample or in a patient. In certain embodiments, the amount of compound in compositions of this invention is such that is effective to measurably inhibit MTHFD2, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of MTHFD2.

The activity of a compound utilized in this invention as an inhibitor of MTHFD2, may be assayed in vitro, in vivo or in a cell line. In vitro assays include assays that determine inhibition of MTHFD2. Alternate in vitro assays quantitate the ability of the inhibitor to bind to MTHFD2. Detailed conditions for assaying a compound utilized in this invention as an inhibitor of MTHFD2, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of MTHFD2 and are therefore useful for treating one or more disorders associated with activity of MTHFD2. Thus, in certain embodiments, the present invention provides a method for treating a MTHFD2-mediated disorder comprising the step of administering to a patient in need thereof a compound of the present invention, or pharmaceutically acceptable composition thereof.

As used herein, the terms "MTHFD2-mediated" disorders, diseases, and/or conditions as used herein means any disease or other deleterious condition in which MTHFD2, is known to play a role. Accordingly, another embodiment of the present invention relates to treating or lessening the severity of one or more diseases in which MTHFD2 is known to play a role.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As described herein, the application of agents, e.g., inhibitory nucleic acids or small molecules, that inhibit SHMT2 or MTHFD2 reduces cancer cell proliferation and thus treat cancer in subjects. Thus, in some embodiments, the methods described herein include administering a therapeutically effective dose of one or more agents that inhibit a mitochondrial 1-carbon (1-C) pathway enzyme, e.g., SHMT2, MTHFD2, and/or MTHFD1L.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of glycine uptake or an increased expression or activity of a mitochondrial 1-c enzyme (e.g., SHMT2, MTHFD2, and/or MTHFD1L) relative to normal tissues or to other cancers of the same tissues; methods known in the art and described herein can be used to identify those cancers. In some embodiments, the methods include obtaining a sample comprising cells of the cancer, determining the level of glycine uptake or protein, mRNA, or activity of one or more mitochondrial 1-c enzymes (e.g., SHMT2, MTHFD2, and/or MTHFD1L) in the sample, and administering a treatment as described herein (e.g., an antifolate or an agent that inhibits MTHFD2, e.g., ebselen). In some embodiments, the cancer is one that is shown herein to have increased levels of glycine uptake.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by targeting MTHFD2 of the serine biosynthetic pathway. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting MTHFD2 activity in a biological sample comprising the step of contacting said biological sample with a compound of this invention, or a composition comprising said compound.

The term "biological sample", as used herein, includes, without limitation, cell cultures or extracts thereof biopsied material obtained from a mammal or extracts thereof and blood, saliva, urine, feces, semen, tears, or other body fluids or extracts thereof.

Another embodiment of the present invention relates to a method of inhibiting MTHFD2 in a patient comprising the step of administering to said patient a compound of the present invention, or a composition comprising said compound.

According to another embodiment, the invention relates to a method of inhibiting MTHFD2 activity in a patient comprising the step of administering to said patient a compound of the present invention, or a composition comprising said compound. In other embodiments, the present invention provides a method for treating a disorder mediated by MTHFD2 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™ Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/ pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, Z STK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib, or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

List of Abbreviations Used in the Experimental Section.
AcOH: acetic acid
ACN: acetonitrile
Ad: adamantyl
Anhyd: anhydrous
Aq: aqueous
BINAP: 2,2'-bis(diphenylphosphino)-1,1'-binaphthyl
Bn: benzyl
Boc: tert-butoxycarbonyl
BPO: benzoyl peroxide
nBuOH: n-butanol
COD: cyclooctadiene
d: days
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DIBAL-H: diisobutylaluminum hydride
DIPEA or DIEA: N,N-diisopropylethylamine
DMA: N,N-dimethyl acetamide
DMAP: 4-dimethylaminopyridine
DMF: N,N-dimethylformamide
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOH: ethanol
h: hours
HATU: N,N,N',N'-tetramethyl-O-(7-azabenzotriazol-1-yl)uronium hexa-fluorophosphate
HPLC: high performance liquid chromatography
IPA: isopropyl alcohol
KHMDS: potassium hexamethyldisilazide
LAH: lithium aluminum hydride
M: molar
MeOH: methanol
MeI: iodomethane
min: minutes
mL: milliliters
mM: millimolar
mmol: millimoles
MOMCl: methyl chloromethyl ether
MsCl: methanesulfonyl chloride
MTBE: methyl tert-butyl ether
NBS: N-bromosuccinimide
NMP: N-methylpyrrolidine
NMR: Nuclear Magnetic Resonance
° C.: degrees Celsius
PBS: phosphate buffered saline
PE: petroleum ether
PPh$_3$: triphenylphosphine
Rel: relative
R.T. or rt: room temperature
sat: saturated
SEMCl: chloromethyl-2-trimethylsilylethyl ether
SFC: supercritical fluid chromatography
tBuOK: potassium tert-butoxide
TEA: triethylamine
Tf: trifluoromethanesulfonate
TfAA: trifluoromethanesulfonic anhydride
TFA: trifluoracetic acid
TIPS: triisopropylsilyl
THF: tetrahydrofuran THP: tetrahydropyran
TLC: thin layer chromatography
TMEDA: tetramethylethylenediamine
pTSA: para-toluenesulfonic acid
Xantphos: 4,5-bis(diphenylphosphino)-9,9-dimethylxanthene General Synthetic Methods.

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine is reported compounds of the invention which have bromine atom(s). Bromine exists as an approximately 1:1 molar ratio of $^{79}$Br:$^{81}$Br. Thus, a compound with a single bromine atom will exhibit two parent mass ions having a difference of 2 amu.

Compounds purified by flash/column chromatography and preparative thin layer chromatography were conducted on silica gel unless otherwise noted. Compounds purified by flash chromatography were purified using a Biotage Isolera™ 1 or Isolera™ 4 Purification Systems or Teledyne Isco CombiFlash® Purification System. Reactions conducted in a microwave reactor were conducted in a Biotage® Emrys Personal Chemistry Optimized Microwave Synthesizer or a Biotage® Initiator Microwave Reactor.

Preparative HPLC (prep-HPLC) Methods
Method A
  Waters XBridge® OBD C18
  (150*25 mm), 5μ
  Solvent A: 10 mM NH$_4$HCO$_3$
  Solvent B: acetonitrile (ACN)
  Gradient: 25-50% ACN (unless otherwise noted)
  Gradient time: 12 min
Method B
  Waters XBridge® OBD C18
  (250*19 mm), 10μ
  Solvent A: 0.1% NH$_4$HCO$_3$
  Solvent B: acetonitrile (ACN)
  Gradient: 45-75% ACN (unless otherwise noted)
  Gradient time: 15 min
Method C
  Phenomenex Luna® C18
  (100*30 mm), 5□
  Solvent A: 0.01% HCl
  Solvent B: acetonitrile (ACN)
  Gradient: 30-60% ACN (unless otherwise noted)
  Gradient time: 12 min
Method D
  Boston Analytics (Shanghai) PHLEX® ODS
  (250*21 mm), 5□
  Solvent A: 0.04% HCl
  Solvent B: acetonitrile (ACN)
  Gradient: 30-60% ACN (unless otherwise noted)
  Gradient time: 15 min
Method E
  Phenomenex Luna® C18
  (100*30 mm), 5□
  Solvent A: 10 mM NH$_4$HCO$_3$
  Solvent B: acetonitrile (ACN)
  Gradient: 30-60% ACN (unless otherwise noted)
  Gradient time: 12 min
Method F
  Waters XBridge® OBD C18
  (250*21.2 mm), 10□
  Solvent A: 10 mM NH$_4$HCO$_3$
  Solvent B: acetonitrile (ACN)
  Gradient: 30-65% ACN (unless otherwise noted)
  Gradient time: 12 min Synthesis of Intermediates
General Schemes Compounds of the invention were synthesized according to the general synthetic methods described in the following schemes. Much of the methodology described below can be found in *Collect. Czech. Chem. Commun.* 1990, 55 2257-2269, *J. Med. Chem.* 1996, 39, 2-9, and *J. Med. Chem.* 1997, 40, 4396-4405.

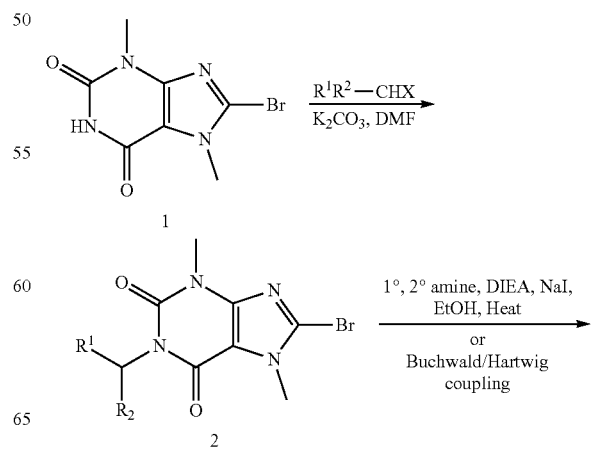

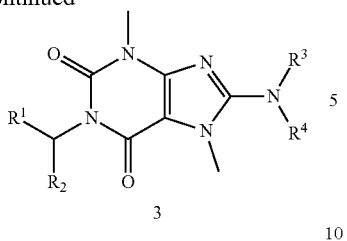

3

Compounds as 3 of the invention can be prepared according to Scheme 1. The commercially available 8-bromo-3,7-dimethyl-3,7-dihydro-1H-purine-2,6-dione 1 can be alkylated at the N1 position using appropriate alkyl and substituted alkyl groups containing an appropriate leaving group (X) and an appropriate base to give intermediate 2. The bromide in Intermediate 2 can be displaced with an appropriate primary, secondary amine or aromatic amine by a nucleophilic aromatic type substitution using DIEA and sodium iodide in ethanol or other appropriate alcoholic solvent or the substitution can be carried out using Buchwald/Hartwig type coupling to provide example compounds of general structure 3.

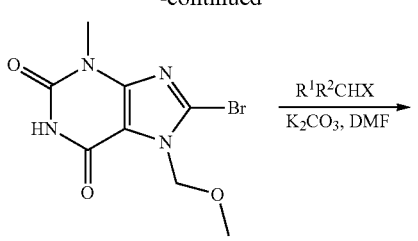

Scheme 2

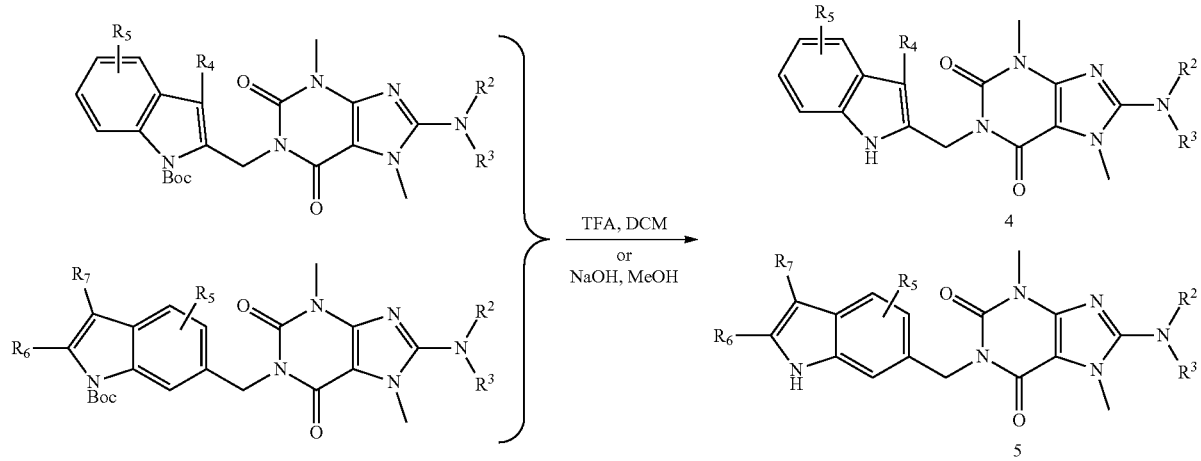

Deprotection of suitable protected intermediates such as those in Scheme 2 can be afforded using TFA in DCM or NaOH in methanol to afford example compounds of general structures 4 and 5.

Scheme 3

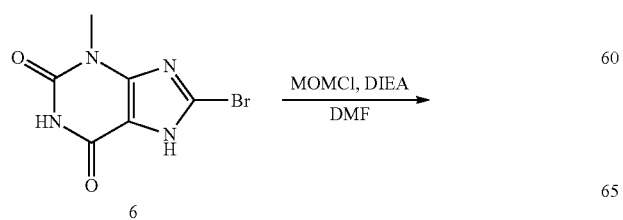

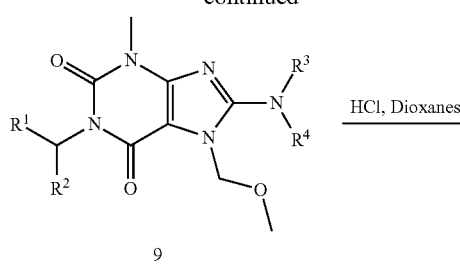

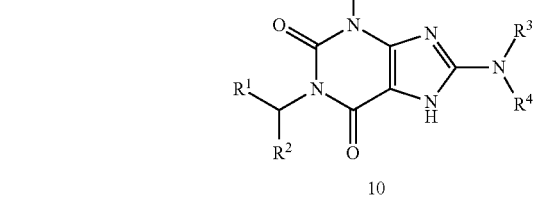

Accessing compounds such as 10 where N7 is hydrogen is shown in Scheme 3. Beginning with commercially available compound 6, N7 can be selectively protected using MOMCl under the conditions shown. Then in an analogous fashion as described in Scheme 1 compound 7 can be functionalized to compounds 8 and then 9. Finally the methoxy methyl protecting group can be removed using HCl in dioxanes to provide example compounds of general structure 10.

-continued

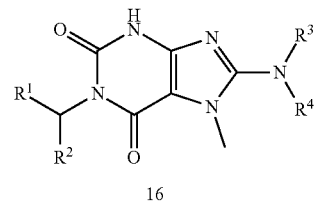

16

Similarly, the methodology of another set of sample compounds for this invention where the N3 substituent is hydrogen is shown in Scheme 4. Beginning with the commercially available compound 11, the N7 can be methylated using the conditions shown to give 12. The N3 position of compound 12 can be selectively protected to give compound 13 using MOMCl. Compound 13 can be elaborated as described in Scheme 1 to provide compounds 14 and then 15. Finally removal of the methoxymethyl protecting group using HCl in dioxanes provides example compounds of general structure 16.

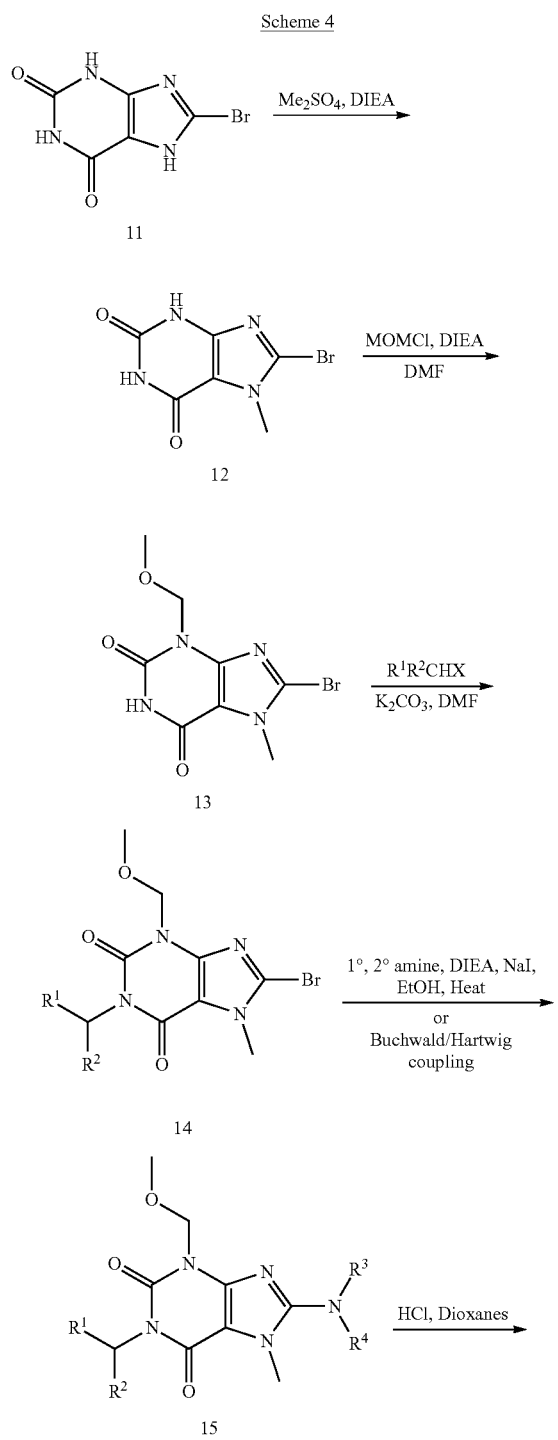

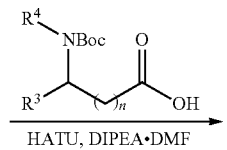

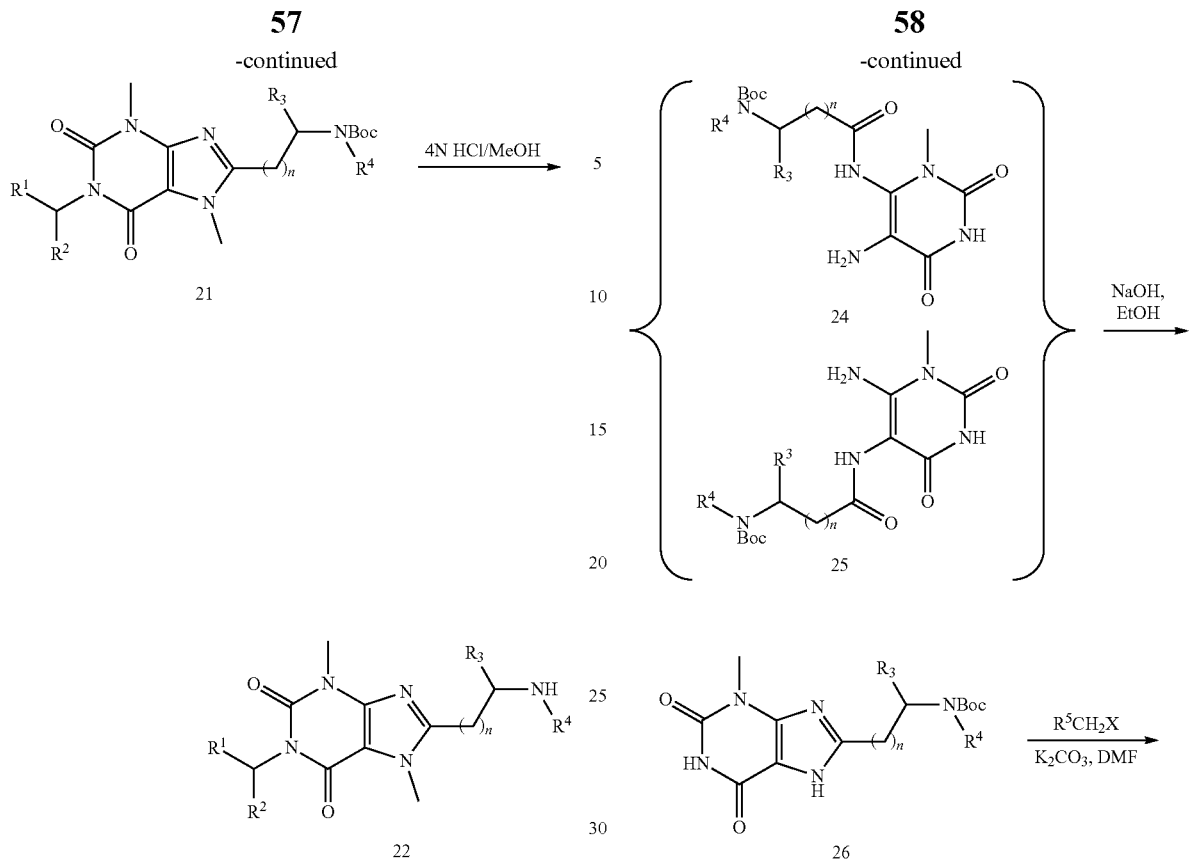

Compounds such as 22 can be accessed as shown in Scheme 5. Commercially available 17 can be reacted with a Boc-protected amino acid using a suitable amide coupling reagent such as HATU to give compounds 18 and 19. Compounds 18 and 19 can be cyclized by reacting them with a base to give compound 20. Compound 20 can be reacted as described in Scheme 1 to give compound 21. The Boc-protecting group can be removed using a strong acid such as TFA in DCM or HCl in methanol to provide sample compounds of general structure 222. An alternative route to the preparation of a similar set of sample compounds of the invention is described in Scheme 6. In this sequence diverse functionalization of compound 26 at N7 can be achieved using a base such as $K_2CO_3$ and the appropriate electrophile.

Scheme 6

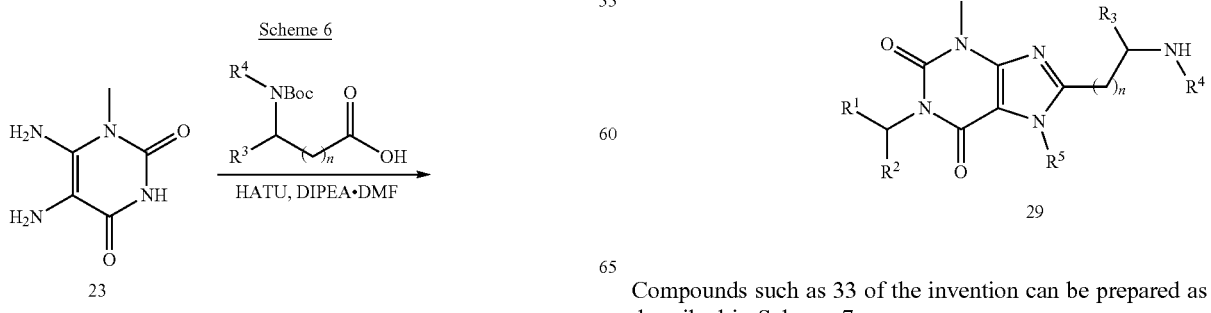

Compounds such as 33 of the invention can be prepared as described in Scheme 7.

Scheme 7

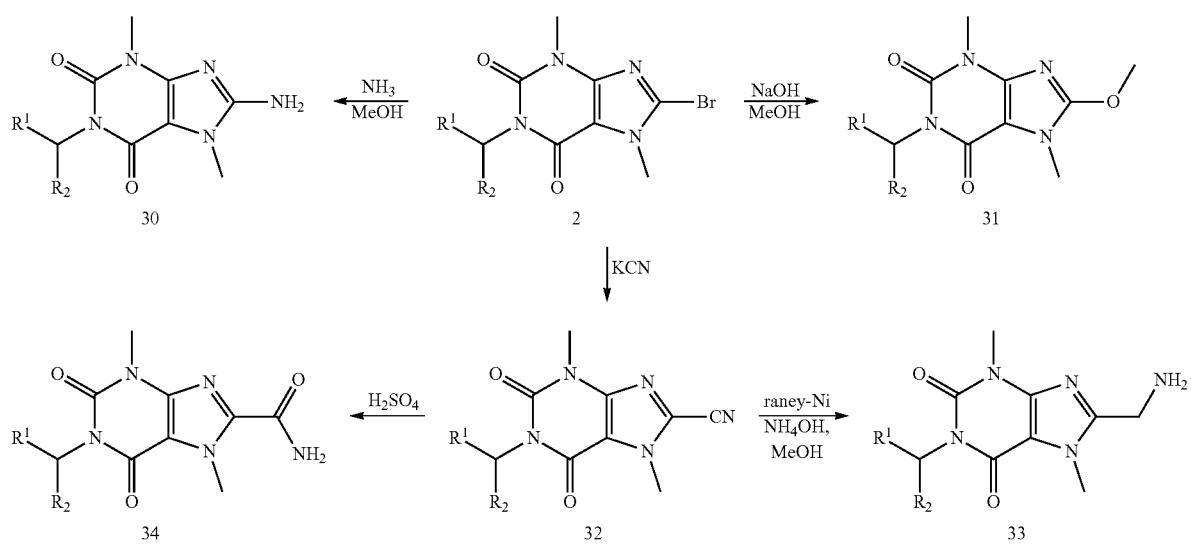

Compound 2 can undergo a displacement reaction with ammonia to give example compounds of general structure 30 or with methoxide to give general structure 31. Additionally the bromide can be displaced with cyanide to give compounds of example compounds of general structure 32. The cyano group of 32 could be hydrolyzed or reduced using the appropriate conditions and reagents to provide compounds of general structures 34 and 33 respectively.

The methodology for another set of sample compounds of the invention is described in Scheme 8. The anion of diethyl malonate or other appropriate malonate ester can displace the bromide of compound 2 to give compound 35. Compound 35 can undergo a decarboxylation reaction using LiCl in DMSO with heat to give example compounds of general structure 36. The ester in 36 can be reduced with an appropriate reducing reagent such as NaBH$_4$, DiBAL-H, LiBH$_4$ to example compounds of the general structure 37.

Scheme 8

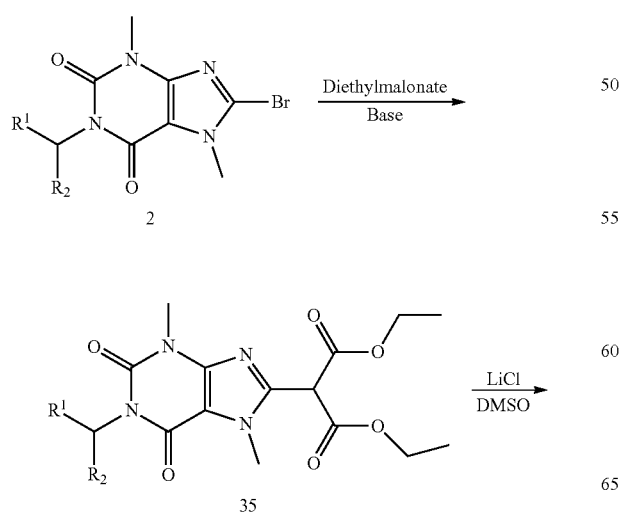

-continued

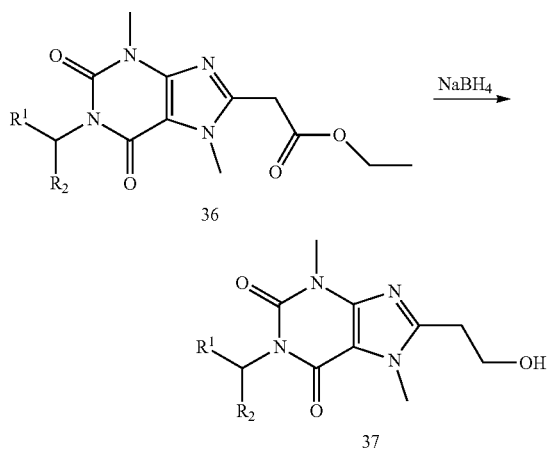

Synthesis of Intermediates

General Synthetic Scheme for the Synthesis of 3-substituted 8-bromo-3,7-dihydro-1H-purine-2,6-diones

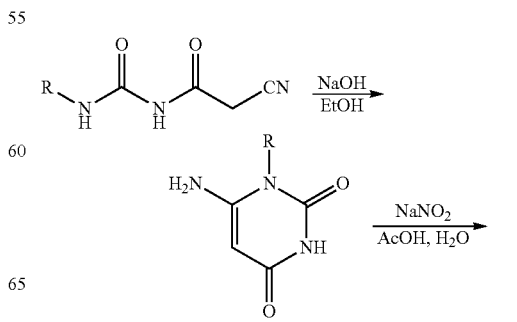

-continued

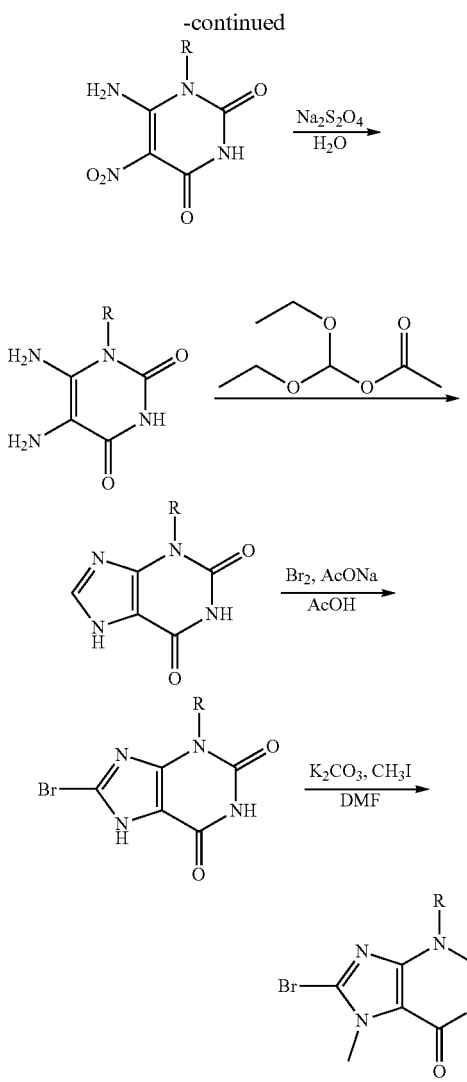

The 8-bromo-3-methyl-3,7-dihydro-1H-purine-2,6-dione and the 8-bromo-3-ethyl-3,7-dihydro-1H-purine-2,6-dione used in the synthesis of many of the compounds of the invention are available from commercial vendors. The synthesis of 8-bromo-3-ethyl-3,7-dihydro-1H-purine-2,6-dione is described below for illustrative purposes.

2-Cyano-N-(ethylcarbamoyl)acetamide

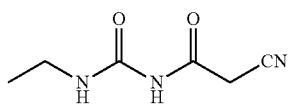

To the solution of 1-ethylurea (10.00 g, 114 mmol) in Ac$_2$O (10 mL) was added 2-cyanoacetic acid (9.69 g, 114 mmol) at rt and the resulting mixture was stirred at 75° C. for 3 h. LCMS showed that desired product was detected. The mixture was cooled to rt, filtered and the filtered cake was washed with MeOH (20 mL), dried under vacuum to give the desired product. ESI: m/z 156.1 (M+H)$^+$.

6-Amino-1-ethylpyrimidine-2,4(1H,3H)-dione

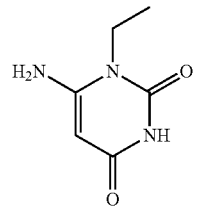

A mixture of 2-cyano-N-(ethylcarbamoyl)acetamide (11.132 g, 71.82 mmol) in EtOH (24 mL) and NaOH solution (2.0 M, 12 mL) was stirred at 75° C. for 3 h. LCMS showed the completion of the reaction. The mixture was cooled to rt, acidified with concentrated HCl to pH=7, the precipitate was collected by filtration to give the desired product, 6.50 g. ESI: m/z 156.1 (M+H)$^+$.

6-Amino-1-ethyl-5-nitrosopyrimidine-2,4(1H,3H)-dione

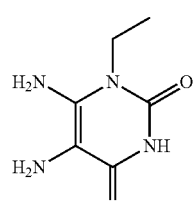

To a stirred solution of compound 6-amino-1-ethylpyrimidine-2,4(1H,3H)-dione (3.00 g, 19.35 mmol) in CH$_3$COOH (50 mL) was added NaNO$_2$ (1.602 g, 23.22 mmol) in H$_2$O (6 mL) dropwise at 0° C. The resulting mixture was stirred at 10° C. for another 30 min and a red solid precipitated out of the reaction mixture. The solids were collected by filtration and dried under vacuum to give the desired product as a red solid, 3.22 g. ESI: m/z 185.1 (M+H)$^+$.

5,6-Diamino-1-ethylpyrimidine-2,4(1H,3H)-dione

A solution of 6-amino-1-ethyl-5-nitrosopyrimidine-2,4 (1H,3H)-dione (3.22 g, 17.50 mmol) in H$_2$O (40 mL) was heated to 80° C. Then Na$_2$S$_2$O$_4$ was added fairly rapidly over a period of 5 min. The resulting mixture was stirred at 90° C. for 30 min. The mixture was cooled to rt and then immersed in a ice bath. The precipitated solids were collected by filtration and dried under vacuum to give the desired product, 2.90 g. ESI: m/z 171.1 (M+H)$^+$.

3-Ethyl-1H-purine-2,6(3H,7H)-dione

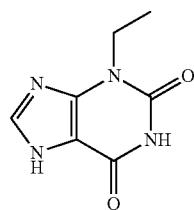

A mixture of 5,6-diamino-1-ethylpyrimidine-2,4(1H,3H)-dione (1.00 g, 5.88 mmol) in diethoxymethyl acetate (8 mL) was stirred at 80° C. for 2 h. The mixture was evaporated to dryness, water (10 mL) was added, and the resulting mixture was refluxed for 30 min. Then the mixture was allowed to concentrate slowly to yield the desired product, 920 mg. ESI: m/z 181.1 (M+H)$^+$.

8-Bromo-3-ethyl-1H-purine-2,6(3H,7H)-dione

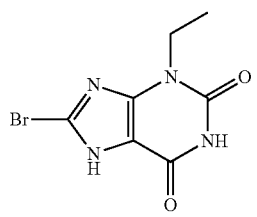

To a solution of compound 3-ethyl-1H-purine-2,6(3H,7H)-dione (920 mg, 5.11 mmol) in CH$_3$COOH (20 mL) was added CH$_3$COONa (838 mg, 10.22 mmol) and the mixture was heated to 50° C. Then Br$_2$ (1.227 g, 7.67 mmol) was added dropwise to the mixture. The resulting solution was heated to 65° C. and stirred at this temperature for 3 h. The mixture was cooled to rt and poured into ice-water (20 mL), filtered and the filtered cake was washed with water (10 mL), dried under vacuum to give the desired product, 490 mg. ESI: m/z 261.0 (M+2+H)$^+$.

8-Bromo-3-ethyl-7-methyl-1H-purine-2,6(3H,7H)-dione

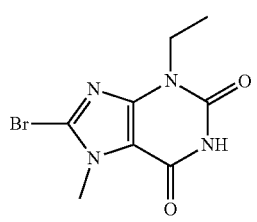

To a solution of compound 8-bromo-3-ethyl-1H-purine-2,6(3H,7H)-dione (490 mg, 1.90 mmol) in DMF (5 mL) was added CH$_3$I (270 mg, 1.90 mmol) and K$_2$CO$_3$ (393 mg, 2.85 mmol). The resulting solution was stirred at 60° C. for 1 h, then cooled to rt, water (15 mL) was added to the mixture and the mixture was extracted with EA (4*10 mL). The combined organic fractions were washed with water (2*5 mL), brine (2*5 mL), dried over Na$_2$SO$_4$ and concentrated to give the crude desired product, 350 mg. ESI: m/z 275.0 (M+2+H)$^+$.

General Synthetic Scheme for the Preparation of N-Boc Chloromethyl Indoles

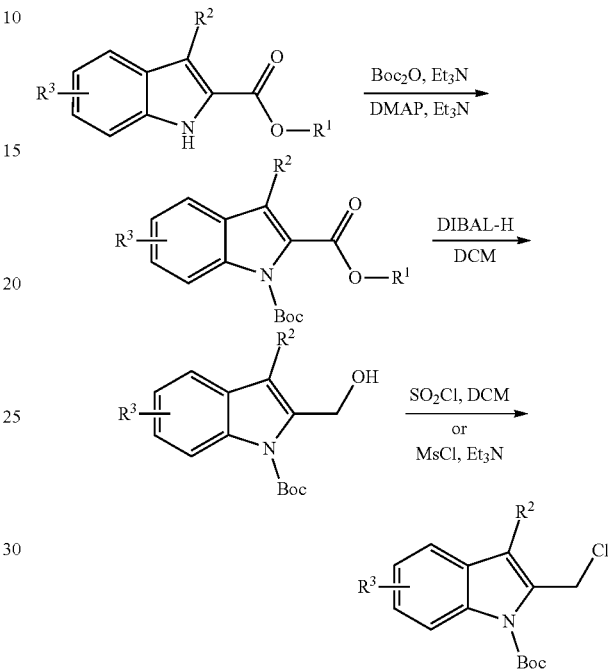

Procedure 1

Illustrative Example 1-tert-butyl 2-methyl 6-chloro-1H-indole-1,2-dicarboxylate

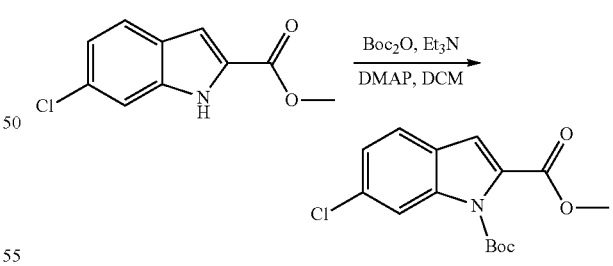

To a solution of methyl 6-chloro-1H-indole-2-carboxylate (4.6 g, 21.9 mmol), Et$_3$N (6.65 g, 65.7 mmol) and DMAP (268 mg, 2.19 mmol) in DCM (70 mL) was added dropwise Boc$_2$O (5.74 g, 26.3 mmol) at 0° C. The mixture was warmed to 25° C. and stirred for 3 h. The reaction mixture was diluted in DCM (60 mL) and washed with water (1*80 mL) and brine (1*80 mL), dried over Na$_2$SO$_4$, concentrated and purified by flash chromatography (0~10% EA/PE) to give the product. ESI 254.1 (M−56+H)$^+$.

The Intermediates in Table 1 were synthesized according to Procedure 1.

TABLE 1

| Name and MS or NMR Data | Structure |
|---|---|
| 1-(tert-butyl) 2-methyl 7-chloro-1H-indole-1,2-dicarboxylate<br>¹H NMR (400 MHz, CDCl₃) 7.59-7.54 (m, 1H), 7.35 (s, 1H), 7.24 (s, 1H), 7.11 (s, 1H), 3.92 (s, 3H), 1.68 (s, 9H) | |
| 1-(tert-butyl) 2-methyl 4-chloro-1H-indole-1,2-dicarboxylate<br>ESI: 310.0 (M + H)⁺ | |
| 1-(tert-butyl) 2-methyl 5-methoxy-1H-indole-1,2-dicarboxylate<br>ESI: m/z 266 (M − 55 + H)⁺ | |
| 1-(tert-butyl) 2-methyl 6-methyl-1H-indole-1,2-dicarboxylate<br>ESI: m/z 234.0 (M − 55 + H)⁺ | |
| 1-(tert-butyl) 2-methyl 5-chloro-1H-indole-1,2-dicarboxylate<br>ESI 310.1 (M + H)⁺ | |
| 1-(tert-butyl) 2-methyl 4-methoxy-1H-indole-1,2-dicarboxylate<br>ESI: 250.0 (M + H − 56)⁺ | |
| 1-(tert-butyl) 2-methyl 4-fluoro-1H-indole-1,2-dicarboxylate<br>ESI: m/z 238 (M + H − 56)⁺ | |
| 1-(tert-butyl) 2-methyl 4-(trifluoromethyl)-1H-indole-1,2-dicarboxylate<br>ESI: 288.0 (M + H − 56)⁺ | |
| 1-(tert-butyl) 2-methyl 1H-pyrrolo[2,3-c]pyridine-1,2-dicarboxylate<br>ESI: m/z 291 (M + H)⁺ | |

TABLE 1-continued

| Name and MS or NMR Data | Structure |
|---|---|
| 1-(tert-butyl) 2-methyl 4-methyl-1H-indole-1,2-dicarboxylate<br>ESI: m/z 234.0 (M − 55 + H)⁺ | |
| 1-(tert-butyl) 2-methyl 3,4-dimethyl-1H-indole-1,2-dicarboxylate<br>ESI: m/z 326 (M + H)⁺ | |
| 1-(tert-butyl) 2-methyl 5-bromo-1H-indole-1,2-dicarboxylate<br>¹H NMR (400 MHz, CDCl₃) δ 8.04 (d, J = 8.4 Hz, 1H), 7.42 (d, J = 7.6 Hz, 1H), 7.26 (d, J = 16 Hz, 1H), 7.16 (s, 1H), 3.94 (s, 3H), 1.62 (s, 9H). | |
| 1-(tert-butyl) 2-methyl 5-methyl-1H-indole-1,2-dicarboxylate<br>ESI: m/z 234 (M − 56 + H)⁺ | |
| 1-(tert-butyl) 2-ethyl 3-methyl-1H-indole-1,2-dicarboxylate ESI: m/z 234.0 (M + H)⁺ | |
| 1-tert-butyl 2-methyl 4-bromo-1H-indole-1,2-dicarboxylate<br>¹H NMR (400 MHz, CDCl₃) δ 8.04 (d, J = 8.4 Hz, 1H), 7.42 (d, J = 7.6 Hz, 1H), 7.26 (d, J = 16 Hz, 1H), 7.16 (s, 1H), 3.94 (s, 3H), 1.62 (s, 9H) | |
| 1-(tert-butyl) 6-methyl 1H-indole-1,6-dicarboxylate<br>ESI: m/z 276.0 (M + H)⁺ | |
| 1-(tert-butyl) 2-methyl 6-chloro-1H-indole-1,2-dicarboxylate<br>ESI: m/z 254 (M − 56 + H)⁺ | |
| 1-(tert-butyl) 2-methyl 1H-indole-1,2-dicarboxylate<br>ESI: 220.0 m/z (M + H − 56)⁺ | |

TABLE 1-continued

| Name and MS or NMR Data | Structure |
|---|---|
| 1-tert-butyl 2-methyl 7-methyl-1H-indole-1,2-dicarboxylate<br>$^1$HNMR: (400 MHz, CDCl$_3$) δ 7.49 (d, J = 7.5 Hz, 1H), 7.21 (s, 1H), 7.17-7.07 (m, 2H), 3.91 (s, 3H), 2.57 (s, 3H), 1.65 (s, 9H) | 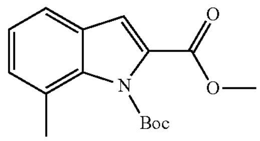 |
| 1-(tert-butyl) 2-methyl 7-fluoro-1H-indole-1,2-dicarboxylate<br>$^1$H NMR (400 MHz, CDCl$_3$) δ 7.43 (d, J = 7.5 Hz, 1H), 7.24-7.05 (m, 3H), 3.96 (s, 3H), 1.68 (s, 9H) | 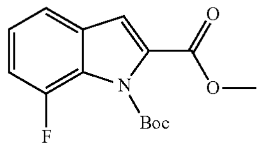 [SMILES: COC(=O)c1cc2cccc(Cl)c2n1C(=O)OC(C)(C)C] |

Procedure 2

Illustrative Example tert-butyl 6-chloro-2-(hydroxymethyl)-1H-indole-1-carboxylate

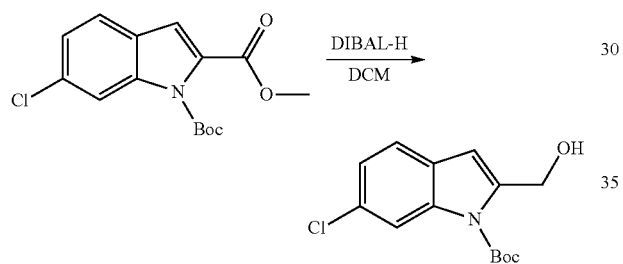

To a solution of 1-tert-butyl 2-methyl 6-chloro-1H-indole-1,2-dicarboxylate (5.0 g, 16.1 mmol) in DCM (100 mL) was added dropwise a solution of DIBAL-H in toluene (48.3 mL, 48.3 mmol, 1M) at −70° C. The mixture was stirred for 4 h at −40° C. The reaction was quenched with water (60 mL). The mixture was filtered and the solid was washed with DCM (50 mL). The organic fraction was washed with brine (1*100 mL), dried over Na$_2$SO$_4$, concentrated and purified by flash chromatography (0~30% EA/PE) to give the product as a white solid (3.0 g); ESI: m/z 304.1 (M+Na)$^+$.

The intermediates in Table 2 were synthesized according to Procedure 2.

TABLE 2

| Name and MS or NMR Data | Structure |
|---|---|
| tert-butyl 7-chloro-2-(hydroxymethyl)-1H-indole-1-carboxylate<br>$^1$H NMR (400 MHz, CDCl$_3$) 7.46 (d, J = 8.0 Hz, 1H), 7.31 (d, J = 7.0 Hz, 1H), 7.20-7.14 (m, 1H), 6.57 (s, 1H), 4.76 (d, J = 7.0 Hz, 2H), 3.35 (t, J = 7.3 Hz, 1H), 1.69 (s, 9H). | 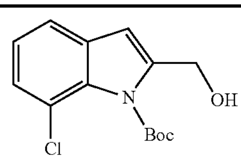 |

TABLE 2-continued

| Name and MS or NMR Data | Structure |
|---|---|
| tert-butyl 4-chloro-2-(hydroxymethyl)-1H-indole-1-carboxylate<br>ESI: m/z 304.1 (M + 23)$^+$ | 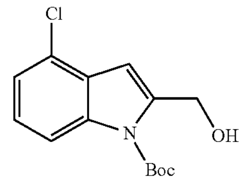 [SMILES: CC(C)(C)OC(=O)n1c(CO)cc2c(Cl)cccc21] |
| tert-butyl 2-(hydroxymethyl)-5-methoxy-1H-indole-1-carboxylate<br>ESI: m/z 204.0 (M − 73)$^+$ | 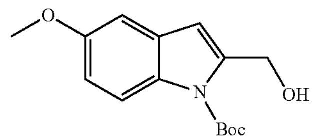 [SMILES: COc1ccc2c(c1)cc(CO)n2C(=O)OC(C)(C)C] |
| tert-butyl 2-(hydroxymethyl)-6-methyl-1H-indole-1-carboxylate<br>ESI: 188.0 (M − 73)$^+$ | 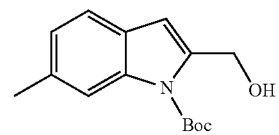 [SMILES: Cc1ccc2cc(CO)n(C(=O)OC(C)(C)C)c2c1] |
| tert-butyl 5-chloro-2-(hydroxymethyl)-1H-indole-1-carboxylate<br>ESI: m/z 208.0 (M − 73)$^+$ | 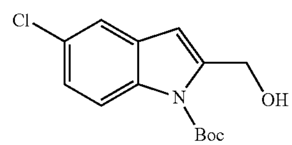 [SMILES: CC(C)(C)OC(=O)n1c(CO)cc2cc(Cl)ccc21] |
| tert-butyl 2-(hydroxymethyl)-4-methoxy-1H-indole-1-carboxylate<br>ESI: 178.0 (M + H − 100)$^+$ | 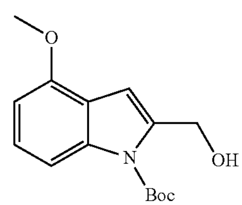 [SMILES: COc1cccc2c1cc(CO)n2C(=O)OC(C)(C)C] |
| tert-butyl 4-fluoro-2-(hydroxymethyl)-1H-indole-1-carboxylate<br>ESI: m/z 192.0 (M + H − 73)$^+$ | 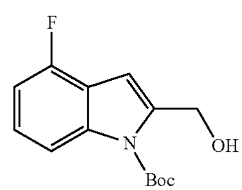 |
| tert-butyl 2-(hydroxymethyl)-4-(trifluoromethyl)-1H-indole-1-carboxylate<br>ESI: 242.0 (M − 73)$^+$ | 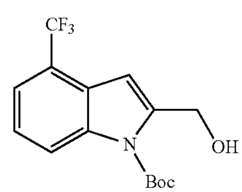 [SMILES: CC(C)(C)OC(=O)n1c(CO)cc2c(C(F)(F)F)cccc21] |
| tert-butyl 2-(hydroxymethyl)-1H-pyrrolo[2,3-c]pyridine-1-carboxylate<br>ESI: m/z 249.0 (M + H)$^+$ | 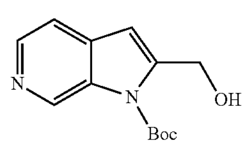 [SMILES: CC(C)(C)OC(=O)n1c(CO)cc2ccncc21] |
| tert-butyl 2-(hydroxymethyl)-4-methyl-1H-indole-1-carboxylate<br>ESI: m/z 188.0 (M + H − 73)$^+$ | 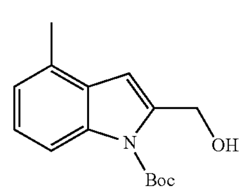 [SMILES: Cc1cccc2c1cc(CO)n2C(=O)OC(C)(C)C] |

TABLE 2-continued

| Name and MS or NMR Data | Structure |
|---|---|
| tert-butyl 2-(hydroxymethyl)-3,4-dimethyl-1H-indole-1-carboxylate<br>ESI: m/z 296.0 (M + H)+ | |
| tert-butyl 5-bromo-2-(hydroxymethyl)-1H-indole-1-carboxylate<br>1H NMR (400 MHz, CDCl3) δ 7.94 (d, J = 8.4 Hz, 1H), 7.90 (d, J = 1.6 Hz, 1H), 7.15 (t, J = 8.0 Hz, 1H), 6.68 (s, 1H), 4.83 (d, J = 1.6 Hz, 2H), 3.59 (t, J = 7.6 Hz, 1H), 1.72 (s, 9H). | |
| tert-butyl 2-(hydroxymethyl)-5-methyl-1H-indole-1-carboxylate<br>ESI: 188.0 (M − 73)+ | |
| tert-butyl 2-(hydroxymethyl)-3-methyl-1H-indole-1-carboxylate<br>1H NMR (400 MHz, CDCl3) δ 7.96-7.94 (d, J = 8.0 Hz, 1H), 7.46-7.44 (d, J = 8.0 Hz, 2H), 7.29-7.23 (m, 2H), 4.80-4.78 (d, J = 7.2 Hz, 2H), 4.12 (br s, 1H), 2.28 (s, 3H), 1.71 (s, 9H). | |
| tert-butyl 2-(hydroxymethyl)-4-methyl-1H-indole-1-carboxylate<br>ESI: m/z 188.0 (M − 73)+ | |
| tert-butyl 7-fluoro-2-(hydroxymethyl)-1H-indole-1-carboxylate<br>1H NMR (400 MHz, CDCl3) δ 7.27 (d, J = 7.5 Hz, 1H), 7.14 (dt, J = 4.2, 7.8 Hz, 1H), 6.98 (dd, J = 7.9, 12.8 Hz, 1H), 6.55 (d, J = 1.8 Hz, 1H), 4.74 (d, J = 7.5 Hz, 2H), 3.67 (t, J = 7.5 Hz, 1H), 1.65 (s, 9H) | |
| tert-butyl 4-bromo-2-(hydroxymethyl)-1H-indole-1-carboxylate<br>1H NMR (400 MHz, CDCl3) δ 7.94 (d, J = 8.4 Hz, 1H), 7.90 (d, J = 1.6 Hz, 1H), 7.15 (t, J = 8.0 Hz, 1H), 6.68 (s, 1H), 4.83 (d, J = 1.6 Hz, 2H), 3.59 (t, J = 7.6 Hz, 1H), 1.72 (s, 9H). | |
| tert-butyl 2-(hydroxymethyl)-1H-indole-1-carboxylate<br>1H NMR (400 MHz, CDCl3) δ 7.99-7.97 (d, J = 8.4 Hz, 1H), 7.50-7.48 (d, J = 7.6 Hz, 1H), 7.28-7.21 (m, 2H), 6.58 (s, 1H), 4.80-4.78 (d, J = 7.2 Hz, 2H), 3.82-3.80 (br s, 1H), 1.71 (s, 9H). | |
| tert-butyl 6-chloro-2-(hydroxymethyl)-1H-indole-1-carboxylate<br>ESI: 304.0 (M + Na)+ | |
| tert-butyl 2-(hydroxymethyl)-7-methyl-1H-indole-1-carboxylate<br>1H NMR (400 MHz, CDCl3) δ 7.41-7.37 (m, 1H), 7.20-7.09 (m, 2H), 6.56 (s, 1H), 4.78 (d, J = 7.0 Hz, 2H), 3.09 (t, J = 7.0 Hz, 1H), 2.52 (s, 3H), 1.70 (s, 9H) | |

Procedure 3

Illustrative Example tert-butyl 6-chloro-2-(chloromethyl)-1H-indole-1-carboxylate

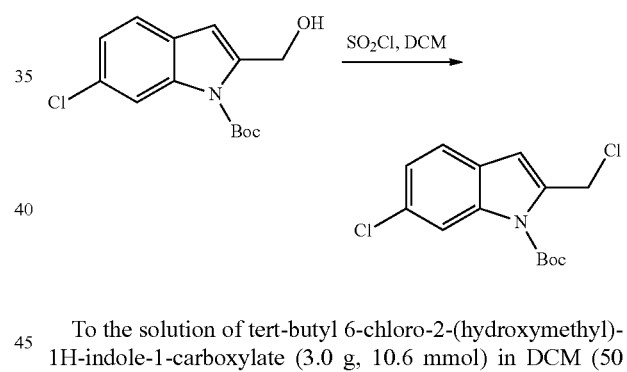

To the solution of tert-butyl 6-chloro-2-(hydroxymethyl)-1H-indole-1-carboxylate (3.0 g, 10.6 mmol) in DCM (50 mL) was added dropwise SOCl2 (1.51 g, 12.72 mmol) at 0° C. The mixture was stirred for 2 h at 25° C. The reaction mixture was diluted in DCM (50 mL) and NaHCO3 (aq) was added to pH=9-10. The organic fraction was washed with water (1*80 mL) and brine (1*80 mL), dried over Na2SO4, concentrated and dried in vacuo to afford the product which was used directly without further purification.

The compounds in Table 3 were synthesized according to Procedure 3 and used without purification.

TABLE 3

| Name | Structure |
|---|---|
| tert-butyl 7-chloro-2-(chloromethyl)-1H-indole-1-carboxylate | 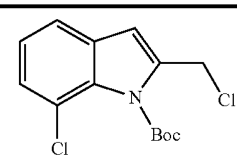 |

TABLE 3-continued

| Name | Structure |
|---|---|
| tert-butyl 4-chloro-2-(chloromethyl)-1H-indole-1-carboxylate | 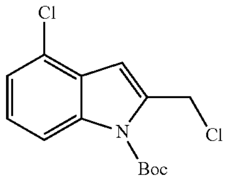 [SMILES: CC(C)(C)OC(=O)n1c(CCl)cc2c(Cl)cccc21] |
| tert-butyl 2-(chloromethyl)-5-methoxy-1H-indole-1-carboxylate | 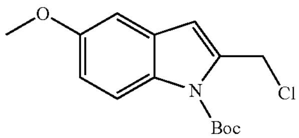 [SMILES: COc1ccc2c(c1)cc(CCl)n2C(=O)OC(C)(C)C] |
| tert-butyl 2-(chloromethyl)-6-methyl-1H-indole-1-carboxylate | 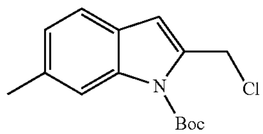 [SMILES: Cc1ccc2cc(CCl)n(C(=O)OC(C)(C)C)c2c1] |
| tert-butyl 5-chloro-2-(chloromethyl)-1H-indole-1-carboxylate | 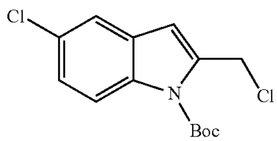 [SMILES: CC(C)(C)OC(=O)n1c(CCl)cc2cc(Cl)ccc21] |
| tert-butyl 2-(chloromethyl)-4-methoxy-1H-indole-1-carboxylate | 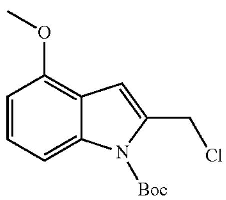 [SMILES: COc1cccc2c1cc(CCl)n2C(=O)OC(C)(C)C] |
| tert-butyl 4-fluoro-2-(chloromethyl)-1H-indole-1-carboxylate | 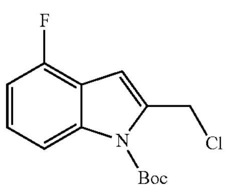 [SMILES: CC(C)(C)OC(=O)n1c(CCl)cc2c(F)cccc21] |
| tert-butyl 2-(chloromethyl)-4-(trifluoromethyl)-1H-indole-1-carboxylate | 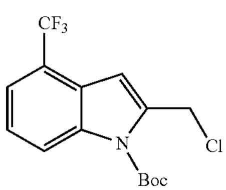 [SMILES: CC(C)(C)OC(=O)n1c(CCl)cc2c(C(F)(F)F)cccc21] |
| tert-butyl 2-(chloromethyl)-1H-pyrrolo[2,3-c]pyridine-1-carboxylate | 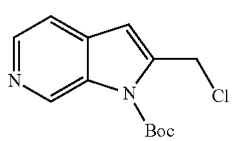 [SMILES: CC(C)(C)OC(=O)n1c(CCl)cc2ccncc21] |
| tert-butyl 2-(chloromethyl)-4-methyl-1H-indole-1-carboxylate | |
| tert-butyl 2-(chloromethyl)-3,4-dimethyl-1H-indole-1-carboxylate | |
| tert-butyl 5-bromo-2-(chloromethyl)-1H-indole-1-carboxylate | |
| tert-butyl 2-(chloromethyl)-5-methyl-1H-indole-1-carboxylate | |
| tert-butyl 2-(chloromethyl)-3-methyl-1H-indole-1-carboxylate | |
| tert-butyl 5-bromo-2-(chloromethyl)-1H-indole-1-carboxylate | |
| tert-butyl 2-(chloromethyl)-4-methyl-1H-indole-1-carboxylate | |
| tert-butyl 2-(chloromethyl)-7-fluoro-1H-indole-1-carboxylate | |
| tert-butyl 4-bromo-2-(chloromethyl)-1H-indole-1-carboxylate | |

Procedure 4

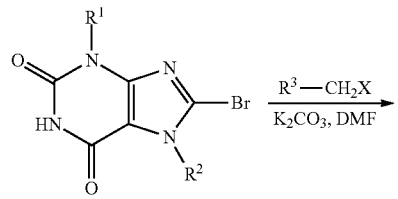

Illustrative Example 8-bromo-1-(3,4-dichlorobenzyl)-3,7-dimethyl-1H-purine-2,6(3H,7H)-dione

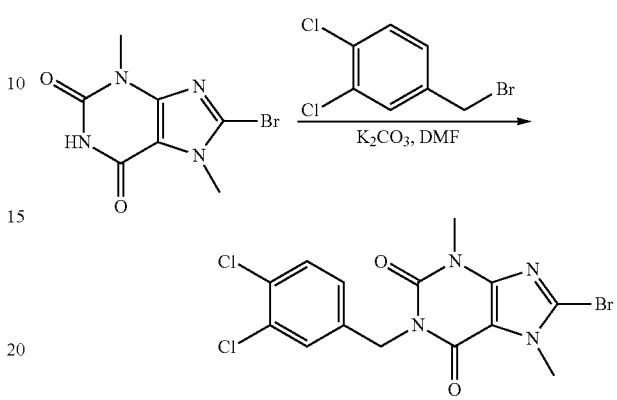

To a solution of 8-bromo-3,7-dimethyl-1H-purine-2,6(3H,7H)-dione (500 mg, 3.14 mmol) and potassium carbonate (800 mg, 9.42 mmol) in DMF (5 mL) was added 4-(bromomethyl)-1,2-dichlorobenzene (556 mg, 3.77 mmol). The mixture was stirred at 50° C. for 5 h. The mixture was then poured into water and filtered. The solid was dried under high vacuum to provide the title compound ESI: m/z 419.2 (M+H)+.

The compounds in Table 4 were synthesized according to Procedure 4.

TABLE 4

| Name | Structure | Mass Spec (ESI) or $^1$H NMR |
| --- | --- | --- |
| 8-bromo-3,7-dimethyl-1-(4-(trifluoromethyl)benzyl)-3,7-dihydro-1H-purine-2,6-dione | 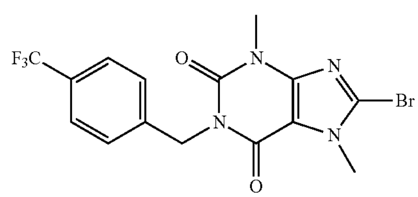 [SMILES: Cn1c(Br)nc2c1c(=O)n(Cc1ccc(C(F)(F)F)cc1)c(=O)n2C] | 417.0 (M + H)+ |
| tert-butyl 2-((8-bromo-3,7-dimethyl-2,6-dioxo-2,3,6,7-tetrahydro-1H-purin-1-yl)methyl)-1H-indole-1-carboxylate | 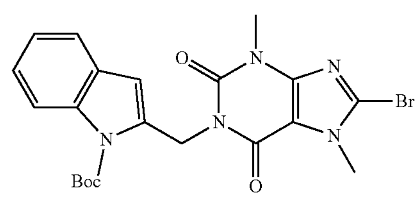 [SMILES: Cn1c(Br)nc2c1c(=O)n(Cc1cc3ccccc3n1C(=O)OC(C)(C)C)c(=O)n2C] | 388.0 (M + H − 100)+ |
| tert-butyl 6-((8-bromo-3,7-dimethyl-2,6-dioxo-2,3,6,7-tetrahydro-1H-purin-1-yl)methyl)-1H-indole-1-carboxylate | 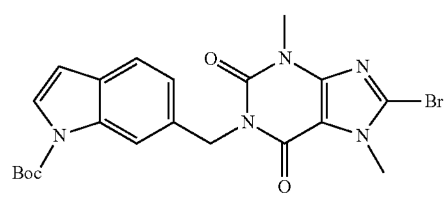 [SMILES: Cn1c(Br)nc2c1c(=O)n(Cc1ccc3ccn(C(=O)OC(C)(C)C)c3c1)c(=O)n2C] | 432.0 (M + H − 56)+ |

TABLE 4-continued

| Name | Structure | Mass Spec (ESI) or ¹H NMR |
|---|---|---|
| 8-bromo-3,7-dimethyl-1-(oxazol-2-ylmethyl)-3,7-dihydro-1H-purine-2,6-dione | 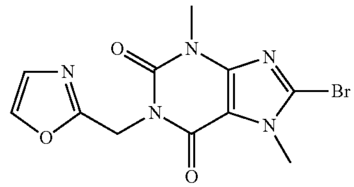 [SMILES: Cn1c(Br)nc2c1c(=O)n(Cc1ncco1)c(=O)n2C] | 339.9 (M + H)+ |
| tert-butyl 2-((8-bromo-3,7-dimethyl-2,6-dioxo-2,3,6,7-tetrahydro-1H-purin-1-yl)methyl)-5-methyl-1H-indole-1-carboxylate | 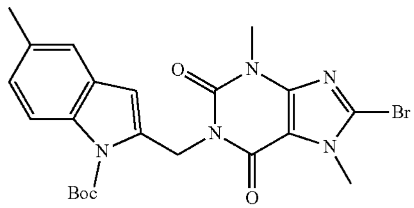 [SMILES: Cc1ccc2c(c1)cc(Cn1c(=O)c3c(nc(Br)n3C)n(C)c1=O)n2C(=O)OC(C)(C)C] | 402.0 (M + H − 100)+ |
| 8-bromo-3,7-dimethyl-1-((3-phenyl-1-((2-(trimethylsilyl)ethoxy)methyl)-1H-pyrazol-5-yl)methyl)-3,7-dihydro-1H-purine-2,6-dione | 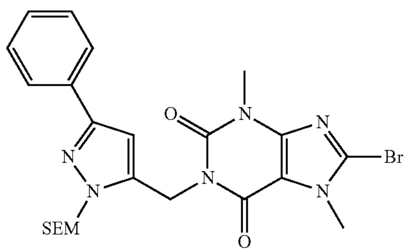 [SMILES: Cn1c(Br)nc2c1c(=O)n(Cc1cc(-c3ccccc3)nn1COCC[Si](C)(C)C)c(=O)n2C] | 545.1 (M + H)+ |
| tert-butyl 2-((8-bromo-3,7-dimethyl-2,6-dioxo-2,3,6,7-tetrahydro-1H-purin-1-yl)methyl)-5-methoxy-1H-indole-1-carboxylate | 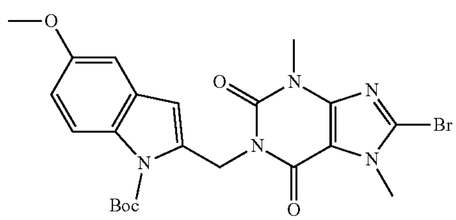 | 420.0 (M + H − 100)+ |
| tert-butyl 2-((8-bromo-3,7-dimethyl-2,6-dioxo-2,3,6,7-tetrahydro-1H-purin-1-yl)methyl)-5-chloro-1H-indole-1-carboxylate | 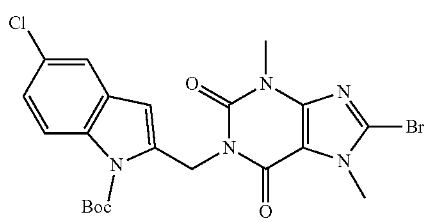 | 424.0 (M + H − 100)+ |
| 4-((8-bromo-3,7-dimethyl-2,6-dioxo-2,3,6,7-tetrahydro-1H-purin-1-yl)methyl)-2-chlorobenzonitrile | 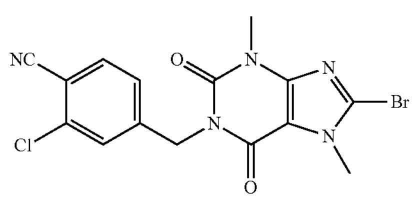 [SMILES: Cn1c(Br)nc2c1c(=O)n(Cc1ccc(C#N)c(Cl)c1)c(=O)n2C] | 408.8 (M + H)+ |
| tert-butyl 2-((8-bromo-3,7-dimethyl-2,6-dioxo-2,3,6,7-tetrahydro-1H-purin-1-yl)methyl)-4-chloro-1H-indole-1-carboxylate | 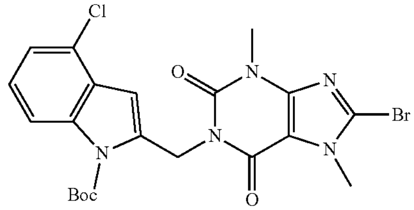 [SMILES: Cn1c(Br)nc2c1c(=O)n(Cc1cc3c(Cl)cccc3n1C(=O)OC(C)(C)C)c(=O)n2C] | 544 (M + 23)+ |

TABLE 4-continued

| Name | Structure | Mass Spec (ESI) or ¹H NMR |
|---|---|---|
| tert-butyl 2-((8-bromo-3,7-dimethyl-2,6-dioxo-2,3,6,7-tetrahydro-1H-purin-1-yl)methyl)-4-fluoro-1H-indole-1-carboxylate | 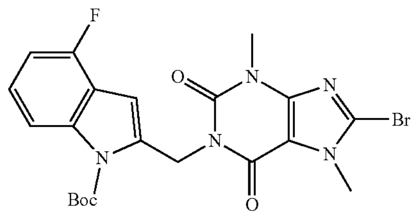 [SMILES: Cn1c(Br)nc2c1c(=O)n(Cc1cc3c(F)cccc3n1C(=O)OC(C)(C)C)c(=O)n2C] | 406.1 (M + H − 100)+ |
| tert-butyl 2-((8-bromo-3,7-dimethyl-2,6-dioxo-2,3,6,7-tetrahydro-1H-purin-1-yl)methyl)-3-chloro-1H-indole-1-carboxylate | 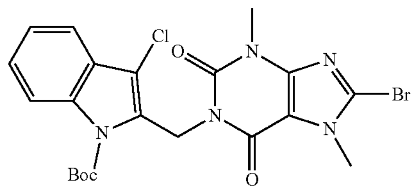 | 422.0 (M + H − 100)+ |
| tert-butyl 2-((8-bromo-3,7-dimethyl-2,6-dioxo-2,3,6,7-tetrahydro-1H-purin-1-yl)methyl)-6-chloro-1H-indole-1-carboxylate | 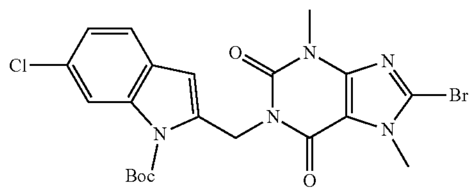 [SMILES: Cn1c(Br)nc2c1c(=O)n(Cc1cc3ccc(Cl)cc3n1C(=O)OC(C)(C)C)c(=O)n2C] | 422.1 (M + H − 100)+ |
| 8-bromo-3,7-dimethyl-1-(4-chlorobenzyl)-3,7-dihydro-1H-purine-2,6-dione | 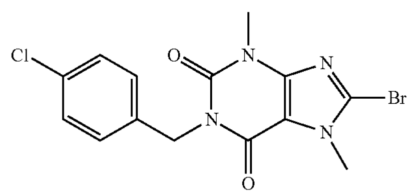 [SMILES: Cn1c(Br)nc2c1c(=O)n(Cc1ccc(Cl)cc1)c(=O)n2C] | 384.85 (M + H)+ |
| 8-bromo-3,7-dimethyl-1-(4-chloro-3-fluorobenzyl)-3,7-dihydro-1H-purine-2,6-dione | 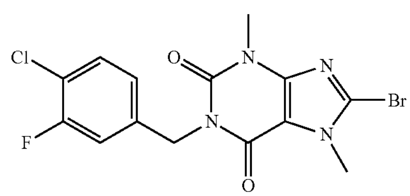 [SMILES: Cn1c(Br)nc2c1c(=O)n(Cc1ccc(Cl)c(F)c1)c(=O)n2C] | 402.8 (M + H)+ |
| 8-bromo-3,7-dimethyl-1-(3,4-difluorobenzyl)-3,7-dihydro-1H-purine-2,6-dione | 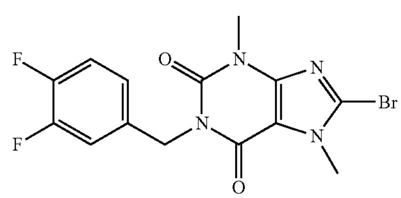 [SMILES: Cn1c(Br)nc2c1c(=O)n(Cc1ccc(F)c(F)c1)c(=O)n2C] | 386.85 (M + H)+ |
| 8-bromo-1-(4-methoxybenzyl)-3,7-dimethyl-3,7-dihydro-1H-purine-2,6-dione | 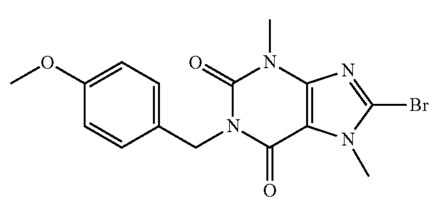 [SMILES: COc1ccc(Cn2c(=O)c3c(nc(Br)n3C)n(C)c2=O)cc1] | 380.85 (M + H)+ |

TABLE 4-continued

| Name | Structure | Mass Spec (ESI) or ¹H NMR |
|---|---|---|
| 1-(benzo[b]thiophen-5-ylmethyl)-8-bromo-3,7-dimethyl-3,7-dihydro-1H-purine-2,6-dione | 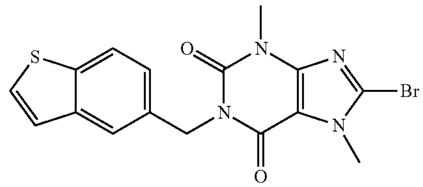 [SMILES: Cn1c(Br)nc2c1c(=O)n(Cc1ccc3sccc3c1)c(=O)n2C] | 406.75 (M + H)+ |
| 8-bromo-3,7-dimethyl-1-phenethyl-3,7-dihydro-1H-purine-2,6-dione | 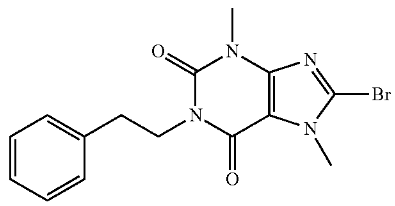 [SMILES: Cn1c(Br)nc2c1c(=O)n(CCc1ccccc1)c(=O)n2C] | 364.8 (M + H)+ |
| 8-bromo-1-(3,4-dichlorophenethyl)-3,7-dimethyl-3,7-dihydro-1H-purine-2,6-dione | 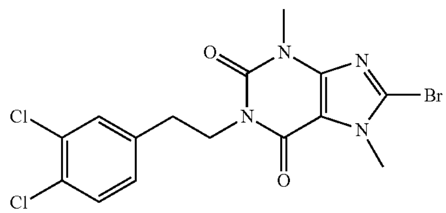 | 364.8 (M + H)+ |
| 8-bromo-1-(4-chloro-3-(trifluoromethyl)benzyl)-3,7-dimethyl-3,7-dihydro-1H-purine-2,6-dione | 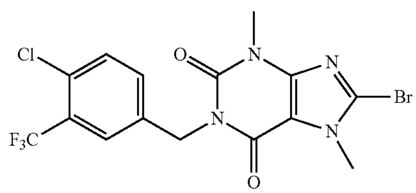 [SMILES: Cn1c(Br)nc2c1c(=O)n(Cc1ccc(Cl)c(C(F)(F)F)c1)c(=O)n2C] | 452.9 (M + H)+ |
| 8-bromo-1-(3-chloro-4-(trifluoromethyl)benzyl)-3,7-dimethyl-3,7-dihydro-1H-purine-2,6-dione | 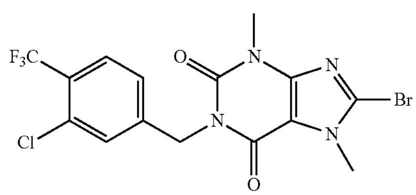 [SMILES: Cn1c(Br)nc2c1c(=O)n(Cc1ccc(C(F)(F)F)c(Cl)c1)c(=O)n2C] | 450.8 (M + H)+ |
| 8-bromo-1-(4-chloro-3-methoxybenzyl)-3,7-dimethyl-3,7-dihydro-1H-purine-2,6-dione | 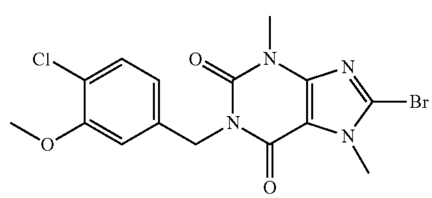 [SMILES: COc1cc(Cn2c(=O)c3c(nc(Br)n3C)n(C)c2=O)ccc1Cl] | 414.8 (M + H)+ |
| methyl 5-((8-bromo-3,7-dimethyl-2,6-dioxo-2,3,6,7-tetrahydro-1H-purin-1-yl)methyl)-2-chlorobenzoate | 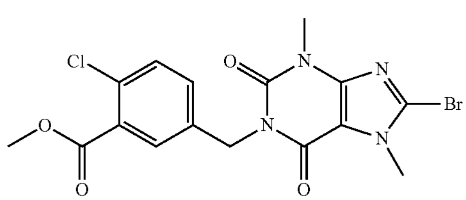 [SMILES: COC(=O)c1cc(Cn2c(=O)c3c(nc(Br)n3C)n(C)c2=O)ccc1Cl] | 442.85 (M + H)+ |

TABLE 4-continued

| Name | Structure | Mass Spec (ESI) or $^1$H NMR |
|---|---|---|
| 8-bromo-1-(1-(3,4-dichlorophenyl)ethyl)-3,7-dimethyl-3,7-dihydro-1H-purine-2,6-dione | 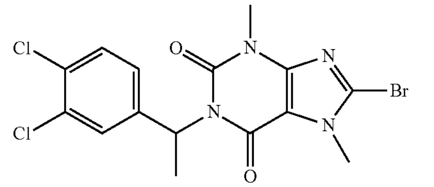 [SMILES: CC(c1ccc(Cl)c(Cl)c1)n1c(=O)c2c(nc(Br)n2C)n(C)c1=O] | 431.0 (M + H)$^+$ |
| tert-butyl 2-((8-bromo-3,7-dimethyl-2,6-dioxo-2,3,6,7-tetrahydro-1H-purin-1-yl)methyl)-1H-benzo[d]imidazole-1-carboxylate | 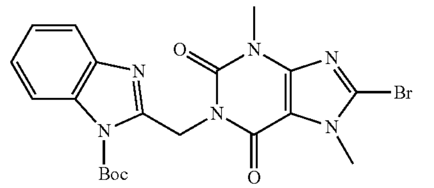 | 388.0 (M + H − 100)$^+$ |
| tert-butyl 2-((8-bromo-3,7-dimethyl-2,6-dioxo-2,3,6,7-tetrahydro-1H-purin-1-yl)methyl)-4-methyl-1H-indole-1-carboxylate | 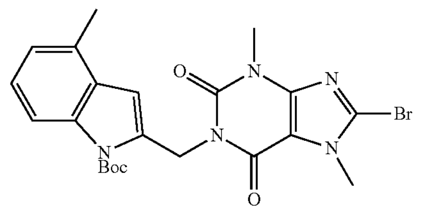 [SMILES: Cc1cccc2c1cc(Cn1c(=O)c3c(nc(Br)n3C)n(C)c1=O)n2C(=O)OC(C)(C)C] | 402.1 (M + H − 100)$^+$ |
| 8-bromo-3,7-dimethyl-1-(naphthalen-2-ylmethyl)-1H-purine-2,6(3H,7H)-dione | 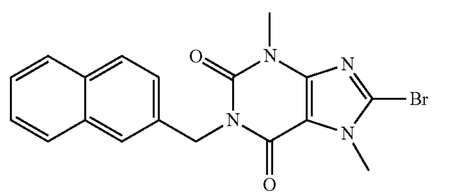 [SMILES: Cn1c(Br)nc2c1c(=O)n(Cc1ccc3ccccc3c1)c(=O)n2C] | 399.1 (M + H)$^+$ |
| tert-butyl 2-((8-bromo-3-ethyl-7-methyl-2,6-dioxo-2,3,6,7-tetrahydro-1H-purin-1-yl)methyl)-4-chloro-1H-indole-1-carboxylate | 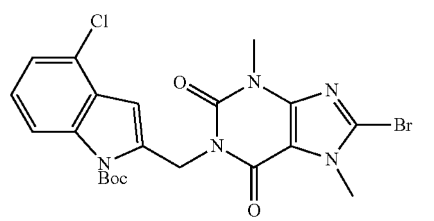 | 536.0 (M + H)$^+$ |
| tert-butyl 2-((8-bromo-3,7-dimethyl-2,6-dioxo-2,3,6,7-tetrahydro-1H-purin-1-yl)methyl)-7-fluoro-1H-indole-1-carboxylate | 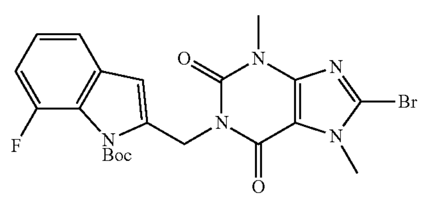 | $^1$H NMR (400 MHz, CDCl$_3$) δ 7.18-7.04 (m, 2 H) 7.00-6.90 (m, 1 H) 6.19-6.12 (s, 1 H) 5.57 (s, 2 H) 4.00 (s, 3 H) 3.62 (s, 3 H) 1.71 (s, 9 H) |
| tert-butyl 2-[(8-bromo-3,7-dimethyl-2,6-dioxo-purin-1-yl)methyl]-7-chloro-indole-1-carboxylate | 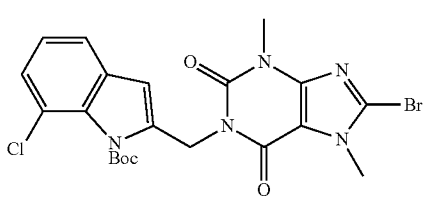 [SMILES: Cn1c(Br)nc2c1c(=O)n(Cc1cc3cccc(Cl)c3n1C(=O)OC(C)(C)C)c(=O)n2C] | $^1$H NMR (400 MHz, CDCl$_3$) 7.26-7.21 (m, 1H), 7.09 (s, 1H), 6.16-6.12 (m, 1H), 5.49 (s, 2H), 5.33 (s, 1H), 4.01-3.99 (m, 3H), 3.62 (s, 3H), 1.72 (s, 9H) |

TABLE 4-continued

| Name | Structure | Mass Spec (ESI) or ¹H NMR |
|---|---|---|
| 8-bromo-1-((5-chloronaphthalen-2-yl)methyl)-3,7-dimethyl-3,7-dihydro-1H-purine-2,6-dione | 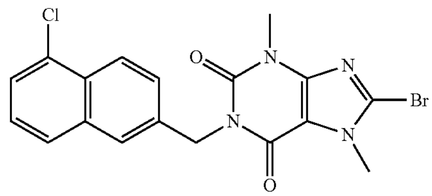 [SMILES: Cn1c(Br)nc2c1c(=O)n(Cc1ccc3c(Cl)cccc3c1)c(=O)n2C] | 435 (M + H)⁺ |
| tert-butyl 4-bromo-2-((8-bromo-3,7-dimethyl-2,6-dioxo-2,3,6,7-tetrahydro-1H-purin-1-yl)methyl)-1H-indole-1-carboxylate | 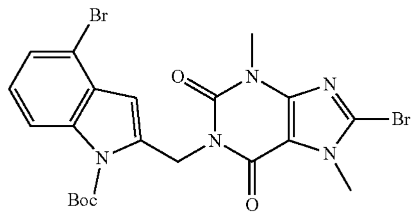 | 580.2 (M + H)⁺ |
| tert-butyl 2-[(8-bromo-3,7-dimethyl-2,6-dioxo-purin-1-yl)methyl]-7-methyl-indole-1-carboxylate | 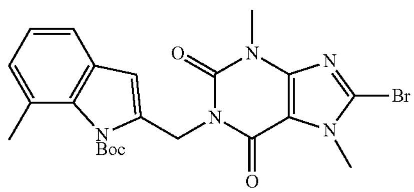 [SMILES: Cc1cccc2cc(Cn3c(=O)c4c(nc(Br)n4C)n(C)c3=O)n(C(=O)OC(C)(C)C)c12] | 402.0 (M + H − 100)⁺ |
| 8-bromo-3-ethyl-7-methyl-1-((5-methylnaphthalen-2-yl)methyl)-1H-purine-2,6(3H,7H)-dione | 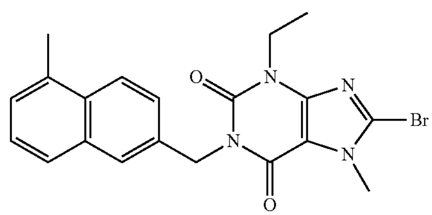 [SMILES: CCn1c(=O)n(Cc2ccc3c(C)cccc3c2)c(=O)c2c1nc(Br)n2C] | 429.0 (M + H + 2)⁺ |

Procedure 5

Illustrative Example 8-bromo-3,7-dimethyl-1-((1-methyl-1H-indol-2-yl)methyl)-1H-purine-2,6(3H,7H)-dione

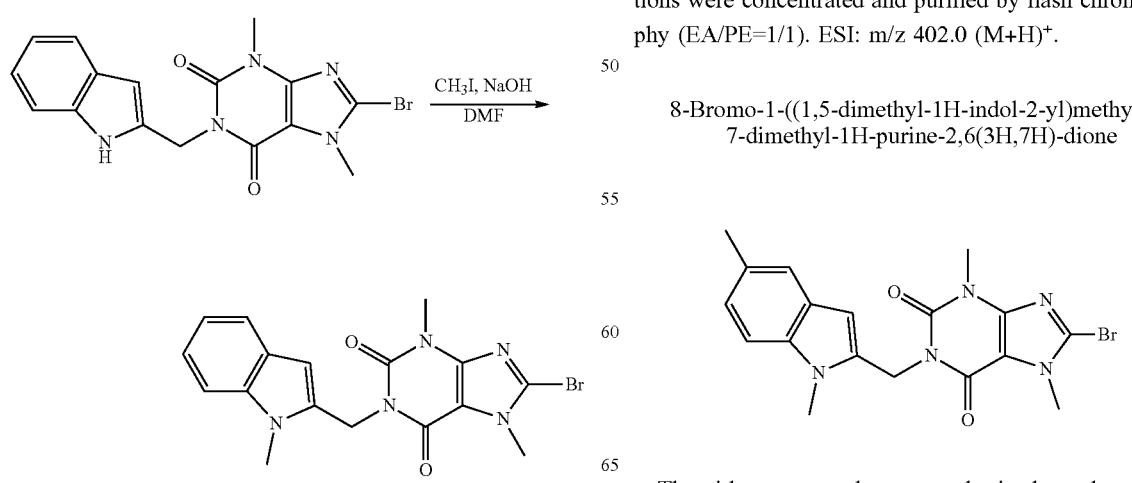

To a solution of 1-((1H-indol-2-yl)methyl)-8-bromo-3,7-dimethyl-1H-purine-2,6(3H,7H)-dione (0.26 mmol, 0.10 g), NaOH (0.78 mmol, 0.03 g) in DMF (5 mL) was added CH₃I (0.78 mmol, 0.11 g). The reaction mixture was stirred at 50° C. for 16 h. The mixture was diluted with water (20 mL) and extracted with EA (2*50 ml). The combined organic fractions were concentrated and purified by flash chromatography (EA/PE=1/1). ESI: m/z 402.0 (M+H)⁺.

8-Bromo-1-((1,5-dimethyl-1H-indol-2-yl)methyl)-3,7-dimethyl-1H-purine-2,6(3H,7H)-dione The title compound was synthesized as described in Procedure 5. ESI: m/z 416.0 (M+H)⁺.

8-bromo-1-((5-methoxy-1-methyl-1H-indol-2-yl)methyl)-3,7-dimethyl-1H-purine-2,6(3H,7H)-dione

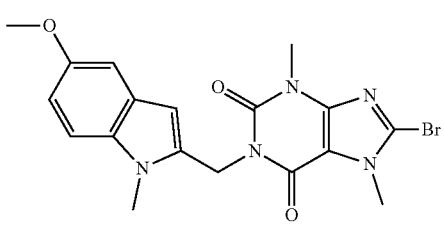 [SMILES: COc1ccc2c(c1)cc(Cn1c(=O)c3c(nc(Br)n3C)n(C)c1=O)n2C]

The title compound was synthesized as described in Procedure 5. ESI: m/z 434.0 (M+H)⁺.

General Synthetic Scheme for the Preparation of methyl (aminopyridyl)propanoates

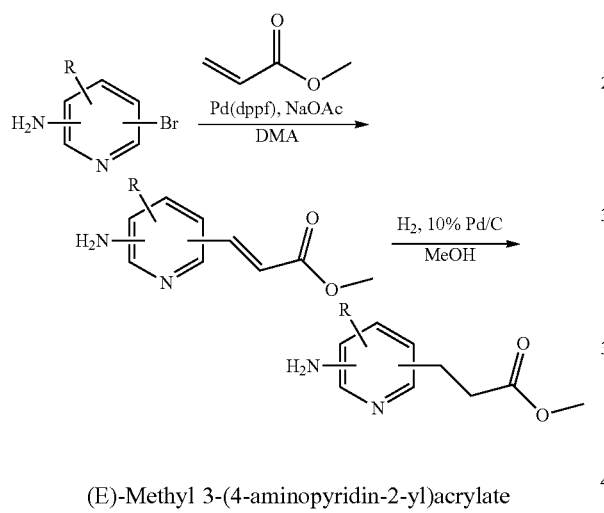

(E)-Methyl 3-(4-aminopyridin-2-yl)acrylate

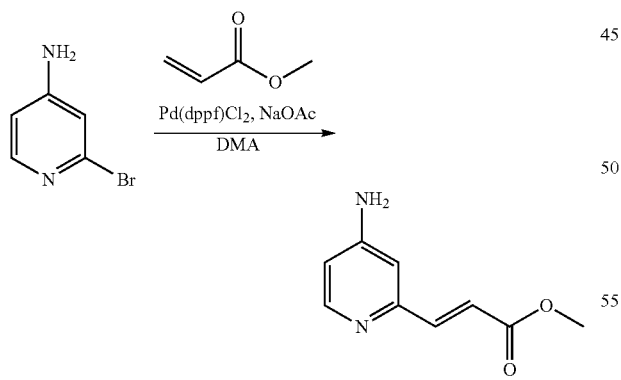

To a solution of 2-bromopyridin-4-amine (1.04 g, 6.0 mmol) and methyl acrylate (1.55 g, 18 mmol) in DMA (10 mL), were added Pd(dppf)Cl₂·CH₂Cl₂ (490 mg, 0.6 mmol) and NaOAc (1.48 g, 18 mmol). The mixture was stirred at 140° C. for 3 h under microwave irradiation. The mixture was cooled, filtered and concentrated. The residue was purified by flash chromatography (DCM/MeOH=10/1). ESI: m/z 179.1 (M+H)⁺.

(E)-Methyl 3-(6-amino-3-chloropyridin-2-yl)acrylate

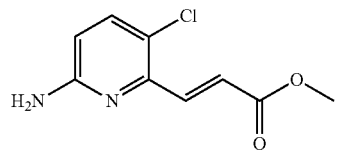

The title compound was synthesized in a similar fashion as described above using 6-bromo-5-chloropyridin-2-amine. ESI: m/z 213.1 (M+H)⁺.

Methyl 3-(6-aminopyridin-2-yl)acrylate

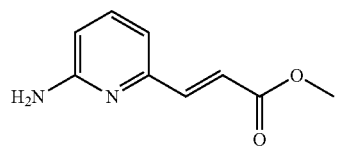

The title compound was synthesized as described above using 6-bromopyridin-2-amine. ESI: m/z 179.1 (M+H)⁺.

Methyl (E)-3-(2-aminopyridin-4-yl)acrylate

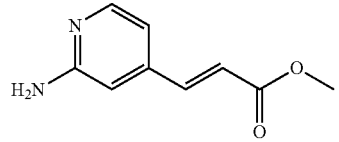

The title compound was synthesized as described above using 4-bromopyridin-2-amine. ESI m/z 179.1 (M+H)⁺.

(E)-Methyl 3-(6-amino-3-methylpyridin-2-yl)acrylate

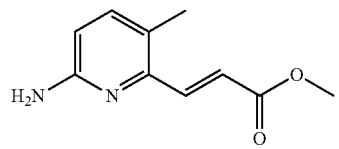

A mixture of (E)-methyl 3-(6-amino-3-chloropyridin-2-yl)acrylate (200 mg, 1.04 mmol), methylboronic acid (625 mg, 10.4 mmol), Pd(OAc)₂ (2 mg, 0.01 mmol), n-BuPAd (7 mg, 0.02 mmol), and Cs₂CO₃ (1014 mg, 3.12 mmol) in H₂O (1 mL) and toluene (4 mL) under Ar atmosphere was heated at 80° C. overnight. The mixture was concentrated and the residue was purified with column chromatography (silica gel, EA/PE=60%) to give the title compound. ESI: m/z 193.2 (M+H)⁺.

Methyl 3-(4-aminopyridin-2-yl)propanoate

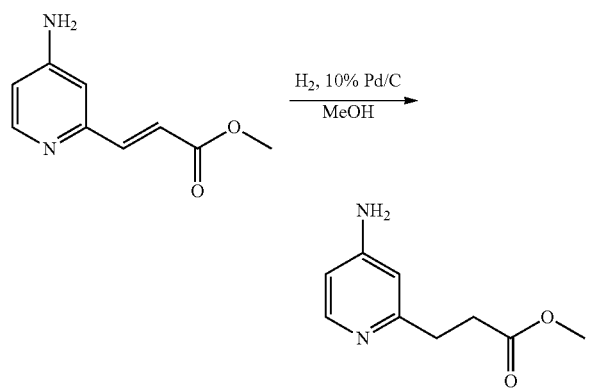

To a solution of (E)-methyl 3-(4-aminopyridin-2-yl)acrylate (200 mg, 1.12 mmol) in MeOH (5 mL), was added Pd/C (20 mg). The mixture was stirred at room temperature for 3 h under $H_2$ atmosphere. The mixture was filtered and concentrated to give methyl 3-(4-aminopyridin-2-yl)propanoate. ESI: m/z 181.1 $(M+H)^+$.

Methyl 3-(6-aminopyridin-2-yl)propanoate

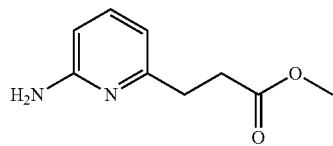

The title compound was synthesized as described above using methyl 3-(6-aminopyridin-2-yl)acrylate. ESI: m/z 181.1 $(M+H)^+$.

Methyl 3-(2-aminopyridin-4-yl)propanoate

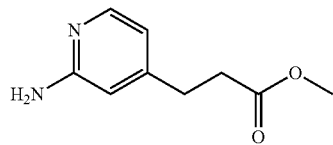

The title compound was synthesized as described above using methyl (E)-3-(2-aminopyridin-4-yl)acrylate. ESI: m/z 181.1 $(M+H)^+$.

Methyl 3-(6-amino-3-methylpyridin-2-yl)propanoate

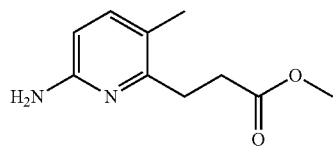

The title compound was synthesized as described above using (E)-methyl 3-(6-amino-3-methylpyridin-2-yl)acrylate. ESI: m/z 195.2 $(M+H)^+$.

Methyl 3-(6-amino-3-chloropyridin-2-yl)propanoate

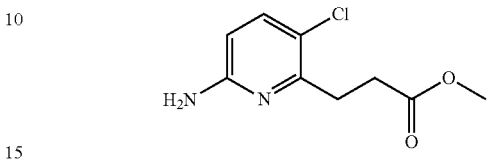

$NaBH_4$ (65 mg, 1.71 mmol) was slowly added to a mixture of (E)-methyl 3-(6-amino-3-methylpyridin-2-yl)acrylate (120 mg, 0.57 mmol) and NiCl (74 mg, 0.57 mmol) in THF (4 mL) and $CH_3OH$ (4 mL) at 0° C. The mixture was stirred at 0° C. for 20 min. The mixture was filtered and the filtrate was purified by column chromatography (EA/PE=30%) to give the product (95 mg). ESI: m/z 215.2 $(M+H)^+$.

Scheme 3: General Synthetic Scheme for the Preparation of Ethyl (aminopyridinyl)cyclopropanecarboxylates

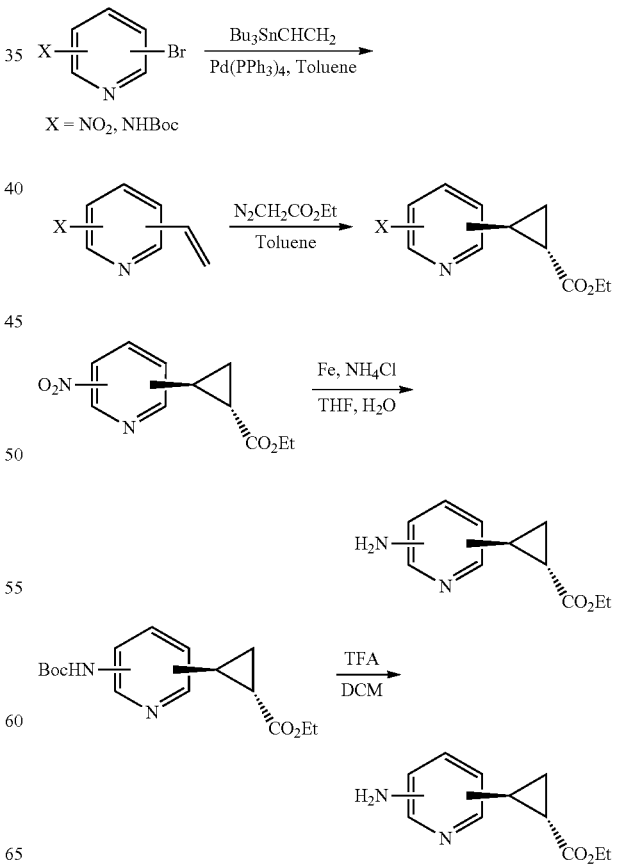

4-nitro-2-vinyl-pyridine

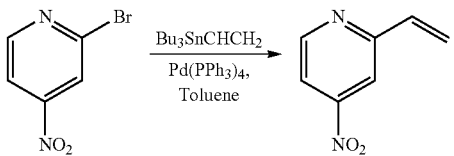

To a mixture of 2-chloro-4-nitro-pyridine (500.00 mg, 3.15 mmol, 1.00 eq) and tributyl(vinyl)stannane (1.30 g, 4.10 mmol, 1.30 eq) in toluene (5.00 mL) was added Pd(PPh$_3$)$_4$ (182.00 mg, 157.50 umol, 0.05 eq) at 15° C. The reaction mixture was degassed with nitrogen. Then the mixture was heated to 100° C. and stirred for 15 hr. The mixture was concentrated to give a crude residue. The residue was purified by column chromatography (PE/EA from 50/1 to 5/1) to give 4-nitro-2-vinyl-pyridine. ESI: m/z 151.0 (M+H)$^+$.

tert-butyl N-(6-vinyl-2-pyridyl)carbamate

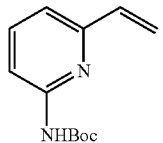

To a mixture of tert-butyl N-(6-bromo-2-pyridyl)carbamate (1.00 g, 3.66 mmol) and tributyl(vinyl)stannane (1.51 g, 4.76 mmol) in toluene (10.00 mL) was added Pd(PPh$_3$)$_4$ (211.47 mg, 183.00 umol) at 15° C. The reaction mixture was degassed with nitrogen. The mixture was heated to 120° C. and stirred for 12 hr. The mixture was concentrated and purified by column chromatography (PE/EA from 1/0 to 50/1) to afford tert-butyl N-(6-vinyl-2-pyridyl)carbamate.

(±)-cis-ethyl 2-(4-nitropyridin-2-yl)cyclopropanecarboxylate and (±)-trans-ethyl 2-(4-nitropyridin-2-yl)cyclopropanecarboxylate

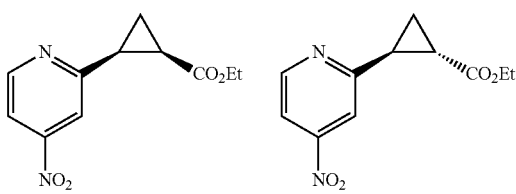 [SMILES: CCOC(=O)[C@@H]1C[C@@H]1c1cc([N+](=O)[O-])ccn1 ; CCOC(=O)[C@H]1C[C@@H]1c1cc([N+](=O)[O-])ccn1]

To a mixture of 4-nitro-2-vinyl-pyridine (1.57 g, 10.46 mmol) in toluene (30.00 mL) was added at reflux (110° C.) ethyl 2-diazoacetate (2.39 g, 20.92 mmol, 2.19 mL) in toluene (30.00 mL) in three portions over 30 minutes. The reaction mixture was refluxed for 15 h. The mixture was concentrated to give a crude residue which was purified by column chromatography (SiO$_2$, PE/EtOAc from 100/1 to 3/1) to provide (±)-trans-ethyl 2-(4-nitropyridin-2-yl)cyclopropanecarboxylate (1.00 g) and (±)-cis-ethyl 2-(4-nitropyridin-2-yl)cyclopropanecarboxylate (200.00 mg). Physical data for (±)-cis-ethyl 2-(4-nitropyridin-2-yl)cyclopropanecarboxylate: $^1$H NMR (400 MHz, CDCl$_3$) δ 8.79-8.80 (d, J=4.8 Hz, 1H), 8.01-8.02 (d, J=2.0 Hz, 1H), 7.85-7.87 (dd, J=4.8 Hz, J=2.0 Hz, 1H), 3.92-3.99 (m, 2H), 2.81-2.87 (m, 1H), 2.26-2.30 (m, 1H), 1.89-1.94 (m, 1H), 1.55-1.159 (m, 2H), 1.07-1.12 (t, J=7.4 Hz, 3H). Physical data for (±)-trans-ethyl 2-(4-nitropyridin-2-yl)cyclopropanecarboxylate: $^1$H NMR (400 MHz CDCl$_3$) δ 8.75-8.74 (m, 1H) 7.98 (s, 1H) 7.84-7.82 (m, 1H) 4.24-4.18 (m, 2H) 2.76-2.72 (m, 1H) 2.36-2.33 (m, 1H) 1.74-1.60 (m, 2H) 1.32-1.28 (m, 3H).

(±)-trans-Ethyl-2-(6-((tert-butoxycarbonyl)amino)pyridin-2-yl)cyclopropanecarboxylate

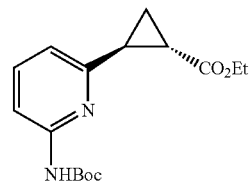 [SMILES: CCOC(=O)[C@H]1C[C@@H]1c1cccc(NC(=O)OC(C)(C)C)n1]

To a solution of tert-butyl N-(6-vinyl-2-pyridyl)carbamate (490.00 mg, 2.22 mmol) in toluene (5.00 mL) at reflux (~120° C.) was added dropwise a solution of ethyl 2-diazoacetate (253.31 mg, 2.22 mmol) in toluene (1.00 mL). The solution was stirred at 120° C. for 12 h. The mixture was concentrated and purified by column chromatography (PE/EA=100 to 20/1) to afford the title compound.

(±)-trans-Ethyl 2-(4-aminopyridin-2-yl)cyclopropanecarboxylate

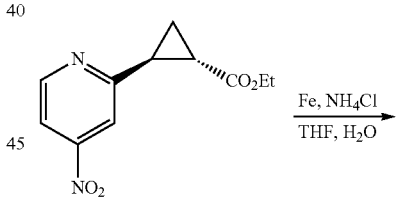

To a mixture of ethyl 2-(4-nitropyridin-2-yl)cyclopropanecarboxylate (200.00 mg, 846.67 umol), Fe (189.15 mg, 3.39 mmol) in THF (500.00 uL) was stirred at 25° C. for 33 hr. The reaction mixture was filtered and the filtrate was concentrated in reduced pressure at 45° C. The residue was poured into ice water (w/w=1/1) (10 mL). The aqueous phase was extracted with ethyl acetate (10 mL*3.). The combined organic phase was washed with brine (10 mL), dried with anhydrous Na$_2$SO$_4$, filtered and concentrated in vacuum. The residue was purified by prep-TLC (DCM/MeOH=10/1). ESI: m/z 207.2 (M+H)$^+$.

Procedure 6: Boc Removal with TFA

Illustrative Example (±)-trans-Ethyl 2-(6-aminopyridin-2-yl)cyclopropanecarboxylate

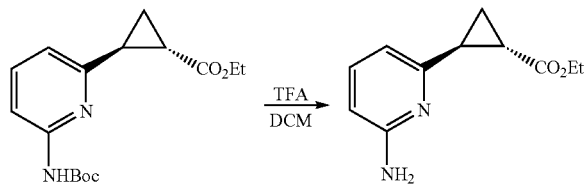 [SMILES: CCOC(=O)[C@H]1C[C@@H]1c1cccc(NC(=O)OC(C)(C)C)n1 ; CCOC(=O)[C@H]1C[C@@H]1c1cccc(N)n1 ; "TFA"]

To a solution of (±)-trans-ethyl 2-(6-((tert-butoxycarbonyl)amino)pyridin-2-yl) cyclopropanecarboxylate (230.00 mg, 750.75 umol) in DCM (5.00 mL) at 0° C. was added dropwise TFA (3.00 mL). The reaction mixture was stirred at 15° C. for 12 hr. The mixture was concentrated and the residue was dissolved in DCM (2 mL). The mixture was made basic with sat.NaHCO$_3$ to pH=~8 and extracted with DCM (5 mL*3). The combined organic fractions were dried over Na$_2$SO$_4$ and concentrated. The residue was purified by prep-TLC (PE/EA=3/1): $^1$HNMR (400 MHz, CDCl$_3$) δ 7.29-7.33 (t, J=7.6 Hz, 1H), 6.58-6.60 (d, J=7.6 Hz, 1H), 6.29-6.31 (d, J=8.0 Hz, 1H), 4.30 (br, 2H), 4.13-1.19 (q, J=7.2 Hz, 2H), 2.42-2.46 (m, 1H), 2.10-2.25 (m, 1H), 1.50-1.65 (m, 2H), 1.25-1.29 (t, J=7.2 Hz, 3H).

Synthesis of (±)-cis-ethyl 2-(6-aminopyridin-2-yl)cyclopropanecarboxylate

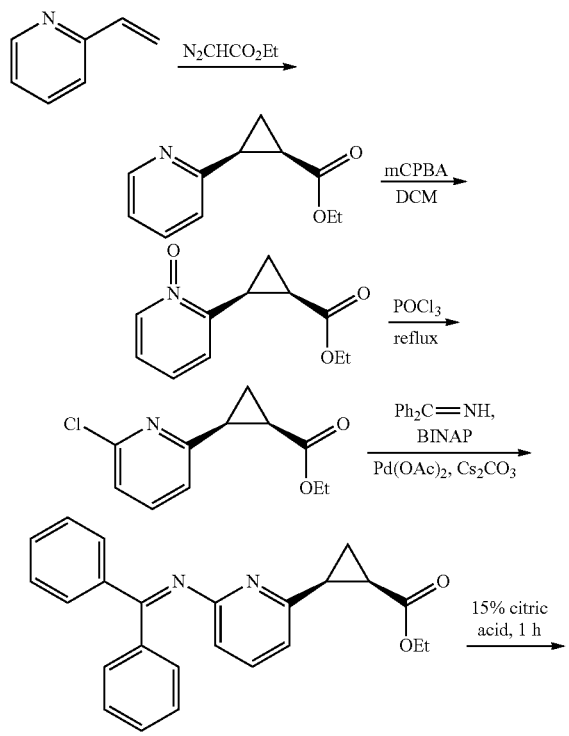

(±)-cis-Ethyl 2-(pyridin-2-yl)cyclopropanecarboxylate and (±)-trans-ethyl 2-(pyridin-2-yl)cyclopropanecarboxylate

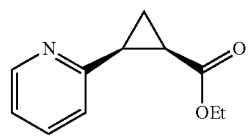 [SMILES: CCOC(=O)[C@@H]1C[C@@H]1c1ccccn1]

To a solution of 2-vinylpyridine (14.30 g, 136.01 mmol, 14.74 mL) in toluene (300.00 mL) was added ethyl 2-diazoacetate (15.52 g, 136.01 mmol, 14.30 mL). The mixture was stirred at 100° C. for 12 hr. The mixture was concentrated. The crude product was purified by column chromatography (PE/EA from 100/1 to 3/1) to afford (±)-trans-ethyl-2-(pyridin-2-yl)cyclopropanecarboxylate (11.30 g) and (±)-cis-ethyl-2-(pyridin-2-yl)cyclopropane carboxylate: Physical data for (±)-cis-ethyl-2-(pyridin-2-yl)cyclopropane carboxylate: $^1$H NMR (400 MHz, CDCl$_3$) δ 8.53-8.52 (m, 1H), 7.63-7.59 (m, 1H), 7.29-7.27 (m, 2H), 7.15-7.12 (m, 1H), 3.96-3.90 (m, 2H), 2.78-2.74 (m, 1H), 2.21-2.19 (m, 1H), 1.86-1.85 (m, 1H), 1.46-1.43 (m, 1H), 1.07-1.03 (t, 3H); ESI m/z 192.1 (M+H)$^+$.

(±)-cis-2-(2-(ethoxycarbonyl)cyclopropyl)pyridine 1-oxide

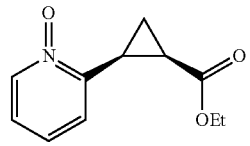 [SMILES: CCOC(=O)[C@@H]1C[C@@H]1c1cccc[n+]1[O-]]

To a solution of (±)-cis-ethyl-2-(2-pyridyl)cyclopropanecarboxylate (1.00 g, 5.23 mmol) in DCM (10.00 mL) at 0° C. was added m-CPBA (1.69 g, 7.85 mmol, 80% purity). The mixture was stirred at 25° C. for 2 hr. The mixture was quenched with sat. Na$_2$SO$_3$ (~20 mL) and basified by NaHCO$_3$ to pH=8. The resulting mixture was extracted with DCM (30 mL*3). The combined organic fractions were washed with brine (10 mL), dried over Na$_2$SO$_4$ and concentrated to afford the title compound. ESI: m/z 208.1 (M+H)$^+$.

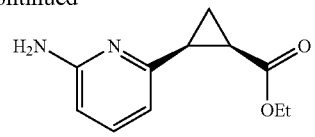

(±)-cis-Ethyl 2-(6-chloropyridin-2-yl)cyclopropanecarboxylate

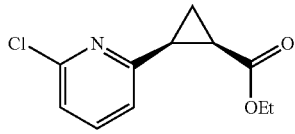 [SMILES: CCOC(=O)[C@@H]1C[C@@H]1c1cccc(Cl)n1]

A solution of (±)-cis-2-((2-(ethoxycarbonyl)cyclopropyl) pyridine 1-oxide (1.20 g, 5.79 mmol) in POCl$_3$ (12.00 mL) was stirred at 100° C. for 12 hr. The mixture was concentrated and dissolved with DCM (20 mL). The mixture was poured into ice-cold sat.NaHCO$_3$ (~40 mL) until pH>8. The aqueous layer was extracted with DCM (40 mL*3). The combine organic fractions were washed with brine (10 mL), dried over Na$_2$SO$_4$ and concentrated. The crude product was purified by column chromatography (PE/EA from 100/1 to 40/1) to afford (±)-cis-ethyl 2-(6-chloropyridin-2-yl) cyclopropanecarboxylate (40.00 mg) and (±)-trans-ethyl 2-(6-chloropyridin-2-yl) cyclopropanecarboxylate (280.00 mg). Physical data for (±)-cis-ethyl 2-(6-chloropyridin-2-yl) cyclopropanecarboxylate: $^1$H NMR (400 MHz, CDCl$_3$) δ 7.59-7.56 (t, 1H), 7.22-7.16 (m, 2H), 7.29-7.27 (m, 2H), 4.01-3.96 (m, 2H), 2.73-2.67 (m, 1H), 2.22-2.20 (m, 1H), 1.83-1.80 (m, 1H), 1.48-1.44 (m, 1H), 1.13-1.09 (t, 3H); ESI: m/z 226.1 (M+H)$^+$.

(±)-cis-Ethyl-2-(6-((diphenylmethylene)amino)pyridin-2-yl)cyclopropanecarboxylate

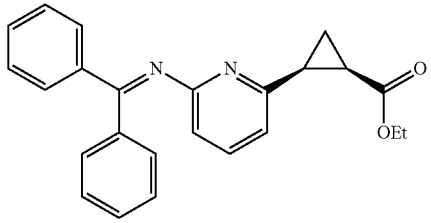 [SMILES: CCOC(=O)[C@@H]1C[C@@H]1c1cccc(N=C(c2ccccc2)c2ccccc2)n1]

To a mixture of (±)-cis-ethyl 2-(6-chloropyridin-2-yl) cyclopropanecarboxylate (178.00 mg, 788.76 umol), diphenylmethanimine (142.95 mg, 788.76 umol, 132.36 uL, 1.00 eq), diphenylmethanimine (142.95 mg, 788.76 umol, 132.36 uL) and Cs$_2$CO$_3$ (770.98 mg, 2.37 mmol) in toluene (3.00 mL) was added Pd(OAc)$_2$ (10.63 mg, 47.33 umol). The mixture was stirred at 110° C. for 12 hr. The mixture was filtered and the filtrate was concentrated to afford the title compound (300.00 mg). ESI: m/z 371.9 (M+H)$^+$.

(±)-cis-Ethyl 2-(6-aminopyridin-2-yl)cyclopropanecarboxylate

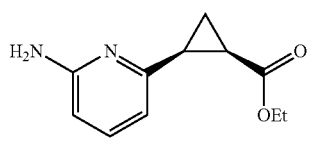 [SMILES: CCOC(=O)[C@@H]1C[C@@H]1c1cccc(N)n1]

To a solution of (±)-cis-ethyl-2-(6-((diphenylmethylene) amino)pyridin-2-yl) cyclopropanecarboxylate (300.00 mg, 809.85 umol) in THF (3.00 mL) at 0° C. was added 15% citric acid (5.00 mL). The solution was stirred at 25° C. for 1 hour. The mixture was cooled to 0° C. and the pH was made basic with sat.NaHCO$_3$(aq) to pH>8. The resulting mixture was extracted with EA (20 mL*3). The combined organic fractions were washed with brine (5 mL), dried over Na$_2$SO$_4$ and concentrated. The crude product was purified by prep-HPLC (column: Luna C18 100*30 5u; liquid phase: [A-TFA/H2O=0.075% v/v; B-ACN]B %: 1%-25%, 12 min]) to afford the title compound. $^1$H NMR (400 MHz, CDCl$_3$) δ 7.67-7.63 (m, 1H), 6.66-6.61 (m, 2H), 4.08-4.02 (m, 2H), 2.69-2.65 (m, 1H), 2.38-2.34 (m, 1H), 1.72-1.68 (m, 1H), 1.59-1.56 (m, 1H), 1.22-1.18 (t, 3H); ESI: m/z 207.1 (M+H)$^+$.

Synthesis of Methyl 3-(4-aminopyridin-2-yl)cyclobutanecarboxylate

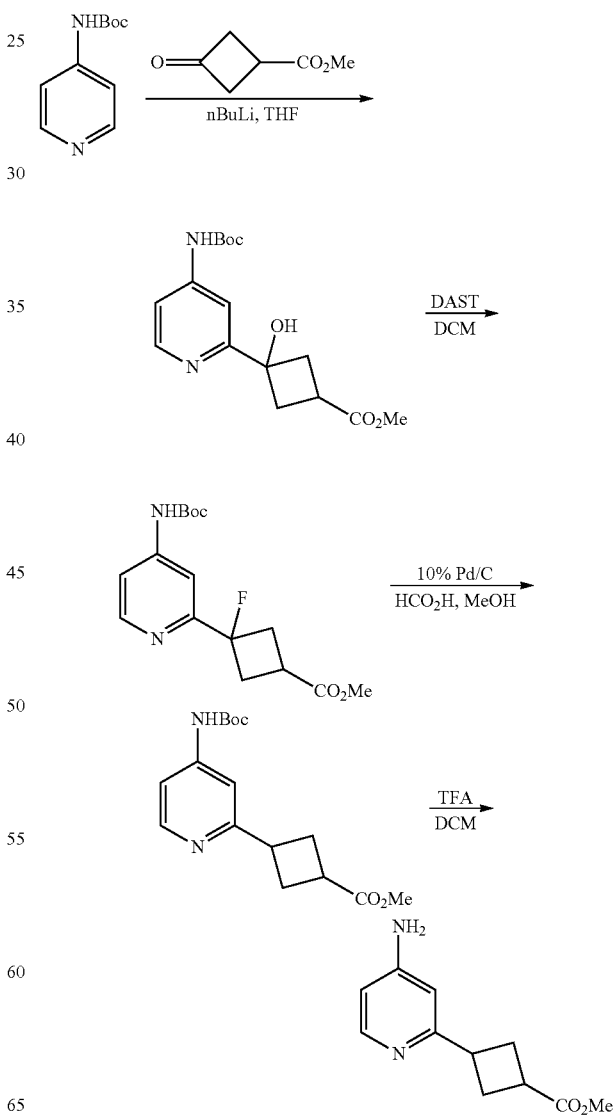

Methyl 3-(4-(tert-butoxycarbonylamino)pyridin-2-yl)-3-hydroxycyclobutanecarboxylate

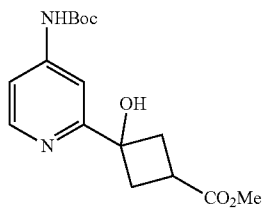 [SMILES: COC(=O)C1CC(O)(c2cc(NC(=O)OC(C)(C)C)ccn2)C1]

To a solution of tert-butyl 2-bromopyridin-4-ylcarbamate (2.0 g, 7.3 mmol) in THF (60 mL) was added n-BuLi (7.3 ml, 18.25 mmol) dropwise at −78° C. under $N_2$. After the reaction mixture was stirred at −78° C. for 1 h, methyl 3-oxocyclobutanecarboxylate (1.87 g, 14.6 mmol) was added in one portion. The resulting mixture was allowed to warm to room temperature over 1 h. The reaction was quenched with sat. $NH_4Cl$ solution (20 mL) and the mixture was extracted with EA (50 mL×2). The combined organic fractions were dried over $Na_2SO_4$, filtered and concentrated. The residue was purified by flash column chromatography to give the product. ESI: m/z 323.1 (M+H)$^+$.

Methyl 3-(4-(tert-butoxycarbonylamino)pyridin-2-yl)-3-fluorocyclobutanecarboxylate

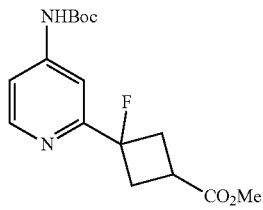 [SMILES: COC(=O)C1CC(F)(c2cc(NC(=O)OC(C)(C)C)ccn2)C1]

To a solution of methyl 3-(4-(tert-butoxycarbonylamino)pyridin-2-yl)-3-hydroxycyclobutanecarboxylate (900 mg, 2.8 mmol) in DCM (25 mL) was added DAST (676 mg, 4.2 mmol) dropwise at −78° C. under $N_2$. After stirring at −78° C. for 5 minute, the reaction mixture was stirred at 0° C. for 1 h. The mixture was quenched with water (10 mL). The pH was adjusted to pH=8 with sat. $NaHCO_3$ solution, and extracted with DCM (30 mL×2). The combined organic fractions were dried over $Na_2SO_4$, filtered and concentrated. The residue was purified by flash column to give the title compound. ESI: m/z 325.2 (M+H)$^+$.

Methyl 3-(4-(tert-butoxycarbonylamino)pyridin-2-yl)cyclobutanecarboxylate

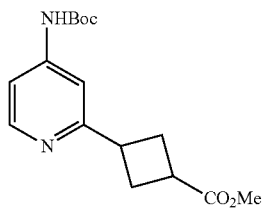

To a solution of methyl 3-(4-(tert-butoxycarbonylamino)pyridin-2-yl)-3-fluorocyclobutane carboxylate (475 mg, 1.47 mmol) in MeOH (20 mL) and formic acid (1 mL) was added 10% Pd/C (200 mg). The resulting mixture was stirred at room temperature overnight under $H_2$. The mixture was filtered through Celite and concentrated. The residue was dissolved in EA (80 mL) and washed with sat. $NaHCO_3$ solution (40 mL×2), brine (30 mL), dried over $Na_2SO_4$, filtered and concentrated in vacuo to give the title compound. ESI: m/z 307.2 (M+H)$^+$ Methyl 3-(4-aminopyridin-2-yl)cyclobutanecarboxylate

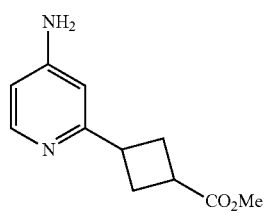 [SMILES: COC(=O)C1CC(c2cc(N)ccn2)C1]

To a solution of methyl 3-(4-(tert-butoxycarbonylamino)pyridin-2-yl)cyclobutanecarboxylate (440 mg, 1.44 mmol) in DCM (8 mL) was added TFA (2 mL) dropwise. The resulting mixture was stirred at room temperature for 2 h. The mixture was concentrated under reduced pressure; 7 N $NH_3$ in methanol (10 mL) was added. The mixture was concentrated. The residue was purified by flash column chromatography to give the title compound. ESI: m/z 207.1 (M+H)$^+$.

Synthesis of 3-(6-aminopyridin-2-yl) cyclopentanol

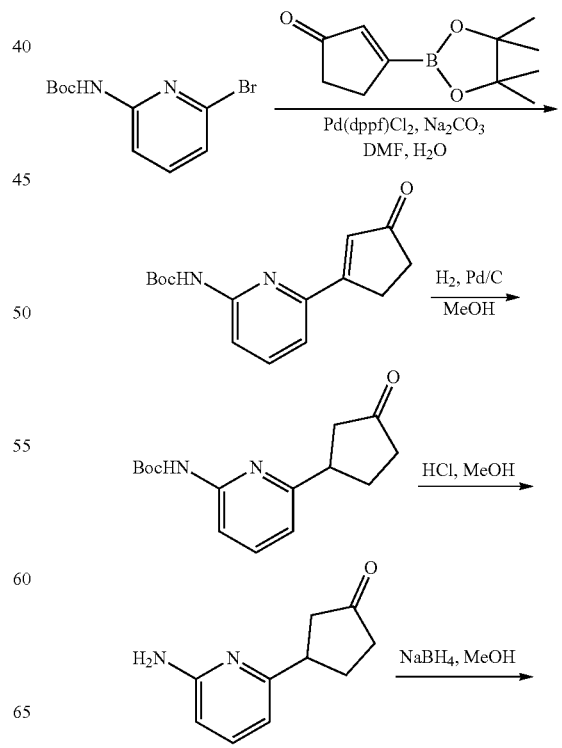

-continued

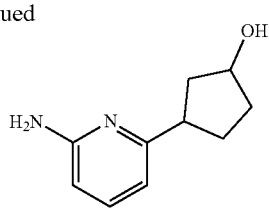

tert-Butyl 6-(3-oxocylopent-1-enyl)pyridine-2-ylcarbamate

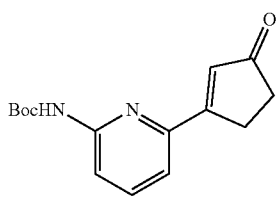 [SMILES: CC(C)(C)OC(=O)Nc1cccc(C2=CC(=O)CC2)n1]

A mixture of 3-(4,4,5,5,-tetramethyl-1,3,2-dioxaborolan-2-yl)cyclopent-2-enone (500 mg, 2.4 mmol), tert-butyl 6-bromopyridin-2-ylcarbamate (656 mg, 2.4 mmol), Pd(dppf)Cl$_2$ (176 mg, 0.24 mmol), Na$_2$CO$_3$ (509 mg, 4.8 mmol), DMF (16 mL) and water (4 mL) was stirred at 100° C. under N$_2$ overnight. The mixture was extracted with EA (60 mL*2), washed with brine (20 mL*3), dried over Na$_2$SO$_4$ and concentrated to dryness. The residue was purified by column chromatography (EA/DCM=0~20%). ESI: m/z 275.2 (M+H)$^+$.

tert-Butyl 6-(3-oxocyclopentyl) pyridine-2-ylcarbamate

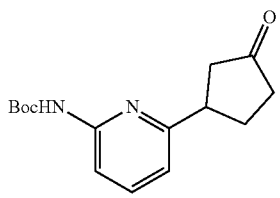 [SMILES: CC(C)(C)OC(=O)Nc1cccc(C2CCC(=O)C2)n1]

A mixture of tert-butyl 6-(3-oxocylopent-1-enyl) pyridine-2-ylcarbamate (220 mg, 0.803 mmol), Pd/C (50 mg) and MeOH (5 mL) was degassed with H$_2$ and stirred at r. t. under H$_2$ overnight. The mixture was filtered and the filtrate was concentrated to dryness. The residue was purified by column chromatography (EA/DCM=0~10%) to give the title compound. ESI: m/z 277.2 (M+H)$^+$.

3-(6-aminopyridin-2-yl) cyclopentanone

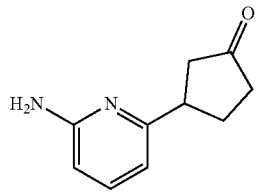 [SMILES: Nc1cccc(C2CCC(=O)C2)n1]

A mixture of tert-butyl 6-(3-oxocyclopentyl) pyridine-2-ylcarbamate (220 mg, 0.796 mmol) and HCl in MeOH (3M, 5 mL, 15 mmol) was stirred at r. t. for 4 h. The mixture was concentrated to dryness. The residue was neutralized with NaHCO$_3$(aq) to pH~7. The mixture was concentrated to dryness. The residue was purified by column chromatography (MeOH/DCM=0~10%) to give the desired product. ESI: m/z 177.2 (M+H)$^+$.

3-(6-aminopyridin-2-yl) cyclopentanol

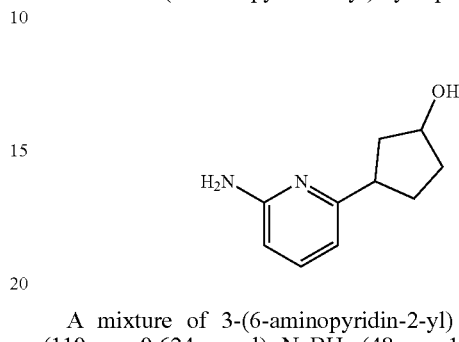

A mixture of 3-(6-aminopyridin-2-yl) cyclopentanone (110 mg, 0.624 mmol), NaBH$_4$ (48 mg, 1.248 mmol) and MeOH (10 mL) was stirred at rt. for 2 h. The mixture was concentrated to dryness, and the residue was purified by column chromatography (MeOH/DCM=0~10%) to give the desired product. ESI: m/z 179.2 (M+H)$^+$.

Synthesis of methyl 3-(4-aminopyrimidin-2-yl)propanoate

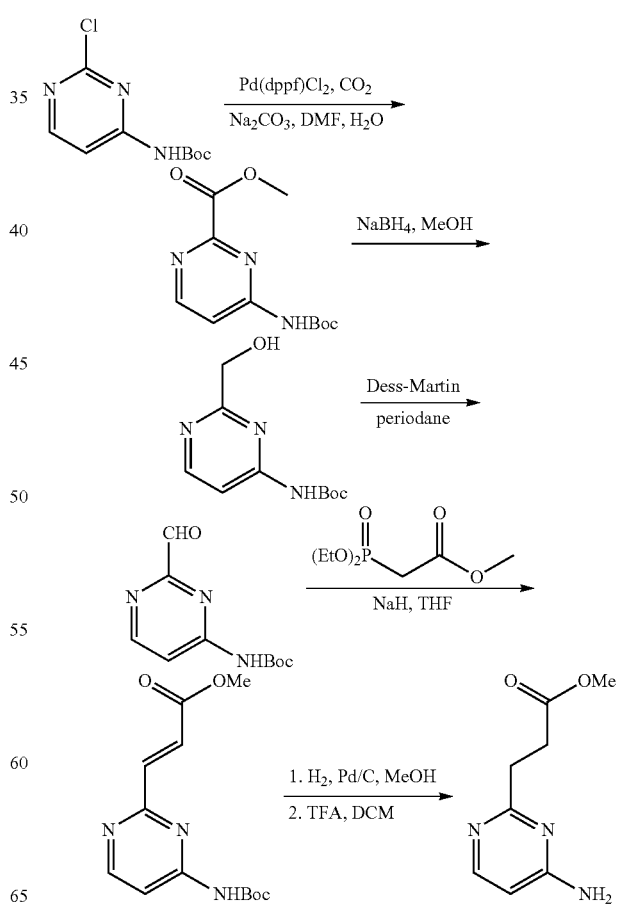

Methyl 4-(tert-butoxycarbonylamino)pyrimidine-2-carboxylate

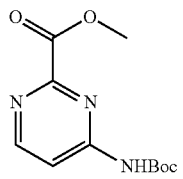 [SMILES: COC(=O)c1nccc(NC(=O)OC(C)(C)C)n1]

A solution of tert-butyl 2-chloropyrimidin-4-ylcarbamate (39.3 mmol, 9.0 g), PdCl₂(dppf) (1.4 mmol, 1.0 g) and triethylamine (55.2 mmol, 7.7 mL) in MeOH (100 mL) was stirred at 100° C. for 12 h in an atmosphere of carbon monoxide with the pressure of 200 psi. The reaction was concentrated and purified by flash chromatography (PE/EA=10/3) to give the product. ESI: m/z 254.2 (M+H)⁺.

tert-butyl 2-(hydroxymethyl)pyrimidin-4-ylcarbamate

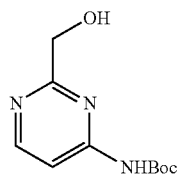

To a solution of methyl 4-(tert-butoxycarbonylamino)pyrimidine-2-carboxylate (9.88 mmol, 2.50 g) in EtOH (20 mL) was added NaBH₄ (10.40 mmol, 0.39 g). The reaction mixture was stirred at 30° C. for 2 h. The reaction was concentrated and purified by flash chromatography (PE/EA=1/3) to give the product. ESI: m/z 226.2 (M+H)⁺.

tert-Butyl 2-(hydroxymethyl)pyrimidin-4-ylcarbamate

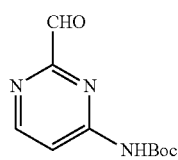

To a solution of tert-butyl 2-(hydroxymethyl)pyrimidin-4-ylcarbamate (8.0 mmol, 1.80 g) in DCM (100 mL) was added Dess-Martin periodinane (16.0 mmol, 6.78 g). The reaction mixture was stirred at 30° C. for 5 h. The reaction was filtered and the filtrate was concentrated. The product was purified by flash chromatography (PE/EA=1/3). ESI: m/z 242.2 (M+H₃O)⁺.

(E)-Methyl 3-(4-(tert-butoxycarbonylamino)pyrimidin-2-yl)acrylate

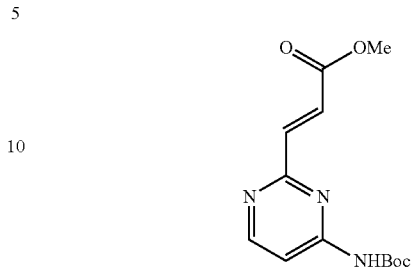

To an ice-cooled solution of NaH (6.30 mmol, 252 mg) in THF (30 mL) was added ethyl 2-(diethoxyphosphoryl)acetate (6.75 mmol, 1.35 ml). The reaction mixture was stirred at 0° C. for 1 h. Then tert-butyl 2-(hydroxymethyl)pyrimidin-4-ylcarbamate (4.50 mmol, 1.02 g) in THF (5 mL) was added dropwise. The final mixture was stirred at 30° C. for 1 h. Sat. NH₄Cl (20 mL) was added to quench the reaction. The organic layer was separated and the aqueous layer was extracted with EA (30 mL*2). The organic fractions were combined, washed with brine (30 mL), dried with Na₂SO₄ and concentrated. The product was purified by flash chromatography (PE/EA=1/1). ESI: m/z 294.2 (M+H)⁺.

Methyl 3-(4-aminopyrimidin-2-yl)propanoate

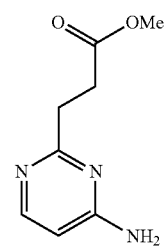 [SMILES: COC(=O)CCc1nccc(N)n1]

To a solution of (E)-methyl 3-(4-(tert-butoxycarbonylamino)pyrimidin-2-yl)acrylate (4.44 mmol, 1.30 g) in EA (60 mL) was added Pd/C (650 mg). The reaction mixture was stirred in an atmosphere of H₂ (1 atm) at 30° C. for 1 h. The reaction was filtered and the filtrate was concentrated. The residue was dissolved in DCM (3 mL) and TFA (1.0 mL). The solution was stirred at 30° C. for 1 h. The solution was concentrated. The residue was dissolved in EA (30 mL), washed with sat. NaHCO₃ (20 mL), dried with Na₂SO₄ and concentrated. The product was purified by flash chromatography (PE/EA=1/1) to give the title compound. ESI: m/z 196.1 (M+H)⁺.

Synthesis of Examples

General Synthetic Method

Procedure 7A and 7B

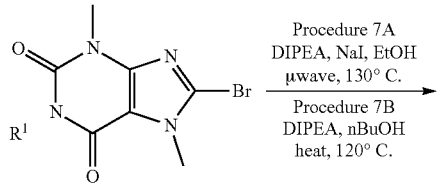

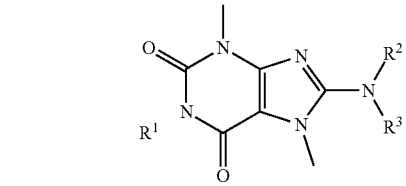

Illustrative Examples

Procedure 7A

Example 112

1-(3,4-dichlorobenzyl)-8-(3,3-difluorocyclobutylamino)-3,7-dimethyl-1H-purine-2,6(3H,7H)-dione

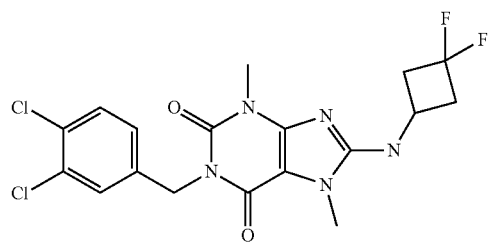 [SMILES: Cn1c(NC2CC(F)(F)C2)nc2c1c(=O)n(Cc1ccc(Cl)c(Cl)c1)c(=O)n2C]

To a solution of 8-bromo-1-(3,4-dichlorobenzyl)-3,7-dimethyl-1H-purine-2,6(3H,7H)-dione (150 mg, 0.36 mmol), 3,3-difluorocyclobutanamine (80 mg, 0.72 mmol) and DIEA (117 mg, 0.9 mmol) in EtOH (8 mL) was added NaI (5 mg). The mixture was stirred at 130° C. for 6 h in a microwave reactor. The reaction mixture was concentrated and purified by column chromatography (PE/EA, 1/1) to provide the title compound. $^1$H NMR (400 MHz, CD$_3$OD) δ 7.51 (s, 1H), 7.39 (d, J=8.4 Hz, 1H), 7.29 (d, J=2.0 Hz, 1H), 5.07 (s, 2H), 4.25 (m, 1H), 3.64 (s, 3H), 3.46 (s, 3H), 3.31 (m, 1H), 2.91 (m, 1H), 1.85-2.07 (m, 5H), 1.61 (m, 1H); ESI: m/z 480.1 (M+H)$^+$.

Procedure 7B

Example 49

1-[(3,4-dichlorophenyl)methyl]-3,7-dimethyl-8-{[(3S)-oxolan-3-yl]amino}-2,3,6,7-tetrahydro-1H-purine-2,6-dione

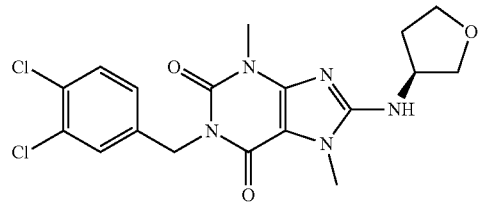 [SMILES: Cn1c(N[C@H]2CCOC2)nc2c1c(=O)n(Cc1ccc(Cl)c(Cl)c1)c(=O)n2C]

(3S)-Oxolan-3-amine hydrochloride (83 mg, 0.67 mmol) was added at room temperature to a stirred suspension of 8-bromo-1-(3,4-dichlorobenzyl)-3,7-dimethyl-1H-purine-2,6(3H,7H)-dione (70 mg, 0.17 mmol) and DIEA (233 μl, 1.34 mmol) in nBuOH (5 ml). The resulting mixture was heated at 120° C. and stirred for 20 h. Further (3S)-oxolan-3-amine hydrochloride (83 mg, 0.67 mmol) and DIEA (233 μl, 1.34 mmol) were added. The temperature was increased to 130° C. and stirring was continued. After 24 h the solvent was removed in vacuo and the residue was purified by prep-HPLC to obtain the title compound. $^1$H NMR (500 MHz, DMSO-d$_6$) δ 7.55 (d, J=8.3 Hz, 1H), 7.51 (d, J=1.9 Hz, 1H), 7.25 (dd, J=8.3, 2.0 Hz, 1H), 7.12 (d, J=6.3 Hz, 1H), 4.98 (s, 2H), 4.47-4.31 (m, 1H), 3.94-3.84 (m, 2H), 3.72 (td, J=8.1, 6.0 Hz, 1H), 3.61 (dd, J=9.0, 4.1 Hz, 1H), 3.58 (s, 3H), 3.35 (s, 3H), 2.38-2.07 (m, 1H), 1.99-1.78 (m, 1H).

Procedure 8A and 8B

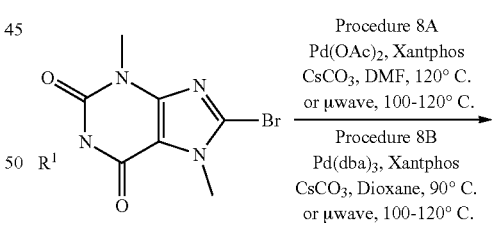

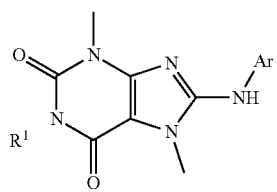

Illustrative Examples

Procedure 8A

Example 109

1-(3,4-dichlorobenzyl)-3,7-dimethyl-8-(2-oxo-2,3,4,5-tetrahydro-1H-benzo[b]azepin-8-ylamino)-1H-purine-2,6(3H,7H)-dione

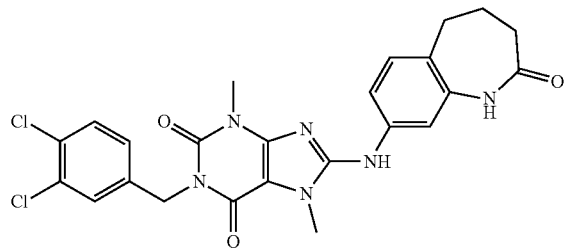 [SMILES: Cn1c(Nc2ccc3c(c2)NC(=O)CCC3)nc2c1c(=O)n(Cc1ccc(Cl)c(Cl)c1)c(=O)n2C]

A solution of 8-bromo-1-(3,4-dichlorobenzyl)-3,7-dimethyl-1H-purine-2,6(3H,7H)-dione (165 mg, 0.40 mmol), 8-amino-4,5-dihydro-1H-benzo[b]azepin-2(3H)-one (106 mg, 0.60 mmol), Pd(OAc)$_2$ (18 mg, 0.08 mmol), Xantphos (92 mg, 0.16 mmol) and Cs$_2$CO$_3$ (391 mg, 1.2 mmol) in DMF (2 mL) was stirred at 120° C. for 1 h. The mixture was purified by Prep-HPLC using Method D (30-70% ACN). $^1$H NMR (400 MHz, DMSO-d$_6$) δ 9.66 (s, 1H), 9.22 (s, 1H), 7.63-7.52 (m, 2H), 7.44 (d, J=2.0 Hz, 1H), 7.37 (dd, J=8.2, 2.1 Hz, 1H), 7.29 (dd, J=8.4, 1.9 Hz, 1H), 7.17 (d, J=8.3 Hz, 1H), 5.02 (s, 2H), 3.77 (s, 3H), 3.44 (s, 3H), 2.63 (t, J=6.9 Hz, 2H), 2.24-2.13 (m, 2H), 2.12-1.99 (m, 2H); ESI: m/z 513.0 (M+H)$^+$.

Procedure 8B

Example 365

3,7-dimethyl-1-[(7-methyl-1H-indol-2-yl)methyl]-8-(4-pyridylamino)purine-2,6-dione

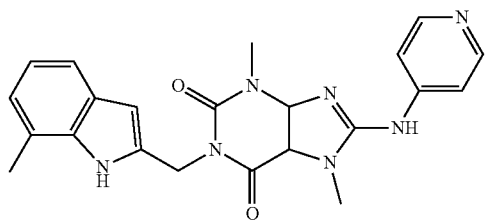 [SMILES: Cc1cccc2cc(CN3C(=O)C4C(N=C(Nc5ccncc5)N4C)N(C)C3=O)[nH]c12]

To a solution of tert-butyl 2-[(8-bromo-3,7-dimethyl-2,6-dioxo-purin-1-yl)methyl]-7-methyl-indole-1-carboxylate (170.00 mg, 338.40 umol) and pyridin-4-amine (47.77 mg, 507.60 umol, 85.30 uL) in dioxane (1.00 mL) was added Cs$_2$CO$_3$ (220.52 mg, 676.80 umol), Pd$_2$(dba)$_3$ (6.20 mg, 6.77 umol) and Xantphos (3.92 mg, 6.77 umol). The mixture was stirred at 90° C. under N$_2$ for 16 hr. The mixture was diluted with DCM (10 mL) and MeOH (4 mL) and filtered. The filtrate was concentrated. The residue was purified by prep-TLC (DCM/MeOH=10/1) to give crude product. The product was purified by prep-HPLC using Method C (24-54% ACN). $^1$H NMR (400 MHz, DMSO-d$_6$) δ 11.35 (br. s., 1H), 10.87 (br. s., 1H), 8.59 (d, J=7.1 Hz, 2H), 8.12 (d, J=6.2 Hz, 2H), 7.20 (d, J=6.6 Hz, 1H), 6.90-6.75 (m, 2H), 6.10 (s, 1H), 5.24 (s, 2H), 3.94 (s, 3H), 3.50 (s, 3H); ESI: m/z 416.2 (M+H)$^+$.

Example 1

1-(3,4-dichlorobenzyl)-8-((2-hydroxyethyl)amino)-3,7-dimethyl-1H-purine-2,6(3H,7H)-dione

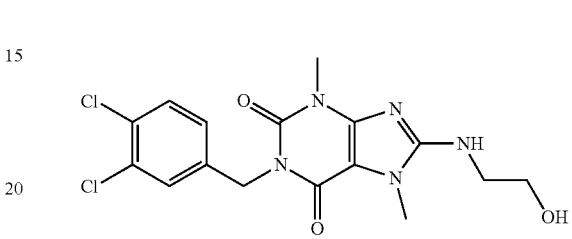

The title compound was synthesized in a similar fashion as described in Procedure 7A using 8-bromo-1-(3,4-dichlorobenzyl)-3,7-dimethyl-1H-purine-2,6(3H,7H)-dione and 2-aminoethanol. The mixture was purified by prep-HPLC using Method C (25-50% ACN) to afford the product. $^1$H NMR (400 MHz, CD$_3$OD) δ 7.51-7.49 (m, 1H), 7.42-7.39 (m, 1H), 7.30-7.26 (m, 1H), 5.06 (s, 2H), 3.72-3.69 (m, 2H), 3.61 (s, 3H), 3.54 (m, 2H), 3.45 (s, 3H); ESI: m/z 398.1 (M+H)$^+$.

Example 8

1-[(3,4-dichlorophenyl)methyl]-8-{[(2S)-2-hydroxypropyl]amino}-3,7-dimethyl-2,3,6,7-tetrahydro-1H-purine-2,6-dione

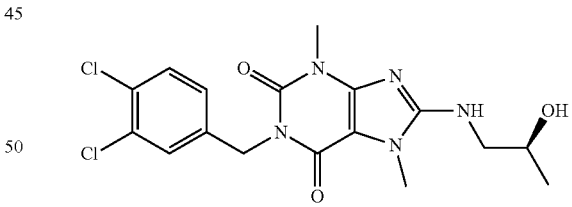

The title compound was synthesized in a similar fashion as described in Procedure 7B using 8-bromo-1-(3,4-dichlorobenzyl)-3,7-dimethyl-1H-purine-2,6(3H,7H)-dione, (S)-1-aminopropan-2-ol, and DMF as solvent (3 h, 130° C.). The product was purified by flash column chromatography (0-8% methanol/DCM). $^1$H NMR (500 MHz, DMSO-d$_6$) δ 7.55 (d, J=8.3 Hz, 1H), 7.52 (d, J=1.9 Hz, 1H), 7.25 (dd, J=8.3, 2.0 Hz, 1H), 7.03 (t, J=5.8 Hz, 1H), 4.98 (s, 2H), 4.75 (d, J=4.5 Hz, 1H), 3.89-3.80 (m, 1H), 3.57 (s, 3H), 3.35 (s, 3H), 3.28-3.23 (m, 2H), 1.08 (d, J=6.2 Hz, 3H); ESI: m/z 412.1 (M+H)$^+$.

Example 9

1-[(3,4-dichlorophenyl)methyl]-8-{[(2R)-2-hydroxypropyl]amino}-3,7-dimethyl-2,3,6,7-tetrahydro-1H-purine-2,6-dione

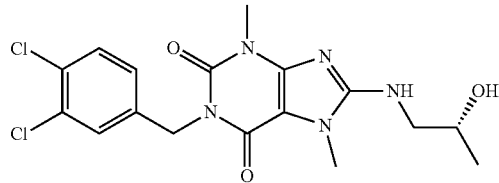

The title compound was synthesized in a similar fashion as described in Procedure 7B using 8-bromo-1-(3,4-dichlorobenzyl)-3,7-dimethyl-1H-purine-2,6(3H,7H)-dione and (R)-1-aminopropan-2-ol. The product was purified by flash chromatography (0-8% methanol/DCM). $^1$H NMR (500 MHz, DMSO-d$_6$) δ 7.55 (d, J=8.3 Hz, 1H), 7.52 (d, J=2.0 Hz, 1H), 7.25 (dd, J=8.3, 2.0 Hz, 1H), 7.04 (t, J=5.8 Hz, 1H), 4.98 (s, 2H), 4.75 (d, J=4.4 Hz, 1H), 3.88-3.80 (m, 1H), 3.57 (s, 3H), 3.35 (s, 3H), 3.28-3.23 (m, 2H), 1.08 (d, J=6.2 Hz, 3H); ESI: m/z 412.2 (M+H)$^+$.

Example 13

1-[(3,4-dichlorophenyl)methyl]-8-{[(2R)-2,3-dihydroxypropyl]amino}-3,7-dimethyl-2,3,6,7-tetrahydro-1H-purine-2,6-dione

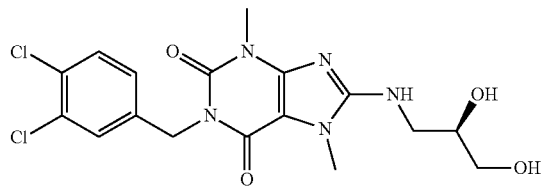 [SMILES: Cn1c(NC[C@@H](O)CO)nc2c1c(=O)n(Cc1ccc(Cl)c(Cl)c1)c(=O)n2C]

The title compound was synthesized in a similar fashion as described in procedure 7B using 8-bromo-1-(3,4-dichlorobenzyl)-3,7-dimethyl-1H-purine-2,6(3H,7H)-dione, (R)-3-aminopropane-1,2-diol, and isopropanol as solvent (48 h, 100° C.). The product was purified by flash column chromatography (0-10% methanol/DCM). $^1$H NMR (500 MHz, DMSO-d$_6$) δ 7.55 (d, J=8.3 Hz, 1H), 7.52 (d, J=2.0 Hz, 1H), 7.26 (dd, J=8.3, 2.0 Hz, 1H), 6.99 (t, J=5.7 Hz, 1H), 4.99 (s, 2H), 4.83 (d, J=4.9 Hz, 1H), 4.61 (t, J=5.8 Hz, 1H), 3.73-3.65 (m, 1H), 3.57 (s, 3H), 3.45 (dt, J=13.3, 5.6 Hz, 1H), 3.37 (t, J=5.6 Hz, 2H), 3.35 (s, 3H), 3.29-3.22 (m, 1H); ESI: m/z 428.1 (M+H)$^+$.

Example 14

1-[(3,4-dichlorophenyl)methyl]-8-{[(2S)-2,3-dihydroxypropyl]amino}-3,7-dimethyl-2,3,6,7-tetrahydro-1H-purine-2,6-dione

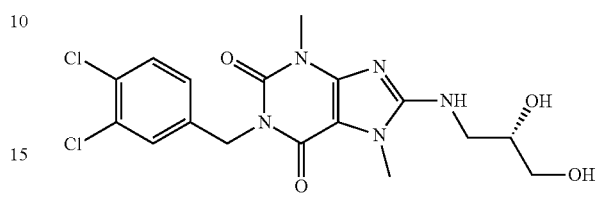

The title compound was synthesized in a similar fashion as described in Procedure 7B using 8-bromo-1-(3,4-dichlorobenzyl)-3,7-dimethyl-1H-purine-2,6(3H,7H)-dione and (S)-3-aminopropane-1,2-diol. The product was purified by flash column chromatography (0-10% methanol/DCM). $^1$H NMR (500 MHz, DMSO-d$_6$) δ 7.55 (d, J=8.3 Hz, 1H), 7.52 (d, J=2.0 Hz, 1H), 7.26 (dd, J=8.3, 2.0 Hz, 1H), 6.99 (t, J=5.7 Hz, 1H), 4.99 (s, 2H), 4.82 (d, J=4.9 Hz, 1H), 4.60 (t, J=5.8 Hz, 1H), 3.72-3.66 (m, 1H), 3.57 (s, 3H), 3.45 (dt, J=13.4, 5.5 Hz, 1H), 3.37 (t, J=5.6 Hz, 2H), 3.35 (s, 3H), 3.28-3.22 (m, 1H); ESI: m/z 428.1 (M+H)$^+$.

Example 15

1-[(4-chlorophenyl)methyl]-8-{[(2R)-2,3-dihydroxypropyl]amino}-3,7-dimethyl-2,3,6,7-tetrahydro-1H-purine-2,6-dione

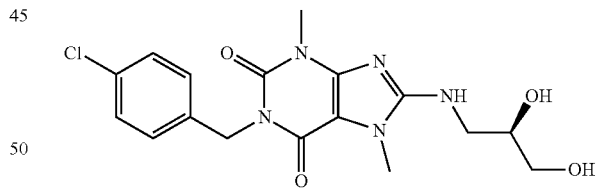

The title compound was synthesized in a similar fashion as described in Procedure 7B using 8-bromo-3,7-dimethyl-1-(4-chlorobenzyl)-3,7-dihydro-1H-purine-2,6-dione, (R)-3-aminopropane-1,2-diol, and NMP as solvent (5 h, 130° C.). The product was purified by prep-HPLC. $^1$H NMR (500 MHz, DMSO-d$_6$) δ 7.37-7.32 (m, 2H), 7.29 (d, J=8.5 Hz, 2H), 6.98 (t, J=5.7 Hz, 1H), 4.99 (s, 2H), 4.83 (d, J=4.9 Hz, 1H), 4.61 (t, J=5.8 Hz, 1H), 3.72-3.65 (m, 1H), 3.57 (s, 3H), 3.45 (dt, J=13.3, 5.5 Hz, 1H), 3.37 (t, J=5.6 Hz, 2H), 3.34 (s, 3H), 3.28-3.22 (m, 1H); ESI: m/z 394.1 (M+H)$^+$.

Example 16

1-[(4-chlorophenyl)methyl]-8-{[(2S)-2,3-dihydroxypropyl]amino}-3,7-dimethyl-2,3,6,7-tetrahydro-1H-purine-2,6-dione

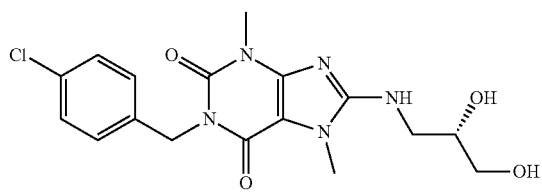 [SMILES: Cn1c(NC[C@H](O)CO)nc2c1c(=O)n(Cc1ccc(Cl)cc1)c(=O)n2C]

The title compound was synthesized in a similar fashion as described in Procedure 7A using 8-bromo-3,7-dimethyl-1-(4-chlorobenzyl)-3,7-dihydro-1H-purine-2,6-dione, (S)-3-aminopropane-1,2-diol. The product was purified by prep-HPLC. $^1$H NMR (500 MHz, DMSO-$d_6$) δ 7.37-7.32 (m, 2H), 7.29 (d, J=8.5 Hz, 2H), 6.98 (t, J=5.7 Hz, 1H), 4.99 (s, 2H), 4.83 (d, J=4.9 Hz, 1H), 4.61 (t, J=5.8 Hz, 1H), 3.72-3.66 (m, 1H), 3.57 (s, 3H), 3.45 (dt, J=13.3, 5.6 Hz, 1H), 3.37 (t, J=5.6 Hz, 2H), 3.34 (s, 3H), 3.29-3.22 (m, 1H); ESI: m/z 394.1 (M+H)$^+$.

Example 17

1-[(4-chlorophenyl)methyl]-8-{[(2R)-2-hydroxypropyl]amino}-3,7-dimethyl-2,3,6,7-tetrahydro-1H-purine-2,6-dione

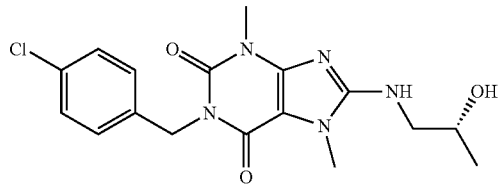 [SMILES: C[C@@H](O)CNc1nc2c(c(=O)n(Cc3ccc(Cl)cc3)c(=O)n2C)n1C]

The title compound was synthesized in a similar fashion as described in Procedure 7B using 8-bromo-3,7-dimethyl-1-(4-chlorobenzyl)-3,7-dihydro-1H-purine-2,6-dione, (R)-1-aminopropan-2-ol and isopropanol as solvent. $^1$H NMR (500 MHz, DMSO-$d_6$) δ 7.34 (d, J=8.5 Hz, 2H), 7.29 (d, J=8.5 Hz, 2H), 7.02 (t, J=5.8 Hz, 1H), 4.98 (s, 2H), 4.76 (s, 1H), 3.84 (h, J=6.1 Hz, 1H), 3.57 (s, 3H), 3.34 (s, 3H), 3.29-3.22 (m, 2H), 1.07 (d, J=6.2 Hz, 3H); ESI: m/z 378.2 (M+H)$^+$.

Example 18

1-[(4-chlorophenyl)methyl]-8-{[(2S)-2-hydroxypropyl]amino}-3,7-dimethyl-2,3,6,7-tetrahydro-1H-purine-2,6-dione

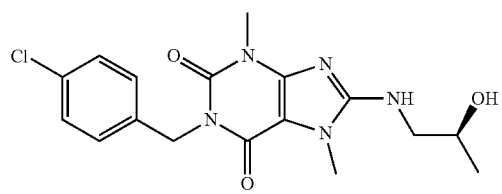 [SMILES: C[C@H](O)CNc1nc2c(c(=O)n(Cc3ccc(Cl)cc3)c(=O)n2C)n1C]

The title compound was synthesized in a similar fashion as described in Procedure 7B using 8-bromo-3,7-dimethyl-1-(4-chlorobenzyl)-3,7-dihydro-1H-purine-2,6-dione, (S)-1-aminopropan-2-ol and isopropanol as solvent. $^1$H NMR (500 MHz, DMSO-$d_6$) δ 7.38-7.32 (m, 2H), 7.29 (d, J=8.5 Hz, 2H), 7.02 (t, J=5.8 Hz, 1H), 4.98 (s, 2H), 4.76 (d, J=4.7 Hz, 1H), 3.84 (hept, J=5.8 Hz, 1H), 3.57 (s, 3H), 3.33 (s, 3H), 3.28-3.23 (m, 2H), 1.07 (d, J=6.2 Hz, 3H); ESI: m/z 378.2 (M+H)$^+$.

Example 21

1-[(3,4-dichlorophenyl)methyl]-3,7-dimethyl-8-(methylamino)-2,3,6,7-tetrahydro-1H-purine-2,6-dione

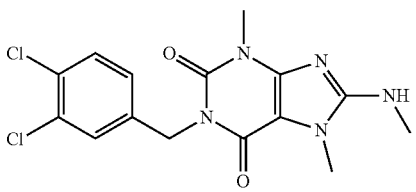 [SMILES: CNc1nc2c(c(=O)n(Cc3ccc(Cl)c(Cl)c3)c(=O)n2C)n1C]

The title compound was synthesized in a similar fashion as described in Procedure 7B using 8-bromo-1-(3,4-dichlorobenzyl)-3,7-dimethyl-1H-purine-2,6(3H,7H)-dione and methylamine hydrochloride. The product was purified by prep-HPLC (acetonitrile/water, 0.1% formic acid). $^1$H NMR (500 MHz, DMSO-$d_6$) δ 7.55 (d, J=8.3 Hz, 1H), 7.52 (d, J=2.0 Hz, 1H), 7.26 (dd, J=8.3, 2.0 Hz, 1H), 7.02 (q, J=4.5 Hz, 1H), 4.98 (s, 2H), 3.54 (s, 3H), 3.36 (s, 3H), 2.90 (d, J=4.6 Hz, 3H); ESI: m/z 368.1 (M+H)$^+$.

Example 22

N-[2-({1-[(3,4-dichlorophenyl)methyl]-3,7-dimethyl-2,6-dioxo-2,3,6,7-tetrahydro-1H-purin-8-yl}amino)ethyl]acetamide

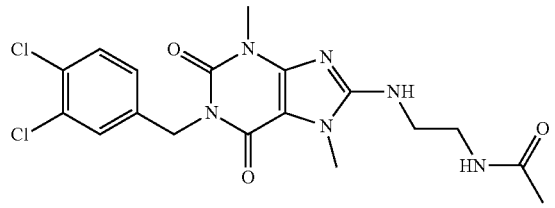 [SMILES: CC(=O)NCCNc1nc2c(c(=O)n(Cc3ccc(Cl)c(Cl)c3)c(=O)n2C)n1C]

The title compound was synthesized in a similar fashion as described in Procedure 7B using 8-bromo-1-(3,4-dichlorobenzyl)-3,7-dimethyl-1H-purine-2,6(3H,7H)-dione, N-(2-aminoethyl)acetamide, and isopropanol as solvent (46 h, 100° C.). The mixture was poured into water. The solid was collected by filtration and washed with water and DCM and dried under high vacuum. $^1$H NMR (500 MHz, DMSO-$d_6$) δ 7.95 (t, J=5.5 Hz, 1H), 7.55 (d, J=8.3 Hz, 1H), 7.51 (d, J=1.9 Hz, 1H), 7.25 (dd, J=8.3, 1.9 Hz, 1H), 7.15 (t, J=5.6 Hz, 1H), 4.99 (s, 2H), 3.55 (s, 3H), 3.40-3.32 (m, 5H), 3.25 (q, J=6.2 Hz, 2H), 1.80 (s, 3H); ESI: m/z 439.1 (M+H)$^+$.

Example 23: 1-[(4-chloro-3-fluorophenyl)methyl]-8-[(3-hydroxypropyl)amino]-3,7-dimethyl-2,3,6,7-tetrahydro-1H-purine-2,6-dione

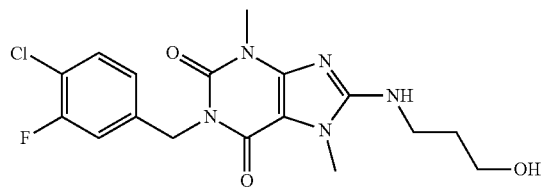 [SMILES: Cn1c(NCCCO)nc2c1c(=O)n(Cc1ccc(Cl)c(F)c1)c(=O)n2C]

The title compound was synthesized in a similar fashion as described in Procedure 7B using 8-bromo-3,7-dimethyl-1-(4-chloro-3-fluorobenzyl)-3,7-dihydro-1H-purine-2,6-dione, 1-amino-3-propanol, and isopropanol used as solvent (20 h, 100° C.), $^1$H NMR (500 MHz, DMSO-$d_6$) δ 7.50 (t, J=8.1 Hz, 1H), 7.28 (dd, J=10.4, 1.9 Hz, 1H), 7.12 (dd, J=8.3, 1.4 Hz, 1H), 7.01 (t, J=5.5 Hz, 1H), 4.99 (s, 2H), 4.49 (t, J=5.2 Hz, 1H), 3.55 (s, 3H), 3.48 (q, J=6.1 Hz, 2H), 3.39 (q, J=6.3 Hz, 2H), 3.35 (s, 3H), 1.73 (p, J=6.6 Hz, 2H); ESI: m/z 396.1 (M+H)$^+$.

Example 24

1-[(4-chloro-3-fluorophenyl)methyl]-8-{[(2R)-2-hydroxypropyl]amino}-3,7-dimethyl-2,3,6,7-tetrahydro-1H-purine-2,6-dione

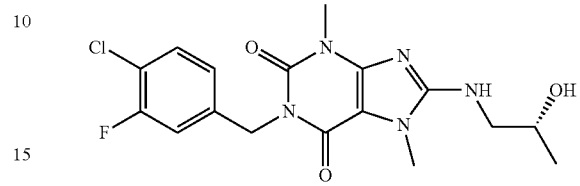

The title compound was synthesized in a similar fashion as described in Procedure 7B using 8-bromo-3,7-dimethyl-1-(4-chloro-3-fluorobenzyl)-3,7-dihydro-1H-purine-2,6-dione, (R)-1-aminopropan-2-ol, and isopropanol used as solvent (20 h, 100° C.). $^1$H NMR (500 MHz, DMSO-$d_6$) δ 7.50 (t, J=8.1 Hz, 1H), 7.28 (dd, J=10.4, 1.9 Hz, 1H), 7.12 (dd, J=8.3, 1.5 Hz, 1H), 7.03 (t, J=5.8 Hz, 1H), 4.99 (s, 2H), 4.75 (d, J=4.6 Hz, 1H), 3.84 (hept, J=5.9 Hz, 1H), 3.57 (s, 3H), 3.35 (s, 3H), 3.25 (td, J=6.1, 2.6 Hz, 2H), 1.08 (d, J=6.2 Hz, 3H); ESI: m/z 396.1 (M+H)$^+$.

Example 25

1-[(4-chloro-3-fluorophenyl)methyl]-8-{[(2S)-2-hydroxypropyl]amino}-3,7-dimethyl-2,3,6,7-tetrahydro-1H-purine-2,6-dione

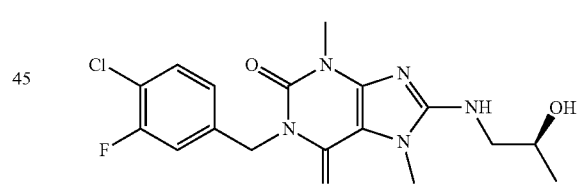

The title compound was synthesized in a similar fashion as described in Procedure 7B using 8-bromo-3,7-dimethyl-1-(4-chloro-3-fluorobenzyl)-3,7-dihydro-1H-purine-2,6-dione, (S)-1-aminopropan-2-ol, and isopropanol used as solvent (20 h, 100° C.). $^1$H NMR (500 MHz, DMSO-$d_6$) δ 7.50 (t, J=8.1 Hz, 1H), 7.28 (dd, J=10.4, 1.9 Hz, 1H), 7.12 (dd, J=8.3, 1.5 Hz, 1H), 7.03 (t, J=5.8 Hz, 1H), 4.99 (s, 2H), 4.75 (d, J=4.7 Hz, 1H), 3.84 (hept, J=5.9 Hz, 1H), 3.57 (s, 3H), 3.35 (s, 3H), 3.25 (td, J=6.1, 2.6 Hz, 2H), 1.08 (d, J=6.2 Hz, 3H); ESI: m/z 396.1 (M+H)$^+$.

Example 26

1-[(4-chlorophenyl)methyl]-8-{[(2R)-4-hydroxybutan-2-yl]amino}-3,7-dimethyl-2,3,6,7-tetrahydro-1H-purine-2,6-dione

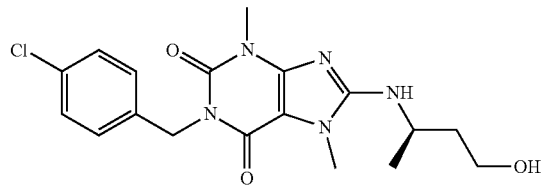 [SMILES: C[C@H](CCO)Nc1nc2c(c(=O)n(Cc3ccc(Cl)cc3)c(=O)n2C)n1C]

The title compound was synthesized in a similar fashion as described in Procedure 7B using 8-bromo-3,7-dimethyl-1-(4-chlorobenzyl)-3,7-dihydro-1H-purine-2,6-dione and (R)-3-aminobutan-1-ol. $^1$H NMR (500 MHz, DMSO-$d_6$) δ 7.37-7.31 (m, 2H), 7.29 (d, J=8.5 Hz, 2H), 6.76 (d, J=8.2 Hz, 1H), 4.98 (s, 2H), 4.48-4.42 (m, 1H), 4.01 (hept, J=7.8 Hz, 1H), 3.55 (s, 3H), 3.50-3.44 (m, 2H), 3.34 (s, 3H), 1.75 (ddt, J=13.8, 7.8, 6.1 Hz, 1H), 1.64 (dq, J=13.3, 6.7 Hz, 1H), 1.19 (d, J=6.5 Hz, 3H); ESI: m/z 392.1 (M+H)$^+$.

Example 27

1-[(3,4-dichlorophenyl)methyl]-8-{[(2R)-4-hydroxybutan-2-yl]amino}-3,7-dimethyl-2,3,6,7-tetrahydro-1H-purine-2,6-dione

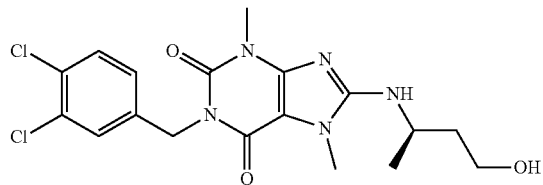 [SMILES: C[C@H](CCO)Nc1nc2c(c(=O)n(Cc3ccc(Cl)c(Cl)c3)c(=O)n2C)n1C]

The title compound was synthesized in a similar fashion as described in Procedure 7B using 8-bromo-1-(3,4-dichlorobenzyl)-3,7-dimethyl-1H-purine-2,6(3H,7H)-dione and (R)-3-aminobutan-1-ol. $^1$H NMR (500 MHz, DMSO-$d_6$) δ 7.55 (d, J=8.3 Hz, 1H), 7.52 (d, J=2.0 Hz, 1H), 7.25 (dd, J=8.3, 2.0 Hz, 1H), 6.78 (d, J=8.1 Hz, 1H), 4.98 (s, 2H), 4.44 (t, J=4.9 Hz, 1H), 4.02 (hept, J=7.7 Hz, 1H), 3.56 (s, 3H), 3.51-3.44 (m, 2H), 3.35 (s, 3H), 1.75 (ddt, J=13.8, 7.8, 6.1 Hz, 1H), 1.64 (dq, J=13.2, 6.7 Hz, 1H), 1.19 (d, J=6.5 Hz, 3H); ESI: m/z 426.1 (M+H)$^+$.

Example 28

1-[(3,4-dichlorophenyl)methyl]-8-[(4-hydroxybutyl)amino]-3,7-dimethyl-2,3,6,7-tetrahydro-1H-purine-2,6-dione

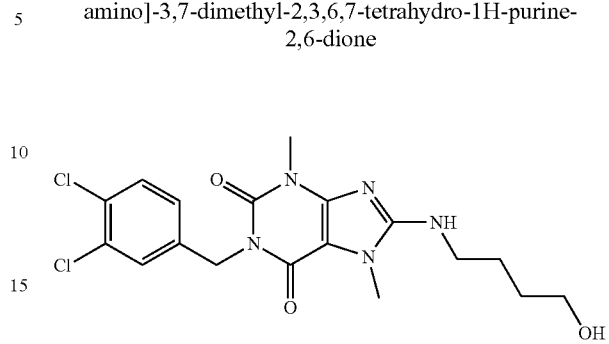

The title compound was synthesized in a similar fashion as described in Procedure 7B using 8-bromo-1-(3,4-dichlorobenzyl)-3,7-dimethyl-1H-purine-2,6(3H,7H)-dione and 1-amino-4-butanol. $^1$H NMR (500 MHz, DMSO-$d_6$) δ 7.55 (d, J=8.3 Hz, 1H), 7.52 (d, J=1.9 Hz, 1H), 7.26 (dd, J=8.3, 2.0 Hz, 1H), 7.04 (t, J=5.6 Hz, 1H), 4.98 (s, 2H), 4.41 (t, J=4.7 Hz, 1H), 3.55 (s, 3H), 3.42 (q, J=5.4, 4.7 Hz, 2H), 3.35 (s, 3H), 3.34-3.33 (tt, J=7.7, 6.9 Hz, 2H), 1.65-1.55 (tt, J=7.5, 6.5 Hz 2H), 1.51-1.44 (m, 2H); ESI: m/z 426.1 (M+H)$^+$.

Example 29

1-[(3,4-difluorophenyl)methyl]-8-[(3-hydroxypropyl)amino]-3,7-dimethyl-2,3,6,7-tetrahydro-1H-purine-2,6-dione

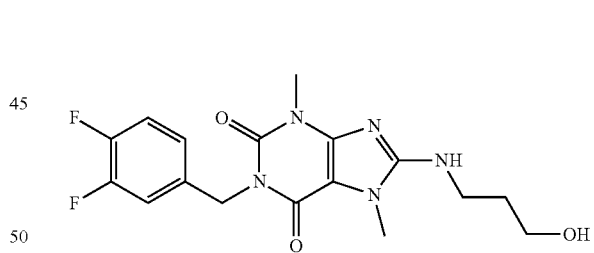

The title compound was synthesized in a similar fashion as described in Procedure 7B using 8-bromo-1-(3,4-difluorobenzyl)-3,7-dimethyl-1H-purine-2,6(3H,7H)-dione and 1-amino-4-butanol. $^1$H NMR (500 MHz, DMSO-$d_6$) δ 7.34 (dd, J=10.7, 8.5 Hz, 1H), 7.31 (ddd, J=11.3, 7.9, 2.0 Hz, 1H), 7.14-7.09 (m, 1H), 7.01 (t, J=5.5 Hz, 1H), 4.98 (s, 2H), 4.49 (t, J=5.2 Hz, 1H), 3.55 (s, 3H), 3.48 (q, J=6.1 Hz, 2H), 3.38 (q, J=6.4 Hz, 2H), 3.35 (s, 3H), 1.73 (p, J=6.4 Hz, 2H); ESI: m/z 380.2 (M+H)$^+$

Example 30

1-[(3,4-difluorophenyl)methyl]-8-{[(2S)-2-hydroxypropyl]amino}-3,7-dimethyl-2,3,6,7-tetrahydro-1H-purine-2,6-dione

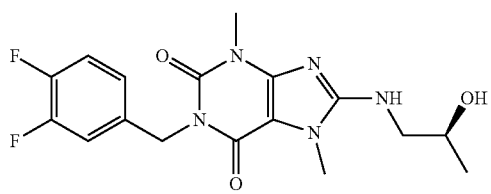 [SMILES: C[C@H](O)CNc1nc2c(c(=O)n(Cc3ccc(F)c(F)c3)c(=O)n2C)n1C]

The title compound was synthesized in a similar fashion as described in Procedure 7B using 8-bromo-1-(3,4-difluorobenzyl)-3,7-dimethyl-1H-purine-2,6(3H,7H)-dione, (S)-1-aminopropan-2-ol, and isopropanol as solvent. $^1$H NMR (500 MHz, DMSO-d$_6$) δ 7.35 (dd, J=10.9, 8.5 Hz, 1H), 7.31 (ddd, J=11.3, 7.9, 2.0, 1H), 7.17-7.07 (m, 1H), 7.02 (t, J=5.8 Hz, 1H), 4.98 (s, 2H), 4.75 (d, J=4.7 Hz, 1H), 3.84 (hept, J=5.9 Hz, 1H), 3.57 (s, 3H), 3.35 (s, 3H), 3.25 (td, J=6.1, 2.7 Hz, 2H), 1.08 (d, J=6.2 Hz, 3H); ESI: m/z 380.1 (M+H)$^+$.

Example 31

1-[(4-chlorophenyl)methyl]-8-{[(2S)-4-hydroxybutan-2-yl]amino}-3,7-dimethyl-2,3,6,7-tetrahydro-1H-purine-2,6-dione

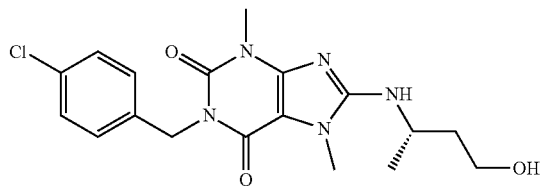 [SMILES: C[C@@H](CCO)Nc1nc2c(c(=O)n(Cc3ccc(Cl)cc3)c(=O)n2C)n1C]

The title compound was synthesized in a similar fashion as described in Procedure 7B using 8-bromo-3,7-dimethyl-1-(4-chlorobenzyl)-3,7-dihydro-1H-purine-2,6-dione and (S)-3-aminobutan-1-ol. $^1$H NMR (500 MHz, DMSO-d$_6$) δ 7.37-7.33 (m, 2H), 7.29 (d, J=8.5 Hz, 2H), 6.77 (d, J=8.2 Hz, 1H), 4.99 (s, 2H), 4.48-4.43 (s, 1H), 4.02 (hept, J=7.7 Hz, 1H), 3.56 (s, 3H), 3.51-3.45 (s, 2H), 3.35 (s, 3H), 1.76 (ddt, J=13.8, 7.8, 6.1 Hz, 1H), 1.65 (dq, J=13.3, 6.7 Hz, 1H), 1.20 (d, J=6.5 Hz, 3H); ESI: m/z 392.1 (M+H)$^+$.

Example 32

1-[(3,4-dichlorophenyl)methyl]-8-{[(2S)-4-hydroxybutan-2-yl]amino}-3,7-dimethyl-2,3,6,7-tetrahydro-1H-purine-2,6-dione

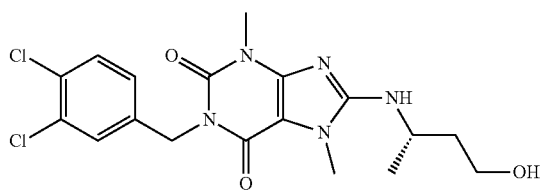 [SMILES: C[C@@H](CCO)Nc1nc2c(c(=O)n(Cc3ccc(Cl)c(Cl)c3)c(=O)n2C)n1C]

The title compound was synthesized in a similar fashion as described in Procedure 7B using 8-bromo-1-(3,4-dichlorobenzyl)-3,7-dimethyl-1H-purine-2,6(3H,7H)-dione and (S)-3-aminobutan-1-ol. $^1$H NMR (500 MHz, DMSO-d$_6$) δ 7.55 (d, J=8.3 Hz, 1H), 7.52 (d, J=2.0 Hz, 1H), 7.25 (dd, J=8.3, 2.0 Hz, 1H), 6.78 (d, J=8.2 Hz, 1H), 4.98 (s, 2H), 4.49-4.41 (s, 1H), 4.02 (dq, J=14.2, 7.7 Hz, 1H), 3.56 (s, 3H), 3.49-3.45 (s, 2H), 3.35 (s, 3H), 1.75 (ddt, J=13.8, 7.8, 6.1 Hz, 1H), 1.64 (dq, J=13.2, 6.6 Hz, 1H), 1.19 (d, J=6.5 Hz, 3H); ESI: m/z 426.1 (M+H)$^+$.

Example 33

1-[(3,4-dichlorophenyl)methyl]-8-[(3-hydroxycyclohexyl)amino]-3,7-dimethyl-2,3,6,7-tetrahydro-1H-purine-2,6-dione

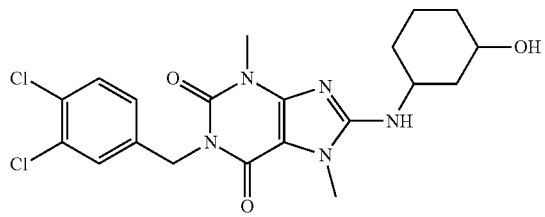 [SMILES: Cn1c(NC2CCCC(O)C2)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and 3-aminocyclohexan-1-ol. $^1$H NMR (500 MHz, DMSO-d$_6$) δ 7.55 (d, J=8.3 Hz, 1H), 7.51 (d, J=1.7 Hz, 1H), 7.26 (dd, J=8.3, 1.8 Hz, 1H), 6.68 (d, J=7.9 Hz, 1H), 4.98 (s, 2H), 4.45 (d, J=3.2 Hz, 1H), 4.13-4.03 (m, 1H), 4.01-3.97 (s, 1H), 3.56 (s, 3H), 3.35 (s, 3H), 1.90-1.78 (m, 2H), 1.74-1.62 (m, 1H), 1.62-1.45 (m, 3H), 1.43-1.25 (m, 2H); ESI: m/z 452.1 (M+H)$^+$.

Example 34

8-{[(2S)-2-hydroxypropyl]amino}-1-[(4-methoxyphenyl)methyl]-3,7-dimethyl-2,3,6,7-tetrahydro-1H-purine-2,6-dione

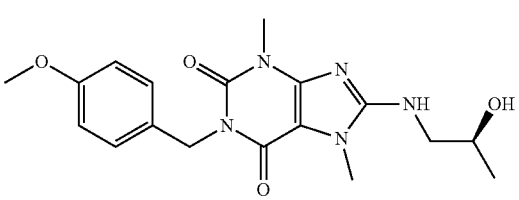 [SMILES: COc1ccc(Cn2c(=O)c3c(nc(NC[C@H](C)O)n3C)n(C)c2=O)cc1]

The title compound was synthesized in a similar fashion as described in Procedure 7B using 8-bromo-1-(4-methoxybenzyl)-3,7-dimethyl-3,7-dihydro-1H-purine-2,6-dione, (S)-1-aminopropan-2-ol, and isopropanol as solvent. $^1$H NMR (500 MHz, Acetone-d$_6$) δ 7.37 (d, J=8.7 Hz, 2H), 6.82 (d, J=8.7 Hz, 2H), 6.22 (t, J=6.3 Hz, 1H), 5.02 (s, 2H), 4.14-4.12 (s, 1H), 4.01-3.95 (m, 1H), 3.75 (s, 3H), 3.68 (s, 3H), 3.52-3.46 (m, 1H), 3.39 (s, 3H), 3.35-3.29 (m, 1H), 1.15 (d, J=6.3 Hz, 3H); ESI: m/z 374.2 (M+H)$^+$.

Example 35

1-[(3,4-dichlorophenyl)methyl]-3,7-dimethyl-8-[(piperidin-4-yl)amino]-2,3,6,7-tetrahydro-1H-purine-2,6-dione

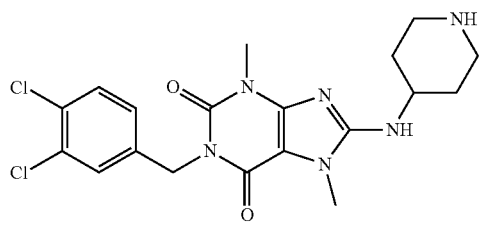 [SMILES: Cn1c(NC2CCNCC2)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and tert-butyl 4-aminopiperidine-1-carboxylate to provide after purification by flash column chromatography tert-butyl 4-({1-[(3,4-dichlorophenyl)methyl]-3,7-dimethyl-2,6-dioxo-2,3,6,7-tetrahydro-1H-purin-8-yl}amino)piperidine-1-carboxylate. This material was stirred in 20% trifluoroacetic acid in dichloromethane (2 h). The mixture was concentrated under reduced pressure and the residue was purified by prep-HPLC (acetonitrile/water, 0.2% ammonium hydroxide) to yield the title compound. $^1$H NMR (500 MHz, DMSO-$d_6$) δ 7.55 (d, J=8.3 Hz, 1H), 7.51 (d, J=1.8 Hz, 1H), 7.25 (dd, J=8.3, 1.9 Hz, 1H), 6.83 (d, J=7.7 Hz, 1H), 4.98 (s, 2H), 3.69 (dtt, J=11.5, 7.9, 4.0 Hz, 1H), 3.56 (s, 3H), 3.34 (s, 3H), 2.95 (d, J=12.4 Hz, 2H), 2.51-2.46 (m, 2H), 1.85 (d, J=9.7 Hz, 2H), 1.38 (qd, J=11.9, 4.0 Hz, 2H); ESI: m/z 437.1 (M+H)$^+$.

Example 36

8-{[(2S)-2-hydroxypropyl]amino}-3,7-dimethyl-1-{[4-(trifluoromethyl)phenyl]methyl}-2,3,6,7-tetrahydro-1H-purine-2,6-dione

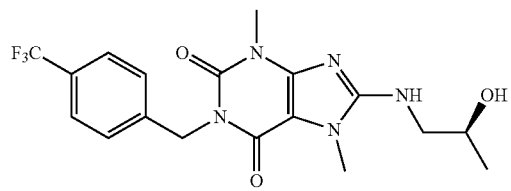 [SMILES: C[C@H](O)CNc1nc2c(c(=O)n(Cc3ccc(C(F)(F)F)cc3)c(=O)n2C)n1C]

The title compound was synthesized in a similar fashion as described in Procedure 7B using 8-bromo-3,7-dimethyl-1-(4-(trifluoromethyl)benzyl)-3,7-dihydro-1H-purine-2,6-dione, (S)-1-aminopropan-2-ol, and isopropanol as solvent. $^1$H NMR (500 MHz, DMSO-$d_6$) δ 7.66 (d, J=8.2 Hz, 2H), 7.47 (d, J=8.1 Hz, 2H), 7.07 (t, J=5.8 Hz, 1H), 5.09 (s, 2H), 4.79 (d, J=4.6 Hz, 1H), 3.85 (hept, J=6.0 Hz, 1H), 3.58 (s, 3H), 3.36 (s, 3H), 3.29-3.24 (m, 2H), 1.08 (d, J=6.2 Hz, 3H); ESI: m/z 412.2 (M+H)$^+$.

Example 37

3-({1-[(3,4-dichlorophenyl)methyl]-3,7-dimethyl-2,6-dioxo-2,3,6,7-tetrahydro-1H-purin-8-yl}amino)propanoic acid

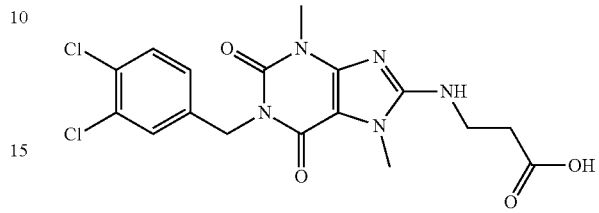

The title compound was synthesized in a similar fashion as described in Procedure 7B using 8-bromo-1-(3,4-dichlorobenzyl)-3,7-dimethyl-1H-purine-2,6(3H,7H)-dione and 3-aminopropanoic acid. $^1$H NMR (500 MHz, DMSO-$d_6$) δ 7.55 (d, J=8.3 Hz, 1H), 7.52 (d, J=1.8 Hz, 1H), 7.25 (dd, J=8.3, 1.9 Hz, 1H), 7.22-7.17 (s, 1H), 4.98 (s, 2H), 3.54 (s, 3H), 3.51 (d, J=7.0 Hz, 2H), 2.55 (t, J=7.0 Hz, 2H). One methyl signal obscured by solvent peak; ESI: m/z 426.1 (M+H)$^+$.

Example 38

(±)-1-[(3,4-dichlorophenyl)methyl]-3,7-dimethyl-8-{[(trans)-4-aminocyclohexyl]amino}-2,3,6,7-tetrahydro-1H-purine-2,6-dione

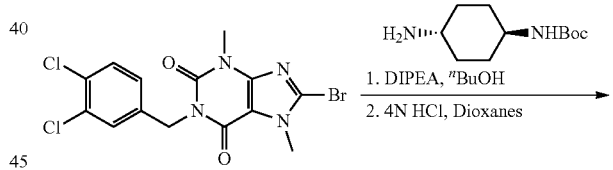

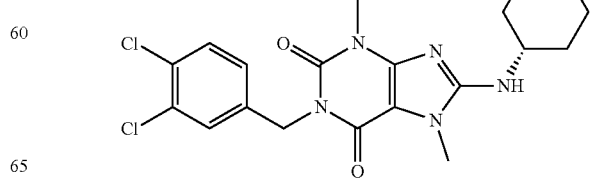

117

(±)-tert-Butyl (trans)-4-((1-(3,4-dichlorobenzyl)-3,7-dimethyl-2,6-dioxo-2,3,6,7-tetrahydro-1H-purin-8-yl)amino)cyclohexyl)carbamate

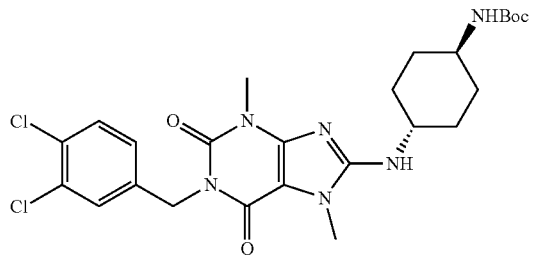 [SMILES: Cn1c(N[C@H]2CC[C@H](NC(=O)OC(C)(C)C)CC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and (±)-tert-butyl trans-4-((1-(3,4-dichlorobenzyl)-3,7-dimethyl-2,6-dioxo-2,3,6,7-tetrahydro-1H-purin-8-yl)amino)cyclohexyl)carbamate.

(±)-1-[(3,4-Dichlorophenyl)methyl]-3,7-dimethyl-8-{[(trans)-4-aminocyclohexyl]amino}-2,3,6,7-tetrahydro-1H-purine-2,6-dione

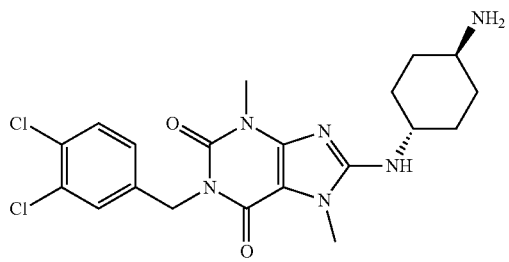 [SMILES: Cn1c(N[C@H]2CC[C@H](N)CC2)nc2c1c(=O)n(Cc1ccc(Cl)c(Cl)c1)c(=O)n2C]

tert-Butyl (±)-trans-4-((1-(3,4-dichlorobenzyl)-3,7-dimethyl-2,6-dioxo-2,3,6,7-tetrahydro-1H-purin-8-yl)amino)cyclohexyl)carbamate (56 mg, 1.0 mmol) was dissolved in dioxanes (2 mL). 4N HCl in dioxanes (5 mL) was added and the mixture was stirred for 24 h at room temperature. The mixture was concentrated under reduced pressure and the residue was dried under high vacuum to provide the title compound as its HCl salt. $^1$H NMR (500 MHz, DMSO-$d_6$) δ 8.09-7.97 (m, 3H), 7.55 (d, J=8.3 Hz, 1H), 7.51 (d, J=1.7 Hz, 1H), 7.25 (dd, J=8.3, 1.8 Hz, 1H), 6.94 (d, J=7.6 Hz, 1H), 4.98 (s, 2H), 3.66-3.59 (m, 1H), 3.56 (s, 3H), 3.35 (s, 3H), 3.03-2.95 (s, 1H), 2.13-1.86 (m, 4H), 1.53-1.28 (m, 4H); ESI: m/z 451.1 (M+H)$^+$.

118

Example 39

(±)-1-[(3,4-dichlorophenyl)methyl]-3,7-dimethyl-8-{[(cis)-4-aminocyclohexyl]amino}-2,3,6,7-tetrahydro-1H-purine-2,6-dione

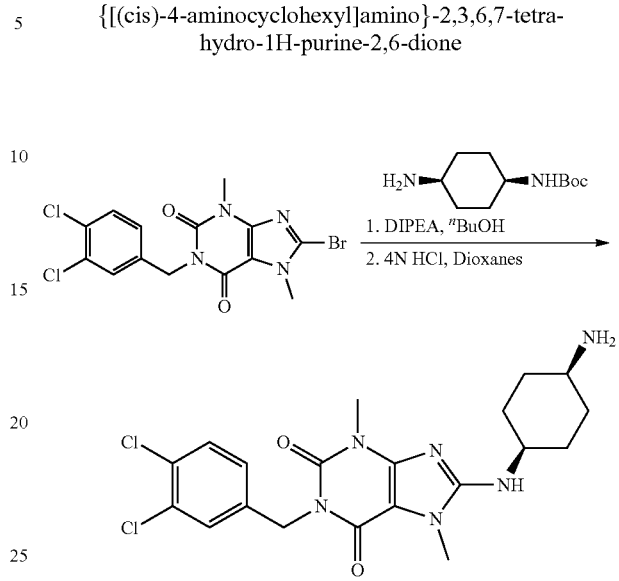

The title compound was synthesized in a similar fashion as described in Procedure 7B using 8-Bromo-1-(3,4-dichlorobenzyl)-3,7-dimethyl-1H-purine-2,6(3H,7H)-dione and tert-butyl cis-4-((1-(3,4-dichlorobenzyl)-3,7-dimethyl-2,6-dioxo-2,3,6,7-tetrahydro-1H-purin-8-yl)amino)cyclohexyl)carbamate. $^1$H NMR (500 MHz, DMSO-$d_6$) δ 7.97 (s, 3H), 7.56 (d, J=8.3 Hz, 1H), 7.52 (d, J=1.8 Hz, 1H), 7.26 (dd, J=8.3, 1.9 Hz, 1H), 6.65 (d, J=4.0 Hz, 1H), 4.99 (s, 2H), 3.87-3.81 (m, 1H), 3.75-3.64 (m, 1H), 3.64 (s, 3H), 3.35 (s, 3H), 2.03-1.90 (m, 2H), 1.73 (d, J=5.3 Hz, 4H), 1.71-1.61 (m, 2H); ESI: m/z 451.3 (M+H)$^+$.

Example 40

1-[(3,4-dichlorophenyl)methyl]-8-{[2-(dimethylamino)ethyl]amino}-3,7-dimethyl-2,3,6,7-tetrahydro-1H-purine-2,6-dione

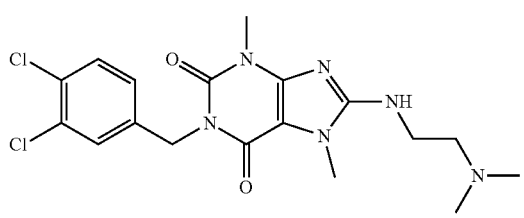 [SMILES: CN(C)CCNc1nc2c(c(=O)n(Cc3ccc(Cl)c(Cl)c3)c(=O)n2C)n1C]

The title compound was synthesized in a similar fashion as described in Procedure 7B using 8-Bromo-1-(3,4-dichlorobenzyl)-3,7-dimethyl-1H-purine-2,6(3H,7H)-dione and N,N-dimethylethane-1,2-diamine. $^1$H NMR (500 MHz, DMSO-$d_6$) δ 7.55 (d, J=8.3 Hz, 1H), 7.52 (d, J=2.0 Hz, 1H), 7.25 (dd, J=8.3, 2.0 Hz, 1H), 7.01 (t, J=5.7 Hz, 1H), 4.98 (s, 2H), 3.55 (s, 3H), 3.41 (q, J=6.6 Hz, 2H), 2.43 (t, J=6.8 Hz, 2H), 2.18 (s, 6H); ESI: m/z 425.1 (M+H)$^+$.

Example 41

(±)-1-[(3,4-dichlorophenyl)methyl]-3,7-dimethyl-8-{[(cis)-4-hydroxycyclohexyl]amino}-2,3,6,7-tetrahydro-1H-purine-2,6-dione

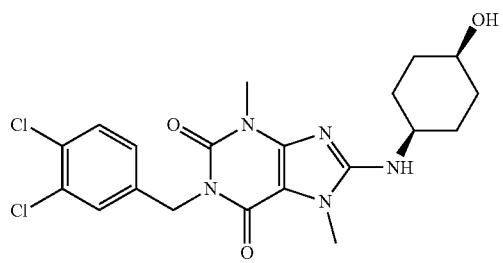 [SMILES: Cn1c(N[C@H]2CC[C@@H](O)CC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and (±)-cis-4-aminocyclohexan-1-ol. $^1$H NMR (500 MHz, DMSO-d$_6$) δ 7.55 (d, J=8.3 Hz, 1H), 7.51 (d, J=1.7 Hz, 1H), 7.25 (dd, J=8.3, 1.8 Hz, 1H), 6.77 (d, J=7.5 Hz, 1H), 4.98 (s, 2H), 4.38 (d, J=2.6 Hz, 1H), 3.80-3.73 (m, 1H), 3.73-3.64 (m, 1H), 3.57 (s, 3H), 3.34 (s, 3H), 1.81-1.71 (m, 2H), 1.71-1.60 (m, 4H), 1.49 (t, J=12.3 Hz, 2H); ESI: m/z 452.1 (M+H)$^+$.

Example 42

1-[(3,4-dichlorophenyl)methyl]-3,7-dimethyl-8-[(1H-pyrazol-4-ylmethyl)amino]-2,3,6,7-tetrahydro-1H-purine-2,6-dione

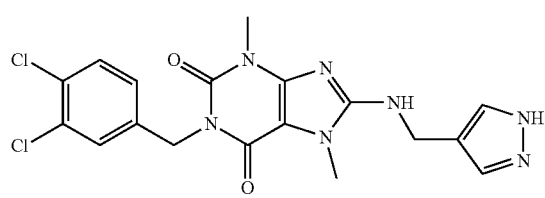 [SMILES: Cn1c(NCc2cn[nH]c2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and (1H-pyrazol-4-yl)methanamine. $^1$H NMR (500 MHz, DMSO-d$_6$) δ 12.66 (s, 1H), 7.67-7.53 (s, 2H), 7.55 (d, J=8.3 Hz), 7.52 (d, J=1.7 Hz, 1H), 7.39 (t, J=5.7 Hz, 1H), 7.25 (dd, J=8.3, 1.8 Hz, 1H), 4.98 (s, 2H), 4.39 (d, J=5.6 Hz, 2H), 3.55 (s, 3H), 3.38 (s, 3H); ESI: m/z 434.1 (M+H)$^+$.

Examples 43 and 71

1-(3,4-dichlorobenzyl)-8-((1S,3R)-3-hydroxycyclopentylamino)-3,7-dimethyl-1H-purine-2,6(3H,7H)-dione and 1-(3,4-dichlorobenzyl)-8-((1R,3S)-3-hydroxycyclopentylamino)-3,7-dimethyl-1H-purine-2,6(3H,7H)-dione

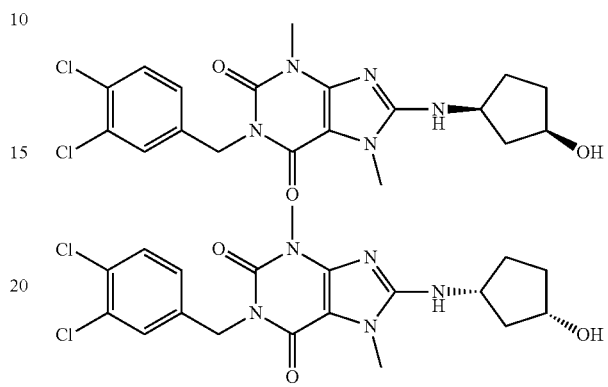

A solution of 8-bromo-1-(3,4-dichlorobenzyl)-3,7-dimethyl-1H-purine-2,6(3H,7H)-dione (740 mg, 1.78 mmol), (±)-cis-3-aminocyclopentanol (360 mg, 3.56 mmol), DIEA (460 mg, 3.56 mmol) and sodium iodide (75 mg, 0.36 mmol) in EtOH (8 mL) was stirred at 130° C. for 6 h in a microwave reactor. The mixture was purified by column chromatography (DCM:MeOH=15:1) and by chiral SFC using a CHIRALCEL® OZ-H/SFC column eluting with 40% MeOH (0.1% DEA) in carbon dioxide.

Example 43: 1-(3,4-dichlorobenzyl)-8-((1S,3R)-3-hydroxycyclopentylamino)-3,7-dimethyl-1H-purine-2,6(3H,7H)-dione or 1-(3,4-dichlorobenzyl)-8-((1R,3S)-3-hydroxycyclopentylamino)-3,7-dimethyl-1H-purine-2,6(3H,7H)-dione; ee 92.8%, retention time=7.08 min); $^1$H NMR (400 MHz, DMSO-d$_6$) δ 7.54 (dd, J=14.1, 5.1 Hz, 2H), 7.25 (dd, J=8.3, 1.9 Hz, 1H), 6.95 (d, J=7.4 Hz, 1H), 4.98 (s, 2H), 4.72 (d, J=4.0 Hz, 1H), 4.09 (dd, J=15.0, 7.7 Hz, 2H), 3.56 (s, 3H), 3.35 (s, 3H), 2.32-2.17 (m, 1H), 1.94 (dd, J=14.9, 7.9 Hz, 1H), 1.81-1.65 (m, 2H), 1.65-1.54 (m, 1H), 1.55-1.41 (m, 1H). ESI: m/z 438.0 (M+H)$^+$.

Example 71: 1-(3,4-dichlorobenzyl)-8-((1S,3R)-3-hydroxycyclopentylamino)-3,7-dimethyl-1H-purine-2,6(3H,7H)-dione or 1-(3,4-dichlorobenzyl)-8-((1R,3S)-3-hydroxycyclopentylamino)-3,7-dimethyl-1H-purine-2,6(3H,7H)-dione (ee 100.0%, retention time=6.24 min,); $^1$H NMR (400 MHz, DMSO-d$_6$) δ 7.54 (dd, J=14.1, 5.1 Hz, 2H), 7.25 (dd, J=8.3, 1.9 Hz, 1H), 6.95 (d, J=7.4 Hz, 1H), 4.98 (s, 2H), 4.72 (d, J=4.0 Hz, 1H), 4.09 (dd, J=15.0, 7.7 Hz, 2H), 3.56 (s, 3H), 3.35 (s, 3H), 2.32-2.17 (m, 1H), 1.94 (dd, J=14.9, 7.9 Hz, 1H), 1.81-1.65 (m, 2H), 1.65-1.54 (m, 1H), 1.55-1.41 (m, 1H). ESI: m/z 438.0 (M+H)$^+$.

Examples 44 and 70

1-(3,4-dichlorobenzyl)-8-((1R,3R)-3-hydroxycyclopentylamino)-3,7-dimethyl-1H-purine-2,6(3H,7H)-dione 1-(3,4-dichlorobenzyl)-8-((1S,3S)-3-hydroxycyclopentylamino)-3,7-dimethyl-1H-purine-2,6(3H,7H)-dione

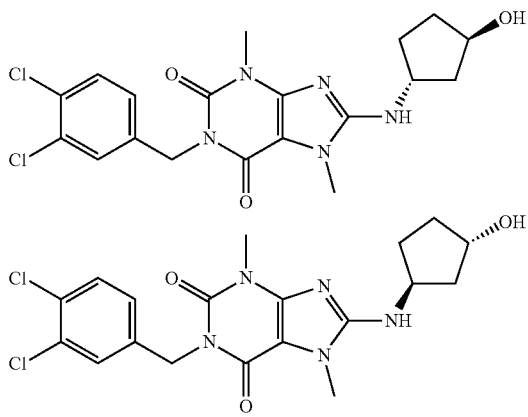

The title compounds were synthesized in a similar fashion as Example 43 using 8-bromo-1-(3,4-dichlorobenzyl)-3,7-dimethyl-1H-purine-2,6(3H,7H)-dione and (±)-trans-3-aminocyclopentanol (184 mg, 1.82 mmol) and DIEA (294 mg, 2.27 mmol) in EtOH (12 mL) was added NaI (10 mg). The mixture was stirred at 130° C. for 6 h under microwave condition. The reaction mixture was concentrated and the residue was purified by flash chromatography (DCM/MeOH=10/1) to give the product as a white solid ESI: m/z 438.1 (M+H)$^+$. The enantiomers were separated by chiral SFC using a CHIRALPAK® IC/SFC column eluting with 20% EtOH (0.1% NH$_4$OH) in carbon dioxide.

Example 44: 1-(3,4-dichlorobenzyl)-8-((1R,3R)-3-hydroxycyclopentylamino)-3,7-dimethyl-1H-purine-2,6(3H,7H)-dione or 1-(3,4-dichlorobenzyl)-8-((1S,3S)-3-hydroxycyclopentylamino)-3,7-dimethyl-1H-purine-2,6(3H,7H)-dione; (ee 98.71%, retention time 4.76 min). $^1$H NMR (400 MHz, DMSO-d$_6$) δ 7.52-7.54 (d, J=8.4 Hz, 1H), 7.49 (d, J=2.0 Hz, 1H), 7.22-7.25 (dd, J=2.0 Hz, J=2.0 Hz, 1H), 6.86-6.88 (d, J=7.2 Hz, 1H), 4.96 (s, 2H), 4.54 (d, J=3.6 Hz, 1H), 4.34 (m, 1H), 4.21 (m, 1H), 3.54 (s, 3H), 3.34 (s, 3H), 3.15-3.17 (d, J=4.2 Hz, 1H), 2.11 (m, 1H), 1.88-1.93 (m, 2H), 1.66-1.72 (m, 1H), 1.44-1.50 (m, 2H). ESI: m/z 438.1 (M+H)$^+$.

Example 70: 1-(3,4-dichlorobenzyl)-8-((1S,3S)-3-hydroxycyclopentylamino)-3,7-dimethyl-1H-purine-2,6(3H,7H)-dione or 1-(3,4-dichlorobenzyl)-8-((1R,3R)-3-hydroxycyclopentylamino)-3,7-dimethyl-1H-purine-2,6(3H,7H)-dione; (ee 100%, retention time 5.19 min). $^1$H NMR (400 MHz, DMSO-d$_6$) δ 7.52-7.54 (d, J=8.4 Hz, 1H), 7.49 (d, J=2.0 Hz, 1H), 7.22-7.25 (dd, J=2.0 Hz, J=2.0 Hz, 1H), 6.86-6.88 (d, J=7.2 Hz, 1H), 4.96 (s, 2H), 4.54 (d, J=3.6 Hz, 1H), 4.34 (m, 1H), 4.21 (m, 1H), 3.54 (s, 3H), 3.34 (s, 3H), 3.15-3.17 (d, J=4.2 Hz, 1H), 2.11 (m, 1H), 1.88-1.93 (m, 2H), 1.66-1.72 (m, 1H), 1.44-1.50 (m, 2H). ESI: m/z 438.1 (M+H)$^+$.

Example 45

1-[(3,4-dichlorophenyl)methyl]-8-[(3-hydroxy-3-methylbutyl)amino]-3,7-dimethyl-2,3,6,7-tetrahydro-1H-purine-2,6-dione

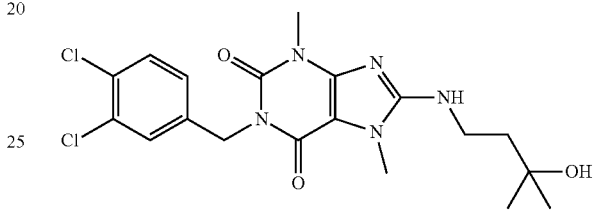

The title compound was synthesized in a similar fashion as described in Procedure 7B using 8-Bromo-1-(3,4-dichlorobenzyl)-3,7-dimethyl-1H-purine-2,6(3H,7H)-dione, 4-amino-2-methylbutan-2-ol and isopropanol as solvent. $^1$H NMR (500 MHz, DMSO-d$_6$) δ 7.55 (d, J=8.3 Hz, 1H), 7.52 (d, J=1.7 Hz, 1H), 7.25 (dd, J=8.3, 1.9 Hz, 1H), 6.96 (t, J=5.4 Hz, 1H), 4.98 (s, 2H), 4.38 (s, 1H), 3.54 (s, 3H), 1.74-1.66 (m, 2H), 1.14 (s, 6H). One methyl and one methylene signal obscured by solvent; ESI: m/z 440.1 (M+H)$^+$.

Example 46

1-[(3,4-dichlorophenyl)methyl]-3,7-dimethyl-8-{[(3S)-oxan-3-yl]amino}-2,3,6,7-tetrahydro-1H-purine-2,6-dione

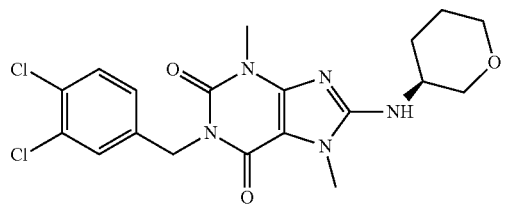 [SMILES: Cn1c(N[C@H]2CCCOC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and (S)-tetrahydro-2H-pyran-3-amine. $^1$H NMR (500 MHz, DMSO-d$_6$) δ 7.55 (d, J=8.3 Hz, 1H), 7.51 (d, J=2.0 Hz, 1H), 7.25 (dd, J=8.3, 2.0 Hz, 1H), 6.84 (d, J=7.7 Hz, 1H), 4.98 (s, 2H), 3.90 (dd, J=10.6, 2.9 Hz, 1H), 3.84-3.73 (m, 2H), 3.57 (s, 3H), 3.40-3.36 (m, 1H), 3.35 (s, 3H), 3.15 (dd, J=10.4, 9.6 Hz, 1H), 2.04-1.95 (m, 1H), 1.76-1.67 (m, 1H), 1.64-1.53 (m, 2H); ESI: m/z 438.1 (M+H)$^+$.

Example 47

1-[(3,4-dichlorophenyl)methyl]-3,7-dimethyl-8-{[(3R)-oxan-3-yl]amino}-2,3,6,7-tetrahydro-1H-purine-2,6-dione

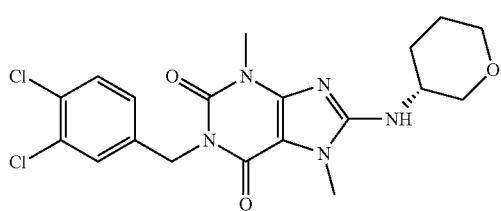 [SMILES: Cn1c(N[C@@H]2CCCOC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and (R)-tetrahydro-2H-pyran-3-amine. $^1$H NMR (500 MHz, DMSO-$d_6$) δ 7.55 (d, J=8.3 Hz, 1H), 7.51 (d, J=2.0 Hz, 1H), 7.25 (dd, J=8.3, 2.0 Hz, 1H), 6.84 (d, J=7.7 Hz, 1H), 4.98 (s, 2H), 3.90 (dd, J=10.7, 2.8 Hz, 1H), 3.85-3.73 (m, 2H), 3.57 (s, 3H), 3.41-3.36 (m, 1H), 3.35 (s, 3H), 3.15 (dd, J=10.4, 9.6 Hz, 1H), 2.04-1.96 (m, 1H), 1.76-1.67 (m, 1H), 1.65-1.53 (m, 2H); ESI: m/z 438.1 (M+H)$^+$.

Example 48

1-[(3,4-dichlorophenyl)methyl]-3,7-dimethyl-8-[(oxan-4-yl)amino]-2,3,6,7-tetrahydro-1H-purine-2,6-dione

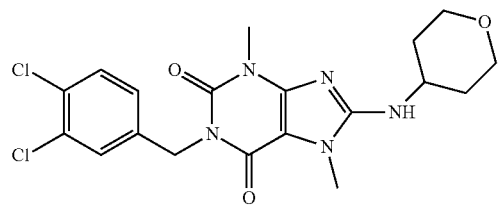 [SMILES: Cn1c(NC2CCOCC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and tetrahydro-2H-pyran-4-amine. $^1$H NMR (500 MHz, DMSO-$d_6$) δ 7.55 (d, J=8.3 Hz, 1H), 7.52 (d, J=2.0 Hz, 1H), 7.26 (dd, J=8.3, 2.0 Hz, 1H), 6.89 (d, J=7.6 Hz, 1H), 4.98 (s, 2H), 3.93-3.82 (m, 3H), 3.58 (s, 3H), 3.39 (td, J=11.7, 1.9 Hz, 2H), 3.35 (s, 3H), 1.92-1.85 (m, 2H), 1.56 (qd, J=12.2, 4.5 Hz, 2H); ESI: m/z 438.1 (M+H)$^+$.

Example 50

(1S,3R)-3-({1-[(3,4-dichlorophenyl)methyl]-3,7-dimethyl-2,6-dioxo-2,3,6,7-tetrahydro-1H-purin-8-yl}amino)cyclopentane-1-carboxylic acid

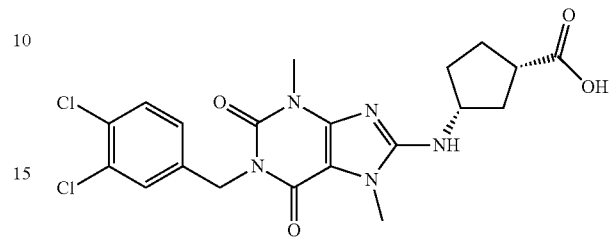

The title compound was synthesized in a similar fashion as described in Procedure 7B using 8-Bromo-1-(3,4-dichlorobenzyl)-3,7-dimethyl-1H-purine-2,6(3H,7H)-dione and (1S,3R)-3-aminocyclopentane-1-carboxylic acid. $^1$H NMR (500 MHz, DMSO-$d_6$) δ 7.55 (d, J=8.3 Hz, 1H), 7.52 (d, J=2.0 Hz, 1H), 7.25 (dd, J=8.3, 2.0 Hz, 1H), 7.13 (s, 1H), 4.98 (s, 2H), 4.21-4.14 (m, 1H), 3.56 (s, 3H), 3.35 (s, 3H), 2.76 (p, J=8.7 Hz, 1H), 2.25 (dt, J=15.0, 7.5 Hz, 1H), 2.01-1.93 (m, 1H), 1.93-1.82 (m, 2H), 1.77 (dt, J=12.6, 8.9 Hz, 1H), 1.62 (dq, J=12.0, 7.3 Hz, 1H); ESI: m/z 466.1 (M+H)$^+$.

Example 51

1-(1-benzothiophen-5-ylmethyl)-8-{[(2S)-4-hydroxybutan-2-yl]amino}-3,7-dimethyl-2,3,6,7-tetrahydro-1H-purine-2,6-dione

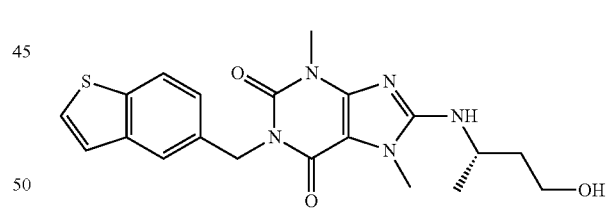

The title compound was synthesized in a similar fashion as described in Procedure 7B using 1-(benzo[b]thiophen-5-ylmethyl)-8-bromo-3,7-dimethyl-3,7-dihydro-1H-purine-2,6-dione and (S)-3-aminobutan-1-ol. $^1$H NMR (500 MHz, DMSO-$d_6$) δ 7.91 (d, J=8.3 Hz, 1H), 7.75 (s, 1H), 7.73 (d, J=5.4 Hz, 1H), 7.43 (d, J=5.4 Hz, 1H), 7.34 (d, J=8.3 Hz, 1H), 6.76 (d, J=8.2 Hz, 1H), 5.14 (s, 2H), 4.46 (t, J=5.0 Hz, 1H), 4.02 (hept, J=6.9 Hz, 1H), 3.58 (s, 3H), 3.51-3.46 (m, 2H), 3.36 (s, 3H), 1.76 (dq, J=13.6, 6.3 Hz, 1H), 1.65 (dq, J=13.1, 6.5 Hz, 1H), 1.20 (d, J=6.5 Hz, 3H); ESI: m/z 414.2 (M+H)$^+$.

Example 52

1-(1-benzothiophen-5-ylmethyl)-8-[(3-hydroxypropyl)amino]-3,7-dimethyl-2,3,6,7-tetrahydro-1H-purine-2,6-dione

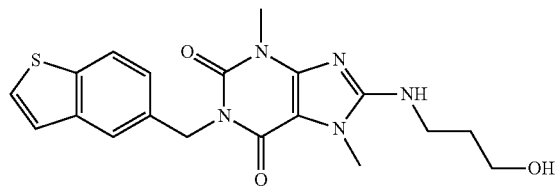 [SMILES: Cn1c(NCCCO)nc2c1c(=O)n(Cc1ccc3sccc3c1)c(=O)n2C]

The title compound was synthesized in a similar fashion as described in Procedure 7B using 1-(benzo[b]thiophen-5-ylmethyl)-8-bromo-3,7-dimethyl-3,7-dihydro-1H-purine-2,6-dione and 3-amino-1-propanol. $^1$H NMR (500 MHz, DMSO-$d_6$) δ 7.90 (d, J=8.4 Hz, 1H), 7.75 (s, 1H), 7.72 (d, J=5.4 Hz, 1H), 7.42 (d, J=5.4 Hz, 1H), 7.33 (d, J=8.4 Hz, 1H), 6.99 (t, J=5.5 Hz, 1H), 5.13 (s, 2H), 4.49 (s, 1H), 3.57 (s, 3H), 3.51-3.44 (m, 2H), 3.39 (q, J=6.6 Hz, 2H), 3.36 (s, 3H), 1.73 (p, J=6.5 Hz, 2H); ESI: m/z 400.2 (M+H)$^+$.

Example 53

1-[(3,4-dichlorophenyl)methyl]-8-[(1,3-dihydroxypropan-2-yl)amino]-3,7-dimethyl-2,3,6,7-tetrahydro-1H-purine-2,6-dione

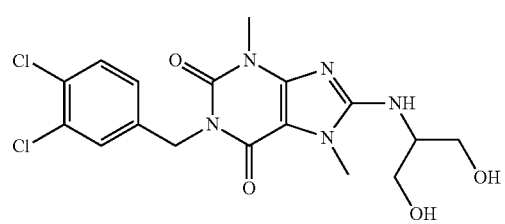 [SMILES: Cn1c(NC(CO)CO)nc2c1c(=O)n(Cc1ccc(Cl)c(Cl)c1)c(=O)n2C]

The title compound was synthesized in a similar fashion as described in described in Procedure 7B using 8-Bromo-1-(3,4-dichlorobenzyl)-3,7-dimethyl-1H-purine-2,6(3H,7H)-dione and 2-aminopropane-1,3-diol. $^1$H NMR (500 MHz, DMSO-$d_6$) δ 7.55 (d, J=8.3 Hz, 1H), 7.51 (d, J=1.8 Hz, 1H), 7.25 (dd, J=8.3, 1.8 Hz, 1H), 6.64 (d, J=8.1 Hz, 1H), 4.99 (s, 2H), 4.66 (t, J=5.5 Hz, 2H), 3.92-3.85 (m, 1H), 3.58 (s, 3H), 3.53 (m, 4H), 3.35 (s, 3H); ESI: m/z 428.1 (M+H)$^+$.

Example 54

1-[(3,4-dichlorophenyl)methyl]-8-{[2-(2-hydroxyethoxy)ethyl]amino}-3,7-dimethyl-2,3,6,7-tetrahydro-1H-purine-2,6-dione

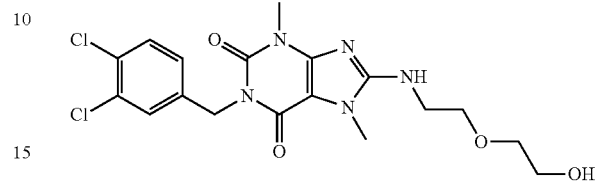

The title compound was synthesized in a similar fashion as described in Procedure 7B using 8-Bromo-1-(3,4-dichlorobenzyl)-3,7-dimethyl-1H-purine-2,6(3H,7H)-dione and 2-(2-aminoethoxy)ethan-1-ol. $^1$H NMR (500 MHz, DMSO-$d_6$) δ 7.55 (d, J=8.3 Hz, 1H), 7.52 (s, 1H), 7.26 (d, J=8.2 Hz, 1H), 7.13 (t, J=5.4 Hz, 1H), 4.98 (s, 2H), 4.59 (t, J=5.3 Hz, 1H), 3.57 (m, 5H), 3.53-3.44 (m, 6H), 3.35 (s, 3H); ESI: m/z 442.1 (M+H)$^+$.

Example 55

(±)-1-(3,4-dichlorobenzyl)-8-(((trans)-4-hydroxycyclohexyl)amino)-3,7-dimethyl-3,7-dihydro-1H-purine-2,6-dione

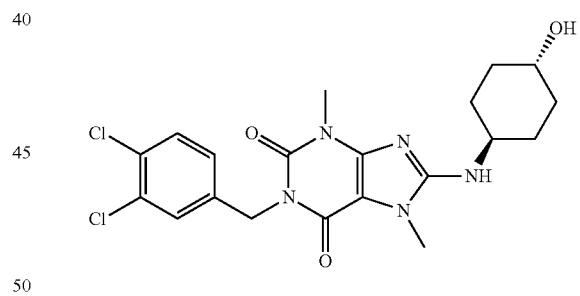

The title compound was synthesized in a similar fashion as described in Procedure 7B using 8-Bromo-1-(3,4-dichlorobenzyl)-3,7-dimethyl-1H-purine-2,6(3H,7H)-dione and trans-4-aminocyclohexan-1-ol. $^1$H NMR (500 MHz, DMSO-$d_6$) δ 7.55 (d, J=8.3 Hz, 1H), 7.51 (s, 1H), 7.25 (d, J=8.3 Hz, 1H), 6.77 (d, J=7.8 Hz, 1H), 4.98 (s, 2H), 4.58 (d, J=4.3 Hz, 1H), 3.66-3.58 (m, 1H), 3.54 (s, 3H), 3.43-3.37 (m, 4H), 1.92 (d, J=11.3 Hz, 2H), 1.85 (d, J=11.0 Hz, 2H), 1.35 (q, J=11.1 Hz, 2H), 1.24 (q, J=10.5 Hz, 2H); ESI: m/z 452.1 (M+H)$^+$.

Example 56

8-[(3-hydroxypropyl)amino]-3,7-dimethyl-1-{[4-(trifluoromethyl)phenyl]methyl}-2,3,6,7-tetrahydro-1H-purine-2,6-dione

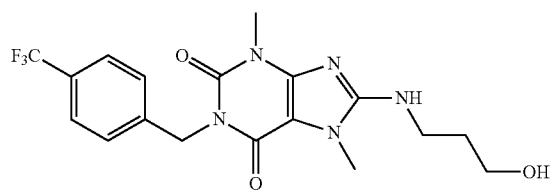 [SMILES: Cn1c(NCCCO)nc2c1c(=O)n(Cc1ccc(C(F)(F)F)cc1)c(=O)n2C]

The title compound was synthesized in a similar fashion as described in Procedure 7B using 8-bromo-3,7-dimethyl-1-(4-(trifluoromethyl)benzyl)-3,7-dihydro-1H-purine-2,6-dione and 3-amino-1-propanol. $^1$H NMR (500 MHz, DMSO-$d_6$) δ 7.65 (d, J=8.2 Hz, 2H), 7.47 (d, J=8.1 Hz, 2H), 7.02 (t, J=5.5 Hz, 1H), 5.09 (s, 2H), 4.49 (t, J=5.1 Hz, 1H), 3.56 (s, 3H), 3.48 (q, J=6.0 Hz, 2H), 3.39 (q, J=6.8 Hz, 2H), 3.36 (s, 3H), 1.73 (p, J=6.4 Hz, 2H); ESI: m/z 412.2 (M+H)$^+$.

Example 57

8-{[(2R)-2-hydroxypropyl]amino}-3,7-dimethyl-1-{[4-(trifluoromethyl)phenyl]methyl}-2,3,6,7-tetrahydro-1H-purine-2,6-dione

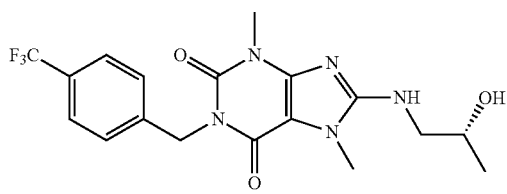 [SMILES: C[C@@H](O)CNc1nc2c(c(=O)n(Cc3ccc(C(F)(F)F)cc3)c(=O)n2C)n1C]

The title compound was synthesized in a similar fashion as described in Procedure 7B using 8-bromo-3,7-dimethyl-1-(4-(trifluoromethyl)benzyl)-3,7-dihydro-1H-purine-2,6-dione, (R)-1-amino-propan-2-ol, and isopropanol as solvent. $^1$H NMR (500 MHz, DMSO-$d_6$) δ 7.65 (d, J=8.2 Hz, 2H), 7.46 (d, J=8.1 Hz, 2H), 7.03 (t, J=5.8 Hz, 1H), 5.09 (s, 2H), 4.75 (d, J=4.6 Hz, 1H), 3.85 (hept, J=6.1 Hz, 1H), 3.57 (s, 3H), 3.35 (s, 3H), 3.29-3.22 (m, 2H), 1.08 (d, J=6.2 Hz, 3H ESI: m/z 412.2 (M+H)$^+$.

Example 59

8-(cyclohexylamino)-1-[(3,4-dichlorophenyl)methyl]-3,7-dimethyl-2,3,6,7-tetrahydro-1H-purine-2,6-dione

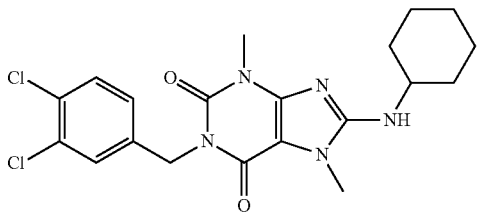 [SMILES: Cn1c(NC2CCCCC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and cyclohexyamine. $^1$H NMR (500 MHz, DMSO-$d_6$) δ 7.55 (d, J=8.3 Hz, 1H), 7.51 (d, J=1.8 Hz, 1H), 7.25 (dd, J=8.3, 1.9 Hz, 1H), 6.78 (d, J=7.8 Hz, 1H), 4.98 (s, 2H), 3.70-3.60 (m, 1H), 3.56 (s, 3H), 3.35 (s, 3H), 1.97-1.89 (m, 2H), 1.79-1.69 (m, 2H), 1.61 (d, J=11.9 Hz, 1H), 1.36-1.25 (m, 4H), 1.20-1.07 (m, 1H); ESI: m/z 436.1 (M+H)$^+$.

Example 60

1-[(3,4-dichlorophenyl)methyl]-3,7-dimethyl-8-{[(3R)-pyrrolidin-3-yl]amino}-2,3,6,7-tetrahydro-1H-purine-2,6-dione

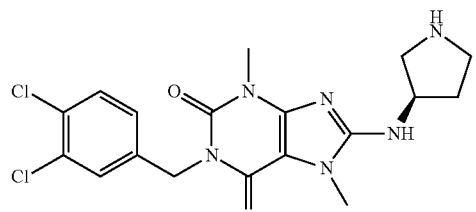

The title compound was synthesized in a similar fashion as described in Procedure 7B using 8-Bromo-1-(3,4-dichlorobenzyl)-3,7-dimethyl-1H-purine-2,6(3H,7H)-dione and tert-butyl (R)-3-aminopyrrolidine-1-carboxylate followed by Boc deprotection as described in Procedure 6. $^1$H NMR (250 MHz, DMSO-$d_6$) δ 9.27 (s, 1H), 9.10 (s, 1H), 7.56 (d, J=8.3 Hz, 1H), 7.51 (d, J=1.9 Hz, 1H), 7.37 (d, J=6.3 Hz, 1H), 7.26 (dd, J=8.3, 2.0 Hz, 1H), 4.99 (s, 2H), 4.46 (q J=5.6 Hz, 1H), 3.71-3.63 (m, 1H), 3.62 (s, 3H), 3.51-3.47 (m, 1H), 3.34-3.18 (m, 2H), 2.33-2.17 (m, 1H), 2.14-1.92 (m, 1H). One methyl signal obscured by solvent peak; ESI: m/z 423.2 (M+H)$^+$.

Example 61

1-[(3,4-dichlorophenyl)methyl]-3,7-dimethyl-8-{[(3S)-pyrrolidin-3-yl]amino}-2,3,6,7-tetrahydro-1H-purine-2,6-dione

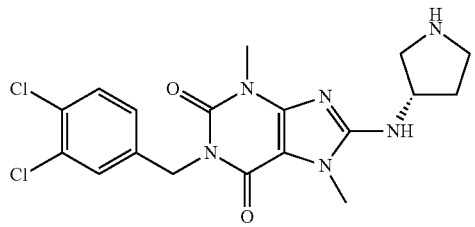 [SMILES: Cn1c(N[C@H]2CCNC2)nc2c1c(=O)n(Cc1ccc(Cl)c(Cl)c1)c(=O)n2C]

The title compound was synthesized in a similar fashion as described in Procedure 7B using 8-Bromo-1-(3,4-dichlorobenzyl)-3,7-dimethyl-1H-purine-2,6(3H,7H)-dione and tert-butyl (S)-3-aminopyrrolidine-1-carboxylate followed by Boc-deprotection as described in procedure 6. $^1$H NMR (250 MHz, DMSO-d$_6$) δ 9.36 (s, 1H), 9.20 (s, 1H), 7.56 (d, J=8.2 Hz, 1H), 7.51 (d, J=1.6 Hz, 1H), 7.41 (d, J=5.7 Hz, 1H), 7.26 (dd, J=8.3, 1.6 Hz, 1H), 4.99 (s, 2H), 4.47 (q, J=4.8 Hz, 1H), 3.74-3.65 (m, 1H), 3.62 (s, 3H), 3.37 (s, 3H), 3.33-3.16 (m, 2H), 2.31-2.17 (m, 1H), 2.14-1.83 (m, 1H); ESI: m/z 423.2 (M+H)$^+$.

Example 62

1-(3,4-dichlorophenyl)-8-[(3-hydroxypropyl)amino]-3,7-dimethyl-2,3,6,7-tetrahydro-1H-purine-2,6-dione

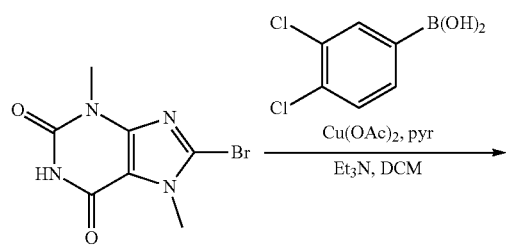

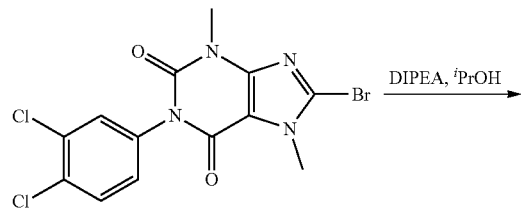

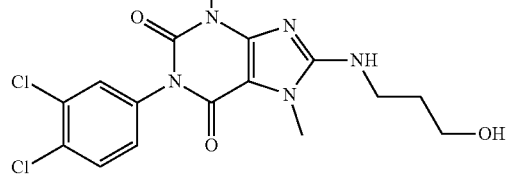

8-bromo-1-(3,4-dichlorophenyl)-3,7-dimethyl-3,7-dihydro-1H-purine-2,6-dione

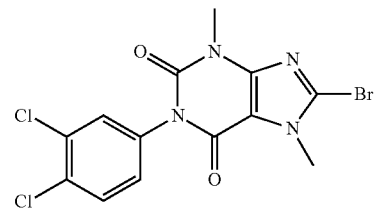 [SMILES: Cn1c(Br)nc2c1c(=O)n(-c1ccc(Cl)c(Cl)c1)c(=O)n2C]

8-Bromo-1-(3,4-dichlorobenzyl)-3,7-dimethyl-1H-purine-2,6(3H,7H)-dione (250 mg, 0.97 mmol) was added to 4 Å molecular sieves (370 mg) in dichloromethane (7.5 ml). (3,4-Dichlorophenyl)boronic acid (368 mg, 1.93 mmol) was added followed by triethylamine (269 μl, 1.93 mmol), pyridine (156 μl, 1.93 mmol) and copper (II) acetate (351 mg, 1.93 mmol). The reaction was stirred at room temperature for 72 h. The mixture was filtered through Celite® and partitioned between dichloromethane and water. The aqueous layer was extracted with dichloromethane three times, the combined organic fractions were washed with sat. NaCl, dried over MgSO$_4$ and concentrated in vacuo. The residue was purified by chromatography (0-100% EA/heptane). ESI: m/z 404.95 (M+H)$^+$.

1-[(3,4-dichlorophenyl)methyl]-3,7-dimethyl-8-{[(3S)-pyrrolidin-3-yl]amino}-2,3,6,7-tetrahydro-1H-purine-2,6-dione

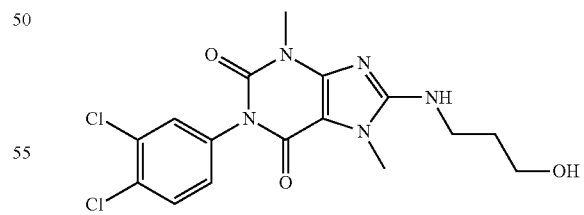

The title compound was synthesized in a similar fashion as described in Procedure 7B using 8-bromo-1-(3,4-dichlorophenyl)-3,7-dimethyl-3,7-dihydro-1H-purine-2,6-dione and 3-aminopropan-1-ol. $^1$H NMR (500 MHz, DMSO-d$_6$) δ 7.71 (d, J=8.5 Hz, 1H), 7.61 (d, J=2.3 Hz, 1H), 7.27 (dd, J=8.5, 2.3 Hz, 1H), 7.06 (t, J=5.5 Hz, 1H), 4.51 (s, 1H), 3.53 (s, 3H), 3.52-3.47 (m, 2H), 3.41 (q, J=6.7 Hz, 2H), 3.36 (s, 3H), 1.75 (p, J=6.5 Hz, 2H); ESI: m/z 398.1 (M+H)$^+$.

Example 63

1-[(3,4-dichlorophenyl)methyl]-3,7-dimethyl-8-{[(3R)-oxolan-3-yl]amino}-2,3,6,7-tetrahydro-1H-purine-2,6-dione

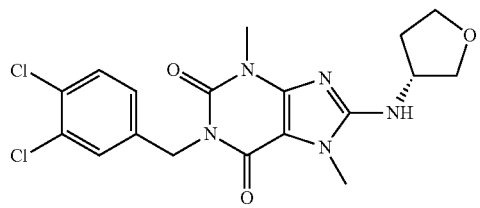 [SMILES: Cn1c(N[C@@H]2CCOC2)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (R)-tetrahydrofuran-3-amine. $^1$H NMR (500 MHz, DMSO-$d_6$) δ 7.56 (d, J=8.3 Hz, 1H), 7.52 (s, 1H), 7.27 (dd, J=8.3, 1.8 Hz, 1H), 7.13 (d, J=6.2 Hz, 1H), 5.00 (s, 2H), 4.42-4.35 (m, 1H), 3.93-3.84 (m, 2H), 3.73 (td, J=8.0, 6.0 Hz, 1H), 3.62 (dd, J=9.0, 4.1 Hz, 1H), 3.59 (s, 3H), 3.37 (s, 3H), 2.22 (dq, J=14.6, 7.7 Hz, 1H), 1.97-1.89 (m, 1H); ESI: m/z 424.1 (M+H)$^+$.

Example 64

(1R,3S)-3-(1-(3,4-dichlorobenzyl)-3,7-dimethyl-2,6-dioxo-2,3,6,7-tetrahydro-1H-purin-8-ylamino)cyclopentanecarboxylic acid

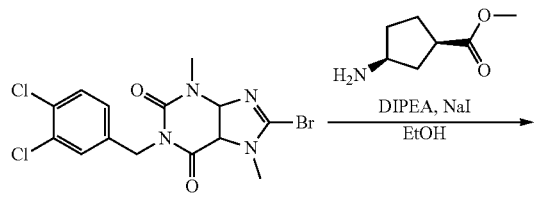

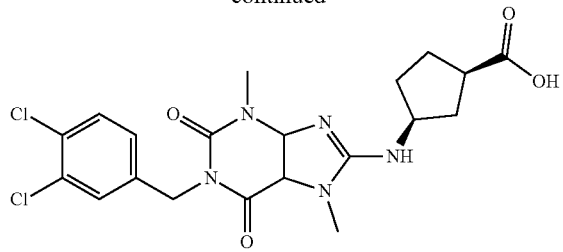

(1R,3S)-Methyl 3-(1-(3,4-dichlorobenzyl)-3,7-dimethyl-2,6-dioxo-2,3,6,7-tetrahydro-1H-purin-8-ylamino)cyclopentanecarboxylate

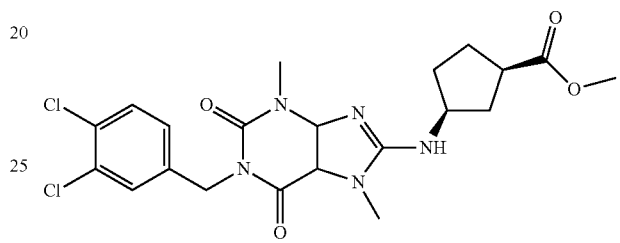

The title compound was synthesized in a similar fashion as Procedure 7A using 8-bromo-1-(3,4-dichlorobenzyl)-3,7-dimethyl-1H-purine-2,6(3H,7H)-dione and methyl (1R,3S)-3-aminocyclopentane-1-carboxylate. The mixture was concentrated and purified by flash chromatography (EA/PE=1/1). ESI: m/z 494.1 (M+H)$^+$.

(1R,3S)-3-(1-(3,4-dichlorobenzyl)-3,7-dimethyl-2,6-dioxo-2,3,6,7-tetrahydro-1H-purin-8-ylamino)cyclopentanecarboxylic acid

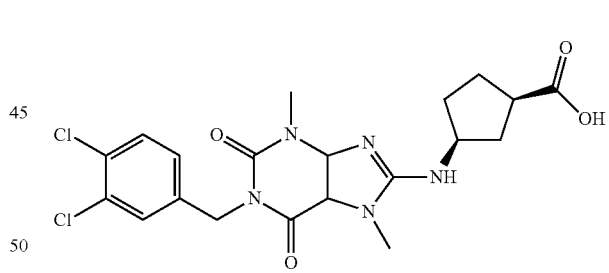

To a solution of (1R,3S)-methyl 3-(1-(3,4-dichlorobenzyl)-3,7-dimethyl-2,6-dioxo-2,3,6,7-tetrahydro-1H-purin-8-ylamino)cyclopentanecarboxylate (0.28 mmol, 140 mg) in methanol (0.5 mL), THF (4 mL), and water (4 mL) was added LiOH (1.12 mmol, 28 mg). The reaction mixture was stirred at 30° C. for 4 h. The mixture was concentrated and the pH was adjusted to 6 by addition of HCl (aq) solution. The mixture was extracted with EA (2*50 mL). The combined organic fractions were concentrated and purified by Prep-HPLC using Method D (30-70% ACN). $^1$H NMR (400 MHz, CD$_3$OD) δ 7.53 (d, J=1.9 Hz, 1H), 7.43 (dd, J=8.3, 2.8 Hz, 1H), 7.30 (dd, J=8.2, 2.1 Hz, 1H), 5.09 (d, J=3.7 Hz, 2H), 4.32 (m, 1H), 3.63 (d, J=1.8 Hz, 3H), 3.49 (d, J=2.0 Hz, 3H), 2.90 (m, 1H), 2.37 (m, 1H), 2.15-1.96 (m, 4H), 1.89 (m, 1H), 1.83-1.73 (m, 1H).); ESI: m/z 466.1 (M+H)$^+$.

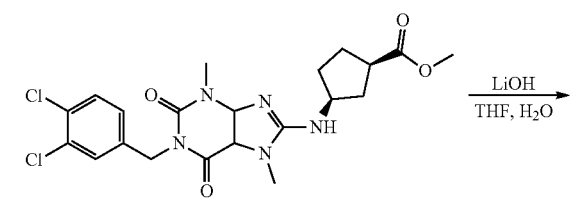

Example 65

8-[(azetidin-3-yl)amino]-1-[(3,4-dichlorophenyl)methyl]-3,7-dimethyl-2,3,6,7-tetrahydro-1H-purine-2,6-dione

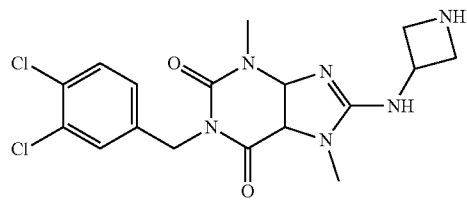 [SMILES: CN1C(=O)N(Cc2ccc(Cl)c(Cl)c2)C(=O)C2C1N=C(NC1CNC1)N2C]

The title compound was synthesized in a similar fashion as described in Procedure 7A using 8-bromo-1-(3,4-dichlorobenzyl)-3,7-dimethyl-1H-purine-2,6(3H,7H)-dione and tert-butyl 3-aminoazetidine-1-carboxylate followed by Boc-deprotection as described in Procedure 6; $^1$H NMR (500 MHz, DMSO-$d_6$) δ 7.59-7.53 (m, 2H), 7.51 (d, J=1.9 Hz, 1H), 7.25 (dd, J=8.3, 2.0 Hz, 1H), 4.98 (s, 2H), 4.60 (s, 1H), 4.12 (s, 0.5H), 3.83 (s, 0.5H), 3.66 (s, 2H), 3.59 (s, 3H), 3.56 (d, J=6.7 Hz, 2H), 3.34 (s, 3H); ESI: m/z 409.1 (M+H)$^+$.

Example 66

1-[(3,4-dichlorophenyl)methyl]-3,7-dimethyl-8-{[(cis)-3-hydroxycyclobutyl]amino}-2,3,6,7-tetrahydro-1H-purine-2,6-dione

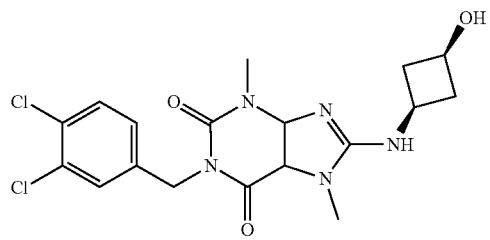 [SMILES: CN1C(=O)N(Cc2ccc(Cl)c(Cl)c2)C(=O)C2C1N=C(N[C@H]1C[C@@H](O)C1)N2C]

The title compound was synthesized in a similar fashion as described in Procedure 7B using 8-bromo-1-(3,4-dichlorobenzyl)-3,7-dimethyl-1H-purine-2,6(3H,7H)-dione and 3-aminocyclobutan-1-ol. The cis-diastereomer was isolated by prep HPLC. $^1$H NMR (500 MHz, DMSO-$d_6$) δ 7.55 (d, J=8.3 Hz, 1H), 7.51 (d, J=2.0 Hz, 1H), 7.25 (dd, J=8.3, 2.0 Hz, 1H), 7.19 (d, J=7.3 Hz, 1H), 5.10 (d, J=5.5 Hz, 1H), 4.98 (s, 2H), 3.89-3.82 (m, 1H), 3.82-3.74 (m, 1H), 3.56 (s, 3H), 3.34 (s, 3H), 2.65-2.59 (m, 2H), 1.92-1.85 (m, 2H); ESI: m/z 424.1 (M+H)$^+$.

Example 67

1-{[4-chloro-3-(trifluoromethyl)phenyl]methyl}-8-[(3-hydroxypropyl)amino]-3,7-dimethyl-2,3,6,7-tetrahydro-1H-purine-2,6-dione

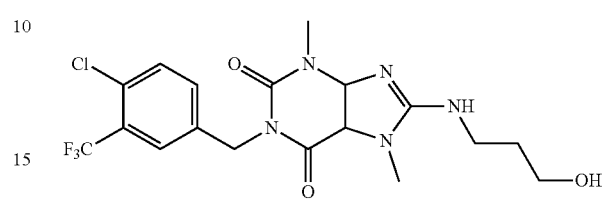

The title compound was synthesized in a similar fashion as described in Procedure 7B using 8-bromo-1-(4-chloro-3-(trifluoromethyl)benzyl)-3,7-dimethyl-3,7-dihydro-1H-purine-2,6-dione and 3-amino-propan-1-ol. $^1$H NMR (500 MHz, DMSO-$d_6$) δ 7.79 (d, J=1.9 Hz, 1H), 7.65 (d, J=8.3 Hz, 1H), 7.56 (dd, J=8.3, 1.8 Hz, 1H), 7.02 (t, J=5.5 Hz, 1H), 5.05 (s, 2H), 4.49 (t, J=5.2 Hz, 1H), 3.55 (s, 3H), 3.48 (q, J=6.2 Hz, 2H), 3.38 (q, J=6.8 Hz, 2H), 3.35 (s, 3H), 1.73 (p, J=6.4 Hz, 2H) ESI: m/z 446.1 (M+H)$^+$.

Example 68

1-[(3,4-dichlorophenyl)methyl]-3,7-dimethyl-8-{[(3S)-piperidin-3-yl]amino}-2,3,6,7-tetrahydro-1H-purine-2,6-dione

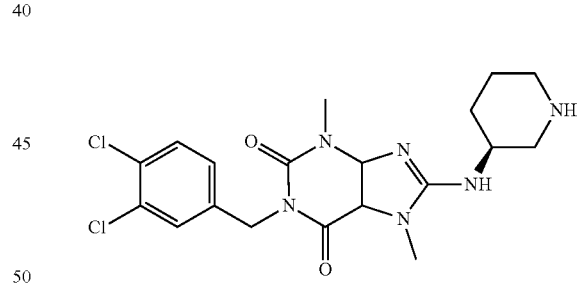

The title compound was synthesized in a similar fashion as described in Procedure 7B using 8-bromo-1-(3,4-dichlorobenzyl)-3,7-dimethyl-1H-purine-2,6(3H,7H)-dione and tert-butyl (S)-3-aminopiperidine-1-carboxylate followed by Boc-deprotection as described in Procedure 6. $^1$H NMR (500 MHz, DMSO-$d_6$) δ 7.55 (d, J=8.3 Hz, 1H), 7.51 (d, J=2.0 Hz, 1H), 7.25 (dd, J=8.3, 2.1 Hz, 1H), 6.72 (d, J=7.9 Hz, 1H), 4.98 (s, 2H), 3.74-3.65 (m, 1H), 3.57 (s, 3H), 3.35 (s, 3H), 3.06 (dd, J=11.7, 3.3 Hz, 1H), 2.79 (d, J=12.2 Hz, 1H), 2.43-2.34 (m, 2H), 1.97-1.91 (m, 1H), 1.67-1.60 (m, 1H), 1.49-1.37 (m, 2H); ESI: m/z 437.2 (M+H)$^+$.

Example 69

1-[(3,4-dichlorophenyl)methyl]-3,7-dimethyl-8-{[(3R)-piperidin-3-yl]amino}-2,3,6,7-tetrahydro-1H-purine-2,6-dione

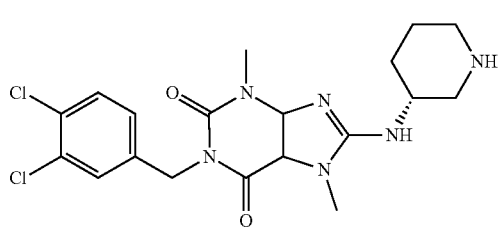 [SMILES: CN1C(=O)N(Cc2ccc(Cl)c(Cl)c2)C(=O)C2C1N=C(N[C@@H]1CCCNC1)N2C]

The title compound was synthesized in a similar fashion as described in Procedure 7B using 8-bromo-1-(3,4-dichlorobenzyl)-3,7-dimethyl-1H-purine-2,6(3H,7H)-dione and tert-butyl (R)-3-aminopiperidine-1-carboxylate followed by Boc-deprotection as described in Procedure 6. $^1$H NMR (500 MHz, DMSO-d$_6$) δ 7.55 (d, J=8.3 Hz, 1H), 7.51 (d, J=2.0 Hz, 1H), 7.25 (dd, J=8.3, 2.0 Hz, 1H), 6.72 (d, J=7.9 Hz, 1H), 4.98 (s, 2H), 3.74-3.66 (m, 1H), 3.56 (s, 3H), 3.35 (s, 3H), 3.06 (dd, J=11.7, 3.4 Hz, 1H), 2.79 (d, J=12.3 Hz, 1H), 2.42-2.33 (m, 2H), 1.93 (d, J=9.7 Hz, 1H), 1.67-1.59 (m, 1H), 1.49-1.35 (m, 2H); ESI: m/z 437.2 (M+H)$^+$.

Example 72

1-[1-(3,4-dichlorophenyl)ethyl]-8-[(3-hydroxypropyl)amino]-3,7-dimethyl-2,3,6,7-tetrahydro-1H-purine-2,6-dione

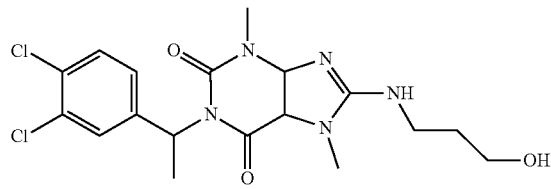 [SMILES: CC(c1ccc(Cl)c(Cl)c1)N1C(=O)C2C(N=C(NCCCO)N2C)N(C)C1=O]

The title compound was synthesized in a similar fashion as described in Procedure 7B using 8-bromo-1-(1-(3,4-dichlorophenyl)ethyl)-3,7-dimethyl-3,7-dihydro-1H-purine-2,6-dione and 3-aminopropan-1-ol. $^1$H NMR (500 MHz, DMSO-d$_6$) δ 7.52 (d, J=8.4 Hz, 1H), 7.46 (d, J=1.8 Hz, 1H), 7.21 (dd, J=8.4, 1.8 Hz, 1H), 7.00 (t, J=5.5 Hz, 1H), 6.14 (q, J=6.7 Hz, 1H), 4.49 (s, 1H), 3.54 (s, 3H), 3.48 (t, J=6.0 Hz, 2H), 3.38 (q, J=6.7 Hz, 2H), 3.29 (s, 3H), 1.77-1.69 (m, 5H); ESI: m/z 426.2 (M+H)$^+$.

Example 73

1-{[3-chloro-4-(trifluoromethyl)phenyl]methyl}-8-[(3-hydroxypropyl)amino]-3,7-dimethyl-2,3,6,7-tetrahydro-1H-purine-2,6-dione

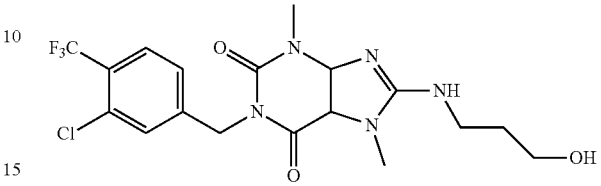

The title compound was synthesized in a similar fashion as Example 49 using 8-bromo-1-(3-chloro-4-(trifluoromethyl)benzyl)-3,7-dimethyl-3,7-dihydro-1H-purine-2,6-dione and 3-aminopropan-1-ol. $^1$H NMR (500 MHz, DMSO-d$_6$) δ 7.78 (d, J=8.2 Hz, 1H), 7.59 (s, 1H), 7.40 (d, J=8.1 Hz, 1H), 7.03 (t, J=5.5 Hz, 1H), 5.07 (s, 2H), 4.49 (t, J=5.2 Hz, 1H), 3.56 (s, 3H), 3.48 (q, J=6.2 Hz, 2H), 3.39 (q, J=6.8 Hz, 2H), 3.36 (s, 3H), 1.74 (p, J=6.4 Hz, 2H); ESI: m/z 446.2 (M+H)$^+$.

Examples 74 and 75

(±)-1-(1-benzothiophen-5-ylmethyl)-8-{[(cis)-3-hydroxycyclopentyl]amino}-3,7-dimethyl-2,3,6,7-tetrahydro-1H-purine-2,6-dione and (±)-1-(1-benzothiophen-5-ylmethyl)-8-{[(trans)-3-hydroxycyclopentyl]amino}-3,7-dimethyl-2,3,6,7-tetrahydro-1H-purine-2,6-dione

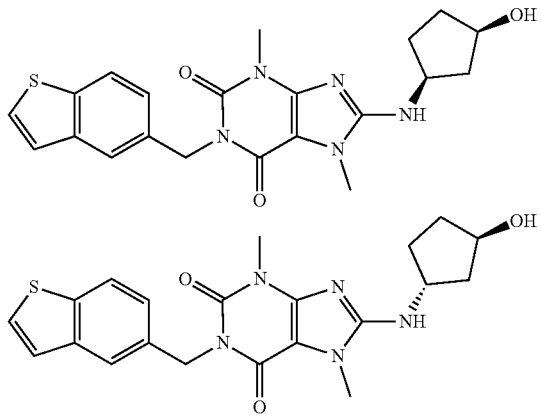

The title compounds were synthesized in a similar fashion as described in Procedure 7B using 1-(benzo[b]thiophen-5-ylmethyl)-8-bromo-3,7-dimethyl-3,7-dihydro-1H-purine-2,6-dione and 3-aminocyclopentan-1-ol. The cis and trans diastereomers were separated by flash chromatography.

Example 74: (±)-1-(1-benzothiophen-5-ylmethyl)-8-{[(cis)-3-hydroxycyclopentyl]amino}-3,7-dimethyl-2,3,6,7-tetrahydro-1H-purine-2,6-dione or (±)-1-(1-benzothiophen-5-ylmethyl)-8-{[(trans)-3-hydroxycyclopentyl]amino}-3,7-dimethyl-2,3,6,7-tetrahydro-1H-purine-2,6-dione; $^1$H NMR (500 MHz, CDCl$_3$) δ 7.94 (d, J=1.3 Hz, 1H), 7.79 (d, J=8.3 Hz, 1H), 7.51 (dd, J=8.3, 1.6 Hz, 1H), 7.38 (d, J=5.4 Hz, 1H), 7.28 (dd, J=5.4, 0.5 Hz, 1H), 5.29 (s, 2H), 4.58-4.41 (m, 2H), 3.97 (d, J=6.7 Hz, 1H), 3.66 (s, 3H), 3.51 (s, 3H), 2.40 (td, J=13.9, 7.8 Hz, 1H), 2.29-2.18 (m, 1H), 2.18-2.06 (m, 1H), 1.80-1.63 (m, 2H), 1.52-1.45 (m, 1H); ESI: m/z 426.1 (M+H)+.

Example 75: (±)-1-(1-benzothiophen-5-ylmethyl)-8-{[(cis)-3-hydroxycyclopentyl]amino}-3,7-dimethyl-2,3,6,7-tetrahydro-1H-purine-2,6-dione or (±)-1-(1-benzothiophen-5-ylmethyl)-8-{[(trans)-3-hydroxycyclopentyl]amino}-3,7-dimethyl-2,3,6,7-tetrahydro-1H-purine-2,6-dione; 1H NMR (500 MHz, CDCl3) δ 7.94 (d, J=1.3 Hz, 1H), 7.79 (d, J=8.3 Hz, 1H), 7.51 (dd, J=8.3, 1.5 Hz, 1H), 7.38 (d, J=5.4 Hz, 1H), 7.29 (d, J=5.4 Hz, 1H), 5.29 (s, 2H), 5.04 (d, J=8.5 Hz, 1H), 4.54-4.43 (m, 1H), 4.43-4.34 (m, 1H), 3.63 (s, 3H), 3.51 (s, 3H), 2.67 (d, J=3.8 Hz, 1H), 2.16-1.94 (m, 3H), 1.93-1.79 (m, 3H); ESI: m/z 426.0 (M+H)+.

Examples 76 and 144

8-((1R,3R)-3-hydroxycyclopentylamino)-3,7-dimethyl-1-(4-(trifluoromethyl)benzyl)-1H-purine-2,6 (3H,7H)-dione and 8-((1S,3S)-3-hydroxycyclopentylamino)-3,7-dimethyl-1-(4-(trifluoromethyl)benzyl)-1H-purine-2,6(3H,7H)-dione

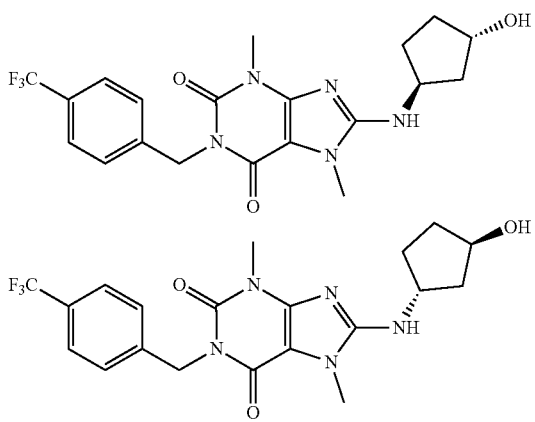

The title compounds were synthesized in a similar fashion as described in Procedure 7A using 8-bromo-3,7-dimethyl-1-(4-(trifluoromethyl)benzyl)-3,7-dihydro-1H-purine-2,6-dione and (±)-(trans)-3-aminocyclopentan-1-ol to provide (±)-8-((trans)-3-hydroxycyclopentylamino)-3,7-dimethyl-1-(4-(trifluoromethyl)benzyl)-1H-purine-2,6(3H,7H)-dione. The enantiomers were separated by chiral SFC using a CHIRALPAK®IC/SFC column eluting with 20% EtOH (0.1% NH4OH) in carbon dioxide.

Example 76: 8-((1R,3R)-3-hydroxycyclopentylamino)-3,7-dimethyl-1-(4-(trifluoromethyl)benzyl)-1H-purine-2,6 (3H,7H)-dione or 8-((1S,3S)-3-hydroxycyclopentylamino)-3,7-dimethyl-1-(4-(trifluoromethyl)benzyl)-1H-purine-2,6 (3H,7H)-dione (ee 99.4%, retention time 3.97 min); 1H NMR (400 MHz, CDCl3) δ 7.57-7.52 (m, 4H), 5.21 (s, 2H), 4.55-4.50 (m, 2H), 4.04 (d, J=6.8 Hz, 1H), 3.65 (s, 3H), 3.51 (s, 3H), 2.43-2.38 (m, 1H), 2.27-2.21 (m, 1H), 2.17-2.10 (m, 1H), 1.78-1.68 (m, 2H), 1.56-1.47 (m, 2H). ESI: m/z 438.1 (M+H)+.

Example 144: 8-((1R,3R)-3-hydroxycyclopentylamino)-3,7-dimethyl-1-(4-(trifluoromethyl)benzyl)-1H-purine-2,6 (3H,7H)-dione or 8-((1S,3S)-3-hydroxycyclopentylamino)-3,7-dimethyl-1-(4-(trifluoromethyl)benzyl)-1H-purine-2,6 (3H,7H)-dione (ee 100%, retention time 3.15 min); 1H NMR (400 MHz, CDCl3) δ 7.57-7.52 (m, 4H), 5.21 (s, 2H), 4.55-4.48 (m, 2H), 4.05 (d, J=6.8 Hz, 1H), 3.65 (s, 3H), 3.51 (s, 3H), 2.43-2.38 (m, 1H), 2.27-2.21 (m, 1H), 2.17-2.10 (m, 1H), 1.78-1.68 (m, 2H), 1.56-1.47 (m, 2H). ESI: m/z 438.1 (M+H)+.

Example 77

(1S,3R)-3-[(3,7-dimethyl-2,6-dioxo-1-{[4-(trifluoromethyl)phenyl]methyl}-2,3,6,7-tetrahydro-1H-purin-8-yl)amino]cyclopentane-1-carboxylic acid

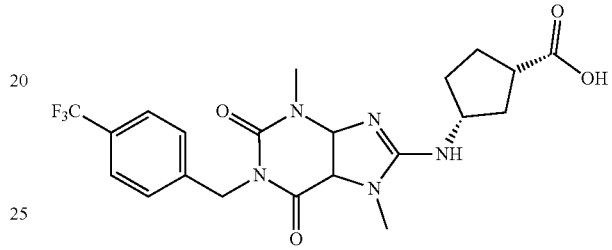

The title compound was synthesized in a similar fashion as described in Procedure 7B using 8-bromo-3,7-dimethyl-1-(4-(trifluoromethyl)benzyl)-3,7-dihydro-1H-purine-2,6-dione and (1S,3R)-3-aminocyclopentane-1-carboxylic acid. 1H NMR (500 MHz, DMSO-d6) δ 12.13 (br s, 1H), 7.65 (d, J=8.2 Hz, 2H), 7.46 (d, J=8.1 Hz, 2H), 7.16 (br s, 1H), 5.09 (s, 2H), 4.20-4.13 (m, 1H), 3.56 (s, 3H), 3.36 (s, 3H), 2.76 (p, J=8.6 Hz, 1H), 2.29-2.19 (m, 1H), 2.01-1.93 (m, 1H), 1.92-1.82 (m, 2H), 1.77 (dt, J=12.7, 8.8 Hz, 1H), 1.67-1.57 (m, 1H); ESI: m/z 466.2 (M+H)+.

Example 173

(±)-1-(3,4-dichlorobenzyl)-8-((cis)-3-hydroxycyclohexylamino)-3,7-dimethyl-1H-purine-2,6(3H,7H)-dione

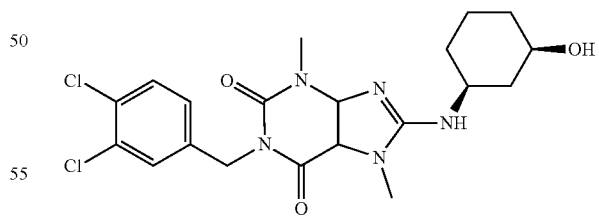

The title compound was synthesized in a similar fashion as described in Procedure 7A using 8-bromo-1-(1-(3,4-dichlorobenzyl)-3,7-dimethyl-3,7-dihydro-1H-purine-2,6-dione and (±)-(cis)-3-aminocyclohexan-1-ol. 1H NMR (400 MHz, DMSO-d6) δ 7.57-7.51 (m, 2H), 7.25 (d, J=8.4 Hz, 1H), 6.85 (d, J=8.0 Hz, 1H), 4.98 (s, 2H), 4.67 (d, J=4.4 Hz, 1H), 3.70-3.66 (m, 1H), 3.56 (s, 3H), 3.47-3.44 (m, 1H), 3.35 (s, 3H), 2.14-2.10 (m, 1H), 1.89-1.78 (m, 2H), 1.72-1.67 (m, 1H), 1.28-1.03 (m, 4H). ESI: m/z 452.0 (M+H)+.

Examples 78 and 79

1-(3,4-dichlorobenzyl)-8-((1S,3R)-3-hydroxycyclohexylamino)-3,7-dimethyl-1H-purine-2,6(3H,7H)-dione and 1-(3,4-dichlorobenzyl)-8-((1R,3S)-3-hydroxycyclohexylamino)-3,7-dimethyl-1H-purine-2,6(3H,7H)-dione

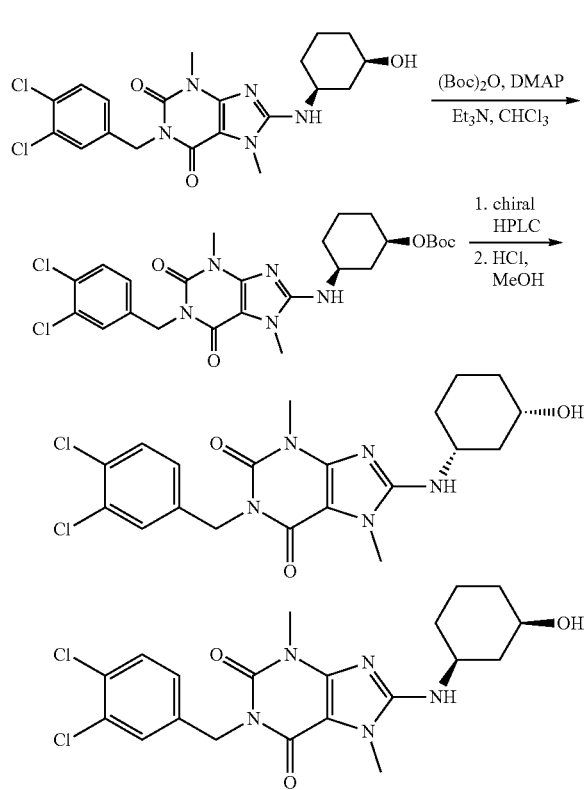

tert-butyl (±)-(cis)-3-(1-(3,4-dichlorobenzyl)-3,7-dimethyl-2,6-dioxo-2,3,6,7-tetrahydro-1H-purin-8-ylamino)cyclohexyl carbonate

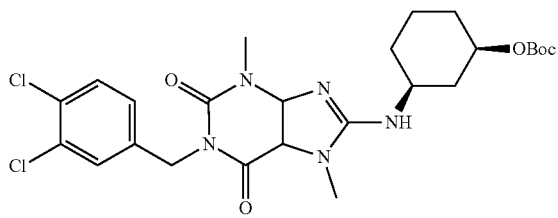

To a solution of (±)-1-(3,4-dichlorobenzyl)-8-((cis)-3-hydroxycyclohexylamino)-3,7-dimethyl-1H-purine-2,6(3H,7H)-dione (275 mg, 0.608 mmol), Et₃N (246.1 mg, 2.43 mmol) and DMAP (22.3 mg, 0.182 mmol) in CHCl₃ (5 mL) was added dropwise a solution of Boc₂O (265.4 mg, 1.22 mmol) in CHCl₃ (2 mL) at 0° C. The mixture was heated to reflux and stirred for 2 h. The reaction mixture was diluted with DCM (30 mL) and washed with water (1*30 mL) and brine (1*30 mL), dried over Na₂SO₄, concentrated and purified by column chromatography (10~30% EA/PE). ESI: m/z 552.2 (M+H)⁺.

1-(3,4-dichlorobenzyl)-8-((1S,3R)-3-hydroxycyclohexylamino)-3,7-dimethyl-1H-purine-2,6(3H,7H)-dione and 1-(3,4-dichlorobenzyl)-8-((1R,3S)-3-hydroxycyclohexylamino)-3,7-dimethyl-1H-purine-2,6(3H,7H)-dione

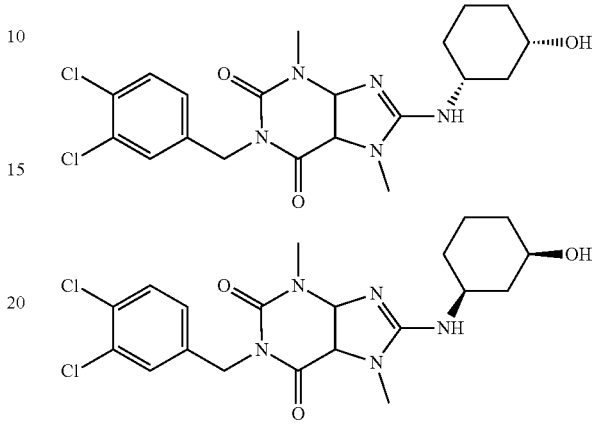

(±)-tert-Butyl (1R,3S)-3-(1-(3,4-dichlorobenzyl)-3,7-dimethyl-2,6-dioxo-2,3,6,7-tetrahydro-1H-purin-8-ylamino)cyclohexyl carbonate (185 mg, 0.33 mmol) was purified by chiral SFC using an CHIRALPAK® AD-H/SFC AD column eluting with 35% MeOH (0.1% NH₄OH) in carbon dioxide to obtain tert-butyl (1R,3S)-3-(1-(3,4-dichlorobenzyl)-3,7-dimethyl-2,6-dioxo-2,3,6,7-tetrahydro-1H-purin-8-ylamino)cyclohexyl carbonate or tert-butyl (1S,3R)-3-(1-(3,4-dichlorobenzyl)-3,7-dimethyl-2,6-dioxo-2,3,6,7-tetrahydro-1H-purin-8-ylamino)cyclohexyl carbonate (ee 99.76%, retention time 3.3 min); ESI: m/z 552.1 (M+H)⁺ and tert-butyl (1R,3S)-3-(1-(3,4-dichlorobenzyl)-3,7-dimethyl-2,6-dioxo-2,3,6,7-tetrahydro-1H-purin-8-ylamino)cyclohexyl carbonate or tert-butyl (1S,3R)-3-(1-(3,4-dichlorobenzyl)-3,7-dimethyl-2,6-dioxo-2,3,6,7-tetrahydro-1H-purin-8-ylamino)cyclohexyl carbonate (ee 99.95%, retention time 5.08 min); ESI: m/z 552.0 (M+H)⁺.

The individual enantiomers (60 mg, 0.109 mmol) were independently treated with HCl/MeOH (2 mL, 2M) and the mixture was stirred for 1 h at 25° C. The reaction mixtures were made basic with aqueous NaHCO₃ solution to pH=9 and extracted with EA (2*20 mL). The combined organic fractions were washed with brine (1*30 mL), dried over Na₂SO₄, concentrated and purified by column chromatography (30~100% EA/PE).

Example 79: 1-(3,4-dichlorobenzyl)-8-((1S,3R)-3-hydroxycyclohexylamino)-3,7-dimethyl-1H-purine-2,6(3H,7H)-dione or 1-(3,4-dichlorobenzyl)-8-((1R,3S)-3-hydroxycyclohexylamino)-3,7-dimethyl-1H-purine-2,6(3H,7H)-dione; ¹H NMR (400 MHz, DMSO-d₆) δ 7.57-7.51 (m, 2H), 7.27-7.24 (m, 1H), 6.86 (d, J=8.4 Hz, 1H), 4.98 (s, 2H), 4.68 (d, J=4.4 Hz, 1H), 3.69-3.66 (m, 2H), 3.56 (s, 3H), 3.47-3.44 (m, 2H), 3.35 (s, 3H), 2.14-2.10 (m, 1H), 1.89-1.78 (m, 2H), 1.72-1.67 (m, 1H), 1.28-1.03 (m, 4H); ESI: m/z 452.0 (M+H)⁺.

Example 78: 1-(3,4-dichlorobenzyl)-8-((1S,3R)-3-hydroxycyclohexylamino)-3,7-dimethyl-1H-purine-2,6(3H,7H)-dione or 1-(3,4-dichlorobenzyl)-8-((1R,3S)-3-hydroxycyclohexylamino)-3,7-dimethyl-1H-purine-2,6(3H,7H)-dione; ¹H NMR (400 MHz, DMSO-d₆) δ 7.57-7.51 (m, 2H), 7.27-7.24 (m, 1H), 6.86 (d, J=8.4 Hz, 1H), 4.98 (s, 2H), 4.68

(d, J=4.4 Hz, 1H), 3.69-3.66 (m, 2H), 3.56 (s, 3H), 3.47-3.44 (m, 2H), 3.35 (s, 3H), 2.14-2.10 (m, 1H), 1.89-1.78 (m, 2H), 1.72-1.67 (m, 1H), 1.28-1.03 (m, 4H); ESI: m/z 452.0 (M+H)⁺.

Example 172

(±)-1-(3,4-dichlorobenzyl)-8-((trans)-3-hydroxycyclohexylamino)-3,7-dimethyl-1H-purine-2,6(3H,7H)-dione

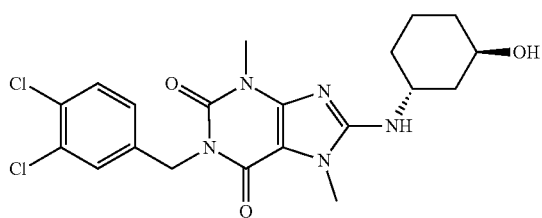 [SMILES: Cn1c(N[C@@H]2CCC[C@@H](O)C2)nc2c1c(=O)n(Cc1ccc(Cl)c(Cl)c1)c(=O)n2C]

The title compound was synthesized in a similar fashion as described in Procedure 7A using 8-bromo-1-(1-(3,4-dichlorobenzyl)-3,7-dimethyl-3,7-dihydro-1H-purine-2,6-dione and (trans)-3-aminocyclohexan-1-ol. ¹H NMR (400 MHz, DMSO-d₆) δ 7.54 (dd, J=14.7, 5.1 Hz, 2H), 7.26 (dd, J=8.4, 2.0 Hz, 1H), 6.70 (d, J=7.9 Hz, 1H), 4.98 (s, 2H), 4.47 (d, J=3.2 Hz, 1H), 4.07 (s, 1H), 3.99 (s, 1H), 3.56 (s, 3H), 3.35 (s, 3H), 1.94-1.74 (m, 2H), 1.73-1.43 (m, 4H), 1.44-1.26 (m, 2H); ESI: m/z 452.1 (M+H)⁺.

Example 80 and 81

1-(3,4-dichlorobenzyl)-8-((1S,3S)-3-hydroxycyclohexylamino)-3,7-dimethyl-1H-purine-2,6(3H,7H)-dione and 1-(3,4-dichlorobenzyl)-8-((1R,3R)-3-hydroxycyclohexylamino)-3,7-dimethyl-1H-purine-2,6(3H,7H)-dione

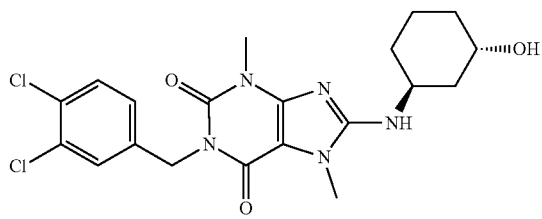

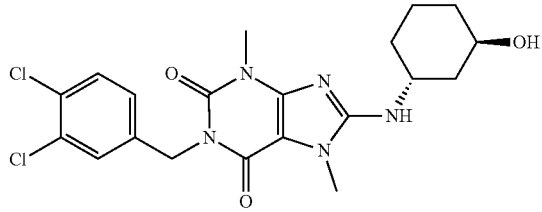

(±)-1-(3,4-Dichlorobenzyl)-8-((trans)-3-hydroxycyclohexylamino)-3,7-dimethyl-1H-purine-2,6(3H,7H)-dione (270 mg, 0.60 mmol) was purified by chiral SFC using a AD column eluting with 35% MeOH (0.1% NH₄OH) in carbon dioxide to obtain 1-(3,4-dichlorobenzyl)-8-((1S,3S)-3-hydroxycyclohexylamino)-3,7-dimethyl-1H-purine-2,6(3H,7H)-dione or 1-(3,4-dichlorobenzyl)-8-((1R,3R)-3-hydroxycyclohexylamino)-3,7-dimethyl-1H-purine-2,6(3H,7H)-dione Example 81: (ee 99.63%, retention time 4.4 min); ¹H NMR (400 MHz, DMSO-d6-d₆) δ 7.57-7.51 (m, 2H), 7.27-7.24 (m, 1H), 7.70 (d, J=7.6 Hz, 1H), 4.98 (s, 2H), 4.47 (d, J=3.2 Hz, 1H), 4.08-3.98 (m, 2H), 3.56 (s, 3H), 3.35 (s, 3H), 1.86-1.80 (m, 2H), 1.68-1.47 (m, 4H), 1.41-1.28 (m, 2H); ESI: m/z 452.1 (M+H)⁺ and 1-(3,4-dichlorobenzyl)-8-((1S,3S)-3-hydroxycyclohexylamino)-3,7-dimethyl-1H-purine-2,6(3H,7H)-dione or 1-(3,4-dichlorobenzyl)-8-((1R,3R)-3-hydroxycyclohexylamino)-3,7-dimethyl-1H-purine-2,6(3H,7H)-dione Example 80: (ee 98.47%, retention time 5.57 min); ¹H NMR (400 MHz, DMSO-d₆) δ 7.57-7.51 (m, 2H), 7.27-7.24 (m, 1H), 7.70 (d, J=7.6 Hz, 1H), 4.98 (s, 2H), 4.47 (d, J=3.2 Hz, 1H), 4.08-3.98 (m, 2H), 3.56 (s, 3H), 3.35 (s, 3H), 1.86-1.80 (m, 2H), 1.68-1.47 (m, 4H), 1.41-1.28 (m, 2H); ESI: m/z 452.0 (M+H)⁺.

Examples 82 and 83

(S)-1-(3,4-dichlorobenzyl)-3,7-dimethyl-8-(6-oxopiperidin-3-ylamino)-1H-purine-2,6(3H,7H)-dione and (R)-1-(3,4-dichlorobenzyl)-3,7-dimethyl-8-(6-oxopiperidin-3-ylamino)-1H-purine-2,6(3H,7H)-dione

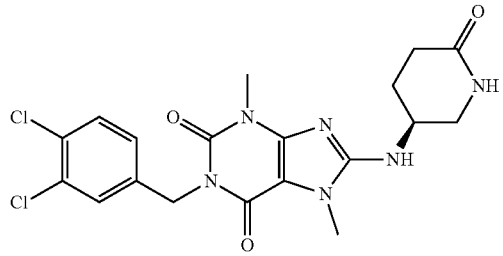

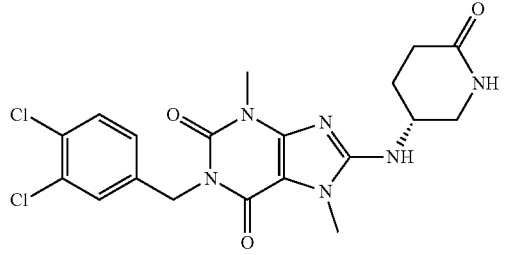

The title compounds were made in a similar fashion as described in Procedure 7A using 8-bromo-1-(3,4-dichlorobenzyl)-3,7-dimethyl-1H-purine-2,6(3H,7H)-dione and 5-aminopiperidin-2-one hydrochloride. The crude was purified by Prep-HPLC using a Method D (30-70 ACN) to give the racemic product. ESI: m/z 451.0 (M+H)⁺. The individual enantiomers were separated by chiral SFC using a AD-H column eluting with 45% MeOH (0.5% NH₄OH) in carbon dioxide to give (S)-1-(3,4-dichlorobenzyl)-3,7-dimethyl-8-(6-oxopiperidin-3-ylamino)-1H-purine-2,6(3H,7H)-dione or (R)-1-(3,4-dichlorobenzyl)-3,7-dimethyl-8-(6-oxopiperidin-3-ylamino)-1H-purine-2,6(3H,7H)-dione Example 83: (ee 100%, retention time 9 min); ¹H NMR (400 MHz, DMSO-d₆) δ 7.79 (s, 1H), 7.59-7.49 (m, 2H), 7.25 (dd, J=8.4, 2.1 Hz, 1H), 7.19 (s, 1H), 4.99 (s, 2H), 3.83-3.74 (m, 1H), 3.58 (s, 3H), 3.35 (s, 3H), 2.26-2.03 (m, 3H), 1.84-1.69 (m, 1H); ESI: m/z 451.0 (M+H)⁺ and (S)-1-(3,4-dichlorobenzyl)-3,7-dimethyl-8-(6-oxopiperidin-3-ylamino)-1H-purine-2,6(3H,7H)-dione or (R)-1-(3,4-dichlorobenzyl)-3,7-dimethyl-8-(6-oxopiperidin-3-ylamino)-1H-purine-2,6(3H, 7H)-dione Example 82: (ee 100%, retention time 6.61 min); ¹H NMR (400 MHz, DMSO-d₆) δ 7.78 (s, 1H), 7.59-7.49 (m, 2H), 7.25 (dd, J=8.3, 2.2 Hz, 1H), 7.17 (t, J=5.8 Hz, 1H), 4.99 (s, 2H), 3.79 (t, J=6.0 Hz, 1H), 3.58 (s, 3H), 3.35 (s, 5H), 2.26-2.14 (m, 1H), 2.14-2.03 (m, 2H), 1.84-1.69 (m, 1H); ESI: m/z 451.0 (M+H)⁺.

Example 84

(±)-1-(3,4-dichlorobenzyl)-8-(((cis)-3-(dimethyl-amino)cyclohexyl)amino)-3,7-dimethyl-3,7-dihydro-1H-purine-2,6-dione or (±)-1-(3,4-dichlorobenzyl)-8-(((trans)-3-(dimethylamino)cyclohexyl)amino)-3,7-dimethyl-3,7-dihydro-1H-purine-2,6-dione

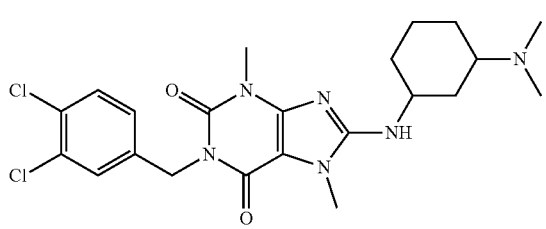 [SMILES: CN(C)C1CCCC(Nc2nc3c(c(=O)n(Cc4ccc(Cl)c(Cl)c4)c(=O)n3C)n2C)C1]

The title compound was made in a similar fashion as described in Procedure 7B using 8-bromo-1-(3,4-dichlorobenzyl)-3,7-dimethyl-1H-purine-2,6(3H,7H)-dione and N¹,N¹-dimethylcyclohexane-1,3-diamine. The mixture was purified by prep-HPLC to yield the product as a single diastereomer of unknown relative and absolute configuration. ¹H NMR (500 MHz, DMSO-d₆) δ 7.55 (d, J=8.3 Hz, 1H), 7.51 (d, J=2.0 Hz, 1H), 7.26 (dd, J=8.3, 2.0 Hz, 1H), 6.89 (d, J=7.9 Hz, 1H), 4.98 (s, 2H), 3.75-3.64 (m, 1H), 3.56 (s, 3H), 3.35 (s, 3H), 2.35-2.27 (m, 1H), 2.19 (s, 6H), 2.10-2.04 (m, 1H), 1.96-1.88 (m, 1H), 1.81-1.71 (m, 2H), 1.33-1.15 (m, 3H), 1.15-1.04 (m, 1H); ESI: m/z 479.2 (M+H)⁺.

Example 85

8-((3-aminocyclohexyl)amino)-1-(3,4-dichlorobenzyl)-3,7-dimethyl-3,7-dihydro-1H-purine-2,6-dione

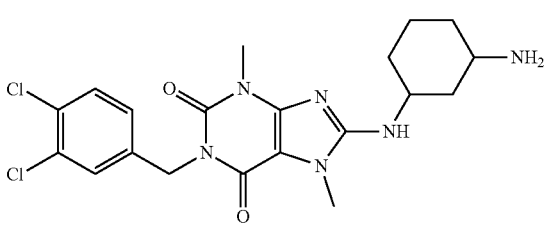 [SMILES: Cn1c(NC2CCCC(N)C2)nc2c1c(=O)n(Cc1ccc(Cl)c(Cl)c1)c(=O)n2C]

The title compound was made in a similar fashion as described in Procedure 7B using 8-bromo-1-(3,4-dichlorobenzyl)-3,7-dimethyl-1H-purine-2,6(3H,7H)-dione and N-Boc-cyclohexane-1,3-diamine followed by Boc-deprotection as described in Procedure 6. ¹H NMR (500 MHz, DMSO-d₆) δ 7.96 (s, 2H), 7.91 (s, 1H), 7.59-7.54 (m, 1H), 7.54-7.49 (m, 1H), 7.29-7.22 (m, 1H), 7.02 (d, J=8.0 Hz, 0.6H), 6.71 (d, J=6.6 Hz, 0.4H), 5.04-4.95 (m, 2H), 4.19-4.10 (m, 0.4H), 3.80-3.69 (m, 0.6H), 3.58 (s, 1.8H), 3.57 (s, 1.8H), 3.48 (s, 1.2H), 3.36 (s, 1.2H), 3.19-3.09 (m, 0.6H), 2.28-2.21 (m, 0.6H), 2.09-2.01 (m, 0.4H), 1.97-1.88 (m, 1.4H), 1.85-1.59 (m, 3H), 1.52-1.33 (m, 1.6H), 1.30-1.17 (m, 1.4H); ESI: m/z 451.2 (M+H)⁺.

Example 86

1-[(3,4-dichlorophenyl)methyl]-3,7-dimethyl-8-[(2-oxopyrrolidin-3-yl)amino]-2,3,6,7-tetrahydro-1H-purine-2,6-dione

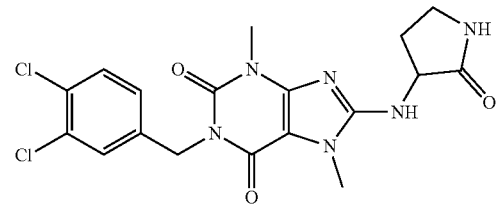 [SMILES: Cn1c(NC2CCNC2=O)nc2c1c(=O)n(Cc1ccc(Cl)c(Cl)c1)c(=O)n2C]

The title compound was made in a similar fashion as described in Procedure 7B using 8-bromo-1-(3,4-dichlorobenzyl)-3,7-dimethyl-1H-purine-2,6(3H,7H)-dione and 3-aminopyrrolidin-2-one. ¹H NMR (500 MHz, DMSO-d₆) δ 7.89 (s, 1H), 7.54 (d, J=8.4 Hz, 1H), 7.52 (s, 1H), 7.34 (d, J=8.1 Hz, 1H), 7.25 (d, J=7.8 Hz, 1H), 4.99 (s, 2H), 4.51 (q, J=8.6 Hz, 1H), 3.59 (s, 3H), 3.34 (s, 3H), 3.26-3.22 (m, 2H), 2.45-2.39 (m, 1H), 2.01 (p, J=10.0, 1H); ESI: m/z 437.1 (M+H)⁺.

Example 87

(1R,3S)-3-{[1-(1-benzothiophen-5-ylmethyl)-3,7-dimethyl-2,6-dioxo-2,3,6,7-tetrahydro-1H-purin-8-yl]amino}cyclopentane-1-carboxylic acid

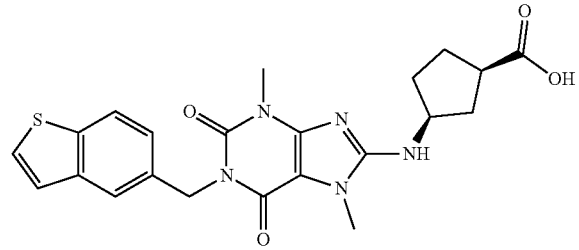 [SMILES: Cn1c(N[C@H]2CC[C@@H](C(=O)O)C2)nc2c1c(=O)n(Cc1ccc3sccc3c1)c(=O)n2C]

The title compound was synthesized in a similar fashion as described in Procedure 7B using 1-(benzo[b]thiophen-5-ylmethyl)-8-bromo-3,7-dimethyl-3,7-dihydro-1H-purine-2,6-dione and (1R,3S)-3-aminocyclopentane-1-carboxylic acid. ¹H NMR (500 MHz, DMSO-d₆) δ 12.12 (s, 1H), 7.91 (d, J=8.3 Hz, 1H), 7.75 (s, 1H), 7.73 (d, J=5.4 Hz, 1H), 7.43 (d, J=5.4 Hz, 1H), 7.34 (dd, J=8.4, 1.2 Hz, 1H), 7.10 (s, 1H), 5.13 (s, 2H), 4.17 (h, J=7.3 Hz, 1H), 3.58 (s, 3H), 3.37 (s, 3H), 2.76 (p, J=8.6 Hz, 1H), 2.31-2.20 (m, 1H), 2.04-1.93 (m, 1H), 1.93-1.83 (m, 2H), 1.78 (dt, J=12.7, 8.9 Hz, 1H), 1.67-1.58 (m, 1H); ESI: m/z 454.2 (M+H)⁺.

Example 88

(±)-1-[(3,4-dichlorophenyl)methyl]-3,7-dimethyl-8-[(5-oxopyrrolidin-3-yl)amino]-2,3,6,7-tetrahydro-1H-purine-2,6-dione

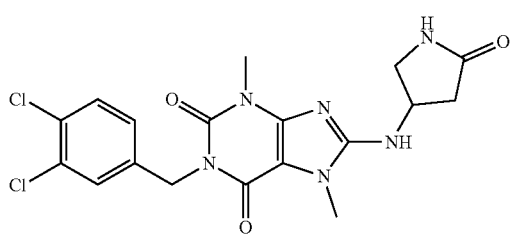 [SMILES: Cn1c(NC2CNC(=O)C2)nc2c1c(=O)n(Cc1ccc(Cl)c(Cl)c1)c(=O)n2C]

The title compound was made in a similar fashion as described in Procedure 7B using 8-bromo-1-(3,4-dichlorobenzyl)-3,7-dimethyl-1H-purine-2,6(3H,7H)-dione and 4-aminopyrrolidin-2-one. $^1$H NMR (500 MHz, DMSO-$d_6$) δ 7.66 (s, 1H), 7.55 (d, J=8.3 Hz, 1H), 7.52 (d, J=1.9 Hz, 1H), 7.35 (d, J=6.5 Hz, 1H), 7.26 (dd, J=8.4, 1.9 Hz, 1H), 4.99 (s, 2H), 4.54-4.44 (m, 1H), 3.62 (dd, J=9.9, 7.1 Hz, 1H), 3.58 (s, 3H), 3.36 (s, 3H), 3.18 (dd, J=10.1, 4.2 Hz, 1H), 2.58 (dd, J=16.8, 8.3 Hz, 1H), 2.24 (dd, J=16.8, 5.1 Hz, 1H); ESI: m/z 437.1 (M+H)$^+$.

Example 89

(±)-1-[(3,4-dichlorophenyl)methyl]-3,7-dimethyl-8-[(2-oxopiperidin-3-yl)amino]-2,3,6,7-tetrahydro-1H-purine-2,6-dione

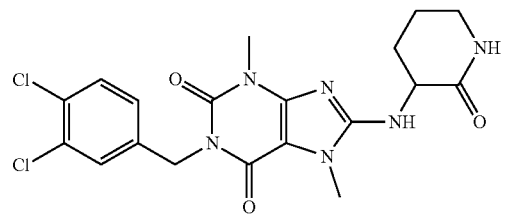 [SMILES: Cn1c(NC2CCCNC2=O)nc2c1c(=O)n(Cc1ccc(Cl)c(Cl)c1)c(=O)n2C]

The title compound was made in a similar fashion as described in Procedure 7B using 8-bromo-1-(3,4-dichlorobenzyl)-3,7-dimethyl-1H-purine-2,6(3H,7H)-dione and 3-aminopiperidin-2-one. $^1$H NMR (500 MHz, DMSO-$d_6$) δ 7.66 (s, 1H), 7.54 (d, J=8.4 Hz, 1H), 7.52 (d, J=1.3 Hz, 1H), 7.25 (d, J=8.1 Hz, 2H), 4.99 (s, 2H), 4.29 (q, J=8.4, 8.0 Hz, 1H), 3.58 (s, 3H), 3.34 (s, 3H), 3.20-3.15 (m, 2H), 2.14-2.06 (m, 1H), 1.92-1.75 (m, 3H); ESI: m/z 451.1 (M+H)$^+$.

Example 90

1-[(3,4-dichlorophenyl)methyl]-8-[(3-hydroxypropyl)amino]-3-methyl-2,3,6,7-tetrahydro-1H-purine-2,6-dione

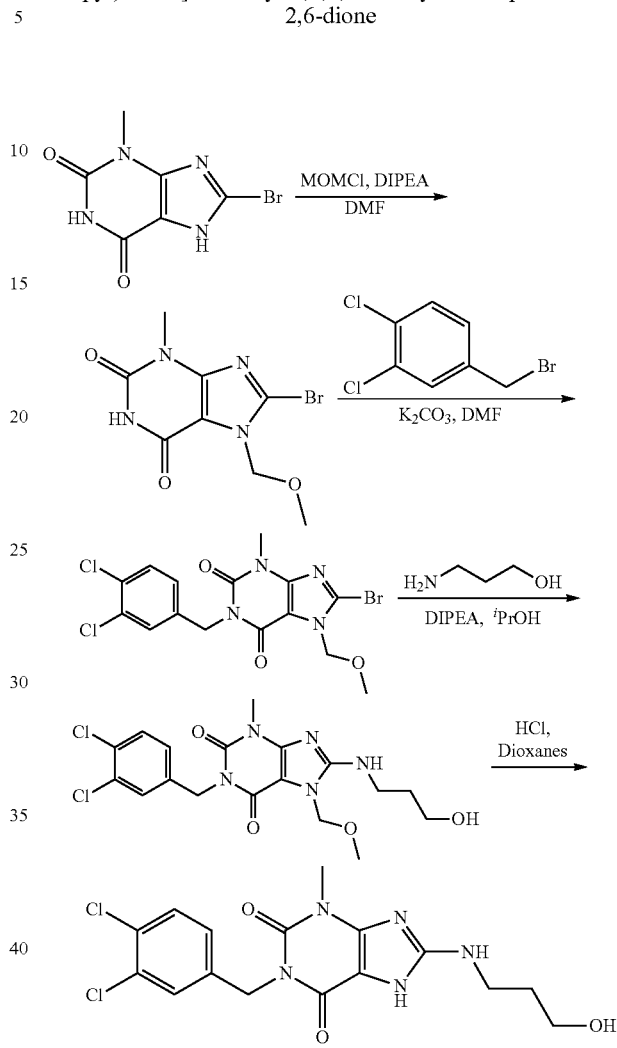

8-bromo-7-(methoxymethyl)-3-methyl-3,7-dihydro-1H-purine-2,6-dione

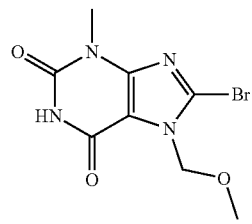 [SMILES: COCn1c(Br)nc2c1c(=O)[nH]c(=O)n2C]

8-Bromo-3-methyl-3,7-dihydro-1H-purine-2,6-dione (1.0 g, 4.1 mmol) was suspended in DMF (14 ml) and DIEA (820 µl, 4.9 mmol) was added. Once full dissolution had occurred chloromethyl methylether (362 µl, 4.3 mmol) was added and the reaction was stirred at room temperature. After 2 h the solid was collected by filtration, washed with water and dried in vacuo. ESI: m/z 288.9 (M+H)$^+$.

8-Bromo-1-(3,4-dichlorobenzyl)-7-(methoxymethyl)-3-methyl-3,7-dihydro-1H-purine-2,6-dione

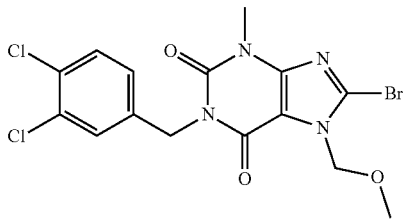 [SMILES: COCn1c(Br)nc2c1c(=O)n(Cc1ccc(Cl)c(Cl)c1)c(=O)n2C]

3,4-Dichlorobenzylbromide (377 μl, 2.6 mmol) was added to a suspension of 8-bromo-7-(methoxymethyl)-3-methyl-3,7-dihydro-1H-purine-2,6-dione (500 mg, 1.7 mmol) and potassium carbonate (477 mg, 3.5 mmol) in DMF (8 ml). The reaction was heated to 90° C. After 1 h the reaction was cooled and poured into water. The aqueous layer was extracted into ethyl acetate three times. The combined organic fractions were washed with sat. NaCl, dried over MgSO$_4$ and concentrated in vacuo. The residue was purified by flash chromatography (0-80% ethyl acetate/heptane). ESI: m/z 448.9 (M+H)$^+$.

1-(3,4-Dichlorobenzyl)-8-((3-hydroxypropyl)amino)-7-(methoxymethyl)-3-methyl-3,7-dihydro-1H-purine-2,6-dione

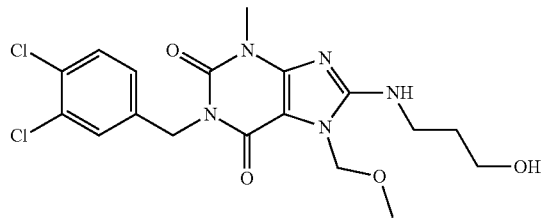 [SMILES: COCn1c(NCCCO)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-7-(methoxymethyl)-3-methyl-3,7-dihydro-1H-purine-2,6-dione and 3-aminopropan-1-ol. ESI: m/z 442.0 (M+H)$^+$.

1-[(3,4-dichlorophenyl)methyl]-8-[(3-hydroxypropyl)amino]-3-methyl-2,3,6,7-tetrahydro-1H-purine-2,6-dione

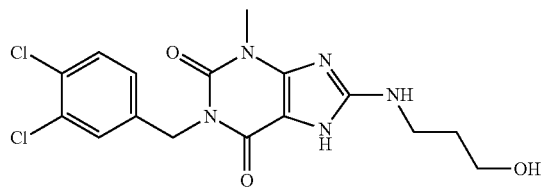 [SMILES: Cn1c(=O)n(Cc2ccc(Cl)c(Cl)c2)c(=O)c2[nH]c(NCCCO)nc21]

HCl in dioxane (197 μl) was added to a solution of 1-(3,4-dichlorobenzyl)-8-((3-hydroxypropyl)amino)-7-(methoxymethyl)-3-methyl-3,7-dihydro-1H-purine-2,6-dione (87 mg, 0.2 mmol) in methanol (2 ml). The reaction was stirred at room temperature for 72 h. Additional 4M HCl in dioxane (2 ml) was added and the reaction heated to 70° C. for 48 h. The solvent was removed in vacuo and the residue was purified by prep HPLC (acetonitrile/water, 0.1% formic acid) to provide the title compound. $^1$H NMR (500 MHz, DMSO-d$_6$) δ 11.56-11.34 (s, 1H), 7.55 (d, J=8.3 Hz, 1H), 7.51 (s, 1H), 7.25 (d, J=6.8 Hz, 1H), 7.15 (t, J=5.6 Hz, 1H), 5.00 (s, 2H), 4.49 (s, 1H), 3.46 (t, J=6.2 Hz, 2H), 3.34 (s, 3H), 3.26 (q, J=6.7 Hz, 2H), 1.66 (p, J=6.5 Hz, 2H); ESI: m/z: 398.1 (M+H)$^+$.

Example 91

(±)-1-[(3,4-dichlorophenyl)methyl]-8-{[(trans)-2-hydroxycyclohexyl]amino}-3,7-dimethyl-2,3,6,7-tetrahydro-1H-purine-2,6-dione±

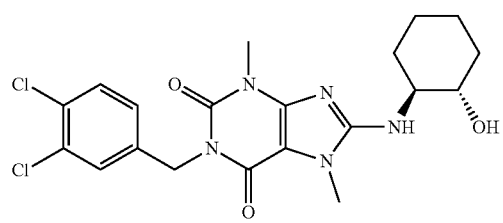 [SMILES: Cn1c(N[C@H]2CCCC[C@@H]2O)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (trans)-2-aminocyclohexan-1-ol. $^1$H NMR (500 MHz, DMSO-d$_6$) δ 7.55 (d, J=8.3 Hz, 1H), 7.51 (d, J=2.0 Hz, 1H), 7.25 (dd, J=8.3, 2.0 Hz, 1H), 6.73 (d, J=8.0 Hz, 1H), 4.99 (s, 2H), 4.65 (d, J=4.6 Hz, 1H), 3.57 (s, 3H), 3.57-3.48 (m, 1H), 3.45-3.38 (m, 1H), 3.35 (s, 3H), 1.92 (t, J=11.2 Hz, 2H), 1.65 (d, J=7.2 Hz, 2H), 1.34-1.13 (m, 4H); ESI: m/z 452.2 (M+H)$^+$.

Example 92

1-[(3,4-dichlorophenyl)methyl]-8-{[(1S,2S)-2-hydroxycyclopentyl]amino}-3,7-dimethyl-2,3,6,7-tetrahydro-1H-purine-2,6-dione

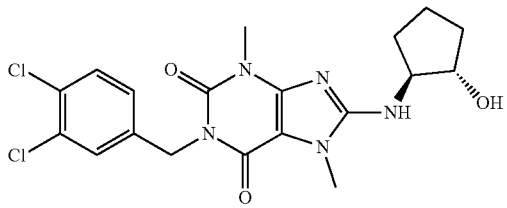 [SMILES: Cn1c(N[C@H]2CCC[C@@H]2O)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (1S,2S)-2-aminocyclopentan-1-ol. $^1$H NMR (500 MHz, DMSO-d$_6$) δ 7.55 (d, J=8.3 Hz, 1H), 7.51 (d, J=1.9 Hz, 1H), 7.25 (dd, J=8.3, 2.0 Hz, 1H), 6.86 (d, J=6.9 Hz, 1H), 4.99 (s, 2H), 4.83 (d, J=4.2 Hz, 1H), 3.99 (p, J=5.4 Hz, 1H), 3.89 (p, J=6.7 Hz, 1H), 3.57 (s, 3H), 3.36 (s, 3H), 2.11-2.03 (m, 1H), 1.95-1.80 (m, 1H), 1.78-1.56 (m, 2H), 1.56-1.40 (m, 2H); ESI: m/z 438.2 (M+H)$^+$.

Example 93

1-[(3,4-dichlorophenyl)methyl]-8-{[(1R,2R)-2-hydroxycyclopentyl]amino}-3,7-dimethyl-2,3,6,7-tetrahydro-1H-purine-2,6-dione

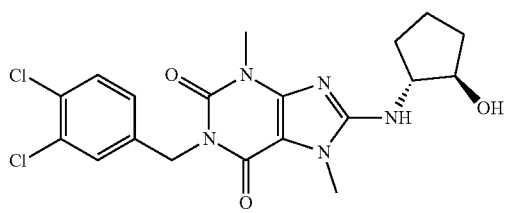 [SMILES: Cn1c(N[C@@H]2CCC[C@H]2O)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (1R,2R)-2-aminocyclopentan-1-ol. $^1$H NMR (500 MHz, DMSO-$d_6$) δ 7.54 (d, J=8.3 Hz, 1H), 7.51 (d, J=1.9 Hz, 1H), 7.25 (dd, J=8.3, 2.0 Hz, 1H), 6.86 (d, J=6.9 Hz, 1H), 4.98 (s, 2H), 4.83 (s, 1H), 3.98 (q, J=5.8 Hz, 1H), 3.88 (p, J=7.1 Hz, 1H), 3.57 (s, 3H), 3.35 (s, 3H), 2.11-2.03 (m, 1H), 1.93-1.82 (m, 1H), 1.72-1.57 (m, 2H), 1.55-1.42 (m, 2H); ESI: m/z 438.2 (M+H)$^+$.

Example 94

1-[(3,4-dichlorophenyl)methyl]-8-{[(1S,2R)-2-hydroxycyclopentyl]amino}-3,7-dimethyl-2,3,6,7-tetrahydro-1H-purine-2,6-dione

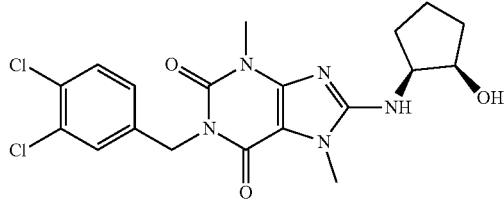 [SMILES: Cn1c(N[C@H]2CCC[C@H]2O)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (1S,2R)-2-aminocyclopentan-1-ol. $^1$H NMR (500 MHz, DMSO-$d_6$) δ 7.56 (d, J=8.3 Hz, 1H), 7.52 (d, J=1.9 Hz, 1H), 7.26 (dd, J=8.3, 2.0 Hz, 1H), 6.57 (d, J=7.8 Hz, 1H), 5.00 (s, 2H), 4.66 (d, J=2.9 Hz, 1H), 4.10 (s, 1H), 4.04-3.88 (m, 1H), 3.61 (s, 3H), 3.36 (s, 3H), 1.92-1.85 (m, 1H), 1.84-1.66 (m, 3H), 1.66-1.57 (m, 1H), 1.55-1.47 (m, 1H); ESI: m/z 438.2 (M+H)$^+$.

Example 95

(±)-1-[(3,4-dichlorophenyl)methyl]-8-{[(cis)-2-hydroxycyclohexyl]amino}-3,7-dimethyl-2,3,6,7-tetrahydro-1H-purine-2,6-dione

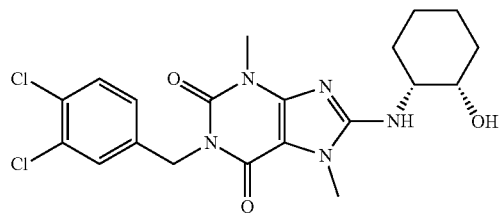 [SMILES: Cn1c(N[C@@H]2CCCC[C@@H]2O)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and (cis)-2-aminocyclohexan-1-ol. $^1$H NMR (500 MHz, DMSO-$d_6$) δ 7.55 (d, J=8.3 Hz, 1H), 7.51 (d, J=1.8 Hz, 1H), 7.25 (dd, J=8.3, 1.9 Hz, 1H), 6.43 (d, J=7.9 Hz, 1H), 4.99 (s, 2H), 4.65 (s, 1H), 3.93 (s, 1H), 3.76-3.70 (m, 1H), 3.60 (s, 3H), 3.34 (s, 3H), 1.80-1.69 (m, 2H), 1.69-1.63 (m, 1H), 1.61-1.50 (m, 2H), 1.47 (d, J=12.8 Hz, 1H), 1.38-1.20 (m, 2H) ESI: m/z 452.2 (M+H)$^+$.

Example 96

1-[(4-chloro-3-methoxyphenyl)methyl]-8-[(3-hydroxypropyl)amino]-3,7-dimethyl-2,3,6,7-tetrahydro-1H-purine-2,6-dione

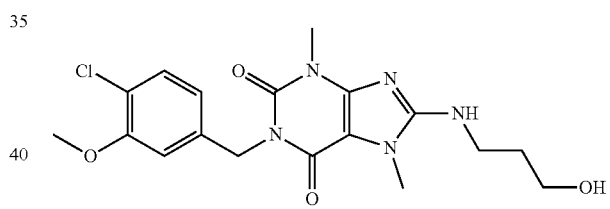

The title compound was made in a similar fashion as described in Procedure 7B using 8-bromo-1-(4-chloro-3-methoxybenzyl)-3,7-dimethyl-3,7-dihydro-1H-purine-2,6-dione and 3-aminopropan-1-ol. $^1$H NMR (500 MHz, DMSO-$d_6$) δ 7.30 (d, J=8.1 Hz, 1H), 7.10 (s, 1H), 7.00 (t, J=5.4 Hz, 1H), 6.76 (d, J=8.1 Hz, 1H), 4.99 (s, 2H), 4.50 (t, J=5.2 Hz, 1H), 3.82 (s, 3H), 3.55 (s, 3H), 3.48 (q, J=6.0 Hz, 2H), 3.39 (q, J=6.4 Hz, 2H), 3.35 (s, 3H), 1.73 (p, J=6.5 Hz, 2H); ESI: m/z 408.2 (M+H)$^+$.

Example 97

1-[(3,4-dichlorophenyl)methyl]-8-[(3-hydroxypropyl)amino]-7-methyl-2,3,6,7-tetrahydro-1H-purine-2,6-dione

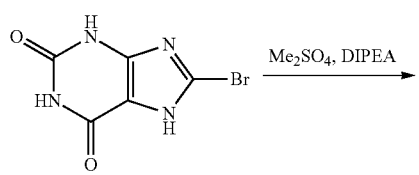

151
-continued

152
8-bromo-3-(methoxymethyl)-7-methyl-3,7-dihydro-1H-purine-2,6-dione

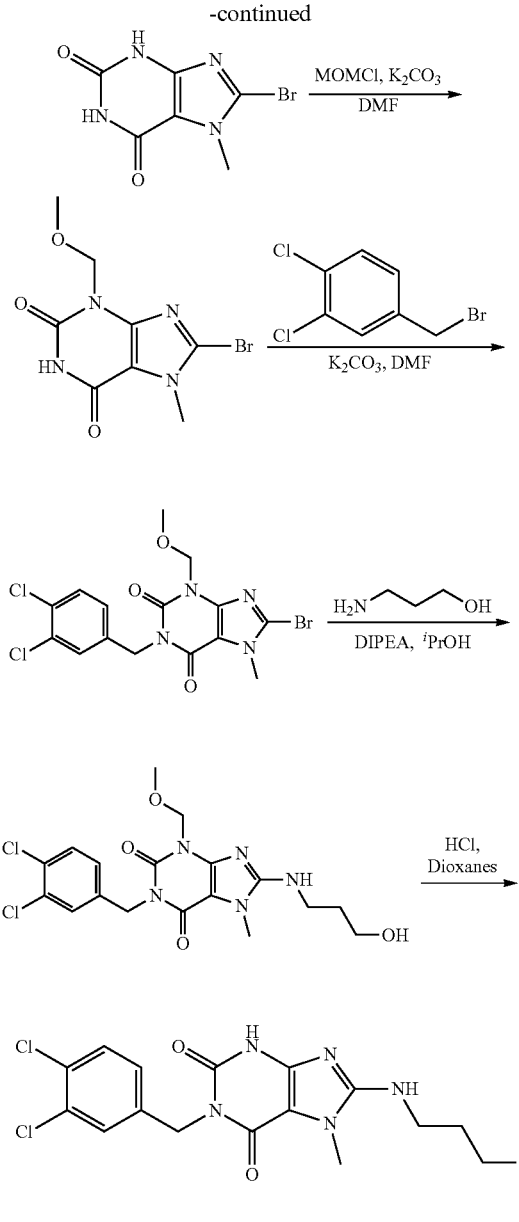

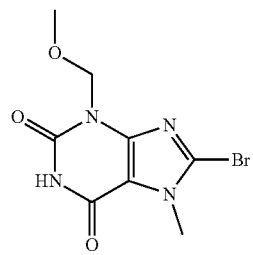 [SMILES: COCn1c(=O)[nH]c(=O)c2c1nc(Br)n2C]

Chloromethyl methylether (76 µl, 1.0 mmol) was added to a suspension of 8-bromo-7-methyl-3,7-dihydro-1H-purine-2,6-dione (245 mg, 1.0 mmol) and potassium carbonate (138 mg, 1.0 mmol) in DMF (10 ml). The reaction was stirred at room temperature for 72 h. The reaction was poured into water and extracted into ethyl acetate three times. The combined organic fractions were washed with sat. NaCl, dried over $MgSO_4$ and concentrated in vacuo. The residue was purified by flash chromatography (0-100% EA/heptane). ESI: m/z 289.0 $(M+H)^+$.

8-Bromo-1-(3,4-dichlorobenzyl)-3-(methoxymethyl)-7-methyl-3,7-dihydro-1H-purine-2,6-dione

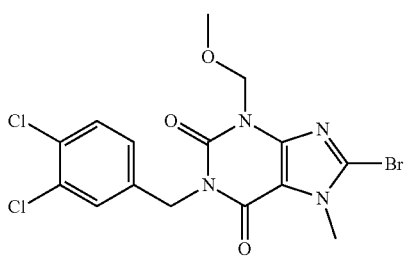 [SMILES: COCn1c(=O)n(Cc2ccc(Cl)c(Cl)c2)c(=O)c2c1nc(Br)n2C]

8-bromo-7-methyl-3,7-dihydro-1H-purine-2,6-dione

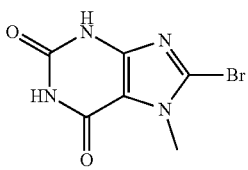

Dimethylsulfate (410 µl, 4.33 mmol) was added to a suspension of 8-bromo-3,7-dihydro-1H-purine-2,6-dione (1.0 g, 4.33 mmol) and DIEA (798 µl, 4.76 mmol) in DMF (45 ml). After 90 minutes the reaction was poured into ice cold water and stirred for 30 minutes. The precipitate was collected by filtration, washed with water and dried in vacuo.

3,4-Dichlorobenzylbromide (27 µl, 0.19 mmol) was added to a suspension of 8-bromo-3-(m ethoxymethyl)-7-methyl-3,7-dihydro-1H-purine-2,6-dione (36 mg, 0.12 mmol) and potassium carbonate (34 mg, 0.25 mmol) in DMF (2 ml). The reaction was heated to 90° C. for 90 minutes, cooled and poured into water. The aqueous layer was extracted with ethyl acetate three times, the combined organic fractions were washed with brine, dried over $MgSO_4$ and concentrated in vacuo. The residue was purified by flash chromatography (0-80% EA/heptane). ESI: m/z 448.9 $(M+H)^+$.

1-(3,4-dichlorobenzyl)-8-((3-hydroxypropyl)amino)-3-(methoxymethyl)-7-methyl-3,7-dihydro-1H-purine-2,6-dione

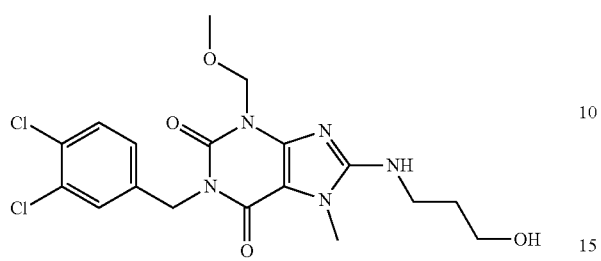

3-Amino-1-propanol (19 μl, 0.25 mmol) and DIEA (44 μl, 0.25 mmol) were added to a suspension of 8-bromo-1-(3,4-dichlorobenzyl)-3-(methoxymethyl)-7-methyl-3,7-dihydro-1H-purine-2,6-dione (56 mg, 0.12 mmol) in isopropanol (2 ml). The reaction was heated to 100° C. for 40 h, cooled and concentrated in vacuo. The residue was purified by flash chromatography (0-50% methanol/DCM). ESI: m/z 442.1 (M+H)+.

1-(3,4-dichlorobenzyl)-8-((3-hydroxypropyl)amino)-7-methyl-3,7-dihydro-1H-purine-2,6-dione

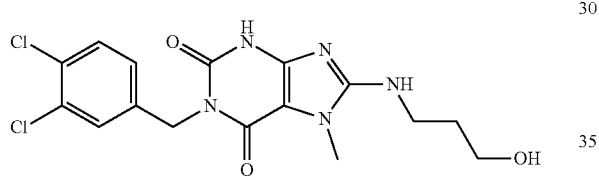

HCl (4M dioxane, 2 ml) was added to a suspension of 1-(3,4-dichlorobenzyl)-8-((3-hydroxypropyl)amino)-3-(methoxymethyl)-7-methyl-3,7-dihydro-1H-purine-2,6-dione (55 mg, 0.12 mmol) in methanol (2 ml). The reaction was stirred at room temperature for 1 h then heated to 75° C. After 72 h the reaction was cooled and concentrated in vacuo. The residue was purified by prep-HPLC (acetonitrile/water, 0.2% ammonium hydroxide). $^1$H NMR (500 MHz, DMSO-$d_6$) δ 11.70 (s, 1H), 7.55 (d, J=8.3 Hz, 1H), 7.49 (d, J=1.9 Hz, 1H), 7.24 (dd, J=8.3, 2.0 Hz, 1H), 6.97 (s, 1H), 4.94 (s, 2H), 4.48 (t, J=5.1 Hz, 1H), 3.52 (s, 3H), 3.46 (q, J=6.1 Hz, 2H), 1.70 (p, J=6.4 Hz, 2H). One methylene signal obscured by solvent peak; ESI: m/z: 398.1 (M+H)+.

Example 98

Ethyl 2-(1-(3,4-dichlorobenzyl)-8-((3-hydroxypropyl)amino)-7-methyl-2,6-dioxo-1,2,6,7-tetrahydro-3H-purin-3-yl)acetate

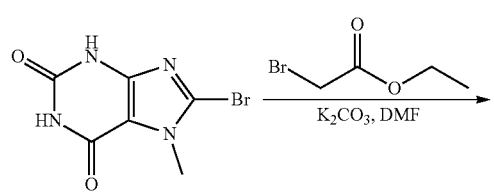

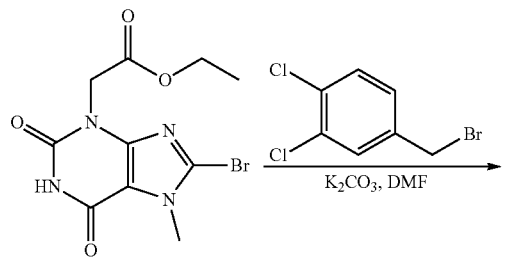

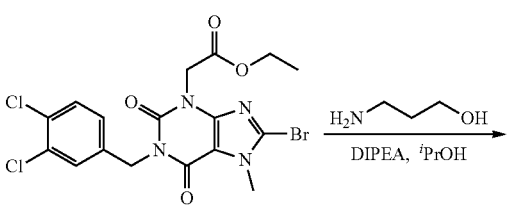

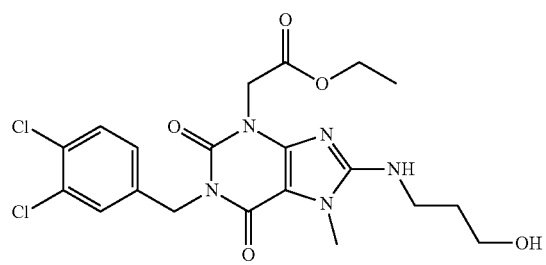

Ethyl 2-(8-bromo-7-methyl-2,6-dioxo-1,2,6,7-tetrahydro-3H-purin-3-yl)acetate

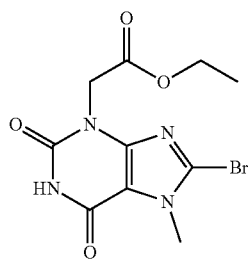 [SMILES: CCOC(=O)Cn1c(=O)[nH]c(=O)c2c1nc(Br)n2C]

Ethyl bromoacetate (90 μl, 0.82 mmol) was added to a suspension of 8-bromo-7-methyl-3,7-dihydro-1H-purine-2,6-dione (200 mg, 0.82 mmol) and potassium carbonate (124 mg, 0.09 mmol) in DMF (10 ml). The reaction was stirred for 72 h then poured into water and extracted with ethyl acetate three times. The combined organic fractions were washed with sat. NaCl, dried over MgSO$_4$ and concentrated in vacuo. The residue was purified by flash column chromatography (0-100% ethyl acetate/heptane). ESI: m/z 333.1 (M+H)+.

Ethyl 2-(8-bromo-1-(3,4-dichlorobenzyl)-7-methyl-2,6-dioxo-1,2,6,7-tetrahydro-3H-purin-3-yl)acetate

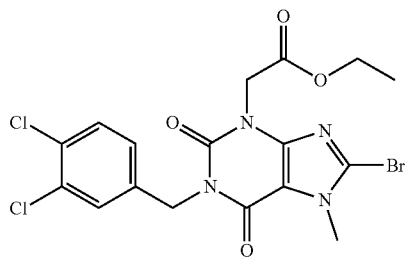 [SMILES: CCOC(=O)Cn1c(=O)n(Cc2ccc(Cl)c(Cl)c2)c(=O)c2c1nc(Br)n2C]

3,4-Dichlorobenzylbromide (61 µl, 0.42 mmol) was added to a suspension of ethyl 2-(8-bromo-7-methyl-2,6-dioxo-1,2,6,7-tetrahydro-3H-purin-3-yl)acetate (93 mg, 0.28 mmol) and potassium carbonate (77 mg, 0.56 mmol) in DMF (3 ml). The reaction was heated to 90° C. for 1 h then cooled and poured into water. The aqueous layer was extracted with ethyl acetate three times, the combined organic fractions were washed with sat. NaCl, dried over MgSO$_4$ and concentrated in vacuo. The residue was purified by flash chromatography (0-75% EA/heptane). ESI: m/z 490.9 (M+H)$^+$.

Ethyl 2-(1-(3,4-dichlorobenzyl)-8-((3-hydroxypropyl)amino)-7-methyl-2,6-dioxo-1,2,6,7-tetrahydro-3H-purin-3-yl)acetate

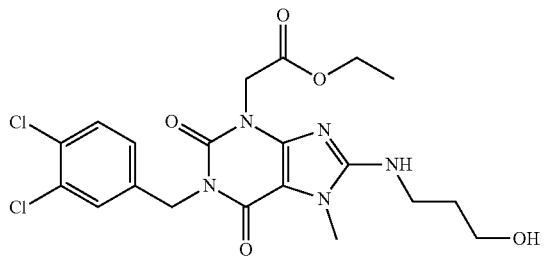 [SMILES: CCOC(=O)Cn1c(=O)n(Cc2ccc(Cl)c(Cl)c2)c(=O)c2c1nc(NCCCO)n2C]

3-Amino-1-propanol (39 µl, 0.51 mmol) and DIEA (90 µl, 0.51 mmol) were added to ethyl 2-(8-bromo-1-(3,4-dichlorobenzyl)-7-methyl-2,6-dioxo-1,2,6,7-tetrahydro-3H-purin-3-yl)acetate (124 mg, 0.25 mmol) in isopropanol (3 ml). The reaction was heated to 100° C. for 20 h then cooled and poured into water. The aqueous layer was extracted with ethyl acetate three times, the combined organic fractions were washed with sat. NaCl, dried over MgSO$_4$ and concentrated in vacuo. The residue was purified by flash chromatography (0-10% methanol/dichloromethane). $^1$H NMR (500 MHz, DMSO-d$_6$) δ 7.57 (d, J=8.3 Hz, 1H), 7.48 (d, J=2.0 Hz, 1H), 7.24 (dd, J=8.3, 2.0 Hz, 1H), 7.08 (t, J=5.6 Hz, 1H), 5.00 (s, 2H), 4.65 (s, 2H), 4.46 (t, J=4.9 Hz, 1H), 4.13 (q, J=7.1 Hz, 2H), 3.56 (s, 3H), 3.46 (q, J=6.0 Hz, 2H), 1.70 (p, J=6.5 Hz, 2H), 1.17 (t, J=7.1 Hz, 3H). One methylene signal obscured by solvent peak; ESI: m/z: 484.2 (M+H)$^+$.

Example 99

1-((1H-benzo[d]imidazol-2-yl)methyl)-8-((1S,3R)-3-hydroxycyclopentylamino)-3,7-dimethyl-1H-purine-2,6(3H,7H)-dione

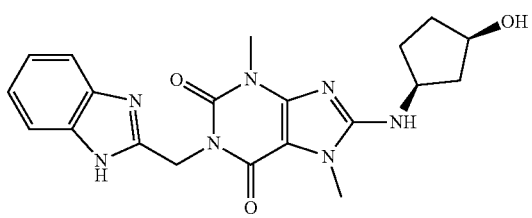 [SMILES: Cn1c(N[C@H]2CC[C@@H](O)C2)nc2c1c(=O)n(Cc1nc3ccccc3[nH]1)c(=O)n2C]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-1H-benzo[d]imidazole-1-carboxylate, (1R,3S)-3-aminocyclopentanol. The mixture was concentrated and purified by flash chromatography (DCM/MeOH: 10/1) to give the crude product. The crude product was purified by Prep-HPLC using Method D (30-70% ACN). $^1$H NMR (400 MHz, DMSO-d$_6$) δ 12.19 (br s, 1H), 7.44 (br s, 2H), 7.12 (s, 2H), 6.97-6.95 (d, J=8.2 Hz, 1H), 5.21 (s, 2H), 4.75 (s, 1H), 4.13-4.11 (m, 2H), 3.57 (s, 3H), 3.37 (s, 3H), 2.30-2.26 (m, 1H), 1.98-1.96 (m, 1H), 1.75-1.51 (m, 4H); ESI: m/z 410.1 (M+H)$^+$.

Example 161

Methyl 1-(3,4-dichlorobenzyl)-3,7-dimethyl-2,6-dioxo-2,3,6,7-tetrahydro-1H-purine-8-carboxylate

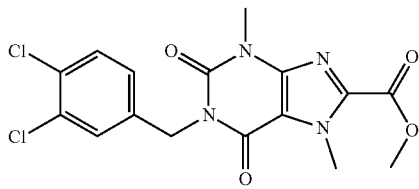 [SMILES: COC(=O)c1nc2c(c(=O)n(Cc3ccc(Cl)c(Cl)c3)c(=O)n2C)n1C]

To a solution of 8-bromo-1-(3,4-dichlorobenzyl)-3,7-dimethyl-1H-purine-2,6(3H,7H)-dione (1.25 g, 3.0 mmol) in MeOH (30 mL) was added Pd(PPh$_3$)$_4$ (347 mg, 0.3 mmol). The mixture was stirred at 100° C. for 24 h under 20 atm CO atmospheres. The mixture was cooled, filtered and concentrated. The residue was purified by flash chromatography (PE/EA=5/10). $^1$H NMR (400 MHz, CDCl$_3$) δ 7.59 (d, J=1.6 Hz, 1H), 7.39-7.36 (m, 2H), 5.13 (s, 2H), 4.37 (s, 3H), 4.03 (s, 3H), 3.61 (s, 3H); ESI: m/z 397.0 (M+H)$^+$.

Example 100

1-(3,4-dichlorobenzyl)-8-(hydroxymethyl)-3,7-dimethyl-1H-purine-2,6(3H,7H)-dione

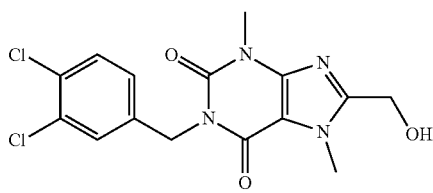 [SMILES: Cn1c(CO)nc2c1c(=O)n(Cc1ccc(Cl)c(Cl)c1)c(=O)n2C]

To a solution of methyl 1-(3,4-dichlorobenzyl)-3,7-dimethyl-2,6-dioxo-2,3,6,7-tetrahydro-1H-purine-8-carboxylate (20 mg, 0.05 mmol) in THF (1 mL), was added NaBH$_4$ (9.2 mg, 0.25 mmol). The mixture was stirred at room temperature for 6 h. The reaction was quenched with MeOH (5 mL), concentrated and the residue was purified by flash chromatography (DCE/MeOH=20/1) to give the title compound. $^1$H NMR (400 MHz, DMSO-d$_6$) δ 7.57-7.55 (m, 2H), 7.29 (dd, J=2.0, 8.4 Hz, 1H), 5.70 (t, J=5.6 Hz, 1H), 5.04 (s, 2H), 4.60 (d, J=5.2 Hz, 2H), 3.92 (s, 3H), 3.47 (s, 3H); ESI: m/z 369.0 (M+H)$^+$.

Example 162 ethyl 2-(1-(3,4-dichlorobenzyl)-3,7-dimethyl-2,6-dioxo-2,3,6,7-tetrahydro-1H-purin-8-yl)acetate

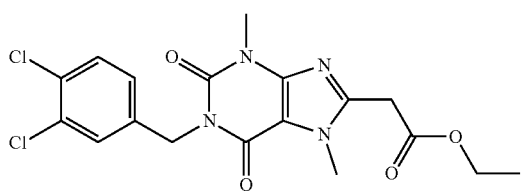 [SMILES: CCOC(=O)Cc1nc2c(c(=O)n(Cc3ccc(Cl)c(Cl)c3)c(=O)n2C)n1C]

To a solution of 8-bromo-1-(3,4-dichlorobenzyl)-3,7-dimethyl-1H-purine-2,6(3H,7H)-dione (418 mg, 1.0 mmol) in DMSO (5 mL), was added diethyl malonate (480 mg, 3.0 mmol) and NaOH (400 mg, 10.0 mmol). The mixture was stirred at 130° C. for 12 h in a microwave. The mixture was cooled, neutralized with 1N HCl and extracted with EA (3*20 mL). The combined organic fractions were dried with Na$_2$SO$_4$, filtered and concentrated. The residue was purified by flash chromatography (PE/EA=2/1) to give the title compound. $^1$H NMR (400 MHz, CDCl$_3$) δ 7.57 (d, J=1.6 Hz, 1H), 7.38-7.34 (m, 2H), 5.12 (s, 2H), 4.22 (q, J=7.2 Hz, 2H), 3.95 (s, 3H), 3.87 (s, 2H), 3.55 (s, 3H), 1.29 (t, J=7.2 Hz, 3H); ESI: m/z 425.1 (M+H)$^+$.

The following compounds were synthesized in a similar fashion as Example 162.

Ethyl 2-(1-(((1H-indol-2-yl)methyl)-3,7-methyl-2,6-dioxo-2,3,6,7-tetrahydro-1H-purin-8-yl)acetate

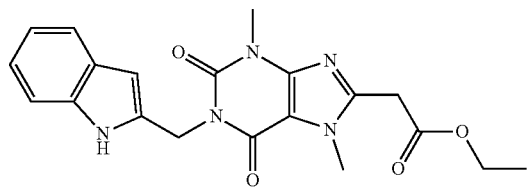

ESI: m/z 396.1 (M+H)$^+$.

Ethyl 2-(1-((5-chloro-1H-indol-2-yl)methyl)-3,7-dimethyl-2,6-dioxo-2,3,6,7-tetrahydro-1H-purin-8-yl)acetate

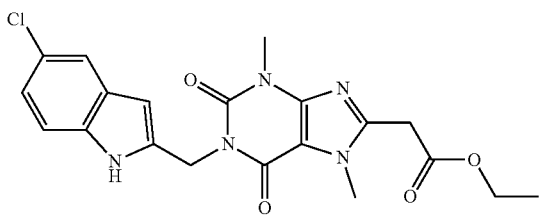 [SMILES: CCOC(=O)Cc1nc2c(c(=O)n(Cc3cc4cc(Cl)ccc4[nH]3)c(=O)n2C)n1C]

ESI: m/z 430.1 (M+H)$^+$

Ethyl 2-(3,7-dimethyl-1-((5-methyl-1H-indol-2-yl)methyl)-2,6-dioxo-2,3,6,7-tetrahydro-1H-purin-8-yl)acetate

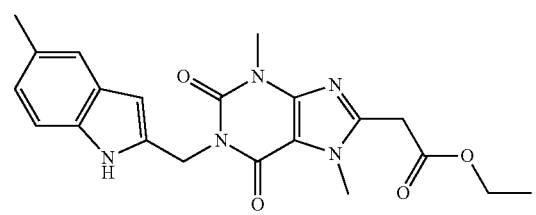 [SMILES: CCOC(=O)Cc1nc2c(c(=O)n(Cc3cc4cc(C)ccc4[nH]3)c(=O)n2C)n1C]

ESI: m/z 410.0 (M+H)$^+$

Example 101

2-(1-(3,4-dichlorobenzyl)-3,7-dimethyl-2,6-dioxo-2,3,6,7-tetrahydro-1H-purin-8-yl)acetic acid

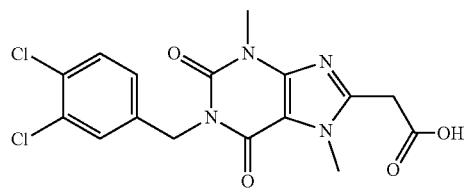 [SMILES: Cn1c(CC(=O)O)nc2c1c(=O)n(Cc1ccc(Cl)c(Cl)c1)c(=O)n2C]

To a solution of ethyl 2-(1-(3,4-dichlorobenzyl)-3,7-dimethyl-2,6-dioxo-2,3,6,7-tetrahydro-1H-purin-8-yl)acetate (40 mg, 0.094 mmol) in THF (4 mL) and water (2 mL) was added LiOH·H$_2$O (12 mg, 0.282 mmol). The mixture was stirred at room temperature for 6 h. The pH was adjusted to 6 using AcOH and the mixture was concentrated. The residue was purified by reversed phase chromatography (C18, CH$_3$CN/H$_2$O=20/80). $^1$H NMR (400 MHz, DMSO-d$_6$) δ 7.56-7.54 (m, 2H), 7.28-7.26 (m, 1H), 5.03 (s, 2H), 3.83-3.82 (m, 5H), 3.40 (s, 3H); ESI: m/z 397.1 (M+H)$^+$.

Example 102

2-(1-(3,4-dichlorobenzyl)-3,7-dimethyl-2,6-dioxo-2,3,6,7-tetrahydro-1H-purin-8-ylamino)ethanesulfonamide

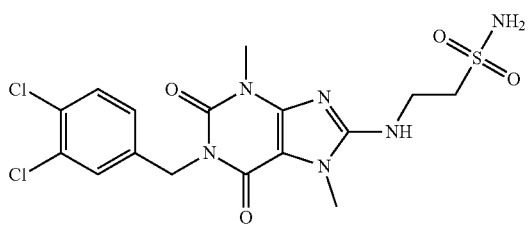 [SMILES: Cn1c(NCCS(N)(=O)=O)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and 2-aminoethanesulfonamide. The reaction mixture was concentrated and the residue was purified by preparative HPLC using Method D. $^1$H NMR (400 MHz, DMSO-d$_6$) δ 7.56 (d, J=8.3 Hz, 1H), 7.51 (d, J=1.9 Hz, 1H), 7.26 (dd, J=8.3, 2.0 Hz, 1H), 5.00 (s, 2H), 3.77-3.69 (m, 2H), 3.55 (s, 3H), 3.38 (s, 3H), 3.37-3.29 (m, 2H); ESI: m/z 463.0 (M+H)$^+$.

Example 103

1-[(4-chloro-3-methoxyphenyl)methyl]-8-{[(1R,2R)-2-hydroxycyclopentyl]amino}-3,7-dimethyl-2,3,6,7-tetrahydro-1H-purine-2,6-dione

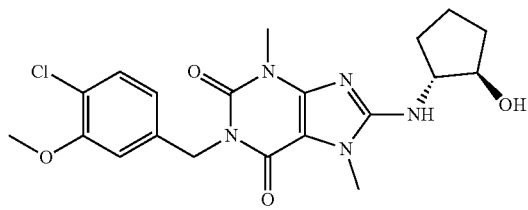 [SMILES: COc1cc(Cn2c(=O)c3c(nc(N[C@@H]4CCC[C@H]4O)n3C)n(C)c2=O)ccc1Cl]

The title compound was synthesized in a similar fashion as described in Procedure 7B using 8-bromo-1-(3,4-dichlorobenzyl)-3,7-dimethyl-1H-purine-2,6(3H,7H)-dione and (1R,2R)-2-aminocyclopentan-1-ol. $^1$H NMR (500 MHz, DMSO-d$_6$) δ 7.30 (d, J=8.1 Hz, 1H), 7.10 (d, J=1.6 Hz, 1H), 6.85 (d, J=6.9 Hz, 1H), 6.76 (dd, J=8.1, 1.7 Hz, 1H), 5.00 (s, 2H), 4.83 (s, 1H), 3.99 (q, J=5.3 Hz, 1H), 3.89 (p, J=6.0 Hz, 1H), 3.82 (s, 3H), 3.58 (s, 3H), 3.36 (s, 3H), 2.11-2.03 (m, 1H), 1.96-1.81 (m, 1H), 1.76-1.58 (m, 2H), 1.58-1.39 (m, 2H); ESI: m/z 343.2 (M+H)$^+$.

Example 104

(S)-1-(3,4-dichlorobenzyl)-3,7-dimethyl-8-((tetrahydrofuran-2-yl)methylamino)-1H-purine-2,6(3H,7H)-dione

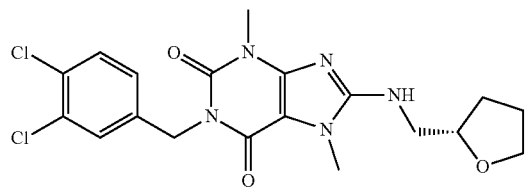 [SMILES: Cn1c(NC[C@@H]2CCCO2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and (S)-(tetrahydrofuran-2-yl)methanamine. $^1$H NMR (400 MHz, DMSO-d$_6$) δ 7.53-7.55 (d, J=8.4 Hz, 1H), 7.51 (d, J=1.6 Hz, 1H), 7.25 (dd, J=2.0 Hz, J=2.0 Hz, 1H), 7.19 (t, J=5.6 Hz, 1H), 4.97 (s, 2H), 4.01 (m, 1H), 3.78 (m, 1H), 3.65 (m, 1H), 3.56 (m, 1H), 3.34-3.37 (m, 5H), 1.79-1.90 (m, 3H), 1.59 (m, 1H); ESI: m/z: 438.1 (M+H)$^+$.

Example 105

(S)-3,7-dimethyl-8-((tetrahydrofuran-2-yl)methylamino)-1-(4-(trifluoromethyl)benzyl)-1H-purine-2,6(3H,7H)-dione

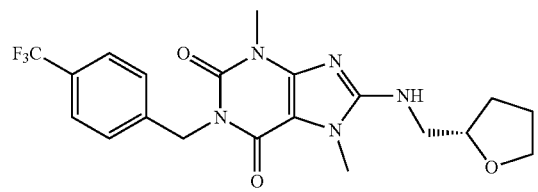 [SMILES: Cn1c(NC[C@@H]2CCCO2)nc2c1c(=O)n(Cc1ccc(C(F)(F)F)cc1)c(=O)n2C]

The title compound was synthesized in a similar fashion as described in Procedure 7A using 8-bromo-3,7-dimethyl-1-(4-(trifluoromethyl)benzyl)-1H-purine-2,6(3H,7H)-dione and (S)-(tetrahydrofuran-2-yl)methanamine. The reaction mixture was concentrated and purified by flash chromatography (PE/EA 1/1); $^1$H NMR (400 MHz, DMSO-d$_6$) δ 7.66 (d, J=8.0 Hz, 2H), 7.46 (d, J=8.0 Hz, 2H), 7.20 (t, J=6.0 Hz, 1H), 5.09 (s, 2H), 4.02-4.05 (m, 1H), 3.77-3.80 (m, 1H), 3.63-3.67 (m, 1H), 3.57 (s, 1H), 3.36-3.37 (m, 5H), 1.81-1.92 (m, 3H), 1.60-1.63 (m, 1H); ESI: m/z 438.1 (M+H)$^+$.

Example 106

1-(3,4-dichlorobenzyl)-8-((1-hydroxycyclohexyl)methylamino)-3,7-dimethyl-1H-purine-2,6(3H,7H)-dione

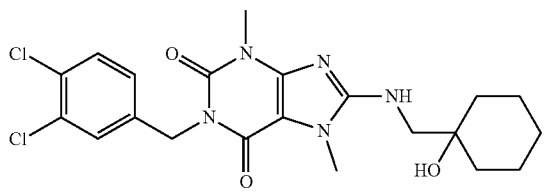 [SMILES: Cn1c(NCC2(O)CCCCC2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and 1-(aminomethyl)cyclohexanol. The mixture was purified by flash chromatography (DCM:MeOH=20:1); $^1$H NMR (400 MHz, CDCl$_3$) δ 7.54 (d, J=1.8 Hz, 1H), 7.32-7.30 (m, 2H), 5.09 (s, 2H), 4.67 (t, J=5.8 Hz, 1H), 3.69 (s, 3H), 3.51 (d, J=5.9 Hz, 2H), 3.49 (s, 3H), 2.68 (s, 1H), 1.59-1.44 (m, 8H), 1.36 (s, 2H); ESI: m/z 466.0 (M+H)$^+$.

Example 107

8-((1-hydroxycyclohexyl)methylamino)-3,7-dimethyl-1-(4-(trifluoromethyl)benzyl)-1H-purine-2,6(3H,7H)-dione

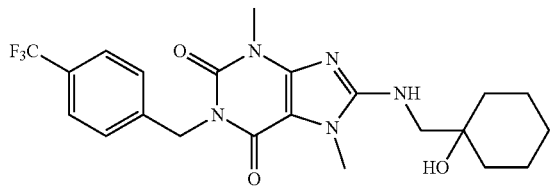 [SMILES: Cn1c(NCC2(O)CCCCC2)nc2c1c(=O)n(Cc1ccc(C(F)(F)F)cc1)c(=O)n2C]

The title compound was synthesized in a similar fashion described in Procedure 7A using 8-bromo-3,7-dimethyl-1-(4-(trifluoromethyl)benzyl)-1H-purine-2,6(3H,7H)-dione and 1-(aminomethyl)cyclohexanol. The product was purified by column chromatography (DCM:MeOH=20:1); $^1$H NMR (400 MHz, CDCl$_3$) δ 7.54 (s, 4H), 5.20 (s, 2H), 4.74 (s, 1H), 3.68 (s, 3H), 3.50 (m, 5H), 2.79 (s, 1H), 1.74 (s, 2H), 1.60 (s, 2H), 1.52 (m, 6H); ESI: m/z 466.0 (M+H)$^+$.

Example 108

1-(3,4-dichlorobenzyl)-8-((1R,2R)-2-hydroxycyclohexylamino)-3,7-dimethyl-1H-purine-2,6(3H,7H)-dione

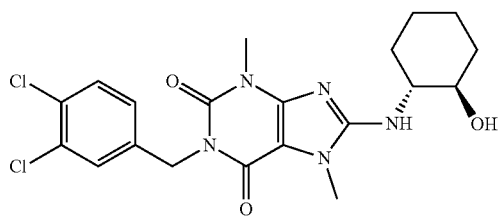 [SMILES: Cn1c(N[C@@H]2CCCC[C@H]2O)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and (1R,2R)-2-aminocyclohexanol. The product was purified by preparative HPLC using Method B. $^1$H NMR (400 MHz, CDCl$_3$) δ 7.53 (d, J=1.6 Hz, 1H), 7.34 (d, J=6.8 Hz, 1H), 7.30 (dd, J=6.4, 1.6 Hz, 1H), 5.09 (s, 2H), 4.22-4.20 (m, 1H), 3.67 (s, 3H), 3.65-3.59 (m, 1H), 3.48 (s, 3H), 3.46-3.43 (m, 1H), 2.17-2.09 (m, 2H), 1.79-1.76 (m, 2H), 1.44-1.22 (m, 5H); ESI: m/z 452.0 (M+H)$^+$.

Example 110

(1S,2R)-2-(3,7-dimethyl-2,6-dioxo-1-(4-(trifluoromethyl)benzyl)-2,3,6,7-tetrahydro-1H-purin-8-ylamino)cyclopentanecarboxylic acid

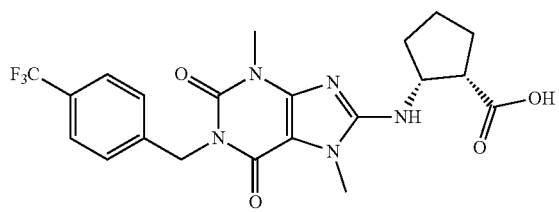 [SMILES: Cn1c(N[C@@H]2CCC[C@@H]2C(=O)O)nc2c1c(=O)n(Cc1ccc(C(F)(F)F)cc1)c(=O)n2C]

To a solution of 8-bromo-1-(4-(trifluoromethyl)benzyl)-3,7-dimethyl-1H-purine-2,6(3H,7H)-dione (200 mg, 0.48 mmol), methyl (1S,2R)-2-aminocyclopentane-1-carboxylate (97 mg, 0.96 mmol) and DIEA (155 mg, 1.2 mmol) in EtOH (8 mL) was added NaI (10 mg). The mixture was stirred at 130° C. for 6 h under microwave condition. The reaction mixture was concentrated and purified by column chromatography (PE/EA, 1/1) to yield methyl (1S,2R)-2-((3,7-dimethyl-2,6-dioxo-1-(4-(trifluoromethyl)benzyl)-2,3,6,7-tetrahydro-1H-purin-8-yl)amino)cyclopentane-1-carboxylate; ESI: m/z 480.1 (M+H)$^+$. This product (200 mg, 0.42 mmol,) was dissolved in THF/MeOH/H$_2$O (10 mL/10 mL/10 mL) and NaOH (67 mg) was added. The solution was stirred for 15 h, then the pH was adjusted to 6-7 with 2 N HCl. The mixture was concentrated. The residue was purified by prep-HPLC using Method D (30-80% ACN). $^1$H NMR (400 MHz, CDCl$_3$) δ 7.55 (t, 4H), 5.30 (t, J=8.0 Hz, 1H), 4.51 (m, 1H), 3.62 (s, 3H), 3.51 (s, 3H), 3.13 (m, 1H), 2.09-2.11 (m, 3H), 1.72-1.86 (m, 3H), 1.35 (d, J=4.4 Hz, 1H); ESI: m/z 466.2 (M+H)$^+$.

Example 111

(1S,2R)-2-(1-(3,4-dichlorobenzyl)-3,7-dimethyl-2,6-dioxo-2,3,6,7-tetrahydro-1H-purin-8-ylamino)cyclopentanecarboxylic acid

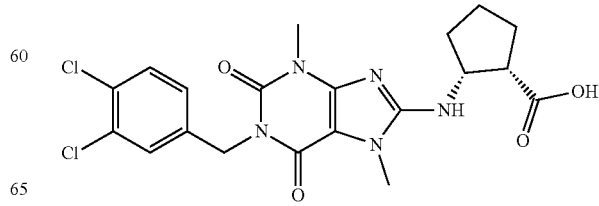

The title compound was made in a similar fashion as Example 110 using 8-bromo-1-(3,4-dichlorobenzyl)-3,7-dimethyl-1H-purine-2,6(3H,7H)-dione and methyl (1S,2R)-2-aminocyclopentane-1-carboxylate. The product was purified by prep-HPLC using Method D (30-80% ACN). $^1$H NMR (400 MHz, CD$_3$OD) δ 7.51 (s, 1H), 7.39 (d, J=8.0 Hz, 1H), 7.28 (dd, J=1.2 Hz, 1.5 Hz, 1H), 5.05 (s, 2H), 4.37 (s, 1H), 3.62 (s, 3H), 3.46 (s, 3H), 3.31 (m, 1H), 2.91 (m, 1H), 1.85-2.07 (m, 5H), 1.61 (m, 1H); ESI: m/z 466.2 (M+H)$^+$.

Example 113

8-((1R,2R)-2-hydroxycyclohexylamino)-3,7-dimethyl-1-(4-(trifluoromethyl)benzyl)-1H-purine-2,6 (3H,7H)-dione

The title compound was synthesized in a similar fashion as described in Procedure 7A using 8-bromo-3,7-dimethyl-1-(4-(trifluoromethyl)benzyl)-1H-purine-2,6(3H,7H)-dione, and (1R,2R)-2-aminocyclohexan-1-ol. The product was purified by prep-HPLC using Method B. $^1$H NMR (400 MHz, CDCl$_3$) δ 7.57-7.46 (m, 4H), 5.20 (s, 2H), 4.17 (d, J=4.4 Hz, 1H), 3.77-3.72 (m, 1H), 3.68 (s, 3H), 3.63-3.60 (m, 1H), 3.53 (s, 3H), 3.46-3.42 (m, 1H), 2.17-2.09 (m, 2H), 1.79-1.77 (m, 2H), 1.39-1.44 (m, 4H); ESI: m/z 452.2 (M+H)$^+$.

Example 114

(±)-3-(1-(3,4-dichlorobenzyl)-3,7-dimethyl-2,6-dioxo-2,3,6,7-tetrahydro-1H-purin-8-ylamino)cyclohexanecarboxylic acid

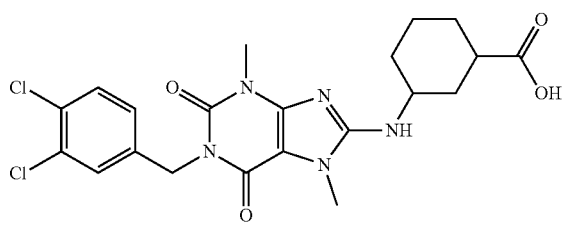 [SMILES: Cn1c(NC2CCCC(C(=O)O)C2)nc2c1c(=O)n(Cc1ccc(Cl)c(Cl)c1)c(=O)n2C]

The title compound was made in a similar fashion as Example 110 using 8-bromo-1-(3,4-dichlorobenzyl)-3,7-dimethyl-1H-purine-2,6(3H,7H)-dione and methyl 3-aminocyclohexanecarboxylate. The product was purified by Prep-HPLC using Method D (30-70% ACN). $^1$H NMR (400 MHz, DMSO-d$_6$) δ 7.56-7.51 (m, 2H), 7.25 (d, J=10.0 Hz, 1H), 6.88 (d, J=8.0 Hz, 1H), 4.98 (s, 2H), 3.59 (s, 3H), 3.35 (s, 3H), 2.35 (m, 1H), 2.07 (m, 1H), 1.95-1.76 (m, 4H), 1.38-1.21 (m, 4H); ESI: m/z 480.1 (M+H)$^+$.

Example 115

(±)-3-(3,7-dimethyl-2,6-dioxo-1-(4-(trifluoromethyl)benzyl)-2,3,6,7-tetrahydro-1H-purin-8-ylamino)cyclohexanecarboxylic acid

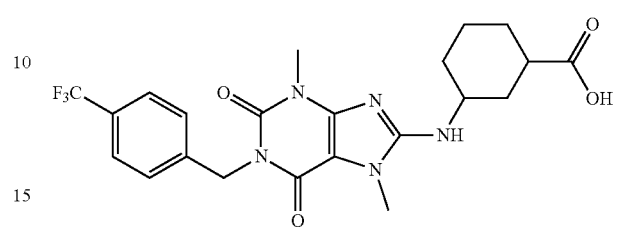

The title compound was made in a similar fashion as Example 110 using 8-bromo-3,7-dimethyl-1-(4-(trifluoromethyl)benzyl)-1H-purine-2,6(3H,7H)-dione and 3-aminocyclohexanecarboxylate. The product was purified by Prep-HPLC using Method D (30-70% ACN). $^1$H NMR (400 MHz, DMSO-d$_6$) δ 12.20 (br s, 1H), 7.65 (d, J=8.4 Hz, 2H), 7.46 (d, J=8.0 Hz, 2H), 6.88 (s, 1H), 4.08 (s, 2H), 3.59 (m, 1H), 3.56 (s, 3H), 3.35 (s, 3H), 2.38-2.31 (m, 1H), 2.17-2.14 (m, 1H), 1.98-1.71 (m, 3H), 1.38-1.16 (m, 3H); ESI: m/z 480.1 (M+H)$^+$.

Example 116

1-(3,4-dichlorobenzyl)-3,7-dimethyl-8-(pyrazin-2-ylmethylamino)-1H-purine-2,6(3H,7H)-dione

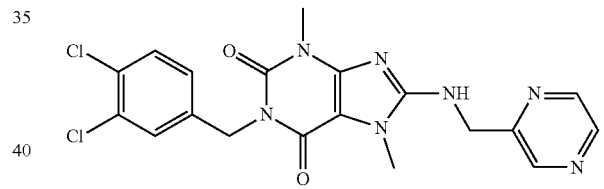

The title compound was synthesized in a similar fashion as described in Procedure 7a using 8-bromo-1-(3,4-dichlorobenzyl)-3,7-dimethyl-1H-purine-2,6(3H,7H)-dione and pyrazin-2-ylmethanamine. The product was purified by flash chromatography (EA/PE=1/1). $^1$H NMR (400 MHz, DMSO-d$_6$) δ 8.71 (s, 1H), 8.60 (s, 1H), 8.55 (s, 1H), 7.86 (m, 1H), 7.55-7.52 (m, 2H), 7.26-7.24 (d, J=10.4 Hz, 1H), 4.98 (s, 2H), 4.68 (d, J=5.6 Hz, 1H), 3.63 (s, 3H), 3.28 (s, 3H); ESI: m/z 446.0 (M+H)$^+$.

Example 117

1-(3,4-dichlorobenzyl)-3,7-dimethyl-8-(pyridin-3-ylmethylamino)-1H-purine-2,6(3H,7H)-dione

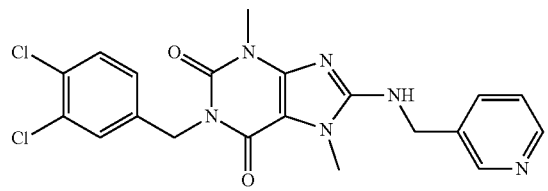 [SMILES: Cn1c(NCc2cccnc2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and pyridin-3-ylmethanamine. The product was recrystalized from MeOH. $^1$HNMR (400 MHz, DMSO-$d_6$) δ 8.05 (d, J=1.6 Hz, 1H), 8.47 (dd, J=3.6, 1.2 Hz, 1H), 7.80-7.78 (m, 1H), 7.72 (t, J=4.8 Hz, 1H), 7.54 (d, J=6.8 Hz, 1H), 7.51 (d, J=1.6 Hz, 1H), 7.37-7.34 (m, 1H), 7.24 (dd, J=6.8, 2.0 Hz, 1H), 4.98 (s, 2H), 4.57 (d, J=4.8 Hz, 2H), 3.60 (s, 3H), 3.33 (s, 3H); ESI: m/z 445.0 (M+H)$^+$.

Example 118: 1-(3,4-dichlorobenzyl)-3,7-dimethyl-8-(pyridin-4-ylmethylamino)-1H-purine-2,6(3H,7H)-dione

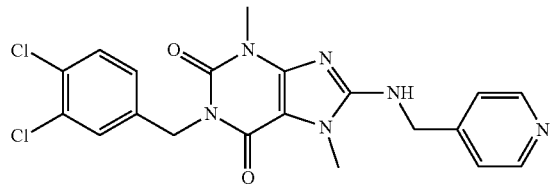 [SMILES: Cn1c(NCc2ccncc2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and pyridin-4-ylmethanamine. The product was purified by column chromatography (PE/EA, 1/1). $^1$HNMR (400 MHz, CD$_3$OD) δ 8.50 (d, J=6.0 Hz, 2H), 7.75-7.78 (t, J=6.0 Hz, 1H), 7.53-7.55 (d, J=8.4 Hz, 2.0 Hz, 1H), 7.51 (s, 1H), 7.35 (d, J=6.0 Hz, 2H), 7.25 (d, J=2.0 Hz, 2H), 4.97 (s, 2H), 4.57 (d, J=6.0 Hz, 2H), 3.63 (s, 3H), 3.28 (s, 3H); ESI: m/z 445.1 (M+H)$^+$.

Example 119

8-(3-amino-1H-pyrazol-1-yl)-1-(3,4-dichlorobenzyl)-3,7-dimethyl-1H-purine-2,6(3H,7H)-dione

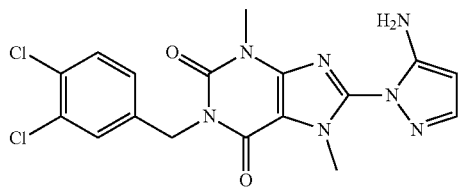 [SMILES: Cn1c(-n2nccc2N)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and 1H-pyrazol-3-amine. The product was purified by prep-HPLC using Method B. $^1$H NMR (400 MHz, DMSO-$d_6$): δ 8.07 (d, J=2.7 Hz, 1H), 7.57 (dd, J=5.1, 3.1 Hz, 2H), 7.31 (dd, J=8.3, 2.0 Hz, 1H), 5.89 (d, J=2.8 Hz, 1H), 5.55 (s, 2H), 5.03 (s, 2H), 4.15 (s, 3H), 3.41 (s, 3H). ESI: m/z 421.1 (M+H)$^+$.

Example 120

(S)-8-(1-cyclohexyl-3-hydroxypropan-2-ylamino)-3,7-dimethyl-1-(4-(trifluoromethyl)benzyl)-1H-purine-2,6(3H,7H)-dione

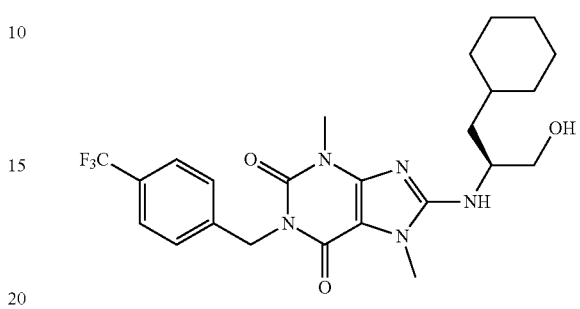

The titled compound was synthesized in a similar fashion as described in Procedure 7A using 8-bromo-3,7-dimethyl-1-(4-(trifluoromethyl)benzyl)-1H-purine-2,6(3H,7H)-dione and (S)-2-amino-3-cyclohexylpropan-1-ol. The product was purified by column chromatography (DCM:MeOH=20:1); $^1$H NMR (400 MHz, DMSO-$d_6$) δ 8.31 (s, 1H), 7.92 (s, 1H), 7.69-7.46 (m, 3H), 7.29 (dd, J=8.4, 2.0 Hz, 1H), 5.03 (s, 2H), 3.77 (s, 3H), 3.46 (s, 3H); ESI: m/z 494.0 (M+H)$^+$.

Example 121

(S)-8-(1-cyclohexyl-3-hydroxypropan-2-ylamino)-1-(3,4-dichlorobenzyl)-3,7-dimethyl-1H-purine-2,6(3H,7H)-dione

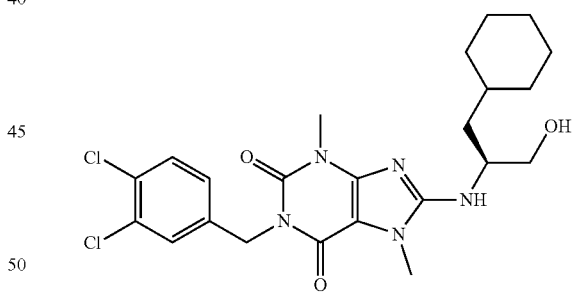

The titled compound was synthesized in a similar fashion as described in Procedure 7A using 8-bromo-1-(3,4-dichlorobenzyl)-3,7-dimethyl-1H-purine-2,6(3H,7H)-dione and (S)-2-amino-3-cyclohexylpropan-1-ol. The product was purified by column chromatography (DCM:MeOH=20:1). $^1$H NMR (400 MHz, CDCl$_3$) δ 7.54 (d, J=1.8 Hz, 1H), 7.36-7.27 (m, 2H), 5.09 (s, 2H), 4.36 (d, J=7.5 Hz, 1H), 4.14-4.03 (m, 1H), 3.82 (dd, J=11.0, 2.5 Hz, 1H), 3.68 (s, 3H), 3.64 (dd, J=11.3, 5.8 Hz, 1H), 3.48 (s, 3H), 3.24 (s, 1H), 1.82-1.79 (m, 1H), 1.73-1.67 (m, 4H), 1.57-1.41 (m, 2H), 1.41-1.28 (m, 1H), 1.22-1.14 (m, 3H), 1.03-0.89 (m, 2H); ESI: m/z 494.0 (M+H)$^+$.

Example 122

1-(3,4-dichlorobenzyl)-3,7-dimethyl-8-(pyridazin-3-ylamino)-1H-purine-2,6(3H,7H)-dione

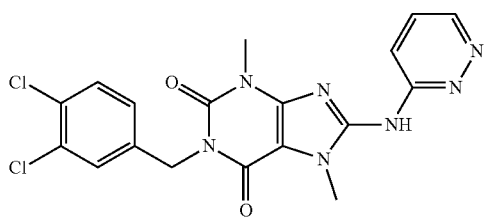 [SMILES: Cn1c(Nc2cccnn2)nc2c1c(=O)n(Cc1ccc(Cl)c(Cl)c1)c(=O)n2C]

The title compound was synthesized in a similar fashion as described in Procedure 8A using of 8-bromo-1-(3,4-dichlorobenzyl)-3,7-dimethyl-1H-purine-2,6(3H,7H)-dione and pyridazin-3-amine. The product was purified by Prep-HPLC using Method D (30-70% ACN). $^1$H NMR (400 MHz, DMSO-d$_6$) δ 8.38 (s, 1H), 7.92 (s, 1H), 7.63-7.47 (m, 3H), 7.29 (dd, J=8.4, 2.0 Hz, 1H), 5.03 (s, 2H), 3.77 (s, 3H), 3.46 (s, 3H); ESI: m/z 432.0 (M+H)$^+$.

Example 123

1-(3,4-dichlorobenzyl)-3,7-dimethyl-8-(oxazol-2-ylamino)-1H-purine-2,6(3H,7H)-dione

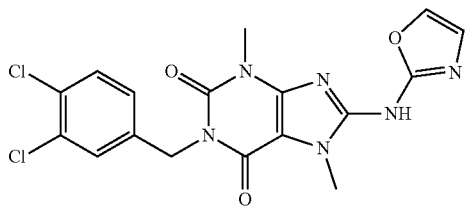 [SMILES: Cn1c(Nc2ncco2)nc2c1c(=O)n(Cc1ccc(Cl)c(Cl)c1)c(=O)n2C]

The title compound was synthesized in a similar fashion as described in Procedure 8A using 8-bromo-1-(3,4-dichlorobenzyl)-3,7-dimethyl-1H-purine-2,6(3H,7H)-dione and oxazol-2-amine. The product was purified by prep-HPLC using Method B. $^1$H NMR (400 MHz, DMSO-d$_6$): δ 7.56 (d, J=8.5 Hz, 3H), 7.35-7.22 (m, 2H), 5.02 (s, 2H), 3.65 (s, 3H), 3.52 (s, 3H); ESI: m/z 421.1 (M+H)$^+$.

Example 124

1-(3,4-dichlorobenzyl)-8-(1-(hydroxymethyl)cyclopentylamino)-3,7-dimethyl-1H-purine-2,6(3H,7H)-dione

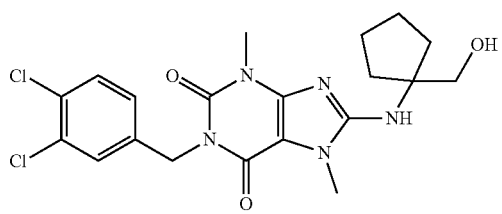 [SMILES: Cn1c(NC2(CO)CCCC2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and (1-aminocyclopentyl)methanol. The product purified by flash chromatography (EA/PE=1/1). $^1$H NMR (400 MHz, DMSO-d$_6$) δ 7.51 (s, 1H), 7.44-7.42 (d, J=8.4 Hz, 1H), 7.29 (d, J=8.0 Hz, 1H), 5.08 (s, 1H), 3.81 (s, 1H), 3.65 (s, 1H), 3.35 (s, 3H), 2.07-2.05 (m, 1H), 1.88-1.80 (m, 4H), 1.69-1.67 (m, 2H); ESI: m/z 452.1 (M+H)$^+$.

Example 125

1-(3,4-dichlorobenzyl)-3,7-dimethyl-8-(pyridin-4-ylamino)-1H-purine-2,6(3H,7H)-dione

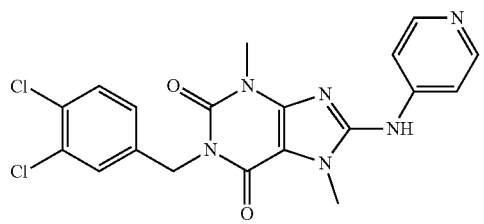 [SMILES: Cn1c(Nc2ccncc2)nc2c1c(=O)n(Cc1ccc(Cl)c(Cl)c1)c(=O)n2C]

The titled compound was synthesized in a similar fashion as described in Procedure 8A using 8-bromo-1-(3,4-dichlorobenzyl)-3,7-dimethyl-1H-purine-2,6(3H,7H)-dione and pyridin-4-amine. After aqueous workup the residue was recrystallized with MeOH. $^1$H NMR (400 MHz, DMSO-d$_6$) δ 9.68 (s, 1H), 8.37 (s, 2H), 7.66 (s, 2H), 7.55-7.58 (d, J=8.8 Hz, 2H), 7.28 (dd, J=2.0 Hz, 1.2 Hz, 2H), 5.02 (s, 2H), 3.81 (s, 3H), 3.44 (s, 3H); ESI: m/z 431.0 (M+H)$^+$.

Example 126

1-(3,4-dichlorobenzyl)-3,7-dimethyl-8-(pyrazin-2-ylamino)-1H-purine-2,6(3H,7H)-dione

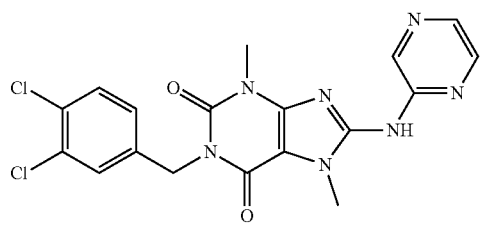 [SMILES: Cn1c(Nc2cnccn2)nc2c1c(=O)n(Cc1ccc(Cl)c(Cl)c1)c(=O)n2C]

The title compound was synthesized in a similar fashion as described in Procedure 8A using of 8-bromo-1-(3,4-dichlorobenzyl)-3,7-dimethyl-1H-purine-2,6(3H,7H)-dione and pyrazin-2-amine. The product was recrystallized with MeOH. $^1$H NMR (400 MHz, DMSO-d$_6$) δ 10.35 (s, 1H), 9.09 (s, 1H), 8.30 (s, 1H), 8.22 (s, 1H), 7.55-7.57 (m, 2H), 7.29 (d, J=1.6 Hz, 1H), 5.03 (s, 2H), 3.78 (s, 3H), 3.42 (s, 3H); ESI: m/z 432.1.0 (M+H)$^+$.

Example 127

1-(3,4-dichlorobenzyl)-3,7-dimethyl-8-(phenylamino)-1H-purine-2,6(3H,7H)-dione

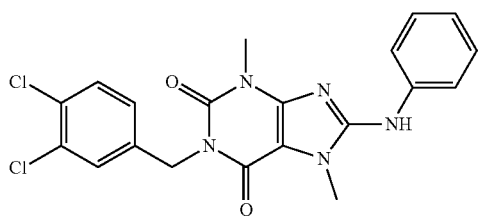

The title compound was synthesized in a similar fashion as described in Procedure 8A using 8-bromo-1-(3,4-dichlorobenzyl)-3,7-dimethyl-1H-purine-2,6(3H,7H)-dione and aniline. The product was purified by Prep-HPLC using Method D (30-70% ACN). $^1$H NMR (400 MHz, DMSO-d$_6$) δ 9.17 (s, 1H), 7.69 (d, J=8.0 Hz, 2H), 7.61-7.53 (m, 2H), 7.38-7.25 (m, 3H), 7.06-6.93 (m, 1H), 5.02 (s, 2H), 3.79 (s, 3H), 3.41 (s, 3H); ESI: m/z 431.0 (M+H)$^+$.

Example 128

8-(1-(hydroxymethyl)cyclopentylamino)-3,7-dimethyl-1-(4-(trifluoromethyl)benzyl)-1H-purine-2,6(3H,7H)-dione

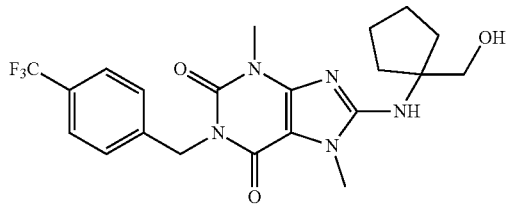 [SMILES: Cn1c(NC2(CO)CCCC2)nc2c1c(=O)n(Cc1ccc(C(F)(F)F)cc1)c(=O)n2C]

The titled compound was synthesized in a similar fashion described in Procedure 7A using 8-bromo-3,7-dimethyl-1-(4-(trifluoromethyl)benzyl)-1H-purine-2,6(3H,7H)-dione and (1-aminocyclopentyl)methanol. The product was purified by Prep-HPLC using Method D (30-70% ACN). $^1$H NMR (400 MHz, CD$_3$OD) δ 7.59-7.57 (d, J=8.4 Hz, 1H), 7.51-7.49 (d, J=7.6 Hz, 1H), 5.19 (s, 2H), 3.82 (s, 2H), 3.65 (s, 3H), 3.47 (s, 3H), 2.11-2.04 (m, 2H), 1.90-1.79 (m, 4H), 1.69-1.63 (m, 2H); ESI: m/z 452.2 (M+H)$^+$.

Example 129

(R)-2-(1-(3,4-dichlorobenzyl)-3,7-dimethyl-2,6-dioxo-2,3,6,7-tetrahydro-1H-purin-8-ylamino)propanoic acid

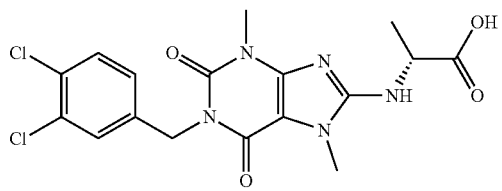 [SMILES: C[C@@H](Nc1nc2c(c(=O)n(Cc3ccc(Cl)c(Cl)c3)c(=O)n2C)n1C)C(=O)O]

To a solution of 8-bromo-1-(3,4-dichlorobenzyl)-3,7-dimethyl-1H-purine-2,6(3H,7H)-dione (150 mg, 0.36 mmol) and (R)-2-aminopropanoic acid (65 mg, 0.72 mmol) in DMSO (3 mL), were added CuI (10 mg, 0.036 mmol) and K$_2$CO$_3$ (150 mg, 0.108 mmol). The mixture was stirred at 120° C. for 1 h under N$_2$ atmosphere in a microwave reactor. The mixture was cooled, quenched with water (5 mL) and extracted with EA (3*10 mL). The combined organic fractions were dried with Na$_2$SO$_4$, filtered and concentrated. The residue was purified by prep-HPLC using Method D (45-75% ACN). $^1$H NMR (500 MHz, DMSO-d$_6$) δ 7.54 (d, J=1.6 Hz, 1H), 7.44 (d, J=8.4 Hz, 1H), 7.30-7.33 (dd, J=1.2 Hz, 1.0 Hz, 1H), 5.10 (s, 2H), 4.51 (m, 1H), 3.71 (s, 3H), 3.46 (s, 3H); ESI; m/z 426.1 (M+H)$^+$.

Example: 130

3-(1-(3,4-dichlorobenzyl)-3,7-dimethyl-2,6-dioxo-2,3,6,7-tetrahydro-1H-purin-8-ylamino)benzonitrile

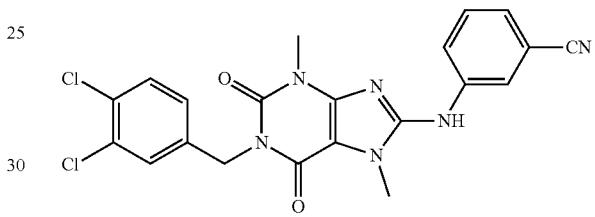

The title compound was synthesized in a similar fashion as described in Procedure 8A using 8-bromo-1-(3,4-dichlorobenzyl)-3,7-dimethyl-1H-purine-2,6(3H,7H)-dione and 3-aminobenzonitrile. The product was purified by flash chromatography (EA/PE=1/1). $^1$H NMR (400 MHz, DMSO-d$_6$) δ 9.54 (s, 1H), 8.13 (s, 1H), 8.02-7.99 (d, J=12.0 Hz, 1H), 7.58-7.51 (d, J=7.2 Hz, 1H), 7.30-7.29 (d, J=5.6 Hz, 1H), 5.02 (s, 2H), 3.80 (s, 3H), 3.43 (s, 3H); ESI: m/z 455.0 (M+H)$^+$.

Example 131

3-(1-(3,4-dichlorobenzyl)-3,7-dimethyl-2,6-dioxo-2,3,6,7-tetrahydro-1H-purin-8-ylamino)propanenitrile

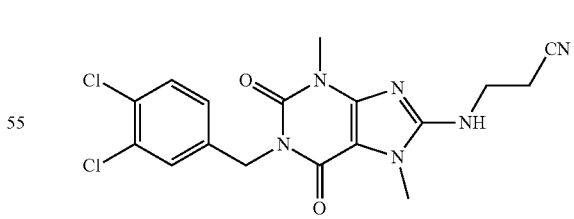

The title compound was synthesized in a similar fashion as described in Procedure 7A using 8-bromo-1-(3,4-dichlorobenzyl)-3,7-dimethyl-1H-purine-2,6(3H,7H)-dione and 3-aminopropanenitrile. The product was purified by prep-HPLC using Method B. $^1$H NMR (400 MHz, DMSO-d$_6$) δ 7.57-7.52 (m, 3H), 7.27-7.24 (m, 1H), 4.99 (s, 2H), 3.57 (d, J=6.0 Hz, 5H), 2.58 (m, 2H). ESI: m/z 407.1 (M+H)$^+$.

Example 132 and 143

8-(3H-1,2,4-triazol-3-ylamino)-1-(3,4-dichlorobenzyl)-3,7-dimethyl-1H-purine-2,6(3H,7H)-dione and 8-(5-amino-1H-1,2,4-triazol-1-yl)-1-(3,4-dichlorobenzyl)-3,7-dimethyl-1H-purine-2,6(3H,7H)-dione Example 132

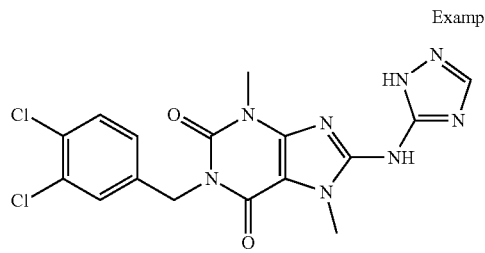

Example 143

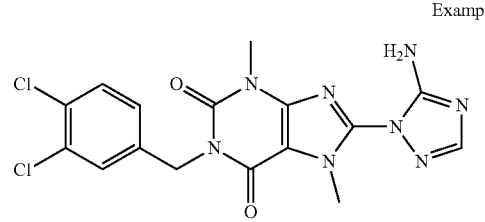

The title compounds were synthesized in a similar fashion as described in Procedure 8A using 8-bromo-1-(3,4-dichlorobenzyl)-3,7-dimethyl-1H-purine-2,6(3H,7H)-dione and 3H-1,2,4-triazol-3-amine. The crude mixture was purified by preparative HPLC using Method B. to give Example 132: 1H NMR (400 MHz, DMSO-$d_6$) δ 7.75 (s, 1H), 7.58 (d, J=8.0 Hz, 2H), 7.30 (s, 3H), 5.06 (s, 2H), 4.01 (s, 3H), 3.48 (s, 3H); ESI: m/z 421.1 (M+H)$^+$; and Example 143; $^1$H NMR (400 MHz, CDCl$_3$): δ 8.55 (s, 1H), 7.58 (d, J=1.6 Hz, 1H), 7.39-7.35 (m, 2H), 5.13 (s, 2H), 4.26 (s, 3H), 3.55 (s, 3H); ESI: m/z 421.1 (M+H)$^+$.

Example 171

(±)-8-((cis)-3-hydroxycyclopentylamino)-3,7-dimethyl-1-(4-(trifluoromethyl)benzyl)-1H-purine-2,6(3H,7H)-dione

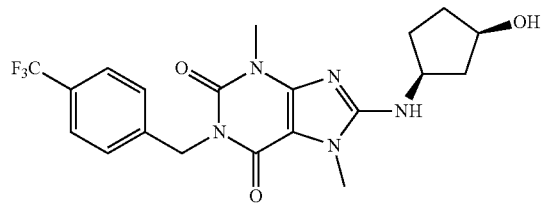 [SMILES: Cn1c(N[C@H]2CC[C@@H](O)C2)nc2c1c(=O)n(Cc1ccc(C(F)(F)F)cc1)c(=O)n2C]

The title compound was prepared in a similar fashion as described in Procedure 7A using 8-bromo-3,7-dimethyl-1-(4-(trifluoromethyl)benzyl)-1H-purine-2,6(3H,7H)-dione and (cis)-3-aminocyclopentanol. The product was purified by flash chromatography (DCM/MeOH=50/1)). $^1$H NMR (400 MHz, CDCl$_3$) δ 7.59-7.52 (m, 4H), 5.20 (s, 2H), 5.15 (d, J=8.8 Hz, 1H), 4.49-4.41 (m, 2H), 3.62 (s, 3H), 3.51 (s, 3H), 2.68 (m, 1H), 2.14-1.95 (m, 3H), 1.89-1.80 (m, 3H), 1.28-1.14 (m, 2H); ESI: m/z 438.1 (M+H)$^+$.

Examples 133 and 156

8-((1S,3R)-3-hydroxycyclopentylamino)-3,7-dimethyl-1-(4-(trifluoromethyl)benzyl)-1H-purine-2,6(3H,7H)-dione and 8-((1R,3S)-3-hydroxycyclopentylamino)-3,7-dimethyl-1-(4-(trifluoromethyl)benzyl)-1H-purine-2,6(3H,7H)-dione

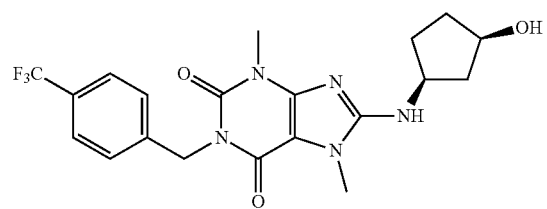

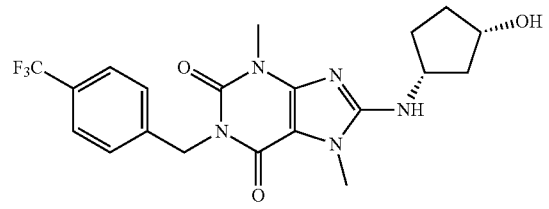

The title compounds were synthesized using a synthetic sequence as described for Example 78 and 79. The racemic tert-butyl carbonate ester was separate into individual enantiomers by chiral SFC using a CHIRALCEL®OJ-H/SFC OJ-H column eluting with 30% MeOH (0.1% NH$_4$OH) in carbon dioxide to give tert-butyl (1R,3S)-3-(3,7-dimethyl-2,6-dioxo-1-(4-(trifluoromethyl)benzyl)-2,3,6,7-tetrahydro-1H-purin-8-ylamino)cyclopentyl carbonate or tert-butyl (1S,3R)-3-(3,7-dimethyl-2,6-dioxo-1-(4-(trifluoromethyl)benzyl)-2,3,6,7-tetrahydro-1H-purin-8-ylamino)cyclopentyl carbonate (ee 99.42%, retention time 4.17 min) and tert-butyl (1R,3S)-3-(3,7-dimethyl-2,6-dioxo-1-(4-(trifluoromethyl)benzyl)-2,3,6,7-tetrahydro-1H-purin-8-ylamino)cyclopentyl carbonate or tert-butyl (1S,3R)-3-(3,7-dimethyl-2,6-dioxo-1-(4-(trifluoromethyl)benzyl)-2,3,6,7-tetrahydro-1H-purin-8-ylamino)cyclopentyl carbonate (ee 99.2%, retention time 4.59 min).

The individual enantiomers were independently treated with TFA in DCM to remove the tert-butyl carbonate groups. The products were purified by preparative HPLC using Method B.

Example 156: 8-((1S,3R)-3-hydroxycyclopentylamino)-3,7-dimethyl-1-(4-(trifluoromethyl)benzyl)-1H-purine-2,6(3H,7H)-dione or 8-((1R,3S)-3-hydroxycyclopentylamino)-3,7-dimethyl-1-(4-(trifluoromethyl)benzyl)-1H-purine-2,6(3H,7H)-dione: $^1$H NMR (400 MHz, CDCl$_3$) δ 7.56-7.51 (m, 4H), 5.20-5.18 (m, 3H), 4.48-4.39 (m, 2H), 3.61 (s, 3H), 3.51 (s, 3H), 2.85 (b, 1H), 2.12-1.97 (m, 3H), 1.87-1.82 (m, 3H); ESI: m/z 438.1 (M+H)$^+$.

Example 133: 8-((1S,3R)-3-hydroxycyclopentylamino)-3,7-dimethyl-1-(4-(trifluoromethyl)benzyl)-1H-purine-2,6(3H,7H)-dione or 8-((1R,3S)-3-hydroxycyclopentylamino)-3,7-dimethyl-1-(4-(trifluoromethyl)benzyl)-1H-purine-2,6(3H,7H)-dione: $^1$H NMR (400 MHz, CDCl$_3$) δ 7.56-7.51 (m, 4H), 5.28 (d, J=8.0 Hz, 1H), 5.20 (s, 2H), 4.45-4.37 (m, 2H), 3.60 (s, 3H), 3.50 (s, 3H), 3.11 (b, 1H), 2.11-1.93 (m, 3H), 1.87-1.80 (m, 3H); ESI: m/z 438.1 (M+H)$^+$.

Example 134

2-(1-(3,4-dichlorobenzyl)-3,7-dimethyl-2,6-dioxo-2,3,6,7-tetrahydro-1H-purin-8-ylamino)acetic acid

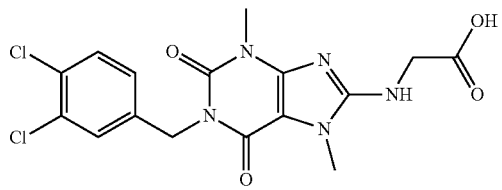 [SMILES: Cn1c(NCC(=O)O)nc2c1c(=O)n(Cc1ccc(Cl)c(Cl)c1)c(=O)n2C]

The title compound was synthesized in a similar fashion as described in Procedure 7A using 8-bromo-3,7-dimethyl-1-(4-(trifluoromethyl)benzyl)-1H-purine-2,6(3H,7H)-dione and 2-aminoacetic acid. The product was purified by chromatography (DCM/MeOH=50/1). $^1$H NMR (400 MHz, CD$_3$OD) δ 7.54 (d, J=1.6 Hz, 1H), 7.44 (d, J=6.8 Hz, 1H), 7.30 (dd, J=6.8, 1.6 Hz, 1H), 5.10 (s, 2H), 4.12 (s, 2H), 3.70 (s, 3H), 3.48 (s, 3H); ESI: m/z 412.0 (M+H)$^+$.

Example 135 and 136

8-(4-amino-1H-pyrazol-1-yl)-1-(3,4-dichlorobenzyl)-3,7-dimethyl-6,7-dihydro-1H-purin-2(3H)-one and 8-(4-amino-1H-pyrazol-1-yl)-1-(3,4-dichlorobenzyl)-3,7-dimethyl-6,7-dihydro-1H-purin-2(3H)-one Example 135

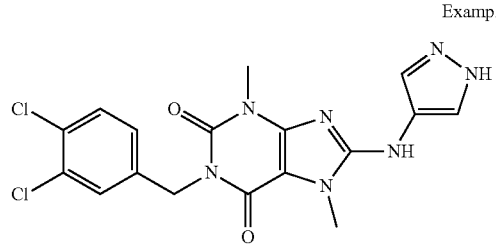

Example 136

The title compounds were synthesized in a similar fashion as described in Procedure 8A using 8-bromo-1-(3,4-dichlorobenzyl)-3,7-dimethyl-3,7-dihydro-1H-purine-2,6-dione and 1H-pyrazol-4-amine. The product was purified by preparative HPLC using Method B (25-55% ACN).

Example 135: $^1$H NMR (400 MHz, DMSO-d6) δ 12.58 (s, 1H), 9.24 (s, 1H), 7.93 (s, 1H), 7.62 (s, 1H), 7.57-7.48 (m, 1H), 7.28 (dd, J=8.3, 1.9 Hz, 1H), 5.01 (s, 2H), 3.71 (s, 3H), 3.42 (s, 3H); ESI: m/z 419.2 (M+H)$^+$.

Example 136: $^1$H NMR (400 MHz, DMSO-d$_6$) δ 7.61 (s, 1H), 7.59-7.55 (m, 2H), 7.52 (s, 1H), 7.31 (dd, J=8.3, 1.8 Hz, 1H), 5.04 (s, 2H), 4.49 (s, 2H), 4.11 (s, 3H), 3.43 (s, 3H); ESI: m/z 419.2 (M+H)$^+$.

Example 137

8-(benzylamino)-1-(3,4-dichlorobenzyl)-3,7-dimethyl-1H-purine-2,6(3H,7H)-dione

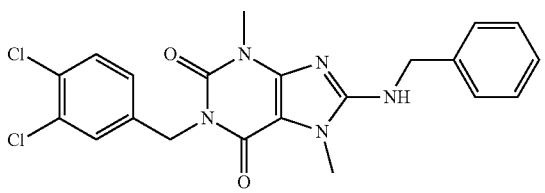 [SMILES: Cn1c(NCc2ccccc2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and benzylamine. The mixture was purified by column chromatography (DCM:MeOH=20:1). $^1$H NMR (400 MHz, DMSO-d$_6$) δ 7.68 (t, J=6.1 Hz, 1H), 7.59-7.50 (m, 2H), 7.41-7.30 (m, 4H), 7.29-7.21 (m, 2H), 4.98 (s, 2H), 4.56 (d, J=6.0 Hz, 2H), 3.61 (s, 3H), 3.33 (s, 3H); ESI: m/z 444.0 (M+H)$^+$.

Example 138

1-(3,4-dichlorobenzyl)-8-(4-hydroxypyrimidin-2-ylamino)-3,7-dimethyl-1H-purine-2,6(3H,7H)-dione

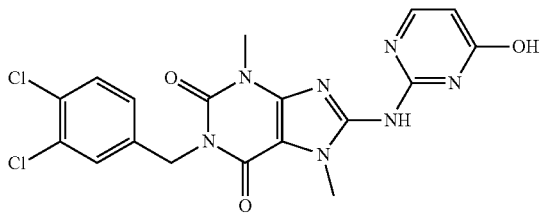 [SMILES: Cn1c(Nc2nccc(O)n2)nc2c1c(=O)n(Cc1ccc(Cl)c(Cl)c1)c(=O)n2C]

The title compound was synthesized as described in Procedure 8A using 8-bromo-1-(3,4-dichlorobenzyl)-3,7-dimethyl-1H-purine-2,6(3H,7H)-dione and 2-aminopyrimidin-4-ol. The product was purified by Prep-HPLC using Method D (30-70% ACN). $^1$H NMR (400 MHz, DMSO-d$_6$) δ 11.99 (s, 1H), 7.66 (d, J=7.6 Hz, 1H), 7.60-7.55 (m, 2H), 7.29 (dd, J=8.4, 1.9 Hz, 1H), 5.68 (d, J=7.6 Hz, 1H), 5.03 (s, 2H), 3.70 (s, 3H), 3.48 (s, 3H); ESI: m/z 448.0 (M+H)$^+$.

Example 139

1-(3,4-dichlorobenzyl)-3,7-dimethyl-8-(pyridin-2-ylmethylamino)-1H-purine-2,6(3H,7H)-dione

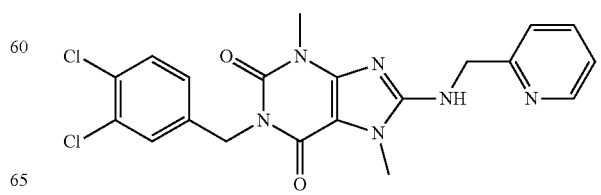

The title compound was synthesized in a similar fashion as described in Procedure 7A using 8-bromo-1-(3,4-dichlorobenzyl)-3,7-dimethyl-1H-purine-2,6(3H,7H)-dione and pyridin-2-ylmethanamine. The product was purified by column chromatography (DCM:MeOH=10:1). $^1$H NMR (400 MHz, DMSO-$d_6$) δ 8.53 (d, J=4.2 Hz, 1H), 7.83-7.71 (m, 2H), 7.57-7.50 (m, 2H), 7.41 (d, J=7.8 Hz, 1H), 7.32-7.21 (m, 2H), 4.98 (s, 2H), 4.65 (d, J=6.0 Hz, 2H), 3.65 (s, 3H), 3.29 (s, 3H); ESI: m/z 452.1 (M+H)$^+$.

Example 140

1-(3,4-dichlorobenzyl)-3,7-dimethyl-8-(2-oxo-1,2-dihydropyrimidin-4-ylamino)-1H-purine-2,6(3H,7H)-dione

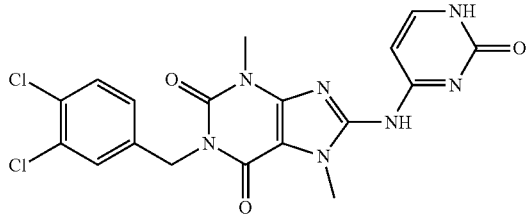 [SMILES: Cn1c(Nc2cc[nH]c(=O)n2)nc2c1c(=O)n(Cc1ccc(Cl)c(Cl)c1)c(=O)n2C]

The title compound was synthesized in a similar fashion as described in Procedure 8A using 8-bromo-1-(3,4-dichlorobenzyl)-3,7-dimethyl-1H-purine-2,6(3H,7H)-dione and 4-aminopyrimidin-2(1H)-one The product was purified by flash chromatography (EA/PE=2/1) to give the crude product. The crude product was purified by Prep-HPLC using Method D (30-70% ACN). $^1$H NMR (400 MHz, DMSO-$d_6$) δ 7.76-7.75 (m, 2H), 7.63-7.57 (m, 3H), 7.31-7.30 (d, J=1.0 Hz, 1H), 5.94-5.92 (d, J=8.0 Hz, 1H), 5.06 (s, 2H), 3.68 (s, 3H), 3.41 (s, 3H); ESI: m/z 448.0 (M+H)$^+$.

Example 141

8-(1H-pyrazol-3-ylamino)-1-(3,4-dichlorobenzyl)-3,7-dimethyl-1H-purine-2,6(3H,7H)-dione

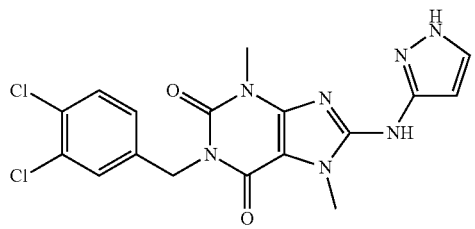 [SMILES: Cn1c(Nc2cc[nH]n2)nc2c1c(=O)n(Cc1ccc(Cl)c(Cl)c1)c(=O)n2C]

The title compound was synthesized in a similar fashion as described in Procedure 8A using 8-bromo-1-((4,5-dichloropyridin-2-yl)methyl)-3,7-dimethyl-1H-purine-2,6(3H,7H)-dione and tert-butyl 3-amino-1H-pyrazole-1-carboxylate. The product was purified by flash chromatography (EA/PE=20%) to afford the Boc-protected product: ESI: m/z 521.1 (M+H)$^+$. The Boc was removed with 6N HCl in methanol. The product was purified by prep-HPLC using Method B. $^1$H NMR (400 MHz, DMSO-$d_6$) δ 12.31 (s, 1H), 9.85 (s, 1H), 7.64-7.54 (m, 3H), 7.29-7.27 (m, 1H), 6.61 (s, 1H), 5.01 (s, 2H), 3.74 (s, 3H), 3.40 (s, 3H); ESI: m/z 420.1 (M+H)$^+$.

Example 142

2-(1-(3,4-dichlorobenzyl)-3,7-dimethyl-2,6-dioxo-2,3,6,7-tetrahydro-1H-purin-8-ylamino)benzonitrile

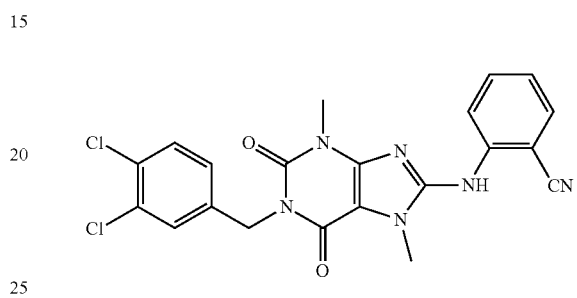

The title compound was synthesized in a similar fashion as described in Procedure 8A using 8-bromo-1-(3,4-dichlorobenzyl)-3,7-dimethyl-1H-purine-2,6(3H,7H)-dione and 2-aminobenzonitrile. The product was purified by flash chromatography (DCM/MeOH=15/1). $^1$H NMR (400 MHz, CDCl$_3$) δ 8.27 (d, J=6.4 Hz, 1H), 7.63-7.58 (m, 3H), 7.38-7.33 (m, 2H), 7.13 (t, J=6.0 Hz, 1H), 6.81 (s, 1H), 5.13 (s, 2H), 3.92 (s, 3H), 3.57 (s, 3H); ESI: m/z 455.0 (M+H)$^+$.

Example 145

8-(3,3-difluorocyclobutylamino)-3,7-dimethyl-1-(4-(trifluoromethyl)benzyl)-1H-purine-2,6(3H,7H)-dione

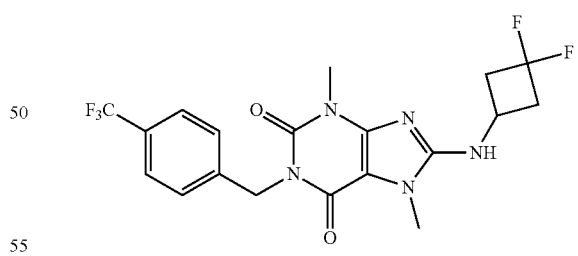

The title compound was synthesized in a similar fashion described in Procedure 7A using 8-bromo-3,7-dimethyl-1-(4-(trifluoromethyl)benzyl)-1H-purine-2,6(3H,7H)-dione and 3,3-difluorocyclobutanamine. The product was purified by preparative HPLC using Method D (45-75% ACN). $^1$H NMR (400 MHz, DMSO-$d_6$) δ 7.66 (d, J=8.2 Hz, 2H), 7.46 (d, J=7.6 Hz, 3H), 5.09 (s, 2H), 4.29-4.05 (m, 1H), 3.59 (s, 3H), 3.36 (s, 3H), 3.11-2.89 (m, 2H), 2.84-2.59 (m, 2H); ESI: m/z 426.1 (M+H)$^+$.

Example 146

1-(3,4-dichlorobenzyl)-3,7-dimethyl-8-(pyridin-2-ylamino)-1H-purine-2,6(3H,7H)-dione

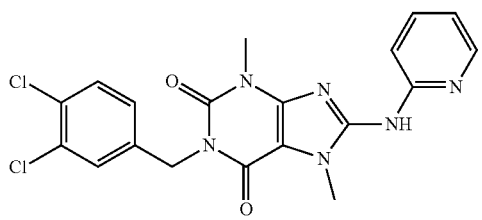 [SMILES: Cn1c(Nc2ccccn2)nc2c1c(=O)n(Cc1ccc(Cl)c(Cl)c1)c(=O)n2C]

The title compound was synthesized in a similar fashion as described in Procedure 8A using 8-bromo-1-(3,4-dichlorobenzyl)-3,7-dimethyl-1H-purine-2,6(3H,7H)-dione and pyridin-2-amine The product was recrystallized from MeOH. $^1$H NMR (400 MHz, DMSO-$d_6$) δ 9.97 (br s, 1H), 8.27-8.22 (m, 1H), 7.79-7.75 (m, 2H), 7.58-7.56 (m, 2H), 7.31-7.29 (m, 1H), 6.98 (br s, 1H), 5.03 (s, 2H), 3.77 (s, 3H), 3.43 (s, 3H); ESI: m/z 431.1 (M+H)$^+$.

Example 147

1-(1-(3,4-dichlorobenzyl)-3,7-dimethyl-2,6-dioxo-2,3,6,7-tetrahydro-1H-purin-8-ylamino)cyclopropanecarboxylic acid

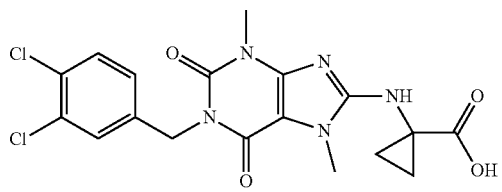 [SMILES: Cn1c(NC2(C(=O)O)CC2)nc2c1c(=O)n(Cc1ccc(Cl)c(Cl)c1)c(=O)n2C]

The title compound was made in a similar fashion as described in Procedure 7A using 8-bromo-1-(3,4-dichlorobenzyl)-3,7-dimethyl-1H-purine-2,6(3H,7H)-dione and 1-aminocyclopropanecarboxylic acid. The product was purified by reverse chromatography (C18, CH$_3$CN/H$_2$O=20/80). $^1$H NMR (400 MHz, CD$_3$OD) δ 7.41 (d, J=1.6 Hz, 1H), 7.33 (d, J=8.4 Hz, 1H), 7.19 (dd, J=1.6, 8.4 Hz, 1H), 4.99 (s, 2H), 3.56 (s, 3H), 3.38 (s, 3H), 1.49-1.46 (m, 2H), 1.14-1.11 (m, 2H); ESI: m/z 438.0 (M+H)$^+$.

Example 148

1-(1-(3,4-dichlorobenzyl)-3,7-dimethyl-2,6-dioxo-2,3,6,7-tetrahydro-1H-purin-8-ylamino)cyclopentanecarboxylic acid

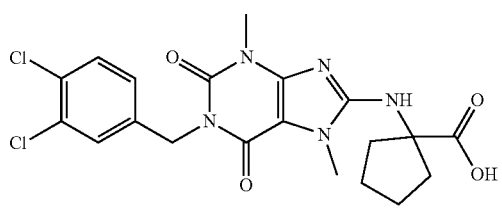 [SMILES: Cn1c(NC2(C(=O)O)CCCC2)nc2c1c(=O)n(Cc1ccc(Cl)c(Cl)c1)c(=O)n2C]

The title compound was synthesized in a similar fashion as described in Procedure 7A using 8-bromo-1-(3,4-dichlorobenzyl)-3,7-dimethyl-1H-purine-2,6(3H,7H)-dione and 1-aminocyclopentanecarboxylic acid. The product was purified by reversed chromatography (C18, CH$_3$CN/H$_2$O=30/70). $^1$H NMR (400 MHz, DMSO-$d_6$) δ 12.33 (br s, 1H), 7.55-7.53 (m, 2H), 7.25 (dd, J=1.6, 8.4 Hz, 1H), 7.14 (s, 1H), 4.99 (s, 2H), 3.63 (s, 3H), 3.30 (s, 3H), 2.21-2.05 (m, 4H), 1.76-1.66 (m, 4H); ESI: m/z 466.2 (M+H)$^+$.

Example 149

1-(3,7-dimethyl-2,6-dioxo-1-(4-(trifluoromethyl)benzyl)-2,3,6,7-tetrahydro-1H-purin-8-ylamino)cyclopentanecarboxylic acid

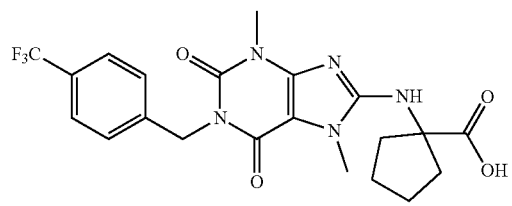 [SMILES: Cn1c(NC2(C(=O)O)CCCC2)nc2c1c(=O)n(Cc1ccc(C(F)(F)F)cc1)c(=O)n2C]

The title compound was synthesized in a similar fashion as described in Procedure 7A using 8-bromo-3,7-dimethyl-1-(4-(trifluoromethyl)benzyl)-1H-purine-2,6(3H,7H)-dione and 1-aminocyclopentanecarboxylic acid. The product was purified by reverse chromatography (C18, CH$_3$CN/H$_2$O=30/70). $^1$H NMR (400 MHz, DMSO-$d_6$) δ 12.31 (br s, 1H), 7.65 (d, J=8.4 Hz, 2H), 7.46 (d, J=8.0 Hz, 2H), 7.14 (s, 1H), 5.09 (s, 2H), 3.63 (s, 3H), 3.17 (s, 3H), 2.20-2.15 (m, 4H), 1.76-1.66 (m, 4H). ESI: m/z 466.2 (M+H)$^+$.

Example 150

8-(6-aminopyridin-2-ylamino)-1-(3,4-dichlorobenzyl)-3,7-dimethyl-1H-purine-2,6(3H,7H)-dione

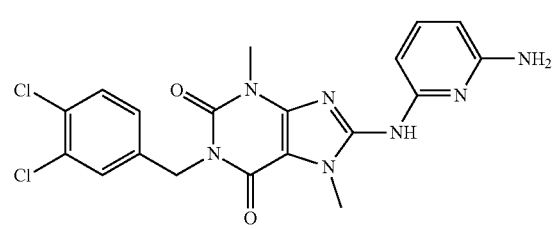 [SMILES: Cn1c(Nc2cccc(N)n2)nc2c1c(=O)n(Cc1ccc(Cl)c(Cl)c1)c(=O)n2C]

The title compound was synthesized in a similar fashion as described in Procedure 8A using 8-bromo-1-(3,4-dichlorobenzyl)-3,7-dimethyl-1H-purine-2,6(3H,7H)-dione and pyridine-2,6-diamine. The product was purified by column chromatography (3050% EA/PE). $^1$H NMR (400 MHz, DMSO-$d_6$) δ 9.37 (s, 1H), 7.58-7.55 (m, 2H), 7.35-7.72 (m, 2H), 6.85-6.83 (m, 1H), 6.07-6.05 (m, 1H), 5.72 (d, J=6.0 Hz, 1H), 5.03 (s, 2H), 3.73 (s, 3H), 3.41 (s, 3H); ESI: m/z 446.0 (M+H)$^+$.

Example 151

2-cyclohexyl-2-((3,7-dimethyl-2,6-dioxo-1-(4-(trifluoromethyl)benzyl)-2,3,6,7-tetrahydro-1H-purin-8-yl)amino)acetic acid

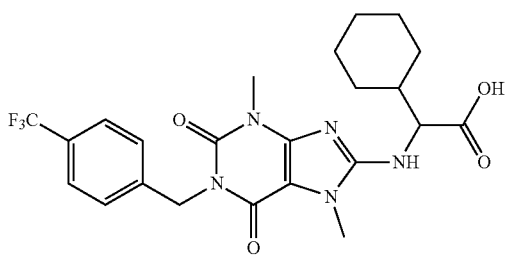 [SMILES: Cn1c(NC(C(=O)O)C2CCCCC2)nc2c1c(=O)n(Cc1ccc(C(F)(F)F)cc1)c(=O)n2C]

The title compound was synthesized in a similar fashion as described in Procedure 7A using 8-bromo-3,7-dimethyl-1-(4-(trifluoromethyl)benzyl)-1H-purine-2,6(3H,7H)-dione and 2-amino-2-cyclohexylacetic acid. The product was purified by prep-HPLC using Method B. $^1$H NMR (400 MHz, CD$_3$OD): δ 7.59 (d, J=8.2 Hz, 2H), 7.51 (d, J=8.1 Hz, 2H), 5.20 (s, 2H), 4.41 (d, J=6.7 Hz, 1H), 3.71 (d, J=7.1 Hz, 3H), 3.50-3.42 (m, 3H), 1.91-1.66 (m, 5H), 1.28 (dt, J=23.3, 13.1 Hz, 5H); ESI: m/z 494.1 (M+H)$^+$.

Example 152

1-(3,4-dichlorobenzyl)-3,7-dimethyl-1H-purine-2,6(3H,7H)-dione

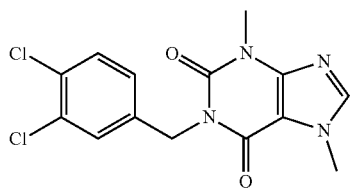 [SMILES: Cn1cnc2c1c(=O)n(Cc1ccc(Cl)c(Cl)c1)c(=O)n2C]

The title compound was made according to Procedure 4 using 3,7-dimethyl-1H-purine-2,6(3H,7H)-dione and 4-(bromomethyl)-1,2-dichlorobenzene. The crude product was purified by column chromatography (PE:EA=10:1 to 1:1). $^1$H NMR (400 MHz, DMSO-d$_6$) δ 8.05 (s, 1H), 7.57 (dd, J=5.0, 3.1 Hz, 2H), 7.29 (dd, J=8.3, 1.8 Hz, 1H), 5.03 (s, 2H), 3.89 (s, 3H), 3.43 (s, 3H); ESI: m/z 339.0 (M+H)$^+$.

Example 153

8-amino-1-(3,4-dichlorobenzyl)-3,7-dimethyl-1H-purine-2,6(3H,7H)-dione

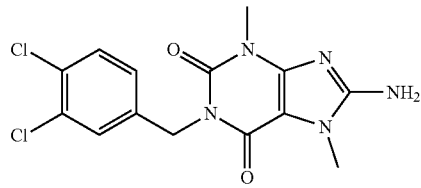 [SMILES: Cn1c(N)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione (200 mg, 0.48 mmol) was dissolved in NH$_3$/MeOH (50 mL) and sealed in a tube. The mixture was heated to 150° C. and stirred at that temperature for 15 h. The reaction mixture was concentrated and purified by column chromatography (PE/EA=1/1) to provide the title compound. $^1$H NMR (400 MHz, DMSO-d$_6$) δ 7.62-7.47 (m, 2H), 7.26 (dd, J=8.3, 1.9 Hz, 1H), 6.96 (s, 2H), 4.98 (s, 2H), 3.56 (s, 3H), 3.33 (s, 3H). ESI: m/z 354.1 (M+H)$^+$.

Example 154

Methyl 4-(1-(3,4-dichlorobenzyl)-3,7-dimethyl-2,6-dioxo-2,3,6,7-tetrahydro-1H-purin-8-ylamino)benzoate

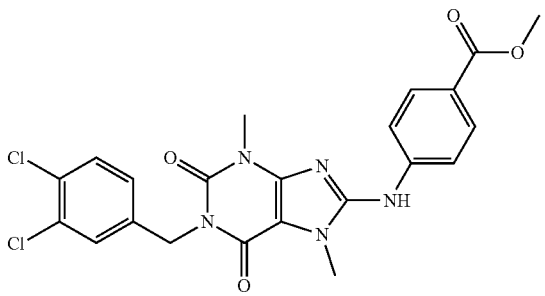 [SMILES: COC(=O)c1ccc(Nc2nc3c(c(=O)n(Cc4ccc(Cl)c(Cl)c4)c(=O)n3C)n2C)cc1]

The title compound was synthesized in a similar fashion as described in Procedure 8A using 8-bromo-1-(3,4-dichlorobenzyl)-3,7-dimethyl-1H-purine-2,6(3H,7H)-dione and methyl 4-aminobenzoate. The product was purified by flash chromatography (EA/PE=2/1). $^1$H NMR (400 MHz, d$_6$-DMSO) δ 9.59 (s, 1H), 7.92-7.90 (d, J=6.8 Hz, 2H), 7.81-7.79 (d, J=6.4 Hz, 2H), 7.57-7.55 (m, 2H), 7.30-7.28 (d, J=8.0 Hz, 1H), 5.02 (s, 2H), 3.81 (s, 6H), 3.43 (s, 3H); ESI: m/z 488.0 (M+H)$^+$.

Example 155

(±)-1-((1H-indol-2-yl)methyl)-8-((cis)-3-hydroxycyclopentylamino)-3,7-dimethyl-1H-purine-2,6(3H,7H)-dione

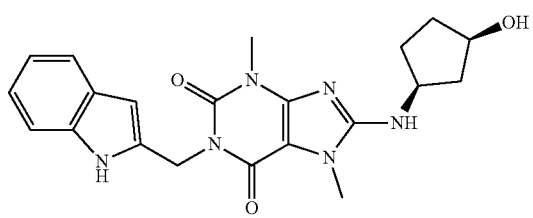 [SMILES: Cn1c(N[C@H]2CC[C@@H](O)C2)nc2c1c(=O)n(Cc1cc3ccccc3[nH]1)c(=O)n2C]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-1H-indole-1-carboxylate and cis-3-aminocyclopentanol. The product was purified by Prep-HPLC using Method D (30-70% ACN). $^1$H NMR (400 MHz, CD$_3$OD) δ 7.42-7.44 (d, J=8.0 Hz, 1H), 7.30-7.32 (d, J=8.0 Hz, 1H), 7.01-7.05 (m, 1H), 6.92-6.96 (m, 1H), 6.35 (s, 1H), 5.26 (s, 2H), 3.63 (s, 3H), 3.50 (s, 3H), 2.31-2.38 (m, 1H), 2.06-2.10 (m, 1H), 1.77-1.88 (m, 3H), 1.61-1.67 (m, 1H); ESI: m/z 409.2 (M+H)⁺.

Example 158

1-(3,4-dichlorobenzyl)-8-(2-hydroxyethyl)-3,7-dimethyl-1H-purine-2,6(3H,7H)-dione

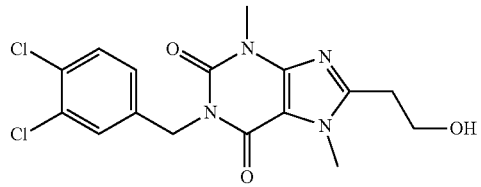 [SMILES: Cn1c(CCO)nc2c1c(=O)n(Cc1ccc(Cl)c(Cl)c1)c(=O)n2C]

To a solution of ethyl 2-(1-(3,4-dichlorobenzyl)-3,7-dimethyl-2,6-dioxo-2,3,6,7-tetrahydro-1H-purin-8-yl)acetate (440 mg, 1.04 mmol) in THF (10 mL), was added NaBH₄ (118 mg, 3.12 mmol). After stirring at room temperature for 6 h, the reaction was quenched with MeOH (10 mL) and concentrated. The residue was purified by flash chromatography (DCM/MeOH=20/1) to give the tile compound. ¹H NMR (400 MHz, CDCl₃) δ 7.56 (d, J=2.0 Hz, 1H), 7.38-7.31 (m, 2H), 5.12 (s, 2H), 4.08 (q, J=5.6 Hz, 2H), 3.93 (s, 3H), 3.55 (s, 3H), 3.37 (t, J=6.4 Hz, 1H), 2.93 (t, J=5.6 Hz, 2H); ESI: m/z 383.1 (M+H)⁺.

Example 157

1-(3,4-dichlorobenzyl)-8-(2-(dimethylamino)ethyl)-3,7-dimethyl-1H-purine-2,6(3H,7H)-dione

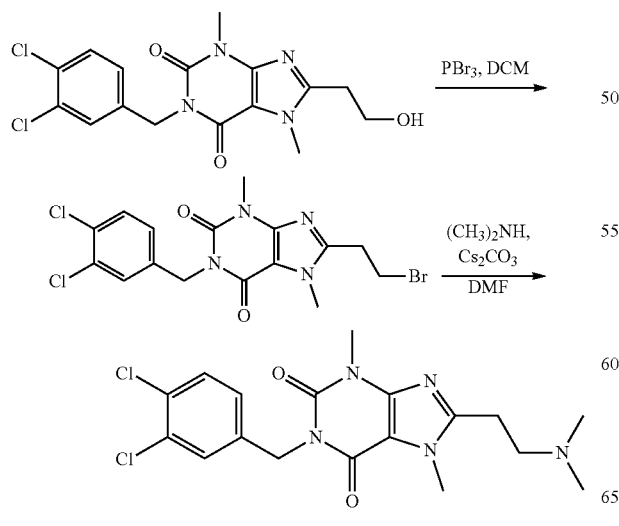

8-(2-bromoethyl)-1-(3,4-dichlorobenzyl)-3,7-dimethyl-1H-purine-2,6(3H,7H)-dione

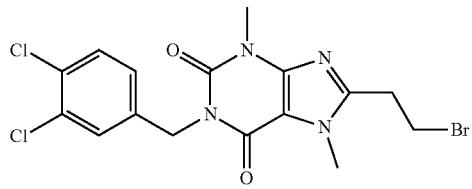 [SMILES: Cn1c(CCBr)nc2c1c(=O)n(Cc1ccc(Cl)c(Cl)c1)c(=O)n2C]

To a solution of 1-(3,4-dichlorobenzyl)-8-(2-hydroxyethyl)-3,7-dimethyl-1H-purine-2,6(3H,7H)-dione (100 mg, 0.261 mmol) in DCM (10 mL) was added PBr₃ (78 mg, 0.288 mmol) at 0° C. The mixture was stirred at this temperature for 1 h. Water (10 mL) was added and the mixture was extracted with DCM (10 mL). The organic fraction was dried over Na₂SO₄ and concentrated to give the title compound. ESI: m/z 447.0 (M+H)⁺.

1-(3,4-Dichlorobenzyl)-8-(2-(dimethylamino)ethyl)-3,7-dimethyl-1H-purine-2,6(3H,7H)-dione

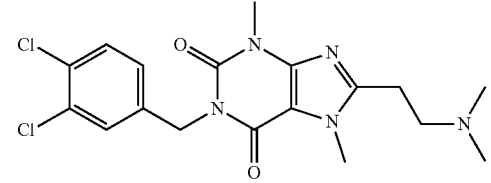 [SMILES: CN(C)CCc1nc2c(c(=O)n(Cc3ccc(Cl)c(Cl)c3)c(=O)n2C)n1C]

To a solution of 8-(2-bromoethyl)-1-(3,4-dichlorobenzyl)-3,7-dimethyl-1H-purine-2,6(3H,7H)-dione (50 mg, 0.112 mmol) in DMF (3 mL) was added dimethylamine (50 mg, 1.12 mmol) and Cs₂CO₃ (73 mg, 0.22 mmol). The mixture was stirred at 50° C. for 15 h. The mixture was cooled, diluted with water (5 mL) and extracted with EA (3*5 mL). The combined organic fractions were dried with Na₂SO₄, filtered and concentrated. The residue was purified by prep-HPLC using a Method F (25-55% ACN). ¹H NMR (400 MHz, CD₃OD) δ 7.40 (d, J=1.9 Hz, 1H), 7.26 (d, J=8.3 Hz, 1H), 7.18 (dd, J=8.3, 2.0 Hz, 1H), 4.93 (s, 2H), 3.81 (s, 3H), 3.38 (s, 3H), 2.90-2.78 (m, 2H), 2.72-2.60 (m, 2H), 2.22 (s, 6H); ESI: m/z 410.1 (M+H)⁺.

Example 159 and 160

1-(3,4-dichlorobenzyl)-3,7-dimethyl-8-(2-morpholinoethyl)-1H-purine-2,6(3H,7H)-dione (159) and 1-(3,4-dichlorobenzyl)-3,7-dimethyl-8-vinyl-1H-purine-2,6(3H,7H)-dione (160)

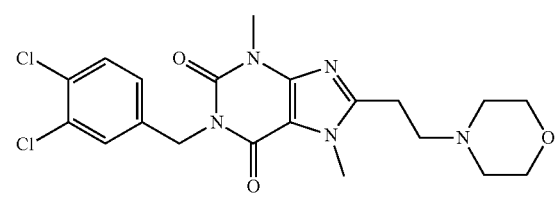

-continued

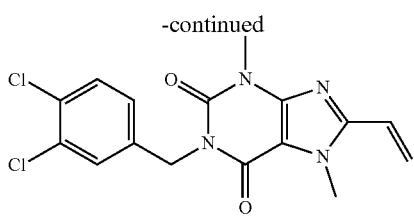

To a solution of 1-(3,4-dichlorobenzyl)-8-(2-hydroxyethyl)-3,7-dimethyl-1H-purine-2,6(3H,7H)-dione (80 mg, 0.21 mmol) in DCM (5 mL) was added MsCl (29 mg, 0.25 mmol) and Et$_3$N (64 mg, 0.63 mmol). After stirring at room temperature for 2 h, the mixture was concentrated. The residue was diluted with DCM (10 mL). To the mixture was added morpholine (92 mg, 1.05 mmol) and Et$_3$N (212 mg, 2.1 mmol). After stirring at reflux for 12 h, the mixture was cooled and concentrated. The residue was purified by flash chromatography (DCM/MeOH=100/1) to give 1-(3,4-dichlorobenzyl)-3,7-dimethyl-8-(2-morpholinoethyl)-1H-purine-2,6(3H,7H)-dione Example 159: $^1$H NMR (400 MHz, CDCl$_3$) δ 7.57 (d, J=1.2 Hz, 1H), 7.37-7.34 (m, 2H), 5.12 (s, 2H), 3.94 (s, 3H), 3.71 (t, J=4.8 Hz, 4H), 3.55 (s, 3H), 2.92 (t, J=7.2 Hz, 2H), 2.78 (t, J=7.2 Hz, 2H), 2.53 (t, J=4.4 Hz, 4H); ESI: m/z 452.1 (M+H)$^+$ and 1-(3,4-dichlorobenzyl)-3,7-dimethyl-8-vinyl-1H-purine-2,6(3H,7H)-dione Example 160: $^1$H NMR (400 MHz, CDCl$_3$) δ 7.57 (d, J=1.6 Hz, 1H), 7.38-7.32 (m, 2H), 6.64 (dd, J=11.2, 17.2 Hz, 1H), 6.46 (dd, J=1.6, 17.2 Hz, 1H), 5.76 (dd, J=1.6, 11.2 Hz, 1H), 5.12 (s, 2H), 4.00 (s, 3H), 3.59 (s, 3H). ESI m/z 365.1 (M+H)$^+$.

Example 163

(±)-1-((1H-indol-6-yl)methyl)-8-((cis)-3-hydroxycyclopentylamino)-3,7-dimethyl-1H-purine-2,6(3H,7H)-dione

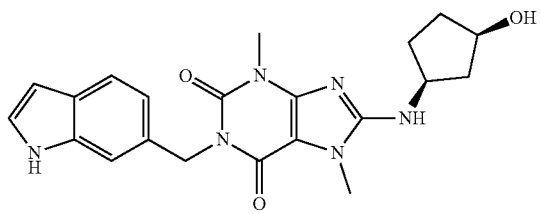 [SMILES: Cn1c(N[C@H]2CC[C@@H](O)C2)nc2c1c(=O)n(Cc1ccc3cc[nH]c3c1)c(=O)n2C]

The title compound was synthesized in a similar fashion as described in Procedure 7A using 6-((8-bromo-3,7-dimethyl-2,6-dioxo-2,3,6,7-tetrahydro-1H-purin-1-yl)methyl)-1H-indole-1-carboxylate and (cis)-3-aminocyclopentanol. The product was purified by Prep-HPLC using Method D (30-70% ACN). $^1$H NMR (400 MHz, CDCl$_3$) δ 8.28 (s, 1H), 7.52-7.55 (m, 2H), 7.27-7.29 (d, J=8.4 Hz, 1H), 7.12-7.13 (m, 1H), 6.45 (s, 1H), 5.26 (s, 2H), 4.45-4.46 (m, 1H), 3.34-3.36 (m, 1H), 3.59 (s, 3H), 3.48 (s, 3H), 1.78-2.09 (m, 7H); ESI: m/z 409.2 (M+H)$^+$.

Example 164

1-[(3,4-dichlorophenyl)methyl]-8-[(3-hydroxy-3-methylcyclopentyl)amino]-3,7-dimethyl-2,3,6,7-tetrahydro-1H-purine-2,6-dione

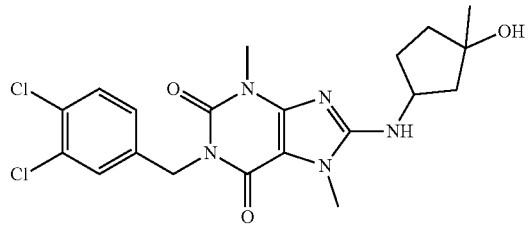 [SMILES: Cn1c(NC2CCC(C)(O)C2)nc2c1c(=O)n(Cc1ccc(Cl)c(Cl)c1)c(=O)n2C]

The title compound was synthesized in a similar fashion as described in Procedure 7B using 8-bromo-1-(3,4-dichlorobenzyl)-3,7-dimethyl-1H-purine-2,6(3H,7H)-dione and 3-amino-1-methylcyclopentan-1-ol. The product was purified by prep-HPLC (acetonitrile/water, 0.2% ammonium hydroxide). The product is a diastereomerically pure racemate of unknown configuration. $^1$H NMR (500 MHz, DMSO-d$_6$) δ 7.56 (d, J=8.3 Hz, 1H), 7.52 (d, J=1.9 Hz, 1H), 7.26 (dd, J=8.3, 2.0 Hz, 1H), 6.92 (d, J=7.4 Hz, 1H), 4.99 (s, 2H), 4.62 (s, 1H), 4.17 (p, J=7.3 Hz, 1H), 3.56 (s, 3H), 3.35 (s, 3H), 2.06-1.98 (m, 2H), 1.87-1.77 (m, 1H), 1.77-1.66 (m, 2H), 1.54-1.46 (m, 1H), 1.24 (s, 3H); ESI: m/z 452.1 (M+H)$^+$.

Example 165

Methyl 2-chloro-5-({8-[(3-hydroxypropyl)amino]-3,7-dimethyl-2,6-dioxo-2,3,6,7-tetrahydro-1H-purin-1-yl}methyl)benzoate

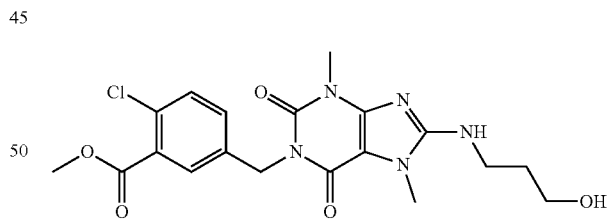

The title compound was synthesized in a similar fashion as described in Procedure 7B using methyl 5-((8-bromo-3,7-dimethyl-2,6-dioxo-2,3,6,7-tetrahydro-1H-purin-1-yl)methyl)-2-chlorobenzoate and 3-aminopropan-1-ol. The product was purified by flash column chromatography (0-10% methanol/DCM). $^1$H NMR (500 MHz, DMSO-d$_6$) δ 7.71 (d, J=2.0 Hz, 1H), 7.50 (d, J=8.3 Hz, 1H), 7.46 (dd, J=8.3, 2.1 Hz, 1H), 7.02 (t, J=5.5 Hz, 1H), 5.01 (s, 2H), 4.49 (t, J=5.1 Hz, 1H), 3.85 (s, 3H), 3.55 (s, 3H), 3.48 (q, J=5.9 Hz, 2H), 3.38 (q, J=6.8 Hz, 2H), 3.35 (s, 3H), 1.73 (p, J=6.5 Hz, 2H); ESI: m/z 436.2 (M+H)$^+$.

Example 166

1-{[4-chloro-3-(hydroxymethyl)phenyl]methyl}-8-[(3-hydroxypropyl)amino]-3,7-dimethyl-2,3,6,7-tetrahydro-1H-purine-2,6-dione

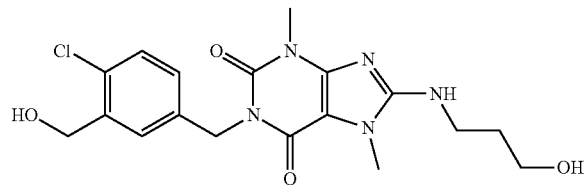 [SMILES: Cn1c(NCCCO)nc2c1c(=O)n(Cc1ccc(Cl)c(CO)c1)c(=O)n2C]

Methyl 2-chloro-5-({8-[(3-hydroxypropyl)amino]-3,7-dimethyl-2,6-dioxo-2,3,6,7-tetrahydro-1H-purin-1-yl}methyl)benzoate (40 mg, 0.09 mmol) in tetrahydrofuran (3 ml) was added to lithium borohydride (8 mg, 0.37 mmol). The reaction was heated to 50° C. for 1 h then cooled and quenched by dropwise addition of water. The mixture was poured into water and extracted into ethyl acetate three times. The combined organic fractions were washed with sat. NaCl, dried over MgSO$_4$ and concentrated in vacuo. The residue was purified by HPLC (acetonitrile/water, 0.2% ammonium hydroxide). $^1$H NMR (500 MHz, DMSO-d$_6$) δ 7.46 (s, 1H), 7.30 (d, J=8.2 Hz, 1H), 7.16 (dd, J=8.2, 1.8 Hz, 1H), 7.00 (t, J=5.4 Hz, 1H), 5.35 (s, 1H), 5.00 (s, 2H), 4.51 (s, 3H), 3.56 (s, 3H), 3.48 (q, J=5.8 Hz, 2H), 3.38 (q, J=6.7 Hz, 2H), 3.35 (s, 3H), 1.73 (p, J=6.5 Hz, 2H); ESI: m/z 408.2 (M+H)$^+$.

Example 167

1-[(3,4-dichlorophenyl)methyl]-8-[(3-hydroxypropyl)amino]-7-methyl-6,7-dihydro-1H-purin-6-one

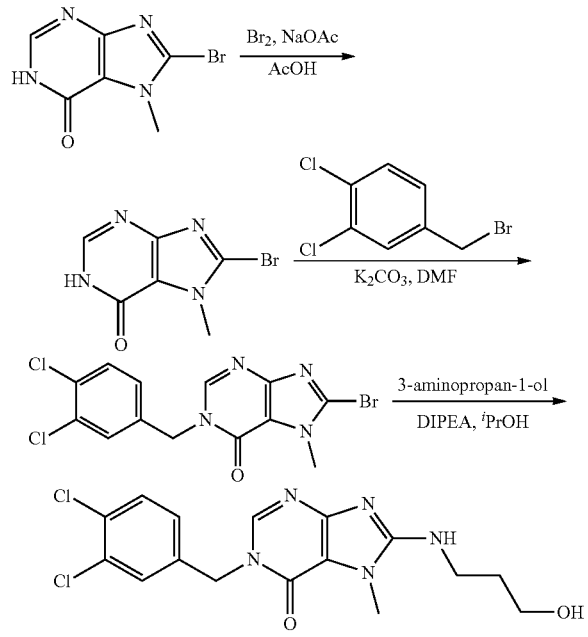

8-bromo-7-methyl-6,7-dihydro-1H-purin-6-one

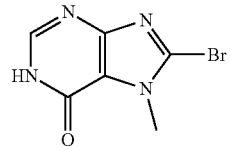

Bromine (512 µl, 9.99 mmol) was added to a suspension of 3-methyl-3,9-dihydro-1H-purine-2,6-dione (250 mg, 1.67 mmol) and sodium acetate (956 mg, 11.66 mmol) in acetic acid (16 ml). The reaction was heated to 80° C. for 2 h. Additional bromine (512 µl, 9.99 mmol) was added and the reaction heated to 80° C. for a further 2 h. The mixture was cooled and concentrated in vacuo, then purified by flash chromatography (0-10% methanol/dichloromethane). $^1$H NMR (500 MHz, DMSO-d$_6$) δ 12.40 (s, 1H), 7.97 (s, 1H), 3.92 (s, 3H).

8-bromo-1-[(3,4-dichlorophenyl)methyl]-7-methyl-6,7-dihydro-1H-purin-6-one

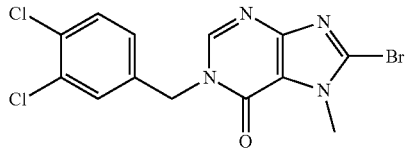 [SMILES: Cn1c(Br)nc2ncn(Cc3ccc(Cl)c(Cl)c3)c(=O)c21]

3,4-Dichlorobenzylbromide (151 µl, 1.04 mmol) was added to a suspension of 8-bromo-7-methyl-6,7-dihydro-1H-purin-6-one (248 mg, 0.87 mmol) and potassium carbonate (143 mg, 1.04 mmol) in DMF (8 ml). The reaction was stirred at room temperature for 1 h. The mixture was quenched into water and extracted into ethyl acetate three times. The combined organic fractions were washed with sat. NaCl, dried over MgSO$_4$ and concentrated in vacuo. The residue was purified by flash chromatography (0-100% EA/heptane). ESI: m/z 388.9 (M+H)$^+$.

1-[(3,4-dichlorophenyl)methyl]-8-[(3-hydroxypropyl)amino]-7-methyl-6,7-dihydro-1H-purin-6-one

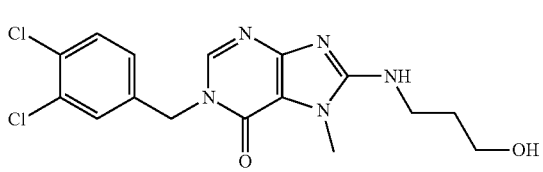 [SMILES: Cn1c(NCCCO)nc2ncn(Cc3ccc(Cl)c(Cl)c3)c(=O)c21]

3-Amino-1-propanol (20 µl, 0.26 mmol) and DIEA (46 µl, 0.26 mmol) were added to a suspension of 8-bromo-1-[(3,4-dichlorophenyl)methyl]-7-methyl-6,7-dihydro-1H-purin-6-one (50 mg, 0.13 mmol) in isopropanol (4 ml). The reaction was heated to 100° C. for 20 h then concentrated in vacuo and purified by HPLC (acetonitrile/water, 0.2% ammonium hydroxide). $^1$H NMR (500 MHz, DMSO-d$_6$) δ 8.31 (s, 1H), 7.60 (d, J=8.3 Hz, 1H), 7.60 (d, J=1.9 Hz, 1H), 7.29 (dd, J=8.3, 1.9 Hz, 1H), 6.91 (t, J=5.6 Hz, 1H), 5.12 (s, 2H), 4.55 (t, J=5.0 Hz, 1H), 3.63 (s, 3H), 3.47 (q, J=5.8 Hz, 2H), 3.38 (q, J=6.6 Hz, 2H), 1.72 (p, J=6.5 Hz, 2H); ESI: m/z 382.2 (M+H)+.

Example 168

(S)-3,7-dimethyl-8-((tetrahydrofuran-2-yl)methyl-amino)-1-(4-(trifluoromethyl)benzyl)-1H-purine-2,6 (3H,7H)-dione

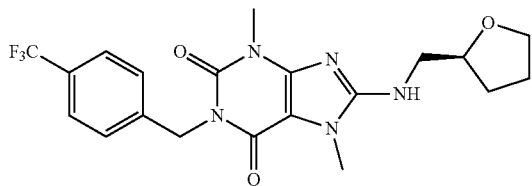 [SMILES: Cn1c(NC[C@@H]2CCCO2)nc2c1c(=O)n(Cc1ccc(C(F)(F)F)cc1)c(=O)n2C]

The title compound was synthesized in a similar fashion as described in Procedure 7A using 8-bromo-3,7-dimethyl-1-(4-(trifluoromethyl)benzyl)-1H-purine-2,6(3H,7H)-dione and (S)-(tetrahydrofuran-2-yl)methanamine. The product was purified by flash chromatography (DCM/MeOH=20/1). $^1$H NMR (400 MHz, DMSO-$d_6$) δ 7.66-7.64 (d, J=8.0 Hz, 2H), 7.46 (d, J=8.0 Hz, 2H), 7.21-7.19 (m, 1H), 5.08 (s, 2H), 4.05-4.01 (m, 1H), 3.79-3.78 (m, 1H), 3.64-3.57 (m, 1H), 3.39-3.35 (m, 5H), 1.91-1.80 (m, 3H), 1.68-1.64 (m, 1H); ESI: m/z 438.0 (M+H)+.

Example 169

(R)-2-(1-(3,4-dichlorobenzyl)-3,7-dimethyl-2,6-di-oxo-2,3,6,7-tetrahydro-1H-purin-8-ylamino)pro-panoic acid

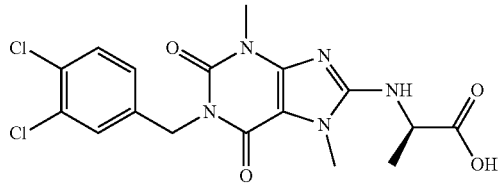 [SMILES: C[C@@H](Nc1nc2c(c(=O)n(Cc3ccc(Cl)c(Cl)c3)c(=O)n2C)n1C)C(=O)O]

The title compound was synthesized in a similar fashion as described in Procedure 7A using 8-bromo-1-(3,4-dichlo-robenzyl)-3,7-dimethyl-1H-purine-2,6(3H,7H)-dione and (R)-2-aminopropanoic acid. The product was purified by Prep-HPLC using Method D (30-70% ACN). $^1$H NMR (400 MHz, DMSO-$d_6$) δ 7.50 (s, 1H), 7.40-7.38 (d, J=8.0 Hz, 1H), 7.28-7.26 (d, J=9.6 Hz, 1H), 5.04 (s, 2H), 4.39-4.38 (m, 1H), 3.66 (s, 3H), 3.44 (s, 3H), 1.51-1.49 (d, J=7.2 Hz, 3H); ESI: m/z 426.1 (M+H)+.

Example 170

(S)-1-(3,4-dichlorobenzyl)-3,7-dimethyl-8-((tetrahy-drofuran-2-yl)methylamino)-1H-purine-2,6(3H,7H)-dione

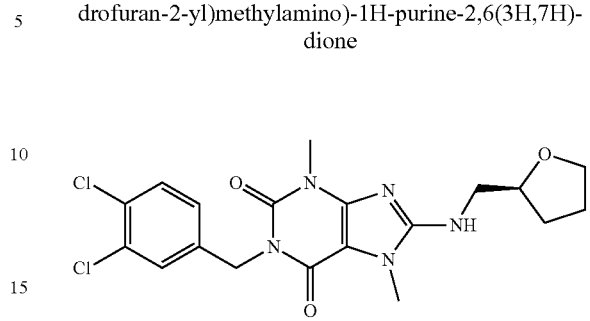

The title compound was synthesized in a similar fashion as described in Procedure 7A using 8-bromo-1-(3,4-dichlo-robenzyl)-3,7-dimethyl-1H-purine-2,6(3H,7H)-dione and (S)-(tetrahydrofuran-2-yl)methanamine. The product was purified by flash chromatography (DCM/MeOH=20/1). $^1$H NMR (400 MHz, d6-DMSO) δ 7.56-7.52 (m, 2H), 7.27-7.20 (m, 2H), 4.98 (s, 2H), 4.03 (m, 1H), 3.64 (m, 1H), 3.58 (m, 1H), 3.38-3.34 (m, 5H), 1.83-1.81 (m, 3H), 1.68-1.64 (m, 1H); ESI: m/z 438.0 (M+H)+.

Example 174

1-((1H-indol-2-yl)methyl)-3,7-dimethyl-8-(pyridin-4-ylamino)-1H-purine-2,6(3H,7H)-dione

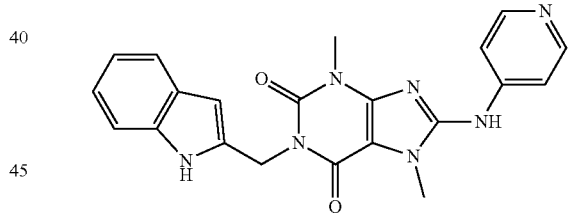

The title compound was synthesized in a similar fashion as described in Procedure 8A using tert-butyl 2-((8-bromo-3,7-dimethyl-2,6-dioxo-2,3,6,7-tetrahydro-1H-purin-1-yl) methyl)-1H-indole-1-carboxylate and pyridin-4-amine hydrochloride. The product was purified by flash chromatography (EA) to give tert-butyl 2-((3,7-dimethyl-2,6-dioxo-8-(pyridin-4-ylamino)-2,3,6,7-tetrahydro-1H-purin-1-yl) methyl)-1H-indole-1-carboxylate. ESI 502.1 (M+H)+. To a solution of tert-butyl 2-((3,7-dimethyl-2,6-dioxo-8-(pyridin-4-ylamino)-2,3,6,7-tetrahydro-1H-purin-1-yl)methyl)-1H-indole-1-carboxylate (0.24 mmol, 120 mg) in DCM (5 mL) was added TFA (0.5 mL). The mixture was stirred at 30° C. for 3 h. The reaction mixture was concentrated and purified by Prep-HPLC using Method D (45-75% ACN). $^1$H NMR (400 MHz, CD$_3$OD) δ 8.37-8.30 (m, 2H), 7.77-7.70 (m, 2H), 7.42 (d, J=7.9 Hz, 1H), 7.30 (d, J=8.1 Hz, 1H), 7.02 (t, J=7.5 Hz, 1H), 6.93 (t, J=7.5 Hz, 1H), 6.37 (s, 1H), 5.28 (s, 2H), 3.88 (s, 3H), 3.57 (s, 3H); ESI: m/z 402.1 (M+H)+.

Example 175

(±)-1-((5-chloro-1H-indol-2-yl)methyl)-8-((cis)-3-hydroxycyclopentylamino)-3,7-dimethyl-1H-purine-2,6(3H,7H)-dione

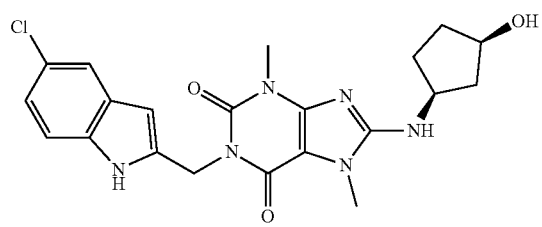 [SMILES: Cn1c(N[C@H]2CC[C@@H](O)C2)nc2c1c(=O)n(Cc1cc3cc(Cl)ccc3[nH]1)c(=O)n2C]

The title compound was made in a similar fashion as described in Procedure 7A using tert-butyl 2-((8-bromo-3,7-dimethyl-2,6-dioxo-2,3,6,7-tetrahydro-1H-purin-1-yl)methyl)-5-chloro-1H-indole-1-carboxylate and (cis)-3-aminocyclopentanol. The product was purified by prep-HPLC using Method B. $^1$H NMR (400 MHz, CD$_3$OD) δ 7.37 (s, 1H), 7.24 (d, J=8.6 Hz, 1H), 6.96 (d, J=8.6 Hz, 1H), 6.30 (s, 1H), 5.20 (s, 2H), 4.26 (dd, J=13.1, 5.9 Hz, 2H), 3.60 (s, 3H), 3.47 (s, 3H), 2.34 (dd, J=13.9, 6.7 Hz, 1H), 2.06 (dd, J=17.1, 11.2 Hz, 1H), 1.92-1.51 (m, 4H); ESI: m/z 443.1 (M+H)$^+$.

Example 176

1-((5-chloro-1H-indol-2-yl)methyl)-3,7-dimethyl-8-(pyridin-4-ylamino)-1H-purine-2,6(3H,7H)-dione

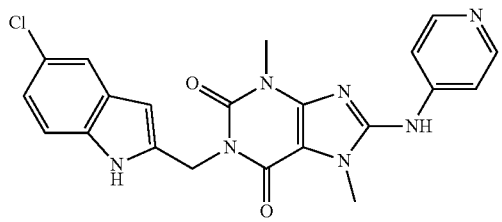 [SMILES: Cn1c(Nc2ccncc2)nc2c1c(=O)n(Cc1cc3cc(Cl)ccc3[nH]1)c(=O)n2C]

The title compound was synthesized in a similar fashion as example 174 using tert-butyl 5-chloro-2-((3,7-dimethyl-2,6-dioxo-8-(pyridin-4-ylamino)-2,3,6,7-tetrahydro-1H-purin-1-yl)methyl)-1H-indole-1-carboxylate and pyridin-4-amine hydrochloride. $^1$H NMR (400 MHz, DMSO-d$_6$) δ 11.10 (s, 1H), 8.38 (d, J=5.8 Hz, 2H), 7.69 (d, J=5.9 Hz, 2H), 7.46 (d, J=1.5 Hz, 1H), 7.35 (d, J=8.6 Hz, 1H), 7.01 (dd, J=8.6, 1.9 Hz, 1H), 6.23 (s, 1H), 5.19 (s, 2H), 3.84 (s, 3H), 3.48 (s, 3H); ESI: m/z 436.1 (M+H)$^+$.

Example 177

(±)-8-((cis)-3-hydroxycyclopentylamino)-3,7-dimethyl-1-((5-methyl-1H-indol-2-yl)methyl)-1H-purine-2,6(3H,7H)-dione

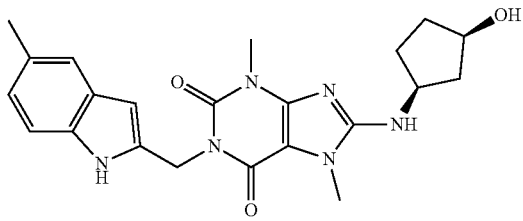 [SMILES: Cc1ccc2[nH]c(Cn3c(=O)c4c(nc(N[C@H]5CC[C@@H](O)C5)n4C)n(C)c3=O)cc2c1]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-5-methyl-1H-indole-1-carboxylate and (cis)-3-aminocyclopentanol. The product was purified by column chromatography (50~100% EA/PE). $^1$H NMR (500 MHz, DMSO-d$_6$) δ 10.62 (s, 1H), 7.22-7.17 (m, 2H), 6.91 (d, J=7.0 Hz, 1H), 6.82 (d, J=7.0 Hz, 1H), 6.09 (d, J=0.5 Hz, 1H), 5.11 (s, 2H), 4.71 (d, J=4.5 Hz, 1H), 4.11-4.07 (m, 2H), 3.58 (s, 3H), 3.37 (s, 3H), 2.32 (s, 3H), 2.29-2.22 (m, 1H), 1.95-1.92 (m, 1H), 1.73-1.47 (m, 4H); ESI: m/z 423.1 (M-Boc+H)$^+$.

Example 178

(±)-1-((5-chloro-1-methyl-1H-indol-2-yl)methyl)-8-((cis)-3-hydroxycyclopentylamino)-3,7-dimethyl-1H-purine-2,6(3H,7H)-dione

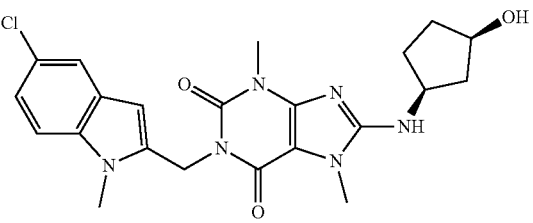 [SMILES: Cn1c(Cn2c(=O)c3c(nc(N[C@H]4CC[C@@H](O)C4)n3C)n(C)c2=O)cc2cc(Cl)ccc21]

The title compound was synthesized in a similar fashion as described in Procedure 7A using 8-bromo-1-((5-chloro-1-methyl-1H-indol-2-yl)methyl)-3,7-dimethyl-1H-purine-2,6(3H,7H)-dione and (cis)-3-aminocyclopentanol. The product was purified by prep-HPLC using Method B. $^1$H NMR (400 MHz, DMSO-d$_6$) δ 7.49-7.38 (m, 2H), 7.13-7.05 (m, 1H), 7.02-6.90 (m, 1H), 6.14 (s, 1H), 5.18 (s, 2H), 4.73 (d, J=4.0 Hz, 1H), 4.18-4.00 (m, 1H), 3.84 (s, 3H), 3.57 (s, 3H), 3.37 (s, 3H), 2.36-2.19 (m, 1H), 2.01-1.88 (m, 1H), 1.78-1.42 (m, 4H); ESI: m/z 457.1 (M+H)$^+$.

Example 179

(±)-8-((cis)-3-hydroxycyclopentylamino)-3,7-dimethyl-1-((1-methyl-1H-indol-2-yl)methyl)-1H-purine-2,6(3H,7H)-dione

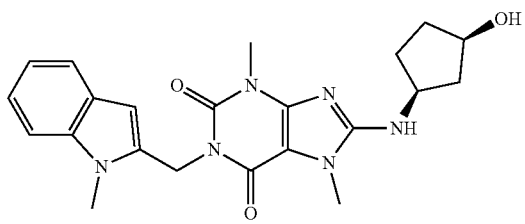 [SMILES: Cn1c(Cn2c(=O)c3c(nc(N[C@H]4CC[C@@H](O)C4)n3C)n(C)c2=O)cc2ccccc21]

The title compound was synthesized in a similar fashion as described in Procedure 7A using 8-bromo-3,7-dimethyl-1-((1-methyl-1H-indol-2-yl)methyl)-3,7-dihydro-1H-purine-2,6-dione and (cis)-3-aminocyclopentanol. The product was purified by flash chromatography (EA/PE=2/1). 1H NMR (400 MHz, DMSO-d$_6$) δ 7.44-7.36 (m, 2H), 7.10-7.06 (m, 1H), 6.97-6.94 (m, 2H), 6.14 (s, 1H), 5.19 (s, 2H), 4.74-4.73 (d, J=4.4 Hz, 1H), 4.13-4.07 (m, 2H), 3.84 (s, 3H), 3.58 (s, 3H), 3.35 (m, 3H), 2.52-2.29 (m, 1H), 2.03-1.89 (m, 1H), 1.79-1.44 (m, 4H); ESI: m/z 423.1 (M+H)$^+$.

Example 180

(±)-8-((cis)-3-hydroxycyclopentylamino)-3,7-dimethyl-1-((3-phenyl-1H-pyrazol-5-yl)methyl)-1H-purine-2,6(3H,7H)-dione

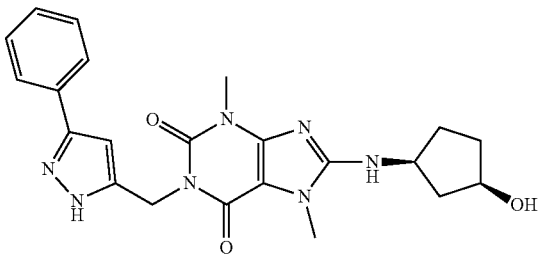 [SMILES: Cn1c(N[C@H]2CC[C@@H](O)C2)nc2c1c(=O)n(Cc1cc(-c3ccccc3)n[nH]1)c(=O)n2C]

To a solution of 8-bromo-3,7-dimethyl-1-((3-phenyl-1-((2-(trimethylsilyl)ethoxy)methyl)-1H-pyrazol-5-yl)methyl)-1H-purine-2,6(3H,7H)-dione (91 mg, 0.17 mmol) and (cis)-3-aminocyclopentanol (34 mg, 0.34 mmol) in EtOH (3 mL), were added NaI (3 mg, 0.017 mmol), DIEA (66 mg, 0.51 mmol). The mixture was stirred at 130° C. for 6 h under microwave. The mixture was cooled and concentrated, the residue was purified by flash chromatography (DCM/MeOH=15/1) to give (±)-8-((cis)-3-hydroxycyclopentylamino)-3,7-dimethyl-1-((3-phenyl-1-((2-(trimethylsilyl)ethoxy)methyl)-1H-pyrazol-5-yl)methyl)-1H-purine-2,6(3H,7H)-dione. ESI: m/z 566.2 (M+H)$^+$. A mixture of 8-((cis)-3-hydroxycyclopentylamino)-3,7-dimethyl-1-((3-phenyl-1-((2-(trimethylsilyl)ethoxy)methyl)-1H-pyrazol-5-yl)methyl)-1H-purine-2,6(3H,7H)-dione (90 mg, 0.21 mmol) and TBAF (548 mg, 2.1 mmol) in THF (5 mL) was sealed in a vial and irradiated in the microwave at 110° C. for 1 h. The mixture was filtered and the filtrate was purified by prep-HPLC using Method B. 1H NMR (400 MHz, CDCl$_3$) δ 7.76-7.74 (m, 2H), 7.38-7.34 (m, 2H), 7.29-7.27 (m, 1H), 6.66 (s, 1H), 5.21 (s, 3H), 4.48-4.36 (m, 2H), 3.59 (s, 3H), 3.51 (s, 3H), 2.13-1.93 (m, 3H), 1.87-1.67 (m, 3H); ESI: m/z 436.1 (M+H)$^+$.

Example 181

3,7-dimethyl-1-((5-methyl-1H-indol-2-yl)methyl)-8-(pyridin-4-ylamino)-1H-purine-2,6(3H,7H)-dione

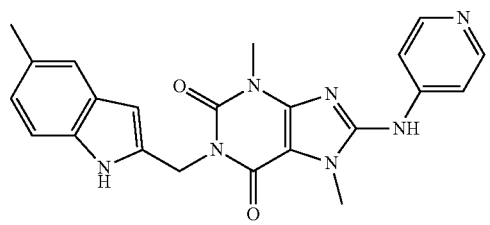 [SMILES: Cc1ccc2[nH]c(Cn3c(=O)c4c(nc(Nc5ccncc5)n4C)n(C)c3=O)cc2c1]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-5-methyl-1H-indole-1-carboxylate and pyridin-4-amine hydrochloride. The product was purified by column chromatography (0~10% MeOH/DCM) to obtain 120 mg of crude product, which was dissolved in TFA (1 mL) and DCM (3 mL) and stirred for 4 h at RT. The reaction mixture was concentrated and dissolved in DCM (50 mL), washed with NaHCO$_3$ aqueous (1*40 mL) and brine (1*40 mL), dried over Na$_2$SO$_4$, concentrated and purified by flash chromatography (50~100% EA/PE). 1H NMR (500 MHz, DMSO-d$_6$) δ 10.68 (s, 1H), 9.68 (s, 1H), 8.38 (s, 2H), 7.66 (s, 2H), 7.21 (d, J=8.5 Hz, 1H), 7.18 (s, 1H), 6.83 (dd, J=8.5, 1.5 Hz, 1H), 6.13 (d, J=1.0 Hz, 1H), 5.17 (s, 2H), 3.83 (s, 3H), 3.48 (s, 3H), 2.32 (s, 3H); ESI: m/z 416.1 (M+H)$^+$.

Example 182

8-((1S,3R)-3-hydroxycyclopentylamino)-1-((5-methoxy-1H-indol-2-yl)methyl)-3,7-dimethyl-1H-purine-2,6(3H,7H)-dione

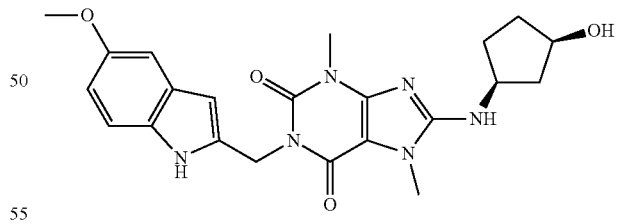

The title compound was synthesized in a similar fashion as described in Procedure 7A using 8 tert-butyl 2-((8-bromo-3,7-dimethyl-2,6-dioxo-2,3,6,7-tetrahydro-1H-purin-1-yl)methyl)-5-methoxy-1H-indole-1-carboxylate and (1R,3S)-3-aminocyclopentanol. The product was purified by prep-HPLC using Method D. 1H NMR (400 MHz, DMSO-d$_6$) δ 10.59 (s, 1H), 7.21 (d, J=8.7 Hz, 1H), 6.98-6.85 (m, 2H), 6.65 (dd, J=8.7, 2.5 Hz, 1H), 6.10 (s, 1H), 5.11 (s, 2H), 4.73 (d, J=4.0 Hz, 1H), 4.15-4.04 (m, 2H), 3.70 (s, 3H), 3.58 (s, 3H), 3.37 (s, 3H), 2.26 (m, 1H), 2.05-1.87 (m, 1H), 1.81-1.54 (m, 3H), 1.49 (m, 1H); ESI: m/z 439.1 (M+H)$^+$.

Example 183

1-((5-methoxy-1H-indol-2-yl)methyl)-3,7-dimethyl-8-(pyridin-4-ylamino)-1H-purine-2,6(3H,7H)-dione

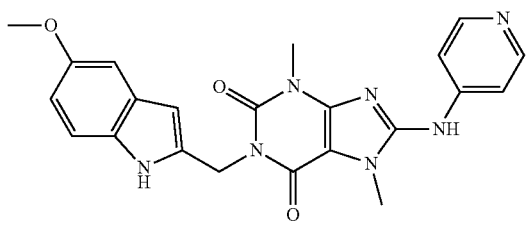 [SMILES: COc1ccc2[nH]c(Cn3c(=O)c4c(nc(Nc5ccncc5)n4C)n(C)c3=O)cc2c1]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-5-methoxy-1H-indole-1-carboxylate and pyrazin-2-amine. The product was purified by flash chromatography (DCM/MeOH=10/1). $^1$H NMR (400 MHz, DMSO-$d_6$) δ 10.67 (s, 1H), 9.69 (s, 1H), 8.37 (s, 2H), 7.66 (s, 1H), 7.22 (d, J=8.8 Hz, 1H), 6.92 (d, J=2.5 Hz, 1H), 6.66 (dd, J=8.8, 2.5 Hz, 1H), 6.16 (s, 1H), 5.16 (s, 2H), 3.83 (s, 3H), 3.70 (s, 3H), 3.48 (s, 3H); ESI: m/z 432.1 (M+H)$^+$.

Examples 184 and 187

(1S,3R)-3-(1-(3,4-dichlorobenzyl)-3,7-dimethyl-2,6-dioxo-2,3,6,7-tetrahydro-1H-purin-8-ylamino)cyclohexanecarboxylic acid and (1R,3S)-3-(1-(3,4-dichlorobenzyl)-3,7-dimethyl-2,6-dioxo-2,3,6,7-tetrahydro-1H-purin-8-ylamino)cyclohexanecarboxylic acid

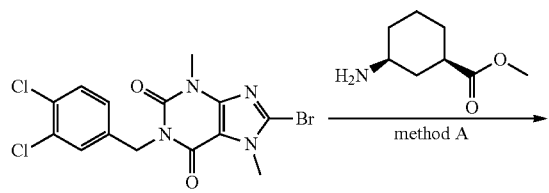

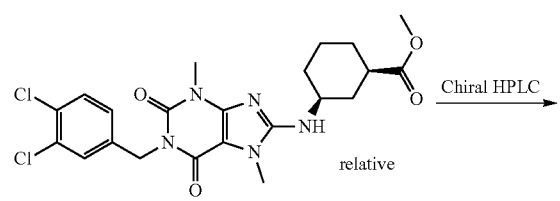

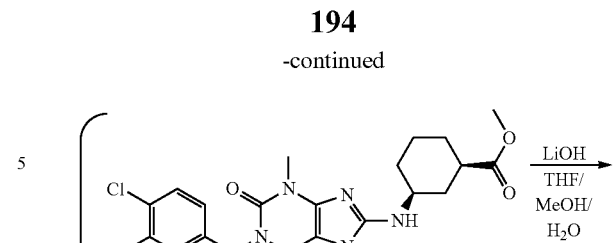

(±)-(cis)-Methyl 3-(1-(3,4-dichlorobenzyl)-3,7-dimethyl-2,6-dioxo-2,3,6,7-tetrahydro-1H-purin-8-ylamino)cyclohexanecarboxylate The title compound was synthesized in a similar fashion as described in Procedure 7A using 8-bromo-1-(3,4-dichlorobenzyl)-3,7-dimethyl-1H-purine-2,6(3H,7H)-dione and cis-methyl 3-aminocyclohexanecarboxylate. The product was purified by Prep-HPLC using Method D. ESI: m/z: 494.0 (M+H)$^+$.

(1S,3R)-Methyl 3-(1-(3,4-dichlorobenzyl)-3,7-dimethyl-2,6-dioxo-2,3,6,7-tetrahydro-1H-purin-8-ylamino)cyclohexanecarboxylate and (1R,3S)-methyl 3-(1-(3,4-dichlorobenzyl)-3,7-dimethyl-2,6-dioxo-2,3,6,7-tetrahydro-1H-purin-8-ylamino)cyclohexanecarboxylate

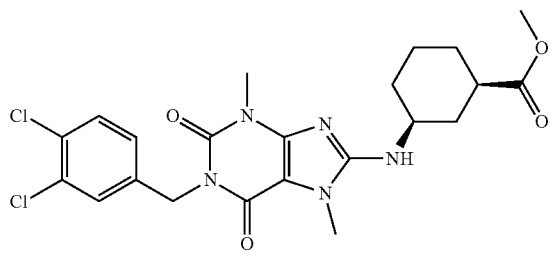 [SMILES: COC(=O)[C@@H]1CCC[C@H](Nc2nc3c(c(=O)n(Cc4ccc(Cl)c(Cl)c4)c(=O)n3C)n2C)C1]

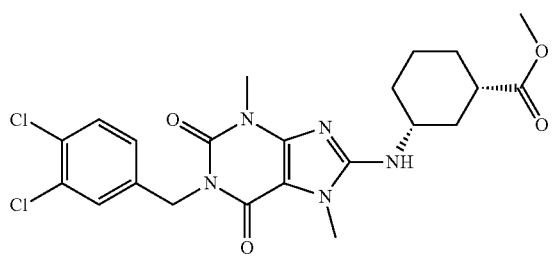

(±)-Cis-methyl 3-(1-(3,4-dichlorobenzyl)-3,7-dimethyl-2,6-dioxo-2,3,6,7-tetrahydro-1H-purin-8-ylamino)cyclohexanecarboxylate (1 g) was separated by chiral SFC using a CHIRALCEL® OD-H/SFC eluting with 10% EtOH (0.1% DEA) in n-Hexane (0.1% DEA) to give two isomers. Isomer 1: (60 mg, ee 100%, retention time 12.36 min) and Isomer 2: (50 mg, ee 100%, retention time 15.55 min).

(1R,3S)-3-(1-(3,4-dichlorobenzyl)-3,7-dimethyl-2,6-dioxo-2,3,6,7-tetrahydro-1H-purin-8-ylamino)cyclohexanecarboxylic acid and (1S,3R)-methyl 3-(1-(3,4-dichlorobenzyl)-3,7-dimethyl-2,6-dioxo-2,3,6,7-tetrahydro-1H-purin-8-ylamino)cyclohexanecarboxylate

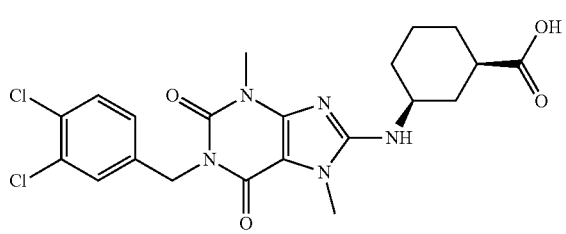

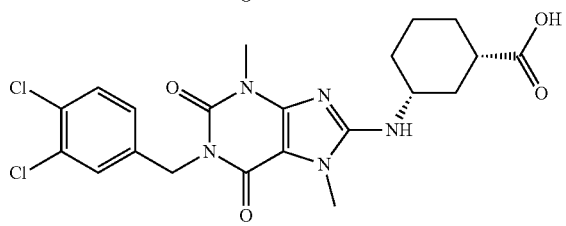

Example 184

(1S,3R)-3-(1-(3,4-dichlorobenzyl)-3,7-dimethyl-2,6-dioxo-2,3,6,7-tetrahydro-1H-purin-8-ylamino)cyclohexanecarboxylic acid or (1R,3S)-3-(1-(3,4-dichlorobenzyl)-3,7-dimethyl-2,6-dioxo-2,3,6,7-tetrahydro-1H-purin-8-ylamino)cyclohexanecarboxylic acid To a solution of methyl ester Isomer 2, with a retention time of 15.55 min (0.10 mmol, 0.05 g) in THF (5 mL), MeOH (0.5 mL) and water (5 mL) was added LiOH (0.3 mmol, 0.007 g). The mixture was stirred at room temperature for 2 h and then concentrated. The pH was adjusted to pH 6 by HCl aqueous solution. The mixture was filtered and the filter cake was dried to afford the title compound. $^1$H NMR (500 MHz, DMSO-$d_6$) δ 12.13 (br s, 1H), 7.59-7.48 (m, 2H), 7.26 (d, J=6.8 Hz, 1H), 6.87 (d, J=7.8 Hz, 1H), 4.98 (s, 2H), 3.77-3.65 (m, 1H), 3.56 (s, 3H) 3.25 (s, 3H), 2.41-2.30 (m, 1H), 2.16-2.14 (m, 1H), 1.98-1.95 (m, 1H), 1.88-1.85 (m, 1H), 1.80-1.76 (m, 1H), 1.38-1.33 (m, 2H), 1.22-1.18 (m, 2H); ESI: m/z 480.0 (M+H)$^+$.

Example 187

(1S,3R)-3-(1-(3,4-dichlorobenzyl)-3,7-dimethyl-2,6-dioxo-2,3,6,7-tetrahydro-1H-purin-8-ylamino)cyclohexanecarboxylic acid or (1R,3S)-3-(1-(3,4-dichlorobenzyl)-3,7-dimethyl-2,6-dioxo-2,3,6,7-tetrahydro-1H-purin-8-ylamino)cyclohexanecarboxylic acid To a solution of methyl ester Isomer 1, with a retention time of 12.75 min (60 mg, 0.12 mmol) in THF (0.6 mL), $H_2O$ (0.1 mL) and MeOH (0.6 mL) was added lithium hydroxide monohydrate (25 mg, 0.6 mmol). The mixture was stirred at rt for 2 h. The mixture was concentrated and diluted with EA (20 mL), neutralized pH value to 5-6 with HCl (1 N) to get white precipitate. The solid was collected by filtration, the filter cake was washed with water to afford the title compound. $^1$H NMR (400 MHz, DMSO-$d_6$) δ 12.13 (br s, 1H), 7.56-7.51 (m, 2H), 7.26-7.24 (d, J=8.0 Hz, 1H), 6.87 (d, J=7.8 Hz, 1H), 4.97 (s, 2H), 3.77-3.66 (m, 1H), 3.55 (s, 3H), 3.34 (s, 3H), 2.38-2.31 (m, 1H), 2.16-2.13 (m, 1H), 2.02-1.92 (m, 1H), 1.90-1.82 (m, 1H), 1.80-1.72 (m, 1H), 1.41-1.31 (m, 2H), 1.20-1.11 (m, 2H); ESI: m/z 480.2 (M+H)$^+$.

Examples 186 and 209

(1S,3S)-3-(1-(3,4-dichlorobenzyl)-3,7-dimethyl-2,6-dioxo-2,3,6,7-tetrahydro-1H-purin-8-ylamino)cyclohexanecarboxylic acid and (1R,3R)-3-(1-(3,4-dichlorobenzyl)-3,7-dimethyl-2,6-dioxo-2,3,6,7-tetrahydro-1H-purin-8-ylamino)cyclohexanecarboxylic acid

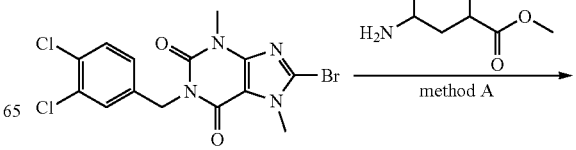

197

-continued

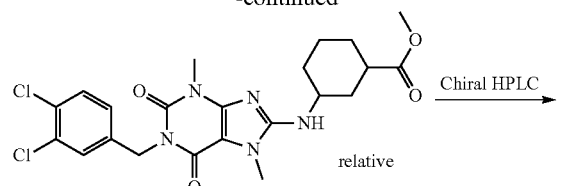

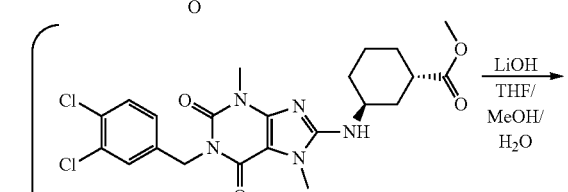

single trans enantiomers of unknown abs. config.

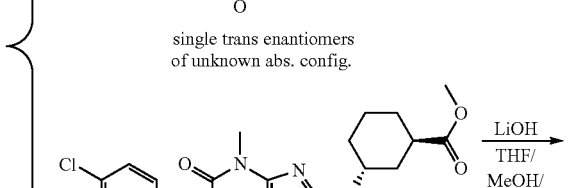

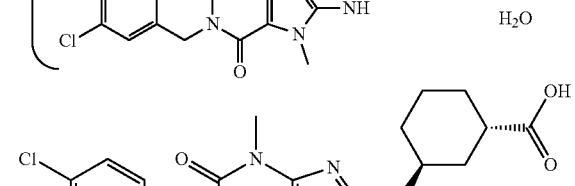


(±)-Methyl 3-(1-(3,4-dichlorobenzyl)-3,7-dimethyl-2,6-dioxo-2,3,6,7-tetrahydro-1H-purin-8-ylamino)cyclohexanecarboxylate

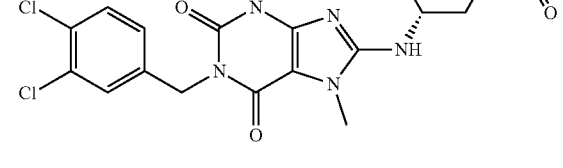

The title compound was synthesized in a similar fashion as described in Procedure 7A using 8-bromo-1-(3,4-dichlorobenzyl)-3,7-dimethyl-1H-purine-2,6(3H,7H)-dione and (±)-methyl 3-aminocyclohexanecarboxylate. The product was purified by Prep-HPLC using Method D. ESI: m/z 508.0 (M+H)+.

198

(1S,3S)-methyl 3-(1-(3,4-dichlorobenzyl)-3,7-dimethyl-2,6-dioxo-2,3,6,7-tetrahydro-1H-purin-8-ylamino)cyclohexanecarboxylate and (1R,3R)-methyl 3-(1-(3,4-dichlorobenzyl)-3,7-dimethyl-2,6-dioxo-2,3,6,7-tetrahydro-1H-purin-8-ylamino)cyclohexanecarboxylate

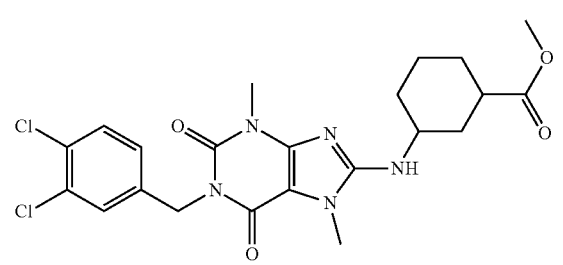 [SMILES: COC(=O)C1CCCC(Nc2nc3c(c(=O)n(Cc4ccc(Cl)c(Cl)c4)c(=O)n3C)n2C)C1]

(±)-Methyl 3-(1-(3,4-dichlorobenzyl)-3,7-dimethyl-2,6-dioxo-2,3,6,7-tetrahydro-1H-purin-8-ylamino)cyclohexanecarboxylate was separated by chiral SFC using a CHIRALCEL® OD-H/SFC column eluting with 10% EtOH (0.1% DEA) in n-Hexane (0.1% DEA) to give 3 fractions. Fraction 1 was a trans isomer (trans-Isomer 1, ee 100%, retention time 10.89 min) and fraction 2 contained a cis isomer (cis-Isomer 1, ee 100%, retention time 15.54 min) and a mixture including two isomers (retention time from 12.36 min to 12.55 min). This mixture was separated by chiral SFC using a CHIRALCEL® OJ-H/SFC column eluting with MeOH (0.5% NH4OH) in carbon dioxide to give the cis-isomer (cis Isomer 2, ee 100%, retention time 12.37 min) and the remaining trans-isomer (trans-Isomer 2, ee 100%, retention time 15.55 min).

(1S,3S)-3-(1-(3,4-dichlorobenzyl)-3,7-dimethyl-2,6-dioxo-2,3,6,7-tetrahydro-1H-purin-8-ylamino)cyclohexanecarboxylic acid and (1R,3R)-3-(1-(3,4-dichlorobenzyl)-3,7-dimethyl-2,6-dioxo-2,3,6,7-tetrahydro-1H-purin-8-ylamino)cyclohexanecarboxylic acid

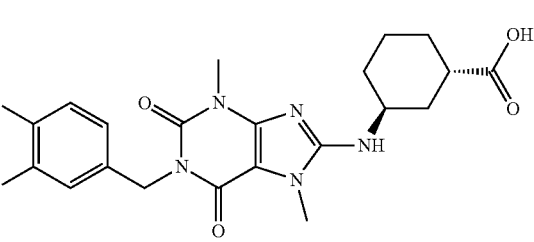

-continued

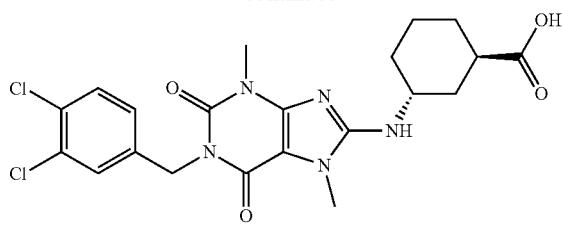

Example 186

(1S,3S)-3-(1-(3,4-dichlorobenzyl)-3,7-dimethyl-2,6-dioxo-2,3,6,7-tetrahydro-1H-purin-8-ylamino)cyclohexanecarboxylic or (1R,3R)-3-(1-(3,4-dichlorobenzyl)-3,7-dimethyl-2,6-dioxo-2,3,6,7-tetrahydro-1H-purin-8-ylamino)cyclohexanecarboxylic acid To a solution of methyl ester trans-Isomer 1 (ret. time: 10.89 min, 0.14 mmol, 0.07 g) in THF (5 mL), MeOH (0.5 mL) and water (5 mL) was added LiOH (0.7 mmol, 0.01 g). The mixture was stirred for 2 h at rt. The mixture was concentrated and the pH was adjusted to pH 6 with HCl aqueous solution. The mixture was filtered and the filter cake was purified by prep-HPLC using Method D to provide the title compound. $^1$H NMR (400 MHz, CD$_3$OD) δ 7.53 (s, 1H), 7.43-7.41 (d, J=8.0 Hz, 1H), 7.30-7.28 (d, J=10.0 Hz, 1H), 5.08 (s, 2H), 3.86-3.79 (m, 1H), 3.62 (s, 3H), 3.48 (s, 3H), 2.46-2.20 (m, 2H), 2.11-1.80 (m, 3H), 1.53-1.33 (m, 4H); ESI: m/z 480.0 (M+H)$^+$.

Example 209

(1S,3S)-3-(1-(3,4-dichlorobenzyl)-3,7-dimethyl-2,6-dioxo-2,3,6,7-tetrahydro-1H-purin-8-ylamino)cyclohexanecarboxylic or (1R,3R)-3-(1-(3,4-dichlorobenzyl)-3,7-dimethyl-2,6-dioxo-2,3,6,7-tetrahydro-1H-purin-8-ylamino)cyclohexanecarboxylic acid A mixture of methyl ester trans-Isomer 2 (ret. time: 15.55 min, 60 mg, 0.12 mmol), lithium hydroxide monohydrate (25 mg, 0.6 mmol) in THF (0.6 mL), H$_2$O (0.1 mL) and MeOH (0.6 mL) was stirred at rt for 2 h. The mixture was concentrated and diluted with EA (20 mL), neutralized pH value to 5-6 with HCl (1N) to get white precipitate that was collected by filtration. The solid was purified by prep-HPLC using Method D. $^1$H NMR (400 MHz, CD$_3$OD) δ 7.51 (s, 1H), 7.41 (d, J=8.3 Hz, 1H), 7.29-7.27 (d, J=8.3 Hz, 1H), 5.06 (s, 2H), 4.12-4.10 (m, 1H), 3.64 (s, 3H), 3.46 (s, 3H), 2.69-2.65 (m, 1H), 2.11-2.05 (m, 1H), 1.90-1.79 (m, 3H), 1.72-1.59 (m, 4H); ESI: m/z: 480.2 (M+H)$^+$.

Example 185

1-((1,5-dimethyl-1H-indol-2-yl)methyl)-8-((1S,3R)-3-hydroxycyclopentylamino)-3,7-dimethyl-1H-purine-2,6(3H,7H)-dione

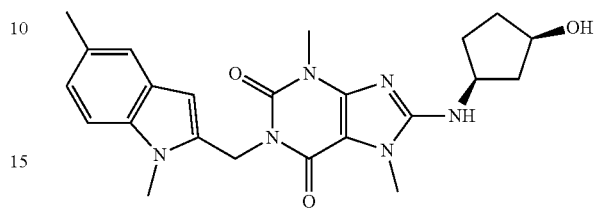

The title compound was synthesized in a similar fashion as described in Procedure 7A using 8-bromo-1-((1,5-dimethyl-1H-indol-2-yl)methyl)-3,7-dimethyl-1H-purine-2,6(3H,7H)-dione and (1R,3S)-3-aminocyclopentanol. The mixture was stirred for 6 h at 130° C. in a microwave reactor. The reaction mixture was poured into water (50 mL) and extracted with EtOAc (2*30 mL). The combined organics were washed with water (1*50 mL) and brine (1*50 mL), dried over Na$_2$SO$_4$, concentrated and purified by column chromatography (5-10% MeOH/DCM) to give the title compound: $^1$H NMR (500 MHz, DMSO-d$_6$) δ 7.27 (d, J=9.0 Hz, 1H), 7.17 (s, 1H), 6.94-6.90 (m, 2H), 6.05 (s, 1H), 5.16 (s, 2H), 4.72 (d, J=4.0 Hz, 1H), 4.13-4.07 (m, 1H), 3.80 (s, 3H), 3.57 (s, 3H), 3.36 (s, 3H), 2.33 (s, 3H), 2.29-2.23 (m, 1H), 1.96-1.93 (m, 1H), 1.74-1.49 (m, 4H); ESI: m/z 437.3 (M+H)$^+$.

Example 188

8-((1S,3R)-3-hydroxycyclopentylamino)-1-((5-methoxy-1-methyl-1H-indol-2-yl)methyl)-3,7-dimethyl-1H-purine-2,6(3H,7H)-dione

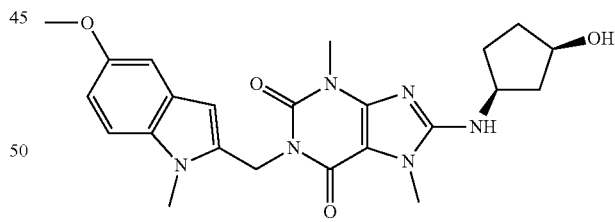

The title compound was synthesized in a similar fashion as described in Procedure 7A using 8-bromo-1-((5-methoxy-1-methyl-1H-indol-2-yl)methyl)-3,7-dimethyl-1H-purine-2,6(3H,7H)-dione and (1R,3S)-3-aminocyclopentanol. The mixture was stirred at 130° C. for 6 h in a microwave reactor. The reaction mixture was concentrated and the residue was purified by preparative HPLC using Method D. $^1$H NMR (400 MHz, DMSO-d$_6$) δ 7.29 (d, J=8.7 Hz, 1H), 6.95 (d, J=7.4 Hz, 1H), 6.91 (d, J=2.4 Hz, 1H), 6.73 (dd, J=8.8, 2.5 Hz, 1H), 6.07 (s, 1H), 5.15 (s, 2H), 4.75 (d, J=4.0 Hz, 1H), 4.17-4.07 (m, 1H), 3.80 (s, 3H), 3.70 (s, 3H), 3.57 (s, 3H), 3.34 (s, 2H), 2.33-2.18 (m, 1H), 2.02-1.87 (m, 1H), 1.79-1.43 (m, 4H); ESI: m/z 453.1 (M+H)$^+$.

Example 189

1-((1H-indol-2-yl)methyl)-3,7-dimethyl-8-(2-oxo-1,2-dihydropyrimidin-4-ylamino)-1H-purine-2,6(3H,7H)-dione

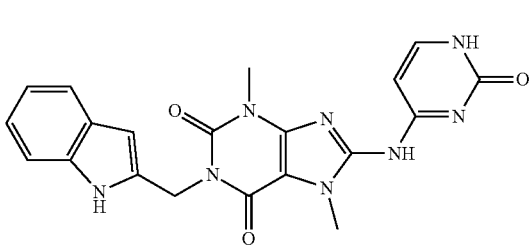 [SMILES: Cn1c(Nc2cc[nH]c(=O)n2)nc2c1c(=O)n(Cc1cc3ccccc3[nH]1)c(=O)n2C]

The title compound was synthesized in a similar fashion as described in Procedure 8A using 1-((1H-indol-2-yl)methyl)-8-bromo-3,7-dimethyl-1H-purine-2,6(3H,7H)-dione and 4-aminopyrimidin-2(1H)-one. The product was purified by preparative HPLC using Method F (25-55% ACN): $^1$H NMR (500 MHz, DMSO-$d_6$) δ 10.93 (s, 1H), 7.79 (s, 2H), 7.65 (d, J=6.0 Hz, 1H), 7.42 (d, J=8.0 Hz, 1H), 7.35 (d, J=8.0 Hz, 1H), 7.02 (t, J=7.5 Hz, 1H), 6.93 (t, J=7.5 Hz, 1H), 6.24 (s, 1H), 5.95 (d, J=7.5 Hz, 1H), 5.23 (s, 2H), 3.70 (s, 3H), 3.44 (s, 3H); ESI: m/z 419.2 (M+H)$^+$.

Example 190

3,7-dimethyl-1-((5-methyl-1H-indol-2-yl)methyl)-8-(2-oxo-1,2-dihydropyrimidin-4-ylamino)-1H-purine-2,6(3H,7H)-dione

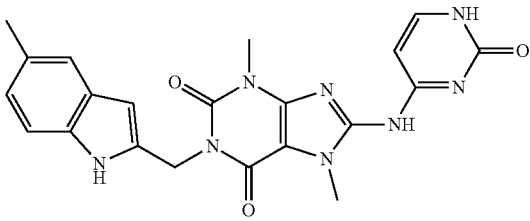 [SMILES: Cc1ccc2[nH]c(Cn3c(=O)c4c(nc(Nc5cc[nH]c(=O)n5)n4C)n(C)c3=O)cc2c1]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-5-methyl-1H-indole-1-carboxylate and 4-aminopyrimidin-2(1H)-one. $^1$H NMR (500 MHz, DMSO-$d_6$) δ 10.75 (s, 1H), 7.77 (s, 2H), 7.63 (d, J=7.5 Hz, 1H), 7.20 (d, J=8.5 Hz, 1H), 6.84 (d, J=8.5 Hz, 1H), 6.13 (s, 1H), 5.93 (d, J=7.0 Hz, 1H), 5.19 (s, 2H), 3.70 (s, 3H), 3.43 (s, 3H), 2.32 (s, 3H); ESI: m/z 433.1 (M+H)$^+$.

Example 191

1-((1H-indol-2-yl)methyl)-8-(4-hydroxypiperidin-1-yl)-3,7-dimethyl-1H-purine-2,6(3H,7H)-dione

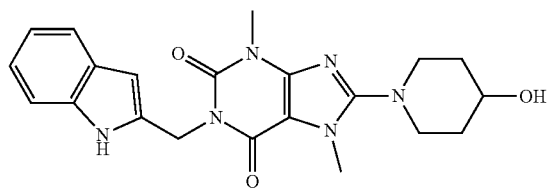 [SMILES: Cn1c(N2CCC(O)CC2)nc2c1c(=O)n(Cc1cc3ccccc3[nH]1)c(=O)n2C]

The title compound was synthesized in a similar fashion as described in Procedure 7A using 1-((1H-indol-2-yl)methyl)-8-bromo-3,7-dimethyl-1H-purine-2,6(3H,7H)-dione and piperidin-4-ol. $^1$H NMR (400 MHz, $d_6$-DMSO) δ 10.82 (s, 1H), 7.40 (d, J=7.7 Hz, 1H), 7.33 (d, J=7.9 Hz, 1H), 7.02-6.98 (m, 1H), 6.94-6.89 (m, 1H), 6.19 (d, J=1.2 Hz, 1H), 5.17 (s, 2H), 4.78 (d, J=3.9 Hz, 1H), 3.70-3.68 (m, 1H), 3.67 (s, 3H), 3.49-3.44 (m, 2H), 3.39 (s, 3H), 3.06-2.99 (m, 2H), 1.86-1.83 (m, 2H), 1.57-1.49 (m, 2H); ESI: m/z 409.1 (M+H)$^+$.

Example 192

1-((1H-indol-2-yl)methyl)-8-(3-hydroxyazetidin-1-yl)-3,7-dimethyl-1H-purine-2,6(3H,7H)-dione

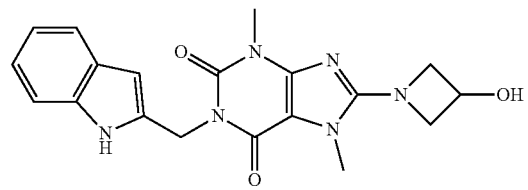 [SMILES: Cn1c(N2CC(O)C2)nc2c1c(=O)n(Cc1cc3ccccc3[nH]1)c(=O)n2C]

The title compound was synthesized in a similar fashion as described in Procedure 7A using 1-((1H-indol-2-yl)methyl)-8-bromo-3,7-dimethyl-1H-purine-2,6(3H,7H)-dione and azetidin-3-ol. $^1$H NMR (400 MHz, DMSO-$d_6$) δ 10.82 (s, 1H), 7.40 (d, J=7.9 Hz, 1H), 7.34 (d, J=7.9 Hz, 1H), 7.02-6.98 (m, 1H), 6.94-6.90 (m, 1H), 6.18 (br s, 1H), 5.80 (d, J=6.1 Hz, 1H), 5.15 (s, 2H), 4.58-4.56 (m, 1H), 4.39-4.36 (m, 2H), 3.97-3.94 (m, 2H), 3.63 (s, 3H), 3.38 (s, 3H); ESI: m/z 381.1 (M+H)$^+$.

Example 193

8-(4-hydroxypiperidin-1-yl)-3,7-dimethyl-1-((5-methyl-1H-indol-2-yl)methyl)-1H-purine-2,6(3H,7H)-dione

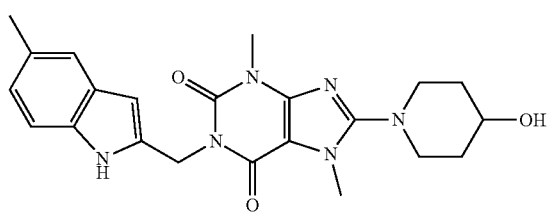 [SMILES: Cc1ccc2[nH]c(Cn3c(=O)c4c(nc(N5CCC(O)CC5)n4C)n(C)c3=O)cc2c1]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-5-methyl-1H-indole-1-carboxylate and piperidin-4-ol (60.7 mg, 0.60 mmol). The product was purified by column chromatography (50~100% EA/PE). $^1$H NMR (400 MHz, DMSO-$d_6$) δ 10.67 (s, 1H), 7.22-7.17 (m, 2H), 6.82 (d, J=8.4 Hz, 1H), 6.10 (s, 1H), 5.14 (s, 2H), 4.78 (d, J=4.0 Hz, 1H), 3.70-3.65 (m, 1H), 3.66 (s, 3H), 3.49-3.44 (m, 2H), 3.39 (s, 3H), 3.06-2.98 (m, 2H), 2.32 (s, 3H), 1.87-1.82 (m, 2H), 1.57-1.48 (m, 2H); ESI: m/z 423.1 (M+H)$^+$.

Example 194

8-(3-hydroxyazetidin-1-yl)-3,7-dimethyl-1-((5-methyl-1H-indol-2-yl)methyl)-1H-purine-2,6(3H,7H)-dione

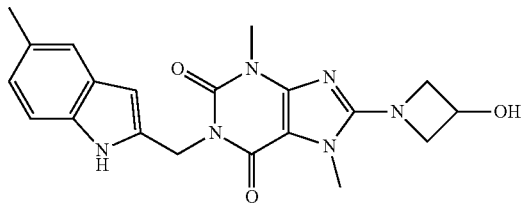 [SMILES: Cc1ccc2[nH]c(Cn3c(=O)c4c(nc(N5CC(O)C5)n4C)n(C)c3=O)cc2c1]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-5-methyl-1H-indole-1-carboxylate and azetidin-3-ol hydrochloride. The product was purified by column chromatography (50~100% EA/PE). $^1$H NMR (400 MHz, DMSO-$d_6$) δ 10.66 (s, 1H), 7.23-7.17 (m, 2H), 6.83 (d, J=8.0 Hz, 1H), 6.09 (s, 1H), 5.81-5.76 (m, 1H), 5.12 (s, 2H), 4.60-4.56 (m, 1H), 4.40-4.35 (m, 2H), 3.97-3.93 (m, 2H), 3.63 (s, 3H), 3.37 (s, 3H), 2.32 (s, 3H); ESI: m/z 395.1 (M+H)$^+$.

Example 195

1-((1H-indol-2-yl)methyl)-8-(2H-1,2,4-triazol-3-ylamino)-3,7-dimethyl-1H-purine-2,6(3H,7H)-dione

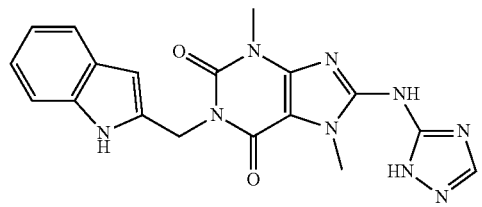 [SMILES: Cn1c(Nc2ncn[nH]2)nc2c1c(=O)n(Cc1cc3ccccc3[nH]1)c(=O)n2C]

The title compound was synthesized in a similar fashion described in Procedure 8A using tert-butyl 2-((8-bromo-3,7-dimethyl-2,6-dioxo-2,3-dihydro-6H-purin-1(7H)-yl)methyl)-1H-indole-1-carboxylate and 4H-1,2,4-triazol-3-amine. The product was purified by flash chromatography (DCM/MeOH=10/1) to give tert-butyl 2-((8-(2H-1,2,4-triazol-3-ylamino)-3,7-dimethyl-2,6-dioxo-2,3-dihydro-6H-purin-1(7H)-yl)methyl)-1H-indole-1-carboxylate. ESI: m/z 392.2 (M+H−100)$^+$.

To a solution of tert-butyl 2-((8-(2H-1,2,4-triazol-3-ylamino)-3,7-dimethyl-2,6-dioxo-2,3-dihydro-6H-purin-1(7H)-yl)methyl)-1H-indole-1-carboxylate (0.31 mmol, 0.15 g) in DCM (4 mL) was added TFA (0.5 mL). The reaction mixture was stirred at 15° C. for 2 h. The mixture was purified by flash chromatography (PE/EA=1/9). $^1$H NMR (400 MHz, CDCl$_3$) δ 10.88 (s, 1H), 7.75 (s, 1H), 7.44-7.33 (m, 2H), 7.29 (s, 2H), 7.06-6.88 (m, 2H), 6.25 (d, J=2.1 Hz, 1H), 5.22 (s, 2H), 4.02 (s, 3H), 3.50 (s, 3H). ESI: m/z 392.2 (M+H)$^+$.

Example 196

1-((5-chloro-1-methyl-1H-indol-2-yl)methyl)-8-(4-hydroxypiperidin-1-yl)-3,7-dimethyl-1H-purine-2,6(3H,7H)-dione

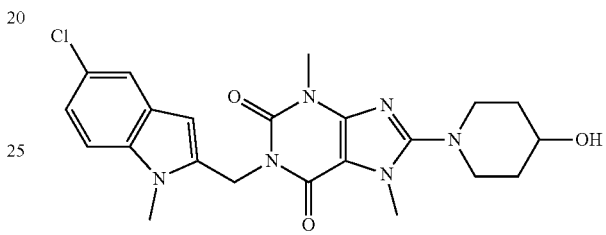

The title compound was synthesized in a similar fashion as described in Procedure 7A using 8-bromo-1-((5-chloro-1-methyl-1H-indol-2-yl)methyl)-3,7-dimethyl-1H-purine-2,6(3H,7H)-dione and piperidin-4-ol. The product was purified by prep-HPLC using Method D. $^1$H NMR (400 MHz, DMSO-$d_6$) δ 7.50-7.40 (m, 2H), 7.09 (dd, J=8.8, 2.0 Hz, 1H), 6.16 (s, 1H), 5.20 (s, 2H), 4.78 (d, J=4.1 Hz, 1H), 3.87 (d, J=19.3 Hz, 3H), 3.73-3.62 (m, 4H), 3.52-3.43 (m, 2H), 3.39 (s, 3H), 3.09-2.99 (m, 2H); ESI: m/z 457.0 (M+H)$^+$.

Example 197

1-((5-chloro-1-methyl-1H-indol-2-yl)methyl)-8-(3-hydroxyazetidin-1-yl)-3,7-dimethyl-1H-purine-2,6(3H,7H)-dione

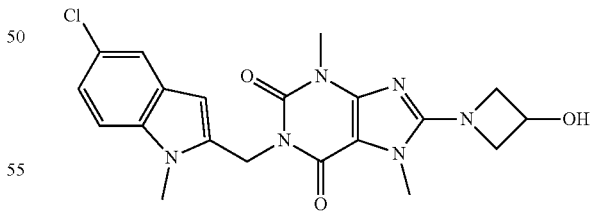

The title compound was synthesized in a similar fashion as described in Procedure 7A using 8-bromo-1-((5-chloro-1-methyl-1H-indol-2-yl)methyl)-3,7-dimethyl-1H-purine-2,6(3H,7H)-dione and azetidin-3-ol. $^1$H NMR (400 MHz, DMSO-$d_6$) δ 7.49-7.42 (m, 2H), 7.09 (dd, J=8.7, 2.0 Hz, 1H), 6.14 (s, 1H), 5.80 (d, J=5.9 Hz, 1H), 5.19 (s, 2H), 4.67-4.50 (m, 1H), 4.46-4.30 (m, 2H), 3.96 (dd, J=8.6, 5.0 Hz, 2H), 3.84 (s, 3H), 3.62 (s, 3H), 3.37 (s, 3H); ESI: m/z 429.1 (M+H)$^+$.

Example 198

1-((5-chloro-1H-indol-2-yl)methyl)-8-(4-hydroxypiperidin-1-yl)-3,7-dimethyl-1H-purine-2,6(3H,7H)-dione

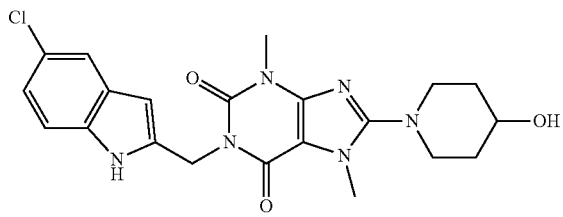 [SMILES: Cn1c(N2CCC(O)CC2)nc2c1c(=O)n(Cc1cc3cc(Cl)ccc3[nH]1)c(=O)n2C]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-5-chloro-1H-indole-1-carboxylate and piperdin-4-ol. $^1$H NMR (400 MHz, DMSO-$d_6$) δ 11.06 (s, 1H), 7.39 (m, 2H), 7.01 (dd, J=8.6, 2.1 Hz, 1H), 6.20 (s, 1H), 5.16 (s, 2H), 4.78 (d, J=4.1 Hz, 1H), 3.76-3.59 (m, 4H), 3.47 (d, J=12.8 Hz, 2H), 3.39 (s, 3H), 3.02 (dd, J=16.1, 6.3 Hz, 2H), 1.84 (d, J=9.4 Hz, 2H), 1.65-1.35 (m, 2H); ESI: m/z 443.0 (M+H)$^+$.

Example 199

1-((5-chloro-1H-indol-2-yl)methyl)-8-(3-hydroxyazetidin-1-yl)-3,7-dimethyl-1H-purine-2,6(3H,7H)-dione

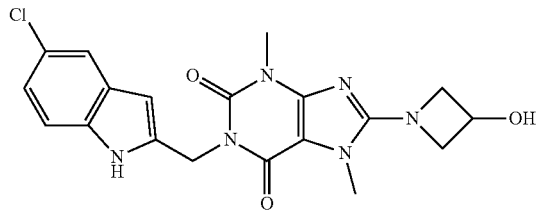 [SMILES: Cn1c(N2CC(O)C2)nc2c1c(=O)n(Cc1cc3cc(Cl)ccc3[nH]1)c(=O)n2C]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-5-chloro-1H-indole-1-carboxylate and azetidin-3-ol. The product was purified by prep-HPLC using Method B. $^1$H NMR (400 MHz, DMSO-$d_6$) δ 11.06 (s, 1H), 7.40 (m, 2H), 7.01 (dd, J=8.6, 2.0 Hz, 1H), 6.20 (s, 1H), 5.79 (d, J=6.3 Hz, 1H), 5.14 (s, 2H), 4.58 (dd, J=11.5, 5.4 Hz, 1H), 4.38 (t, J=7.6 Hz, 2H), 3.95 (dd, J=8.4, 5.0 Hz, 2H), 3.63 (s, 3H), 3.38 (s, 3H); ESI: m/z 415.0 (M+H)$^+$.

Example 200

1-((5-chloro-1H-indol-2-yl)methyl)-3,7-dimethyl-8-(pyridazin-3-ylamino)-1H-purine-2,6(3H,7H)-dione

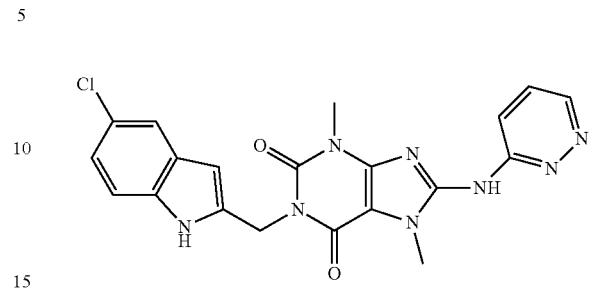

The title compound was synthesized in a similar fashion described in Example 181 using tert-butyl 5-chloro-2-((3,7-dimethyl-2,6-dioxo-8-(pyridazin-3-ylamino)-2,3,6,7-tetrahydro-1H-purin-1-yl)methyl)-1H-indole-1-carboxylate and pyridazin-3-amine. $^1$H NMR (400 MHz, DMSO-$d_6$) δ 11.09 (s, 1H), 8.42 (s, 1H), 7.92 (s, 1H), 7.62-7.50 (m, 1H), 7.46 (d, J=1.7 Hz, 1H), 7.35 (d, J=8.6 Hz, 1H), 7.01 (dd, J=8.6, 2.0 Hz, 1H), 6.24 (s, 1H), 5.18 (s, 2H), 3.79 (s, 3H), 3.48 (s, 3H); ESI: m/z 437.1 (M+H)$^+$.

Example 201

1-((1H-indol-2-yl)methyl)-3,7-dimethyl-8-(pyridazin-3-ylamino)-1H-purine-2,6(3H,7H)-dione

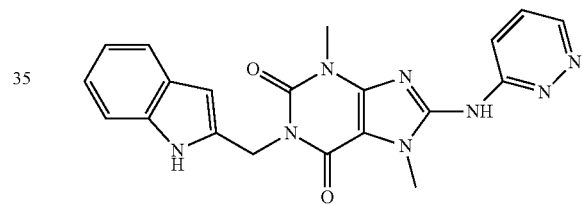

The title compound was synthesized in similar fashion as Example 181 using 1-((1H-indol-2-yl)methyl)-8-bromo-3,7-dimethyl-1H-purine-2,6(3H,7H)-dione and pyridazin-3-amine. $^1$H NMR (400 MHz, DMSO-$d_6$) δ 10.87 (s, 1H), 9.73 (b, 1H), 8.35 (m, 2H), 7.66 (m, 2H), 6.96-6.91 (m, 2H), 6.44 (dd, J=6.8, 2.0 Hz, 1H), 6.20 (d, J=1.6 Hz, 1H), 5.16 (s, 2H), 3.82 (s, 3H), 3.80 (s, 3H), 3.47 (s, 3H): ESI: m/z 432.1 (M+H)$^+$.

Example 202

8-(1H-1,2,4-triazol-5-ylamino)-3,7-dimethyl-1-((5-methyl-1H-indol-2-yl)methyl)-1H-purine-2,6(3H,7H)-dione

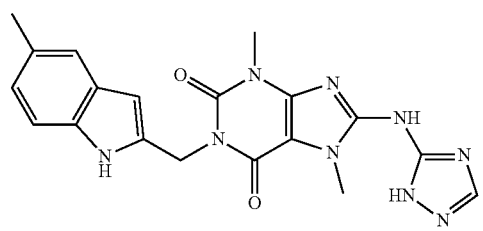 [SMILES: Cc1ccc2[nH]c(Cn3c(=O)c4c(nc(Nc5ncn[nH]5)n4C)n(C)c3=O)cc2c1]

The title compound was synthesized in a similar fashion as Example 181 using tert-butyl 2-((8-bromo-3,7-dimethyl-2,6-dioxo-2,3,6,7-tetrahydro-1H-purin-1-yl)methyl)-5-methyl-1H-indole-1-carboxylate and 1H-1,2,4-triazol-5-amine. $^1$H NMR (400 MHz, DMSO-d$_6$) δ 10.76 (s, 1H), 7.76 (s, 1H), 7.35-7.17 (m, 4H), 6.86-6.83 (m, 1H), 6.15 (s, 1H), 5.20 (s, 2H), 4.02 (s, 3H), 3.54 (s, 3H), 2.32 (s, 3H); ESI: m/z 406.1 (M+H)$^+$.

Example 203

1-((5-chloro-1-methyl-1H-indol-2-yl)methyl)-3,7-dimethyl-8-(pyridazin-3-ylamino)-1H-purine-2,6(3H,7H)-dione

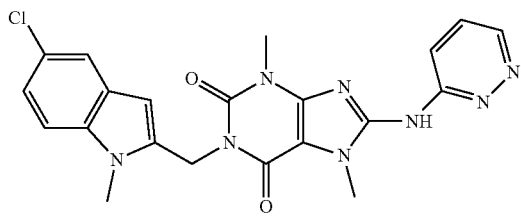 [SMILES: Cn1c(Cn2c(=O)c3c(nc(Nc4cccnn4)n3C)n(C)c2=O)cc2cc(Cl)ccc21]

The title compound was synthesized in a similar fashion as Procedure 8A using of 8-bromo-1-((5-chloro-1-methyl-1H-indol-2-yl)methyl)-3,7-dimethyl-1H-purine-2,6(3H,7H)-dione and pyridazin-3-amine. The product was purified by preparative HPLC using Method D. $^1$H NMR (400 MHz, DMSO-d$_6$) δ 7.94 (s, 1H), 7.61-7.51 (m, 1H), 7.51-7.41 (m, 2H), 7.09 (dd, J=8.8, 2.0 Hz, 1H), 6.19 (s, 1H), 5.23 (s, 2H), 3.86 (s, 3H), 3.78 (s, 3H), 3.48 (s, 3H). ESI: m/z 451.0 (M+H)$^+$.

Example 204

1-((5-chloro-1-methyl-1H-indol-2-yl)methyl)-3,7-dimethyl-8-(pyrimidin-4-ylamino)-1H-purine-2,6(3H,7H)-dione

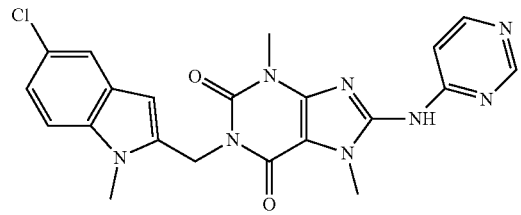 [SMILES: Cn1c(Cn2c(=O)c3c(nc(Nc4ccncn4)n3C)n(C)c2=O)cc2cc(Cl)ccc21]

The title compound was synthesized in a similar fashion as Procedure 8A using 8-bromo-1-((5-chloro-1-methyl-1H-indol-2-yl)methyl)-3,7-dimethyl-1H-purine-2,6(3H,7H)-dione and pyridazin-3-amine the product was purified by preparative HPLC using Method D. $^1$H NMR (400 MHz, DMSO-d$_6$) δ 8.75 (s, 1H), 8.52 (d, J=5.0 Hz, 1H), 7.83-7.62 (m, 1H), 7.52-7.40 (m, 2H), 7.10 (dd, J=8.8, 2.0 Hz, 1H), 6.20 (s, 1H), 5.24 (s, 2H), 3.86 (s, 3H), 3.80 (s, 3H), 3.47 (s, 3H): ESI: m/z 451.0 (M+H)$^+$.

Example 205

3,7-dimethyl-1-((5-methyl-1H-indol-2-yl)methyl)-8-(pyrimidin-4-ylamino)-1H-purine-2,6(3H,7H)-dione

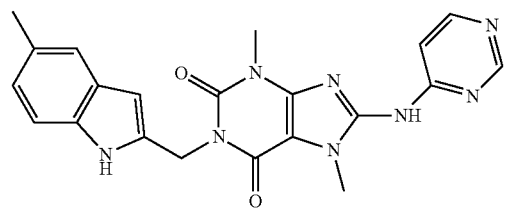 [SMILES: Cc1ccc2[nH]c(Cn3c(=O)c4c(nc(Nc5ccncn5)n4C)n(C)c3=O)cc2c1]

The title compound was synthesized in a similar fashion as Example 181 using tert-butyl 2-((8-bromo-3,7-dimethyl-2,6-dioxo-2,3,6,7-tetrahydro-1H-purin-1-yl)methyl)-5-methyl-1H-indole-1-carboxylate and pyrimidin-4-amine. $^1$H NMR (400 MHz, DMSO-d$_6$) δ 10.71 (br s, 2H), 8.74 (s, 1H), 8.51 (d, J=5.2 Hz, 1H), 7.70 (d, J=4.4 Hz, 1H), 7.23-7.18 (m, 2H), 6.83 (d, J=8.0 Hz, 1H), 6.14 (s, 1H), 5.17 (s, 2H), 3.81 (s, 3H), 3.46 (s, 3H), 2.32 (s, 3H); ESI: m/z 417.1 (M+H)$^+$.

Example 206

1-((5-chloro-1H-indol-2-yl)methyl)-3,7-dimethyl-8-(2-oxo-1,2-dihydropyrimidin-4-ylamino)-1H-purine-2,6(3H,7H)-dione

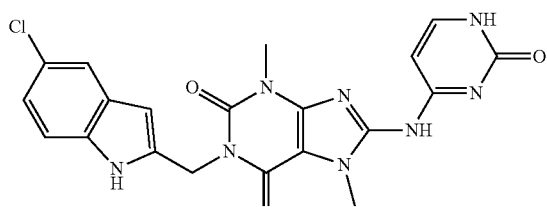

The title compound was synthesized in a similar fashion as Example 181 using tert-butyl 2-((8-bromo-3,7-dimethyl-2,6-dioxo-2,3,6,7-tetrahydro-1H-purin-1-yl)methyl)-5-chloro-1H-indole-1-carboxylate and pyrimidin-4-amine. $^1$H NMR (400 MHz, DMSO-d$_6$) δ 11.15 (s, 1H), 7.78 (s, 2H), 7.64 (d, J=7.4 Hz, 1H), 7.46 (d, J=1.9 Hz, 1H), 7.34 (d, J=8.6 Hz, 1H), 7.02 (dd, J=8.6, 2.1 Hz, 1H), 6.24 (s, 1H), 5.94 (d, J=7.5 Hz, 1H), 5.21 (s, 2H), 3.70 (s, 3H), 3.44 (s, 3H); ESI: m/z 453.1 (M+H)$^+$.

Example 207

8-(1H-1,2,4-triazol-5-ylamino)-1-((5-chloro-1H-indol-2-yl)methyl)-3,7-dimethyl-1H-purine-2,6(3H,7H)-dione

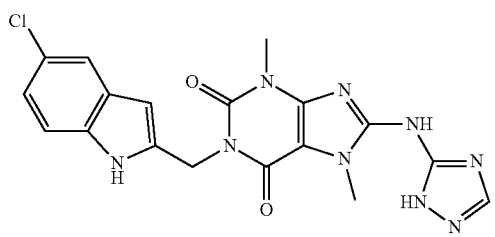 [SMILES: Cn1c(Nc2ncn[nH]2)nc2c1c(=O)n(Cc1cc3cc(Cl)ccc3[nH]1)c(=O)n2C]

The title compound was made in a similar fashion as Procedure 8A using tert-butyl 2-((8-bromo-3,7-dimethyl-2,6-dioxo-2,3,6,7-tetrahydro-1H-purin-1-yl)methyl)-5-chloro-1H-indole-1-carboxylate and pyrimidin-4-amine. $^1$H NMR (400 MHz, DMSO-$d_6$) δ 12.94 (s, 1H), 11.08 (s, 1H), 8.01 (s, 1H), 7.56-7.15 (m, 2H), 7.01 (d, J=8.6 Hz, 1H), 6.22 (s, 1H), 5.17 (s, 2H), 3.70 (s, 3H), 3.55 (s, 3H). ESI: m/z 426.1 (M+H)$^+$.

Example 208

1-((5-chloro-1H-indol-2-yl)methyl)-3,7-dimethyl-8-(pyrimidin-4-ylamino)-1H-purine-2,6(3H,7H)-dione

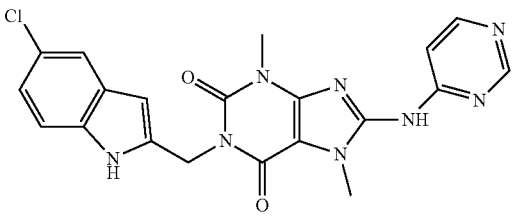 [SMILES: Cn1c(Nc2ccncn2)nc2c1c(=O)n(Cc1cc3cc(Cl)ccc3[nH]1)c(=O)n2C]

The title compound was synthesized in a similar fashion as Example 181 using tert-butyl 2-((8-bromo-3,7-dimethyl-2,6-dioxo-2,3,6,7-tetrahydro-1H-purin-1-yl)methyl)-5-chloro-1H-indole-1-carboxylate and pyrimidin-4-amine. $^1$H NMR (400 MHz, DMSO-$d_6$) δ 11.10 (s, 1H), 10.71 (s, 1H), 8.74 (s, 1H), 8.51 (d, J=5.9 Hz, 1H), 7.70 (d, J=5.8 Hz, 1H), 7.41 (m, 2H), 7.01 (dd, J=8.6, 2.0 Hz, 1H), 6.25 (s, 1H), 5.19 (s, 2H), 3.81 (s, 3H), 3.46 (s, 3H); ESI: m/z 437.1 (M+H)$^+$.

Example 210

8-(2-hydroxyethyl)-3,7-dimethyl-1-((5-methyl-1H-indol-2-yl)methyl)-1H-purine-2,6(3H,7H)-dione

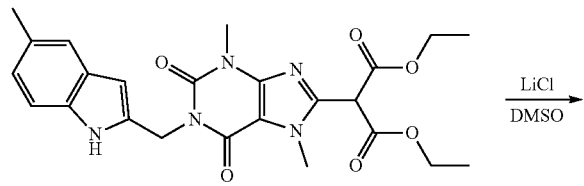

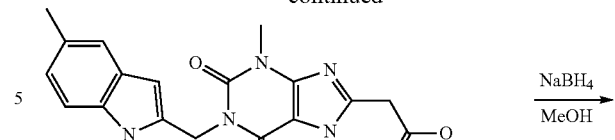

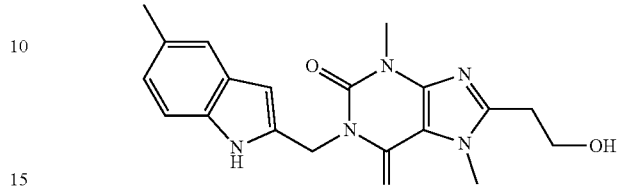

Diethyl 2-(3,7-dimethyl-1-((5-methyl-1H-indol-2-yl)methyl)-2,6-dioxo-2,3,6,7-tetrahydro-1H-purin-8-yl)malonate

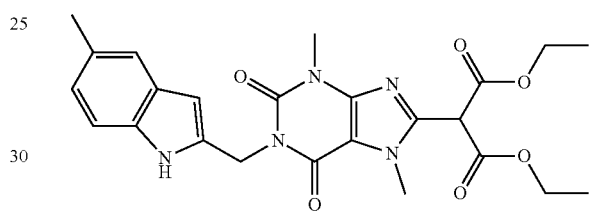

A mixture of tert-butyl 2-((8-bromo-3,7-dimethyl-2,6-dioxo-2,3,6,7-tetrahydro-1H-purin-1-yl)methyl)-5-methyl-1H-indole-1-carboxylate (502 mg, 1.0 mmol), diethyl malonate (481 mg, 3.0 mmol) and KOH (561 mg, 10 mmol) in DMF (8 mL) was stirred for 3 h at 100° C. in a microwave reactor. The reaction mixture was filtered and rinsed with EtOAc (40 mL). The filtrate was neutralized with HCl (2M) and extracted with EtOAc (2*40 mL). The combined organic fractions were washed with water (3*80 mL) and brine (1*80 mL), dried over Na$_2$SO$_4$, concentrated to afford the title compound. ESI 482.0 (M+H)$^+$.

Ethyl 2-(3,7-dimethyl-1-((5-methyl-1H-indol-2-yl)methyl)-2,6-dioxo-2,3,6,7-tetrahydro-1H-purin-8-yl)acetate

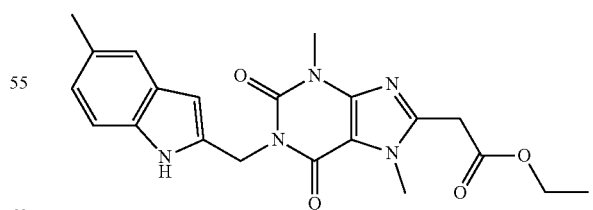

A mixture of diethyl 2-(3,7-dimethyl-1-((5-methyl-1H-indol-2-yl)methyl)-2,6-dioxo-2,3,6,7-tetrahydro-1H-purin-8-yl)malonate (482 mg, 1.0 mmol) and lithium chloride monohydrate (181.2 mg, 3.0 mmol) in DMSO (3 mL) was stirred for 1 h at 100° C. in a microwave reactor. The reaction mixture was poured into water (30 mL) and the 8-(2-hydroxyethyl)-3,7-dimethyl-1-((5-methyl-1H-indol-2-yl)methyl)-1H-purine-2,6(3H,7H)-dione

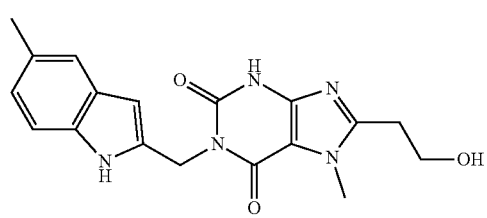 [SMILES: Cc1ccc2[nH]c(Cn3c(=O)[nH]c4nc(CCO)n(C)c4c3=O)cc2c1]

To a solution of ethyl 2-(3,7-dimethyl-1-((5-methyl-1H-indol-2-yl)methyl)-2,6-dioxo-2,3,6,7-tetrahydro-1H-purin-8-yl)acetate (450 mg, 1.1 mmol) in MeOH (10 mL) was added in portions NaBH₄ (302.8 mg, 8.0 mmol) at 0° C. The mixture was stirred for 16 h at 25° C. The reaction mixture was poured into water (30 mL) and extracted with EA (2*30 mL). The combined organic fractions were washed with brine (1*50 mL), dried over Na₂SO₄, concentrated and purified by prep-HPLC using Method F. (41-48% ACN). ¹H NMR (400 MHz, DMSO-d₆) δ 10.70 (s, 1H), 7.23-7.17 (m, 2H), 6.83 (dd, J=8.0 Hz, 0.8 Hz, 1H), 6.11 (s, 1H), 5.16 (s, 2H), 4.85 (t, J=5.4 Hz, 1H), 3.88 (s, 3H), 3.79-3.72 (m, 2H), 3.43 (s, 3H), 2.91 (t, J=6.4 Hz, 2H), 2.32 (s, 3H); ESI: m/z 368.2 (M+H)⁺.

Example 211

(±)-1-(3,4-dichlorobenzyl)-3,7-dimethyl-8-(2-oxopiperidin-4-ylamino)-1H-purine-2,6(3H,7H)-dione

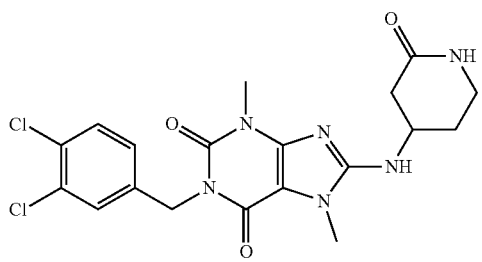 [SMILES: Cn1c(NC2CCNC(=O)C2)nc2c1c(=O)n(Cc1ccc(Cl)c(Cl)c1)c(=O)n2C]

The title compound was synthesized in a similar fashion as described in procedure 7A using 8-bromo-1-(3,4-dichlorobenzyl)-3,7-dimethyl-1H-purine-2,6(3H,7H)-dione and 4-aminopiperidin-2-one acetate. The product was purified by Prep-HPLC using Method D (30-70% ACN). ¹H NMR (400 MHz, CD₃OD) δ 7.52 (d, J=2.0 Hz, 1H), 7.41 (d, J=8.3 Hz, 1H), 7.29 (dd, J=8.4, 2.0 Hz, 1H), 5.05 (s, 2H), 4.26-4.24 (m, 1H), 3.64 (s, 3H), 3.47 (s, 3H), 3.44-3.34 (m, 2H), 2.82 (m, 1H), 2.41 (dd, J=17.6, 9.3 Hz, 1H), 2.26-2.14 (m, 1H), 1.91-1.86 (m, 1H); ESI: m/z 451.0 (M+H)⁺.

Example 212

1-((1H-indol-2-yl)methyl)-8-(2-hydroxyethyl)-3,7-dimethyl-1H-purine-2,6(3H,7H)-dione

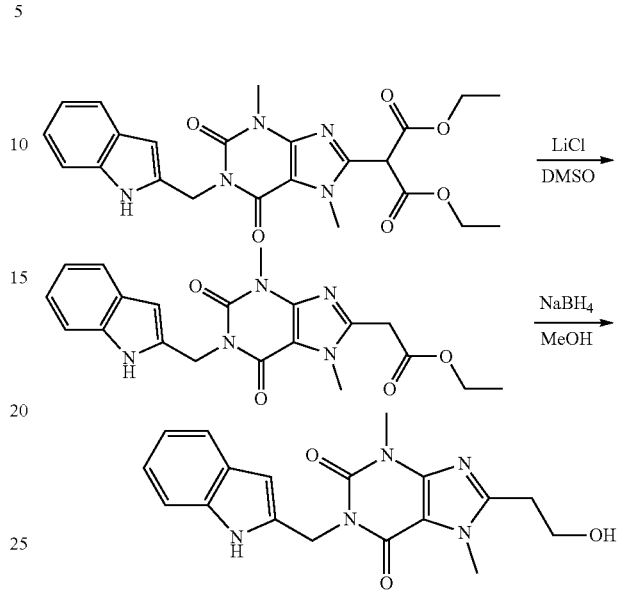

Diethyl 2-(1-((1H-indol-2-yl)methyl)-3,7-dimethyl-2,6-dioxo-2,3,6,7-tetrahydro-1H-purin-8-yl)malonate

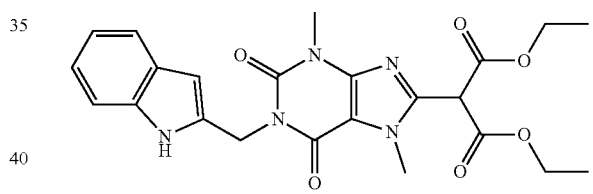

To a solution of tert-butyl 2-((8-bromo-3,7-dimethyl-2,6-dioxo-2,3-dihydro-6H-purin-1(7H)-yl)methyl)-1H-indole-1-carboxylate (1.64 mmol, 0.80 g), diethyl malonate (4.92 mmol, 0.78 g) in DMF (10 mL) was added KOH (16.4 mmol, 0.91 g). The mixture was stirred at 100° C. for 3 h in a microwave reactor. The mixture was diluted with water (100 mL) and extracted with EA (2*100 mL). The combined organic fractions were concentrated and purified by flash chromatography (PE/EA=1/1) to give the product as yellow solid. ESI: m/z 468.1 (M+H)⁺.

Ethyl 2-(1-((1H-indol-2-yl)methyl)-3,7-dimethyl-2,6-dioxo-2,3,6,7-tetrahydro-1H-purin-8-yl)acetate

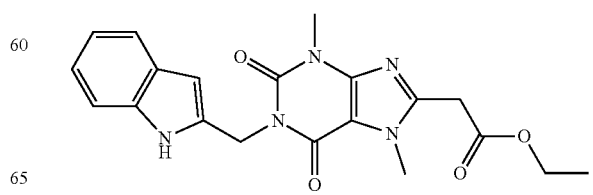

To a solution of diethyl 2-(141H-indol-2-yl)methyl)-3,7-dimethyl-2,6-dioxo-2,3,6,7-tetrahydro-1H-purin-8-yl)malonate (1.64 mmol, 0.70 g) in DMSO (5 mL) was added LiCl·H$_2$O (4.90 mmol, 0.29 g). The mixture was stirred at 100° C. for 2 h in a microwave reactor. The mixture was treated with water (100 mL) and extracted with EA (2*100 mL). The combined organic fractions were concentrated and purified by flash chromatography (PE/EA=1/1) to give the product. ESI: m/z 396.1 (M+H)$^+$.

1-((1H-indol-2-yl)methyl)-8-(2-hydroxyethyl)-3,7-dimethyl-1H-purine-2,6(3H,7H)-dione

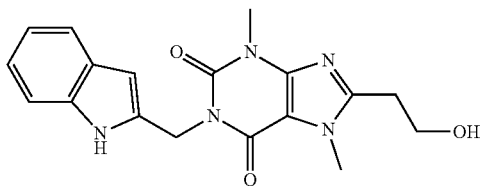 [SMILES: Cn1c(CCO)nc2c1c(=O)n(Cc1cc3ccccc3[nH]1)c(=O)n2C]

To a solution of ethyl 2-(1-((1H-indol-2-yl)methyl)-3,7-dimethyl-2,6-dioxo-2,3,6,7-tetrahydro-1H-purin-8-yl)acetate (0.18 mmol, 0.07 g) in THF (10 mL) was added NaBH$_4$ (1.8 mmol, 0.68 g). The mixture was stirred at 70° C. for 3 h. The mixture was concentrated and purified by Prep-HPLC using Method D (30-70% ACN) to give the title compound: $^1$H NMR (400 MHz, CD$_3$OD) δ 7.40-7.32 (m, 1H), 7.24 (dd, J=8.3, 1.1 Hz, 1H), 7.02-6.93 (m, 1H), 6.89-6.85 (m, 1H), 6.32 (s, 1H), 5.20 (s, 2H), 3.94-3.84 (m, 5H), 3.48 (s, 3H), 2.90 (t, J=6.2 Hz, 2H); ESI: m/z 354.1 (M+H)$^+$.

Example 213

(S)-1-((1H-indol-2-yl)methyl)-3,7-dimethyl-8-(2-oxopiperidin-3-ylamino)-1H-purine-2,6(3H,7H)-dione

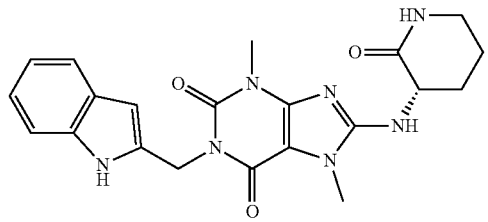 [SMILES: Cn1c(N[C@H]2CCCNC2=O)nc2c1c(=O)n(Cc1cc3ccccc3[nH]1)c(=O)n2C]

The title compound was synthesized in a similar fashion as described in procedure 7A using 1-((1H-indol-2-yl)methyl)-8-bromo-3,7-dimethyl-1H-purine-2,6(3H,7H)-dione and (S)-3-aminopiperidin-2-one. The product was purified by preparative HPLC using Method F (33-63% ACN). $^1$H NMR (400 MHz, CDCl$_3$) δ 9.11 (s, 1H), 7.54 (d, J=7.6 Hz, 1H), 7.31 (d, J=8.0 Hz, 1H), 7.14-7.02 (m, 2H), 6.58 (m, 1H), 5.79 (b, 1H), 5.53-5.52 (m, 1H), 5.30 (s, 2H), 4.28-4.23 (m, 1H), 3.71 (s, 3H), 3.51 (s, 3H), 3.43-3.40 (m, 2H), 2.83-2.78 (m, 1H), 2.04-1.98 (m, 2H), 1.67-1.64 (m, 1H). ESI: m/z 422.2 (M+H)$^+$.

Example 214

(±)-1-((1H-indol-2-yl)methyl)-3,7-dimethyl-8-(5-oxopyrrolidin-3-ylamino)-1H-purine-2,6(3H,7H)-dione

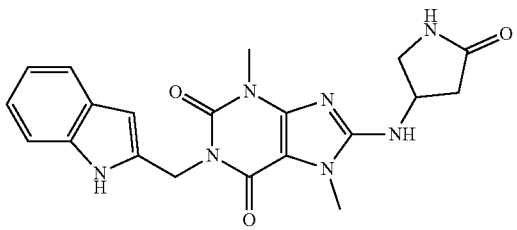 [SMILES: Cn1c(NC2CNC(=O)C2)nc2c1c(=O)n(Cc1cc3ccccc3[nH]1)c(=O)n2C]

The title compound was synthesized in a similar fashion as described in procedure 7A using 1-((1H-indol-2-yl)methyl)-8-bromo-3,7-dimethyl-1H-purine-2,6(3H,7H)-dione and 4-aminopyrrolidin-2-one. The product was purified by preparative HPLC using Method F (30-65% ACN). $^1$HNMR (400 MHz, CDCl$_3$) δ 9.08 (s, 1H), 7.54 (d, J=7.2 Hz, 1H), 7.31 (d, J=8.4 Hz, 1H), 7.15-7.02 (m, 2H), 6.58 (m, 1H), 5.56 (b, 1H), 5.29 (s, 2H), 5.10 (d, J=6.8 Hz, 1H), 4.72-4.68 (m, 1H), 3.84-3.80 (m, 1H), 3.69 (s, 3H), 3.50 (s, 3H), 3.42-3.39 (m, 1H), 2.85-2.78 (m, 1H), 2.37-2.32 (m, 1H); ESI: m/z 408.2 (M+H)$^+$.

Example 215

(±)-1-((1H-indol-2-yl)methyl)-3,7-dimethyl-8-(2-oxopiperidin-4-ylamino)-1H-purine-2,6(3H,7H)-dione

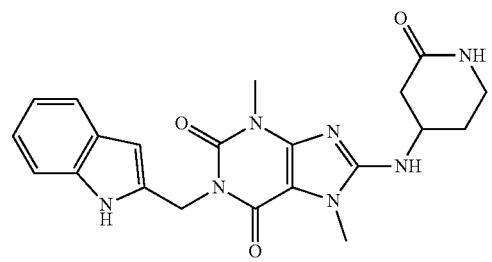 [SMILES: Cn1c(NC2CCNC(=O)C2)nc2c1c(=O)n(Cc1cc3ccccc3[nH]1)c(=O)n2C]

The title compound was made in a similar fashion as described in procedure 7A using 1-((1H-indol-2-yl)methyl)-8-bromo-3,7-dimethyl-1H-purine-2,6(3H,7H)-dione and 4-aminopiperidin-2-one. The product was purified by preparative HPLC using method F (33-60% ACN). $^1$H NMR (400 MHz, CDCl$_3$) δ 9.08 (s, 1H), 7.54 (d, J=7.6 Hz, 1H), 7.31 (d, J=8.0 Hz, 1H), 7.15-7.02 (m, 2H), 6.58 (m, 1H), 5.79 (b, 1H), 5.29 (s, 2H), 4.32-4.26 (m, 2H), 3.69 (s, 3H), 3.50 (s, 3H), 3.44-3.42 (m, 2H), 2.94-2.88 (m, 1H), 2.41-2.34 (m, 1H), 2.23-2.17 (m, 1H), 1.99-1.94 (m, 1H); ESI: m/z 422.2 (M+H)$^+$.

Example 216

1-((1H-indol-2-yl)methyl)-3,7-dimethyl-8-(pyrimidin-4-ylamino)-1H-purine-2,6(3H,7H)-dione

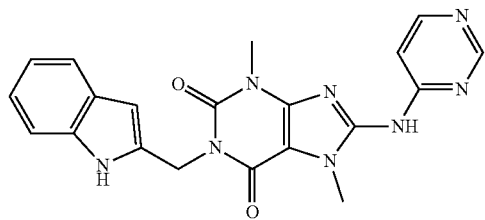 [SMILES: Cn1c(Nc2ccncn2)nc2c1c(=O)n(Cc1cc3ccccc3[nH]1)c(=O)n2C]

The title compound was synthesized in a similar fashion as described in Procedure 8A using 1-((1H-indol-2-yl)methyl)-8-bromo-3,7-dimethyl-1H-purine-2,6(3H,7H)-dione and pyrimidin-4-amine. The product was purified by flash chromatography (DCM/MeOH=10/1) and by Prep-HPLC using Method F. 1H NMR (400 MHz, DMSO-$d_6$) δ 8.69 (s, 1H), 8.46 (d, J=8.0 Hz, 1H), 7.59 (d, J=8.0 Hz, 1H), 7.41-7.33 (m, 1H), 7.03-6.89 (m, 2H), 6.25 (d, J=2.0 Hz, 1H), 5.21 (s, 2H), 3.80 (s, 3H), 3.42 (s, 3H); ESI: m/z 403.1 (M+H)$^+$.

Example 217

1-((1H-indol-2-yl)methyl)-8-(5-amino-1H-pyrazol-1-yl)-3,7-dimethyl-1H-purine-2,6(3H,7H)-dione

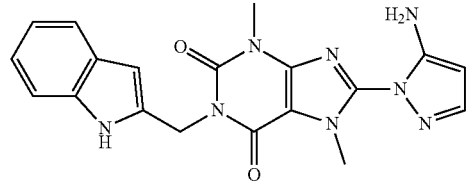 [SMILES: Cn1c(-n2nccc2N)nc2c1c(=O)n(Cc1cc3ccccc3[nH]1)c(=O)n2C]

The title compound was synthesized in a similar fashion as described in procedure 7A using 1-((1H-indol-2-yl)methyl)-8-bromo-3,7-dimethyl-1H-purine-2,6(3H,7H)-dione and 1H-pyrazol-5-amine. The product was purified by prep-HPLC using Method F. $^1$H NMR (400 MHz, CDCl$_3$) δ 9.03 (s, 1H), 8.00 (d, J=2.8 Hz, 1H), 7.55 (d, J=8.0 Hz, 1H), 7.34-7.32 (m, 1H), 7.16-7.12 (m, 1H), 7.07-7.03 (m, 1H), 6.61 (d, J=1.2 Hz, 1H), 5.90 (d, J=2.8 Hz, 1H), 5.33 (s, 2H), 4.29 (s, 3H), 3.96 (b, 2H), 3.56 (s, 3H). ESI: m/z: 391.1 (M+H)$^+$.

Example 218

8-(5-amino-1H-pyrazol-1-yl)-3,7-dimethyl-1-((5-methyl-1H-indol-2-yl)methyl)-1H-purine-2,6(3H,7H)-dione

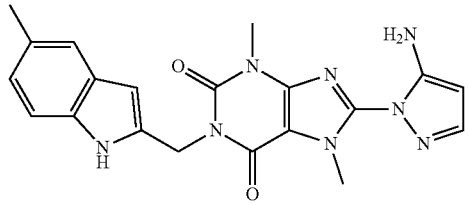 [SMILES: Cc1ccc2[nH]c(Cn3c(=O)c4c(nc(-n5nccc5N)n4C)n(C)c3=O)cc2c1]

The title compound was synthesized in a similar fashion as Example 181 using tert-butyl 2-((8-bromo-3,7-dimethyl-2,6-dioxo-2,3,6,7-tetrahydro-1H-purin-1-yl)methyl)-5-methyl-1H-indole-1-carboxylate and 1H-pyrazol-3-amine. $^1$HNMR (500 MHz, DMSO-$d_6$) δ 10.70 (s, 1H), 8.07 (d, J=3.0 Hz, 1H), 7.23-7.18 (m, 2H), 6.84 (dd, J=8.0 Hz, 1.3 Hz, 1H), 6.14 (d, J=1.0 Hz, 1H), 5.89 (d, J=3.0 Hz, 1H), 5.53 (s, 2H), 5.17 (s, 2H), 4.17 (s, 3H), 3.44 (s, 3H), 2.32 (s, 3H); ESI: m/z 405.1 (M+H)$^+$.

Example 219

8-(5-amino-1H-pyrazol-1-yl)-1-((5-chloro-1H-indol-2-yl)methyl)-3,7-dimethyl-1H-purine-2,6(3H,7H)-dione

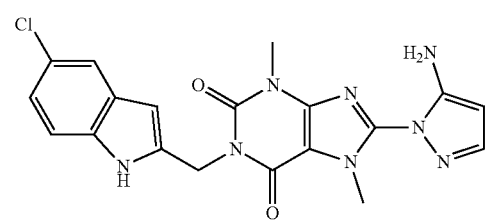 [SMILES: Cn1c(-n2nccc2N)nc2c1c(=O)n(Cc1cc3cc(Cl)ccc3[nH]1)c(=O)n2C]

The title compound was synthesized in a similar fashion as example 181 using tert-butyl 2-((8-bromo-3,7-dimethyl-2,6-dioxo-2,3,6,7-tetrahydro-1H-purin-1-yl)methyl)-5-chloro-1H-indole-1-carboxylate and 1H-pyrazol-3-amine. $^1$HNMR (400 MHz, DMSO-$d_6$) δ 11.11 (s, 1H), 8.08 (d, J=2.7 Hz, 1H), 7.46 (d, J=1.9 Hz, 1H), 7.35 (d, J=8.6 Hz, 1H), 7.01 (dd, J=8.6, 2.0 Hz, 1H), 6.25 (s, 1H), 5.89 (d, J=2.8 Hz, 1H), 5.55 (s, 2H), 5.19 (s, 2H), 4.17 (s, 3H), 3.44 (s, 3H); ESI: m/z 425.1 (M+H)$^+$.

Example 220

8-(5-amino-1H-pyrazol-1-yl)-1-((5-chloro-1-methyl-1H-indol-2-yl)methyl)-3,7-dimethyl-1H-purine-2,6(3H,7H)-dione

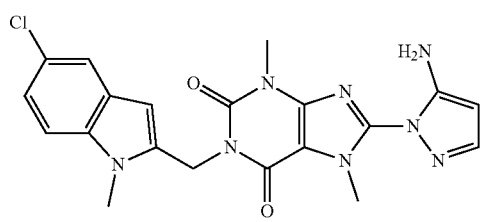 [SMILES: Cn1c(Cn2c(=O)c3c(nc(-n4nccc4N)n3C)n(C)c2=O)cc2cc(Cl)ccc21]

The title compound was synthesized in a similar fashion as described in procedure 8A using 8-bromo-1-((5-chloro-1-methyl-1H-indol-2-yl)methyl)-3,7-dimethyl-1H-purine-2,6(3H,7H)-dione and 1H-pyrazol-3-amine. The product was purified by preparative HPLC using Method B. $^1$H NMR (400 MHz, DMSO-$d_6$) δ 8.08 (d, J=2.7 Hz, 1H), 7.47 (dd, J=5.4, 3.3 Hz, 2H), 7.10 (dd, J=8.8, 2.0 Hz, 1H), 6.22 (s, 1H), 5.90 (d, J=2.7 Hz, 1H), 5.56 (s, 2H), 5.23 (s, 2H), 4.16 (s, 3H), 3.86 (s, 3H), 3.44 (s, 3H). ESI: m/z 439.1 (M+H)$^+$.

Example 221

(R)-1-((1H-indol-2-yl)methyl)-3,7-dimethyl-8-(2-oxopiperidin-3-ylamino)-1H-purine-2,6(3H,7H)-dione

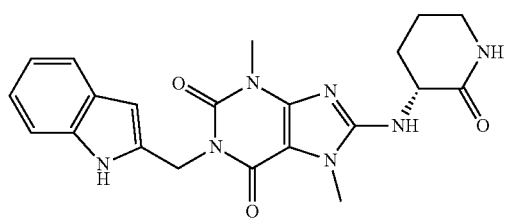 [SMILES: Cn1c(N[C@@H]2CCCNC2=O)nc2c1c(=O)n(Cc1cc3ccccc3[nH]1)c(=O)n2C]

The title compound was synthesized in a similar fashion as described in procedure 8A using tert-butyl 2-((8-bromo-3,7-dimethyl-2,6-dioxo-2,3,6,7-tetrahydro-1H-purin-1-yl)methyl)-1H-indole-1-carboxylate and (R)-3-aminopiperidin-2-one. The product was purified by prep-HPLC using Method B. $^1$H NMR (400 MHz, DMSO-$d_6$) δ 10.80 (s, 1H), 7.68 (s, 1H), 7.45-7.14 (m, 3H), 7.07-6.84 (m, 2H), 6.18 (s, 1H), 5.15 (s, 2H), 4.38-4.18 (m, 1H), 3.60 (s, 3H), 3.36 (s, 3H), 3.18 (s, 2H), 2.11 (d, J=7.1 Hz, 1H), 1.94-1.74 (m, 3H); ESI: m/z 422.0 (M+H)$^+$.

Example 222

(±)-1-((1H-indol-2-yl)methyl)-3,7-dimethyl-8-(2-oxopyrrolidin-3-ylamino)-1H-purine-2,6(3H,7H)-dione

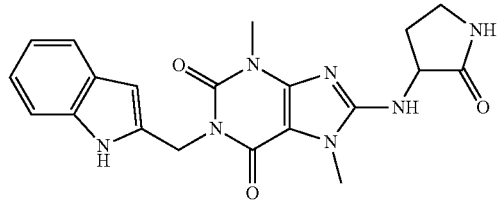 [SMILES: Cn1c(NC2CCNC2=O)nc2c1c(=O)n(Cc1cc3ccccc3[nH]1)c(=O)n2C]

The title compound was synthesized in a similar fashion as example 112 using tert-butyl 2-((8-bromo-3,7-dimethyl-2,6-dioxo-2,3,6,7-tetrahydro-1H-purin-1-yl)methyl)-1H-indole-1-carboxylate and 3-aminopyrrolidin-2-one. The product was purified by preparative HPLC using Method F (33-63% ACN). $^1$H NMR (400 MHz, CDCl$_3$) δ 9.11 (s, 1H), 7.54 (d, J=8.0 Hz, 1H), 7.30 (d, J=8.0 Hz, 1H), 7.12 (t, J=8.0 Hz, 1H), 7.03 (t, J=8.0 Hz, 1H), 6.58 (b, 1H), 5.87 (b, 1H), 5.29 (s, 2H), 5.14 (d, J=3.2 Hz, 1H), 4.44-4.38 (m, 1H), 3.69 (s, 3H), 3.50 (s, 3H), 3.47-3.44 (m, 2H), 2.99-2.89 (m, 1H), 2.08-1.97 (m, 1H). ESI: m/z 408.1 (M+H)$^+$.

Example 223

1-((5-chloro-1H-indol-2-yl)methyl)-8-(2-hydroxyethyl)-3,7-dimethyl-1H-purine-2,6(3H,7H)-dione

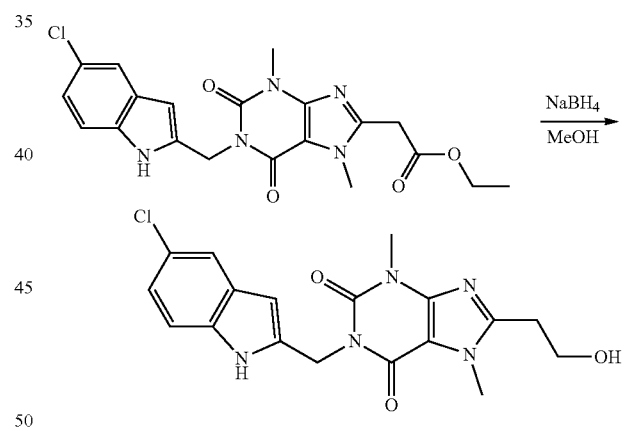

Ethyl 2-(1-((5-chloro-1H-indol-2-yl)methyl)-3,7-dimethyl-2,6-dioxo-2,3,6,7-tetrahydro-1H-purin-8-yl)acetate

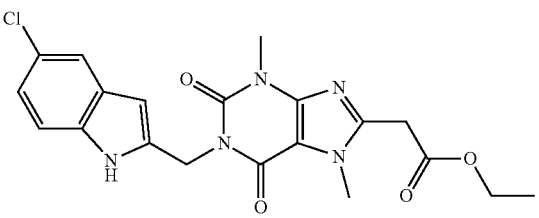 [SMILES: CCOC(=O)Cc1nc2c(c(=O)n(Cc3cc4cc(Cl)ccc4[nH]3)c(=O)n2C)n1C]

The title compound was synthesized in a similar fashion as example 210 using tert-butyl 2-((8-bromo-3,7-dimethyl-2,6-dioxo-2,3,6,7-tetrahydro-1H-purin-1-yl)methyl)-5-chloro-1H-indole-1-carboxylate and diethyl malonate. The product was purified by flash chromatography (PE/EA=2/1) to give diethyl 2-(1-((5-chloro-1H-indol-2-yl)methyl)-3,7-dimethyl-2,6-dioxo-2,3,6,7-tetrahydro-1H-purin-8-yl)malonate. ESI: m/z 502.1 (M+H)⁺. This product and LiCl·H₂O (96 mg, 1.20 mmol) in DMSO (3 mL) was sealed in a vial which was irradiated in the microwave at 100° C. for 2 h. The reaction mixture was treated with water (20 mL) and extracted with DCM (2*100 mL). The combined organic fractions were dried with Na₂SO₄, filtered and concentrated. The residue was purified with column chromatography (EA/PE=60%) to give the title compound. ESI: m/z 430.1 (M+H)⁺.

1-((5-chloro-1H-indol-2-yl)methyl)-8-(2-hydroxyethyl)-3,7-dimethyl-1H-purine-2,6(3H,7H)-dione

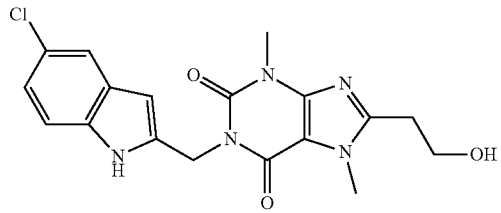 [SMILES: Cn1c(CCO)nc2c1c(=O)n(Cc1cc3cc(Cl)ccc3[nH]1)c(=O)n2C]

To a solution of ethyl 2-(1-((5-chloro-1H-indol-2-yl)methyl)-3,7-dimethyl-2,6-dioxo-2,3,6,7-tetrahydro-1H-purin-8-yl)acetate (100 mg, 0.233 mmol) in THF (4 mL) was added NaBH₄ (13 mg, 0.35 mmol). The mixture was stirred at room temperature for 6 h. The reaction was quenched by MeOH (5 mL). The mixture was concentrated and the residue was purified by prep-HPLC using Method B. ¹H NMR (400 MHz, DMSO-d₆) δ 11.11 (s, 1H), 7.58-7.24 (m, 2H), 7.01 (d, J=8.6 Hz, 1H), 6.21 (s, 1H), 5.18 (s, 2H), 4.87 (t, J=5.1 Hz, 1H), 4.04-3.62 (m, 5H), 3.44 (s, 3H), 2.92 (t, J=6.2 Hz, 2H); ESI: m/z 388.0 (M+H)⁺.

Example 224

1-((5-chloro-1-methyl-1H-indol-2-yl)methyl)-3,7-dimethyl-8-(2-oxo-1,2-dihydropyrimidin-4-ylamino)-1H-purine-2,6(3H,7H)-dione

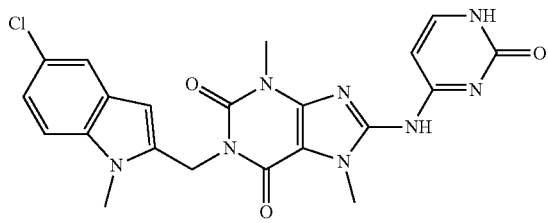 [SMILES: Cn1c(Cn2c(=O)c3c(nc(Nc4cc[nH]c(=O)n4)n3C)n(C)c2=O)cc2cc(Cl)ccc21]

The title compound was synthesized in a similar fashion as example 129 using 8-bromo-1-((5-chloro-1-methyl-1H-indol-2-yl)methyl)-3,7-dimethyl-1H-purine-2,6(3H,7H)-dione and 4-aminopyrimidin-2(1H)-one. The product was purified by prep-HPLC using Method F (48-65% ACN). ¹H NMR (400 MHz, d₆-DMSO) δ 7.77-7.76 (m, 2H), 7.63 (d, J=7.4 Hz, 1H), 7.47-7.45 (m, 2H), 7.09 (dd, J=8.7, 1.9 Hz, 1H), 6.18 (s, 1H), 5.93 (d, J=7.4 Hz, 1H), 5.25 (s, 2H), 3.85 (s, 3H), 3.68 (s, 3H), 3.43 (s, 3H). ESI: m/z 467.7 (M+H)⁺.

Example 225

1-((5-chloro-1-methyl-1H-indol-2-yl)methyl)-3,7-dimethyl-8-(2-morpholinoethyl)-1H-purine-2,6(3H,7H)-dione

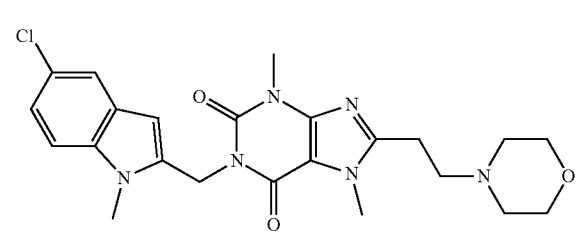 [SMILES: Cn1c(Cn2c(=O)c3c(nc(CCN4CCOCC4)n3C)n(C)c2=O)cc2cc(Cl)ccc21]

To a solution of 1-((5-chloro-1-methyl-1H-indol-2-yl)methyl)-8-(2-hydroxyethyl)-3,7-dimethyl-1H-purine-2,6(3H,7H)-dione (330 mg, 0.82 mmol) in DCM (10 mL), was added Et₃N (167 mg, 1.64 mmol) and MSCl (187 mg, 1.64 mmol) at 25° C. The mixture was stirred at 25° C. for 15 h. The mixture was concentrated to afford 2-(1-((5-chloro-1-methyl-1H-indol-2-yl)methyl)-3,7-dimethyl-2,6-dioxo-2,3,6,7-tetrahydro-1H-purin-8-yl)ethyl methanesulfonate which was used in the next step without further purification; ESI: m/z 480.1 (M+H)⁺. To a solution of this product (330 mg, 0.82 mmol) in THF (15 mL) was added morpholine (240 mg, 2.75 mmol) at 25° C. The mixture was stirred at 80° C. for 6 h. The mixture was concentrated. The residue was purified by prep-HPLC using Method D (45-47% ACN). ¹H NMR (400 MHz, DMSO-d₆) δ 7.55-7.33 (m, 2H), 7.09 (dd, J=8.8, 1.9 Hz, 1H), 6.17 (s, 1H), 5.22 (s, 2H), 3.86 (d, J=7.3 Hz, 6H), 3.64-3.51 (m, 4H), 3.43 (s, 3H), 2.94 (t, J=7.5 Hz, 2H), 2.69 (t, J=7.5 Hz, 2H), 2.50 (s, 4H); ESI: m/z 471.1 (M+H)⁺.

Example 226

1-((1H-indol-2-yl)methyl)-3,7-dimethyl-8-(2-morpholinoethyl)-1H-purine-2,6(3H,7H)-dione

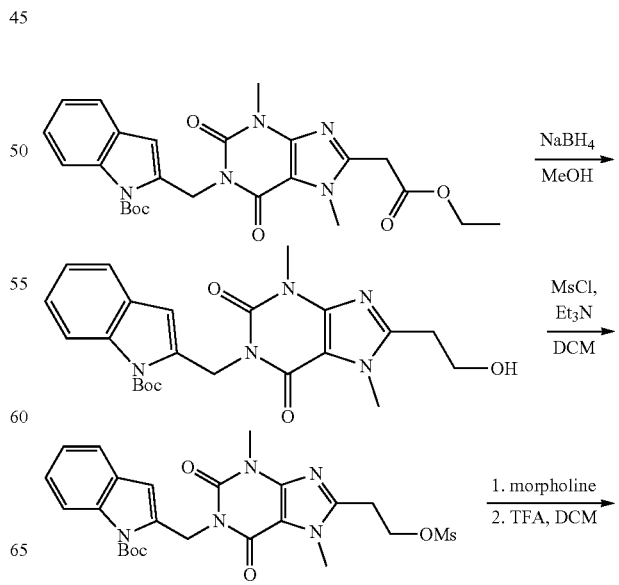

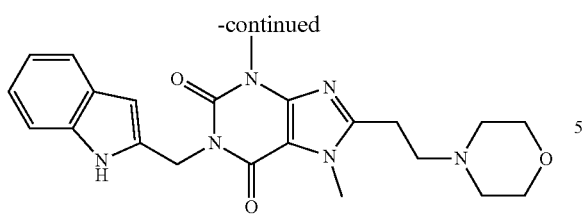

tert-Butyl 2-((8-(2-ethoxy-2-oxoethyl)-3,7-dimethyl-2,6-dioxo-2,3-dihydro-6H-purin-1(7H)-yl)methyl)-1H-indole-1-carboxylate

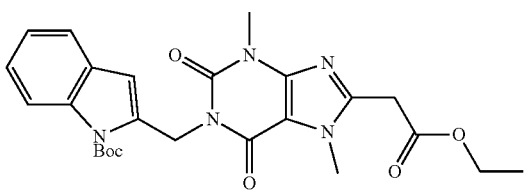 [SMILES: CCOC(=O)Cc1nc2c(c(=O)n(Cc3cc4ccccc4n3C(=O)OC(C)(C)C)c(=O)n2C)n1C]

To a solution of ethyl 2-(1-((1H-indol-2-yl)methyl)-3,7-dimethyl-2,6-dioxo-2,3,6,7-tetrahydro-1H-purin-8-yl)acetate (1.0 mmol, 0.40 g), TEA (3.0 mmol, 0.30 g), DMAP (0.1 mmol, 0.01 g) in DCM (10 mL) was added (Boc)$_2$O (1.5 mmol, 0.33 g). The mixture was stirred at 28° C. for 16 h. The reaction mixture was concentrated and purified by flash chromatography (PE/EA=1/1) to give the title compound. ESI: m/z 496.1 (M+H−100)$^+$.

tert-Butyl 2-((8-(2-hydroxyethyl)-3,7-dimethyl-2,6-dioxo-2,3-dihydro-6H-purin-1(7H)-yl)methyl)-1H-indole-1-carboxylate

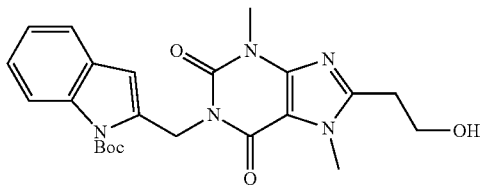 [SMILES: Cn1c(CCO)nc2c1c(=O)n(Cc1cc3ccccc3n1C(=O)OC(C)(C)C)c(=O)n2C]

To a solution of tert-butyl 2-((8-(2-ethoxy-2-oxoethyl)-3,7-dimethyl-2,6-dioxo-2,3-dihydro-6H-purin-1(7H)-yl)methyl)-1H-indole-1-carboxylate (0.2 mmol, 0.10 g) in MeOH (10 mL) was added NaBH$_4$ (0.6 mmol, 0.22 g). The mixture was stirred at 70° C. for 6 h. The reaction mixture was concentrated and purified by flash chromatography (PE/EA=1/2). ESI: m/z 354.1 (M+H−100)$^+$.

tert-Butyl 2-((3,7-dimethyl-8-(2-((methylsulfonyl)oxy)ethyl)-2,6-dioxo-2,3,6,7-tetrahydro-1H-purin-1-yl)methyl)-1H-indole-1-carboxylate

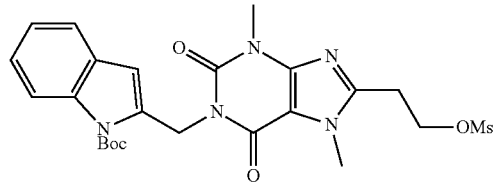 [SMILES: Cn1c(CCOS(C)(=O)=O)nc2c1c(=O)n(Cc1cc3ccccc3n1C(=O)OC(C)(C)C)c(=O)n2C]

A solution of tert-butyl 2-((8-(2-hydroxyethyl)-3,7-dimethyl-2,6-dioxo-2,3-dihydro-6H-purin-1(7H)-yl)methyl)-1H-indole-1-carboxylate (0.13 mmol, 0.06 g) and TEA (0.39 mmol, 0.04 g) in DMF (10 mL) at 0° C. was treated with MsCl (0.26 mmol, 0.030 g). The reaction mixture was stirred at 0° C. for 2 h. The mixture was concentrated and used to the next step without further purification.

1-((1H-Indol-2-yl)methyl)-3,7-dimethyl-8-(2-morpholinoethyl)-1H-purine-2,6(3H,7H)-dione

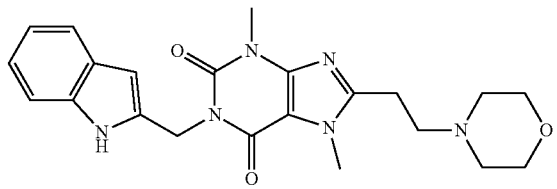 [SMILES: Cn1c(CCN2CCOCC2)nc2c1c(=O)n(Cc1cc3ccccc3[nH]1)c(=O)n2C]

To a solution of tert-butyl 2-((3,7-dimethyl-8-(2-((methylsulfonyl)oxy)ethyl)-2,6-dioxo-2,3,6,7-tetrahydro-1H-purin-1-yl)methyl)-1H-indole-1-carboxylate (0.12 mmol, 0.060 g) in THF (10 mL) was added morpholine (0.36 mmol, 0.03 g). The mixture was stirred at 70° C. for 16 h. The mixture was concentrated and purified by flash chromatography (PE/EA=1/2) to give tert-butyl 2-((3,7-dimethyl-8-(2-morpholinoethyl)-2,6-dioxo-2,3-dihydro-6H-purin-1(7H)-yl)methyl)-1H-indole-1-carboxylate; ESI m/z 423.1 (M+H−100)$^+$. To a solution of this product (0.11 mmol, 0.06 g) in DCM (2 mL) was added TFA (1 mL). The mixture was stirred at 30° C. for 16 h. The mixture was concentrated and purified by Prep-HPLC using Method D (30-70% ACN) to give the title compound: $^1$H NMR (400 MHz, CD$_3$OD) δ 7.39 (dd, J=8.0, 2.6 Hz, 1H), 7.27 (dd, J=8.4, 3.0 Hz, 1H), 7.00 (td, J=7.7, 2.4 Hz, 1H), 6.91 (td, J=7.5, 2.4 Hz, 1H), 6.34 (s, 1H), 5.23 (d, J=4.4 Hz, 2H), 3.93-3.86 (m, 3H), 3.69 (t, J=4.7 Hz, 4H), 3.50 (d, J=2.9 Hz, 3H), 2.94 (q, J=6.9 Hz, 2H), 2.80 (s, 2H), 2.56 (s, 3H); ESI: m/z 423.3 (M+H)$^+$.

Example 227

3,7-dimethyl-1-((5-methyl-1H-indol-2-yl)methyl)-8-(2-morpholinoethyl)-1H-purine-2,6(3H,7H)-dione

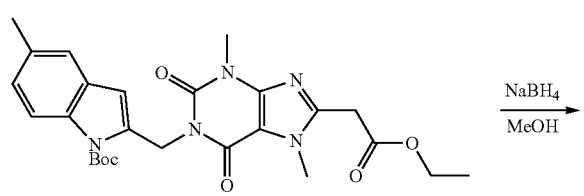

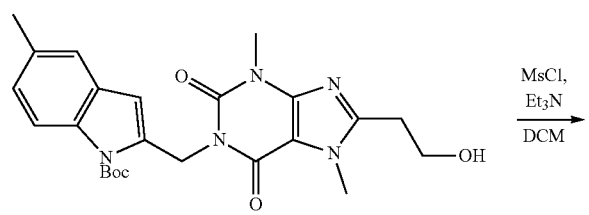

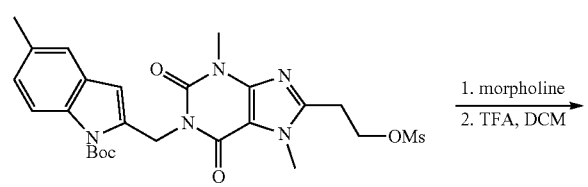

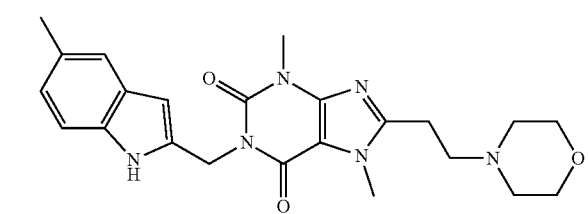

tert-Butyl 2-((8-(2-ethoxy-2-oxoethyl)-3,7-dimethyl-2,6-dioxo-2,3,6,7-tetrahydro-1H-purin-1-yl)methyl)-5-methyl-1H-indole-1-carboxylate

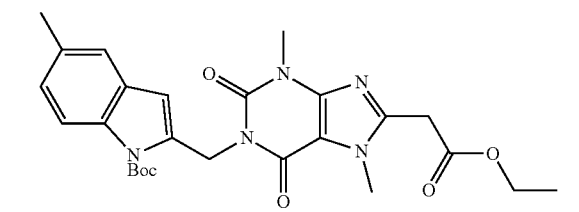 [SMILES: CCOC(=O)Cc1nc2c(c(=O)n(Cc3cc4cc(C)ccc4n3C(=O)OC(C)(C)C)c(=O)n2C)n1C]

The title compound was synthesized in a similar fashion as described in step 1, Example 226 using ethyl 2-(3,7-dimethyl-1-((5-methyl-1H-indol-2-yl)methyl)-2,6-dioxo-2,3,6,7-tetrahydro-1H-purin-8-yl)acetate. The product was purified by column chromatography (20~50% EtOAc/PE). ESI: m/z 510.1 (M+H)⁺.

tert-Butyl 2-((8-(2-hydroxyethyl)-3,7-dimethyl-2,6-dioxo-2,3,6,7-tetrahydro-1H-purin-1-yl)methyl)-5-methyl-1H-indole-1-carboxylate

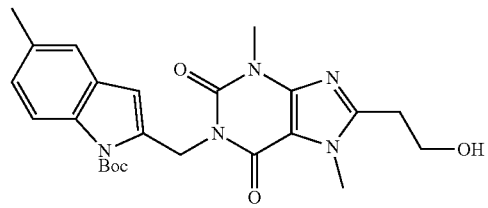 [SMILES: Cc1ccc2c(c1)cc(Cn1c(=O)c3c(nc(CCO)n3C)n(C)c1=O)n2C(=O)OC(C)(C)C]

The title compound was synthesized in a similar fashion as described in step 2, Example 226 using tert-butyl 2-((8-(2-ethoxy-2-oxoethyl)-3,7-dimethyl-2,6-dioxo-2,3,6,7-tetrahydro-1H-purin-1-yl)methyl)-5-methyl-1H-indole-1-carboxylate. The product was purified column chromatography (20~40% EtOAc/PE) to give the title compound. ESI: m/z 368.1 (M−Boc+H)⁺.

tert-Butyl 2-((3,7-dimethyl-8-(2-(methylsulfonyloxy)ethyl)-2,6-dioxo-2,3,6,7-tetrahydro-1H-purin-1-yl)methyl)-5-methyl-1H-indole-1-carboxylate

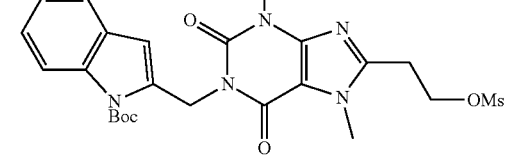

The title compound was synthesized in a similar fashion as described in step 3, Example 226 using tert-butyl 2-((8-(2-hydroxyethyl)-3,7-dimethyl-2,6-dioxo-2,3,6,7-tetrahydro-1H-purin-1-yl)methyl)-5-methyl-1H-indole-1-carboxylate. The product was used in the next step without purification. ESI: m/z 546.0 (M+H)⁺.

3,7-Dimethyl-1-((5-methyl-1H-indol-2-yl)methyl)-8-(2-morpholinoethyl)-1H-purine-2,6(3H,7H)-dione

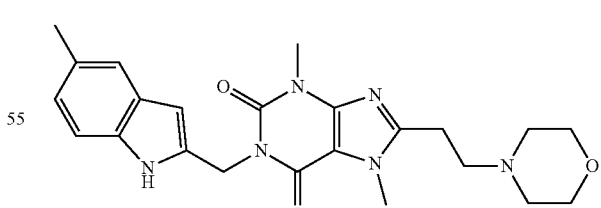

A mixture of tert-butyl 2-((3,7-dimethyl-8-(2-(methylsulfonyloxy)ethyl)-2,6-dioxo-2,3,6,7-tetrahydro-1H-purin-1-yl)methyl)-5-methyl-1H-indole-1-carboxylate (233.5 mg, 0.428 mmol) and morpholine (1.49 g, 17.12 mmol) in THF (10 mL) was heated to reflux and stirred for 16 h. The reaction mixture was poured into water (40 mL) and extracted with EtOAc (2*30 mL). The combined organics were washed with brine (1*50 mL), dried over Na$_2$SO$_4$, concentrated and purified by column chromatography (50~100% EtOAc/PE) to give tert-butyl 2-((3,7-dimethyl-8-(2-morpholinoethyl)-2,6-dioxo-2,3,6,7-tetrahydro-1H-purin-1-yl)methyl)-5-methyl-1H-indole-1-carboxylate; ESI: m/z 537.2 (M−Boc+H)$^+$. A mixture of this product (180 mg, 0.335 mmol) in TFA (1 mL) and DCM (3 mL) was stirred for 2 h at 25° C. The reaction mixture was concentrated and dissolved in DCM (50 mL), washed with NaHCO$_3$ aqueous (1*40 mL) and brine (1*40 mL), dried over Na$_2$SO$_4$, concentrated and purified by column chromatography (5-10% MeOH/DCM) to give the title compound: $^1$H NMR (400 MHz, CDCl$_3$) δ 8.91 (br s, 1H), 7.33 (s, 1H), 7.20 (d, J=8.4 Hz, 1H), 6.96 (d, J=8.0 Hz, 1H), 6.51 (s, 1H), 5.29 (s, 2H), 3.95 (s, 3H), 3.71-3.67 (m, 4H), 3.56 (s, 3H), 2.90 (t, J=7.4 Hz, 2H), 2.76 (t, J=7.2 Hz, 2H), 2.51-2.49 (m, 4H), 2.40 (s, 3H); ESI: m/z 437.1 (M+H)$^+$.

Example 228

(S)-1-((1H-indol-2-yl)methyl)-3,7-dimethyl-8-(6-oxopiperidin-3-ylamino)-1H-purine-2,6(3H,7H)-dione or (R)-1-((1H-indol-2-yl)methyl)-3,7-dimethyl-8-(6-oxopiperidin-3-ylamino)-1H-purine-2,6(3H,7H)-dione

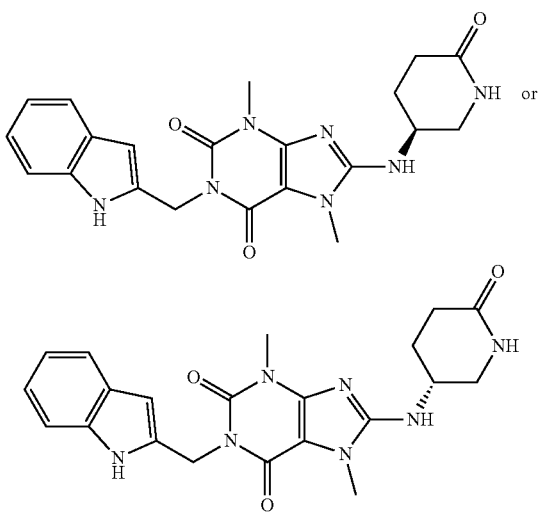

The title compound was synthesized in a similar fashion as described in procedure 7A using 1-((1H-indol-2-yl)methyl)-8-bromo-3,7-dimethyl-1H-purine-2,6(3H,7H)-dione and 5-aminopiperidin-2-one. The product was purified by prep-HPLC using Method F to provide the racemic product. The enantiomers were separated by chiral HPLC using a DAICEL® ChiralPak IA column eluting with n-hexanes (0.1% DEA) and EtOH (0.1% DEA) (1:1). Example 228: (100% ee, retention time 22.55, in); 1H NMR (400 MHz, CDCl$_3$) δ 9.10 (s, 1H), 7.54 (d, J=8.0 Hz, 1H), 7.31 (d, J=8.0 Hz, 1H), 7.14-7.11 (m, 2H), 7.04 (t, J=7.2 Hz, 1H), 6.58 (b, 1H), 5.29 (s, 2H), 5.11 (t, J=6.4 Hz, 1H), 3.98-3.95 (m, 1H), 3.75-3.72 (m, 1H), 3.70 (s, 3H), 3.50 (s, 3H), 3.34-3.27 (m, 1H), 2.38-2.25 (m, 3H), 1.82-1.77 (m, 1H); (5.8 mg); ESI: m/z 422.1 (M+H)$^+$. The second enantiomer: (100% ee, retention time 15.43 min).

Example 229

1-((5-chloro-1H-indol-2-yl)methyl)-3,7-dimethyl-8-(2-morpholinoethyl)-1H-purine-2,6(3H,7H)-dione

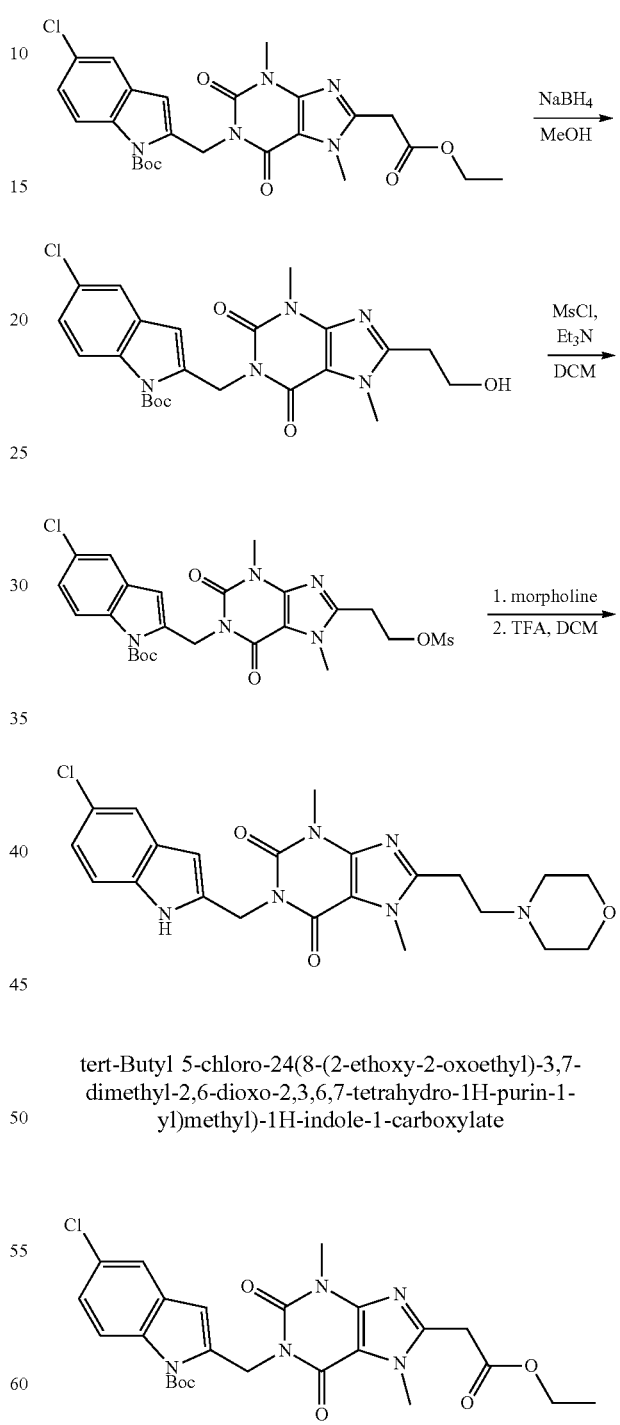

tert-Butyl 5-chloro-24(8-(2-ethoxy-2-oxoethyl)-3,7-dimethyl-2,6-dioxo-2,3,6,7-tetrahydro-1H-purin-1-yl)methyl)-1H-indole-1-carboxylate The title compound was synthesized in a similar fashion as described in step 1, Example 226 using ethyl 2-(1-((5-chloro-1H-indol-2-yl)methyl)-3,7-dimethyl-2,6-dioxo-2,3,6,7-tetrahydro-1H-purin-8-yl)acetate.

tert-Butyl 5-chloro-2-((8-(2-hydroxyethyl)-3,7-dimethyl-2,6-dioxo-2,3,6,7-tetrahydro-1H-purin-1-yl)methyl)-1H-indole-1-carboxylate

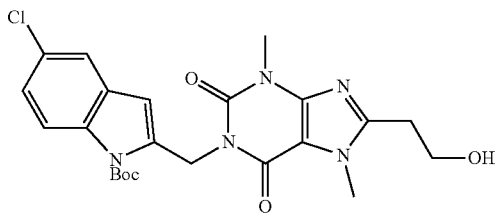 [SMILES: Cn1c(CCO)nc2c1c(=O)n(Cc1cc3cc(Cl)ccc3n1C(=O)OC(C)(C)C)c(=O)n2C]

The title compound was synthesized in a similar fashion as described in step 2, Example 226 using tert-Butyl 5-chloro-2-((8-(2-ethoxy-2-oxoethyl)-3,7-dimethyl-2,6-dioxo-2,3,6,7-tetrahydro-1H-purin-1-yl)methyl)-1H-indole-1-carboxylate.

tert-Butyl 5-chloro-2-((3,7-dimethyl-8-(2-(methylsulfonyloxy)ethyl)-2,6-dioxo-2,3,6,7-tetrahydro-1H-purin-1-yl)methyl)-1H-indole-1-carboxylate

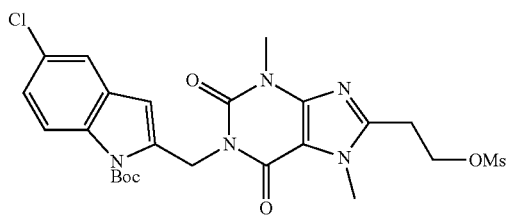 [SMILES: Cn1c(CCOS(C)(=O)=O)nc2c1c(=O)n(Cc1cc3cc(Cl)ccc3n1C(=O)OC(C)(C)C)c(=O)n2C]

The title compound was synthesized in a similar fashion as described in step 3, Example 226 using tert-butyl 5-chloro-2-((8-(2-hydroxyethyl)-3,7-dimethyl-2,6-dioxo-2,3,6,7-tetrahydro-1H-purin-1-yl)methyl)-1H-indole-1-carboxylate. The product was used in the next step without purification. ESI: m/z 566.1 (M+H)$^+$.

1-((5-Chloro-1H-indol-2-yl)methyl)-3,7-dimethyl-8-(2-morpholinoethyl)-1H-purine-2,6(3H,7H)-dione

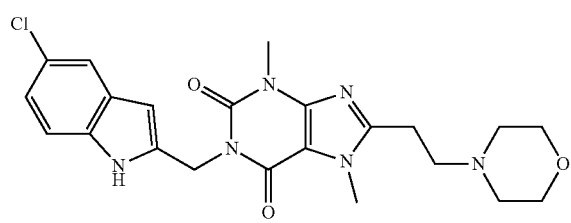 [SMILES: Cn1c(CCN2CCOCC2)nc2c1c(=O)n(Cc1cc3cc(Cl)ccc3[nH]1)c(=O)n2C]

A mixture of tert-butyl 5-chloro-2-((3,7-dimethyl-8-(2-(methylsulfonyloxy)ethyl)-2,6-dioxo-2,3,6,7-tetrahydro-1H-purin-1-yl)methyl)-1H-indole-1-carboxylate (20 mg, 0.035 mmol), and morpholine (31 mg, 0.35 mmol) in THF (2 mL) was stirred at R.T. for 2 h. The mixture was concentrated to afford crude tert-butyl 5-chloro-2-((3,7-dimethyl-8-(2-morpholinoethyl)-2,6-dioxo-2,3,6,7-tetrahydro-1H-purin-1-yl)methyl)-1H-indole-1-carboxylate; ESI: m/z 557.1 (M+H)$^+$. A mixture of this product (20 mg, 0.035 mmol) in TFA (1 mL) and DCM (1 mL) was stirred at R.T. for 2 h. and concentrated. The residue was purified by prep-HPLC using Method B to provide the title compound. $^1$H NMR (400 MHz, DMSO-d$_6$): δ 11.10 (s, 1H), 7.58-7.22 (m, 2H), 7.01 (d, J=8.6 Hz, 1H), 6.22 (s, 1H), 5.18 (s, 2H), 3.88 (s, 3H), 3.56 (s, 4H), 3.43 (s, 3H), 2.94 (t, J=7.4 Hz, 2H), 2.68 (t, J=7.3 Hz, 2H), 2.44 (s, 4H); ESI: m/z 457.1 (M+H)$^+$.

Example 230

8-(5-amino-1H-1,2,4-triazol-1-yl)-1-((5-chloro-1-methyl-1H-indol-2-yl)methyl)-3,7-dimethyl-1H-purine-2,6(3H,7H)-dione

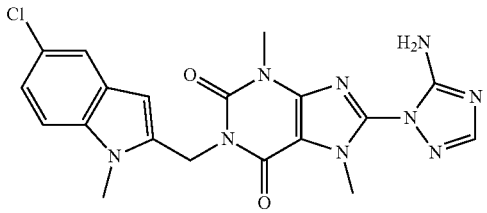 [SMILES: Cn1c(Cn2c(=O)c3c(nc(-n4ncnc4N)n3C)n(C)c2=O)cc2cc(Cl)ccc21]

The title compound was synthesized in a similar fashion and Example 129 using 8-bromo-1-((5-chloro-1-methyl-1H-indol-2-yl)methyl)-3,7-dimethyl-1H-purine-2,6(3H,7H)-dione and 1H-1,2,4-triazol-5-amine. The product was purified by prep-HPLC using Method F (35-55% ACN). $^1$H NMR (400 MHz, d$_6$-DMSO) δ 7.75 (s, 1H), 7.48-7.46 (m, 2H), 7.30 (br s, 2H), 7.11-7.08 (m, 1H), 6.21 (s, 1H), 5.26 (s, 2H), 4.00 (s, 3H), 3.86 (s, 3H), 3.49 (s, 3H). ESI: m/z 440.0 (M+H)$^+$.

Example 231

1-((1H-indol-2-yl)methyl)-8-amino-3,7-dimethyl-1H-purine-2,6(3H,7H)-dione

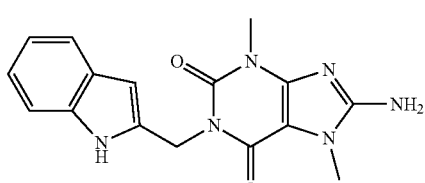

To a solution of tert-butyl 2-((8-bromo-3,7-dimethyl-2,6-dioxo-2,3-dihydro-6H-purin-1(7H)-yl)methyl)-1H-indole-1-carboxylate (1 mmol, 0.487 g) was added NH$_3$H$_2$O (15 mL). The reaction mixture was stirred at 145° C. for 16 h. The mixture was concentrated and purified by Prep-HPLC using Method D (30-70% ACN). $^1$H NMR (400 MHz, CD$_3$OD) δ 7.43 (d, J=7.8 Hz, 1H), 7.31 (dd, J=8.3, 1.1 Hz, 1H), 7.03 (ddd, J=8.1, 6.9, 1.2 Hz, 1H), 6.94 (m, 1H), 6.35 (s, 1H), 5.26 (s, 2H), 3.67 (s, 3H), 3.46 (s, 3H). ESI: m/z: 325.1 (M+H)$^+$.

Example 232

8-amino-3,7-dimethyl-1-((5-methyl-1H-indol-2-yl)methyl)-1H-purine-2,6(3H,7H)-dione

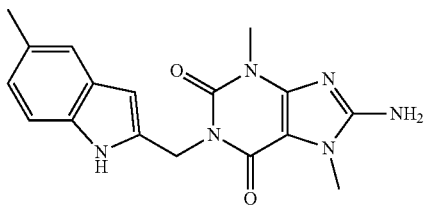 [SMILES: Cc1ccc2[nH]c(Cn3c(=O)c4c(nc(N)n4C)n(C)c3=O)cc2c1]

The title compound was made in a similar fashion as Example 331 using 8-bromo-3,7-dimethyl-1-((5-methyl-1H-indol-2-yl)methyl)-1H-purine-2,6(3H,7H)-dione. $^1$H NMR (400 MHz, DMSO-$d_6$) δ 10.63 (br s, 1H), 7.23-7.17 (m, 2H), 6.95 (s, 2H), 6.82 (d, J=8.8 Hz, 1H), 6.09 (s, 1H), 5.11 (s, 2H), 3.57 (s, 3H), 3.35 (s, 3H), 2.32 (s, 3H); ESI: m/z 339.1 (M+H)$^+$.

Example 233

1-((1,5-dimethyl-1H-indol-2-yl)methyl)-3,7-dimethyl-1H-purine-2,6(3H,7H)-dione

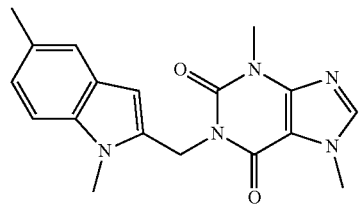 [SMILES: Cc1ccc2c(c1)cc(Cn1c(=O)c3c(ncn3C)n(C)c1=O)n2C]

A mixture of 8-bromo-1-((1,5-dimethyl-1H-indol-2-yl)methyl)-3,7-dimethyl-1H-purine-2,6(3H,7H)-dione (85 mg, 0.204 mmol) and Pd/C (20 mg) in MeOH (6 mL) and THF (4 mL) was stirred for 18 h at 25° C. under $H_2$ (balloon). The reaction mixture was filtered and the filtrate was concentrated. The residue was purified by flash chromatography (10% MeOH/DCM). $^1$H NMR (400 MHz, DMSO-$d_6$) δ 8.06 (s, 1H), 7.29 (d, J=8.4 Hz, 1H), 7.18 (s, 1H), 6.92 (d, J=8.8 Hz, 1H), 6.10 (s, 1H), 5.21 (s, 2H), 3.90 (s, 3H), 3.82 (s, 3H), 3.45 (s, 3H), 2.33 (s, 3H); ESI: m/z 338.2 (M+H)$^+$.

Example 234

1-((1H-indol-2-yl)methyl)-3,7-dimethyl-1H-purine-2,6(3H,7H)-dione

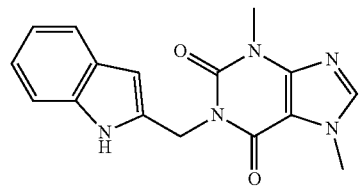 [SMILES: Cn1cnc2c1c(=O)n(Cc1cc3ccccc3[nH]1)c(=O)n2C]

tert-Butyl 2-((8-bromo-3,7-dimethyl-2,6-dioxo-2,3,6,7-tetrahydro-1H-purin-1-yl)methyl)-1H-indole-1-carboxylate was treated with Pd/C and hydrogen as described in Example 233. The resulting product was dissolved in DCM (5 mL) and treated with TFA (1 mL). The reaction mixture was stirred at 5° C. for 5 h. The mixture was concentrated and adjusted to pH 8 by addition of $Na_2CO_3$ aqueous solution. The mixture was extracted with EA (2*50 mL). The combined organic fractions were concentrated and purified by Prep-HPLC using Method D (30-70% ACN). $^1$H NMR (400 MHz, DMSO-$d_6$) δ 10.86 (s, 1H), 8.05 (s, 1H), 7.40 (d, J=7.8 Hz, 1H), 7.33 (d, J=8.0 Hz, 1H), 7.06-6.97 (m, 1H), 6.97-6.88 (m, 1H), 6.23 (d, J=2.0 Hz, 1H), 5.19 (s, 2H), 3.90 (s, 3H), 3.45 (s, 3H). ESI: m/z 310.1 (M+H)$^+$.

Example 235

3,7-dimethyl-1-((1-methyl-1H-indol-2-yl)methyl)-1H-purine-2,6(3H,7H)-dione

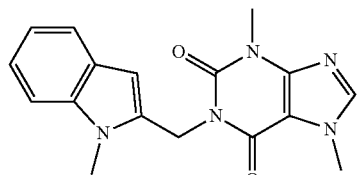

To a solution of 1-((1H-indol-2-yl)methyl)-3,7-dimethyl-1H-purine-2,6(3H,7H)-dione (0.32 mmol, 0.1 g), KOH (0.96 mmol, 0.05 g) in DMF (5 mL) was added $CH_3I$ (0.64 mmol, 0.09 g). The reaction mixture was stirred at 30° C. for 16 h. The mixture was treated with water (30 mL). The mixture was extracted with EA (2*100 mL). The combined organic fractions were concentrated and purified by Prep-HPLC using Method D (30-70% ACN). $^1$H NMR (400 MHz, DMSO-$d_6$) δ 8.06 (s, 1H), 7.45-7.37 (m, 2H), 7.14-7.05 (m, 1H), 6.97 (t, J=7.5 Hz, 1H), 6.20 (s, 1H), 5.24 (s, 2H), 3.90 (s, 3H), 3.85 (s, 3H), 3.45 (s, 3H); ESI: m/z 324.1 (M+H)$^+$.

Example 236

3,7-dimethyl-1-((5-methyl-1H-indol-2-yl)methyl)-1H-purine-2,6(3H,7H)-dione

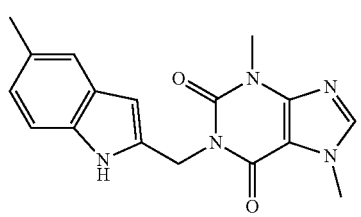 [SMILES: Cc1ccc2[nH]c(Cn3c(=O)c4c(ncn4C)n(C)c3=O)cc2c1]

The title compound was synthesized in a similar fashion as example 234 using tert-butyl 2-((8-bromo-3,7-dimethyl-2,6-dioxo-2,3,6,7-tetrahydro-1H-purin-1-yl)methyl)-5-methyl-1H-indole-1-carboxylate. The product was purified by flash chromatography (100% EA) and prep-HPLC using Method D. $^1$H NMR (400 MHz, DMSO-$d_6$) δ 10.71 (br s, 1H), 8.06 (s, 1H), 7.23-7.18 (m, 2H), 6.85-6.82 (m, 1H), 6.13 (s, 1H), 5.17 (s, 2H), 3.90 (s, 3H), 3.45 (s, 3H), 2.32 (s, 3H); ESI: m/z 324.1 (M+H)⁺.

Example 237

8-amino-1-((5-chloro-1-methyl-1H-indol-2-yl)methyl)-3,7-dimethyl-1H-purine-2,6(3H,7H)-dione

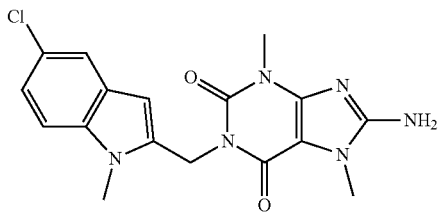 [SMILES: Cn1c(Cn2c(=O)c3c(nc(N)n3C)n(C)c2=O)cc2cc(Cl)ccc21]

The title compound was synthesized in a similar fashion as Example 231 using 8-bromo-1-((5-chloro-1-methyl-1H-indol-2-yl)methyl)-3,7-dimethyl-1H-purine-2,6(3H,7H)-dione. The product was purified by prep-HPLC using Method D. ¹H NMR (500 MHz, CDCl₃) δ 8.88 (s, 1H), 7.51 (s, 1H), 7.21 (d, J=8.8 Hz, 1H), 7.01 (d, J=2.2 Hz, 1H), 6.81 (dd, J=8.8, 2.4 Hz, 1H), 6.54 (s, 1H), 5.30 (s, 2H), 4.00 (s, 3H), 3.82 (s, 3H), 3.60 (s, 3H); ESI: m/z 373.1 (M+H)⁺.

Example 239

1-((5-methoxy-1H-indol-2-yl)methyl)-3,7-dimethyl-1H-purine-2,6(3H,7H)-dione

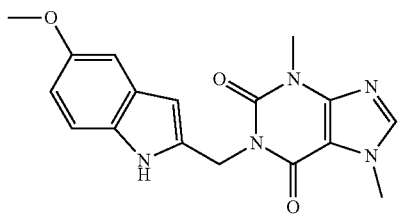 [SMILES: COc1ccc2[nH]c(Cn3c(=O)c4c(ncn4C)n(C)c3=O)cc2c1]

A solution of 3,7-dimethyl-1H-purine-2,6(3H,7H)-dione (520 mg, 2.89 mmol), tert-butyl 2-(chloromethyl)-5-methoxy-1H-indole-1-carboxylate (1.02 g, 3.47 mmol), and Na₂CO₃ (624 mg, 5.78 mmol) in DMF (6 mL) was stirred and heated to 50° C. overnight. The mixture was poured into water and extracted with EA (2*40 mL). The combined organic fractions were dried with Na₂SO₄, filtered and concentrated. The residue was purified by flash chromatography (PE/EA=4/1) to provide tert-butyl 2-((3,7-dimethyl-2,6-dioxo-2,3,6,7-tetrahydro-1H-purin-1-yl)methyl)-5-methoxy-1H-indole-1-carboxylate ESI: m/z 340.1 (M+H)⁺. This product (500 mg, 1.13 mmol) was dissolved in HCl/MeOH (20 mL), The mixture was stirred at rt for 15 h, and concentrated. The residue was purified by prep-HPLC using Method D. ¹H NMR (500 MHz, CDCl₃) δ 8.88 (s, 1H), 7.51 (s, 1H), 7.20 (s, 1H), 7.01 (d, J=2.2 Hz, 1H), 6.81 (dd, J=8.8, 2.4 Hz, 1H), 6.54 (s, 1H), 5.30 (s, 2H), 4.00 (s, 3H), 3.82 (s, 3H), 3.60 (s, 3H); ESI: m/z 340.1 (M+H)⁺.

Example 238

1-((5-methoxy-1-methyl-1H-indol-2-yl)methyl)-3,7-dimethyl-1H-purine-2,6(3H,7H)-dione

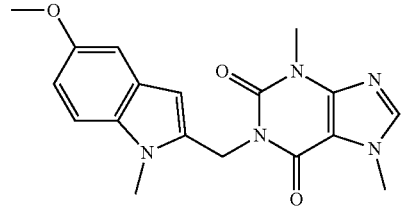 [SMILES: COc1ccc2c(c1)cc(Cn1c(=O)c3c(ncn3C)n(C)c1=O)n2C]

To a solution of 1-((5-methoxy-1H-indol-2-yl)methyl)-3,7-dimethyl-1H-purine-2,6(3H,7H)-dione (200 mg, 0.59 mmol) in DMF (3 mL), was added KOH (132 mg, 2.36 mmol), and MeI (335 mg, 2.36 mmol). The mixture was stirred at room temperature for 20 h. The reaction mixture was washed with water (10 mL) and extracted with EA (3*5 mL). The combined organic layers were dried with Na₂SO₄, filtered and concentrated. The residue was purified by preparative HPLC using Method D. ¹H NMR (500 MHz, CDCl₃) δ 8.88 (s, 1H), 7.51 (s, 1H), 7.21 (d, J=8.8 Hz, 1H), 7.01 (d, J=2.2 Hz, 1H), 6.81 (dd, J=8.8, 2.4 Hz, 1H), 6.54 (s, 1H), 5.30 (s, 2H), 4.00 (s, 3H), 3.82 (s, 3H), 3.60 (s, 3H); ESI: m/z 354.1 (M+H)⁺.

Example 240

1-((5-chloro-1H-indol-2-yl)methyl)-3,7-dimethyl-1H-purine-2,6(3H,7H)-dione

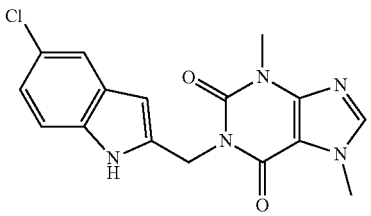 [SMILES: Cn1cnc2c1c(=O)n(Cc1cc3cc(Cl)ccc3[nH]1)c(=O)n2C]

The title compound was synthesized in a similar fashion as Example 239 using 3,7-dimethyl-1H-purine-2,6(3H,7H)-dione and tert-butyl 5-chloro-2-(chloromethyl)-1H-indole-1-carboxylate. The product was purified by preparative HPLC using Method B. ¹H NMR (400 MHz, DMSO-d₆) δ 11.11 (s, 1H), 8.06 (s, 1H), 7.46 (s, 1H), 7.34 (d, J=8.8 Hz, 1H), 7.01 (dd, J=8.6, 2.0 Hz, 1H), 6.24 (s, 1H), 5.18 (s, 2H), 3.90 (s, 3H), 3.45 (s, 3H); ESI m/z 344.1 (M+H)⁺.

Example 241

8-amino-1-((5-chloro-1H-indol-2-yl)methyl)-3,7-dimethyl-1H-purine-2,6(3H,7H)-dione

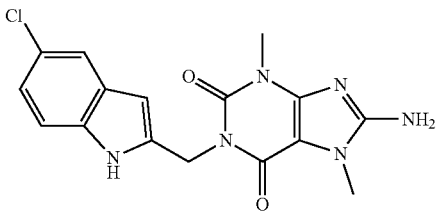 [SMILES: Cn1c(N)nc2c1c(=O)n(Cc1cc3cc(Cl)ccc3[nH]1)c(=O)n2C]

A solution of tert-butyl 2-((8-bromo-3,7-dimethyl-2,6-dioxo-2,3,6,7-tetrahydro-1H-purin-1-yl)methyl)-5-chloro-1H-indole-1-carboxylate (100 mg, 0.19 mmol) in 1N NH$_3$ methanol solution (5 mL) in a sealed vial was stirred at 140° C. overnight. The mixture was concentrated, and the residue was purified by prep-HPLC using Method B. $^1$H NMR (400 MHz, DMSO-d$_6$) δ 11.04 (s, 1H), 7.45 (d, J=1.8 Hz, 1H), 7.34 (d, J=8.6 Hz, 1H), 7.08-6.83 (m, 3H), 6.19 (s, 1H), 5.13 (s, 2H), 3.57 (s, 3H), 3.35 (s, 3H); ESI: m/z 359.0 (M+H)$^+$.

Example 242

1-((5-chloro-1-methyl-1H-indol-2-yl)methyl)-3,7-dimethyl-1H-purine-2,6(3H,7H)-dione

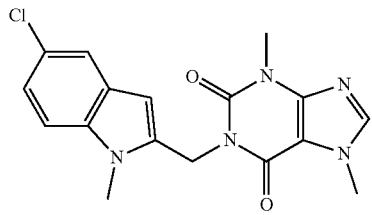 [SMILES: Cn1cnc2c1c(=O)n(Cc1cc3cc(Cl)ccc3n1C)c(=O)n2C]

The title compound was synthesized in a similar fashion as Example 238 using 1-((5-chloro-1H-indol-2-yl)methyl)-3,7-dimethyl-1H-purine-2,6(3H,7H)-dione. $^1$H NMR (400 MHz, DMSO-d$_6$) δ 8.07 (s, 1H), 7.53-7.21 (m, 2H), 7.09 (dd, J=8.8, 2.0 Hz, 1H), 6.19 (s, 1H), 5.23 (s, 2H), 3.89 (s, 3H), 3.86 (s, 3H), 3.44 (s, 3H). ESI: m/z 358.1 (M+H)$^+$.

Example 243

8-amino-1-((5-methoxy-1H-indol-2-yl)methyl)-3,7-dimethyl-1H-purine-2,6(3H,7H)-dione

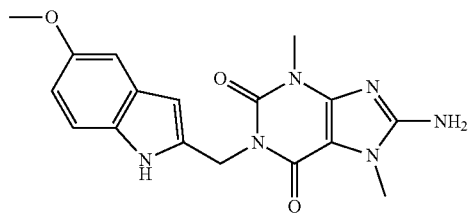 [SMILES: COc1ccc2[nH]c(Cn3c(=O)c4c(nc(N)n4C)n(C)c3=O)cc2c1]

The title compound was synthesized in a similar fashion as example 231 using tert-butyl 2-((8-bromo-3,7-dimethyl-2,6-dioxo-2,3,6,7-tetrahydro-1H-purin-1-yl)methyl)-5-methoxy-1H-indole-1-carboxylate. $^1$H NMR (400 MHz, CD$_3$OD) δ 7.09 (d, J=8.8 Hz, 1H), 6.85 (d, J=2.4 Hz, 1H), 6.60 (dd, J=8.8, 2.4 Hz, 1H), 6.19 (s, 1H), 5.13 (s, 2H), 3.67 (s, 3H), 3.57 (s, 3H), 3.36 (s, 3H); ESI: m/z 355.1 (M+H)$^+$.

Example 244

1-(3,4-dichlorobenzyl)-3,7-dimethyl-2,6-dioxo-2,3,6,7-tetrahydro-1H-purine-8-carboxamide

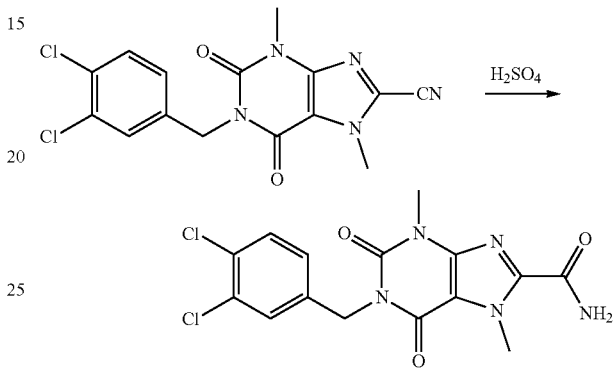

1-(3,4-Dichlorobenzyl)-3,7-dimethyl-2,6-dioxo-2,3,6,7-tetrahydro-1H-purine-8-carbonitrile

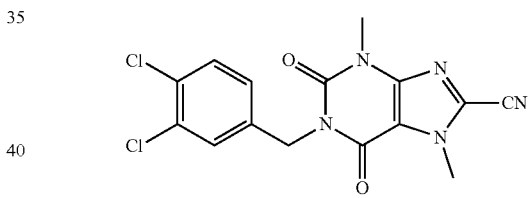

To a solution of 8-bromo-1-(3,4-dichlorobenzyl)-3,7-dimethyl-1H-purine-2,6(3H,7H)-dione (300 mg, 0.72 mmol) in DMF (3 mL) was added coppercyanide (192 mg, 2.16 mmol). The resulting mixture was stirred at 110° C. in microwave for 2 h. The residue was diluted with DCM (10 mL), quenched with sat.NH$_4$Cl and extracted with DCM (3*20 mL). The combined organic fractions were dried with Na$_2$SO$_4$, filtered and concentrated. The residue was purified with column chromatography (PE/EA=3/1) to give the title compound.

1-(3,4-dichlorobenzyl)-3,7-dimethyl-2,6-dioxo-2,3,6,7-tetrahydro-1H-purine-8-carboxamide

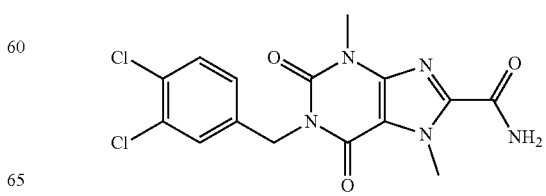

A solution of 1-(3,4-dichlorobenzyl)-3,7-dimethyl-2,6-dioxo-2,3,6,7-tetrahydro-1H-purine-8-carbonitrile (30 mg, 0.082 mmol) in H$_2$SO$_4$ (1 mL) was stirred at room temperature for 0.5 h. The mixture was neutralized with sat.Cs$_2$CO$_3$ and extracted with DCM (3*20 mL). The combined organic fractions were dried with Na$_2$SO$_4$ and concentrated. The residue was purified by prep-HPLC using Method F (33-63% ACN). $^1$H NMR (400 MHz, DMSO-d$_6$) δ 8.06 (b, 2H), 7.58-7.56 (m, 2H), 7.31 (dd, J=6.4, 1.6 Hz, 1H), 5.04 (s, 2H), 4.21 (s, 3H), 3.45 (s, 3H); ESI: m/z 382.0 (M+H)$^+$.

Example 245

1-(3,4-dichlorobenzyl)-3,7-dimethyl-8-(oxetan-3-ylamino)-1H-purine-2,6(3H,7H)-dione

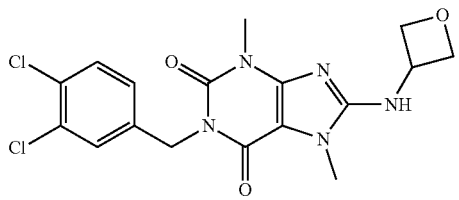 [SMILES: Cn1c(NC2COC2)nc2c1c(=O)n(Cc1ccc(Cl)c(Cl)c1)c(=O)n2C]

The title compound was synthesized in a similar fashion as described in procedure 7A using 8-bromo-1-(3,4-dichlorobenzyl)-3,7-dimethyl-1H-purine-2,6(3H,7H)-dione and oxetan-3-amine. The product was purified by flash chromatography (PE/EA, 1/1). $^1$H NMR (500 MHz, CD$_3$OD) δ 7.41 (d, J=1.9 Hz, 1H), 7.30 (d, J=8.3 Hz, 1H), 7.18 (dd, J=8.3, 2.0 Hz, 1H), 4.98-4.89 (m, 3H), 4.87-4.82 (m, 3H), 4.58 (t, J=6.5 Hz, 2H), 3.55 (s, 3H), 3.32 (s, 3H); ESI: m/z 410.1 (M+H)$^+$.

Example 246

2-(1-(3,4-dichlorobenzyl)-3-methyl-2,6-dioxo-2,3-dihydro-1H-purin-7(6H)-yl)acetamide

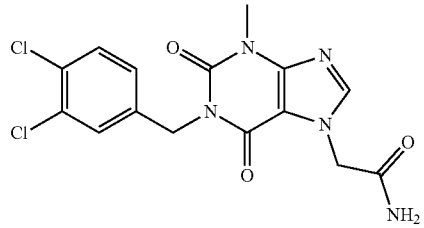 [SMILES: Cn1c(=O)n(Cc2ccc(Cl)c(Cl)c2)c(=O)c2c1ncn2CC(N)=O]

To a solution of 2-(3-methyl-2,6-dioxo-2,3-dihydro-1H-purin-7(6H)-yl)acetamide (150 mg, 0.67 mmol) and 4-(bromomethyl)-1,2-dichlorobenzene (209 mg, 0.87 mmol) in DMF (5 mL) was added K$_2$CO$_3$ (278 mg, 2.01 mmol). The mixture was stirred at 60° C. for 16 h, and then diluted with water (5 mL) and extracted with EA (3*10 mL). The combined organic fractions were dried with Na$_2$SO$_4$, filtered and concentrated. The residue was purified by prep-HPLC using Method F (40-45% ACN). $^1$H NMR (400 MHz, DMSO-d$_6$) δ 8.04 (s, 1H), 7.66 (br s, 1H), 7.57-7.54 (m, 2H), 7.29-7.25 (m, 2H), 5.00 (s, 2H), 4.93 (s, 2H), 3.44 (s, 3H); ESI: m/z 382.0 (M+H)$^+$.

Example 247

(±)-2-chloro-4-((8-((trans)-3-hydroxycyclopentylamino)-3,7-dimethyl-2,6-dioxo-2,3,6,7-tetrahydro-1H-purin-1-yl)methyl)benzonitrile

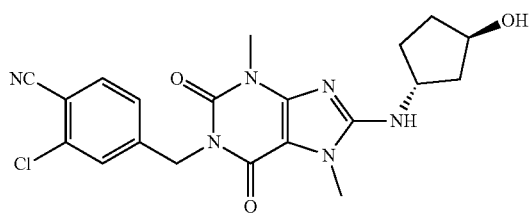 [SMILES: Cn1c(N[C@@H]2CC[C@@H](O)C2)nc2c1c(=O)n(Cc1ccc(C#N)c(Cl)c1)c(=O)n2C]

The title compound was synthesized in a similar fashion as described in procedure 7A using 4-((8-bromo-3,7-dimethyl-2,6-dioxo-2,3,6,7-tetrahydro-1H-purin-1-yl)methyl)-2-chlorobenzonitrile and (trans)-3-aminocyclopentanol. The product purified by prep-HPLC using Method D. $^1$H NMR (400 MHz, DMSO-d$_6$) δ 7.90 (d, J=8.1 Hz, 1H), 7.61 (s, 1H), 7.39 (d, J=9.4 Hz, 1H), 6.91 (d, J=7.4 Hz, 1H), 5.07 (s, 2H), 4.55 (d, J=3.7 Hz, 1H), 4.37 (dd, J=15.0, 7.3 Hz, 1H), 4.22 (s, 1H), 3.55 (s, 3H), 3.36 (s, 3H), 2.13 (d, J=4.9 Hz, 1H), 2.00-1.85 (m, 2H), 1.76-1.64 (m, 1H), 1.55-1.39 (m, 2H); ESI: m/z 429.1 (M+H)$^+$.

Example 248

1-(3,4-dichlorobenzyl)-7-(2-hydroxyethyl)-3-methyl-1H-purine-2,6(3H,7H)-dione

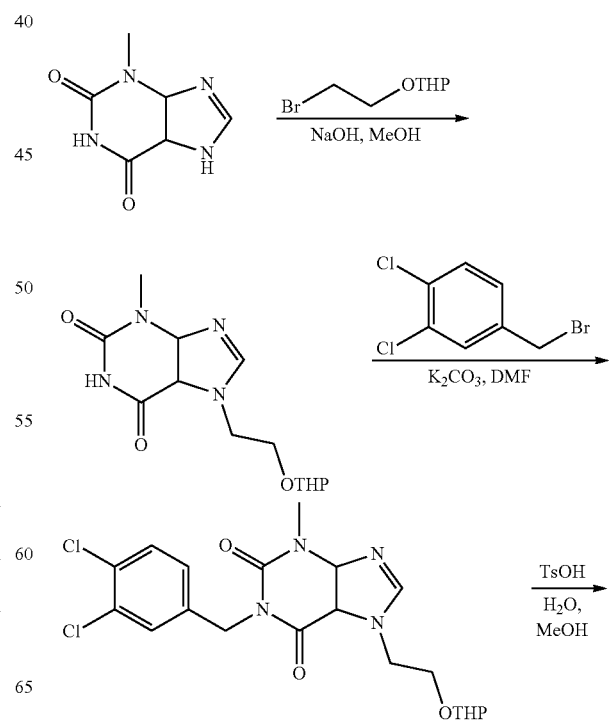

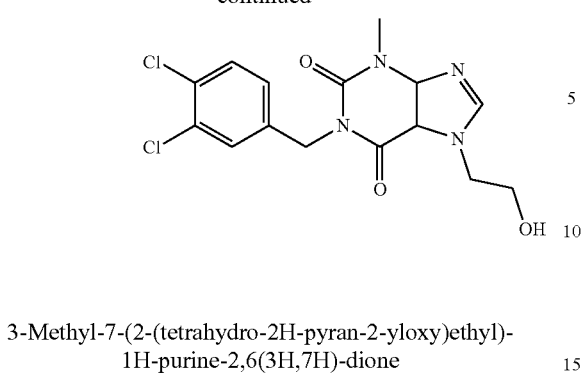

3-Methyl-7-(2-(tetrahydro-2H-pyran-2-yloxy)ethyl)-1H-purine-2,6(3H,7H)-dione

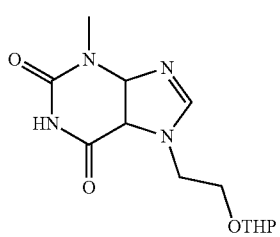

A solution of 3-methyl-1H-purine-2,6(3H,7H)-dione (166 mg, 1.0 mmol) in 10% NaOH (2 mL), MeOH (4 mL) was stirred at 70° C. for 1 h. To the mixture was added 2-(2-bromoethoxy)tetrahydro-2H-pyran (230 mg, 1.1 mmol). After the addition the mixture was stirred at 70° C. for 12 h. The mixture was cooled to room temperature and a white precipitate was formed. The solid was collected by filtration, washed with acetone and dried under vacuum. ESI: m/z 295.1 (M+H)$^+$.

1-(3,4-dichlorobenzyl)-3-methyl-7-(2-(tetrahydro-2H-pyran-2-yloxy)ethyl)-1H-purine-2,6(3H,7H)-dione

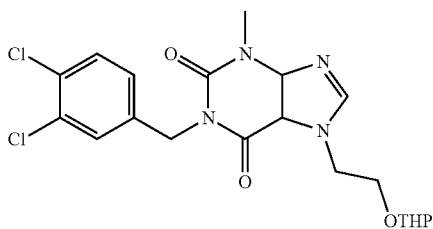

To a solution of methyl 3-methyl-7-(2-(tetrahydro-2H-pyran-2-yloxy)ethyl)-1H-purine-2,6(3H,7H)-dione (160 mg, 0.54 mmol) and 4-(bromomethyl)-1,2-dichlorobenzene (168 mg, 0.70 mmol) in DMF (5 mL), was added K$_2$CO$_3$ (224 mg, 1.62 mmol). The mixture was stirred at 60° C. for 16 h. The reaction was quenched with water (5 mL) and the mixture was extracted with EA (3*10 mL). The combined organic fractions were dried with Na$_2$SO$_4$, filtered and concentrated. ESI: m/z 453.1 (M+H)$^+$.

1-(3,4-dichlorobenzyl)-7-(2-hydroxyethyl)-3-methyl-1H-purine-2,6(3H,7H)-dione

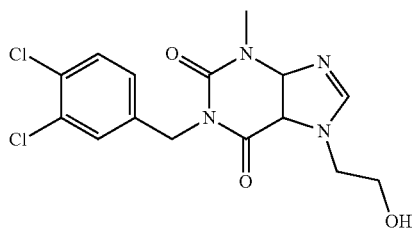 [SMILES: CN1C(=O)N(Cc2ccc(Cl)c(Cl)c2)C(=O)C2C1N=CN2CCO]

To a solution of 1-(3,4-dichlorobenzyl)-3-methyl-7-(2-(tetrahydro-2H-pyran-2-yloxy)ethyl)-1H-purine-2,6(3H,7H)-dione (180 mg, 0.40 mmol) in MeOH (2 mL) and water (1 mL), was added TsOH (14 mg, 0.08 mmol). The mixture was stirred at room temperature for 3 h. The mixture was filtered and the filtrate was concentrated. The residue was purified by prep-HPLC using Method F. $^1$H NMR (400 MHz, DMSO-d$_6$) δ 8.04 (s, 1H), 7.57-7.55 (m, 2H), 7.28 (dd, J=2.0, 8.4 Hz, 1H), 5.02 (s, 2H), 4.94 (t, J=5.2 Hz, 1H), 4.28 (t, J=5.2 Hz, 2H), 3.69 (t, J=5.2 Hz, 2H), 3.43 (s, 3H); ESI: m/z 369.0 (M+H)$^+$.

Example 249

1-(4-chloro-3-methoxybenzyl)-3,7-dimethyl-1H-purine-2,6(3H,7H)-dione

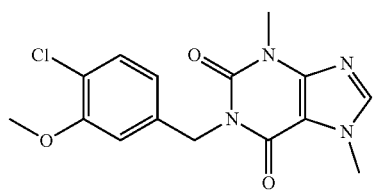 [SMILES: COc1cc(Cn2c(=O)c3c(ncn3C)n(C)c2=O)ccc1Cl]

The title compound was synthesized as described in Procedure 4 using 3,7-dimethyl-1H-purine-2,6(3H,7H)-dione and 4-(bromomethyl)-1-chloro-2-methoxybenzene. The residue was purified by preparative HPLC using Method D. $^1$H NMR (400 MHz, DMSO-d$_6$) δ 8.05 (s, 1H), 7.31 (d, J=8.1 Hz, 1H), 7.14 (d, J=1.5 Hz, 1H), 6.80 (dd, J=8.1, 1.6 Hz, 1H), 5.04 (s, 2H), 3.89 (s, 3H), 3.83 (s, 3H), 3.44 (d, J=8.8 Hz, 3H); ESI: m/z 335.0 (M+H)$^+$.

Example 250

1-(3,4-dichlorobenzyl)-3-ethyl-7-methyl-1H-purine-2,6(3H,7H)-dione

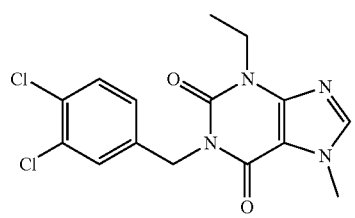 [SMILES: CCn1c(=O)n(Cc2ccc(Cl)c(Cl)c2)c(=O)c2c1ncn2C]

The title compound was synthesized according to procedure 4 using 3-ethyl-7-methyl-1H-purine-2,6(3H,7H)-dione and 4-(bromomethyl)-1,2-dichlorobenzene. The crude product was purified by Prep-HPLC using Method D (30-70% ACN). $^1$H NMR (400 MHz, DMSO-$d_6$) δ 8.06 (s, 1H), 7.57 (dd, J=5.1, 3.2 Hz, 2H), 7.29 (dd, J=8.3, 2.0 Hz, 1H), 5.04 (s, 2H), 4.02 (q, J=7.0 Hz, 2H), 3.89 (s, 3H), 1.22 (t, J=7.0 Hz, 3H); ESI: m/z 353.0 (M+H)$^+$.

Example 251

1-(3,4-dichlorobenzyl)-3-methyl-1H-purine-2,6(3H,7H)-dione

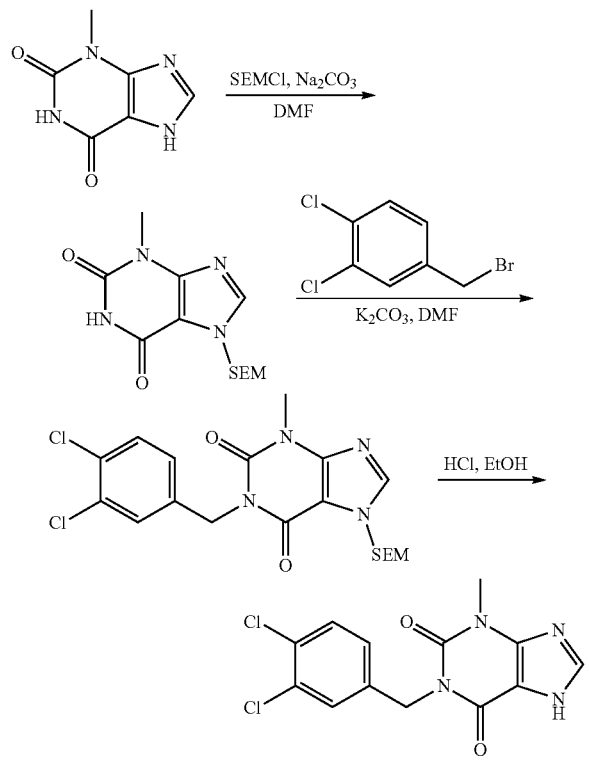

3-Methyl-7-(2-(trimethylsilyl)ethoxy)methyl)-1H-purine-2,6(3H,7H)-dione

A mixture of 3-methyl-1H-purine-2,6(3H,7H)-dione (1000 mg, 6.02 mmol), SEMCl (1440 mg, 8.43 mmol), and Na$_2$CO$_3$ (1661 mg, 12.04 mmol) in DMF (6 mL) was stirred at rt. overnight. The reaction mixture was diluted with water (50 mL) and extracted with EA (3*50 mL). The combined organic fractions were dried with Na$_2$SO$_4$, filtered and concentrated. The residue was purified with column chromatography (DCM/MeOH=10%); ESI: m/z 297.1 (M+H)$^+$.

1-(3,4-dichlorobenzyl)-3-methyl-7-((2-(trimethylsilyl)ethoxy)methyl)-1H-purine-2,6(3H,7H)-dione

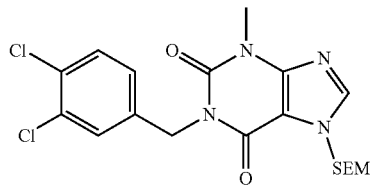 [SMILES: Cn1c(=O)n(Cc2ccc(Cl)c(Cl)c2)c(=O)c2c1ncn2COCC[Si](C)(C)C]

A solution of 3-methyl-7-((2-(trimethylsilyl)ethoxy)methyl)-1H-purine-2,6(3H,7H)-dione (40 mg, 0.135 mmol), 4-(bromomethyl)-1,2-dichlorobenzene (35.5 mg, 0.148 mmol) and K$_2$CO$_3$ (56 mg, 0.41 mmol) in DMF (2 mL) was stirred and heated to 50° C. for 16 h. The mixture was poured into water and extracted with EA (2*40 mL). The combined organic fractions were dried with Na$_2$SO$_4$, filtered and concentrated. The residue was purified with column chromatography (DCM/MeOH=20/1); ESI: m/z 455.0 (M−28)$^+$.

1-(3,4-dichlorobenzyl)-3-methyl-1H-purine-2,6(3H,7H)-dione

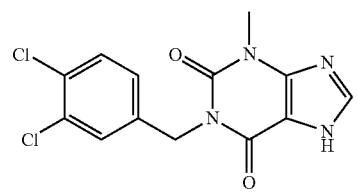 [SMILES: Cn1c(=O)n(Cc2ccc(Cl)c(Cl)c2)c(=O)c2[nH]cnc21]

To a solution of 1-(3,4-dichlorobenzyl)-3-methyl-7-((2-(trimethylsilyl)ethoxy)methyl)-1H-purine-2,6(3H,7H)-dione (50 mg, 0.11 mmol) in EtOH (5 mL), was added HCl (1 mL, 5M). After stirring at 70° C. for 1 h, the mixture was concentrated. The residue was diluted with DCM (10 mL) and sat.NaHCO$_3$ and extracted with DCM (3*20 mL). The combined organic fractions were dried with Na$_2$SO$_4$, filtered and concentrated. The residue was purified by prep-HPLC using method F (33-61% ACN). $^1$H NMR (400 MHz, CDCl$_3$) δ 7.80 (s, 1H), 7.59 (d, J=1.6 Hz, 1H), 7.36 (s, 1H), 7.35 (d, J=2.0 Hz, 1H), 5.17 (s, 2H), 3.64 (s, 3H); ESI: m/z 325.1 (M+H)$^+$.

Example 252

1-(4-chloro-3-(methoxymethyl)benzyl)-3,7-dimethyl-1H-purine-2,6(3H,7H)-dione

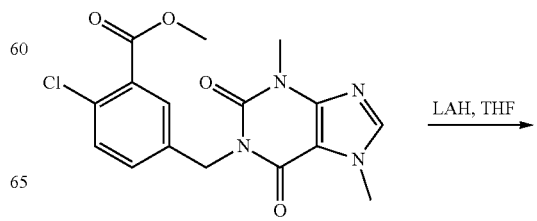

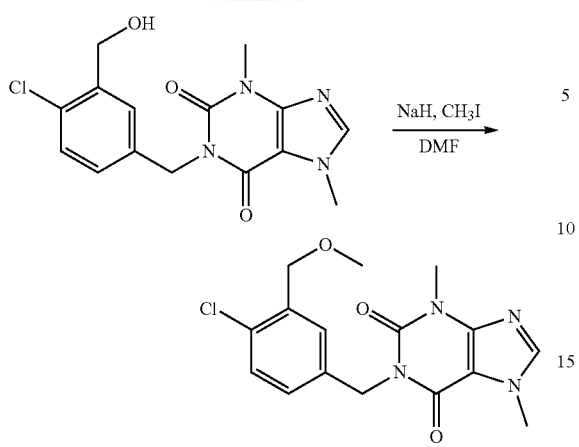

Methyl 2-chloro-5-((3,7-dimethyl-2,6-dioxo-2,3,6,7-tetrahydro-1H-purin-1-yl)methyl)benzoate

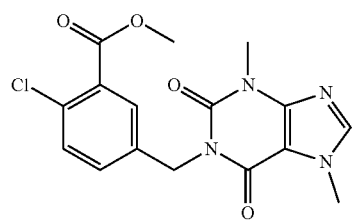 [SMILES: COC(=O)c1cc(Cn2c(=O)c3c(ncn3C)n(C)c2=O)ccc1Cl]

The title compound was synthesized in a similar fashion as described in Procedure 4 using 3,7-dimethyl-1H-purine-2,6(3H,7H)-dione and methyl 5-(bromomethyl)-2-chlorobenzoate. The product was purified by prep-HPLC using method D; ESI: m/z 363.0 (M+H)⁺.

1-(4-chloro-3-(hydroxymethyl)benzyl)-3,7-dimethyl-1H-purine-2,6(3H,7H)-dione

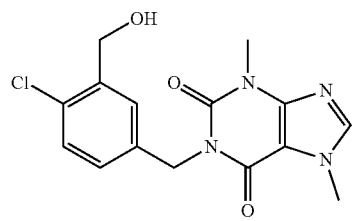 [SMILES: Cn1cnc2c1c(=O)n(Cc1ccc(Cl)c(CO)c1)c(=O)n2C]

To a solution of methyl 2-chloro-5-((3,7-dimethyl-2,6-dioxo-2,3,6,7-tetrahydro-1H-purin-1-yl)methyl)benzoate (500 mg, 1.38 mmol) in THF (500 mL) was added LAH (88 mg, 1.45 mmol) at 0° C. The mixture was stirred at 0° C. for 2 h. The reaction was quenched with (0.09 ml) H₂O, (0.09 ml) NaOH (15%) and (0.264 ml) H₂O. The mixture was filtered, and concentrated. The residue was purified by prep-HPLC using method D. ESI: m/z 335.0 (M+H)⁺.

1-(4-chloro-3-(methoxymethyl)benzyl)-3,7-dimethyl-1H-purine-2,6(3H,7H)-dione

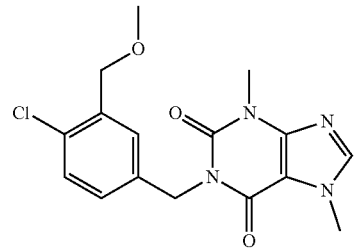 [SMILES: COCc1cc(Cn2c(=O)c3c(ncn3C)n(C)c2=O)ccc1Cl]

To a solution of 1-(4-chloro-3-(hydroxymethyl)benzyl)-3,7-dimethyl-1H-purine-2,6(3H,7H)-dione (600 mg, 1.8 mmol) in DMF (10 mL) was added NaH (60% in oil, 143 mg, 3.6 mmol). The mixture was stirred for 0.5 h and MeI (510 mg, 3.6 mmol) was added. The mixture was stirred at room temperature for 15 h. The reaction mixture was diluted with water (10 mL) and extracted with EA (3*5 mL). The combined organic fractions were dried with Na₂SO₄, filtered and concentrated. The residue was purified by prep-HPLC using Method D. ¹H NMR (400 MHz, DMSO) δ 8.05 (s, 1H), 7.44 (s, 1H), 7.37 (d, J=8.2 Hz, 1H), 7.28-7.18 (m, 1H), 5.04 (s, 2H), 4.44 (s, 2H), 3.89 (s, 3H), 3.42 (s, 3H), 3.35 (s, 3H); ESI: m/z 349.0 (M+H)⁺.

Example 253

1-(3,4-dichlorobenzyl)-9-methyl-1H-purine-2,6(3H,9H)-dione

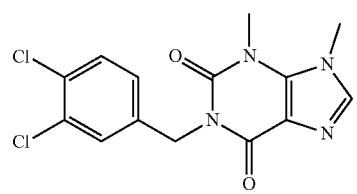 [SMILES: Cn1cnc2c(=O)n(Cc3ccc(Cl)c(Cl)c3)c(=O)n(C)c21]

The title compound was synthesized in a similar fashion as described in Procedure 4 using 3,9-dimethyl-1H-purine-2,6(3H,9H)-dione and 4-(bromomethyl)-1,2-dichlorobenzene. The reaction mixture was filtered and the filtrate was diluted with water (10 mL), extracted with EA (2*5 mL). The combined organic fractions were dried with Na₂SO₄, filtered and concentrated. The product was purified by preparative HPLC using Method D. ¹H NMR (400 MHz, DMSO-d₆) δ 7.71 (s, 1H), 7.57 (d, J=8.3 Hz, 1H), 7.52 (d, J=1.8 Hz, 1H), 7.26 (dd, J=8.3, 1.9 Hz, 1H), 5.04 (s, 2H), 3.93 (s, 3H), 3.68 (s, 3H); ESI: m/z 339.1 (M+H)⁺.

Example 254

(±)-1-(3,4-dichlorobenzyl)-8-(3-(hydroxymethyl)cyclohexylamino)-3,7-dimethyl-1H-purine-2,6(3H,7H)-dione

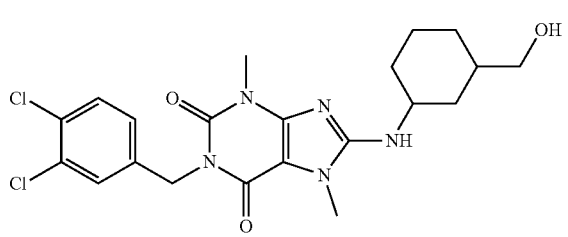 [SMILES: Cn1c(NC2CCCC(CO)C2)nc2c1c(=O)n(Cc1ccc(Cl)c(Cl)c1)c(=O)n2C]

At −78° C. to a solution of methyl 3-(1-(3,4-dichlorobenzyl)-3,7-dimethyl-2,6-dioxo-2,3,6,7-tetrahydro-1H-purin-8-ylamino)cyclohexanecarboxylate (0.2 mmol, 0.1 g) in THF (2 mL) was added DIBAL-H in toluene (0.5 mL, 1N). The reaction mixture was stirred at −40° C. for 2 h. The mixture was diluted with water (2 mL). The mixture was stirred at 10° C. for 1 h. The mixture was extracted with EA (2*50 mL). The organic fractions were concentrated and purified by Prep-HPLC using Method D (30-70% ACN). $^1$H NMR (400 MHz, CD$_3$OD) δ 7.52 (d, J=2.0 Hz, 1H), 7.41 (d, J=8.3 Hz, 1H), 7.29 (dd, J=8.3, 2.1 Hz, 1H), 5.05 (s, 2H), 3.82 (m, 1H), 3.60 (s, 3H), 3.47 (s, 3H), 3.44-3.33 (m, 2H), 2.19-2.03 (m, 2H), 1.87 (m, 1H), 1.79 (d, J=13.0 Hz, 1H), 1.63 (m, 1H), 1.43 (m, 1H), 1.27 (m, 1H), 1.09-0.85 (m, 2H); ESI: m/z 466.0 (M+H)$^+$.

Example 255

1-(3,4-dichlorobenzyl)-8-(3-(hydroxymethyl)cyclopentylamino)-3,7-dimethyl-1H-purine-2,6(3H,7H)-dione

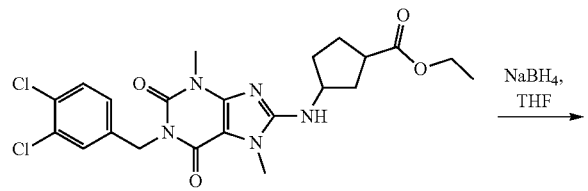

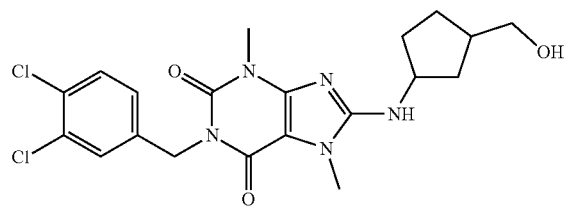

Ethyl 3-(1-(3,4-dichlorobenzyl)-3,7-dimethyl-2,6-dioxo-2,3,6,7-tetrahydro-1H-purin-8-ylamino)cyclopentanecarboxylate

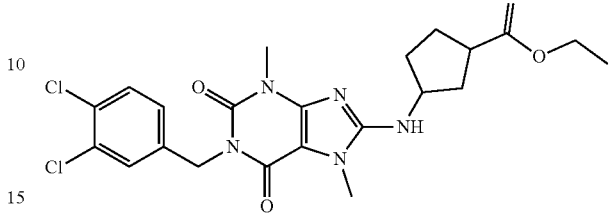

The title compound was synthesized in a similar fashion as described in procedure 7A using 8-bromo-1-(3,4-dichlorobenzyl)-3,7-dimethyl-1H-purine-2,6(3H,7H)-dione and ethyl 3-aminocyclopentanecarboxylate. The product was purified by flash chromatography (PE/EA=1/1); ESI: m/z 494.0 (M+H)$^+$.

1-(3,4-dichlorobenzyl)-8-(3-(hydroxymethyl)cyclopentylamino)-3,7-dimethyl-1H-purine-2,6(3H,7H)-dione

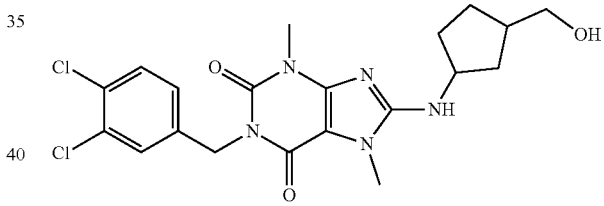

To a solution of ethyl 3-(1-(3,4-dichlorobenzyl)-3,7-dimethyl-2,6-dioxo-2,3,6,7-tetrahydro-1H-purin-8-ylamino)cyclopentanecarboxylate (0.3 mmol, 0.15 g) in THF (10 mL) at −18° C. was added in NaBH$_4$ (1.2 mmol, 0.04 g). The reaction mixture was stirred at 50° C. for 6 h. The mixture was diluted with MeOH (10 mL). The mixture was concentrated and purified by flash chromatography (EA) to give the crude product. The crude product was purified by Prep-HPLC using Method D (30-70% ACN). $^1$H NMR (400 MHz, Methanol-d$_4$) δ 7.52 (d, J=1.9 Hz, 1H), 7.42 (d, J=8.3 Hz, 1H), 7.29 (dd, J=8.3, 2.0 Hz, 1H), 5.06 (s, 2H), 4.28-4.25 (m, 1H), 3.60 (s, 3H), 3.56-3.51 (m, 2H), 3.48 (s, 3H), 2.34-2.13 (m, 2H), 2.10-1.97 (m, 1H), 1.87-1.74 (m, 1H), 1.73-1.51 (m, 2H), 1.34-1.31 (m, 1H); ESI: m/z 451.9 (M+H)$^+$.

Example 256

2-chloro-5-((3,7-dimethyl-2,6-dioxo-2,3,6,7-tetrahydro-1H-purin-1-yl)methyl)benzonitrile

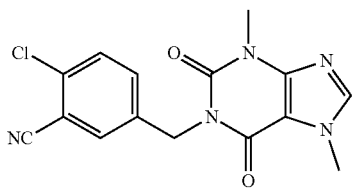 [SMILES: Cn1cnc2c1c(=O)n(Cc1ccc(Cl)c(C#N)c1)c(=O)n2C]

The title compound was synthesized in a similar fashion as described in procedure 4 using 5-(bromomethyl)-2-chlorobenzonitrile and 3,7-dimethyl-1H-purine-2,6(3H,7H)-dione. The product was purified by prep-HPLC using Method F. $^1$H NMR (400 MHz, DMSO-d$_6$) δ 8.06 (s, 1H), 7.89 (d, J=1.6 Hz, 1H), 7.68 (s, 1H), 6.87 (d, J=2.0 Hz, 1H), 5.06 (s, 2H), 3.88 (s, 3H), 3.42 (s, 3H); ESI: m/z 330.1 (M+H)$^+$.

Example 257

2-((3,7-dimethyl-2,6-dioxo-2,3,6,7-tetrahydro-1H-purin-1-yl)methyl)-1H-indole-5-carbonitrile

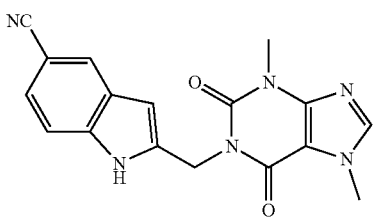 [SMILES: Cn1cnc2c1c(=O)n(Cc1cc3cc(C#N)ccc3[nH]1)c(=O)n2C]

tert-Butyl 5-bromo-2-((3,7-dimethyl-2,6-dioxo-2,3,6,7-tetrahydro-1H-purin-1-yl)methyl)-1H-indole-1-carboxylate (150 mg, 0.31 mmol) and CuCN (83 mg, 0.92 mmol) in NMP (4 mL) in a sealed vial was irradiated in a micromave at 180° C. for 5 h. The mixture was filtered and the filtrate was purified by prep-HPLC using Method B. $^1$H NMR (400 MHz, DMSO-d$_6$) δ 11.52 (s, 1H), 8.06 (s, 1H), 7.95 (s, 1H), 7.49 (d, J=8.4 Hz, 1H), 7.36 (dd, J=8.4, 1.5 Hz, 1H), 6.39 (s, 1H), 5.20 (s, 2H), 3.89 (s, 3H), 3.44 (s, 3H); ESI: m/z 335.0 (M+H)$^+$.

Example 258

(±)-(cis)-ethyl 3-(1-(3,4-dichlorobenzyl)-3,7-dimethyl-2,6-dioxo-2,3,6,7-tetrahydro-1H-purin-8-ylamino)cyclobutanecarboxylate

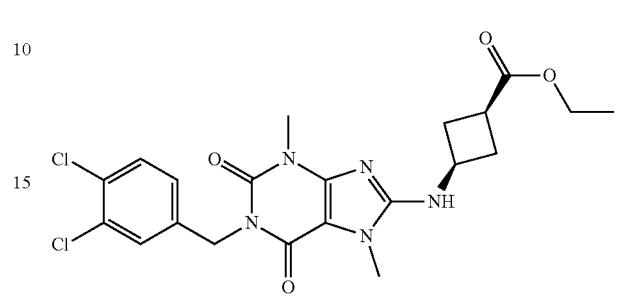

The title compound was synthesized in a similar fashion as described in procedure 7A using 8-bromo-1-(3,4-dichlorobenzyl)-3,7-dimethyl-1H-purine-2,6(3H,7H)-dione and cis-ethyl 3-aminocyclobutanecarboxylate. The product was purified by flash chromatography (PE/EA=1/2). $^1$H NMR (400 MHz, CD$_3$OD) δ 7.52 (s, 1H), 7.42-7.40 (d, J=8.0 Hz, 1H), 7.30-7.28 (d, J=6.0 Hz, 1H), 5.06 (s, 2H), 4.37-4.35 (m, 1H), 4.16-4.11 (q, J=7.1 Hz, 2H), 3.62 (m, 3H), 3.45 (s, 3H), 2.87-3.84 (m, 1H), 2.71-2.59 (m, 2H), 2.34-2.26 (m, 2H), 1.26 (t, J=7.1 Hz, 3H); ESI: m/z 480.0 (M+H)$^+$.

Example 259

(±)-(cis)-3-(1-(3,4-dichlorobenzyl)-3,7-dimethyl-2,6-dioxo-2,3,6,7-tetrahydro-1H-purin-8-ylamino)cyclobutanecarboxylic acid

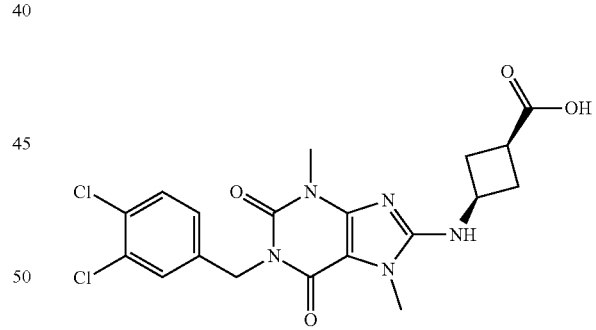

To a solution of (±)-(cis)-ethyl 3-(1-(3,4-dichlorobenzyl)-3,7-dimethyl-2,6-dioxo-2,3,6,7-tetrahydro-1H-purin-8-ylamino)cyclobutanecarboxylate (0.42 mmol, 0.20 g) in water (4 mL), MeOH (1 mL) and THF (4 mL) was added LiOH (1.26 mmol, 0.03 g). The mixture was stirred 4 h at room temperature. The mixture was concentrated and the pH was adjusted 6.0 by addition of aqueous HCl solution. The mixture was filtered and the filter cake was washed with water (10 mL) and dried under high vacuum. $^1$H NMR (400 MHz, DMSO-d$_6$) δ 12.21 (br s, 1H), 7.51-7.56 (m, 2H), 7.37 (d, J=8.0 Hz, 1H), 7.25 (dd, J=8.3, 2.0 Hz, 1H), 4.98 (s, 2H), 4.27-4.24 (m, 1H), 3.56 (s, 3H), 3.35 (s, 5H), 2.77-2.74 (m, 1H), 2.24-2.21 (m, 2H); ESI: m/z 451.9 (M+H)$^+$.

Example 260

3-(1-((1H-indol-6-yl)methyl)-3,7-dimethyl-2,6-dioxo-2,3,6,7-tetrahydro-1H-purin-8-ylamino)cyclohexanecarboxylic acid

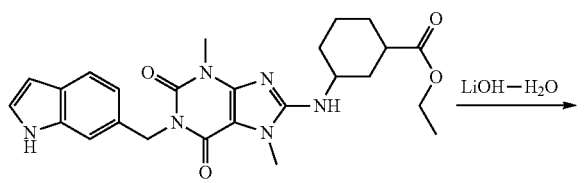

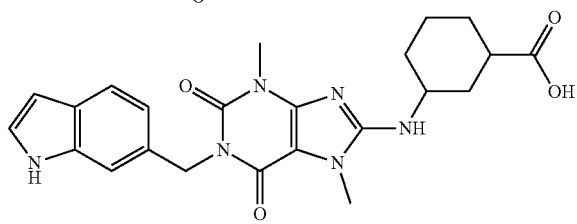

Ethyl 3-(1-((1H-indol-6-yl)methyl)-3,7-dimethyl-2,6-dioxo-2,3,6,7-tetrahydro-1H-purin-8-ylamino)cyclohexanecarboxylate

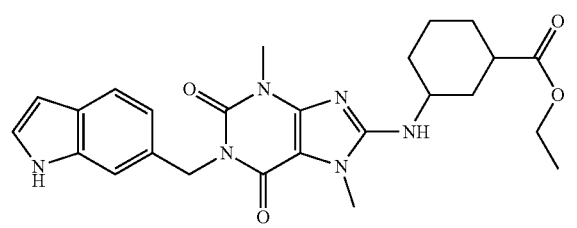 [SMILES: CCOC(=O)C1CCCC(Nc2nc3c(c(=O)n(Cc4ccc5cc[nH]c5c4)c(=O)n3C)n2C)C1]

The title compound was synthesized in a similar fashion as described in Procedure 7a using tert-butyl 6-((8-bromo-3,7-dimethyl-2,6-dioxo-2,3,6,7-tetrahydro-1H-purin-1-yl)methyl)-1H-indole-1-carboxylate and ethyl 3-aminocyclohexanecarboxylate. The product was purified by was purified by flash chromatography (PE/EA=50%); ESI: m/z 479.2 (M+H)⁺.

3-(1-((1H-Indol-6-yl)methyl)-3,7-dimethyl-2,6-dioxo-2,3,6,7-tetrahydro-1H-purin-8-ylamino)cyclohexanecarboxylic acid

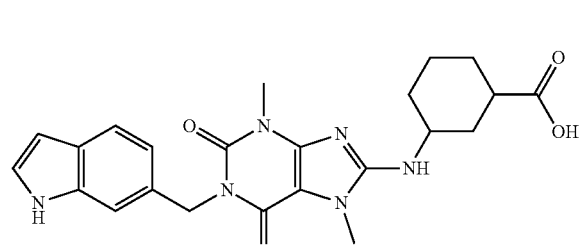

A mixture of ethyl 3-(1-((1H-indol-6-yl)methyl)-3,7-dimethyl-2,6-dioxo-2,3,6,7-tetrahydro-1H-purin-8-ylamino)cyclohexanecarboxylate (100 mg, 0.21 mmol) and LiOH·H₂O (44 mg, 1.05 mmol) in EtOH (10 mL) was stirred at rt. overnight. The mixture was concentrated and purified by prep-HPLC using Shimadzu Shim-Pack PRC-ODS column (20*250 mm), two connected in series eluting with 45%-75% acetonitrile in water (0.05% TFA). ¹H NMR (400 MHz, CD₃OD) δ 10.96 (s, 1H), 7.42 (d, J=8.2 Hz, 1H), 7.29 (dd, J=8.3, 5.6 Hz, 2H), 7.00 (d, J=8.2 Hz, 1H), 6.87-6.79 (□, 1H), 6.35 (s, 1H), 5.09 (s, 2H), 3.57 (s, 3H), 3.35 (s, 3H), 2.35 (t, J=12.1 Hz, 1H), 2.15 (d, J=12.5 Hz, 1H), 2.02-1.53 (m, 4H), 1.36 (m, 2H), 1.26-1.15 (m, 2H); ESI: m/z 451.2 (M+H)⁺.

Example 261

(±)-1-(3,4-dichlorobenzyl)-8-((cis)-3-(hydroxymethyl)cyclobutylamino)-3,7-dimethyl-1H-purine-2,6(3H,7H)-dione

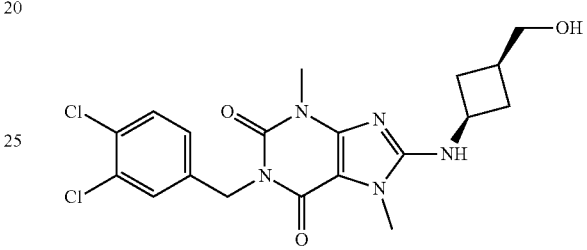

To a solution of (±)-(cis)-ethyl 3-(1-(3,4-dichlorobenzyl)-3,7-dimethyl-2,6-dioxo-2,3,6,7-tetrahydro-1H-purin-8-ylamino)cyclobutanecarboxylate (0.31 mmol, 0.15 g), in THF (10 mL) was added NaBH₄ (1.5 mmol, 0.06 g). The mixture was stirred at 50° C. for 5 h. The reaction was quenched with methanol (2 mL). The mixture was diluted with aqueous NaHCO₃ (20 mL) and extracted with EA (2*50 mL). The combined organic fractions were concentrated and purified by Prep-HPLC using Method D (30-70% ACN). ¹H NMR (400 MHz, CD₃OD) δ 7.51 (s, 1H), 7.40 (dd, J=8.3, 2.5 Hz, 1H), 7.29-7.27 (d, J=8.3, 1H), 5.03 (s, 2H), 4.32-4.27 (m, 1H), 3.60 (s, 3H), 3.55-3.54 (d, J=6.0 Hz, 2H), 3.46 (s, 3H), 2.49-2.46 (m, 2H), 2.25-2.10 (m, 1H), 1.83-1.80 (m, 2H); ESI: m/z 438.0 (M+H)⁺.

Example 262

1-(3,4-dichlorobenzyl)-8-((1R,3R)-3-hydroxycyclopentylamino)-3,9-dimethyl-1H-purine-2,6(3H,9H)-dione

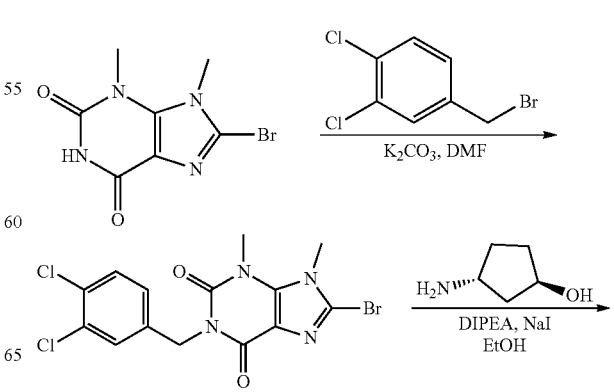

-continued

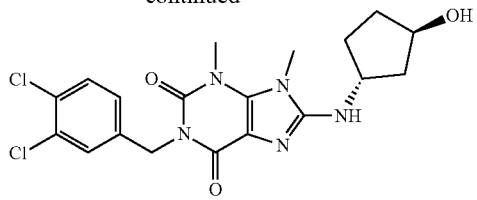

8-bromo-3,9-dimethyl-1H-purine-2,6(3H,9H)-dione

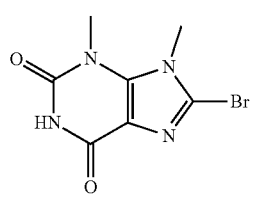

To a solution of 3,9-dimethyl-1H-purine-2,6(3H,9H)-dione (1.20 g, 6.67 mmol) in HOAc (10 mL) was added Br$_2$ (2 mL). The mixture was stirred at 60° C. for 2 h. The precipitate was collected, washed with water and dried to provide the title compound. ESI: m/z 259 (M+H)$^+$.

8-Bromo-1-(3,4-dichlorobenzyl)-3,9-dimethyl-1H-purine-2,6(3H,9H)-dione

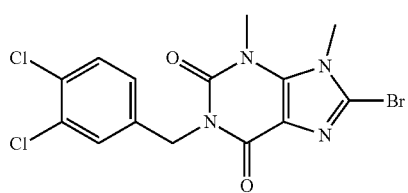 [SMILES: Cn1c(Br)nc2c(=O)n(Cc3ccc(Cl)c(Cl)c3)c(=O)n(C)c21]

The title compound was synthesized in a similar fashion as described in Procedure 4 using 8-bromo-3,9-dimethyl-1H-purine-2,6(3H,9H)-dione and 4-(bromomethyl)-1,2-dichlorobenzene. ESI: m/z 416.8 (M+H)$^+$.

1-(3,4-Dichlorobenzyl)-8-((1R,3R)-3-hydroxycyclopentylamino)-3,9-dimethyl-1H-purine-2,6(3H,9H)-dione

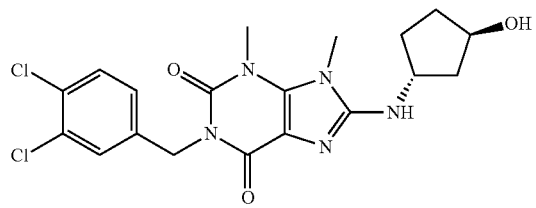 [SMILES: Cn1c(N[C@@H]2CC[C@@H](O)C2)nc2c(=O)n(Cc3ccc(Cl)c(Cl)c3)c(=O)n(C)c21]

The title compound was synthesized in a similar fashion as described in Procedure 7A using 8-bromo-1-(3,4-dichlorobenzyl)-3,9-dimethyl-1H-purine-2,6(3H,9H)-dione and (1R,3R)-3-aminocyclopentanol. The product was purified by prep-HPLC using Method D. $^1$H NMR (400 MHz, DMSO) δ 7.57 (d, J=8.3 Hz, 1H), 7.49 (d, J=1.9 Hz, 1H), 7.25 (dd, J=8.3, 2.0 Hz, 1H), 6.11 (d, J=6.7 Hz, 1H), 5.02 (s, 2H), 4.51 (d, J=3.9 Hz, 1H), 4.19 (dd, J=13.3, 5.4 Hz, 2H), 3.62 (d, J=10.3 Hz, 6H), 2.19-2.03 (m, 1H), 1.93 (dd, J=11.7, 8.1 Hz, 2H), 1.69-1.55 (m, 1H), 1.53-1.37 (m, 2H); ESI: m/z 438.0 (M+H)$^+$.

Example 263

1-((1H-indol-6-yl)methyl)-3,7-dimethyl-1H-purine-2,6(3H,7H)-dione

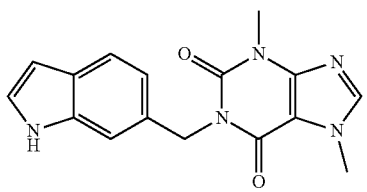 [SMILES: Cn1cnc2c1c(=O)n(Cc1ccc3cc[nH]c3c1)c(=O)n2C]

To a solution of 3,7-dimethyl-1H-purine-2,6(3H,7H)-dione (3.7 mmol, 0.68 g), K$_2$CO$_3$ (11.3 mmol, 1.56 g) in DMF (5 mL) was added tert-butyl 6-(chloromethyl)-1H-indole-1-carboxylate (3.7 mmol, 1.00 g). The reaction mixture was stirred at 50° C. for 16 h. The reaction was treated with water (30 mL) and extracted with EA (2*30 mL). The combined organic fractions were concentrated and purified by flash chromatography (PE/EA=1/2) to give tert-butyl 6-((3,7-dimethyl-2,6-dioxo-2,3,6,7-tetrahydro-1H-purin-1-yl)methyl)-1H-indole-1-carboxylate; ESI: m/z: 410.0 (M+H)$^+$.

To a solution of tert-butyl 6-((3,7-dimethyl-2,6-dioxo-2,3,6,7-tetrahydro-1H-purin-1-yl)methyl)-1H-indole-1-carboxylate (0.24 mmol, 0.1 g) in ethanol (15 mL) was added DIEA (0.73 mmol, 0.09 g). The mixture was stirred at 130° C. for 2 h in microwave reactor. The mixture was concentrated and purified by Prep-HPLC using Method D (30-70% ACN). $^1$H NMR (400 MHz, DMSO-d$_6$) δ 10.99 (s, 1H), 8.03 (s, 1H), 7.44 (d, J=8.1 Hz, 1H), 7.36 (s, 1H), 7.30 (t, J=2.8 Hz, 1H), 7.03 (dd, J=8.2, 1.5 Hz, 1H), 6.36 (s, 1H), 5.14 (s, 2H), 3.89 (s, 3H), 3.43 (s, 3H); ESI: m/z 310.1 (M+H)$^+$.

Example 264

(±)-cis-4-((1-(3,4-dichlorobenzyl)-3,7-dimethyl-2,6-dioxo-2,3,6,7-tetrahydro-1H-purin-8-yl)amino)cyclohexanecarboxylic acid

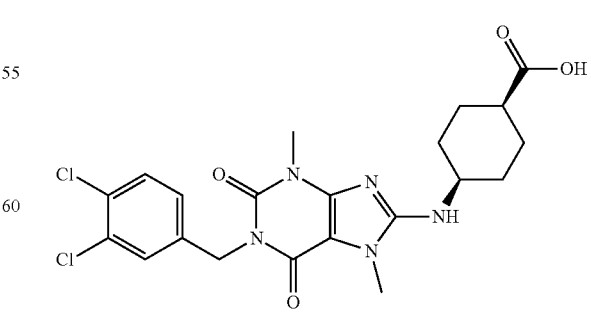

The title compound was synthesized in a similar fashion as described in Procedure 7a using 8-bromo-1-[(3,4-dichlorophenyl)methyl]-3,7-dimethyl-purine-2,6-dione and cis-4-aminocyclohexanecarboxylic acid The product was purified by prep-HPLC using Method A. $^1$H NMR: (400 MHz, CD$_3$OD) δ 7.55 (d, J=8.4 Hz, 1H), 7.52 (d, J=1.8 Hz, 1H), 7.26 (dd, J=2.2, 8.4 Hz, 1H), 6.78 (d, J=7.5 Hz, 1H), 4.98 (s, 2H), 3.76 (br, 1H), 3.57 (s, 3H), 3.35 (s, 3H), 2.54-2.56 (m, 1H), 2.47-2.44 (m, 1H), 2.00 (m, 2H), 1.80-1.51 (m, 6H); ESI; m/z 480.2 (M+H)$^+$.

Example 265

1-(3,4-dichlorobenzyl)-8-(3-(1-hydroxyethyl)cyclopentylamino)-3,7-dimethyl-1H-purine-2,6(3H,7H)-dione

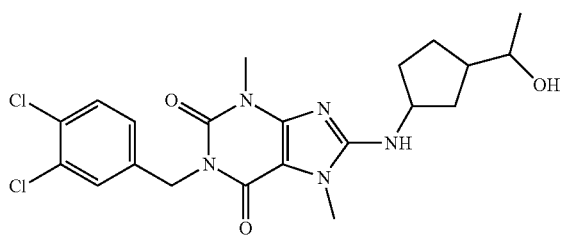 [SMILES: CC(O)C1CCC(Nc2nc3c(c(=O)n(Cc4ccc(Cl)c(Cl)c4)c(=O)n3C)n2C)C1]

The title compound was synthesized in a similar fashion as described in Procedure 7a using 8-bromo-1-(3,4-dichlorobenzyl)-3,7-dimethyl-1H-purine-2,6(3H,7H)-dione and 1-(3-aminocyclopentyl)ethanol. The product was purified by prep-HPLC using Method B. $^1$H NMR (400 MHz, DMSO-d$_6$) δ 7.53 (dd, J=14.1, 5.0 Hz, 2H), 7.26 (dd, J=8.3, 1.9 Hz, 1H), 6.95 (dd, J=7.3, 3.6 Hz, 1H), 4.98 (s, 2H), 4.60 (t, J=5.2 Hz, 1H), 4.12 (d, J=6.8 Hz, 1H), 3.58-3.27 (m, 4H), 3.35 (s, 3H), 2.05-2.01 (m, 1H), 1.95-1.68 (m, 2H), 1.68-1.14 (m, 4H), 1.05 (dd, J=6.2, 2.0 Hz, 3H); ESI: m/z 466.0 (M+H)$^+$.

Example 266

(1R,3R)-ethyl 3-(1-(3,4-dichlorobenzyl)-3,7-dimethyl-2,6-dioxo-2,3,6,7-tetrahydro-1H-purin-8-yl)cyclobutanecarboxylate

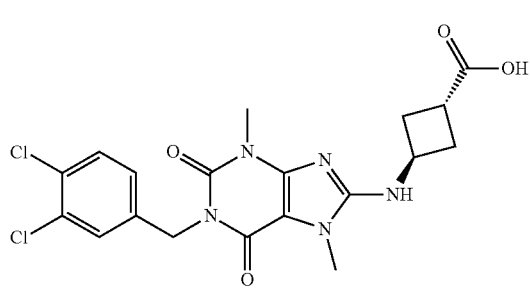 [SMILES: Cn1c(N[C@H]2C[C@H](C(=O)O)C2)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione (291 mg, 0.70 mmol), (1R,3R)-ethyl 3-aminocyclobutanecarboxylate (300 mg, 2.10 mmol) were coupled in a similar fashion as described in Procedure 7A.

The product was purified by column chromatography (PE/EA=70%) to give the (1R,3R)-ethyl 3-(1-(3,4-dichlorobenzyl)-3,7-dimethyl-2,6-dioxo-2,3,6,7-tetrahydro-1H-purin-8-yl)cyclobutanecarboxylate; ESI: m/z 480.2 (M+H)$^+$. A mixture of this product (100 mg, 0.21 mmol) and LiOH-H$_2$O (44 mg, 1.05 mmol) in EtOH (10 mL) and H$_2$O (2 mL) was stirred at R.T. overnight. The mixture was concentrated. The residue was purified by prep-HPLC using Shimadzu Shim-Pack PRC-ODS column (20*250 mm, 15µ), two connected in series eluting with 45%-75% acetonitrile in water (0.05% TFA) to provide the title compound. $^1$H NMR (400 MHz, DMSO-d$_6$): δ 12.24 (s, 1H), 7.53 (dd, J=14.4, 5.1 Hz, 2H), 7.37-7.10 (m, 2H), 4.98 (s, 2H), 4.46 (dd, J=15.6, 7.7 Hz, 1H), 3.58 (s, 3H), 3.34 (d, J=4.7 Hz, 5H), 2.96 (dd, J=11.5, 8.0 Hz, 1H), 2.33 (dt, J=12.4, 10.0 Hz, 2H); ESI: m/z 452.2 (M+H)$^+$.

Example 267

1-(3,4-dichlorobenzyl)-8-(3-(methoxymethyl)cyclopentylamino)-3,7-dimethyl-1H-purine-2,6(3H,7H)-dione

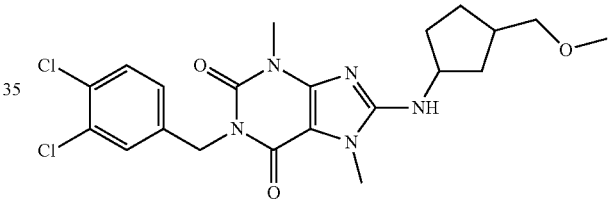

1-(3,4-dichlorobenzyl)-8-(3-(hydroxymethyl)cyclopentylamino)-3,7-dimethyl-1H-purine-2,6(3H,7H)-dione

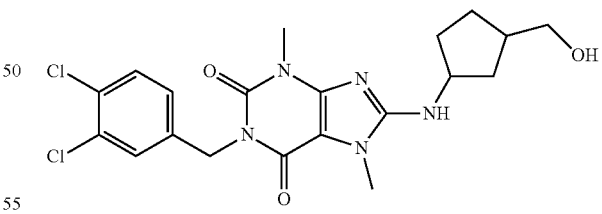

To a solution of ethyl 3-(1-(3,4-dichlorobenzyl)-3,7-dimethyl-2,6-dioxo-2,3,6,7-tetrahydro-1H-purin-8-ylamino)cyclopentanecarboxylate (0.3 mmol, 0.15 g), in THF (10 mL) was added NaBH$_4$ (0.9 mmol, 0.04 g). The mixture was stirred at 80° C. for 16 h. The mixture was diluted with water (50 mL) and extracted with EA (2*50 mL). The combined organic fractions were concentrated to give the product; ESI: m/z: 452.2 (M+H)$^+$.

Example 267

1-(3,4-dichlorobenzyl)-8-(3-(methoxymethyl)cyclopentylamino)-3,7-dimethyl-1H-purine-2,6(3H,7H)-dione

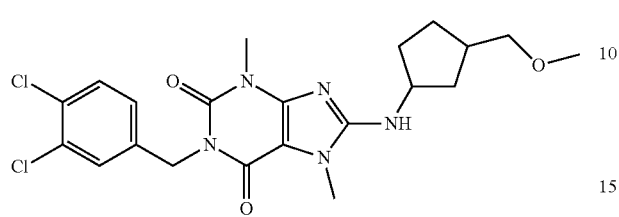

At 0° C. to a solution of 1-(3,4-dichlorobenzyl)-8-(3-(hydroxymethyl)cyclopentylamino)-3,7-dimethyl-1H-purine-2,6(3H,7H)-dione (0.24 mmol, 0.11 g) in DCM (1 mL) was added BF$_3$·Et$_2$O (0.48 mmol, 0.03 g). The mixture was stirred at 0° C. for 5 min then to the mixture was added TMSCHN$_2$ (0.73 mmol, 0.08 g). The mixture was stirred at 15° C. for 16 h. The mixture was diluted with water (20 mL) and extracted with EA (2*50 mL). The combined organic fractions were concentrated to give the crude product. The crude product was purified by Prep-HPLC using Method D (30-70% ACN). $^1$H NMR (500 MHz, DMSO-d$_6$) δ 7.58-7.49 (m, 2H), 7.25 (dd, J=8.3, 2.0 Hz, 1H), 6.91 (d, J=7.2 Hz, 1H), 4.98 (s, 2H), 4.14-4.12 (m, 1H), 3.56 (s, 3H), 3.34-3.21 (m, 7H), 2.20-2.10 (m, 2H), 2.20-1.91 (m, 1H), 1.71-1.65 (m, 1H), 1.58-1.52 (m, 1H), 1.48-1.41 (m, 1H), 1.30-1.24 (m, 1H); ESI: m/z 466.0 (M+H)$^+$.

Example 268

1-(3,4-dichlorobenzyl)-8-((1R,3R)-3-(hydroxymethyl)cyclobutyl)-3,7-dimethyl-3,7-dihydro-1H-purine-2,6-dione

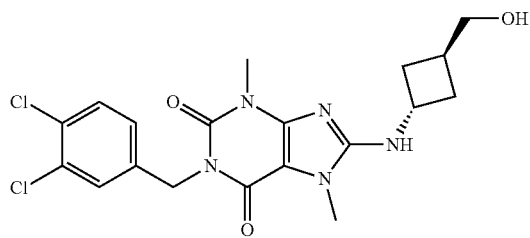 [SMILES: Cn1c(N[C@H]2C[C@H](CO)C2)nc2c1c(=O)n(Cc1ccc(Cl)c(Cl)c1)c(=O)n2C]

NaBH$_4$ (24 mg, 0.63 mmol) was slowly added to a solution of ethyl (1R,3R)-3-((1-(3,4-dichlorobenzyl)-3,7-dimethyl-2,6-dioxo-2,3,6,7-tetrahydro-1H-purin-8-yl)amino)cyclobutane-1-carboxylate (100 mg, 0.21 mmol) in EtOH (10 mL) at 0° C. The solution was stirred at 50° C. for 6 h. The reaction was quenched with water (30 mL). The mixture was concentrated and the residue was purified by prep-HPLC using Method B. $^1$H NMR (400 MHz, DMSO-d$_6$) δ 7.53 (dd, J=15.6, 5.1 Hz, 2H), 7.34-7.15 (m, 2H), 4.98 (s, 2H), 4.64 (t, J=5.3 Hz, 1H), 4.34 (dd, J=15.4, 7.7 Hz, 1H), 3.57 (d, J=5.6 Hz, 3H), 3.50-3.43 (m, 2H), 3.34 (s, 3H), 2.26 (d, J=6.2 Hz, 1H), 2.11 (dd, J=17.5, 8.5 Hz, 4H); ESI: m/z 437.9 (M+H)$^+$.

Example 269

4-[[1-[(3,4-dichlorophenyl)methyl]-3,7-dimethyl-2,6-dioxo-purin-8-yl]amino]benzoic acid

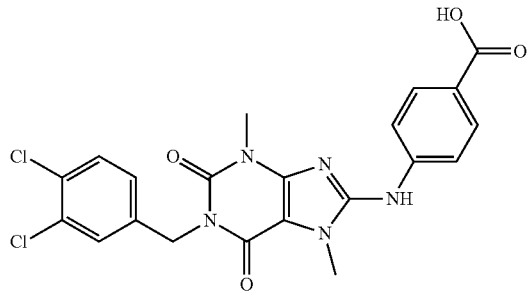 [SMILES: Cn1c(Nc2ccc(C(=O)O)cc2)nc2c1c(=O)n(Cc1ccc(Cl)c(Cl)c1)c(=O)n2C]

8-Bromo-1-[(3,4-dichlorophenyl)methyl]-3,7-dimethyl-purine-2,6-dione and methyl 4-aminobenzoate were coupled as described in Procedure 8B. The product was purified by column chromatography (DCM/MeOH 100/0 to 20/1) to provide 4-[[1-[(3,4-dichlorophenyl)methyl]-3,7-dimethyl-2,6-dioxo-purin-8-yl]amino]benzoate. A mixture of this product (850.00 mg, 1.74 mmol, 1.00 eq) in 6N NaOH (1.00 mL), MeOH (4.00 mL) and THF (4.00 mL) was heated to reflux (80-90° C.) for 18 hr. The mixture was cooled to room temperature (20° C.) and concentrated. The residue was acidified by 3N HCl at 0° C. to pH=1. The solid was collected by filtration, dried under high vacuum to give a crude product which was washed with a solution of DCM/t-BuOMe (1/1, 20 mL). $^1$H NMR (400 MHz, DMSO-d$_6$) δ 9.57 (s, 1H), 7.90 (d, J=9.26 Hz, 2H), 7.78 (d, J=8.82 Hz, 2H), 7.53-7.62 (m, 2H), 7.30 (dd, J=8.38, 2.21 Hz, 1H), 5.03 (s, 2H), 3.76-3.87 (m, 3H), 3.41-3.50 (m, 3H); ESI: m/z 474.1 (M+H)$^+$.

Example 313

4-[[1-[(3,4-dichlorophenyl)methyl]-3,7-dimethyl-2,6-dioxo-purin-8-yl]amino]benzamide

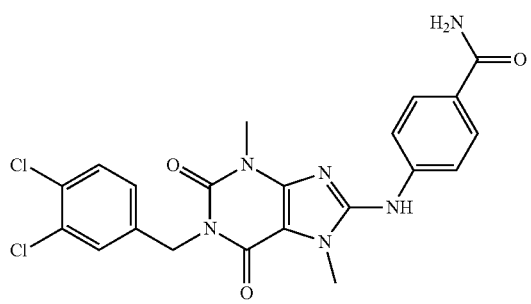 [SMILES: Cn1c(Nc2ccc(C(N)=O)cc2)nc2c1c(=O)n(Cc1ccc(Cl)c(Cl)c1)c(=O)n2C]

To a suspension of 4-[[1-[(3,4-dichlorophenyl)methyl]-3,7-dimethyl-2,6-dioxo-purin-8-yl]amino]benzoic acid (200.00 mg, 421.67 umol, 1.00 eq) in DCM (3.00 mL) was added (COCl)$_2$ (535.23 mg, 4.22 mmol, 10.00 eq) at 0° C., then 2 drops of DMF was added. After the addition, the mixture was warmed slowly to room temperature (20° C.), and stirred for 1 hr. The mixture was concentrated in vacuum. Then sat NH$_3$ in THF (3.00 mL) was added at 0° C. The mixture was warmed to 20° C. and stirred for 1 hr. The mixture was concentrated to give a crude product which was purified by prep-HPLC using Method A. $^1$H NMR (400 MHz, DMSO-$d_6$) δ 9.45 (br. s., 1H), 7.86 (d, J=8.53 Hz, 2H), 7.81 (br. s., 1H), 7.74 (d, J=9.03 Hz, 2H), 7.51-7.63 (m, 2H), 7.30 (dd, J=8.03, 2.01 Hz, 1H), 7.19 (br. s., 1H), 5.04 (s, 2H), 3.82 (s, 3H), 3.44 (s, 3H); ESI: m/z 473.1/475.1 (M+H)$^+$.

Example 270

4-((1-(3,4-dichlorobenzyl)-3,7-dimethyl-2,6-dioxo-2,3,6,7-tetrahydro-1H-purin-8-yl)(hydroxy)methyl)cyclohexanecarboxylic acid

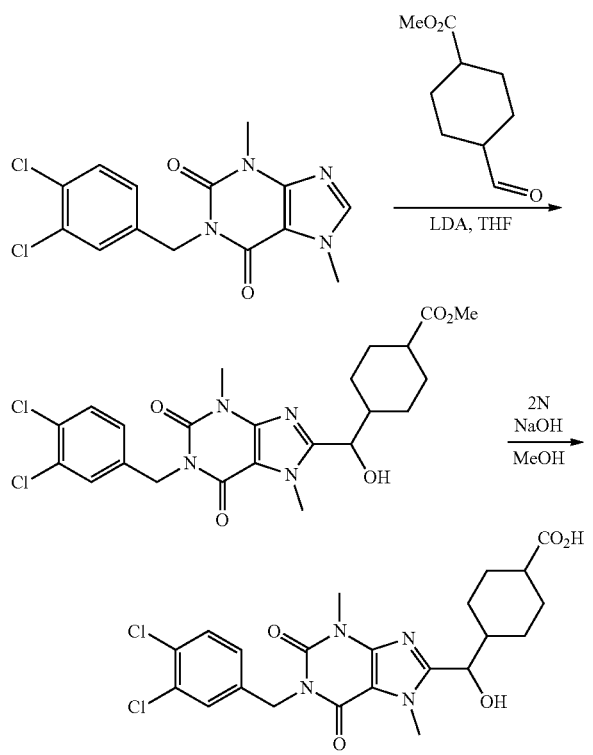

Methyl 4-((1-(3,4-dichlorobenzyl)-3,7-dimethyl-2,6-dioxo-2,3,6,7-tetrahydro-1H-purin-8-yl)(hydroxy)methyl)cyclohexanecarboxylate

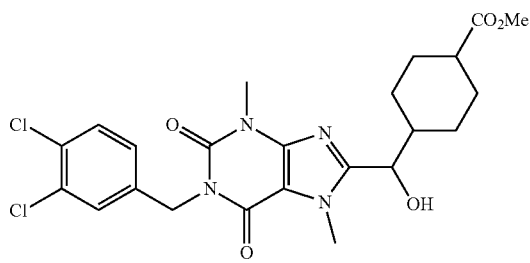 [SMILES: COC(=O)C1CCC(C(O)c2nc3c(c(=O)n(Cc4ccc(Cl)c(Cl)c4)c(=O)n3C)n2C)CC1]

To a solution of 1-[(3,4-dichlorophenyl)methyl]-3,7-dimethyl-purine-2,6-dione (2.00 g, 5.90 mmol, 1.00 eq) in THF (20 mL) was added LDA (821.13 mg, 7.67 mmol, 1.30 eq) dropwise at −78° C. The mixture was stirred at −78° C. for 0.5 h. A solution of methyl 4-formylcyclohexanecarboxylate (1.00 g, 5.90 mmol, 1.00 eq) in THF (20 mL) was added dropwise at −78° C. The mixture was stirred at −78° C. for another 0.5 h. The reaction was quenched with sat. NH$_4$Cl aq (3 mL). EA (20 mL) was added and the layers were separated. The organic fraction was washed with brine (10 mL), dried over Na$_2$SO$_4$ and concentrated. The crude product was purified by Prep-HPLC Method C. ESI: m/z 509.1/511.1 (M+H)$^+$.

4-((1-(3,4-dichlorobenzyl)-3,7-dimethyl-2,6-dioxo-2,3,6,7-tetrahydro-1H-purin-8-yl)(hydroxy)methyl)cyclohexanecarboxylic acid

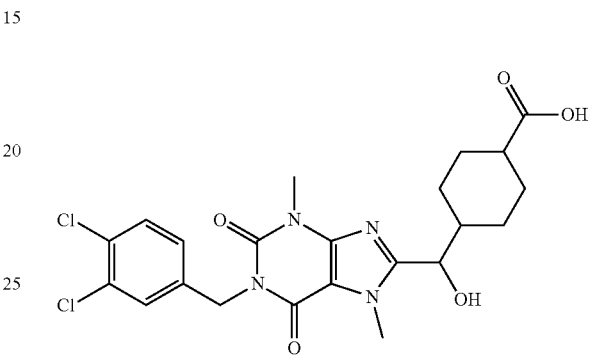

To a solution of methyl 4-[[1-[(3,4-dichlorophenyl)methyl]-3,7-dimethyl-2,6-dioxo-purin-8-yl]-hydroxy-methyl]cyclohexanecarboxylate (140.00 mg, 274.84 umol, 1.00 eq) in MeOH (2.00 mL) was added 2N NaOH (1.10 mmol, 4.00 eq). The reaction mixture was stirred at 15° C. for 40 hr. The pH of the mixture was adjusted to pH=5 with 2N HCl and extracted with EA (50 mL*3). The combined organic fractions were washed with brine (20 mL), dried over Na$_2$SO$_4$, and concentrated. The crude product was washed with MTBE (5 mL) and then filtered. The solid was dried to give the title compound. $^1$H NMR (400 MHz DMSO-$d_6$) δ 12.09 (br, 1H), 7.56-7.58 (d, J=8 Hz, 2H), 5.75 (br, 1H), 5.04 (s, 2H), 4.52 (m, 1H), 3.96 (s, 3H), 3.42 (s, 3H), 1.85-2.00 (m, 4H), 1.38-1.47 (m, 3H), 1.11-1.20 (m, 2H); ESI: m/z 495.2 (M+H)$^+$.

Example 271

8-(cyclopropylamino)-1-[(3,4-dichlorophenyl)methyl]-3,7-dimethyl-purine-2,6-dione

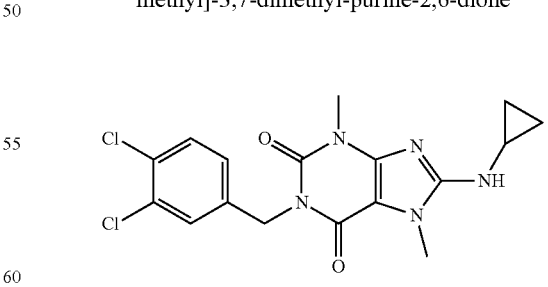

The title compound was synthesized in a similar fashion as described in Procedure 7A using 8-bromo-1-[(3,4-dichlorophenyl)methyl]-3,7-dimethyl-purine-2,6-dione and cyclopropanamine. The product was purified by prep-HPLC using Method A. $^1$H NMR (400 MHz, DMSO-$d_6$) δ 7.60-7.51 (m, 2H), 7.32-7.23 (m, 2H), 5.78-5.76 (m, 1H), 5.00 (s, 2H), 3.54 (s, 3H), 3.39 (s, 3H), 2.79-2.73 (m, 1H), 0.75-0.69 (m, 2H), 0.57-0.51 (m, 2H); ESI: m/z 394.1 (M+H)⁺.

Example 272

(±)-trans-4-[[1-[(3,4-dichlorophenyl)methyl]-3,7-dimethyl-2,6-dioxo-purin-8-yl]amino]cyclohexanecarboxylic acid

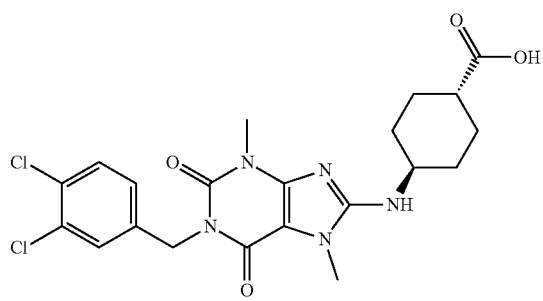 [SMILES: Cn1c(N[C@H]2CC[C@H](C(=O)O)CC2)nc2c1c(=O)n(Cc1ccc(Cl)c(Cl)c1)c(=O)n2C]

The title compound was synthesized in a similar fashion as described in Procedure 7A using 8-bromo-1-[(3,4-dichlorophenyl)methyl]-3,7-dimethyl-purine-2,6-dione and 4-aminocyclohexanecarboxylic acid. The product was purified by prep-HPLC (0.05% HCl-ACN). $^1$H NMR (400 MHz DMSO-$d_6$) δ 7.57-7.52 (m, 2H), 7.28-7.25 (m, 1H), 6.88-6.86 (m, 1H), 5.77 (s, 1H), 4.99 (s, 2H), 3.87 (m, 1H), 3.57 (s, 3H), 3.36 (s, 3H), 2.20-2.18 (m, 1H), 2.02-1.95 (m, 4H), 1.46-1.34 (m, 4H); ESI: m/z 480 (M+H)⁺.

Example 273

1-[(3,4-dichlorophenyl)methyl]-8-(2-methoxyethylamino)-3,7-dimethyl-purine-2,6-dione

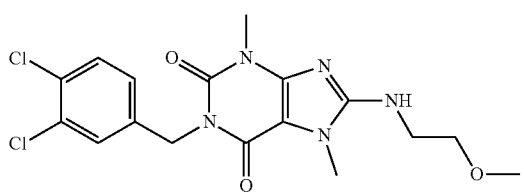 [SMILES: COCCNc1nc2c(c(=O)n(Cc3ccc(Cl)c(Cl)c3)c(=O)n2C)n1C]

The title compound was synthesized in a similar fashion as described in Procedure 7A using 8-bromo-1-[(3,4-dichlorophenyl)methyl]-3,7-dimethyl-purine-2,6-dione and 2-methoxyethanamine. The product was purified by prep-HPLC using Method A. $^1$H NMR (400 MHz, CD$_3$OD) δ 7.53-7.51 (m, 1H), 7.44-7.40 (m, 1H), 7.31-7.27 (m, 1H), 5.09-5.06 (m, 2H), 3.62 (s, 3H), 3.61-3.56 (m, 4H), 3.47 (s, 3H), 3.37 (s, 3H); ESI: m/z: 412.2 (M+H)⁺.

Example 274

N-[1-[(3,4-dichlorophenyl)methyl]-3,7-dimethyl-2,6-dioxo-purin-8-yl]acetamide

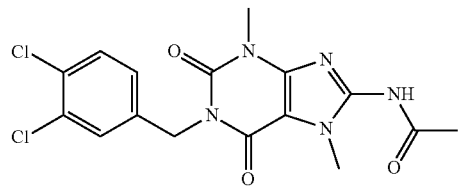 [SMILES: CC(=O)Nc1nc2c(c(=O)n(Cc3ccc(Cl)c(Cl)c3)c(=O)n2C)n1C]

To a mixture of 8-bromo-1-[(3,4-dichlorophenyl)methyl]-3,7-dimethyl-purine-2,6-dione (100.00 mg, 239.19 umol), acetamide (28.26 mg, 478.38 umol), $^t$BuONa (45.97 mg, 478.38 umol) and BINAP (2.98 mg, 4.78 umol) was added Pd$_2$(dba)$_3$ (4.38 mg, 4.78 umol) under N$_2$ atmosphere. The mixture was stirred at 120° C. for 12 h. The mixture was poured into ice-water (5 mL) and extracted with EA (5 mL*3). The combined organic fractions were dried over Na$_2$SO$_4$ and concentrated. The residue was purified by prep-HPLC using Method A. $^1$H NMR (400 MHz, CD$_3$OD) δ 7.56-7.53 (m, 1H), 7.42 (s, 1H), 7.34-7.30 (m, 1H), 5.13-5.19 (m, 2H), 3.78 (s, 3H), 3.49 (s, 3H), 2.20 (s, 3H); ESI: m/z 396.1 (M+H)⁺.

Example 275

1-(3,4-dichlorobenzyl)-8-((1R,3S)-3-(hydroxymethyl)cyclopentylamino)-3,7-dimethyl-1H-purine-2,6(3H,7H)-dione

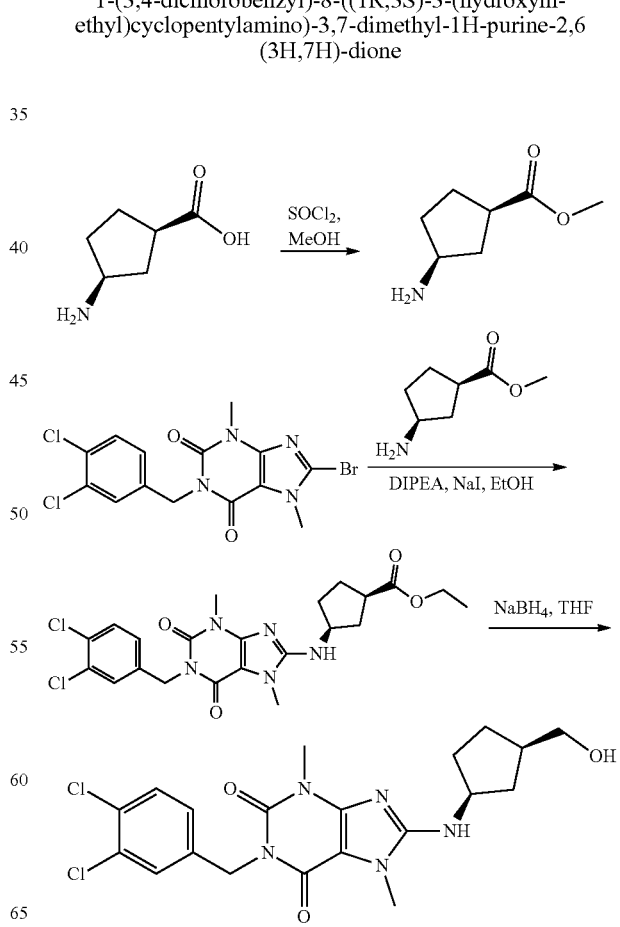

Methyl (1R,3S)-3-aminocyclopentane-1-carboxylate

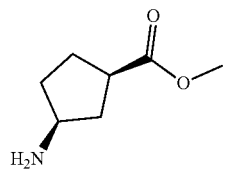

To a solution of (1R,3S)-3-aminocyclopentanecarboxylic acid (27.1 mmol, 3.5 g) in MeOH (35 mL) at 0° C. was added SOCl$_2$ (54.2 mmol, 6.4 g). The mixture was stirred at 75° C. for 16 h. The mixture was concentrated. The residue was suspended in DCM (30 mL) and ACN (30 mL) and treated with Na$_2$CO$_3$ (7.9 g, 75 mmol) and trimethylamine (3 mL). The mixture was stirred at room temperature for 16 h. The mixture was filtered and concentrated. The product was used in the next step without further purification. ESI: m/z 144.3 (m+1)$^+$.

(1R,3S)-Ethyl 3-(1-(3,4-dichlorobenzyl)-3,7-dimethyl-2,6-dioxo-2,3,6,7-tetrahydro-1H-purin-8-ylamino)cyclopentanecarboxylate

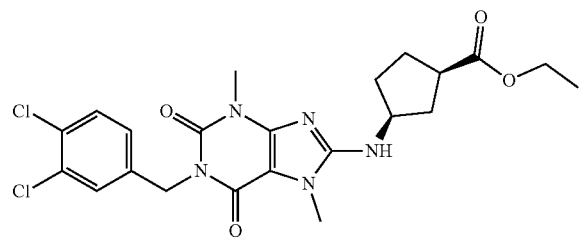 [SMILES: CCOC(=O)[C@@H]1CC[C@H](Nc2nc3c(c(=O)n(Cc4ccc(Cl)c(Cl)c4)c(=O)n3C)n2C)C1]

The title compound was synthesized in a similar fashion as described in Procedure 7A using (1R,3S)-ethyl 3-aminocyclopentanecarboxylate and 8-bromo-1-(3,4-dichlorobenzyl)-3,7-dimethyl-1H-purine-2,6(3H,7H)-dione. The crude product was purified by flash chromatography (PE/EA=1/1). ESI: m/z 494.2 (M+H)$^+$.

1-(3,4-Dichlorobenzyl)-8-((1R,3S)-3-(hydroxymethyl)cyclopentylamino)-3,7-dimethyl-1H-purine-2,6(3H,7H)-dione

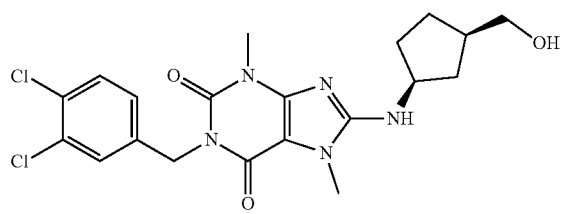 [SMILES: Cn1c(N[C@H]2CC[C@@H](CO)C2)nc2c1c(=O)n(Cc1ccc(Cl)c(Cl)c1)c(=O)n2C]

To a solution of (1R,3S)-ethyl 3-(1-(3,4-dichlorobenzyl)-3,7-dimethyl-2,6-dioxo-2,3,6,7-tetrahydro-1H-purin-8-ylamino)cyclopentanecarboxylate (0.42 mmol, 0.20 g) in THF (10 mL) was added NaBH$_4$ (1.67 mmol, 0.06 g). The mixture was stirred at 65° C. for 16 h. The mixture was diluted with water (40 mL) and extracted with EA (2*100 mL). The combined organic fractions were concentrated to give the crude product. The crude product was purified by Prep-HPLC using Method D (30-70% ACN). $^1$H NMR (400 MHz, CD$_3$OD) δ 7.48 (d, J=1.9 Hz, 1H), 7.33 (dd, J=8.3, 2.7 Hz, 1H), 7.25-7.23 (m, 1H), 4.97 (s, 2H), 4.23-4.20 (m, 1H), 3.55-3.52 (m, 5H), 3.42 (s, 3H), 2.27-2.18 (m, 2H), 2.01-1.98 (m, 1H), 1.78-1.75 (m, 1H), 1.64-1.58 (m, 2H), 1.33-1.30 (m, 1H); ESI: m/z 452.0 (M+H)$^+$.

Example 276

(1S,3R)-ethyl 3-(1-(3,4-dichlorobenzyl)-3,7-dimethyl-2,6-dioxo-2,3,6,7-tetrahydro-1H-purin-8-ylamino)cyclopentanecarboxylate

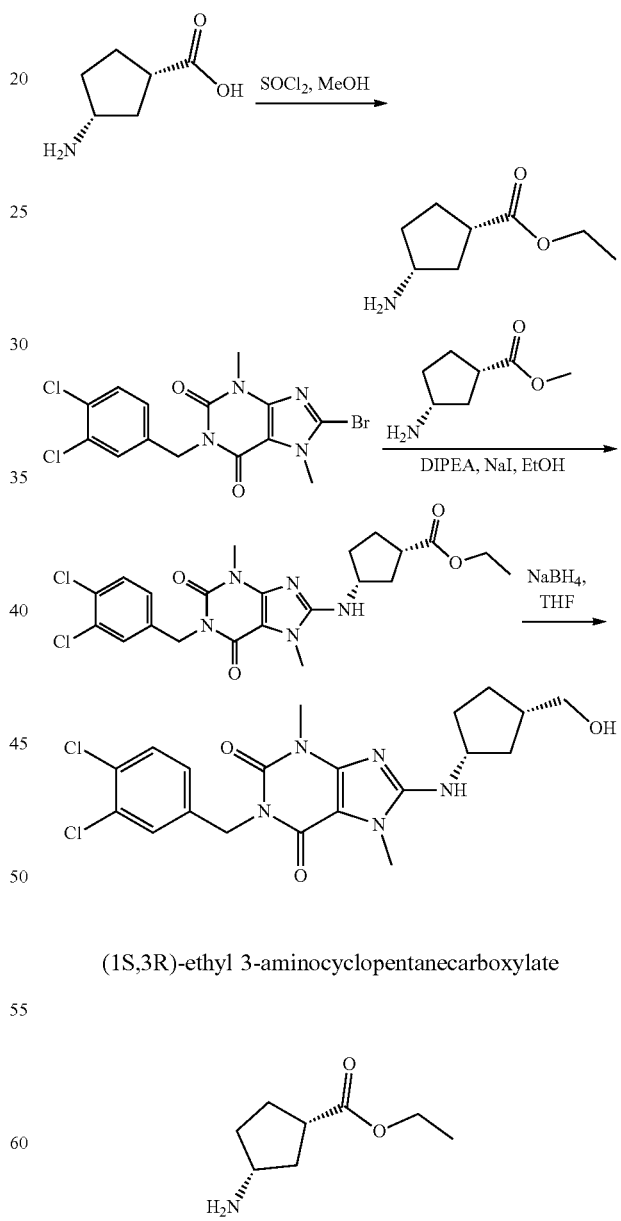

(1S,3R)-ethyl 3-aminocyclopentanecarboxylate

The title compound was synthesized in a similar fashion as (1R,3S)-ethyl 3-aminocyclopentanecarboxylate using ethanol; ESI: m/z 158.1 (M+H)$^+$.

261

(1S,3R)-ethyl 3-(1-(3,4-dichlorobenzyl)-3,7-dimethyl-2,6-dioxo-2,3,6,7-tetrahydro-1H-purin-8-ylamino)cyclopentanecarboxylate

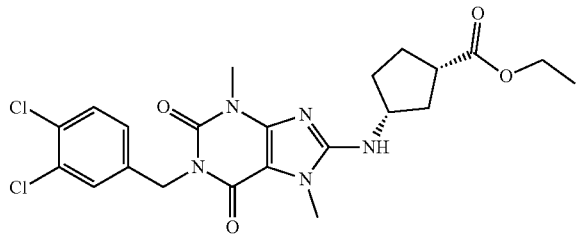 [SMILES: CCOC(=O)[C@H]1CC[C@@H](Nc2nc3c(c(=O)n(Cc4ccc(Cl)c(Cl)c4)c(=O)n3C)n2C)C1]

The title compound was synthesized in a similar fashion as (1S,3R)-ethyl 3-(1-(3,4-dichlorobenzyl)-3,7-dimethyl-2,6-dioxo-2,3,6,7-tetrahydro-1H-purin-8-ylamino)cyclopentanecarboxylate; ESI: m/z 494.2 (M+H)+.

262

1-(3,4-dichlorobenzyl)-8-((1R,3S)-3-(hydroxymethyl)cyclopentylamino)-3,7-dimethyl-1H-purine-2,6(3H,7H)-dione

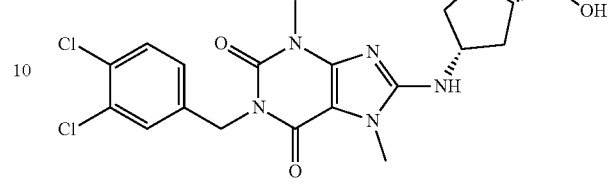

The title compound was synthesized in a similar fashion as Example 275. $^1$H NMR (400 MHz, CD$_3$OD) δ 7.52-7.49 (m, 1H), 7.45-7.34 (m, 1H), 7.29-7.27 (m, 1H), 5.05-5.03 (m, 2H), 4.26-4.24 (m, 1H), 3.59-3.57 (m, 3H), 3.54-3.52 (m, 2H), 3.47-3.44 (m, 3H), 2.24-2.20 (m, 2H), 2.08-1.97 (m, 1H), 1.80-1.75 (m, 1H), 1.72-1.52 (m, 2H), 1.33-1.30 (m, 1H); ESI: m/z 451.9 (M+H)+.

Example 277

3-(4-(1-(3,4-dichlorobenzyl)-3,7-dimethyl-2,6-dioxo-2,3,6,7-tetrahydro-1H-purin-8-ylamino)pyridin-2-yl)propanoic acid

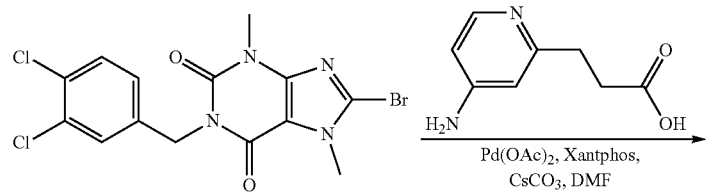

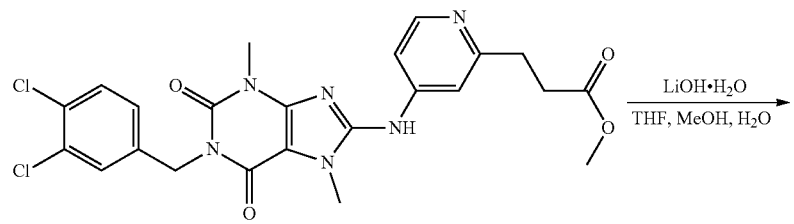

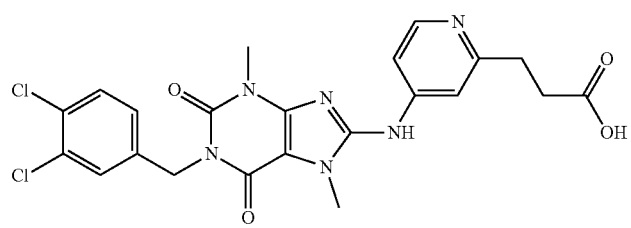

263

Methyl 3-(4-(1-(3,4-dichlorobenzyl)-3,7-dimethyl-2,6-dioxo-2,3,6,7-tetrahydro-1H-purin-8-ylamino)pyridin-2-yl)propanoate

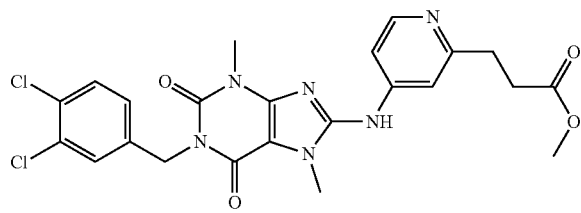 [SMILES: COC(=O)CCc1cc(Nc2nc3c(c(=O)n(Cc4ccc(Cl)c(Cl)c4)c(=O)n3C)n2C)ccn1]

The title compound was synthesized in a similar fashion as described in Procedure 8A using 8-bromo-1-(3,4-dichlorobenzyl)-3,7-dimethyl-1H-purine-2,6(3H,7H)-dione and methyl 3-(4-aminopyridin-2-yl)propanoate. The product was purified by reverse chromatography (C18, CH₃CN/H₂O=30/70). ESI: m/z: 517.0 (M+H)⁺.

3-(4-(1-(3,4-Dichlorobenzyl)-3,7-dimethyl-2,6-dioxo-2,3,6,7-tetrahydro-1H-purin-8-ylamino)pyridin-2-yl)propanoic acid

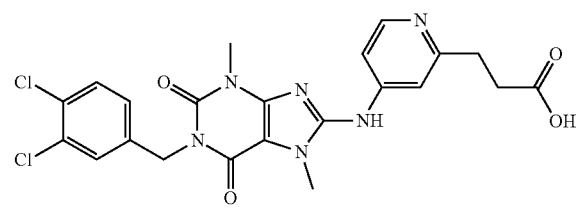 [SMILES: Cn1c(Nc2ccnc(CCC(=O)O)c2)nc2c1c(=O)n(Cc1ccc(Cl)c(Cl)c1)c(=O)n2C]

To a solution of methyl 3-(4-(1-(3,4-dichlorobenzyl)-3,7-dimethyl-2,6-dioxo-2,3,6,7-tetrahydro-1H-purin-8-ylamino)pyridin-2-yl)propanoate (150 mg, 0.29 mmol) in MeOH (2 mL) and water (2 mL), was added LiOH·H₂O (61 mg, 1.45 mmol). The mixture was stirred at 50° C. for 2 h. The mixture was cooled to room temperature and the pH was adjusted to 5~6 using 2 M HCl. The mixture was concentrated and the residue was purified by prep-thin layer chromatography (DCM/MeOH=5/1). ¹H NMR (400 MHz, DMSO-d₆) δ 8.26 (d, J=4.4 Hz, 1H), 7.59-7.51 (m, 4H), 7.30 (dd, J=1.6, 8.4 Hz, 1H), 5.04 (s, 2H), 3.81 (s, 3H), 3.46 (s, 3H), 2.91 (t, J=7.2 Hz, 2H), 2.64 (t, J=7.2 Hz, 2H); ESI: m/z 503.0 (M+H)⁺.

Example 278

1-[(3,4-dichlorophenyl)methyl]-3,7-dimethyl-8-(2,2,2-trifluoroethylamino)purine-2,6-dione

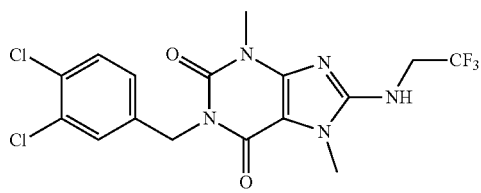 [SMILES: Cn1c(NCC(F)(F)F)nc2c1c(=O)n(Cc1ccc(Cl)c(Cl)c1)c(=O)n2C]

The title compound was synthesized in a similar fashion as described in Procedure 7A using 8-bromo-1-[(3,4-dichlorophenyl)methyl]-3,7-dimethyl-purine-2,6-dione and 2,2,2-trifluoroethanamine. The product was purified by prep-HPLC (column: Luna C18 (100*30) 5 u; liquid phase: [A-TFA/H₂O=0.075% v/v; B-MeOH]B %: 60%-80%, 12 min]) and prep-HPLC (column: Luna C18 (100*30) 5 u; liquid phase: [A-HCl/H₂O=0.04% v/v; B-ACN]B %: 43%-73%, 12 min]). ¹H NMR (400 MHz, CD₃OD) δ 7.52-7.50 (m, 1H), 7.43-7.39 (m, 1H), 7.30-7.26 (m, 1H), 5.08-5.05 (m, 2H), 4.20-4.12 (m, 2H), 3.66 (s, 3H), 3.46 (s, 3H); ESI: m/z 436.1 (M+H)⁺.

Example 279

(±)-trans-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

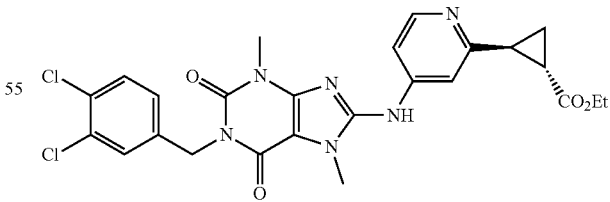

(±)-trans-ethyl 2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate The title compound was synthesized in a similar fashion as described in Procedure 8A using ethyl 2-(4-aminopyridin-2-yl)cyclopropanecarboxylate and 8-bromo-1-[(3,4-dichlorophenyl)methyl]-3,7-dimethyl-purine-2,6-dione. The product was purified by prep-TLC (DCM/MeOH=10/1). ES: m/z 543.2,545.2 (M+H)⁺.

(±)-trans-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

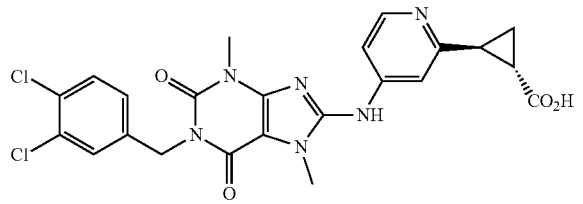 [SMILES: Cn1c(Nc2ccnc([C@H]3C[C@@H]3C(=O)O)c2)nc2c1c(=O)n(Cc1ccc(Cl)c(Cl)c1)c(=O)n2C]

A mixture of ethyl 2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate (114.00 mg, 209.79 umol) in MeOH (1.50 mL) and THF (1.50 mL) was added 1N NaOH (16.78 mg, 419.58 umol) dropwise at 10° C. The mixture was concentrated under reduced pressure at 45° C. The residue was diluted with water (10 mL) and stirred for 20 min. The aqueous phase was extracted with ethyl acetate (10 mL*3). The aqueous fraction was concentrated in vacuum. The pH was acidified to pH=1 (3N HCl). The mixture was filtered, and the solid was washed with water (5 mL), and dried under high vacuum. $^1$H NMR (400 MHz, DMSO-$d_6$) δ 8.28 (br. s., 1H), 7.66 (br. s., 1H), 7.54-7.60 (m, 2H), 7.30 (d, J=7.9 Hz, 1H), 5.04 (s, 2H), 3.82 (s, 3H), 3.46 (s, 3H), 1.97-2.07 (m, 1H), 1.46 (br. s., 2H); ESI: m/z 515.2 (M+H)$^+$.

Example 281

3-(2-(1-(3,4-dichlorobenzyl)-3,7-dimethyl-2,6-dioxo-2,3,6,7-tetrahydro-1H-purin-8-ylamino)pyridin-4-yl)propanoic acid

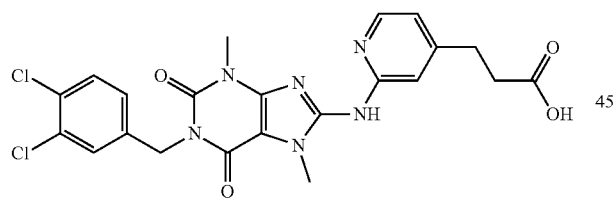

Methyl 3-(2-aminopyridin-4-yl)propanoate and 8-bromo-1-(3,4-dichlorobenzyl)-3,7-dimethyl-1H-purine-2,6(3H,7H)-dione were coupled in a similar fashion as described in Procedure 8A. The product was purified by flash chromatography (DCM/MeOH=9/1) to provide methyl 3-(2-(1-(3,4-dichlorobenzyl)-3,7-dimethyl-2,6-dioxo-2,3,6,7-tetrahydro-1H-purin-8-ylamino)pyridin-4-yl)propanoate; ESI: m/z 516.8 (M+H)$^+$. This product (0.1 mmol, 50 mg) and LiOH-H$_2$O (0.4 mmol, 16 mg) in MeOH (10 mL) and H$_2$O (5 mL) was heated to 40° C. and stirred for 3 h. The mixture was concentrated under reduced pressure. The aqueous layer was cooled to 5° C. and acidified to pH 7 using 3 N HCl. The solid was collected by filtration and dried under high vacuum. $^1$H NMR (400 MHz, DMSO-$d_6$) δ 8.10 (s, 1H), 7.70-7.56 (m, 3H), 7.31-7.28 (m, 1H), 6.84 (s, 1H), 5.03 (s, 2H), 3.75 (s, 3H), 3.45 (s, 3H), 2.84-2.80 (m, 2H), 2.62-2.58 (m, 2H); ESI: m/z 503.0 (M+H)$^+$.

Example 282

3-(6-(1-(3,4-dichlorobenzyl)-3,7-dimethyl-2,6-dioxo-2,3,6,7-tetrahydro-1H-purin-8-ylamino)pyridin-2-yl)propanoic acid

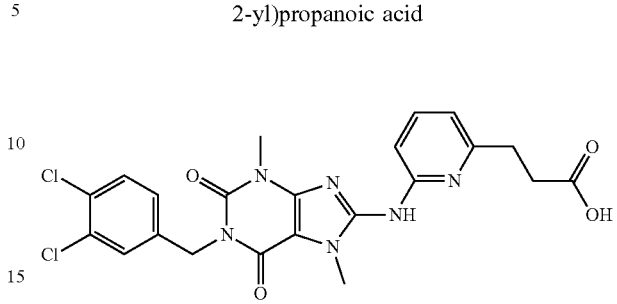

8-Bromo-1-(3,4-dichlorobenzyl)-3,7-dimethyl-1H-purine-2,6(3H,7H)-dione and methyl 3-(6-aminopyridin-2-yl)propanoate were coupled in a similar fashion as described in procedure 8A. The product was purified by flash chromatography (30~60% EA/PE) and prep-TLC (75% EA/PE) to provide methyl 3-(6-(1-(3,4-dichlorobenzyl)-3,7-dimethyl-2,6-dioxo-2,3,6,7-tetrahydro-1H-purin-8-ylamino)pyridin-2-yl)propanoate; ESI: m/z 517.1 (M+H)$^+$. A mixture of methyl 3-(6-(1-(3,4-dichlorobenzyl)-3,7-dimethyl-2,6-dioxo-2,3,6,7-tetrahydro-1H-purin-8-ylamino)pyridin-2-yl)propanoate (150 mg, 0.29 mmol) and lithium hydroxide monohydrate (61 mg, 1.45 mmol) in H$_2$O (0.5 mL), MeOH (2 mL) and THF (2 mL) was heated to 40° C. and stirred for 1 h. The reaction mixture was concentrated. The residue was dissolved in water (20 mL) and washed with EA (1*10 mL). The aqueous layer was acidified with HCl (0.5M) to PH=6~7 and the precipitate was collected and rinsed with water (10 mL) and dried under high vacuum to afford the title compound. $^1$H NMR (400 MHz, DMSO-$d_6$) δ 12.23 (br s, 1H), 9.90 (br s, 1H), 7.68-7.56 (m, 4H), 7.29 (d, J=6.8 Hz, 1H), 6.86 (d, J=6.8 Hz, 1H), 5.03 (s, 2H), 3.78 (s, 3H), 3.42 (s, 3H), 2.89 (t, J=7.2 Hz, 2H), 2.65 (t, J=7.2 Hz, 2H); ESI: m/z 503.0 (M+H)$^+$.

Example 283

3-(4-(1-(3,4-dichlorobenzyl)-3,7-dimethyl-2,6-dioxo-2,3,6,7-tetrahydro-1H-purin-8-ylamino)pyridin-2-yl)propanamide

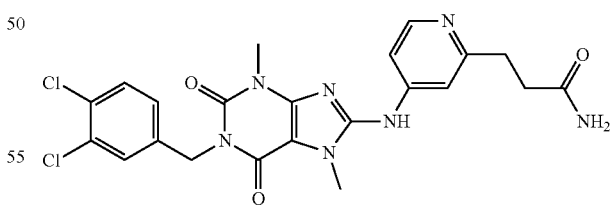

HATU (68 mg, 0.18 mmol) and DIEA (46 mg, 0.36 mmol) were added into DMF solution of 3-(4-(1-(3,4-dichlorobenzyl)-3,7-dimethyl-2,6-dioxo-2,3,6,7-tetrahydro-1H-purin-8-ylamino)pyridin-2-yl)propanoic acid (40 mg, 0.13 mmol) and the resulting reaction mixture was stirred at room temperature for several minutes. Then NH$_4$Cl (194 mg, 3.6 mmol) was added and the mixture was stirred for one hour. The mixture was filtered and the filtrate was purified by prep-HPLC. $^1$H NMR (400 MHz, DMSO-$d_6$) δ 9.63 (b, 1H), 8.28 (d, J=5.6 Hz, 1H), 7.58-7.54 (m, 3H), 7.48 (s, 1H), 7.33 (b, 1H), 7.28 (dd, J=8.4, 2.0 Hz, 1H), 6.76 (b, 1H), 5.03 (s, 2H), 3.81 (s, 3H), 3.45 (s, 3H), 2.89-2.82 (m, 2H), 2.47-2.45 (m, 2H). ESI: m/z 501.9 (M+H)+.

Example 284

(±)-trans-1-(3,4-dichlorobenzyl)-8-((2-(2-(hydroxymethyl)cyclopropyl)pyridin-4-yl)amino)-3,7-dimethyl-1H-purine-2,6(3H,7H)-dione

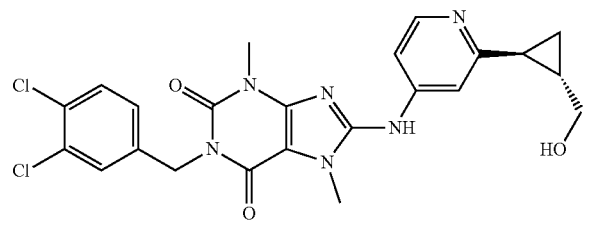 [SMILES: Cn1c(Nc2ccnc([C@H]3C[C@@H]3CO)c2)nc2c1c(=O)n(Cc1ccc(Cl)c(Cl)c1)c(=O)n2C]

To a solution of (±)-trans-ethyl 2-[4-[[1-[(3,4-dichlorophenyl)methyl]-3,7-dimethyl-2,6-dioxo-purin-8-yl]amino]-2-pyridyl]cyclopropanecarboxylate (100.00 mg, 184.03 umol) in dry THF (3.00 mL) was added LiAlH₄ (10.48 mg, 276.05 umol) at 0° C. After the addition the mixture was warmed slowly to 25° C. and stirred for 2 hr. The reaction was quenched with water (0.3 mL) at 0° C., and 15% NaOH (0.3 mL) was added. The mixture was stirred for 2 min and then diluted with EA (2 mL), and filtered through a pad of celite. The layers were separated and the aqueous fraction was extrated with EA (2 mL*3). The combined organic fractions were combined and dried over Na₂SO₄, filtered and concentrated to give a crude product which was purified by prep-TLC (DCM/Methanol=20/1,) to give the title compound. ¹H NMR (400 MHz, CD₃OD) δ 8.21 (d, J=6.5 Hz, 1H), 7.66-7.51 (m, 3H), 7.46 (d, J=8.5 Hz, 1H), 7.39-7.31 (m, 1H), 5.14 (s, 2H), 3.91 (s, 3H), 3.68-3.70 (m, 1H), 3.56 (s, 3H), 3.51-3.53 (m, 1H), 2.10-1.99 (m, 1H), 1.67-1.69 (m, 1H), 1.27-1.18 (m, 1H), 1.09-1.11 (m, 1H); ESI: m/z 501.2 (M+H)+.

Examples 337 and 338

1-(3,4-dichlorobenzyl)-8-((2-((1R,2R)-2-(hydroxymethyl)cyclopropyl)pyridin-4-yl)amino)-3,7-dimethyl-1H-purine-2,6(3H,7H)-dione and 1-(3,4-dichlorobenzyl)-8-((2-((1S,2S)-2-(hydroxymethyl)cyclopropyl)pyridin-4-yl)amino)-3,7-dimethyl-1H-purine-2,6(3H,7H)-dione

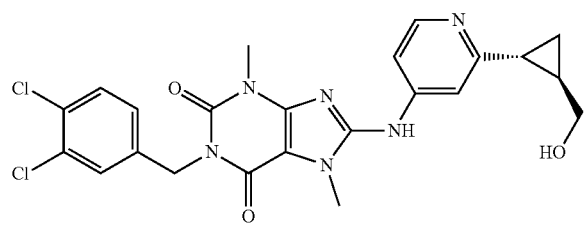

-continued

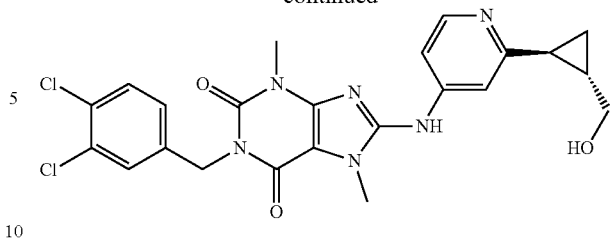

(±)-trans-1-(3,4-dichlorobenzyl)-8-((2-(2-(hydroxymethyl)cyclopropyl)pyridin-4-yl)amino)-3,7-dimethyl-1H-purine-2,6(3H,7H)-dione was separated into individual enantiomers by chiral-SFC using a CHIRALPAK®IC/SFC column (5μ, 250*30 mm) eluting with 45% IPA (0.1% NH₄OH) in CO₂.

Example 338: 1-(3,4-dichlorobenzyl)-8-((2-((1R,2R)-2-(hydroxymethyl)cyclopropyl)pyridin-4-yl)amino)-3,7-dimethyl-1H-purine-2,6(3H,7H)-dione or 1-(3,4-dichlorobenzyl)-8-((2-((1S,2S)-2-(hydroxymethyl)cyclopropyl)pyridin-4-yl)amino)-3,7-dimethyl-1H-purine-2,6(3H,7H)-dione (retention time 16.0 min, ee %: 100%), ¹H NMR (400 MHz, CD₃OD) δ 8.32 (d, J=7.0 Hz, 1H), 7.92 (d, J=5.0 Hz, 1H), 7.83 (br. s., 1H), 7.58 (s, 1H), 7.43-7.50 (m, 1H), 7.33-7.41 (m, 1H), 5.15 (s, 2H), 3.98 (s, 3H), 3.72-3.85 (m, 1H), 3.59 (s, 3H), 3.55 (dd, J=11.5, 6.5 Hz, 1H), 2.21 (dt, J=8.8, 4.6 Hz, 1H), 1.71-1.83 (m, 1H), 1.30-1.49 (m, 2H); ESI: m/z 501.2 (M+H)+.

Example 337: 1-(3,4-dichlorobenzyl)-8-((2-((1R,2R)-2-(hydroxymethyl)cyclopropyl)pyridin-4-yl)amino)-3,7-dimethyl-1H-purine-2,6(3H,7H)-dione or 1-(3,4-dichlorobenzyl)-8-((2-((1S,2S)-2-(hydroxymethyl)cyclopropyl)pyridin-4-yl)amino)-3,7-dimethyl-1H-purine-2,6(3H,7H)-dione (retention time: 12.6 min, ee %: 100). ¹H NMR (400 MHz, DMSO-d₆) δ 8.24 (d, J=5.7 Hz, 1H), 7.48-7.61 (m, 4H), 7.30 (d, J=7.9 Hz, 1H), 5.04 (s, 2H), 4.64 (br. s., 1H), 3.83 (s, 3H), 3.51 (br. s., 1H), 3.46 (s, 3H), 1.95 (br. s., 1H), 1.55 (br. s., 1H), 1.04-1.11 (m, 1H), 0.97 (br. s., 1H); ESI: m/z 501.2 (M+H)+.

Example 285

1-((4-chloro-1H-indol-2-yl)methyl)-3,7-dimethyl-8-(pyridin-4-ylamino)-1H-purine-2,6(3H,7H)-dione

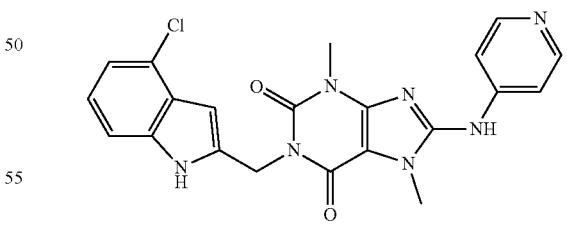

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and pyridin-4-amine hydrochloride. The product was purified by prep-HPLC using method B. ¹H NMR (400 MHz, CDCl₃) δ 9.22 (br s, 1H), 8.50 (d, J=5.5 Hz, 2H), 7.44 (d, J=5.3 Hz, 2H), 7.26-7.24 (m, 1H), 7.08 (d, J=4.4 Hz, 2H), 6.75 (s, 1H), 5.36 (s, 2H), 3.93 (s, 3H), 3.64 (s, 3H); ESI: m/z 436.7 (M+H)+.

Example 286

3-((1-(3,4-dichlorobenzyl)-3,7-dimethyl-2,6-dioxo-2,3,6,7-tetrahydro-1H-purin-8-yl)amino)benzoic acid

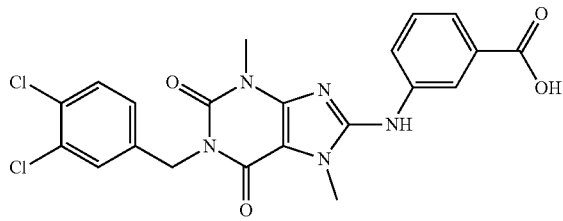 [SMILES: Cn1c(Nc2cccc(C(=O)O)c2)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione and ethyl 3-aminobenzoate were coupled in a similar fashion as described in Procedure 8B. The crude product was purified by prep-TLC (PE/EA=1:1) to afford ethyl 3-((1-(3,4-dichlorobenzyl)-3,7-dimethyl-2,6-dioxo-2,3,6,7-tetrahydro-1H-purin-8-yl)amino)benzoate: $^1$H NMR (400 MHz, CDCl$_3$) δ 8.04 (s, 1H) 7.73-7.68 (m, 2H) 7.50 (s, 1H) 7.38-7.28 (m, 3H) 6.22 (s, 1H) 5.06 (s, 2H) 4.35-4.29 (q, 2H) 3.78 (s, 3H) 3.50 (s, 3H) 1.35-1.31 (t, 3H). To this product (90.00 mg, 179.16 umol) in THF (5.00 mL) and MeOH (1.50 mL) was added 1N NaOH (400.00 uL). The mixture was stirred at 23° C. for 16 hr. The mixture was concentrated and redissolved in THF (5 mL) and 3N NaOH (200.00 uL) and then the mixture was stirred at 50° C. for 3 hr. The mixture was concentrated and the residue was acidified with 3N HCl until pH=1. The mixture was filtered and the solid was washed with H$_2$O (10 mL*3) and DCM (10 mL*2). The solid was dissolved in DMSO (1 mL) and purified by prep-HPLC using Method C. $^1$H NMR (400 MHz, DMSO-d6) δ 9.41 (s, 1H), 8.29 (s, 1H), 8.03 (m, 1H), 7.57-7.59 (m, 3H), 7.46-7.48 (m, 1H), 7.29-7.31 (m, 1H), 5.04 (s, 2H), 3.81 (s, 3H), 3.43 (s, 3H), 2.30 (s, 3H); ESI: m/z 474.1 (M+H)$^+$.

Example 287

2-(3-((1-(3,4-dichlorobenzyl)-3,7-dimethyl-2,6-dioxo-2,3,6,7-tetrahydro-1H-purin-8-yl)amino)phenyl)acetic acid

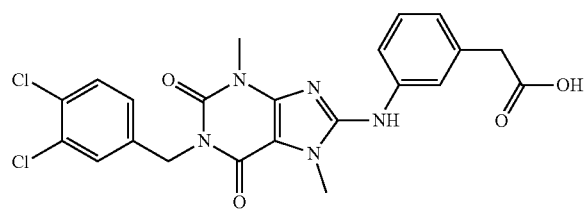 [SMILES: Cn1c(Nc2cccc(CC(=O)O)c2)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione and methyl 2-(3-aminophenyl)acetate were coupled in a similar fashion as described in procedure 8B. The product was purified by prep-TLC (PE/EA=1/1) to provide methyl 2-(3-((1-(3,4-dichlorobenzyl)-3,7-dimethyl-2,6-dioxo-2,3,6,7-tetrahydro-1H-purin-8-yl)amino)phenyl)acetate: $^1$H NMR (400 MHz, CDCl$_3$) δ 7.65 (s, 1H) 7.48-7.25 (m, 2H) 6.94-7.03 (m, 1H) 6.27 (s, 1H) 5.15 (s, 2H) 3.82 (s, 3H) 3.73 (s, 3H) 3.65 (s, 2H) 3.58 (s, 3H). To a solution of this product (90.00 mg, 179.16 umol) in THF (4.00 mL) was added 3N NaOH (200.00 uL). The mixture was stirred at 25° C. for 16 h and at 60° C. for 3 hr. The mixture was concentrated the aqueous residue was acidified with 3N HCl until pH=1. The mixture was filtered and washed with H$_2$O (10 mL*2). The solid was dissolved in DMSO (1 mL) and was purified by prep-HPLC using Method C (38-68% ACN). $^1$H NMR (400 MHz, DMSO-d$_6$) δ 3.43 (s, 3H), 3.55 (s, 2H), 3.79 (s, 3H), 5.04 (s, 2H), 6.84-6.93 (m, 1H), 7.24-7.33 (m, 2H), 7.57 (s, 3H), 7.61-7.67 (m, 1H), 9.15-9.25 (m, 1H); ESI: m/z 488.1/490.2 (M+H)$^+$.

Example 288

2-(4-((1-(3,4-dichlorobenzyl)-3,7-dimethyl-2,6-dioxo-2,3,6,7-tetrahydro-1H-purin-8-yl)amino)phenyl)acetic acid

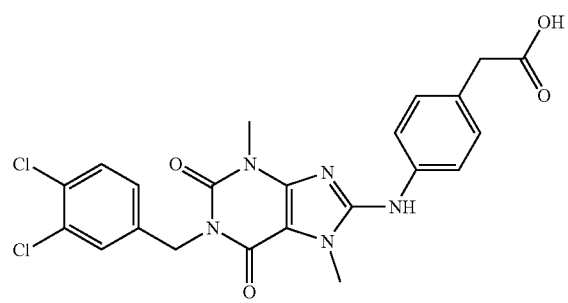 [SMILES: Cn1c(Nc2ccc(CC(=O)O)cc2)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione and ethyl 2-(4-aminophenyl)acetate were coupled in a similar fashion as described in procedure 8B. The product was purified by column chromatography (DCM/MeOH 100/0 to 20/1) to afford ethyl 2-(4-((1-(3,4-dichlorobenzyl)-3,7-dimethyl-2,6-dioxo-2,3,6,7-tetrahydro-1H-purin-8-yl)amino)phenyl)acetate: ESI: m/z 516.2 (M+H)$^+$. This product was treated with aqueous NaOH as described in Example 287. The product was purified by Prep-HPLC using Method C. $^1$H NMR (400 MHz, DMSO-d$_6$) δ 9.12 (s, 1H), 7.49-7.61 (m, 4H), 7.26 (d, J=8.4 Hz, 1H), 7.17 (d, J=8.4 Hz, 2H), 4.99 (s, 2H), 3.75 (s, 3H), 3.48 (s, 2H), 3.38 (s, 3H); ESI: m/z 488.1 (M+H)$^+$.

Example 289

(1R,3R)-3-(1-((1H-indol-2-yl)methyl)-3,7-dimethyl-2,6-dioxo-2,3,6,7-tetrahydro-1H-purin-8-ylamino)cyclobutanecarboxylic acid

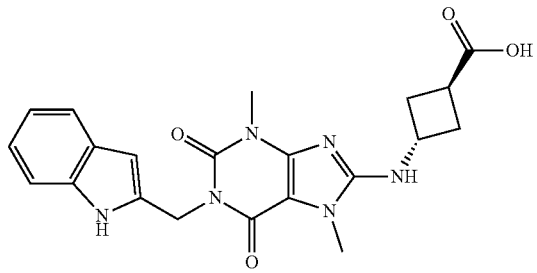 [SMILES: Cn1c(N[C@H]2C[C@H](C(=O)O)C2)nc2c1c(=O)n(Cc1cc3ccccc3[nH]1)c(=O)n2C]

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-1H-indole-1-carboxylate and (1R,3R)-ethyl 3-aminocyclobutanecarboxylate. The product was purified by prep-HPLC using Method D. $^1$H NMR (400 MHz, DMSO-$d_6$) δ 12.23 (s, 1H), 10.78 (s, 1H), 7.39 (d, J=7.9 Hz, 1H), 7.35-7.24 (m, 2H), 7.00 (t, J=7.5 Hz, 1H), 6.91 (t, J=7.3 Hz, 1H), 6.18 (s, 1H), 5.14 (s, 2H), 4.56-4.36 (m, 1H), 3.59 (s, 3H), 3.37 (s, 3H), 3.02-2.89 (m, 1H), 2.46-2.25 (m, 4H); ESI: m/z 423.1 (M+H)$^+$.

Example 290

1-((1H-pyrrolo[2,3-b]pyridin-2-yl)methyl)-3,7-dimethyl-1H-purine-2,6(3H,7H)-dione

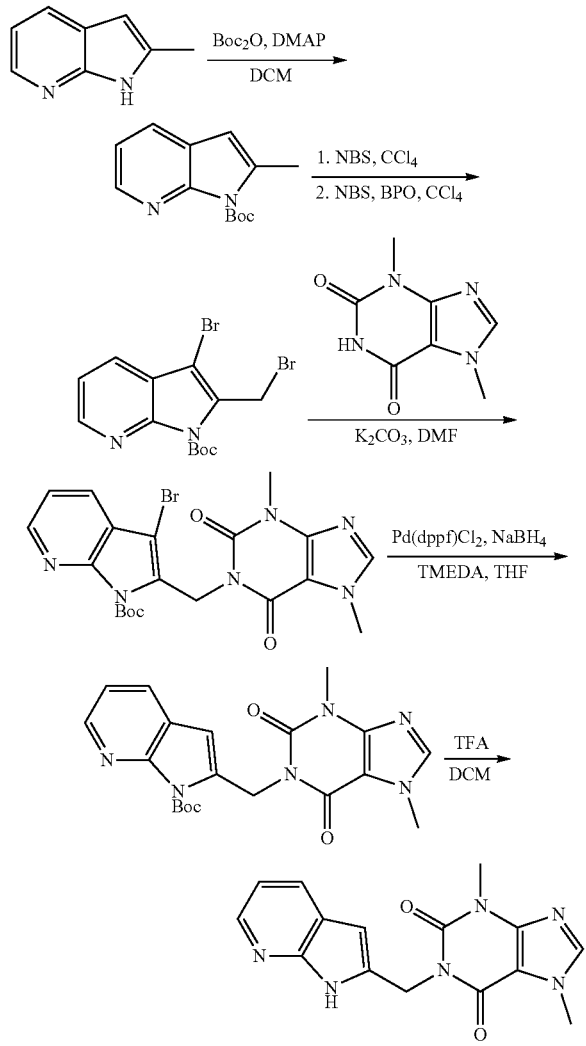

Tert-butyl 3-bromo-2-methyl-1H-pyrrolo[2,3-b]pyridine-1-carboxylate

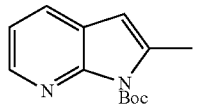 [SMILES: Cc1cc2cccnc2n1C(=O)OC(C)(C)C]

To a solution of 2-methyl-1H-pyrrolo[2,3-b]pyridine (3.0 g, 22.7 mmol) in DCM (30 mL), was added (Boc)$_2$O (5.2 g, 23.8 mmol) and DMAP (277 mg, 2.27 mmol). The reaction mixture was stirred at 30° C. for 3 h. The reaction mixture was concentrated and the residue was purified by flash chromatography (silica gel, PE/EA=10/1) to give the product. ESI: m/z 233.2 (M+H)$^+$.

tert-Butyl 3-bromo-2-(bromomethyl)-1H-pyrrolo[2,3-b]pyridine-1-carboxylate

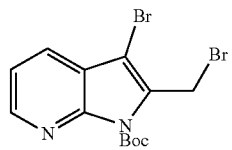 [SMILES: CC(C)(C)OC(=O)n1c(CBr)c(Br)c2cccnc21]

To a solution of tert-butyl 2-methyl-1H-pyrrolo[2,3-b]pyridine-1-carboxylate (3.0 g, 12.93 mmol) in CCl$_4$ (30 mL), was added NBS (2.42 g, 13.57 mmol). The reaction mixture was stirred at 30° C. for 15 h. The mixture was cooled, filtered and concentrated. The residue was purified by flash chromatography (PE/EA=8/1) to give tert-butyl 3-bromo-2-methyl-1H-pyrrolo[2,3-b]pyridine-1-carboxylate; ESI: m/z 255.0 (M+H−56)$^+$.

To a solution of tert-butyl 3-bromo-2-methyl-1H-pyrrolo[2,3-b]pyridine-1-carboxylate (2.4 g, 7.74 mmol) in CCl$_4$ (30 mL) was added BPO (5 mg) and NBS (1.44 g, 8.08 mmol). The reaction mixture was stirred at 85° C. for 2 h. The mixture was cooled, filtered and concentrated. The residue was purified by flash chromatography (PE/EA=8/1) to give the title compound.

tert-Butyl 3-bromo-2-((3,7-dimethyl-2,6-dioxo-2,3,6,7-tetrahydro-1H-purin-1-yl)methyl)-1H-pyrrolo[2,3-b]pyridine-1-carboxylate

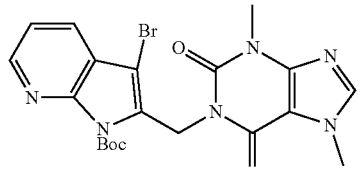

To a solution of tert-butyl 3-bromo-2-(bromomethyl)-1H-pyrrolo[2,3-b]pyridine-1-carboxylate (1.0 g, 2.57 mmol) in DMF (10 mL) was added 3,7-dimethyl-1H-purine-2,6(3H,7H)-dione (460 mg, 2.57 mmol) and K$_2$CO$_3$ (1.06 g, 7.71 mmol). The reaction mixture was stirred at 60° C. for 3 h. The reaction mixture was filtered and the filtrate was diluted with water (20 mL) and extracted with EA (2*30 mL). The combined organic layers were dried with Na₂SO₄, filtered and concentrated. The residue was purified by flash chromatography (PE/EA=4/1); ESI: m/z 389.0 (M+H−100)⁺.

tert-Butyl 2-((3,7-dimethyl-2,6-dioxo-2,3,6,7-tetrahydro-1H-purin-1-yl)methyl)-1H-pyrrolo[2,3-b]pyridine-1-carboxylate

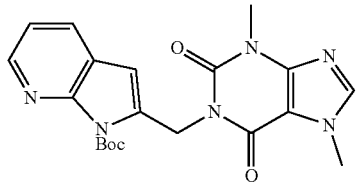 [SMILES: Cn1cnc2c1c(=O)n(Cc1cc3cccnc3[nH]1)c(=O)n2C]

To a solution of tert-butyl 3-bromo-2-((3,7-dimethyl-2,6-dioxo-2,3,6,7-tetrahydro-1H-purin-1-yl)methyl)-1H-pyrrolo[2,3-b]pyridine-1-carboxylate (100 mg, 0.2 mmol) in THF (15 mL), was added Pd(dppf)Cl₂·CH₂Cl₂ (16 mg, 0.02 mmol), TMEDA (5 mg, 0.04 mmol) and NaBH₄ (23 mg, 0.6 mmol). The mixture was stirred at room temperature for 16 h. The mixture was diluted with water (10 mL) and extracted with EA (3*30 mL). The combined organic fractions were dried with Na₂SO₄, filtered and concentrated. The compound was sued in the next step without further purification; ESI: m/z 411.3 (M+H)⁺.

1-((1H-pyrrolo[2,3-b]pyridin-2-yl)methyl)-3,7-dimethyl-1H-purine-2,6(3H,7H)-dione

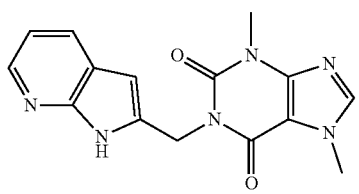

To a solution of tert-butyl 2-((3,7-dimethyl-2,6-dioxo-2,3,6,7-tetrahydro-1H-purin-1-yl)methyl)-1H-pyrrolo[2,3-b]pyridine-1-carboxylate (80 mg, 0.20 mmol) in DCM (1 mL), was added TFA (1 mL). After stirring at room temperature for 2 h, the mixture was concentrated. The residue was diluted with DCM (10 mL), and sat. NaHCO₃, and extracted with DCM (3*20 mL). The combined organic fractions were dried with Na₂SO₄, filtered and concentrated. The residue was purified by prep-HPLC using Method B. ¹H NMR (400 MHz, DMSO-d₆) δ 11.51 (s, 1H), 8.12 (dd, J=1.6, 4.8 Hz, 1H), 8.06 (s, 1H), 7.79 (dd, J=1.2, 8.0 Hz, 1H), 6.99 (dd, J=4.8, 7.6 Hz, 1H), 6.16 (s, 1H), 5.23 (s, 2H), 3.90 (s, 3H), 3.45 (s, 3H). ESI: m/z 311.2 (M+H)⁺.

Example 291

3-(3-(1-(3,4-dichlorobenzyl)-3,7-dimethyl-2,6-dioxo-2,3,6,7-tetrahydro-1H-purin-8-ylamino)phenyl)propanoic acid

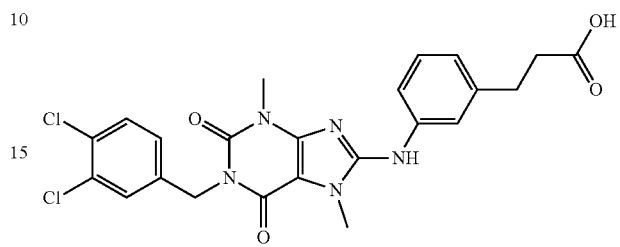

The title compound was synthesized in a similar fashion as described in Procedure 8A using 8-bromo-1-(3,4-dichlorobenzyl)-3,7-dimethyl-1H-purine-2,6(3H,7H)-dione and 3-(3-aminophenyl)propanoic acid. The product was purified by prep-HPLC using Shimadzu Shim-Pack PRC-ODS columns (20*250 mm, 150, two connected in series eluting with 45%-75% acetonitrile in water (0.05% TFA). ¹H NMR (400 MHz, CDCl₃) δ 7.50 (d, J=1.5 Hz, 1H), 7.28 (dd, J=8.4, 4.9 Hz, 2H), 7.18-7.14 (m, 2H), 6.86 (d, J=6.9 Hz, 1H), 6.59 (s, 1H), 5.05 (s, 2H), 3.68 (s, 3H), 3.47 (s, 3H), 2.88 (t, J=7.4 Hz, 2H), 2.62 (t, J=7.4 Hz, 2H); ESI: m/z 502.1 (M+H)⁺.

Example 292

3-(6-(1-(3,4-dichlorobenzyl)-3,7-dimethyl-2,6-dioxo-2,3,6,7-tetrahydro-1H-purin-8-ylamino)pyridin-2-yl)propanamide

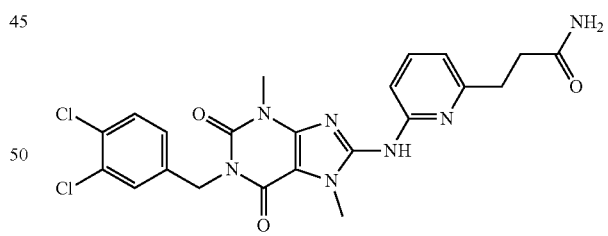

HATU (68 mg, 0.18 mmol) and DIEA (46 mg, 0.36 mmol) were added into a DMF solution of 3-(6-(1-(3,4-dichlorobenzyl)-3,7-dimethyl-2,6-dioxo-2,3,6,7-tetrahydro-1H-purin-8-ylamino)pyridin-2-yl)propanoic acid (60 mg, 0.12 mmol) and the resulting reaction mixture was stirred at room temperature for several minutes. Then NH₄Cl (194 mg, 3.6 mmol) was added. After 1 h the mixture was filtered and the filtrate was purified by prep-HPLC. ¹H NMR (400 MHz, DMSO-d₆) δ 9.86 (b, 1H), 7.67-7.64 (m, 2H), 7.58-7.55 (m, 2H), 7.31-7.28 (m, 2H), 6.85 (d, J=6.4 Hz, 1H), 6.77 (b, 1H), 5.03 (s, 2H), 3.78 (s, 3H), 3.42 (s, 3H), 2.88-2.84 (m, 2H), 2.49-2.44 (m, 2H); ESI: m/z 502.1 (M+H)⁺.

Example 293

1-(3,4-dichlorobenzyl)-8-(6-(3-hydroxypropyl)pyridin-2-ylamino)-3,7-dimethyl-1H-purine-2,6(3H,7H)-dione

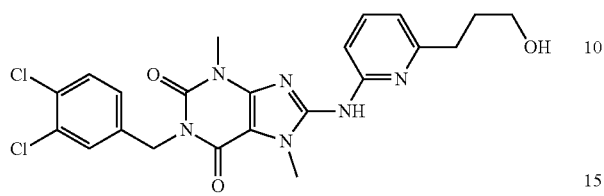

To a suspension of methyl 3-(6-(1-(3,4-dichlorobenzyl)-3,7-dimethyl-2,6-dioxo-2,3,6,7-tetrahydro-1H-purin-8-ylamino)pyridin-2-yl)propanoate (140 mg, 0.27 mmol) in MeOH (3 mL) and THF (3 mL) was added NaBH$_4$ (204 mg, 5.4 mmol) at 0° C. over 30 min. The mixture was warmed to 25° C. and stirred for 48 h. The reaction mixture was poured into water (40 mL) and extracted with EA (2*30 mL). The combined organic fractions were washed with brine (1*50 mL), dried over Na$_2$SO$_4$, concentrated and purified by flash chromatography (100% EA). $^1$H NMR (400 MHz, DMSO-d$_6$) δ 9.86 (br s, 1H), 7.68-7.55 (m, 4H), 7.31-7.28 (m, 1H), 6.84 (s, 1H), 5.03 (s, 2H), 4.50-4.48 (m, 1H), 3.38 (s, 3H), 3.46-3.40 (m, 5H), 2.68 (t, J=7.6 Hz, 2H), 1.85-1.74 (m, 2H); ESI: m/z 489.1 (M+H)$^+$.

Example 294

3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid

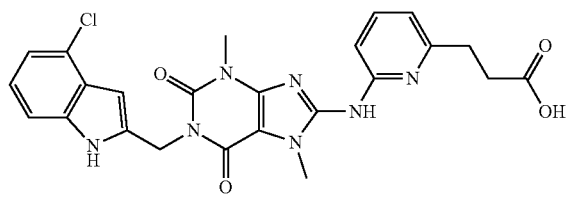 [SMILES: Cn1c(Nc2cccc(CCC(=O)O)n2)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and methyl 3-(6-aminopyridin-2-yl)propanoate were coupled in a similar fashion as described in Procedure 8A. The product was purified by flash chromatography (30~70% EA/PE) to provide methyl 3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoate; ESI: m/z 522.1 (M+H)$^+$. A mixture of this product (155 mg, 0.30 mmol) and lithium hydroxide monohydrate (38 mg, 0.90 mmol) in H$_2$O (0.5 mL), MeOH (2 mL) and THF (2 mL) was heated to 40° C. and stirred for 1 h. The reaction mixture was concentrated and dissolved in water (20 mL) and washed with EA (1*10 mL). The aqueous layer was acidified with HCl (0.5M) to PH=6-7 and the precipitate was collected and rinsed with water (10 mL). The residue was triturated with EA/MeOH (10 mL, 10:1 v/v) to provide the title compound. $^1$H NMR (400 MHz, DMSO-d$_6$) δ 12.16 (br s, 1H), 11.27 (s, 1H), 9.81 (br s, 1H), 7.67-7.61 (m, 2H), 7.35-7.31 (m, 1H), 7.04-7.00 (m, 2H), 6.87-6.85 (m, 1H), 6.28 (s, 1H), 5.21 (s, 2H), 3.80 (s, 3H), 3.45 (s, 3H), 2.89 (t, J=7.6 Hz, 2H), 2.66 (t, J=7.6 Hz, 2H). ESI: m/z 508.2 (M+H)$^+$.

Example 295

1-((1H-indol-2-yl)methyl)-8-((1R,3R)-3-(hydroxymethyl)cyclobutylamino)-3,7-dimethyl-1H-purine-2,6(3H,7H)-dione

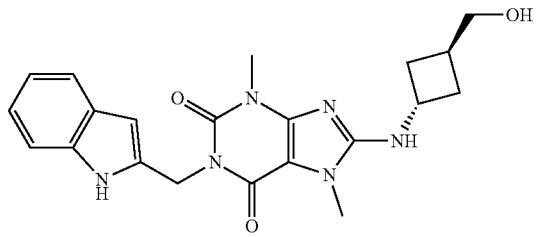 [SMILES: Cn1c(N[C@H]2C[C@H](CO)C2)nc2c1c(=O)n(Cc1cc3ccccc3[nH]1)c(=O)n2C]

A mixture of (1R,3R)-3-(1-((1H-indol-2-yl)methyl)-3,7-dimethyl-2,6-dioxo-2,3,6,7-tetrahydro-1H-purin-8-ylamino)cyclobutanecarboxylic acid (100 mg, 0.236 mmol) in THF (5 mL) was added BH$_3$/THF (1M in THF) (0.5 mL). The reaction mixture was stirred at stirred at rt for 0.5 h. The resulting solution was concentrated and purified by prep-HPLC Method B (34-64% ACN). $^1$H NMR (400 MHz, DMSO-d$_6$) δ 10.77 (s, 1H), 7.39 (d, J=7.9 Hz, 1H), 7.33 (d, J=8.2 Hz, 1H), 7.21 (d, J=7.3 Hz, 1H), 7.00 (t, J=7.2 Hz, 1H), 6.92 (t, J=7.4 Hz, 1H), 6.18 (s, 1H), 5.14 (s, 2H), 4.59 (t, J=5.3 Hz, 1H), 4.39-4.28 (m, 1H), 4.14-4.03 (m, 1H), 3.59 (s, 3H), 3.53-3.44 (m, 2H), 3.37 (s, 3H), 2.20-2.02 (m, 4H); ESI: m/z 409.1 (M+H)$^+$.

Example 296

(±)-trans-2-(4-((1-(3,4-Dichlorobenzyl)-3,7-dimethyl-2,6-dioxo-2,3,6,7-tetrahydro-1H-purin-8-yl)amino)pyridin-2-yl)cyclopropanecarboxamide

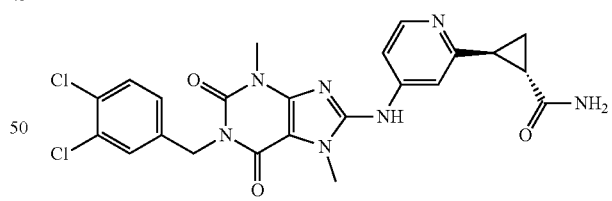

A suspension of (±)-trans-ethyl 2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate (100.00 mg, 184.03 umol, 1.00 eq) in NH$_3$ (g) in MeOH (5.00 mL) was sealed in a tube and heated to 100° C. for 18 hr. Additional NH$_3$ in MeOH (5.00 mL) was added and the mixture was heated to 100° C. for 48 h. The mixture was concentrated to give a crude product which was purified by prep-HPLC (column: Waters Xbridge 150*25 5 u; liquid phase: [A-HCl/H$_2$O=0.04% v/v; B-ACN]B %: 25%-55%, 12 min]). $^1$H NMR (400 MHz, CD$_3$OD) δ 8.36 (d, J=6.53 Hz, 1H), 7.94 (br. s., 1H), 7.85 (br. s., 1H), 7.59 (d, J=1.51 Hz, 1H), 7.47 (d, J=8.03 Hz, 1H), 7.34-7.41 (m, 1H), 5.16

(s, 2H), 3.98 (s, 3H), 3.60 (s, 3H), 2.67-2.72 (m, 1H), 2.25-2.31 (m, 1H), 1.76-1.82 (m, 1H), 1.57-1.66 (m, 1H); ESI: m/z 514.2 (M+H)+.

Example 297

4-[[1-(1H-indol-2-ylmethyl)-3,7-dimethyl-2,6-dioxo-purin-8-yl]amino]benzoic acid

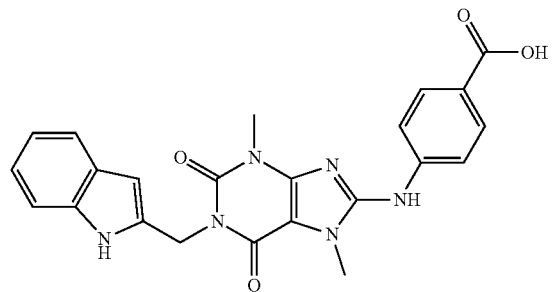 [SMILES: Cn1c(Nc2ccc(C(=O)O)cc2)nc2c1c(=O)n(Cc1cc3ccccc3[nH]1)c(=O)n2C]

The title compound was synthesized in a similar fashion as Example 294 using tert-butyl 2-[(8-bromo-3,7-dimethyl-2,6-dioxo-purin-1-yl)methyl]indole-1-carboxylate and methyl 4-aminobenzoate. The product was purified by Prep-HPLC using Method C (20-70% B). ¹H NMR (400 MHz, DMSO-d₆) δ 12.54-12.66 (m, 1H), 10.80-10.88 (m, 1H), 9.52-9.59 (m, 1H), 7.88-7.95 (m, 2H), 7.74-7.83 (m, 2H), 7.39-7.46 (m, 1H), 7.30-7.37 (m, 1H), 6.99-7.07 (m, 1H), 6.91-6.96 (m, 1H), 6.21-6.26 (m, 1H), 5.19-5.23 (m, 1H), 3.85 (s, 1H), 3.48 (s, 1H); ESI: m/z 445.2 (M+H)+.

Example 298

1-(3,4-dichlorobenzyl)-8-((4-(hydroxymethyl)phenyl)amino)-3,7-dimethyl-3,7-dihydro-1H-purine-2,6-dione

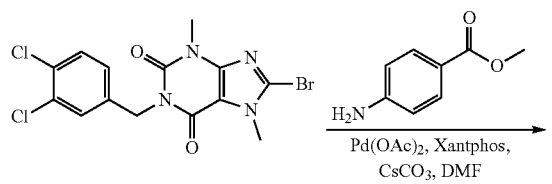

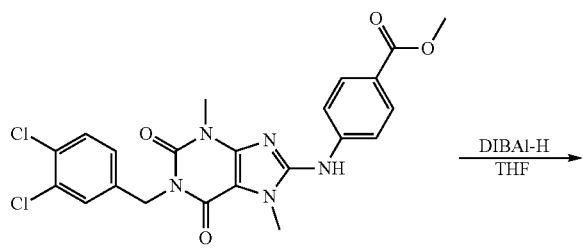

Methyl 4-[[1-[(3,4-dichlorophenyl)methyl]-3,7-dimethyl-2,6-dioxo-purin-8-yl]amino]benzoate

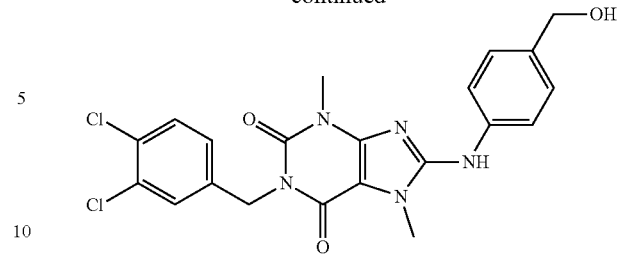

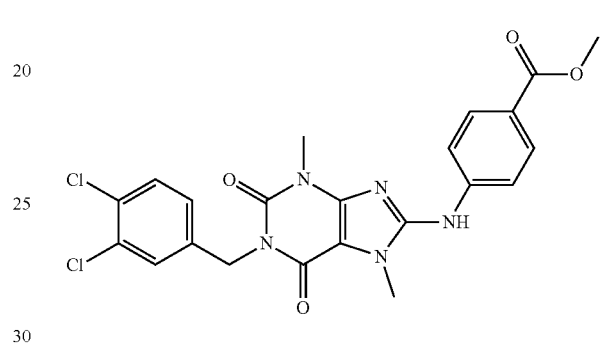

The title compound was synthesized in a similar fashion as described in Procedure 8B using 8-bromo-1-[(3,4-dichlorophenyl)methyl]-3,7-dimethyl-purine-2,6-dione and methyl 4-aminobenzoate. The product was purified by column chromatography (PE/EA from 20/1 to 1/5 to DCM/MeOH=20/1). ¹H NMR (400 MHz, CDCl₃) δ 8.37 (s, 1H), 7.92-7.94 (m, 2H), 7.59-7.61 (m, 2H), 7.51 (s, 1H), 7.26-7.28 (m, 2H), 7.23 (m, 1H), 5.06 (s, 2H), 3.78-3.83 (s, 6H), 3.51 (s, 3H).

1-(3,4-dichlorobenzyl)-8-((4-(hydroxymethyl)phenyl)amino)-3,7-dimethyl-3,7-dihydro-1H-purine-2,6-dione

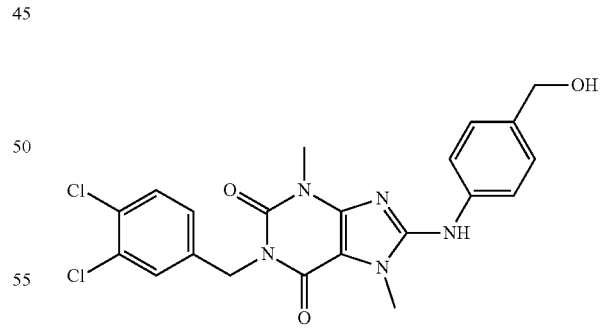

To a solution of methyl 4-[[1-[(3,4-dichlorophenyl)methyl]-3,7-dimethyl-2,6-dioxo-purin-8-yl]amino]benzoate (350.00 mg, 716.74 umol) in toluene (4.00 mL) at −40° C. under N₂ atmosphere was added DIBAL-H (1 M, 2.15 mL). The mixture was stirred at −40° C. for 0.5 hr. Then the mixture was warmed to 20° C. for 3 hr. The reaction was quenched with KHSO₄ (0.35M, 2 mL) at −20° C., then warmed to 20° C. The resulting mixture was filtered through celite. The filtrate was extracted with EA (5 mL*3). The combined organic fractions were dried over Na$_2$SO$_4$ and concentrated. The residue was purified by prep-HPLC using Method C $^1$H NMR (400 MHz, CD$_3$OD) δ 7.66-7.61 (m, 2H), 7.58-7.56 (m, 1H), 7.48-7.44 (m, 1H), 7.36-7.29 (m, 3H), 5.13 (s, 2H), 4.63-4.55 (m, 2H), 3.85 (s, 3H), 3.54 (s, 3H). ESI: m/z 460.2 (M+H)$^+$.

Example 299

(±)-trans-2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

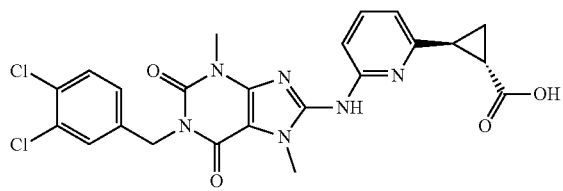 [SMILES: Cn1c(Nc2cccc([C@H]3C[C@@H]3C(=O)O)n2)nc2c1c(=O)n(Cc1ccc(Cl)c(Cl)c1)c(=O)n2C]

8-Bromo-1-[(3,4-dichlorophenyl)methyl]-3,7-dimethyl-purine-2,6-dione and trans-ethyl 2-(6-aminopyridin-2-yl)cyclopropanecarboxylate were coupled in a similar fashion as described in Procedure 8B to afford (±)-trans-ethyl 2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate. The ethyl ester was hydrolyzed in a similar fashion as described in Example 294 using sodium hydroxide. The product was purified by prep-HPLC using Method C to afford the title compound. $^1$H NMR (400 MHz, DMSO-d$_6$) δ 9.75 (m, 1H), 7.56-7.66 (m, 4H), 7.29-7.32 (m, 1H), 7.090-7.03 (m, 1H), 5.04 (s, 2H), 3.79 (s, 3H), 3.43 (s, 3H), 2.55 (s, 1H), 2.02-2.05 (m, 1H), 1.41-1.49 (m, 2H); ESI: m/z 515.2 (M+H)$^+$.

Examples 300 and 301

(1R,2R)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid and (1S,2S)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

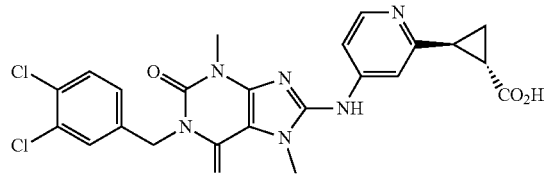

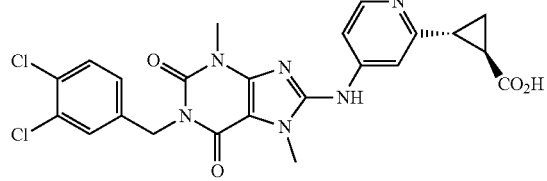

(±)-trans-2-(4-((1-(3,4-Dichlorobenzyl)-3,7-dimethyl-2,6-dioxo-2,3,6,7-tetrahydro-1H-purin-8-yl)amino)pyridin-2-yl)cyclopropanecarboxylic acid (140 mg) was separated into single isomers by chiral-SFC using a CHIRALPAK® AD-H/SFC column eluting with 35% MeOH (0.1% NH$_4$OH) in CO$_2$.

Example 300

(1R,2R)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid or (1S,2S)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid (retention time: 8.2 min.); $^1$H NMR (400 MHz, DMSO-d$_6$) δ 8.24 (d, J=6.0 Hz, 1H), 7.64 (br. s., 1H), 7.54-7.61 (m, 2H), 7.49 (d, J=4.5 Hz, 1H), 7.30 (d, J=8.0 Hz, 1H), 5.04 (s, 2H), 3.82 (s, 3H), 3.47 (s, 3H), 2.38-2.44 (m, 1H), 1.98 (br. s., 1H), 1.41 (br. s., 2H); ESI: m/z 515.2 (M+H)$^+$.

Example 301

(1S,2S)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid or (1R,2R)-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid (retention time 11.5 min); $^1$H NMR (400 MHz, DMSO-d$_6$) δ 8.44 (d, J=7.0 Hz, 1H), 7.90 (br. s., 1H), 7.81 (br. s., 1H), 7.55-7.64 (m, 2H), 7.31 (d, J=8.5 Hz, 1H), 5.06 (s, 2H), 3.91 (s, 3H), 3.48 (s, 4H), 2.76 (br. s., 1H), 2.20 (br. s., 1H), 1.53-1.71 (m, 2H); ESI: m/z 515.2 (M+H)$^+$.

Example 302

1-((4-chloro-1H-indol-2-yl)methyl)-3,7-dimethyl-8-(pyridin-2-ylamino)-1H-purine-2,6(3H, 7H)-dione

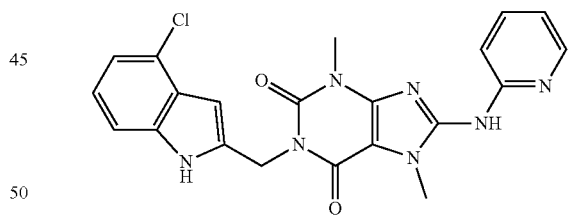

tert-butyl 4-chloro-2-((3,7-dimethyl-2,6-dioxo-8-(pyridin-2-ylamino)-2,3,6,7-tetrahydro-1H-purin-1-yl)methyl)-1H-indole-1-carboxylate was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and pyridin-2-amine. The product was purified by flash chromatography (EA/PE=2/1); ESI: m/z 536.1 (M+H)$^+$. tert-Butyl 4-chloro-2-((3,7-dimethyl-2,6-dioxo-8-(pyridin-2-ylamino)-2,3,6,7-tetrahydro-1H-purin-1-yl)methyl)-1H-indole-1-carboxylate (0.15 mmol, 80 mg) in DCM (2 mL) was treated with TFA (2 mL). The reaction mixture was stirred at 30° C. for 3 h. The reaction mixture was concentrated and purified by Prep-HPLC using method D. $^1$H NMR (400 MHz, DMSO-d$_6$) δ 11.26 (s, 1H), 9.95 (br s, 1H), 8.19 (br s, 1H), 7.74 (br s, 1H), 7.34-7.32 (m, 1H), 7.02-7.00 (m, 3H), 6.27 (s, 1H), 5.20 (s, 2H), 3.88 (s, 3H), 3.46 (s, 3H); ESI: m/z 436.1 (M+H)⁺.

Example 303

4-(1-(3,4-dichlorobenzyl)-3,7-dimethyl-2,6-dioxo-2,3,6,7-tetrahydro-1H-purin-8-ylamino)picolinic acid

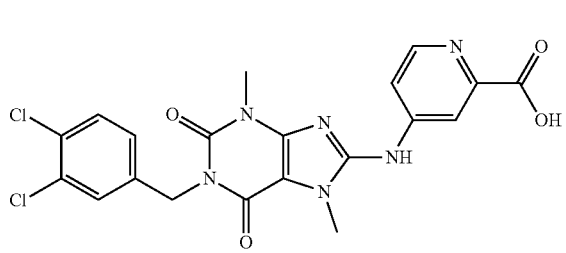 [SMILES: Cn1c(Nc2ccnc(C(=O)O)c2)nc2c1c(=O)n(Cc1ccc(Cl)c(Cl)c1)c(=O)n2C]

8-Bromo-1-(3,4-dichlorobenzyl)-3,7-dimethyl-1H-purine-2,6(3H,7H)-dione and methyl 4-aminopicolinate were coupled in a similar fashion as described in Procedure 8A to afford methyl 4-(1-(3,4-dichlorobenzyl)-3,7-dimethyl-2,6-dioxo-2,3,6,7-tetrahydro-1H-purin-8-ylamino)picolinate; ESI: m/z 489. A mixture of methyl 4-(1-(3,4-dichlorobenzyl)-3,7-dimethyl-2,6-dioxo-2,3,6,7-tetrahydro-1H-purin-8-ylamino)picolinate (120 mg, 0.25 mmol), LiOH·H₂O (30 mg, 1.23 mmol) in THF (10 mL) and H₂O (2 mL) was stirred at rt. overnight. The mixture was concentrated and then diluted with water (20 mL) and filtered. The solid was washed with water (20 mL) and recrystallized from DMSO. ¹H NMR (400 MHz, DMSO-d₆) δ 8.59-8.14 (m, 2H), 7.93 (m, 1H), 7.44 (m, 4H), 5.07 (s, 2H), 3.85 (s, 3H), 3.48 (s, 3H); ESI: m/z 475.0 (M+H)⁺.

Example 304

3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanamide

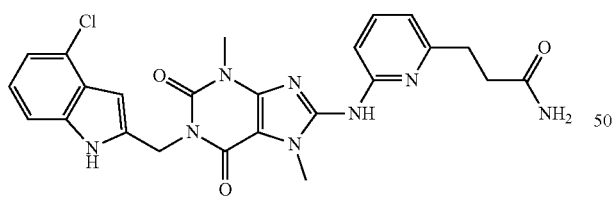

A mixture of 3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid (80 mg, 0.16 mmol), NH₄Cl (128 mg, 2.4 mmol), HATU (73 mg, 0.19 mmol) and DIEA (62 mg, 0.48 mmol) in DMF (3 mL) was stirred for 16 h at 25° C. The reaction mixture was poured into water (30 mL) and the precipitate was collected, dried in vacuo, and purified by flash chromatography (10% MeOH/DCM). ¹H NMR (400 MHz, DMSO-d₆) δ 11.27 (br s, 1H), 9.86 (br s, 1H), 7.67-7.63 (m, 2H), 7.35-7.30 (m, 2H), 7.05-6.98 (m, 2H), 6.88-6.77 (m, 2H), 6.28 (s, 1H), 5.21 (s, 2H), 3.80 (s, 3H), 3.46 (s, 3H), 2.87 (t, J=7.6 Hz, 2H), 2.46 (t, J=7.6 Hz, 2H); ESI: m/z 507.1 (M+H)⁺.

Example 305

1-((4-chloro-1H-indol-2-yl)methyl)-8-((1R,3R)-3-(hydroxymethyl)cyclobutylamino)-3,7-dimethyl-1H-purine-2,6(3H,7H)-dione

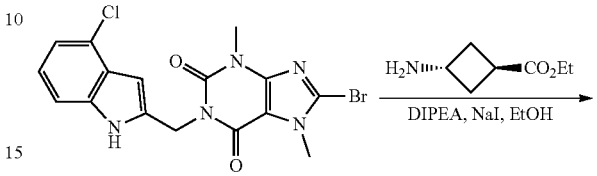

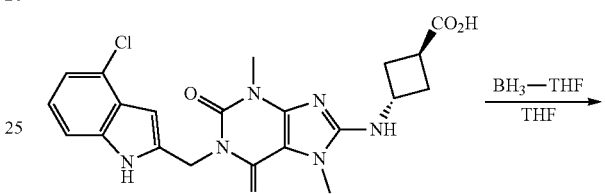

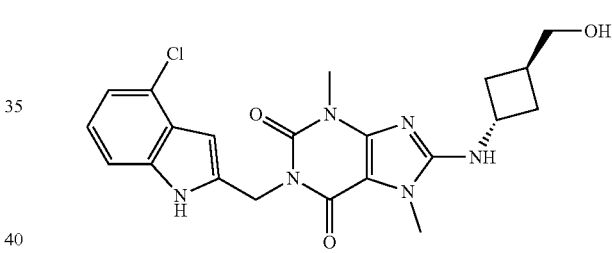

(1R,3R)-3-(1-((4-chloro-1H-indol-2-yl)methyl)-3,7-dimethyl-2,6-dioxo-2,3,6,7-tetrahydro-1H-purin-8-ylamino)cyclobutanecarboxylic acid

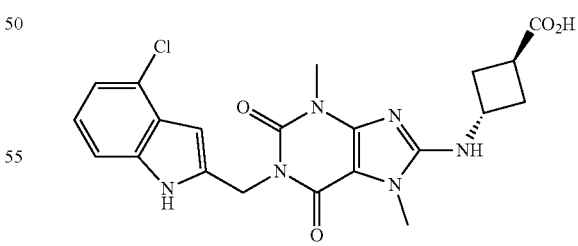

The title compound was synthesized in a similar fashion as described in Procedure 7A using tert-butyl 2-((8-bromo-3,7-dimethyl-2,6-dioxo-2,3,6,7-tetrahydro-1H-purin-1-yl)methyl)-4-chloro-1H-indole-1-carboxylate and (1R,3R)-ethyl 3-aminocyclobutanecarboxylate. The product was purified by preparative HPLC using Method D; ESI: m/z 457.2 (M+H)⁺.

1-((4-Chloro-1H-indol-2-yl)methyl)-8-((1R,3R)-3-(hydroxymethyl)cyclobutylamino)-3,7-dimethyl-1H-purine-2,6(3H,7H)-dione

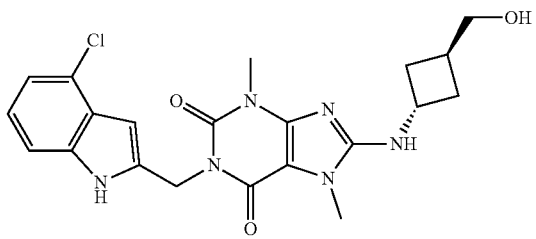

A mixture of (1R,3R)-3-(1-((4-chloro-1H-indol-2-yl)methyl)-3,7-dimethyl-2,6-dioxo-2,3,6,7-tetrahydro-1H-purin-8-ylamino)cyclobutanecarboxylic acid (100 mg, 0.22 mmol) in THF (5 mL) was added BH₃/THF (1M in THF) (0.5 mL). The reaction mixture was stirred at stirred at rt for 0.5 h. The resulting solution was concentrated and purified by prep-HPLC using Method D. ¹H NMR (400 MHz, DMSO-d₆) δ 11.22 (s, 1H), 7.38-7.28 (m, 1H), 7.23 (d, J=7.3 Hz, 1H), 7.07-6.95 (m, 2H), 6.22 (d, J=1.2 Hz, 1H), 5.16 (s, 2H), 4.61 (t, J=5.3 Hz, 1H), 4.41-4.27 (m, 1H), 3.59 (s, 3H), 3.50-3.42 (m, 2H), 3.37 (s, 3H), 2.33-2.20 (m, 1H), 2.20-2.06 (m, 4H); ESI: m/z 443.1 (M+H)⁺.

Example 306

3-(7-(2-amino-2-oxoethyl)-1-(3,4-dichlorobenzyl)-3-methyl-2,6-dioxo-2,3,6,7-tetrahydro-1H-purin-8-ylamino)cyclohexanecarboxylic acid

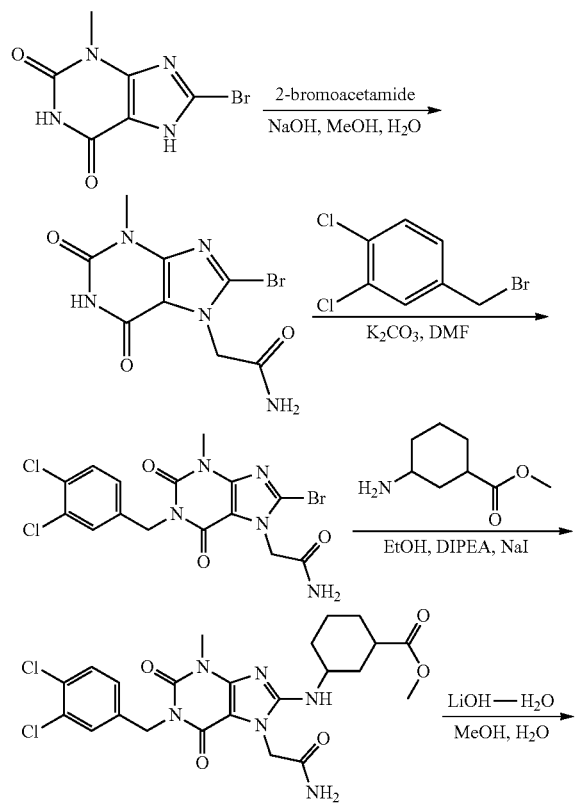

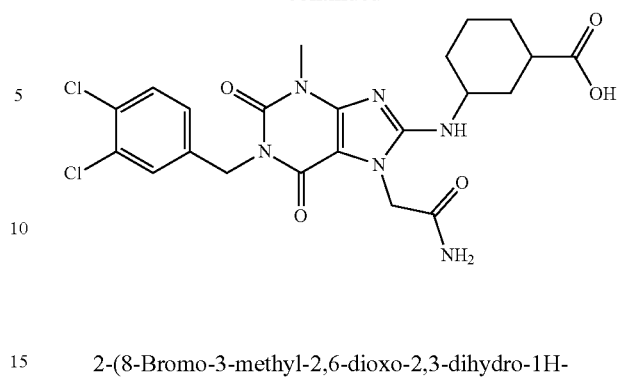

2-(8-Bromo-3-methyl-2,6-dioxo-2,3-dihydro-1H-purin-7(6H)-yl)acetamide

A solution of 8-bromo-3-methyl-1H-purine-2,6(3H,7H)-dione (244 m g, 1.00 mmol) and NaOH (44 mg, 1.10 mmol) in MeOH (4 mL) and H₂O (2 mL) was stirred at 80° C. for 1 h. Then 2-bromoacetamide (274 mg, 2.00 mmol) was added to the solution. The resulting mixture was stirred at 80° C. overnight. The mixture was cooled to rt and diluted with water (6 mL). The solid was collected by filtration, washed with water (2*5 mL), dried under vacuum; ESI: m/z 304.0 (M+2+H)⁺.

2-(8-Bromo-1-(3,4-dichlorobenzyl)-3-methyl-2,6-dioxo-2,3-dihydro-1H-purin-7(6H)-yl)acetamide To a solution of 2-(8-bromo-3-methyl-2,6-dioxo-2,3-dihydro-1H-purin-7(6H)-yl)acetamide (216 mg, 0.72 mmol) in DMF (5 mL) was added 4-(bromomethyl)-1,2-dichlorobenzene (224 mg, 0.94 mmol) and K₂CO₃ (298 mg, 2.16 mmol). The resulting solution was stirred at 60° C. for 4 h. After cooling to room temperature the mixture was diluted with water (5 ml). The solid was collected by filtration, washed with water (2*5 mL) and dried under vacuo; ESI: m/z 460.0 (M+H)⁺.

Methyl 3-(7-(2-amino-2-oxoethyl)-1-(3,4-dichlorobenzyl)-3-methyl-2,6-dioxo-2,3,6,7-tetrahydro-1H-purin-8-ylamino)cyclohexanecarboxylate

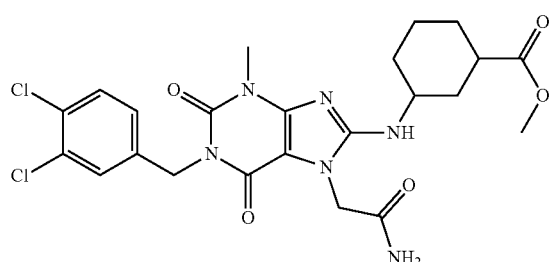

The title compound was synthesized in a similar fashion as described in procedure 7A using 2-(8-bromo-1-(3,4-dichlorobenzyl)-3-methyl-2,6-dioxo-2,3-dihydro-1H-purin-7(6H)-yl)acetamide and methyl 3-aminocyclohexanecarboxylate. The product was purified by Prep-HPLC using Method B. ESI: m/z 551.2 (M+H)$^+$.

3-(7-(2-Amino-2-oxoethyl)-1-(3,4-dichlorobenzyl)-3-methyl-2,6-dioxo-2,3,6,7-tetrahydro-1H-purin-8-ylamino)cyclohexanecarboxylic acid

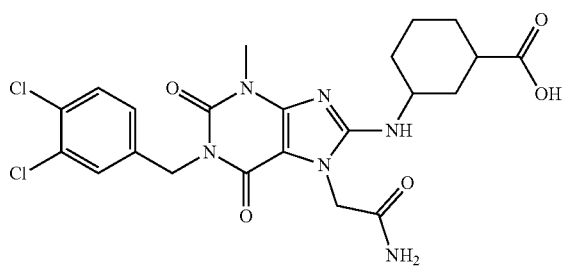 [SMILES: Cn1c(=O)n(Cc2ccc(Cl)c(Cl)c2)c(=O)c2c1nc(NC1CCCC(C(=O)O)C1)n2CC(N)=O]

To a solution of methyl 3-(7-(2-amino-2-oxoethyl)-1-(3,4-dichlorobenzyl)-3-methyl-2,6-dioxo-2,3,6,7-tetrahydro-1H-purin-8-ylamino)cyclohexanecarboxylate (80 mg, 0.15 mmol) in MeOH (2 mL) and H$_2$O (2 mL) was added LiOH (0.60 mL, 1 M in H$_2$O, 0.60 mmol). The resulting mixture was stirred at 50° C. for 3 h. The product was purified by Prep-HPLC using Method B. $^1$H NMR (400 MHz, DMSO-d$_6$) δ 7.55 (d, J=8.3 Hz, 1H), 7.50 (d, J=1.9 Hz, 1H), 7.47 (s, 1H), 7.24 (dd, J=8.3, 1.9 Hz, 1H), 7.14 (s, 1H), 7.05 (s, 1H), 4.96 (s, 2H), 4.74-4.54 (m, 2H), 3.72-3.69 (m, 1H), 3.37 (s, 3H), 2.32 (t, J=12.0 Hz, 1H), 2.17-2.05 (m, 1H), 1.97-1.67 (m, 3H), 1.42-1.10 (m, 4H); ESI: m/z 523.2 (M+H)$^+$.

Example 307

3-(7-(carboxymethyl)-1-(3,4-dichlorobenzyl)-3-methyl-2,6-dioxo-2,3,6,7-tetrahydro-1H-purin-8-ylamino)cyclohexanecarboxylic acid

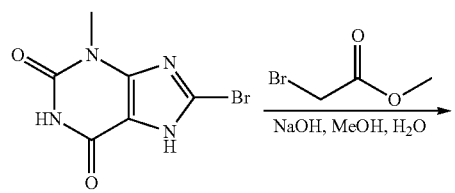

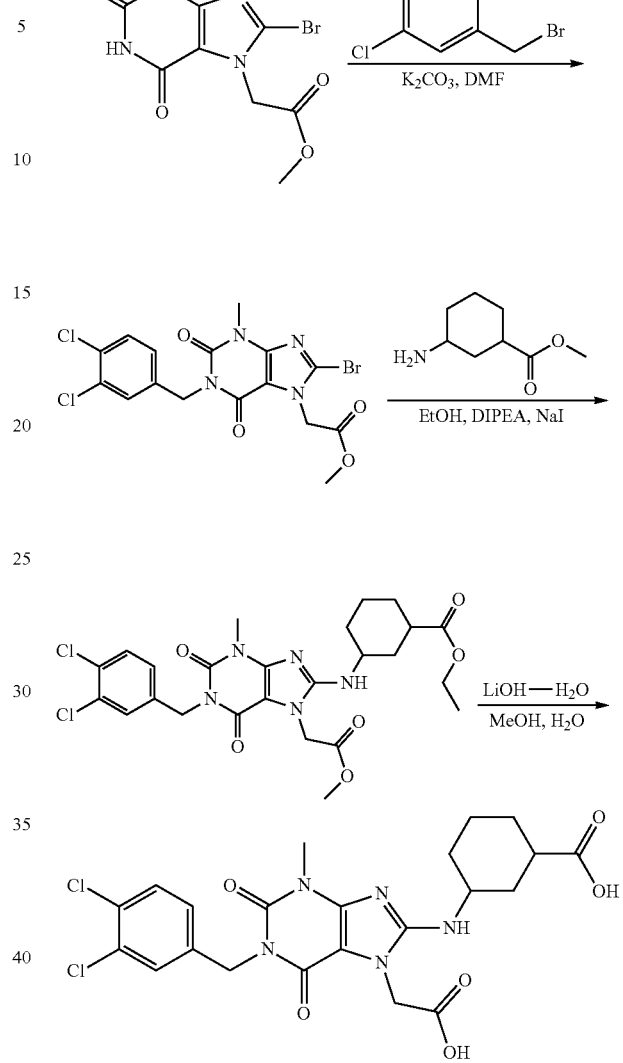

Methyl 2-(8-bromo-3-methyl-2,6-dioxo-2,3-dihydro-1H-purin-7(6H)-yl)acetate

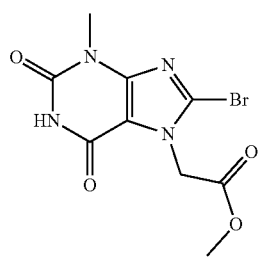 [SMILES: COC(=O)Cn1c(Br)nc2c1c(=O)[nH]c(=O)n2C]

The title compound was synthesized in a similar fashion as Example 306 using of 8-bromo-3-methyl-1H-purine-2,6(3H,7H)-dione and methyl 2-bromoacetate. ESI: m/z 319.0 (M+2+H)$^+$.

Methyl 2-(8-bromo-1-(3,4-dichlorobenzyl)-3-methyl-2,6-dioxo-2,3-dihydro-1H-purin-7(6H)-yl)acetate

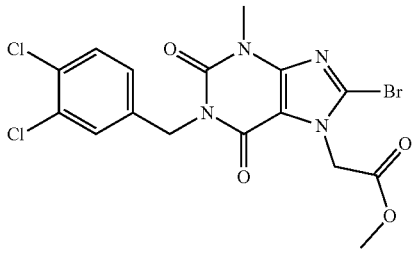 [SMILES: COC(=O)Cn1c(Br)nc2c1c(=O)n(Cc1ccc(Cl)c(Cl)c1)c(=O)n2C]

The title compound was synthesized in a similar fashion as Example 306 using 2-(8-bromo-3-methyl-2,6-dioxo-2,3-dihydro-1H-purin-7(6H)-yl)acetate and 4-(bromomethyl)-1,2-dichlorobenzene. The product was purified by column chromatography (PE/EA, 5/1 to 1/1); ESI: m/z 474.9 (M+H)+.

Ethyl 3-(1-(3,4-dichlorobenzyl)-7-(2-methoxy-2-oxoethyl)-3-methyl-2,6-dioxo-2,3,6,7-tetrahydro-1H-purin-8-ylamino)cyclohexanecarboxylate

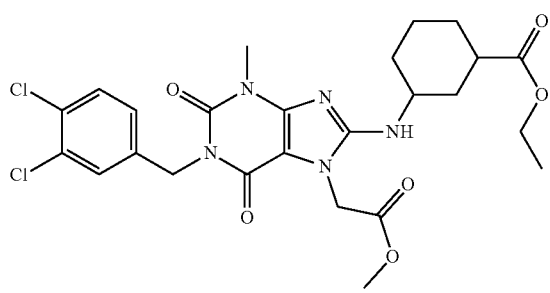 [SMILES: CCOC(=O)C1CCCC(Nc2nc3c(c(=O)n(Cc4ccc(Cl)c(Cl)c4)c(=O)n3C)n2CC(=O)OC)C1]

The title compound was synthesized as described in Example 306 using methyl 2-(8-bromo-1-(3,4-dichlorobenzyl)-3-methyl-2,6-dioxo-2,3-dihydro-1H-purin-7(6H)-yl)acetate. The product was purified by Prep-HPLC using Method B. ESI: m/z 566.2 (M+H)+.

3-(7-(Carboxymethyl)-1-(3,4-dichlorobenzyl)-3-methyl-2,6-dioxo-2,3,6,7-tetrahydro-1H-purin-8-ylamino)cyclohexanecarboxylic acid

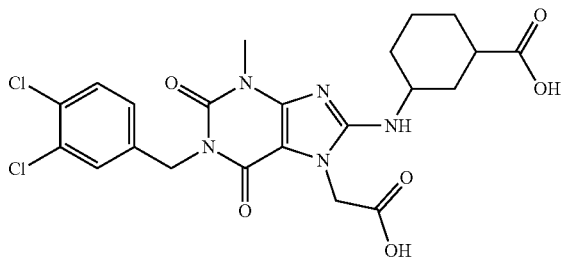 [SMILES: Cn1c(=O)n(Cc2ccc(Cl)c(Cl)c2)c(=O)c2c1nc(NC1CCCC(C(=O)O)C1)n2CC(=O)O]

To a solution of ethyl 3-(1-(3,4-dichlorobenzyl)-7-(2-methoxy-2-oxoethyl)-3-methyl-2,6-dioxo-2,3,6,7-tetrahydro-1H-purin-8-ylamino)cyclohexanecarboxylate (60 mg, 0.10 mmol) in MeOH (2 mL) and H$_2$O (2 mL) was added LiOH (0.40 mL, 1M in H$_2$O, 0.40 mmol). The resulting mixture was stirred at 50° C. for 4 h. After cooling the mixture was filtered and the filtrate was purified by Prep-HPLC using Method B. $^1$H NMR (400 MHz, DMSO-d$_6$) δ 7.52 (dd, J=12.8, 5.0 Hz, 2H), 7.24 (dd, J=8.3, 1.7 Hz, 1H), 7.11 (s, 1H), 4.96 (s, 2H), 4.51 (s, 2H), 3.66 (s, 1H), 3.36 (s, 3H), 2.32 (t, J=12.1 Hz, 1H), 2.13 (d, J=11.9 Hz, 1H), 1.98-1.71 (m, 3H), 1.42-1.10 (m, 4H); ESI: m/z 524.2 (M+H)+.

Example 308

3-(1-((4-chloro-1H-indol-2-yl)methyl)-3,7-dimethyl-2,6-dioxo-2,3,6,7-tetrahydro-1H-purin-8-ylamino)cyclohexanecarboxylic acid

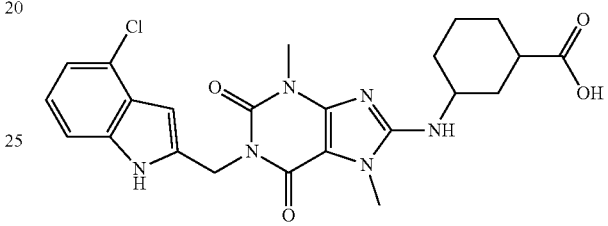

tert-Butyl 2-((8-bromo-3,7-dimethyl-2,6-dioxo-2,3,6,7-tetrahydro-1H-purin-1-yl)methyl)-4-chloro-1H-indole-1-carboxylate and ethyl-3-aminocyclohexane carboxylate were coupled in similar fashion as described in Procedure 7a. The product was purified by flash chromatography (EA/PE=2/1) to give ethyl 3-(1-((4-chloro-1H-indol-2-yl)methyl)-3,7-dimethyl-2,6-dioxo-2,3,6,7-tetrahydro-1H-purin-8-ylamino)cyclohexanecarboxylate; ESI: m/z 513.2 (M+H)+. To a solution of this product (0.1 mmol, 50 mg), in methanol (1 mL) THF (5 mL), and water (5 mL) was added LiOH (0.4 mmol, 10 mg). The reaction mixture was stirred at 30° C. for 4 h. The mixture was concentrated and the pH was adjusted to pH 6 by addition of HCl aqueous solution. The mixture was extracted with DCM (2*30 mL). The combined organic fractions were concentrated and purified by Prep-HPLC using Method D (30-70% ACN). $^1$H NMR (400 MHz, CD$_3$OD) δ 7.28-7.26 (m, 1H), 7.00-6.97 (m, 2H), 6.43 (s, 1H), 5.28 (s, 2H), 3.82 (m, 1H), 3.64 (s, 3H), 3.52 (s, 3H), 2.38-2.17 (m, 2H), 2.03-2.18 (m, 3H), 1.48-1.33 (m, 4H); ESI: m/z 485.2 (M+H)+.

Example 309

3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylic acid

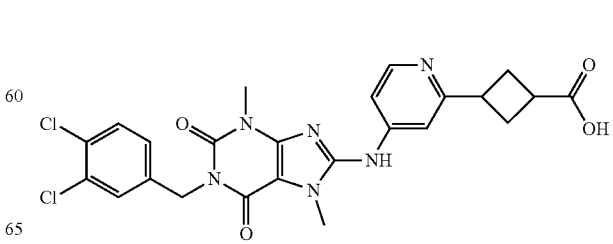

Methyl 3-(4-aminopyridin-2-yl)cyclobutanecarboxylate and 8-bromo-1-(3,4-dichlorobenzyl)-3,7-dimethyl-1H-purine-2,6(3H,7H)-dione were coupled in a similar fashion as described in Procedure 8A to provide methyl 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylate; ESI: m/z 543.2 (M+H)⁺. To a solution of this product (60 mg, 0.11 mmol) in MeOH (4 mL) and water (2 mL) was added LiOH·H₂O (14 mg, 0.33 mmol). The resulting reaction mixture was stirred at room temperature overnight. The mixture was concentrated under reduced pressure. The residue was diluted with water (3 mL). The pH of the mixture was adjusted 6 with 1 N HCl solution. The precipitate was collected by filtration and washed with water (5 mL), and dried under vacuum. ¹H NMR (400 MHz, DMSO-d₆) δ 12.24 (s, 1H), 10.17 (s, 1H), 8.34-8.39 (m, 1H), 7.66-7.78 (m, 2H), 7.56 (m, 2H), 7.29 (d, J=8.4 Hz, 1H), 5.03 (s, 2H), 3.84 (s, 3H), 3.52-3.73 (m, 1H), 3.45-3.46 (m, 3H), 3.07-3.16 (m, 1H), 2.30-2.59 (m, 4H); ESI: m/z 529.1 (M+H)⁺.

Example 310

1-((4-fluoro-1H-indol-2-yl)methyl)-3,7-dimethyl-8-(pyridin-4-ylamino)-1H-purine-2,6(3H,7H)-dione

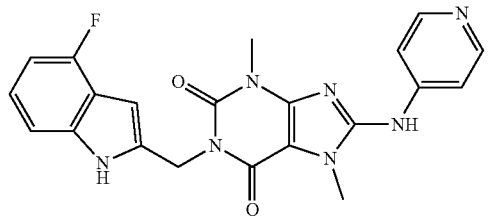

The title compound was synthesized in a similar fashion as described in Procedure 8a using tert-butyl 2-((8-bromo-3,7-dimethyl-2,6-dioxo-2,3,6,7-tetrahydro-1H-purin-1-yl)methyl)-4-fluoro-1H-indole-1-carboxylate and pyridin-4-amine hydrochloride. The product was purified by column chromatography CH₃OH/DCM=5%) to afford tert-butyl 2-((3,7-dimethyl-2,6-dioxo-8-(pyridin-4-ylamino)-2,3,6,7-tetrahydro-1H-purin-1-yl)methyl)-4-fluoro-1H-indole-1-carboxylate; ESI 520.2 (M+H−100)⁺. A mixture of this product (200 mg, 0.39 mmol) in TFA (10 mL) and DCM (10 mL) was stirred at rt. for 3 h. The mixture was concentrated and the product was purified by prep-HPLC using Method B. ¹H NMR (400 MHz, CD₃OD) δ 8.36 (d, J=6.7 Hz, 2H), 7.79 (dd, J=5.2, 1.5 Hz, 2H), 7.14 (d, J=8.2 Hz, 1H), 7.00 (dd, J=7.9, 5.2 Hz, 1H), 6.63 (dd, J=10.6, 7.8 Hz, 1H), 6.44 (s, 1H), 5.30 (s, 2H), 3.92 (s, 3H), 3.60 (s, 3H); ESI: m/z 420.2 (M+H)⁺.

Example 311

1-((3-chloro-1H-indol-2-yl)methyl)-3,7-dimethyl-8-(pyridin-4-ylamino)-1H-purine-2,6(3H,7H)-dione

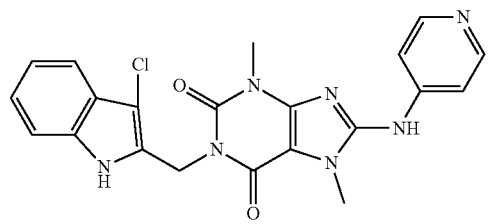 [SMILES: Cn1c(Nc2ccncc2)nc2c1c(=O)n(Cc1[nH]c3ccccc3c1Cl)c(=O)n2C]

The title compound was synthesized in a similar fashion as described in procedure 8A using tert-butyl 2-((8-bromo-3,7-dimethyl-2,6-dioxo-2,3,6,7-tetrahydro-1H-purin-1-yl)methyl)-3-chloro-1H-indole-1-carboxylate and pyridin-4-amine hydrochloride. The product was purified by prep-HPLC using Method B (25-50% B). ¹H NMR (400 MHz, DMSO-d₆) δ 11.02 (s, 1H), 9.70 (br s, 1H), 8.40 (s, 2H), 7.68 (s, 2H), 7.42-7.36 (m, 2H), 7.13-7.08 (m, 2H), 5.25 (s, 2H), 3.84 (s, 3H), 3.49 (s, 3H); ESI 436.1 (M+H)⁺.

Example 312

1-((6-chloro-1H-indol-2-yl)methyl)-3,7-dimethyl-8-(pyridin-4-ylamino)-1H-purine-2,6(3H,7H)-dione

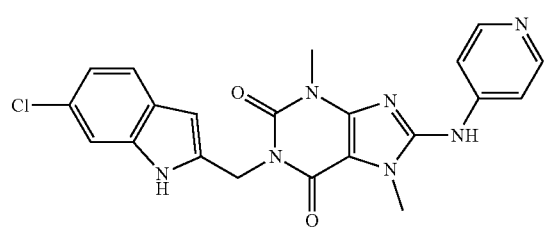 [SMILES: Cn1c(Nc2ccncc2)nc2c1c(=O)n(Cc1cc3ccc(Cl)cc3[nH]1)c(=O)n2C]

The title compound was synthesized in a similar fashion as described in procedure 8A using tert-butyl 2-((8-bromo-3,7-dimethyl-2,6-dioxo-2,3,6,7-tetrahydro-1H-purin-1-yl)methyl)-6-chloro-1H-indole-1-carboxylate and pyridin-4-amine hydrochloride. The product was purified by flash chromatography (0~10% MeOH/DCM) and prep-HPLC using Method B (60-70% ACN) ¹H NMR (400 MHz, DMSO-d₆) δ 11.00 (s, 1H), 9.66 (s, 1H), 8.40-8.37 (m, 2H), 7.67-7.65 (m, 2H), 7.44-7.37 (m, 2H), 6.96-6.93 (m, 1H), 6.27 (s, 1H), 5.18 (s, 2H), 3.83 (s, 3H), 3.48 (s, 3H); ESI: m/z 436.1 (M+H)⁺.

Example 314

2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetic acid

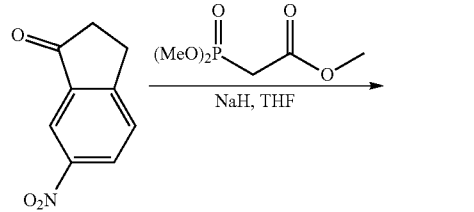

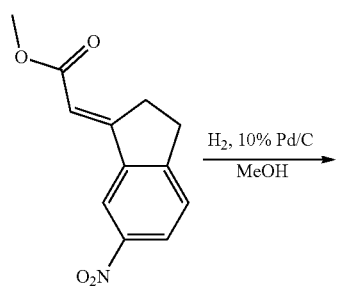

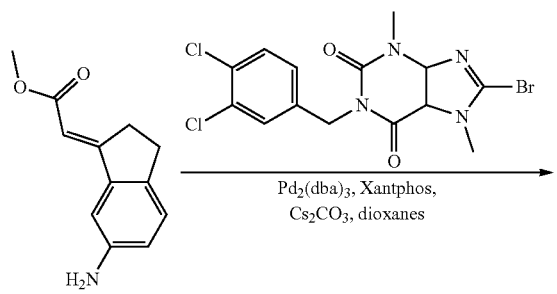

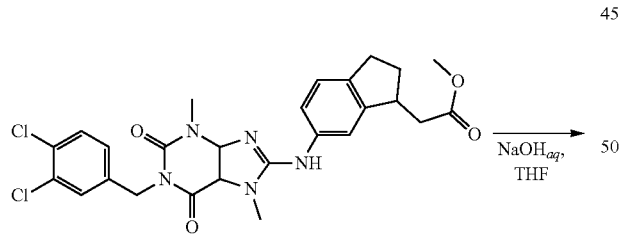

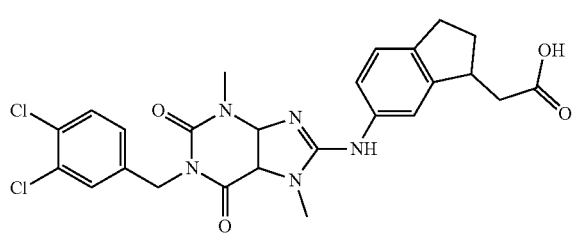

Methyl 2-(6-nitro-2,3-dihydro-1H-inden-1-ylidene)acetate

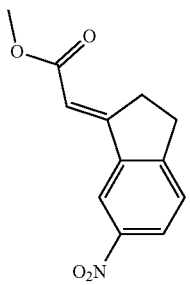 [SMILES: COC(=O)/C=C1\CCc2ccc([N+](=O)[O-])cc21]

To a solution of methyl 2-(dimethoxyphosphoryl)acetate (1.23 g, 6.78 mmol, 2.00 eq) in THF (8.00 mL) was added KHMDS (1 M, 6.78 mL, 2.00 eq) at 0° C. The mixture was stirred at 0° C. under N₂ for 15 min. 6-nitro-2,3-dihydro-1H-inden-1-one (600 mg, 3.39 mmol, 1.00 eq) in THF (5.00 mL) was added dropwise. The mixture was stirred at 25° C. (r.t) for 16 hr. The reaction was quenched with 1N HCl (30 mL). The mixture was extracted with EA (30 mL*3). The combined organic fractions were washed with brine (20 mL), dried over Na₂SO₄ and concentrated. The product was purified by column chromatography (PE/EA from 15/1 to 8/1) to provide the title compound. ¹H NMR (400 MHz CDCl₃) δ 8.44 (s, 1H) 8.25-8.22 (m, 1H) 7.52-7.50 (d, J=8.4, 1H) 6.46 (s, 1H) 3.81 (s, 3H) 3.45-3.41 (m, 2H) 3.21-3.20 (m, 2H).

Methyl 2-(6-amino-2,3-dihydro-1H-inden-1-yl)acetate

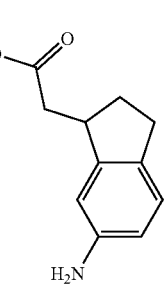

To a solution of methyl 2-(6-nitro-2,3-dihydro-1H-inden-1-ylidene)acetate (300.00 mg, 1.29 mmol, 1.00 eq) in MeOH (30.00 mL) was added Pd—C (10%, 1 g) under N₂. The mixture was stirred under H₂ (50 psi) at 50° C. for 16 hr. The reaction mixture was filtered and the filtrate was concentrated to give crude product which was used without further purification. ¹H NMR (400 MHz CDCl₃) δ 7.03-7.01 (d, J=8.4, 1H) 6.55-6.54 (m, 2H) 3.53-3.51 (m, 1H) 2.81-2.73 (m, 2H) 2.47-2.37 (m, 2H) 1.76-1.70 (m, 2H); ESI: m/z 206.1 (M+H)⁺.

Methyl 2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetate

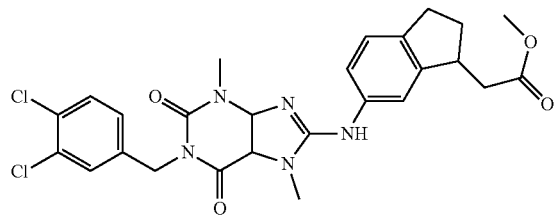 [SMILES: COC(=O)CC1CCc2ccc(NC3=NC4C(C(=O)N(Cc5ccc(Cl)c(Cl)c5)C(=O)N4C)N3C)cc21]

To a solution of methyl 2-(6-amino-2,3-dihydro-1H-inden-1-yl)acetate (200.00 mg, 974.42 umol, 2.00 eq) and 8-bromo-1-(3,4-dichlorobenzyl)-3,7-dimethyl-1H-purine-2,6(3H,7H)-dione (203.69 mg, 487.21 umol, 1.00 eq) in dioxane (5.00 mL) was added $Cs_2CO_3$ (317.49 mg, 974.42 umol, 2.00 eq), Xantphos (5.64 mg, 9.74 umol, 0.02 eq) and $Pd_2(dba)_3$ (8.92 mg, 9.74 umol, 0.02 eq). The product was purified by prep-TLC (PE/EA=1/1). $^1$H NMR (400 MHz, $CDCl_3$) δ 7.64-7.57 (s, 1H) 7.42-7.34 (m, 2H) 7.34-7.31 (m, 1H) 7.26-7.19 (m, 2H) 6.17 (s, 1H) 5.15 (s, 2H) 3.82 (s, 3H) 3.74 (s, 3H) 3.58-3.50 (m, 4H) 2.99-2.82 (m, 2H) 2.81-2.72 (m, 1H) 2.56-2.48 (m, 1H) 2.48-2.37 (m, 1H) 1.87-1.73 (m, 1H); ESI: m/z 542.2 $(M+H)^+$.

2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetic acid

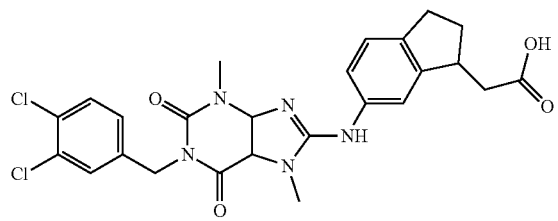 [SMILES: CN1C(=O)N(Cc2ccc(Cl)c(Cl)c2)C(=O)C2C1N=C(Nc1ccc3c(c1)C(CC(=O)O)CC3)N2C]

To a solution of methyl 2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetate (140.00 mg, 258.11 umol, 1.00 eq) in THF (3.00 mL) was added 3N NaOH (500.00 uL). The mixture was stirred at 25° C. for 16 hr. The mixture was stirred at 60° C. for 2 hr. The mixture was concentrated. The residue was dissolved in $H_2O$ (0.5 mL) and acidified with 3N HCl (0.6 mL) until pH=1 at 0° C. The mixture was concentrated to give crude product which was purified by prep-HPLC using Method C. $^1$H NMR (400 MHz, DMSO-$d_6$) δ 1.63-1.75 (m, 1H), 2.26-2.44 (m, 3H), 2.59-2.87 (m, 3H), 3.39-3.43 (m, 4H), 3.72-3.80 (m, 3H), 4.98-5.08 (m, 2H), 7.07-7.21 (m, 1H), 7.26-7.33 (m, 1H), 7.38-7.46 (m, 1H), 7.53-7.61 (m, 3H), 9.08-9.13 (m, 1H); ESI: m/z 528.2/530.2 $(M+H)^+$.

Example 315

(±)-trans-2-[6-[[1-[(4-chloro-1H-indol-2-yl)methyl]-3,7-dimethyl-2,6-dioxo-purin-8-yl] amino]-2-pyridyl]cyclopropanecarboxylic acid

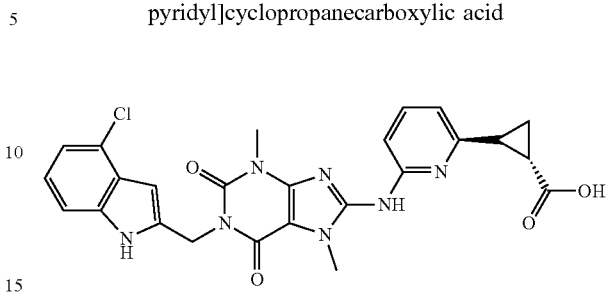

Ethyl 2-(6-amino-2-pyridyl)cyclopropanecarboxylate and tert-butyl 2-[(8-bromo-3,7-dimethyl-2,6-dioxo-purin-1-yl)methyl]-4-chloro-indole-1-carboxylate were coupled in a similar fashion as described in Procedure 8B. The crude product was purified by chromatography (PE/EA, 10/1 to 1/1). (±)-trans-tert-Butyl 4-chloro-2-[[8-[[6-(2-ethoxycarbonylcyclopropyl)-2-pyridyl]amino]-3,7-dimethyl-2,6-dioxo-purin-1-yl]methyl]indole-1-carboxylate and (±)-trans-ethyl 2-[6-[[1-[(4-chloro-1H-indol-2-yl)methyl]-3,7-dimethyl-2,6-dioxo-purin-8-yl]amino]-2-pyridyl]cyclopropanecarboxylate were obtained as products. To a solution of trans-ethyl 2-[6-[[1-[(4-chloro-1H-indol-2-yl)methyl]-3,7-dimethyl-2,6-dioxo-purin-8-yl]amino]-2-pyridyl]cyclopropanecarboxylate (50.00 mg, 91.24 umol) in THF (500.00 uL) was added 2N NaOH (500.00 uL). The mixture was stirred at 40° C. and stirred for another 18 h. The reaction mixture was cooled to 0° C. and adjusted to pH=4-5 with 2N HCl. The mixture was extracted with EA (5 mL*3). The combined organic fractions were washed with brine (2 mL), dried over $Na_2SO_4$, and concentrated. The crude product was purified by Prep-HPLC using Method C (30-60% ACN). $^1$H NMR (400 MHz, DMSO-$d_6$) δ 11.27-11.30 (m, 1H) 9.64-9.78 (m, 1H) 7.63-7.69 (m, 1H) 7.57-7.62 (m, 1H) 7.32-7.37 (m, 1H) 6.99-7.06 (m, 3H) 6.29 (s, 1H) 5.22 (s, 2H) 3.81 (s, 3H) 3.46 (s, 3H) 2.43-2.45 (m, 1H) 2.02-2.07 (m, 1H) 1.40-1.49 (m, 2H). ESI: m/z 520.2 (M+H).

Example 398

(1R,2R)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid or (1S,2S)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid

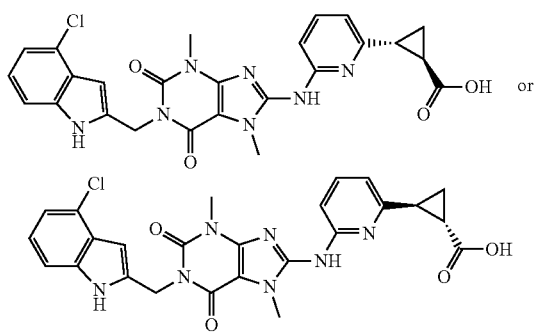

(±)-trans-2-(6-((1-((4-Chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid was separated into individual eneatiomers by SFC using a CHIRALPAK® AS-H/SFC column eluting with 40% MeOH (0.1% NH$_4$OH) in CO$_2$ to give Example 398: (1R,2R)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid or (1S,2S)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid (retention time: 12.7 min, ee %:100%). $^1$H NMR (400 MHz DMSO-d$_6$) δ 8.09 (t, J=8.16 Hz, 1H), 7.51-7.57 (m, 1H), 7.21-7.29 (m, 1H), 6.91-7.02 (m, 1H), 5.31 (s, 2H), 3.99 (s, 3H), 3.61 (s, 3H), 2.77-2.85 (m, 1H), 2.26-2.34 (m, 1H), 1.70-1.77 (m, 1H); ESI: m/z 520.2 (M+H)$^+$. Peak 2 (retention time 15.9 min) was not of high enough ee % for further characterization.

Example 316

3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylic acid

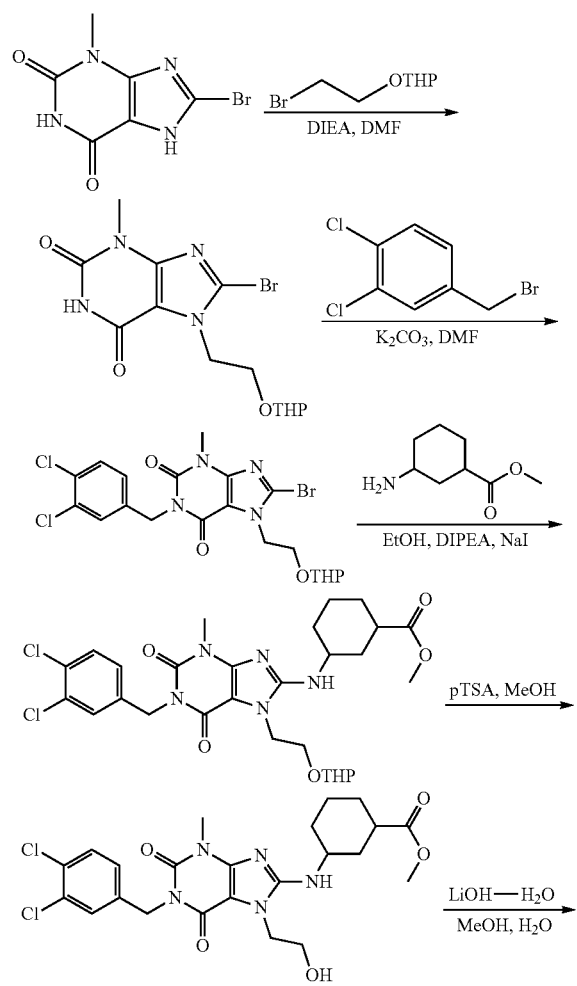

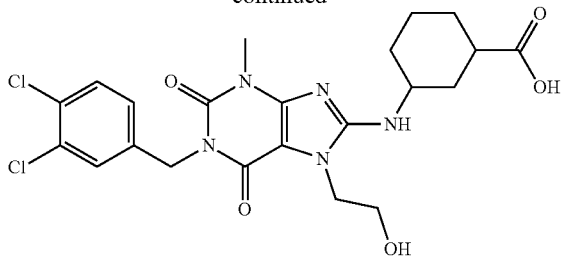

8-Bromo-3-methyl-7-(2-((tetrahydro-2H-pyran-2-yl)oxy)ethyl)-3,7-dihydro-1H-purine-2,6-dione

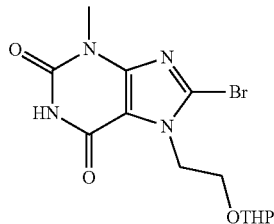

A solution of 8-bromo-3-methyl-1H-purine-2,6(3H,7H)-dione (2.0 g, 8.2 mmol), 2-(2-bromoethoxy)tetrahydro-2H-pyran (3.4 g, 16.4 mmol), DIEA (3.2 g, 24.6 mmol) in DMF (20 mL) was stirred and heated to 80° C. for 18 h. The mixture was concentrated under vacuum. The residue was purified by column chromatography (EA:PE=0:100 to 50:50); ESI; m/z 373.0 (M+H)$^+$.

8-bromo-1-(3,4-dichlorobenzyl)-3-methyl-7-(2-((tetrahydro-2H-pyran-2-yl)oxy)ethyl)-3,7-dihydro-1H-purine-2,6-dione

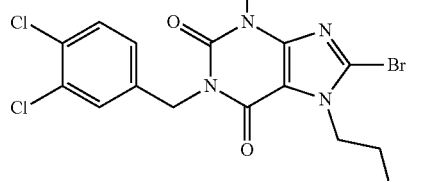

A solution of 8-Bromo-3-methyl-7-(2-((tetrahydro-2H-pyran-2-yl)oxy)ethyl)-3,7-dihydro-1H-purine-2,6-dione (1.0 g, 2.68 mmol), 4-(bromomethyl)-1,2-dichlorobenzene (832 mg, 3.50 mmol) and K$_2$CO$_3$ (1.11 g, 8.04 mmol) in DMF (20 mL) was stirred and heated to 80° C. for 3 h. The mixture was concentrated under vacuum. The residue was purified by column chromatography (EA:PE=0:100 to 50:50). ESI: m/z 530.0 (M+H)$^+$.

Ethyl 3-(1-(3,4-dichlorobenzyl)-3-methyl-2,6-dioxo-7-(2-(tetrahydro-2H-pyran-2-yloxy)ethyl)-2,3,6,7-tetrahydro-1H-purin-8-ylamino)cyclohexanecarboxylate

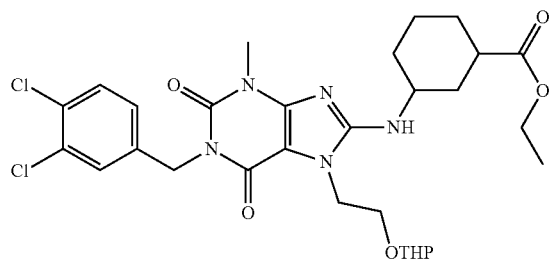

The title compound was synthesized in a similar fashion as described in Procedure 7A using 8-bromo-1-(3,4-dichlorobenzyl)-3-methyl-7-(2-(tetrahydro-2H-pyran-2-yloxy)ethyl)-1H-purine-2,6(3H,7H)-dione and ethyl 3-aminocyclohexane carboxylate. The product was purified by Prep-HPLC using Method D. ESI: m/z 622.2 (M+H)+.

Ethyl 3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylate

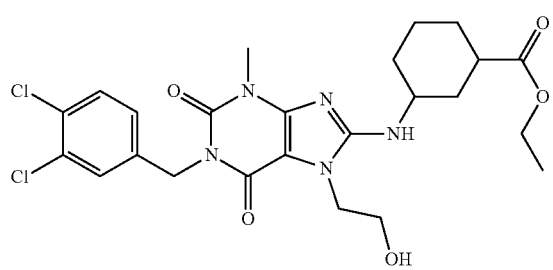 [SMILES: CCOC(=O)C1CCCC(Nc2nc3c(c(=O)n(Cc4ccc(Cl)c(Cl)c4)c(=O)n3C)n2CCO)C1]

To a solution of Ethyl 3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylate (50 mg, 0.081 mmol), p-toluenesulfonic acid (2.8 mg, 0.0162 mmol) in MeOH (2 mL), the mixture was stirred at 25° C. for 2 h. The mixture was concentrated under vacuum. The residue was purified by column chromatography (EA:PE=0:100 to 50:50, MeOH:DCM=0:100 to 5:95); ESI: m/z 538.1 (M+H)+.

3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylic acid

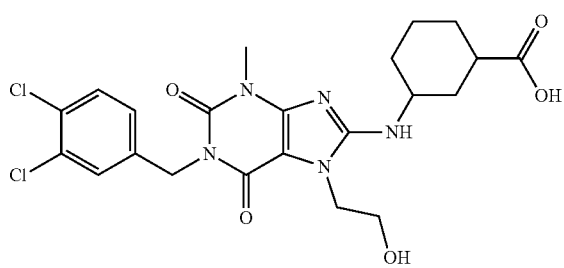 [SMILES: Cn1c(=O)n(Cc2ccc(Cl)c(Cl)c2)c(=O)c2c1nc(NC1CCCC(C(=O)O)C1)n2CCO]

A solution of ethyl 3-(1-(3,4-dichlorobenzyl)-7-(2-hydroxyethyl)-3-methyl-2,6-dioxo-2,3,6,7-tetrahydro-1H-purin-8-ylamino)cyclohexanecarboxylate (40 mg, 0.074 mmol), p-toluenesulfonic acid (9.4 mg, 0.223 mmol) in MeOH (2 mL) and H2O (1 mL) was stirred at 25° C. for 2 h. The mixture was concentrated under vacuum. The residue was purified by Prep-HPLC using Method D. $^1$H NMR (400 MHz, CD$_3$OD) δ 7.54 (d, J=2.1 Hz, 1H), 7.44 (d, J=8.3 Hz, 1H), 7.31 (dd, J=8.3, 2.1 Hz, 1H), 5.10 (s, 2H), 4.23-4.15 (m, 2H), 3.83 (t, J=5.1 Hz, 3H), 3.51 (s, 3H), 2.27 (t, J=13.0 Hz, 2H), 2.05 (d, J=12.0 Hz, 1H), 1.98-1.82 (m, 2H), 1.53-1.23 (m, 4H). ESI: m/z 510.2 (M+H)+.

Example 317

1-((1H-indol-2-yl)methyl)-8-((1S,3R)-3-(hydroxymethyl)cyclopentylamino)-3,7-dimethyl-1H-purine-2,6(3H,7H)-dione

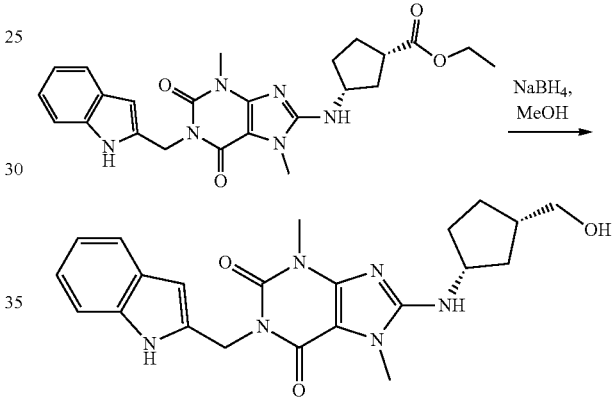

(1R,3S)-ethyl 3-(1-((1H-indol-2-yl)methyl)-3,7-dimethyl-2,6-dioxo-2,3,6,7-tetrahydro-1H-purin-8-ylamino)cyclopentanecarboxylate

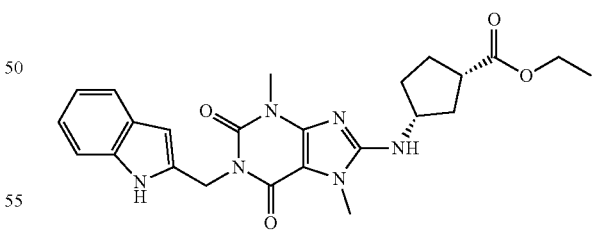

To a solution of tert-butyl 2-((8-bromo-3,7-dimethyl-2,6-dioxo-2,3,6,7-tetrahydro-1H-purin-1-yl)methyl)-1H-indole-1-carboxylate (0.4 mmol, 200 mg), (1R,3S)-methyl 3-aminocyclopentane carboxylate (1.2 mmol, 176 mg), DIEA (1.2 mmol, 154 mg) in ethanol (5 mL) was added NaI (0.04 mmol, 6 mg). The reaction mixture was stirred at 130° C. for 6 h in a microwave reactor. The mixture was concentrated and purified by flash chromatography (EA/PE=2/1); ESI: m/z 465.2 (M+H)+.

299

1-((1H-indol-2-yl)methyl)-8-((1S,3R)-3-(hydroxymethyl)cyclopentylamino)-3,7-dimethyl-1H-purine-2,6(3H,7H)-dione

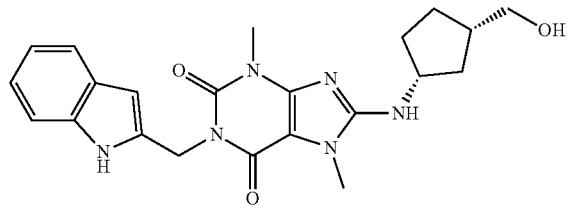 [SMILES: Cn1c(N[C@@H]2CC[C@H](CO)C2)nc2c1c(=O)n(Cc1cc3ccccc3[nH]1)c(=O)n2C]

To a solution of (1R,3S)-ethyl 3-(1-((1H-indol-2-yl)methyl)-3,7-dimethyl-2,6-dioxo-2,3,6,7-tetrahydro-1H-purin-8-ylamino)cyclopentanecarboxylate (0.13 mmol, 0.06 g) in methanol (5 mL) was added NaBH$_4$ (1.3 mmol, 0.05 g). The mixture was stirred at 70° C. for 16 h. The mixture was diluted with water (40 mL) and extracted with EA (2*100 mL). The combined organic fractions were concentrated to give the crude product. The crude product was purified by Prep-HPLC using Method D (30-70% ACN). $^1$H NMR (400 MHz, CH$_3$OD) δ 7.41-7.30 (d, J=4.4 Hz, 2H), 7.02-6.94 (d, J=10.4 Hz, 2H), 6.35 (s, 1H), 5.25 (s, 2H), 4.27 (br s, 1H), 3.62-3.61 (m, 3H), 3.60-3.49 (m, 5H), 2.29-2.17 (m, 2H), 2.04-2.01 (m, 1H), 1.66-1.51 (m, 2H), 1.34-1.30 (m, 1H); ESI: m/z 423.3 (M+H)$^+$.

Example 318

3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylic acid

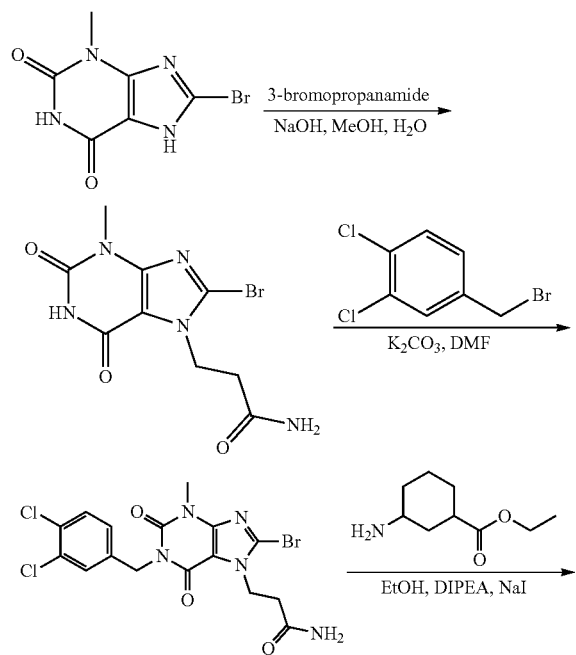

300

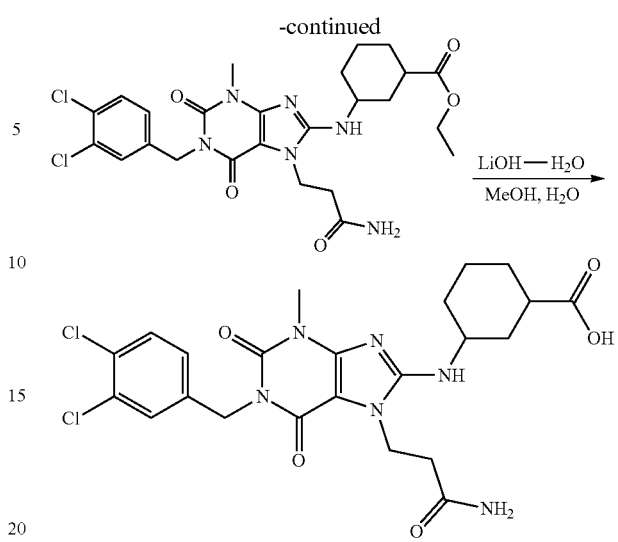

3-(8-bromo-3-methyl-2,6-dioxo-2,3-dihydro-1H-purin-7(6H)-yl)propanamide

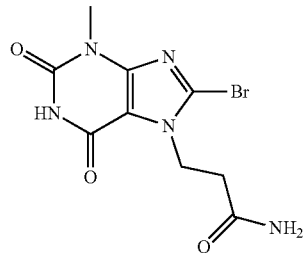 [SMILES: Cn1c(=O)[nH]c(=O)c2c1nc(Br)n2CCC(N)=O]

A solution of 8-bromo-3-methyl-1H-purine-2,6(3H,7H)-dione (244 mg, 1.0 mmol), 3-bromopropanamide (227 mg, 1.5 mmol) and DIEA (387 mg, 3.0 mmol) in DMF (5 mL) was stirred at 80° C. for 18 h. The mixture was concentrated. The residue was purified by column chromatography (EA:PE=0:100 to 50:50); ESI: m/z 316.0 (M+H)$^+$.

3-(8-Bromo-1-(3,4-dichlorobenzyl)-3-methyl-2,6-dioxo-2,3-dihydro-1H-purin-7(6H)-yl)propanamide

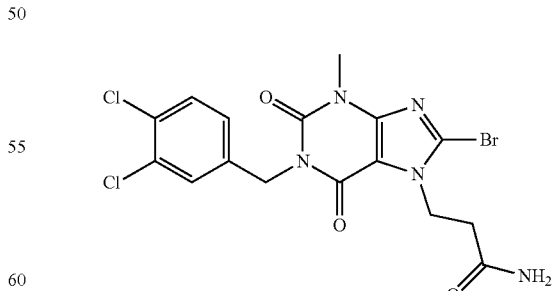

A solution of 3-(8-bromo-3-methyl-2,6-dioxo-2,3-dihydro-1H-purin-7(6H)-yl)propanamide (200 mg, 0.635 mmol), 4-(bromomethyl)-1,2-dichlorobenzene (193 mg, 0.825 mmol), K$_2$CO$_3$ (263 mg, 1.905 mmol) in DMF (5 mL) was heated to 60° C. for 2 h. The mixture was cooled to room temperature and diluted with water (10 mL). The mixture was filtered and the filter cake was dried to give the title compound. ESI: m/z 473.9 (M+H)+.

Ethyl 3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylate

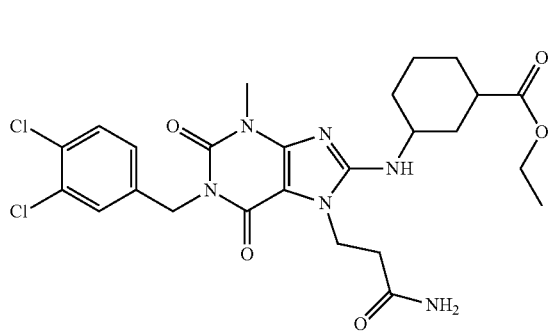 [SMILES: CCOC(=O)C1CCCC(Nc2nc3c(c(=O)n(Cc4ccc(Cl)c(Cl)c4)c(=O)n3C)n2CCC(N)=O)C1]

The title compound was synthesized in a similar fashion as example 112 using 3-(8-bromo-1-(3,4-dichlorobenzyl)-3-methyl-2,6-dioxo-2,3-dihydro-1H-purin-7(6H)-yl)propanamide and ethyl 3-aminocyclohexanecarboxylate. The product was purified by Prep-HPLC using Method D. ESI: m/z 565.2 (M+H)+.

3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylic acid

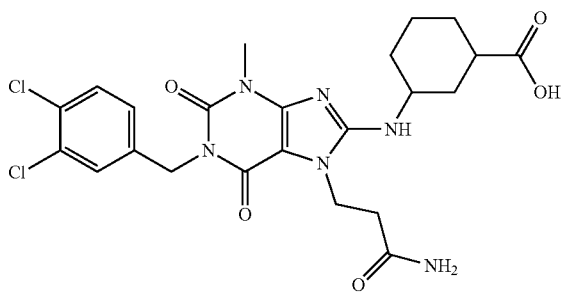 [SMILES: Cn1c(=O)n(Cc2ccc(Cl)c(Cl)c2)c(=O)c2c1nc(NC1CCCC(C(=O)O)C1)n2CCC(N)=O]

A solution of ethyl 3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylate (35 mg, 0.062 mmol), LiOH·H2O (7.8 mg, 0.186 mmol) in MeOH (1 mL), H2O (1 mL) was heated to 50° C. for 1 h. The mixture was filtered and the filtrate was purified by Prep-HPLC using Method D. $^1$H NMR (400 MHz, DMSO-$d_6$) δ 7.53-7.56 (m, 2H), 7.25-7.28 (dd, J=2 Hz, 1.6 Hz, 1H), 7.10 (s, 1H), 4.99 (s, 2H), 4.12-4.15 (m, 2H), 3.66-3.69 (m, 1H), 3.35 (s, 3H), 2.55-2.58 (m, 2H), 2.31-2.37 (m, 1H), 2.12-2.15 (m, 1H), 1.74-1.96 (m, 3H), 1.15-1.38 (m, 4H); ESI: m/z 537.2 (M+H)+.

Example 319

3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxamide

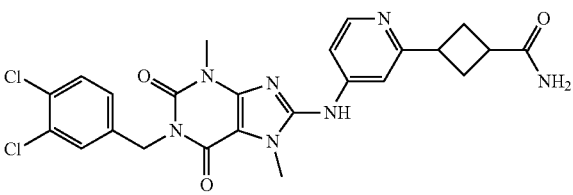 [SMILES: Cn1c(Nc2ccnc(C3CC(C(N)=O)C3)c2)nc2c1c(=O)n(Cc1ccc(Cl)c(Cl)c1)c(=O)n2C]

To a solution of methyl 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylate (60 mg, 0.11 mmol) in MeOH (4 mL) and water (2 mL) was added LiOH·H2O (14 mg, 0.33 mmol). The resulting reaction mixture was stirred at room temperature overnight. The mixture was concentrated and the residue was diluted with water (3 mL). The pH was adjusted to 6.0 with 1 N HCl. The precipitate was collected by filtration and the filter cake was washed with water (5 mL), and dried under vacuum to afford 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylic acid: $^1$H NMR (400 MHz, DMSO-$d_6$) δ 12.24 (s, 1H), 10.17 (s, 1H), 8.34-8.39 (m, 1H), 7.66-7.78 (m, 2H), 7.56 (m, 2H), 7.29 (d, J=8.4 Hz, 1H), 5.03 (s, 2H), 3.84 (s, 3H), 3.52-3.73 (m, 1H), 3.45-3.46 (m, 3H), 3.07-3.16 (m, 1H), 2.30-2.59 (m, 4H); ESI: m/z 529.1 (M+H)+.

To a solution of 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylic acid (100 mg, 019 mmol) in DMF (3 mL) was added HATU (110 mg, 0.29 mmol), DIEA (122 mg, 0.95 mmol), NH4Cl (100 mg, 1.9 mmol). The resulting mixture was stirred at room temperature overnight. The mixture was poured into water (15 ml). The precipitate was collected by filtration. The solid was washed with water (10 ml×2), ether (10 ml), and a mixture of ether/MeOH=20:1 (10 mL), and dried under vacuum to give the title compound as a pale yellow solid: $^1$H NMR (400 MHz, CDCl3) δ 8.23-8.30 (m, 1H), 7.71-7.83 (m, 1H), 7.56-7.60 (m, 1H), 7.55 (d, J=2.0 Hz, 1H), 7.42 (d, J=8.4 Hz, 1H), 7.32 (d, J=8.4 Hz, 2.0 Hz, 1H), 5.09 (s, 2H), 3.88 (s, 3H), 3.74-3.82 (m, 1H), 3.55-3.56 (m, 3H), 3.13-3.21 (m, 1H), 2.41-2.69 (m, 4H); ESI; m/z 528.1 (M+H)+.

Example 320

1-(3,4-dichlorobenzyl)-8-(2-(3-(hydroxymethyl)cyclobutyl)pyridin-4-ylamino)-3,7-dimethyl-1H-purine-2,6(3H,7H)-dione

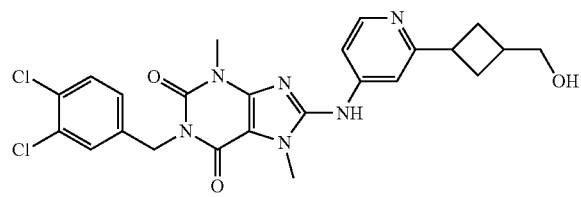 [SMILES: Cn1c(Nc2ccnc(C3CC(CO)C3)c2)nc2c1c(=O)n(Cc1ccc(Cl)c(Cl)c1)c(=O)n2C]

To a solution of methyl 3-(4-(1-(3,4-dichlorobenzyl)-3,7-dimethyl-2,6-dioxo-2,3,6,7-tetrahydro-1H-purin-8-ylamino)pyridin-2-yl)cyclobutanecarboxylate (80 mg, 0.15 mmol) in THF (5 mL) was added LiAlH$_4$ (0.23 ml, 0.23 mmol) dropwise at 0° C. The resulting reaction mixture was stirred at 0° C. for 2 hours, and quenched with water (1.0 mL). The solvent was concentrated and the residue was purified by Prep-TLC (DCM/7N NH$_3$ in MeOH=15:1). $^1$H NMR (400 MHz, CDCl$_3$) δ 8.21-8.26 (m, 1H), 7.70-7.74 (m, 1H), 7.52-7.55 (m, 2H), 7.42 (d, J=8.4 Hz, 1H), 7.32 (d, J=8.4 Hz, 1H), 5.09 (s, 2H), 3.87 (s, 3H), 3.45-3.72 (m, 6H), 2.34-2.54 (m, 3H), 2.22-2.28 (m, 1H), 1.96-2.04 (m, 1H); ESI: m/z 515.2 (M+H)$^+$.

Example 321

(±)-trans-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid

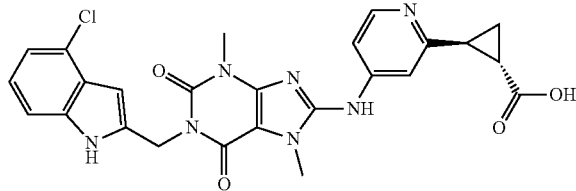 [SMILES: Cn1c(Nc2ccnc([C@H]3C[C@@H]3C(=O)O)c2)nc2c1c(=O)n(Cc1cc3c(Cl)cccc3[nH]1)c(=O)n2C]

tert-Butyl 2-[(8-bromo-3,7-dimethyl-2,6-dioxo-purin-1-yl)methyl]-4-chloro-indole-1-carboxylate and trans-ethyl 2-(4-aminopyridin-2-yl)cyclopropanecarboxylate were coupled in a similar fashion as described in Procedure 8B. The product was purified by Prep-TLC (DCM/MeOH=10/1) to give (±)-trans-tert-butyl 4-chloro-2-((8-((2-(2-(ethoxycarbonyl)cyclopropyl)pyridin-4-yl)amino)-3,7-dimethyl-2,6-dioxo-2,3,6,7-tetrahydro-1H-purin-1-yl)methyl)-1H-indole-1-carboxylate and (±)-trans-ethyl 2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylate. To a solution of (±)-trans-4-chloro-2-((8-((2-(2-(ethoxycarbonyl)cyclopropyl)pyridine-4-yl)amino)-3,7-dimethyl-2,6-dioxo-2,3,6,7-tetrahydro-1H-purin-1-yl)methyl)-1H-indole-1-carboxylate (30.00 mg, 54.75 umol) in THF (500.00 uL) was added 2N NaOH (500.00 uL). The reaction mixture was stirred at 25° C. for 15 hr and 50° C. for 2 h. The mixture was cooled to 0° C. and the pH was adjusted to 5 with 2N HCl. The mixture was extracted with EA (2 mL*3). The combined organic fractions were washed with brine (1 mL), dried over Na$_2$SO$_4$, concentrated in vacuum. The crude product was purified by prep-HPLC using Method C (23-53% ACN). $^1$H NMR (400 MHz, CD$_3$OD) δ 8.36 (d, J=7.03 Hz, 1H), 7.94-8.02 (m, 1H), 7.81-7.89 (m, 1H), 7.29 (d, J=8.03 Hz, 1H), 6.94-7.10 (m, 2H), 6.46 (s, 1H), 5.34 (s, 2H), 3.99 (s, 3H), 3.62 (s, 3H), 2.75-2.82 (m, 1H), 2.25-2.31 (m, 1H), 1.79-1.85 (m, 1H), 1.63-1.70 (m, 1H); ESI: m/z 520.2/522.2 (M+H)$^+$.

Example 322 and 363

(1R,2R)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic and (1S,2S)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid

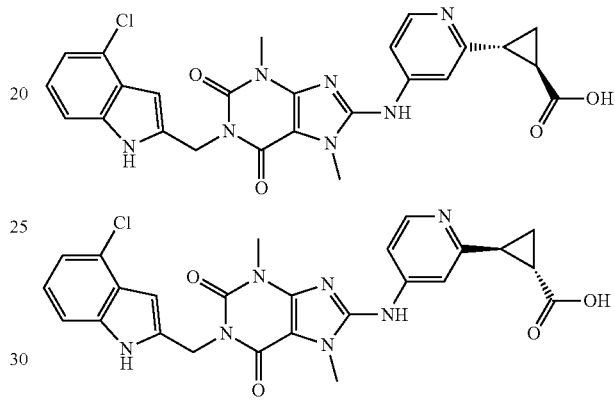

(±)-trans-2-(4-((1-((4-Chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid was separated into individual eneantiomers by SFC using a CHIRALPAK®AD-H/SFC column eluting with 50% EtOH (0.1% NH$_4$OH) in CO$_2$.

Example 322: (1R,2R)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid or (1S,2S)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid (peak 1, retention time: 8.7 min): $^1$H NMR (400 MHz, DMSO-d$_6$) δ 14.33-14.60 (m, 1H), 11.51-11.70 (m, 1H), 8.40-8.62 (m, 2H), 7.47-7.65 (m, 2H), 7.23-7.35 (m, 3H), 4.90-5.02 (m, 2H), 4.51-4.67 (m, 2H), 4.33-4.46 (m, 2H); ESI: m/z 520/522 (M+H)$^+$.

Example 363: (1S,2S)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid or (1R,2R)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid (peak 2, retention time 10.8) $^1$H NMR (400 MHz, DMSO-d$_6$) δ 14.33-14.60 (m, 1H), 11.51-11.70 (m, 1H), 8.40-8.62 (m, 2H), 7.47-7.65 (m, 2H), 7.23-7.35 (m, 3H), 4.90-5.02 (m, 2H), 4.51-4.67 (m, 2H), 4.33-4.46 (m, 2H); ESI: m/z 520/522 (M+H)$^+$.

Example 323

1-(3,4-dichlorobenzyl)-8-((3-(2-hydroxyethyl)-2,3-dihydro-1H-inden-5-yl)amino)-3,7-dimethyl-1H-purine-2,6(3H,7H)-dione

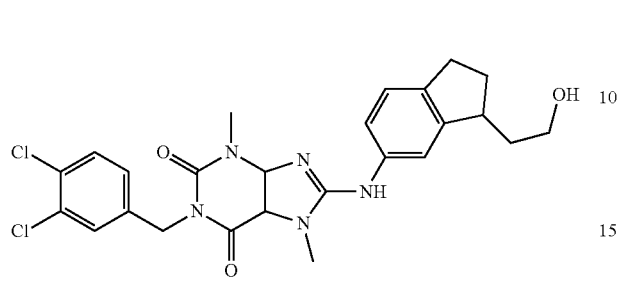

Methyl 2-(6-((1-(3,4-dichlorobenzyl)-3,7-dimethyl-2,6-dioxo-2,3,6,7-tetrahydro-1H-purin-8-yl)amino)-2,3-dihydro-1H-inden-1-yl)acetate (180.00 mg, 331.85 umol) in THF (5.00 mL) was treated with DIBAL-H (1 M, 829.63 uL) at −40° C. The mixture was stirred at −40° C. for 40 min. The mixture was quenched with MeOH (10 mL) −40° C. Then H$_2$O (5 mL) was added to the above solution at 0° C. The mixture was concentrated and the aqueous residue was extracted with DCM (20 mL*3). The combined organic fractions were washed with brine (10 mL), dried over Na$_2$SO$_4$ and concentrated to give crude product which was purified by prep-TLC (PE/EA=1/1) then further purified by prep-HPLC using Method C (50-70% ACN). $^1$H NMR (400 MHz, DMSO-d$_6$) δ 1.47-1.71 (m, 2H), 1.88-1.99 (m, 1H), 2.18-2.30 (m, 1H), 2.70-2.88 (m, 2H), 3.08-3.23 (m, 1H), 3.42 (s, 3H), 3.52-3.63 (m, 2H), 3.78 (s, 3H), 4.47-4.52 (m, 1H), 4.99-5.09 (m, 2H), 7.11-7.19 (m, 1H), 7.26-7.34 (m, 1H), 7.38-7.46 (m, 1H), 7.51-7.66 (m, 3H), 9.06 (s, 1H); ESI: m/z 514.2 (M+H)$^+$.

Example 324

1-(3,4-dichlorobenzyl)-8-((2-(hydroxymethyl)-2,3-dihydro-1H-inden-5-yl)amino)-3,7-dimethyl-1H-purine-2,6(3H,7H)-dione Methyl 5-((1-(3,4-dichlorobenzyl)-3,7-dimethyl-2,6-dioxo-2,3,6,7-tetrahydro-1H-purin-8-yl)amino)-2,3-dihydro-1H-indene-2-carboxylate

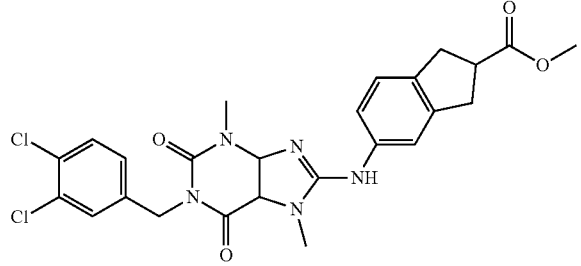 [SMILES: COC(=O)C1Cc2ccc(NC3=NC4C(C(=O)N(Cc5ccc(Cl)c(Cl)c5)C(=O)N4C)N3C)cc2C1]

The title compound was synthesized in a similar fashion as described in Procedure 8B using 8-bromo-1-(3,4-dichlorobenzyl)-3,7-dimethyl-1H-purine-2,6(3H,7H)-dione and methyl 5-amino-2,3-dihydro-1H-indene-2-carboxylate: $^1$H NMR (400 MHz, CDCl$_3$) δ 67.60 (s, 1H) 7.38-7.33 (m, 3H) 7.19 (s, 2H) 6.14 (s, 1H) 5.15 (s, 2H) 3.81 (s, 3H) 3.75 (s, 3H) 3.57 (s, 3H) 3.41-3.23 (m, 5H).

1-(3,4-dichlorobenzyl)-8-((2-(hydroxymethyl)-2,3-dihydro-1H-inden-5-yl)amino)-3,7-dimethyl-1H-purine-2,6(3H,7H)-dione

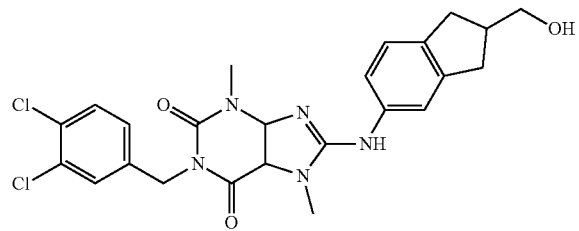 [SMILES: CN1C(=O)N(Cc2ccc(Cl)c(Cl)c2)C(=O)C2C1N=C(Nc1ccc3c(c1)CC(CO)C3)N2C]

To a solution of methyl 5-((1-(3,4-dichlorobenzyl)-3,7-dimethyl-2,6-dioxo-2,3,6,7-tetrahydro-1H-purin-8-yl)

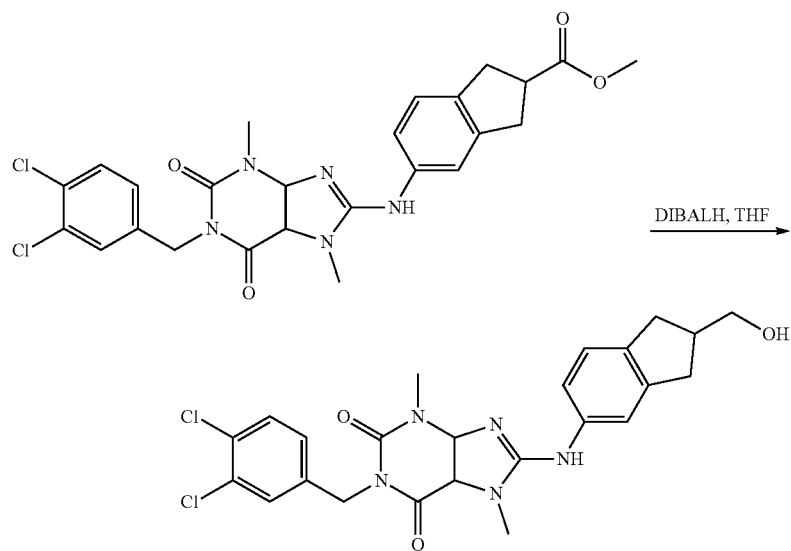

amino)-2,3-dihydro-1H-indene-2-carboxylate (180.00 mg, 340.66 umol) in THF (1.00 mL) was added dropwise DIBAL-H (1 M, 1.3 mL) at −40° C. The mixture was stirred at −40° C. The reaction was quenched with MeOH (10 mL) and H₂O (20 mL) at −40° C. The mixture was extracted with DCM (30 mL*3). The combined organic fractions were washed with brine (15 mL), dried over Na₂SO₄, and concentrated to give crude product which was purified by prep-TLC (EA). ¹H NMR (400 MHz CDCl₃) δ 2.69-2.84 (m, 3H), 3.00-3.16 (m, 2H), 3.58 (s, 3H), 3.66-3.74 (m, 2H), 3.78-3.85 (m, 3H), 5.09-5.20 (m, 2H), 6.04-6.18 (m, 1H), 7.19 (s, 2H), 7.30-7.34 (m, 1H), 7.34-7.43 (m, 2H), 7.58-7.64 (m, 1H); ESI: m/z 500.2 (M+H)⁺.

Example 325

(±)-1-(3,4-dichlorobenzyl)-8-((trans)-3-(hydroxymethyl)cyclopentylamino)-3,7-dimethyl-1H-purine-2,6 (3H,7H)-dione

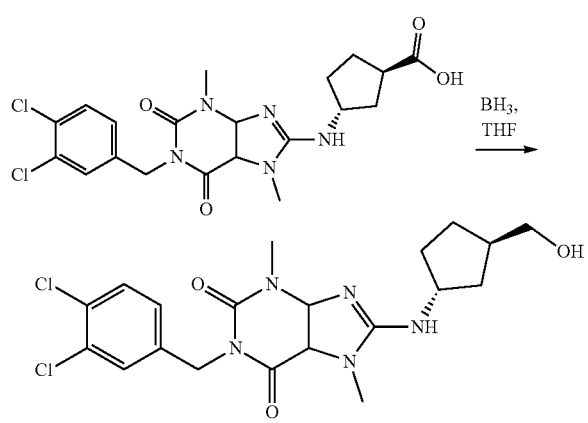

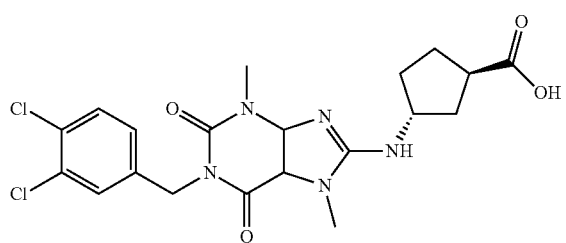 [SMILES: CN1C(=O)N(Cc2ccc(Cl)c(Cl)c2)C(=O)C2C1N=C(N[C@@H]1CC[C@@H](C(=O)O)C1)N2C]

(±)-Ethyl 3-(1-(3,4-dichlorobenzyl)-3,7-dimethyl-2,6-dioxo-2,3,6,7-tetrahydro-1H-purin-8-ylamino)cyclopentanecarboxylate was synthesized in a similar fashion as (1R, 3S)-ethyl 3-(1-(3,4-dichlorobenzyl)-3,7-dimethyl-2,6-dioxo-2,3,6,7-tetrahydro-1H-purin-8-ylamino) cyclopentanecarboxylate described in Example 275. To a solution of ethyl 3-(1-(3,4-dichlorobenzyl)-3,7-dimethyl-2,6-dioxo-2,3,6,7-tetrahydro-1H-purin-8-ylamino)cyclopentanecarboxylate (0.6 mmol, 0.30 g) in methanol (10 mL) was added CH₃ONa (2.4 mmol, 0.13 g). The mixture was stirred at 50° C. for 16 h. The mixture was treated with water (40 mL) and adjusted to pH 5 by addition of NaHCO₃ aqueous solution. The mixture was filtered and the filter cake was dried to give the crude product. The crude product was purified by chiral SFC using a OZ-H column eluting with 20% EtOH (0.1% DEA) in n-Hexane to give two isomers (Retention time=20.606 min, 28.496 min). After comparing the data of cis-structure (Example 276), the isomer (Retention time=20.606 min) was assigned as a trans-structure. ¹H NMR (400 MHz, CD₃OD) δ 7.53 (s, 1H), 7.43-7.41 (d, J=8.4 Hz, 1H), 7.31-7.29 (d, J=8.8 Hz, 1H), 5.07 (s, 2H), 4.37-4.33 (m, 1H), 3.63 (s, 3H), 3.49 (s, 3H), 2.85-2.81 (m, 1H), 2.21-2.19 (m, 1H), 2.03-1.84 (m, 5H); ESI 466.1 (M+H)⁺.

(±)-1-(3,4-dichlorobenzyl)-8-((trans)-3-(hydroxymethyl)cyclopentylamino)-3,7-dimethyl-1H-purine-2,6 (3H,7H)-dione

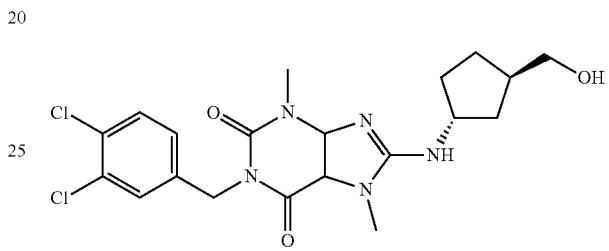

To a solution of (±)-(trans)-3-(1-(3,4-dichlorobenzyl)-3,7-dimethyl-2,6-dioxo-2,3,6,7-tetrahydro-1H-purin-8-ylamino)cyclopentanecarboxylic acid (0.09 mmol, 0.04 g) in THF (1 mL) was added BH₃ in THF (0.2 mL). The mixture was stirred at 0° C. for 0.3 h. The mixture was diluted with methanol and concentrated. The residue was treated with NaHCO₃ aqueous solution (20 mL) and extracted with EA (2*20 mL). The combined organic fractions were concentrated and purified by Prep-HPLC using Method D. ¹H NMR (400 MHz, CD₃OD) δ 7.53-7.52 (m, 1H), 7.43-7.41 (m, 1H), 7.30-7.28 (m, 1H), 5.07 (s, 2H), 4.31-4.24 (m, 1H), 3.61-3.59 (m, 3H), 3.55-3.53 (m, 2H), 3.48-3.47 (m, 3H), 2.32-2.19 (m, 2H), 2.06-2.01 (m, 1H), 1.85-1.77 (m, 1H) 1.67-1.57 (m, 2H), 1.37-1.30 (m, 1H); ESI: m/z 452.2 (M+H)⁺.

Example 326

3,7-dimethyl-1-((6-methyl-1H-indol-2-yl)methyl)-8-(pyridin-4-ylamino)-1H-purine-2,6(3H,7H)-dione

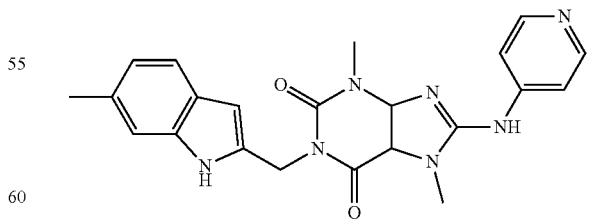

The tert-butyl 2-((3,7-dimethyl-2,6-dioxo-8-(pyridin-4-ylamino)-2,3,6,7-tetrahydro-1H-purin-1-yl)methyl)-6-methyl-1H-indole-1-carboxylate was synthesized in s similar fashion described in Procedure 8A using tert-butyl 2-((8-bromo-3,7-dimethyl-2,6-dioxo-2,3,6,7-tetrahydro-1H- purin-1-yl)methyl)-6-methyl-1H-indole-1-carboxylate and pyridin-4-amine hydrochloride; ESI: m/z 516.3 (M+H)⁺.

A mixture of tert-butyl 2-((3,7-dimethyl-2,6-dioxo-8-(pyridin-4-ylamino)-2,3,6,7-tetrahydro-1H-purin-1-yl)methyl)-6-methyl-1H-indole-1-carboxylate (100 mg, 0.19 mmol) in DCM (10 mL) was treated with TFA (0.5 mL). The reaction mixture was stirred at stirred at rt for 2 h. The resulting solution was concentrated and purified by prep-HPLC using Method D. ¹H NMR (400 MHz, CD₃OD) δ 8.35 (s, 2H), 7.74 (s, 2H), 7.32 (d, J=8.0 Hz, 1H), 7.14 (s, 1H), 6.81 (d, J=7.1 Hz, 1H), 6.34 (s, 1H), 5.29 (s, 2H), 3.92 (s, 3H), 3.60 (s, 3H), 2.40 (s, 3H); ESI: m/z 416.1 (M+H)⁺.

Example 327

8-((1R,3R)-3-(hydroxymethyl)cyclobutylamino)-3,7-dimethyl-1-((4-methyl-1H-indol-2-yl)methyl)-1H-purine-2,6(3H,7H)-dione

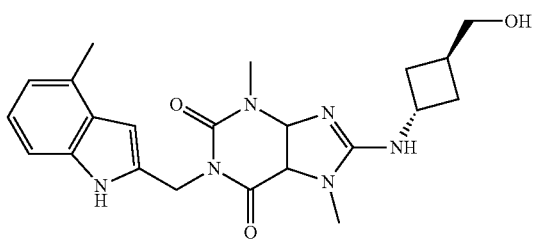 [SMILES: Cc1cccc2[nH]c(CN3C(=O)C4C(N=C(N[C@H]5C[C@H](CO)C5)N4C)N(C)C3=O)cc12]

To a solution of 1-((4-chloro-1H-indol-2-yl)methyl)-8-((1R,3R)-3-(hydroxymethyl)cyclobutylamino)-3,7-dimethyl-1H-purine-2,6(3H,7H)-dione (10.0 mg, 0.023 mmol), methylboronic acid (27 mg, 0.45 mmol) in Toluene/H₂O (0.5 mL/0.2 mL), were added Pd(OAc)₂ (2 mg, 0.023 mmol), n-BuP(Ad)₂ (2 mg, 0.012 mmol) and Cs₂CO₃ (22 mg, 0.069 mmol). The mixture was stirred at 100° C. for 2 h under microwave radiation. The mixture was cooled, diluted with water (3 mL) and extracted with EA (3*3 mL). The combined organic fractions were dried with Na₂SO₄, filtered and concentrated. The residue was purified by prep-HPLC using Method D. ¹H NMR (400 MHz, CD₃OD) δ 7.16 (d, J=8.1 Hz, 1H), 6.98-6.92 (m, 1H), 6.76 (d, J=7.1 Hz, 1H), 6.41 (s, 1H), 5.28 (s, 2H), 3.84-3.61 (m, 5H), 3.52 (s, 3H), 2.44 (d, J=17.9 Hz, 3H), 2.35-2.16 (m, 4H). ESI: m/z 423.3 (M+H)⁺.

Example 328

1-((4-methyl-1H-indol-2-yl)methyl)-3,7-dimethyl-8-(pyridin-4-ylamino)-1H-purine-2,6(3H,7H)-dione

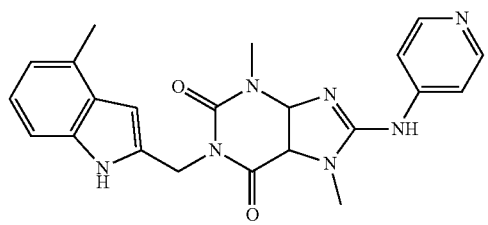 [SMILES: Cc1cccc2[nH]c(CN3C(=O)C4C(N=C(Nc5ccncc5)N4C)N(C)C3=O)cc12]

The tert-butyl 2-((3,7-dimethyl-2,6-dioxo-8-(pyridin-4-ylamino)-2,3,6,7-tetrahydro-1H-purin-1-yl)methyl)-4-methyl-1H-indole-1-carboxylate was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4-methyl-1H-indole-1-carboxylate and pyridin-4-amine hydrochloride. The product was purified by column chromatography (EA/PE=100%) to get tert-butyl 2-((3,7-dimethyl-2,6-dioxo-8-(pyridin-4-ylamino)-2,3,6,7-tetrahydro-1H-purin-1-yl)methyl)-4-methyl-1H-indole-1-carboxylate; ESI: m/z 516.2 (M+H–100)⁺.

A mixture of this product (100 mg, 0.19 mmol) in TFA (2 mL) and DCM (2 mL) was stirred at rt. for 3 h. The mixture was concentrated. The product was purified by prep-HPLC using Method B (45-75% ACN). ¹H NMR (400 MHz, DMSO-d₆) δ 10.80 (s, 1H), 8.36 (s, 2H), 7.66 (d, J=4.0 Hz, 2H), 7.17 (d, J=8.0 Hz, 1H), 6.98-6.84 (m, 1H), 6.73 (d, J=7.1 Hz, 1H), 6.24 (d, J=1.1 Hz, 1H), 5.19 (s, 2H), 3.83 (s, 3H), 3.48 (s, 3H), 2.39 (s, 3H); ESI: m/z 416.2 (M+H)⁺.

Example 329

3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N,N-dimethylpropanamide

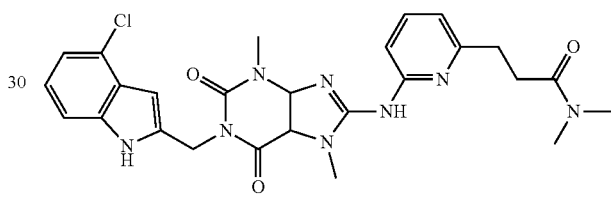

A mixture of 3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid (35 mg, 0.069 mmol), dimethylamine hydrochloride (85 mg, 1.04 mmol), HATU (40 mg, 0.104 mmol) and DIEA (45 mg, 0.345 mmol) in DMF (2 mL) was stirred for 1 h at 25° C. The reaction mixture was poured into water (20 mL) and the precipitate was collected by filtration, dried in vacuo, and purified by prep-HPLC using Method A. ¹H NMR (400 MHz, DMSO-d₆) δ 11.28 (br s, 1H), 9.82 (br s, 1H), 7.67-7.55 (m, 2H), 7.35-7.32 (m, 1H), 7.05-6.98 (m, 2H), 6.90-6.88 (m, 1H), 6.28 (s, 1H), 5.21 (s, 2H), 3.78 (s, 3H), 3.45 (s, 3H), 2.92 (s, 3H), 2.87 (t, J=7.6 Hz, 2H), 2.79 (s, 3H), 2.69 (t, J=7.6 Hz, 2H); ESI: m/z 535.2 (M+H)⁺.

Example 330

3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N-methylpropanamide

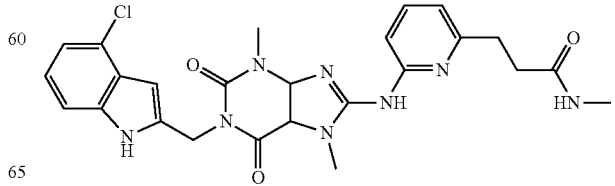

The title compound was synthesized in a similar fashion as example 329 using methanamine hydrochloride. The product was purified by prep-HPLC using Method A (35-65% ACN). $^1$H NMR (400 MHz, DMSO-d$_6$) δ 11.27 (br s, 1H), 9.85 (br s, 1H), 7.78-7.60 (m, 3H), 7.35-7.30 (m, 1H), 7.06-6.98 (m, 2H), 6.86-6.81 (m, 1H), 6.28 (s, 1H), 5.21 (s, 2H), 3.80 (s, 3H), 3.45 (s, 3H), 2.87 (t, J=8.0 Hz, 2H), 2.55 (s, 3H), 2.46 (t, J=8.0 Hz, 2H). ESI: m/z 521.2 (M+H)$^+$.

Example 331

4-[[1-[(4-chloro-1H-indol-2-yl)methyl]-3,7-dimethyl-2,6-dioxo-purin-8-yl]amino]benzoic acid

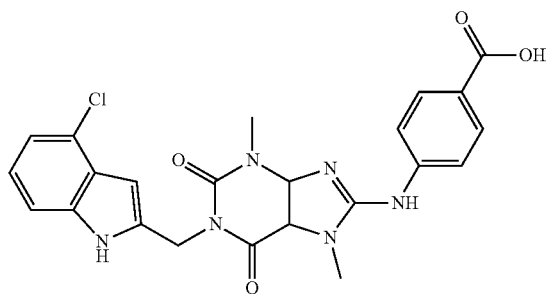 [SMILES: CN1C(=O)N(Cc2cc3c(Cl)cccc3[nH]2)C(=O)C2C1N=C(Nc1ccc(C(=O)O)cc1)N2C]

The title compound was synthesized in a similar fashion as procedure 8B using tert-butyl 2-[(8-bromo-3,7-dimethyl-2,6-dioxo-purin-1-yl)methyl]-4-chloro-indole-1-carboxylate and methyl 4-aminobenzoate. The product was purified by prep-TLC (petroleum ether/ethyl acetate=1/1) to obtain a mixture of tert-butyl 4-chloro-2-((8-((4-(methoxycarbonyl)phenyl)amino)-3,7-dimethyl-2,6-dioxo-2,3,6,7-tetrahydro-1H-purin-1-yl)methyl)-1H-indole-1-carboxylate and methyl 4-((1-((4-chloro-1H-indol-2-yl)methyl)-3,7-dimethyl-2,6-dioxo-2,3,6,7-tetrahydro-1H-purin-8-yl)amino)benzoate (de-Boc product).

The mixture of tert-butyl 4-chloro-2-((8-((4-(methoxycarbonyl)phenyl)amino)-3,7-dimethyl-2,6-dioxo-2,3,6,7-tetrahydro-1H-purin-1-yl)methyl)-1H-indole-1-carboxylate and methyl 4-((1-((4-chloro-1H-indol-2-yl)methyl)-3,7-dimethyl-2,6-dioxo-2,3,6,7-tetrahydro-1H-purin-8-yl)amino)benzoate (de-Boc product) (70.00 mg) was dissolved in 2N NaOH (500.00 uL), MeOH (1.00 mL) and THF (1.00 mL). The mixture was stirred for 15 h at 25° C. and 50° C. for 3 h. The mixture was concentrated in vacuum. The mixture was acidified with 3N HCl to pH=1-2 at 0° C. and concentrated. The residue was purified by prep-HPLC using Method C (30-60% ACN). $^1$H NMR (40 MHz, 400 MHz, DMSO-d$_6$) δ 11.28 (br. s., 1H), 9.58 (s, 1H), 7.87-7.95 (m, 2H), 7.73-7.82 (m, 2H), 7.34 (ddd, J=6.62, 2.21, 0.88 Hz, 1H), 6.97-7.06 (m, 2H), 6.27 (d, J=1.76 Hz, 1H), 5.21 (s, 2H), 3.77-3.90 (m, 3H), 3.48 (s, 3H). ESI: m/z 479.2 (M+H)$^+$.

Example 332

(±)-cis-2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

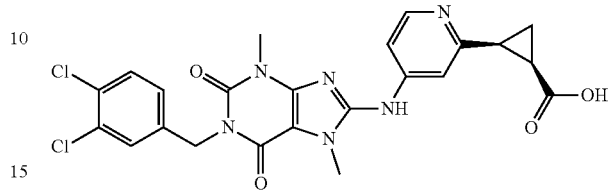

The title compound was synthesized in a similar fashion as described in Procedure 8B using 8-bromo-1-[(3,4-dichlorophenyl)methyl]-3,7-dimethyl-purine-2,6-dione and (±)-cis-ethyl 2-(4-aminopyridin-2-yl)cyclopropanecarboxylate. The product was purified by prep-TLC (DCM/MeOH=10/1) to give (±)-cis-ethyl 2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate: $^1$H NMR (400 MHz, CDCl$_3$) δ 8.38 (s, 1H), 7.61 (s, 1H), 7.28-7.41 (m, 4H), 5.15 (s, 2H), 3.97-4.01 (q, J=7.2 Hz, 2H), 3.89 (s, 3H), 3.61 (s, 3H), 2.73-2.75 (m, 1H), 2.23-2.27 (m, 1H), 1.80-1.82 (m, 1H), 1.25-1.35 (m, 1H), 1.10-1.14 (t, J=7.2 Hz, 3H).

To a solution of (±)-cis-ethyl 2-(4-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate (30.00 mg, 55.21 umol) in THF (1.00 mL) and MeOH (1.00 mL) was added 2N NaOH (500.00 uL) at 25° C. The mixture was stirred for 15 h at 25° C. The mixture was concentrated. The aqueous residue was acidified with 3N HCl at 0° C. to pH=1-2. The solid was collected by filtration, washed with H$_2$O (2 mL), TBME (5 mL) and dried under high vacuum. $^1$H NMR (400 MHz, DMSO-d$_6$) δ 11.57 (s, 1H), 8.47 (d, J=7.03 Hz, 1H), 8.08 (br. s., 2H), 7.51-7.66 (m, 2H), 7.32 (dd, J=8.03, 2.01 Hz, 1H), 5.06 (s, 2H), 3.96 (s, 3H), 3.48 (s, 3H), 2.91 (q, J=8.53 Hz, 1H), 2.22-2.31 (m, 1H), 1.60-1.71 (m, 2H); ESI: m/z 515.2 (M+H)$^+$.

Example 333

1-[(4-chloro-1H-indol-2-yl)methyl]-8-[(2-methoxy-4-pyridyl)amino]-3,7-dimethyl-purine-2,6-dione

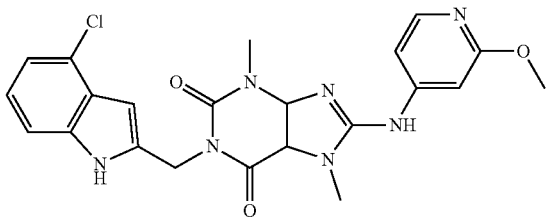 [SMILES: COc1cc(NC2=NC3C(C(=O)N(Cc4cc5c(Cl)cccc5[nH]4)C(=O)N3C)N2C)ccn1]

The title compound was synthesized in a similar fashion as Procedure 8B using tert-butyl 2-[(8-bromo-3,7-dimethyl-2,6-dioxo-purin-1-yl)methyl]-4-chloro-indole-1-carboxylate and 2-methoxypyridin-4-amine. The product was purified by prep-HPLC using Method C (25-50% ACN). $^1$H NMR (400 MHz DMSO-d$_6$) δ 11.30 (s, 1H), 8.05 (d, J=6.0

Hz, 1H), 7.42-7.26 (m, 3H), 7.07-6.96 (m, 2H), 6.27 (s, 1H), 5.21 (s, 2H), 3.90 (s, 3H), 3.86 (s, 3H), 3.48 (s, 3H); ESI: m/z 466.2 (M+H)+.

Example 334

1-[(4-chloro-1H-indol-2-yl)methyl]-8-[(2-trifluoromethyl-4-pyridyl)amino]-3,7-dimethyl-purine-2,6-dione

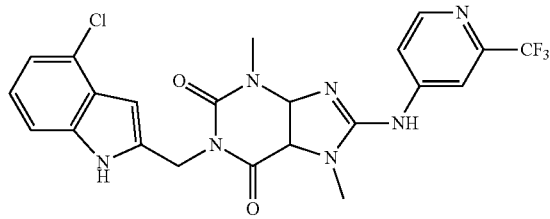

The title compound was synthesized in a similar fashion as Procedure 8B using tert-butyl 2-[(8-bromo-3,7-dimethyl-2,6-dioxo-purin-1-yl)methyl]-4-chloro-indole-1-carboxylate and 2-(trifluoromethyl)pyridin-4-amine. The product was purified by prep-HPLC using Method A (40-65% ACN). $^1$H NMR (400 MHz, DMSO-d$_6$) δ 11.31 (br. s., 1H), 10.12 (s, 1H), 8.57 (d, J=5.3 Hz, 1H), 8.19 (d, J=2.2 Hz, 1H), 8.03-7.94 (m, 1H), 7.34 (dd, J=2.4, 6.4 Hz, 1H), 7.07-6.96 (m, 2H), 6.25 (s, 1H), 5.20 (s, 2H), 3.84 (s, 3H), 3.47 (s, 3H); ESI: m/z 504.2 (M+H)+.

Example 335

(±)-trans-1-((4-chloro-1H-indol-2-yl)methyl)-8-((6-(-2-(hydroxymethyl)cyclopropyl)pyridin-2-yl)amino)-3,7-dimethyl-1H-purine-2,6(3H,7H)-dione

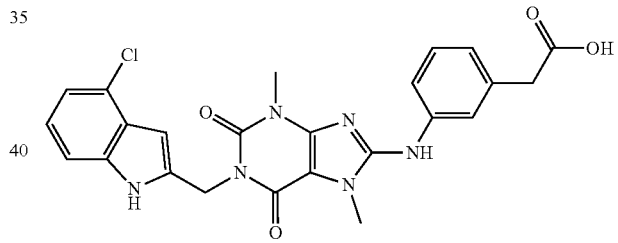

To a solution of (±)-trans-tert-butyl 4-chloro-2-((8-((6-(-2-(ethoxycarbonyl)cyclopropyl)pyridin-2-yl)amino)-3,7-dimethyl-2,6-dioxo-2,3,6,7-tetrahydro-1H-purin-1-yl)methyl)-1H-indole-1-carboxylate (60.00 mg, 92.58 umol) in toluene (1.00 mL) was added DIBAL-H (1 M, 231.45 uL) dropwise at −40° C. under N$_2$. The reaction mixture was stirred at −40° C. for 20 mins. The reaction was quenched with MeOH (0.5 mL) and H$_2$O (1 mL). The reaction mixture warmed to 25° C. and stirred for 10 mins. The mixture was extracted with DCM (1 mL*3), the combined organic fractions were washed with brine (0.5 mL), dried over Na$_2$SO$_4$, concentrated in vacuum. The crude product was purified by Prep-HPLC using Method C (35-55% ACN). $^1$H NMR (400 MHz, DMSO-d$_6$) δ 14.33-14.60 (m, 1H), 11.51-11.70 (m, 1H), 8.40-8.62 (m, 2H), 7.47-7.65 (m, 2H), 7.23-7.35 (m, 3H), 4.90-5.02 (m, 2H), 4.51-4.67 (m, 2H), 4.33-4.46 (m, 2H); ESI: m/z 506.2 (M+H)+.

Example 336

N-[1-[(4-chloro-1H-indol-2-yl)methyl]-3,7-dimethyl-2,6-dioxo-purin-8-yl]methanesulfonamide

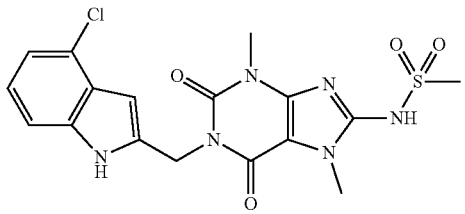 [SMILES: Cn1c(NS(C)(=O)=O)nc2c1c(=O)n(Cc1cc3c(Cl)cccc3[nH]1)c(=O)n2C]

The title compound was synthesized in a similar fashion as Procedure 8B using tert-butyl 2-[(8-bromo-3,7-dimethyl-2,6-dioxo-purin-1-yl)methyl]-4-chloro-indole-1-carboxylate and methanesulfonamide. The product was purified by prep-HPLC using method E (15-45% ACN). $^1$H NMR (400 MHz, CD$_3$OD) δ 7.26 (m, 1H), 6.95-7.00 (m, 2H), 6.41 (s, 1H), 5.28 (s, 2H), 3.61 (s, 3H), 3.52 (s, 3H), 3.15 (s, 3H); ESI: m/z 437.1 (M+H)+.

Example 339

2-(3-((1-((4-chloro-1H-indol-2-yl)methyl)-3,7-dimethyl-2,6-dioxo-2,3,6,7-tetrahydro-1H-purin-8-yl)amino)phenyl)acetic acid tert-Butyl 2-((8-bromo-3,7-dimethyl-2,6-dioxo-2,3,6,7-tetrahydro-1H-purin-1-yl)methyl)-4-chloro-1H-indole-1-carboxylate and methyl 2-(3-aminophenyl)acetate were coupled according to Procedure 8B. The product was purified by prep-TLC (PE/EA=1/1,) to provide tert-butyl-4-chloro-2-((8-((3-(2-methoxy-2-oxoethyl)phenyl)amino)-3,7-dimethyl-2,6-dioxo-2,3,6,7-tetrahydro-1H-purin-1-yl)methyl)-1H-indole-1-carboxylate (70.00 mg, containing de-Boc product).

To a mixture of the product obtained above (70.00 mg, 115.31 umol,) in THF (1.00 mL) and MeOH (1.00 mL) was added 2N NaOH (500.00 uL) dropwise at 25° C. The mixture was stirred at 25° C. for 13 hr. The mixture was concentrated under reduced pressure at 45° C. The residue was diluted with water (2 mL) and stirred for 20 min. The aqueous phase was extracted with EA (10 mL*3). The water layer was concentrated under reduced pressure. The aqueous residue was acidified to 1 (3N HCl). The mixture was evaporated in vacuo. The residue was purified by prep-HPLC using Method C (35-65% ACN). $^1$H NMR (400 MHz, DMSO-d$_6$) δ 11.27 (br. s., 1H), 9.20 (s, 1H), 7.63 (d, J=9.0 Hz, 1H), 7.57 (s, 1H), 7.33 (d, J=8.5 Hz, 1H), 7.26 (t, J=8.0

Hz, 1H), 6.98-7.06 (m, 2H), 6.88 (d, J=7.5 Hz, 1H), 6.26 (s, 1H), 5.20 (s, 2H), 3.80 (s, 3H), 3.54 (s, 2H), 3.45 (s, 3H); ESI: m/z 493.2 (M+H)⁺.

Example 340

3,7-dimethyl-1-((3-methyl-1H-indol-2-yl)methyl)-8-(pyridin-4-ylamino)-1H-purine-2,6(3H,7H)-dione

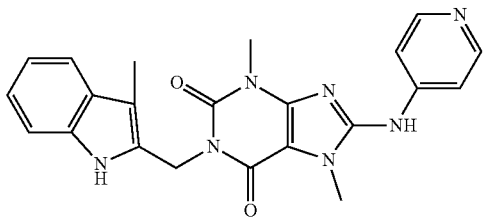 [SMILES: Cc1c(Cn2c(=O)c3c(nc(Nc4ccncc4)n3C)n(C)c2=O)[nH]c2ccccc12]

tert-Butyl 2-((8-bromo-3,7-dimethyl-2,6-dioxo-2,3,6,7-tetrahydro-1H-purin-1-yl)methyl)-3-methyl-1H-indole-1-carboxylate and pyridin-4-amine hydrochloride were reacted in a similar fashion as described in procedure 8A. The product was purified by flash chromatography (EA/PE=1/1) to give tert-butyl 2-((3,7-dimethyl-2,6-dioxo-8-(pyridin-4-ylamino)-2,3,6,7-tetrahydro-1H-purin-1-yl)methyl)-3-methyl-1H-indole-1-carboxylate; ESI: m/z 516.3 (M+H)⁺.

The product obtained above was dissolved in DCM (2 mL) and treated with TFA (2 mL). The reaction mixture was stirred at 20° C. for 2 h. The reaction mixture was concentrated and the pH was adjusted to pH=8 by addition of NaHCO₃ aq. solution. The mixture was extracted with EA (2*20 mL). The combined organic fractions were concentrated and purified by Prep-HPLC using Method D (50-70% ACN). ¹H NMR (400 MHz, CD₃OD) δ 8.34 (br s, 1H), 7.71 (d, J=5.2 Hz, 1H), 7.43-7.41 (m, 1H), 7.27-7.25 (m, 1H), 7.04-6.95 (m, 2H), 5.30 (s, 2H), 3.89 (s, 3H), 3.58 (s, 3H), 2.41 (s, 3H); ESI: m/z 416.1 (M+H)⁺.

Example 341

3-(7-(2-carboxyethyl)-1-(3,4-dichlorobenzyl)-3-methyl-2,6-dioxo-2,3,6,7-tetrahydro-1H-purin-8-ylamino)cyclohexanecarboxylic acid

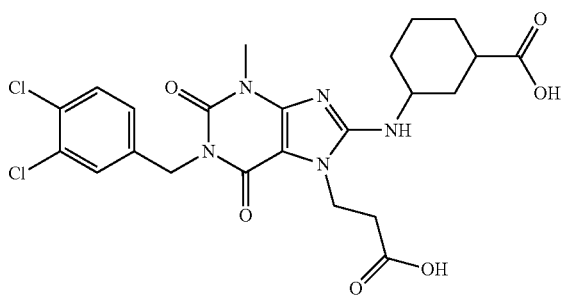 [SMILES: Cn1c(=O)n(Cc2ccc(Cl)c(Cl)c2)c(=O)c2c1nc(NC1CCCC(C(=O)O)C1)n2CCC(=O)O]

To a solution of methyl 3-(7-(3-amino-3-oxopropyl)-1-(3,4-dichlorobenzyl)-3-methyl-2,6-dioxo-2,3,6,7-tetrahydro-1H-purin-8-ylamino)cyclohexanecarboxylate (40 mg, 0.07 mmol) in MeOH (2 mL) and H₂O (2 mL) was added NaOH (14 mg, 0.35 mmol). The resulting mixture was stirred at 50° C. for 48 h. The mixture was filtered and the filtrate was purified by Prep-HPLC using Method B (25-55% ACN). ¹H NMR (400 MHz, DMSO-d₆) δ 7.54 (dd, J=8.5, 5.1 Hz, 2H), 7.25 (dd, J=8.4, 1.9 Hz, 1H), 4.98 (s, 2H), 4.10 (d, J=7.0 Hz, 2H), 3.60 (s, 2H), 3.46-3.40 (m, 3H), 2.38-2.24 (m, 2H), 2.19-2.10 (m, 1H), 2.00-1.68 (m, 4H), 1.39-1.14 (m, 4H); ESI: m/z 538.2 (M+H)⁺.

Example 342

3-(3,7-dimethyl-1-((4-methyl-1H-indol-2-yl)methyl)-2,6-dioxo-2,3,6,7-tetrahydro-1H-purin-8-ylamino)cyclohexanecarboxylic acid

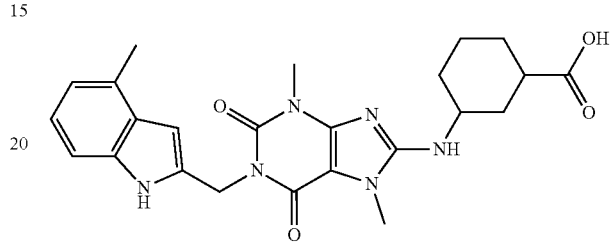

To a mixture of 3-(1-((4-chloro-1H-indol-2-yl)methyl)-3,7-dimethyl-2,6-dioxo-2,3,6,7-tetrahydro-1H-purin-8-ylamino)cyclohexanecarboxylic acid (20 mg, 0.04 mmol), Cs₂CO₃ (40 mg, 0.12 mmol), Pd(OAc)₂ (9 mg, 0.004 mmol), methylboronic acid (5 mg, 0.08 mmol) in toluene (1 mL), H₂O (0.2 mL) was added n-BuP(Ad)₂ (28 mg, 0.008 mmol). The mixture was stirred at 100° C. for 2 h in a microwave reactor. The mixture was diluted with water (20 mL) and extracted with EA (2*50 mL). The combined organic fractions were concentrated and purified by Prep-HPLC using Method D. ¹H NMR (400 MHz, CD₃OD) δ 7.16 (d, J=8.1 Hz, 1H), 6.95 (dd, J=8.2, 7.1 Hz, 1H), 6.76 (d, J=7.3 Hz, 1H), 6.41 (s, 1H), 5.29 (s, 2H), 3.92-3.78 (m, 1H), 3.66 (s, 3H), 3.53 (s, 3H), 2.46 (s, 3H), 2.34-2.25 (m, 1H), 2.06 (m, 1H), 2.02-1.88 (m, 1H), 1.52-1.34 (m, 4H); ESI: m/z 465.3 9M+H)⁺.

Example 343

1-((4-chloro-1H-indol-2-yl)methyl)-3,7-dimethyl-8-(pyridin-3-ylamino)-1H-purine-2,6(3H,7H)-dione

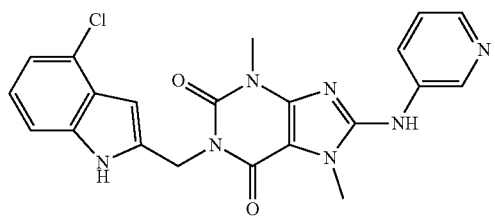 [SMILES: Cn1c(Nc2cccnc2)nc2c1c(=O)n(Cc1cc3c(Cl)cccc3[nH]1)c(=O)n2C]

The title compound was synthesized in a similar fashion as procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and pyridin-3-amine. The product was purified by flash chromatography (DCM/MeOH=10/1); ESI: m/z 536.2 (M+H)⁺. The Boc protecting group was removed from this compound according to Procedure 6. The product was purified by purified by Prep-HPLC using Method D (50-70% ACN). ¹H NMR (400

MHz, DMSO-$d_6$) δ 11.29 (br s, 1H), 9.42 (s, 1H), 8.87 (s, 1H), 8.24 (m, 2H), 7.34 (m, 2H), 7.02-7.00 (m, 2H), 6.26 (s, 1H), 5.20 (s, 2H), 3.83 (s, 3H), 3.45 (m, 1H); ESI: m/z 436.1 (M+H)$^+$.

Example 344

1-(3,4-diclorobenzyl)-8-(2-(3-hydroxylcyclobutyl)pyridine-4-ylamino)-3,7-dimethyl-1-H-purine-2,6(3H,7H)-dione

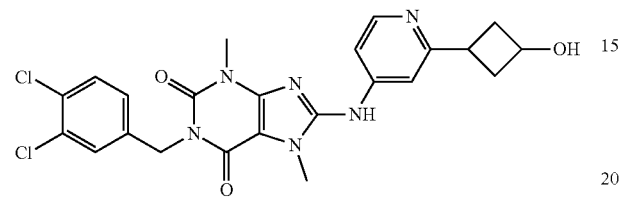

The title compound was synthesized according to Procedure 8A using 3-(4-aminopyridin-2-yl) cyclobutanol and 8-bromo-1-(3,4-dichlorobenzyl)-3,7-dimethyl-1H-purine-2,6(3H,7H)-dione. The product was purified by prep-HPLC using Method D (30-60% ACN). $^1$H NMR (400 MHz, CD$_3$OD) δ 8.28 (d, J=4.0 Hz, 1H), 7.78 (s, 1H), 7.58 (s, 1H), 7.55 (d, J=4.4 Hz, 1H), 7.46 (d, J=8.4 Hz, 1H), 7.35 (d, J=8.4 Hz, 1H), 5.14 (s, 2H), 4.50-4.54 (m, 1H), 3.90 (s, 3H), 3.60-3.63 (m, 1H), 3.58 (s, 3H), 2.10 (m, 1H), 2.46-2.61 (m, 2H), 2.40-2.46 (m, 2H); ESI: m/z 501.2 (M+H)$^+$.

Example 345

2-[4-[[1-[(4-chloro-1H-indol-2-yl)methyl]-3,7-dimethyl-2,6-dioxo-purin-8-yl]amino]phenyl]acetic acid

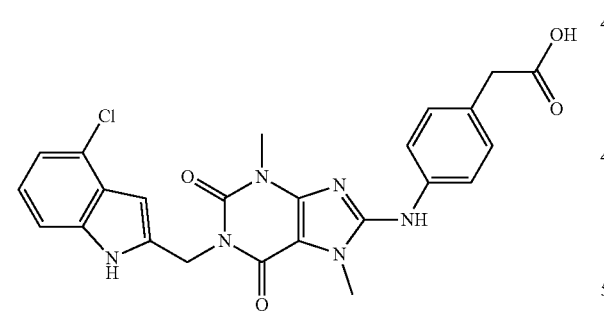

tert-Butyl 4-chloro-2-((8-((4-(2-ethoxy-2-oxoethyl)phenyl)amino)-3,7-dimethyl-2,6-dioxo-2,3,6,7-tetrahydro-1H-purin-1-yl)methyl)-1H-indole-1-carboxylate was synthesized in a similar fashion as Procedure 8B using tert-butyl 2-[(8-bromo-3,7-dimethyl-2,6-dioxo-purin-1-yl)methyl]-4-chloro-indole-1-carboxylate and ethyl 2-(4-aminophenyl)acetate. The product was purified by prep-TLC (PE/EA=2/1) to obtain a mixture of tert-butyl 4-chloro-2-((8-((4-(2-ethoxy-2-oxoethyl)phenyl)amino)-3,7-dimethyl-2,6-dioxo-2,3,6,7-tetrahydro-1H-purin-1-yl)methyl)-1H-indole-1-carboxylate and ethyl 2-(4-((1-((4-chloro-1H-indol-2-yl)methyl)-3,7-dimethyl-2,6-dioxo-2,3,6,7-tetrahydro-1H-purin-8-yl)amino)phenyl)acetate. This product was dissolved in THF (3.00 mL) and MeOH (3.00 mL) and treated with 3N NaOH (1.00 mL). The mixture was stirred at 25° C. for 16 hr. The mixture was concentrated and the aqueous residue was acidified with 3N HCl at 0° C. to pH=1. The mixture was concentrated to give crude product which was purified by prep-HPLC using Method C (37-67% ACN). $^1$H NMR (400 MHz DMSO-$d_6$) δ 11.27 (br. s., 1H), 9.16 (s, 1H), 7.60 (d, J=8.8 Hz, 2H), 7.33 (d, J=9.3 Hz, 1H), 7.20 (d, J=8.4 Hz, 2H), 7.06-6.95 (m, 2H), 6.26 (br. s., 1H), 5.20 (s, 2H), 3.80 (s, 3H), 3.51 (s, 2H), 3.44 (s, 3H); ESI: m/z 493.2 (M+H)$^+$.

Example 346

3-[[1-[(4-chloro-1H-indol-2-yl)methyl]-3,7-dimethyl-2,6-dioxo-purin-8-yl]amino]benzoic acid

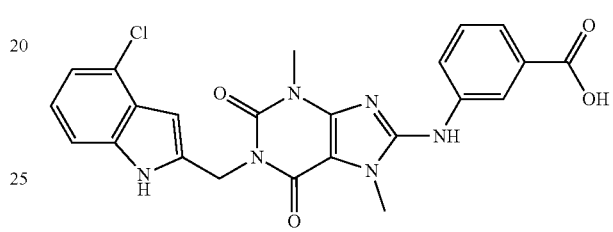

The title compound was synthesized in a similar fashion as example 345 using 3-aminobenzoate. The product was purified by prep-HPLC using Method C (37-67% ACN). $^1$H NMR (400 MHz, DMSO-$d_6$) δ 11.25 (br. s., 1H), 9.38 (s, 1H), 8.26 (br. s., 1H), 8.01 (d, J=10.1 Hz, 1H), 7.54 (d, J=7.9 Hz, 1H), 7.46-7.40 (m, 1H), 7.31 (d, J=6.6 Hz, 1H), 7.04-6.96 (m, 2H), 6.24 (s, 1H), 5.18 (s, 2H), 3.80 (s, 3H), 3.44 (s, 3H); ESI: m/z 479.2 (M+H)$^+$.

Example 347

1-((4-chloro-1H-indol-2-yl)methyl)-8-((1S,2R)-2-hydroxycyclopentylamino)-3,7-dimethyl-1H-purine-2,6(3H,7H)-dione

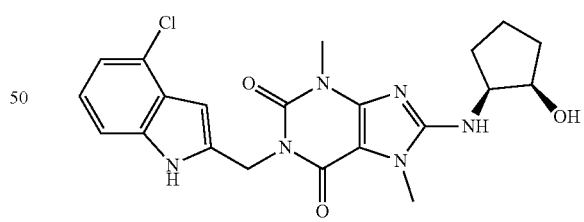

The title compound was synthesized according to Procedure 7A using tert-butyl 2-((8-bromo-3,7-dimethyl-2,6-dioxo-2,3,6,7-tetrahydro-1H-purin-1-yl)methyl)-4-chloro-1H-indole-1-carboxylate and (1R,2S)-2-aminocyclopentanol. The product was purified by prep-HPLC using Method D. $^1$H NMR (400 MHz, DMSO-$d_6$) δ 11.24 (s, 1H), 7.32 (dd, J=6.4, 1.8 Hz, 1H), 7.05-6.94 (m, 2H), 6.57 (d, J=7.8 Hz, 1H), 6.21 (s, 1H), 5.16 (s, 2H), 4.66 (d, J=3.7 Hz, 1H), 4.17-4.04 (m, 1H), 4.02-3.89 (m, 1H), 3.61 (s, 3H), 3.37 (s, 3H), 1.94-1.83 (m, 1H), 1.82-1.65 (m, 3H), 1.63-1.44 (m, 2H); ESI: m/z 443.2 (M+H)$^+$.

Example 348

1-((4-bromo-1H-indol-2-yl)methyl)-3,7-dimethyl-8-(pyridin-4-ylamino)-1H-purine-2, 6(3H,7H)-dione

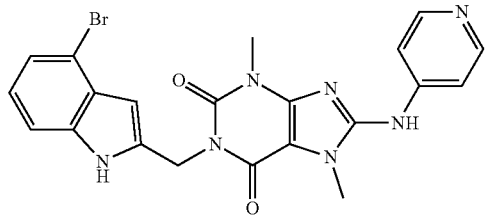 [SMILES: Cn1c(Nc2ccncc2)nc2c1c(=O)n(Cc1cc3c(Br)cccc3[nH]1)c(=O)n2C]

A solution of tert-butyl 4-bromo-2-(chloromethyl)-1H-indole-1-carboxylate (0.7 mmol, 250 mg), tert-butyl 3,7-dimethyl-2,6-dioxo-8-(pyridin-4-ylamino)-2,3,6,7-tetrahydro-1H-purine-1-carboxylate (0.2 mmol, 120 mg) and $K_2CO_3$ (0.3 mmol, 42 mg) in DMF (6 mL) was stirred and heated to 50° C. overnight. The mixture was poured into water and extracted with EA (2*40 mL). The combined organic fractions were dried with $Na_2SO_4$, filtered and concentrated. The residue was purified by flash chromatography (DCM/MeOH=10/1) to give tert-butyl 4-bromo-2-((3,7-dimethyl-2,6-dioxo-8-(pyridin-4-ylamino)-2,3,6,7-tetrahydro-1H-purin-1-yl)methyl)-1H-indole-1-carboxylate; ESI: m/z: 580.2 (M+H)$^+$. To a solution of this product (0.06 mmol, 60 mg) in DCM (4 mL) was added TFA (2 mL). The mixture was stirred at 25° C. for 2 h. The mixture was purified by Prep-HPLC using Method D to give the title compound. $^1$H NMR (400 MHz, $d_6$-DMSO) δ 11.73 (s, 1H), 10.68 (s, 1H), 7.87 (d, J=7.2 Hz, 2H), 7.58-7.16 (m, 4H), 7.06 (t, J=1.6 Hz, 1H), 6.47 (s, 1H), 5.33 (s, 2H), 3.63 (s, 3H), 3.35 (s, 3H); ESI: m/z 480.1 (M+H)$^+$.

Example 349

3,7-dimethyl-1-(naphthalen-2-ylmethyl)-8-(pyridin-4-ylamino)-1H-purine-2,6(3H,7H)-dione

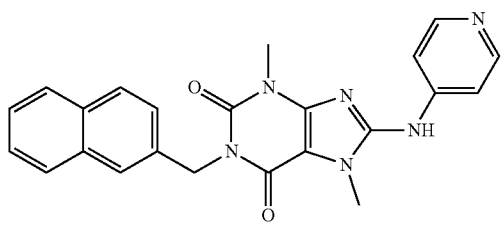 [SMILES: Cn1c(Nc2ccncc2)nc2c1c(=O)n(Cc1ccc3ccccc3c1)c(=O)n2C]

The title compound was synthesized in a similar fashion as Procedure 8A using 8-bromo-3,7-dimethyl-1-(naphthalen-2-ylmethyl)-1H-purine-2,6(3H,7H)-dione and pyridin-4-amine hydrochloride. The mixture was purified by column chromatography (DCM/MeOH from 50/1 to 5/1) to give the crude product. The crude product was purified by Prep-HPLC using Method B (30-65% ACN). $^1$H NMR (400 MHz, DMSO-$d_6$) δ 9.68 (s, 1H), 8.37 (s, 2H), 7.86 (dd, J=8.7, 5.1 Hz, 3H), 7.77 (s, 1H), 7.67 (d, J=4.2 Hz, 2H), 7.54-7.39 (m, 3H), 5.21 (s, 2H), 3.82 (s, 3H), 3.46 (s, 3H); ESI: m/z 413.2 (M+H)$^+$.

Example 350

2-((3,7-dimethyl-2,6-dioxo-8-(pyridin-4-ylamino)-2,3,6,7-tetrahydro-1H-purin-1-yl)methyl)-1H-indole-4-carbonitrile

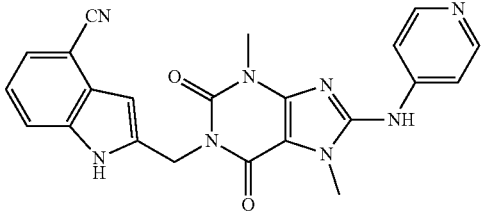

A solution of 1-((4-bromo-1H-indol-2-yl)methyl)-3,7-dimethyl-8-(pyridin-4-ylamino)-1H-purine-2, 6 (3H, 7H)-dione (0.02 mmol, 10 mg), Zn(CN)$_2$ (0.05 mmol, 6 mg), Zn (0.01 mmol, 1 mg), Pd(dppf)Cl$_2$ (0.003 mmol, 2 mg), and Pd$_2$(dba)$_3$ (0.002 mmol, 2 mg) in DMF (4 mL) was placed in microware reactor (120° C., 4 h). The mixture was poured into water and extracted with EA (2*30 mL). The combined organic fractions were dried with Na$_2$SO$_4$, filtered and concentrated. The mixture was purified by Prep-HPLC using Method D. $^1$H NMR (400 MHz, $d_6$-DMSO) δ 12.04 (s, 1H), 10.68 (s, 1H), 7.88 (d, J=7.6 Hz, 2H), 7.74 (d, J=8.0 Hz, 1H), 7.66-6.96 (m, 4H), 6.65 (s, 1H), 5.38 (s, 2H), 3.63 (s, 3H), 3.33 (s, 3H); ESI: m/z 427.2 (M+H)$^+$.

Example 351

1-((4-chloro-1H-indol-2-yl)methyl)-8-(6-(3-hydroxycyclopentyl) pyridin-2-ylamino)-3,7-dimethyl-1H-purine 2,6(3H,7H)-dione

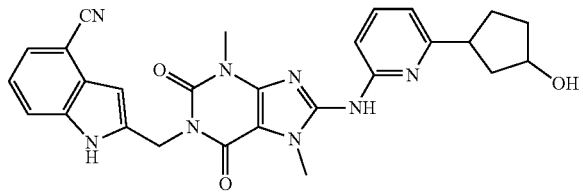 [SMILES: Cn1c(Nc2cccc(C3CCC(O)C3)n2)nc2c1c(=O)n(Cc1cc3c(C#N)cccc3[nH]1)c(=O)n2C]

The title compound was synthesized in a similar fashion as Procedure 8A using 3-(6-aminopyridin-2-yl)cyclopentanol and 8-bromo-1-((4-chloro-1H-indol-2-yl)methyl-3,7-dimethyl-1H-purine-2,6(3H,7H)-indole. The mixture was poured into water (10 ml) and filtered. The filter cake was purified by prep-HPLC using Method D (30-60% ACN). ESI: m/z 620.2 (M+H)$^+$. This product was subjected to TFA in DCM according to procedure 6. The residue was purified by prep-HPLC using Method D (30-70% ACN). $^1$H NMR (400 MHz, DMSO-$d_6$) δ 11.28 (s, 1H), 9.73 (br s, 1H), 7.63 (t, J=7.8 Hz, 1H), 7.56 (d, J=8.3 Hz, 1H), 7.34 (d, J=6.5, 2.6 Hz, 1H), 7.07-6.97 (m, 2H), 6.87 (d, J=7.1 Hz, 1H), 6.28 (s, 1H), 5.21 (s, 2H), 4.51 (s, 1H), 4.29 (s, 1H), 3.80 (s, 3H), 3.45 (s, 3H), 1.99 (s, 1H), 1.87 (dd, J=9.5, 4.3 Hz, 2H), 1.75-1.63 (m, 2H), 1.56 (s, 1H); ESI: m/z 520.2 (M+H)$^+$.

Example 352

1-(3,4-diclorobenzyl)-8-(6-(3-hydroxycyclobutyl)pyridine-2-ylamino)-3,7-dimethyl-1H-purine-2,6(3H,7H)-dione

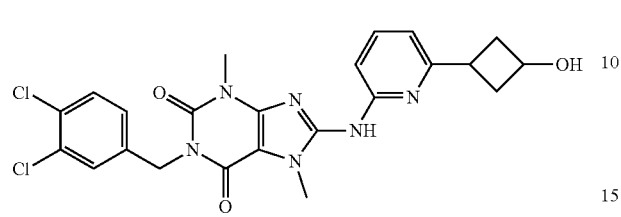

The title compound was synthesized according to procedure 8A using 3-(6-aminopyridin-2-yl)cyclobutanol and 8-bromo-1-(3,4-dichlorobenzyl)-3,7-dimethyl-1H-purine-2,6(3H,7H)-dione. The product was purified by prep-HPLC using Method D (30-60% ACN). $^1$H NMR (400 MHz, CD$_3$OD) δ 9.76 (s, 1H), 7.56-7.65 (m, 4H), 7.30 (d, J=8.4 Hz, 1H), 6.88 (s, 1H), 5.03 (s, 3H), 4.07-4.41 (m, 1H), 3.79 (s, 3H), 3.42 (s, 3H), 2.03-2.51 (m, 4H); ESI: m/z 501.2 (M+H)$^+$.

Example 353

8-(2-amino-1H-benzo[d]imidazol-1-yl)-1-((4-chloro-1H-indol-2-yl)methyl)-3,7-dimethyl-1H-purine-2,6(3H,7H)-dione

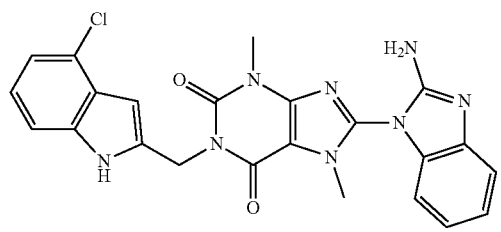 [SMILES: Cn1c(-n2c(N)nc3ccccc32)nc2c1c(=O)n(Cc1cc3c(Cl)cccc3[nH]1)c(=O)n2C]

1H-benzo[d]imidazol-2-amine (0.24 mmol, 32 mg), tert-butyl 2-((8-bromo-3,7-dimethyl-2,6-dioxo-2,3,6,7-tetrahydro-1H-purin-1-yl)methyl)-4-chloro-1H-indole-1-carboxylate (0.12 mmol, 60 mg), CuI (0.012 mmol, 2.3 mg) and Cs$_2$CO$_3$ (0.36 mmol, 117 mg) in DMF (2 mL) was stirred at 100° C. for 1 h in a microwave reactor. Water (10 mL) was added and the solution was extracted with EA (10 mL*3). The organic layers were combined, washed with brine (30 mL), dried with Na$_2$SO$_4$ and concentrated to get the crude tert-butyl 2-((8-(2-amino-1H-benzo[d]imidazol-1-yl)-3,7-dimethyl-2,6-dioxo-2,3,6,7-tetrahydro-1H-purin-1-yl)methyl)-4-chloro-1H-indole-1-carboxylate, which was used in the next step without further purification.
A solution of tert-butyl 2-((8-(2-amino-1H-benzo[d]imidazol-1-yl)-3,7-dimethyl-2,6-dioxo-2,3,6,7-tetrahydro-1H-purin-1-yl)methyl)-4-chloro-1H-indole-1-carboxylate (0.12 mmol, 69 mg) in DCM/TFA (1 mL/1 mL) was stirred at 30° C. for 1 h. The solution was concentrated. The product was purified by prep-HPLC using Method B (45-75% ACN). $^1$H NMR (400 MHz, DMSO-d$_6$) δ 11.41 (s, 1H), 7.36 (m, 1H), 7.24 (m, 1H), 7.07 (m, 4H), 6.95 (m, 1H), 6.80 (s, 1H), 6.33 (s, 1H), 5.28 (s, 1H), 3.71 (s, 3H); ESI: m/z 475.2 (M+H)$^+$.

Example 354

1-((4-chloro-1H-indol-2-yl)methyl)-3,7-dimethyl-8-(pyrazin-2-ylamino)-1H-purine-2,6(3H,7H)-dione

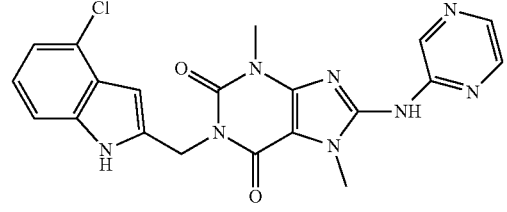 [SMILES: Cn1c(Nc2cnccn2)nc2c1c(=O)n(Cc1cc3c(Cl)cccc3[nH]1)c(=O)n2C]

The title compound was synthesized in a similar fashion as procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and pyrazin-2-amine. The product was purified by prep-HPLC using method D. $^1$H NMR (400 MHz, DMSO-d$_6$) δ 11.31 (s, 1H), 10.38 (s, 1H), 9.10 (s, 1H), 8.31 (s, 1H), 8.23 (s, 1H), 7.43-7.24 (m, 1H), 7.14-6.79 (m, 2H), 6.28 (s, 1H), 5.21 (s, 2H), 3.81 (s, 3H), 3.46 (s, 3H); ESI: m/z 516.3 (M+H)$^+$.

Example 355

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid

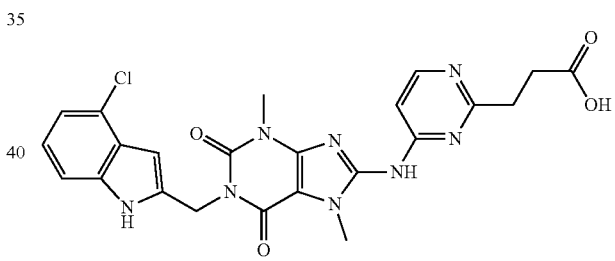

Methyl 3-(4-aminopyrimidin-2-yl)propanoate and tert-butyl 2-((8-bromo-3,7-dimethyl-2,6-dioxo-2,3,6,7-tetrahydro-1H-purin-1-yl)methyl)-4-chloro-1H-indole-1-carboxylate were coupled in a similar fashion as described in procedure 8A. The product was purified by flash chromatography (PE/EA=2/1) to afford tert-butyl 4-chloro-2-((8-((2-(3-methoxy-3-oxopropyl)pyrimidin-4-yl)amino)-3,7-dimethyl-2,6-dioxo-2,3,6,7-tetrahydro-1H-purin-1-yl)methyl)-1H-indole-1-carboxylate; ESI: m/z 637.2 (M+H)$^+$. To a solution of this product (0.55 mmol, 350 mg) in DCM (6 mL) was added TFA (2 mL). The reaction mixture was stirred at 30° C. for 2 h. The reaction was concentrated. The residue was dissolved in EA (30 mL) washed with sat. aq. NaHCO$_3$, dried with Na$_2$SO$_4$ and concentrated. The product was purified by flash chromatography (PE/EA=1/1) to afford methyl 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoate (260 mg). ESI: m/z 537.2 (M+H)$^+$. This product was dissolved in MeOH/THF/H$_2$O (5 mL/5 mL/5 mL) and treated with LiOH (2.60 mmol, 108 mg). The reaction mixture was stirred at 30° C. for 5 h. The solution was concentrated to half volume. The pH of the solution was adjusted to pH=5.0 with aqueous HCl (1N). The solid was collected by filtration and dried under high vacuum. $^1$H NMR (400 MHz, DMSO-$d_6$) δ 11.30 (s, 1H), 9.36 (d, J=6.0 Hz, 1H), 7.56 (d, J=6.4 Hz, 1H), 7.32 (dd, J=2.4, 6.4 Hz, 1H), 7.01 (m, 1H), 6.28 (s, 1H), 5.21 (s, 2H), 3.80 (s, 3H), 3.46 (s, 3H), 2.94 (t, J=7.2 Hz, 2H), 2.66 (t, J=7.2 Hz, 2H); ESI: m/z 509.2 (M+H)$^+$.

Example 356

1-[(4-chloro-1H-indol-2-yl)methyl]-8-(1H-imidazol-2-ylamino)-3,7-dimethyl-purine-2,6-dione

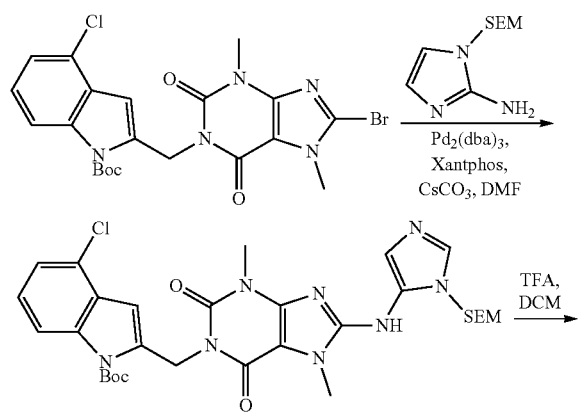

tert-Butyl 4-chloro-2-[[3,7-dimethyl-2,6-dioxo-8-[[1-(2-trimethylsilylethoxymethyl)imidazol-2-yl]amino]purin-1-yl]methyl]indole-1-carboxylate

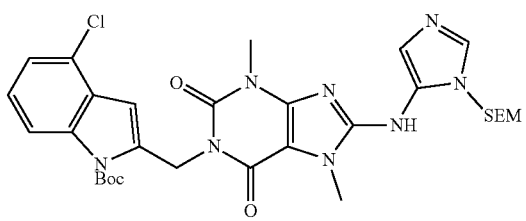 [SMILES: Cn1c(Nc2cncn2COCC[Si](C)(C)C)nc2c1c(=O)n(Cc1cc3c(Cl)cccc3n1C(=O)OC(C)(C)C)c(=O)n2C]

The title compound was synthesized in a similar fashion as Procedure 8B using tert-butyl 2-[(8-bromo-3,7-dimethyl-2,6-dioxo-purin-1-yl)methyl]-4-chloro-indole-1-carboxylate and 1-(2-trimethylsilyl ethoxymethyl)imidazol-2-amine. The product was purified by prep-TLC (PE/EA=1/2).

1-[(4-chloro-1H-indol-2-yl)methyl]-8-(1H-imidazol-2-ylamino)-3,7-dimethyl-purine-2,6-dione

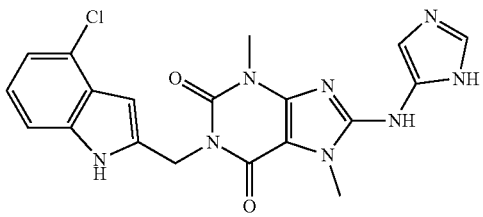 [SMILES: Cn1c(Nc2cnc[nH]2)nc2c1c(=O)n(Cc1cc3c(Cl)cccc3[nH]1)c(=O)n2C]

To a solution of tert-butyl 4-chloro-2-[[3,7-dimethyl-2,6-dioxo-8-[[1-(2-trimethylsilyl ethoxymethyl)imidazol-2-yl]amino]purin-1-yl]methyl]indole-1-carboxylate (90.00 mg, 137.36 umol, 1.00 eq) in DCM (2.00 mL) was added TFA (500.00 uL) at 0° C. The mixture was warmed slowly to 25° C. and stirred for 1.5 hr. The mixture was concentrated in vacuo. The residue was treated with Et$_3$N to pH=8 at 0° C. The mixture was concentrated to give a crude product which was purified by prep-HPLC using Method C (20-50% ACN). $^1$H NMR (400 MHz, CD$_3$OD) δ 7.26 (d, J=8.4 Hz, 1H), 7.07 (s, 2H), 7.01-6.93 (m, 2H), 6.42 (s, 1H), 5.30 (s, 2H), 3.86 (s, 3H), 3.62 (s, 3H); ESI: m/z 425.2 (M+H)$^+$.

Example 357

(±)-cis-2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

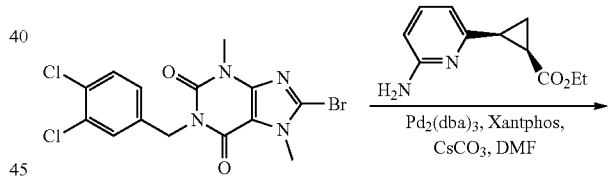

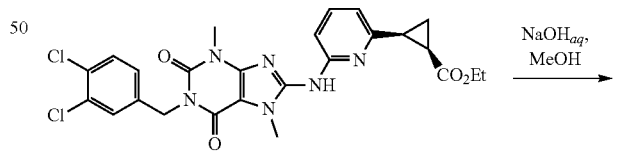

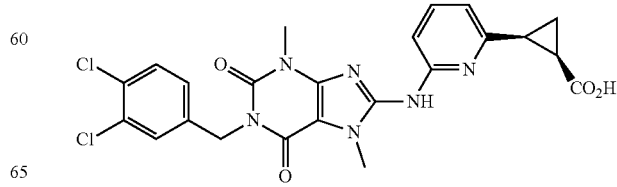

325 cis-Ethyl 2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylate

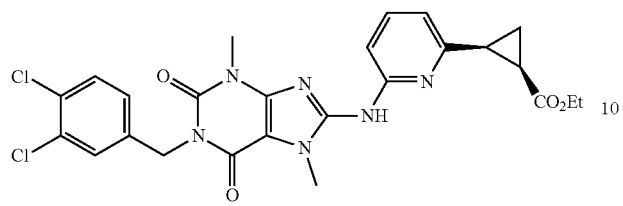

The title compound was synthesized in a similar fashion as procedure 8B using cis-ethyl-2-(6-aminopyridin-2-yl)cyclopropane carboxylate and 8-bromo-1-[(3,4-dichlorophenyl)methyl]-3,7-dimethyl-purine-2,6-dione. The product was purified by prep-TLC (PE/EA=2/1); ESI: m/z 543.2 (M+H)$^+$.

(±)-cis-2-(6-((1-(3,4-dichlorobenzyl)-3,7-dimethyl-2,6-dioxo-2,3,6,7-tetrahydro-1H-purin-8-yl)amino)pyridin-2-yl)cyclopropanecarboxylic acid

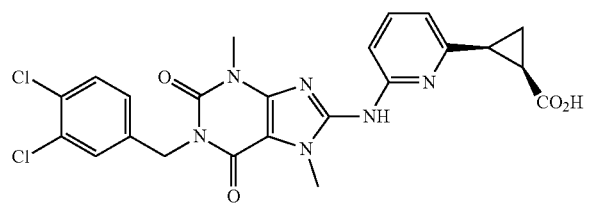 [SMILES: Cn1c(Nc2cccc([C@H]3C[C@H]3C(=O)O)n2)nc2c1c(=O)n(Cc1ccc(Cl)c(Cl)c1)c(=O)n2C]

To a mixture of cis-ethyl-2-[6-[[1-[(3,4-dichlorophenyl)methyl]-3,7-dimethyl-2,6-dioxopurin-8-yl]amino]-2-pyridyl]cyclopropanecarboxylate (100.00 mg, 184.03 umol) in THF (1.00 mL) and MeOH (1.00 mL) was added NaOH/H$_2$O (3 M, 1.00 mL). The mixture was stirred at 25° C. for 12 hr. The mixture was concentrated. The residue was acidified with 3M HCl to pH=1 and the resulting mixture was extracted with DCM (10 mL*3). The combined organic fractions were washed with brine (2 mL), dried over Na$_2$SO$_4$ and concentrated. The crude product was purified by prep-HPLC using Method C (25-60% ACN). $^1$H NMR (400 MHz, DMSO-d$_6$) δ 7.89 (m, 1H), 7.77 (m, 1H), 7.57 (m, 2H), 7.32-7.29 (m, 1H), 7.07 (m, 1H), 5.04 (s, 2H), 3.86 (s, 3H), 3.46 (s, 3H), 2.75 (m, 1H), 2.15-2.12 (m, 1H), 1.67 (m, 1H), 1.46 (m, 1H). ESI: m/z 515.2 (M+H)$^+$.

Example 358

8-(aminomethyl)-1-[(4-chloro-1H-indol-2-yl)methyl]-3,7-dimethyl-purine-2,6-dione

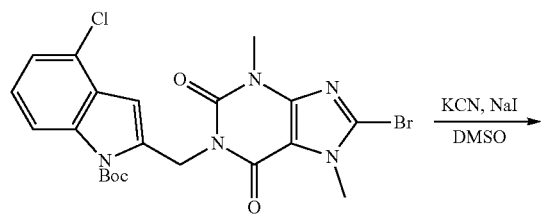

326

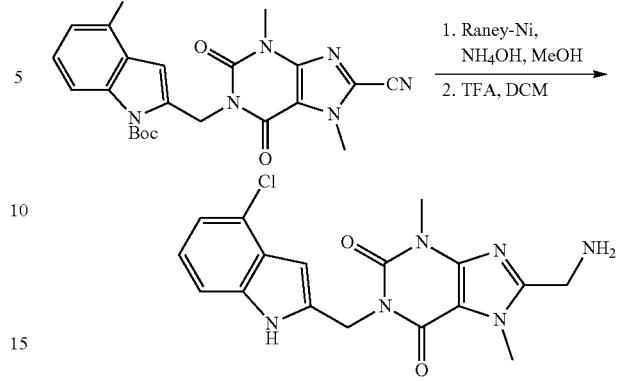

tert-Butyl 4-chloro-2-[(8-cyano-3,7-dimethyl-2,6-dioxo-purin-1-yl)methyl]indole-1-carboxylate

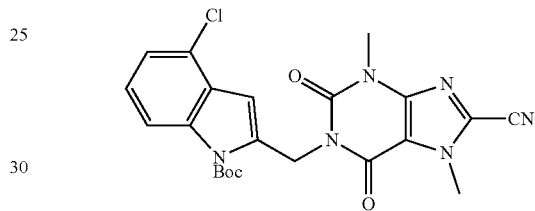

To a mixture of tert-butyl 2-[(8-bromo-3,7-dimethyl-2,6-dioxo-purin-1-yl)methyl]-4-chloro-indole-1-carboxylate (300.00 mg, 286.93 umol) and NaI (21.50 mg, 143.46 umol) in DMSO (5.00 mL) was added KCN (22.42 mg, 344.31 umol, 14.75 uL). The reaction mixture was stirred at 25° C. for 12 hr. The mixture was poured into ice-water (10 mL) and extracted with EA (15 mL*3). The combined organic fractions were washed with brine (5 mL), dried over Na$_2$SO$_4$ and concentrated. The crude product was purified by prep-TLC (PE/EA=2/1) to afford the title compound; $^1$H NMR (400 MHz, CDCl$_3$) δ 8.07-7.92 (m, 1H), 7.19-7.15 (m, 2H), 6.17 (s, 1H), 5.60 (s, 2H), 4.21 (s, 3H), 3.65 (s, 3H), 1.73 (s, 9H); ESI: m/z 369.1 (M+H-Boc)$^+$.

8-(Aminomethyl)-1-[(4-chloro-1H-indol-2-yl)methyl]-3,7-dimethyl-purine-2,6-dione

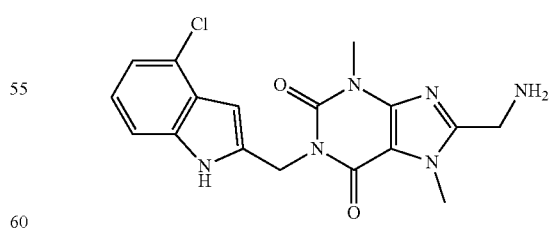

A mixture of tert-butyl 4-chloro-2-[(8-cyano-3,7-dimethyl-2,6-dioxo-purin-1-yl)methyl]indole-1-carboxylate (70.00 mg, 149.29 umol) and Raney-Ni (12.79 mg, 149.29 umol) in MeOH (20.00 mL) and NH$_4$OH (500.00 uL) was stirred at 25° C. under H$_2$ atmosphere (50 psi) for 1 hr. The mixture was filtered through celite. The filtrate was concentrated to afford the tert-butyl 2-[[8-(aminomethyl)-3,7-dimethyl-2,6-dioxo-purin-1-yl]methyl]-4-chloro-indole-1-carboxylate (ESI: m/z 473.3 (M+H)$^+$) which was used directly without further purification.

To a solution of tert-butyl 2-[[8-(aminomethyl)-3,7-dimethyl-2,6-dioxo-purin-1-yl]methyl]-4-chloro-indole-1-carboxylate (70.00 mg, 148.02 umol) in MeOH (1.00 mL) was added HCl/MeOH (4M, 20.00 mL). The reaction mixture was stirred at 25° C. for 2 hr. The mixture was concentrated, dissolved in MeOH (1 mL). and 1M NaOH (2 mL). The mixture was stirred at 25° C. for 12 hr. The mixture was concentrated and purified by prep-HPLC using Method C (10-50% ACN) to afford the title compound. $^1$H NMR (400 MHz, CD$_3$OD) δ 7.25-7.27 (m, 1H), 6.94-7.00 (m, 2H), 6.41 (s, 1H), 5.31 (s, 2H), 4.36 (s, 2H), 3.97 (s, 3H), 3.57 (s, 3H); ESI: m/z 373.2 (M+H)$^+$.

Example 359

4-chloro-24(8-(((1R,2S)-2-hydroxycyclopentyl)amino)-3,7-dimethyl-2,6-dioxo-2,3,6,7-tetrahydro-1H-purin-1-yl)methyl)-1H-indole-1-carboxylic acid

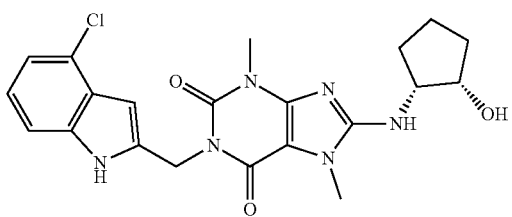 [SMILES: Cn1c(N[C@@H]2CCC[C@@H]2O)nc2c1c(=O)n(Cc1cc3c(Cl)cccc3[nH]1)c(=O)n2C]

The title compound was synthesized in a similar fashion as Procedure 7A using 8-bromo-1-((4-chloro-1H-indol-2-yl)methyl)-3,7-dimethyl-1H-purine-2,6(3H,7H)-dione and (1S,2R)-2-aminocyclopentanol. The product was purified by prep-HPLC using Method D. $^1$H NMR (400 MHz, DMSO-d$_6$) δ 11.26 (s, 1H), 7.33 (dd, J=6.0, 2.2 Hz, 1H), 7.05-6.94 (m, 2H), 6.58 (d, J=7.8 Hz, 1H), 6.21 (s, 1H), 5.16 (s, 2H), 4.67 (d, J=3.7 Hz, 1H), 4.09 (s, 1H), 3.96 (s, 1H), 3.62 (s, 3H), 3.38 (s, 3H), 1.87 (s, 1H), 1.73 (s, 3H), 1.65-1.41 (m, 2H).); ESI 443.1 (M+H)$^+$.

Example 360

2-(1-((4-chloro-1H-indol-2-yl)methyl)-3,7-dimethyl-2,6-dioxo-2,3,6,7-tetrahydro-1H-purin-8-ylamino)acetamide

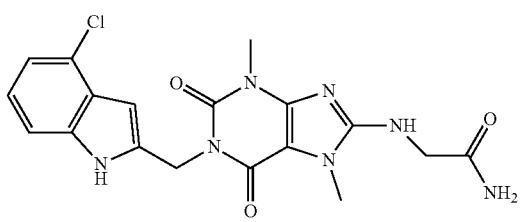 [SMILES: Cn1c(NCC(N)=O)nc2c1c(=O)n(Cc1cc3c(Cl)cccc3[nH]1)c(=O)n2C]

The title compound was synthesized in a similar fashion as Procedure 7A using tert-butyl 2-((8-bromo-3,7-dimethyl-2,6-dioxo-2,3,6,7-tetrahydro-1H-purin-1-yl)methyl)-4-chloro-1H-indole-1-carboxylate and 2-amino-2-oxoethyl-carbamate. The product was purified by prep-HPLC using Method D. $^1$H NMR (400 MHz, DMSO-d$_6$) δ 11.25 (s, 2H), 7.45 (s, 1H), 7.38 (t, J=6.0 Hz, 1H), 7.33 (dd, J=6.4, 1.9 Hz, 1H), 7.10 (s, 1H), 7.07-6.90 (m, 2H), 6.22 (s, 1H), 5.17 (s, 2H), 3.87 (d, J=6.0 Hz, 2H), 3.63 (s, 3H), 3.37 (s, 3H); ESI: m/z 416.1 (M+H)$^+$.

Example 361

1-((4-chloro-1H-indol-2-yl)methyl)-3-ethyl-7-methyl-8-(pyridin-4-ylamino)-1H-purine-2,6(3H,7H)-dione

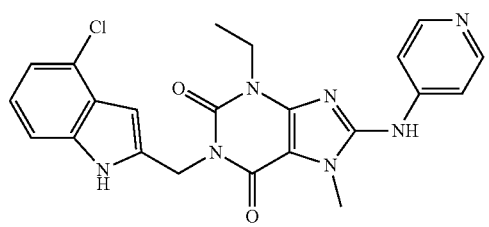 [SMILES: CCn1c(=O)n(Cc2cc3c(Cl)cccc3[nH]2)c(=O)c2c1nc(Nc1ccncc1)n2C]

tert-Butyl 2-((8-bromo-3-ethyl-7-methyl-2,6-dioxo-2,3,6,7-tetrahydro-1H-purin-1-yl)methyl)-4-chloro-1H-indole-1-carboxylate and pyridin-4-amine hydrochloride were coupled in a similar fashion as described in Procedure 8A. The product was purified by column chromatography (DCM/MeOH from 50/1 to 5/1) to give tert-butyl 4-chloro-2-((3-ethyl-7-methyl-2,6-dioxo-8-(pyridin-4-ylamino)-2,3,6,7-tetrahydro-1H-purin-1-yl)methyl)-1H-indole-1-carboxylate; ESI: m/z 550.1 (M+H)$^+$. The Boc was removed according to Procedure 6 and the product was purified by Prep-HPLC using Method D (34-64% ACN) to provide the title compound. $^1$H NMR (400 MHz, CD$_3$OD) δ 8.34-8.36 (d, J=6.0 Hz, 2H), 7.33-7.35 (d, J=5.2 Hz, 2H), 7.28-7.30 (d, J=8.0 Hz, 1H), 6.96-7.03 (m, 2H), 6.45 (s, 1H), 5.32 (s, 1H), 4.18-4.24 (m, 2H), 3.92 (s, 1H), 1.31-1.39 (m, 3H); ESI: m/z 450.2 (M+H)$^+$.

Example 362

1-((4-chloro-1H-indol-2-yl)methyl)-3,7-dimethyl-8-(pyrimidin-4-ylamino)-3,7-dihydro-1H-purine-2,6-dione

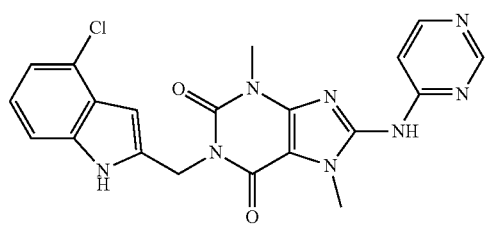 [SMILES: Cn1c(Nc2ccncn2)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and pyrimidin-4-amine were coupled in a similar fashion as described in Procedure 8A. The product was purified by flash chromatography (DCM/MeOH=20/1) to give the crude product (50 mg). The product was purified by Prep-HPLC using Method D (45-75% ACN). $^1$H NMR (400 MHz, DMSO-d$_6$) δ 11.29 (s, 1H), 10.69 (br s, 1H), 8.74 (s, 1H), 8.51-8.50 (d, J=4.0 Hz, 1H), 7.71-7.70 (d, J=4.0 Hz, 1H), 7.34-7.32 (m, 1H), 7.02-7.01 (m, 2H), 6.28 (s, 1H), 5.21 (s, 2H), 3.80 (s, 3H), 3.47 (s, 3H)); ESI: m/z 437.1 (M+H)⁺.

Example 364

(±)-trans-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxamide

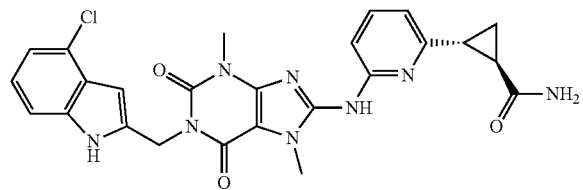 [SMILES: Cn1c(Nc2cccc([C@@H]3C[C@H]3C(N)=O)n2)nc2c1c(=O)n(Cc1cc3c(Cl)cccc3[nH]1)c(=O)n2C]

To a solution of (±)-trans-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid (20.00 mg, 38.47 umol) in THF (200.00 uL) was added pyridine (0.50 uL), (Boc)₂O (10.91 mg, 50.01 umol, 11.49 uL) NH₄HCO₃ (3.95 mg, 50.01 umol, 4.12 uL). The reaction mixture was stirred at 25° C. for 1 hr. The reaction mixture was poured into H₂O (0.5 mL) and extracted with EA (2 mL*3). The combined organic fractions were washed with brine (0.5 mL), dried over Na₂SO₄, concentrated in vacuum. The crude product was purified by prep-HPLC using Method C. ¹H NMR (400 MHz, DMSO-d₆) δ 14.33-14.60 (m, 1H), 11.51-11.70 (m, 1H), 8.40-8.62 (m, 2H), 7.47-7.65 (m, 2H), 7.23-7.35 (m, 3H), 4.90-5.02 (m, 2H), 4.51-4.67 (m, 2H), 4.33-4.46 (m, 2H); ESI: m/z 519.2 (M+H)⁺.

Example 366

1-[(7-fluoro-1H-indol-2-yl)methyl]-3,7-dimethyl-8-(4-pyridylamino)purine-2,6-dione

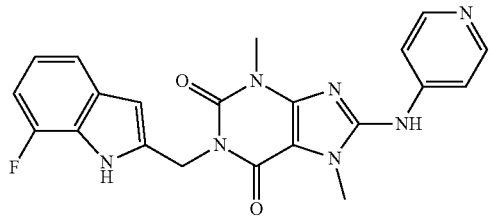 [SMILES: Cn1c(Nc2ccncc2)nc2c1c(=O)n(Cc1cc3cccc(F)c3[nH]1)c(=O)n2C]

The title compound was synthesized in a similar fashion as Procedure 8B using tert-butyl 2-[(8-bromo-3,7-dimethyl-2,6-dioxo-purin-1-yl)methyl]-7-fluoro-indole-1-carboxylate and pyridin-4-amine. The product was purified by prep-TLC (DCM/MeOH=10/1) and then purified by prep-HPLC using Method C (25-55% ACN). ¹H NMR (400 MHz DMSO-d₆) δ 1.46 (br. s., 1H), 8.58 (d, J=6.6 Hz, 2H), 8.06 (d, J=6.2 Hz, 2H), 7.23 (d, J=7.5 Hz, 1H), 6.94-6.82 (m, 2H), 6.24 (br. s., 1H), 5.24 (s, 2H), 3.92 (s, 3H), 3.50 (s, 3H); ESI: m/z 420.2 (M+H)⁺.

Example 367

1-[(4-chloro-1H-indol-2-yl)methyl]-3,7-dimethyl-8-(4-methylsulfonylanilino)purine-2,6-dione

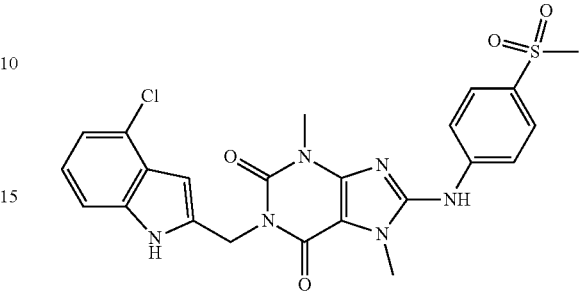

The title compound was synthesized in a similar fashion as procedure 8B using tert-butyl 2-[(8-bromo-3,7-dimethyl-2,6-dioxo-purin-1-yl)methyl]-4-chloro-indole-1-carboxylate and 4-methylsulfonylaniline. The product was purified by prep-TLC (EA) and then by prep-HPLC using Method C (35-70% ACN). ¹H NMR (400 MHz, DMSO-d₆) δ 11.28 (br. s., 1H), 9.73 (s, 1H), 7.99-7.78 (m, 4H), 7.38-7.28 (m, 1H), 7.07-6.95 (m, 2H), 6.27 (s, 1H), 5.21 (s, 2H), 3.85 (s, 3H), 3.47 (s, 3H), 3.16 (s, 3H); ESI: m/z 513.2 (M+H)⁺.

Example 368

(±)-cis-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid

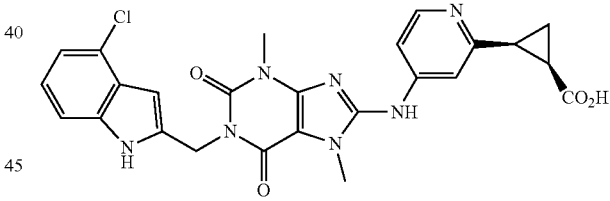

tert-Butyl 2-[(8-bromo-3,7-dimethyl-2,6-dioxo-purin-1-yl)methyl]-4-chloro-indole-1-carboxylate and cis-ethyl 2-(4-aminopyridin-2-yl)cyclopropanecarboxylate were coupled in a similar fashion as described in Procedure 8B. The product was purified by prep-TLC (DCM/MeOH=30/1) to obtain (±)-cis-tert-butyl 4-chloro-2-((8-((2-(-2-(ethoxycarbonyl)cyclopropyl)pyridin-4-yl)amino)-3,7-dimethyl-2,6-dioxo-2,3,6,7-tetrahydro-1H-purin-1-yl)methyl)-1H-indole-1-carboxylate. To a solution of this product (25.00 mg, 38.57 umol) in THF (1.00 mL) and MeOH (1.00 mL) was added 3N NaOH (500.00 uL) at 25° C. The mixture was stirred for 15 h at 25° C. The mixture was concentrated. The residue was acidified with 3N HCl to pH=1-2 at 0° C. and concentrated. The product was purified by prep-HPLC using Method D (20-50% ACN). ¹H NMR (400 MHz, DMSO-d₆) δ 11.34 (s, 1H), 8.47 (d, J=7.0 Hz, 1H), 7.94 (br. s., 2H), 7.40-7.32 (m, 1H), 7.11-6.96 (m, 2H), 6.28 (s, 1H), 5.24 (s, 2H), 3.91 (s, 3H), 3.50 (s, 3H), 2.85 2.87 (m, 1H), 2.22-2.27 (m, 1H), 1.67-1.56 (m, 2H); ESI: m/z 520.2 (M+H)⁺.

Example 369

3-(7-(2-aminoethyl)-1-(3,4-dichlorobenzyl)-3-methyl-2,6-dioxo-2,3,6,7-tetrahydro-1H-purin-8-ylamino)cyclohexanecarboxylic acid

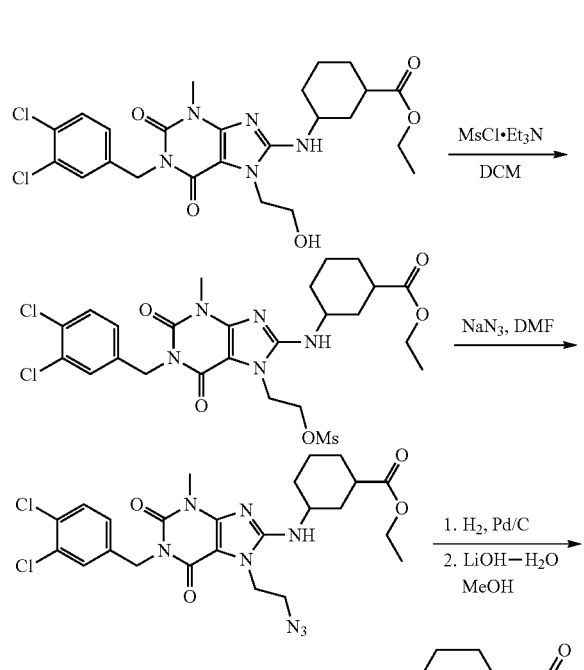

Ethyl 3-(1-(3,4-dichlorobenzyl)-3-methyl-7-(2-(methylsulfonyloxy)ethyl)-2,6-dioxo-2,3,6,7-tetrahydro-1H-purin-8-ylamino)cyclohexanecarboxylate

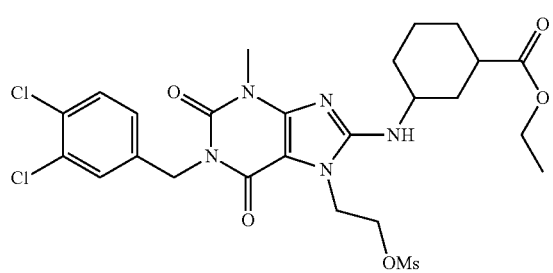 [SMILES: CCOC(=O)C1CCCC(Nc2nc3c(c(=O)n(Cc4ccc(Cl)c(Cl)c4)c(=O)n3C)n2CCOS(C)(=O)=O)C1]

A solution of ethyl 3-(7-(2-aminoethyl)-1-((4-chloro-1H-indol-2-yl)methyl)-3-methyl-2,6-dioxo-2,3,6,7-tetrahydro-1H-purin-8-ylamino)cyclohexanecarboxylate (200 mg, 0.37 mmol), TEA (112 mg, 1.11 mmol) in DCM (5 mL) at 0° C. was treated with MsCl (84.4 mg, 0.74 mmol). The mixture was stirred at 0° C. for 2 h. The mixture was concentrated and the residue was used without further purification.

Ethyl 3-(7-(2-azidoethyl)-1-(3,4-dichlorobenzyl)-3-methyl-2,6-dioxo-2,3,6,7-tetrahydro-1H-purin-8-ylamino)cyclohexanecarboxylate

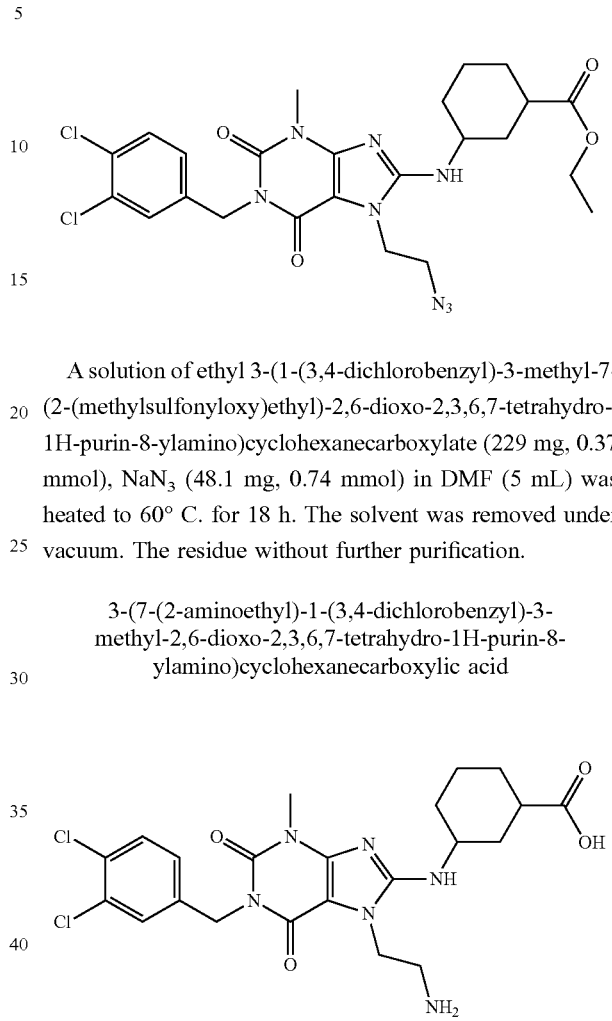

A solution of ethyl 3-(1-(3,4-dichlorobenzyl)-3-methyl-7-(2-(methylsulfonyloxy)ethyl)-2,6-dioxo-2,3,6,7-tetrahydro-1H-purin-8-ylamino)cyclohexanecarboxylate (229 mg, 0.37 mmol), NaN$_3$ (48.1 mg, 0.74 mmol) in DMF (5 mL) was heated to 60° C. for 18 h. The solvent was removed under vacuum. The residue without further purification.

3-(7-(2-aminoethyl)-1-(3,4-dichlorobenzyl)-3-methyl-2,6-dioxo-2,3,6,7-tetrahydro-1H-purin-8-ylamino)cyclohexanecarboxylic acid A solution of ethyl 3-(7-(2-azidoethyl)-1-(3,4-dichlorobenzyl)-3-methyl-2,6-dioxo-2,3,6,7-tetrahydro-1H-purin-8-ylamino)cyclohexanecarboxylate (208 mg, 0.37 mmol), Pd/C (21 mg) in EA (3 mL), was stirred at 25° C. under H$_2$ for 1 h. The mixture was filtered; the filtrate was concentrated under vacuum. The residue was purified by prep-TLC to give ethyl 3-(7-(2-aminoethyl)-1-(3,4-dichlorobenzyl)-3-methyl-2,6-dioxo-2,3,6,7-tetrahydro-1H-purin-8-ylamino)cyclohexanecarboxylate; ESI m/z 537.2 (M+H)$^+$. A solution of this product (30 mg, 0.056 mmol), and LiOH·H$_2$O (7 mg, 0.168 mmol) in MeOH (2 mL) was stirred and heated to 50° C. for 1 h. The mixture was filtered and the filtrate was purified by Prep-HPLC using Method D. $^1$H NMR (400 MHz, CD$_3$OD) δ 7.43 (s, 1H), 7.32-7.34 (d, J=8.0 Hz, 1H), 7.18-7.20 (d, J=8.4 Hz, 1H), 4.99 (s, 2H), 4.03-4.08 (m, 1H), 3.73-3.76 (m, 1H), 3.39 (s, 3H), 2.90-2.93 (m, 2H), 2.19-2.13 (m, 1H), 2.05-2.09 (m, 1H), 1.72-1.89 (m, 3H), 1.18-1.48 (m, 4H); ESI: m/z 509.2 (M+H)$^+$.

Example 370

1-((4-methoxy-1H-indol-2-yl)methyl)-3,7-dimethyl-8-(pyridin-4-ylamino)-1H-purine-2,6(3H,7H)-dione

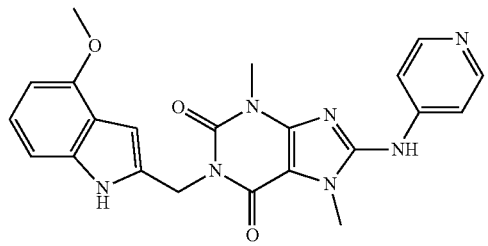

tert-Butyl 2-((8-bromo-3,7-dimethyl-2,6-dioxo-2,3,6,7-tetrahydro-1H-purin-1-yl)methyl)-4-methoxy-1H-indole-1-carboxylate and pyridin-4-amine were coupled in a similar fashion as described in Procedure 8A. The product was purified by flash chromatography (DCM/MeOH=10/1) to give tert-butyl 2-((3,7-dimethyl-2,6-dioxo-8-(pyridin-4-ylamino)-2,3,6,7-tetrahydro-1H-purin-1-yl)methyl)-4-methoxy-1H-indole-1-carboxylate; ESI 532.2 (M+H)$^+$. The Boc protecting group was removed according to Procedure 6 and the product was purified by prep-HPLC using Method B (33-61% ACN). $^1$H NMR (400 MHz, DMSO-d$_6$) δ 10.87 (s, 1H), 9.73 (b, 1H), 8.35 (m, 2H), 7.66 (m, 2H), 6.96-6.91 (m, 2H), 6.44 (dd, J=6.8, 2.0 Hz, 1H), 6.20 (d, J=1.6 Hz, 1H), 5.16 (s, 2H), 3.82 (s, 3H), 3.80 (s, 3H), 3.47 (s, 3H); ESI: m/z 432.1 (M+H)$^+$.

Example 371

8-(3-aminopiperidin-1-yl)-1-((4-chloro-1H-indol-2-yl)methyl)-3,7-dimethyl-1H-purine-2,6(3H,7H)-dione

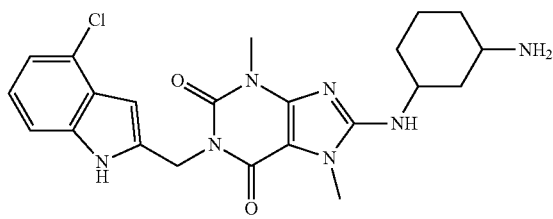 [SMILES: Cn1c(NC2CCCC(N)C2)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and tert-butylpiperidin-3-ylcarbamate were coupled in a similar fashion as described in procedure 7A. The product was purified by flash chromatography (DCM/MeOH=10/1) to give tert-butyl 2-((8-(3-(tert-butoxycarbonylamino)piperidin-1-yl)-3,7-dimethyl-2,6-dioxo-2,3,6,7-tetrahydro-1H-purin-1-yl)methyl)-4-chloro-1H-indole-1-carboxylate; ESI: m/z 542.2 (M+H)$^+$.

The Boc protecting group was removed according Procedure 6. The product was purified by prep-HPLC using Method B (33-61% ACN). $^1$H NMR (400 MHz, DMSO-d$_6$) δ 11.26 (s, 1H), 7.33-7.30 (m, 1H), 7.02-6.99 (m, 2H), 6.24 (m, 1H), 5.18 (s, 2H), 3.67 (s, 3H), 3.50-3.43 (m, 2H), 3.40 (s, 3H), 2.90-2.78 (m, 2H), 2.68-2.61 (m, 1H), 1.90-1.56 (m, 3H), 1.24-1.14 (m, 1H); ESI: m/z 442.0 (M+H)$^+$.

Example 372

(±)-cis-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropane-1-carboxylic acid

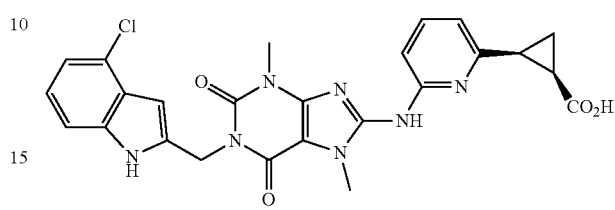

tert-Butyl 2-[(8-bromo-3,7-dimethyl-2,6-dioxo-purin-1-yl)methyl]-4-chloro-indole-1-carboxylate and cis-ethyl 2-(6-aminopyridin-2-yl) cyclopropanecarboxylate were coupled in a similar fashion as described in Procedure 8A. The crude product was purified by prep-TLC (PE/EA=3/1) to afford a mixture of cis-tert-butyl 4-chloro-2-((8-((6-((2-(ethoxycarbonyl)cyclopropyl)pyridin-2-yl)amino)-3,7-dimethyl-2,6-dioxo-2,3,6,7-tetrahydro-1H-purin-1-yl)methyl)-1H-indole-1-carboxylate (ESI: m/z 648.3 (M+H)$^+$) and cis-ethyl 2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylate (ESI: m/z 548.4 (M+H)$^+$. To a mixture of these products in THF (1.50 mL) and MeOH (1.50 mL) was added 3M NaOH (1.00 mL). The mixture was stirred at 25° C. for 12 h. The mixture was concentrated and the aqueous residue was acidified with 3M HCl to pH=1. The mixture was concentrated. The crude product was purified by prep-HPLC using Method C (15-45% ACN). $^1$H NMR (400 MHz, DMSO-d$_6$) δ 7.72-7.68 (m, 1H), 7.58 (m, 1H), 7.04-7.02 (m, 1H), 7.02-6.92 (m, 2H), 6.90 (m, 1H), 6.28 (m, 1H), 5.22 (s, 2H), 3.81 (s, 3H), 3.47 (s, 3H), 2.68-2.64 (m, 1H), 2.12-2.07 (m, 1H), 1.65-1.62 (m, 1H), 1.40-1.38 (m, 1H); ESI: m/z 520.2 (M+H)$^+$.

Example 373

1-[(7-chloro-1H-indol-2-yl)methyl]-3,7-dimethyl-8-(4-pyridylamino)purine-2,6-dione

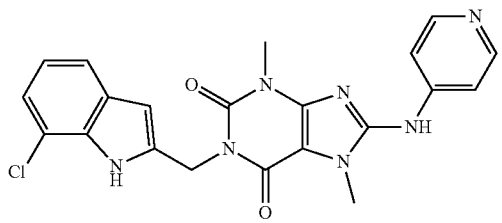 [SMILES: Cn1c(Nc2ccncc2)nc2c1c(=O)n(Cc1cc3cccc(Cl)c3[nH]1)c(=O)n2C]

tert-Butyl 2-[(8-bromo-3,7-dimethyl-2,6-dioxo-purin-1-yl)methyl]-7-chloro-indole-1-carboxylate and pyridin-4-amine were coupled in a similar fashion as described in procedure 8B. The product was purified by prep-TLC (silica gel, DCM/MeOH=20/1) to give tert-butyl 7-chloro-2-[[3,7-dimethyl-2,6-dioxo-8-(4-pyridylamino) purin-1-yl]methyl] indole-1-carboxylate. To a solution of this product (120.00 mg, 223.89 umol) in THF (2.00 mL) was added MeOH (2.00 mL) and 1N NaOH (1.00 mL) and the was stirred 16 h at rt. The mixture was concentrated to give crude product which was purified by prep-HPLC using Method A (40-65% ACN). $^1$H NMR: (400 MHz, DMSO-d$_6$) δ 8.36 (br. s., 2H), 7.65 (d, J=5.3 Hz, 2H), 7.37 (d, J=7.9 Hz, 1H), 7.10 (d, J=7.5 Hz, 1H), 6.98-6.88 (m, 1H), 6.20 (s, 1H), 5.24 (s, 2H), 3.82 (s, 3H), 3.48 (s, 3H); ESI: m/z 436.1 (M+H)$^+$.

Example 374

3,7-dimethyl-1-((4-phenyl-1H-indol-2-yl)methyl)-8-(pyridin-4-ylamino)-1H-purine-2,6(3H,7H)-dione

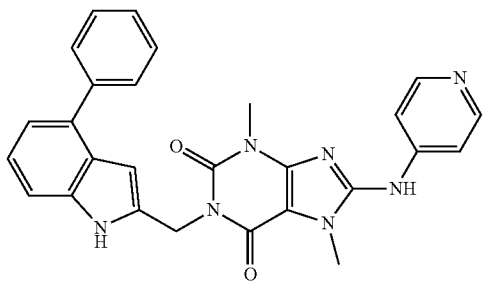 [SMILES: Cn1c(Nc2ccncc2)nc2c1c(=O)n(Cc1cc3c(-c4ccccc4)cccc3[nH]1)c(=O)n2C]

To a solution of tert-butyl 4-chloro-2-((3,7-dimethyl-2,6-dioxo-8-(pyridin-4-ylamino)-2,3,6,7-tetrahydro-1H-purin-1-yl)methyl)-1H-indole-1-carboxylate (0.03 mmol, 18 mg) in toluene/H$_2$O (3 mL/1 mL) was added phenylboronic acid (0.09 mmol, 11 mg), Pd(OAc)$_2$ (0.015 mmol, 3.4 mg), n-BuP(Ad)$_2$ (0.03 mmol, 11 mg), and Cs$_2$CO$_3$ (0.06 mmol, 20 mg). The reaction mixture was stirred under N$_2$ at 100° C. for 2 h in a microwave apparatus. Water (10 mL) was added and the solution was extracted with EA (10 mL*3). The organic fractions were combined, washed with brine (30 mL), dried with Na$_2$SO$_4$ and concentrated to get the crude tert-butyl 2-((3,7-dimethyl-2,6-dioxo-8-(pyridin-4-ylamino)-2,3,6,7-tetrahydro-1H-purin-1-yl)methyl)-4-phenyl-1H-indole-1-carboxylate, which was used for next step without further purification.

A solution of tert-butyl 2-((3,7-dimethyl-2,6-dioxo-8-(pyridin-4-ylamino)-2,3,6,7-tetrahydro-1H-purin-1-yl)methyl)-4-phenyl-1H-indole-1-carboxylate (0.03 mmol, 17 mg) in DCM/TFA (1 mL/1 mL) was stirred at 30° C. for 1 h. The solution was concentrated. The product was purified by prep-HPLC using Method B (45-75% ACN). $^1$H NMR (400 MHz, DMSO-d$_6$) δ 8.21 (m, 2H), 7.61 (d, J=5.2 Hz, 2H), 7.51 (m, 2H), 7.32 (m, 2H), 7.22 (m, 2H), 7.02 (m, 1H), 6.92 (m, 1H), 6.46 (s, 1H), 5.22 (s, 1H), 3.79 (s, 3H), 3.48 (s, 3H). ESI: m/z 478.2 (M+H)$^+$.

Example 375

1-((1-chloronaphthalen-2-yl)methyl)-3,7-dimethyl-8-(pyridin-4-ylamino)-1H-purine-2,6(3H,7H)-dione

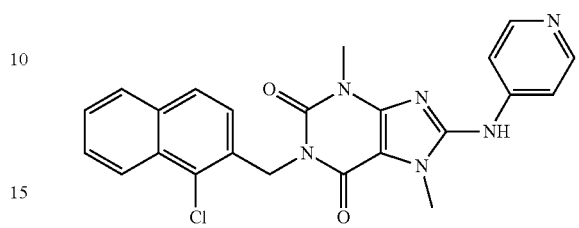

The title compound was synthesized in a similar fashion as Procedure 8A using 8-bromo-1-((1-chloronaphthalen-2-yl)methyl)-3,7-dimethyl-1H-purine-2,6(3H,7H)-dione and pyridin-4-amine hydrochloride. The product was purified by prep-HPLC using Method D. $^1$H NMR (400 MHz, DMSO-d$_6$) δ 9.72 (s, 1H), 8.41 (s, 2H), 8.25 (d, J=8.5 Hz, 1H), 7.98 (d, J=8.1 Hz, 1H), 7.85 (d, J=8.6 Hz, 1H), 7.77-7.65 (m, 3H), 7.61 (t, J=7.3 Hz, 1H), 7.15 (d, J=8.5 Hz, 1H), 5.34 (s, 2H), 3.83 (s, 3H), 3.49 (s, 3H); ESI: m/z 447.1 (M+H)$^+$.

Example 376

8-(3-aminopyrrolidin-1-yl)-1-((4-chloro-1H-indol-2-yl)methyl)-7-methyl-1H-purine-2,6(3H,7H)-dione

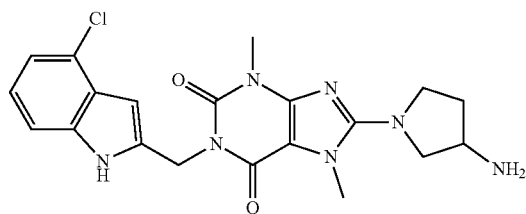 [SMILES: Cn1c(N2CCC(N)C2)nc2c1c(=O)n(Cc1cc3c(Cl)cccc3[nH]1)c(=O)n2C]

The title compound was synthesized in a similar fashion as described in procedure 7A using tert-butyl 2-((8-bromo-3,7-dimethyl-2,6-dioxo-2,3,6,7-tetrahydro-1H-purin-1-yl)methyl)-4-chloro-1H-indole-1-carboxylate and tert-butyl pyrrolidin-3-ylcarbamate. The product was purified by flash chromatography (DCM/MeOH=10/1) to give tert-butyl 2-((8-(3-(tert-butoxycarbonylamino)pyrrolidin-1-yl)-3,7-dimethyl-2,6-dioxo-2,3,6,7-tetrahydro-1H-purin-1-yl)methyl)-4-chloro-1H-indole-1-carboxylate; ESI: m/z 528.2 (M+H)$^+$.

The boc protecting groups were removed according to procedure 6. The product was purified by prep-HPLC using Method D (33-61% ACN). $^1$H NMR (400 MHz, DMSO-d$_6$) δ 11.25 (s, 1H), 7.34-7.32 (m, 1H), 7.03-6.99 (m, 2H), 6.22 (d, J=1.2 Hz, 1.0H), 5.16 (s, 2H), 3.80 (s, 3H), 3.77-3.50 (m, 4H), 3.38 (s, 3H), 3.28-3.23 (m, 1H), 2.02-1.90 (m, 3H), 1.68-1.62 (m, 1H); ESI: m/z 428.1 (M+H)$^+$.

Example 377

3-(6-(1-((4-chloro-1H-indol-2-yl)methyl)-3,7-dimethyl-2,6-dioxo-2,3,6,7-tetrahydro-1H-purin-8-ylamino)-3-methylpyridin-2-yl)propanoic acid

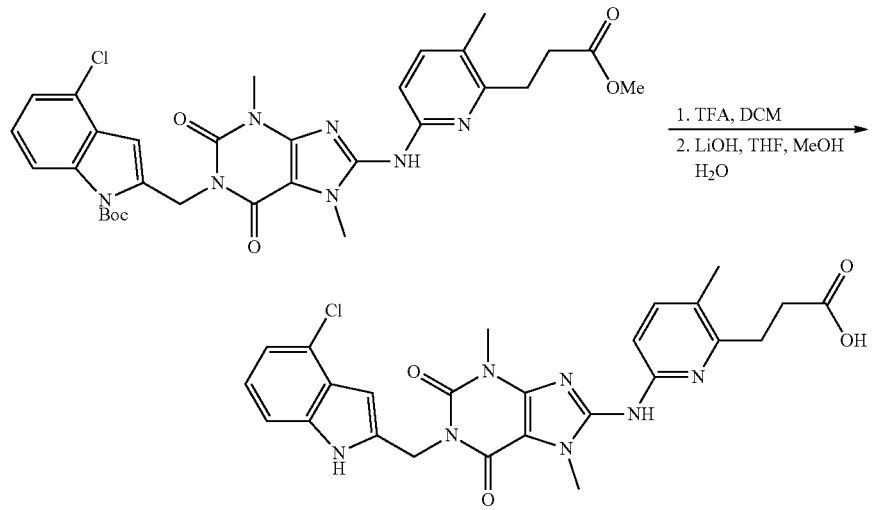

tert-Butyl 4-chloro-2-((8-(6-(3-methoxy-3-oxopropyl)-5-methylpyridin-2-ylamino)-3,7-dimethyl-2,6-dioxo-2,3,6,7-tetrahydro-1H-purin-1-yl)methyl)-1H-indole-1-carboxylate

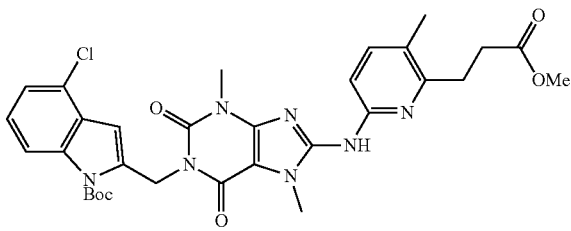 [SMILES: COC(=O)CCc1nc(Nc2nc3c(c(=O)n(Cc4cc5c(Cl)cccc5n4C(=O)OC(C)(C)C)c(=O)n3C)n2C)ccc1C]

The title compound was synthesized in a similar fashion as described in Procedure 8A using methyl 3-(6-amino-3-methylpyridin-2-yl)propanoate and tert-butyl 2-((8-bromo-3,7-dimethyl-2,6-dioxo-2,3,6,7-tetrahydro-1H-purin-1-yl)methyl)-4-chloro-1H-indole-1-carboxylate. The product was purified by column chromatography (eluting EA/PE=70%); ESI: m/z 536.2 (M+H−100)+.

3-(6-(1-((4-chloro-1H-indol-2-yl)methyl)-3,7-dimethyl-2,6-dioxo-2,3,6,7-tetrahydro-1H-purin-8-ylamino)-3-methylpyridin-2-yl)propanoic acid

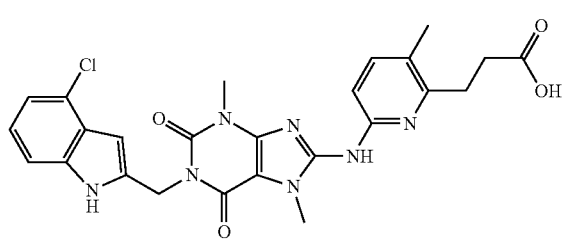 [SMILES: Cc1ccc(Nc2nc3c(c(=O)n(Cc4cc5c(Cl)cccc5[nH]4)c(=O)n3C)n2C)nc1CCC(=O)O]

tert-Butyl 4-chloro-2-((8-(6-(3-methoxy-3-oxopropyl)-5-methylpyridin-2-ylamino)-3,7-dimethyl-2,6-dioxo-2,3,6,7-tetrahydro-1H-purin-1-yl)methyl)-1H-indole-1-carboxylate (20 mg, 0.03 mmol) in TFA (2 mL) and DCM (2 mL) was stirred at rt. for 3 h. The mixture was concentrated and the product was directly used in the next step. A solution of this product (0.037 mmol, 20 mg) and LiOH (0.37 mmol, 14 mg) in MeOH (3 mL) and H₂O (1 mL) was stirred at rt. for 3 h. The mixture was concentrated. The residue was purified by prep-HPLC using Method B. $^1$H NMR (400 MHz, CD$_3$OD) δ 7.38 (s, 2H), 7.21-7.11 (m, 1H), 6.96-6.80 (m, 2H), 6.35 (s, 1H), 5.39 (s, 2H), 5.22 (s, 3H), 3.75 (s, 3H), 3.48 (s, 3H), 2.17 (s, 4H); ESI: m/z 522.2 (M+H)+.

Example 378

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanamide

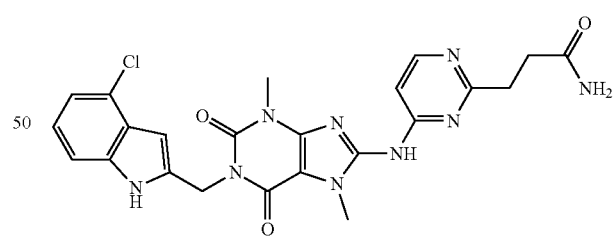

A mixture of 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid (0.04 mmol, 20 mg), NH₄Cl (0.8 mmol, 42 mg), HATU (0.08 mmol, 31 mg) and Et₃N (0.12 mmol, 12 mg) in DMF (2 mL) was stirred at 30° C. for 12 h. The mixture was purified directly by prep-HPLC using Method B. $^1$H NMR (400 MHz, DMSO-d$_6$) δ 11.30 (s, 1H), 10.51 (br s, 1H), 8.42 (s, 1H), 7.56 (s, 1H), 7.32 (m, 1H), 7.01 (m, 1H), 6.77 (s, 1H), 6.28 (d, J=1.2 Hz, 1H), 5.21 (s, 2H), 3.81 (s, 3H), 3.47 (s, 3H), 2.95 (m, 2H), 2.53 (m, 2H); ESI: m/z 508.1 (M+H)+.

Example 379

2-((8-(2-aminoacetamido)-3,7-dimethyl-2,6-dioxo-2,3,6,7-tetrahydro-1H-purin-1-yl)methyl)-4-chloro-1H-indole-1-carboxylic acid

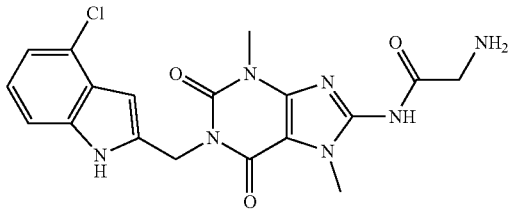 [SMILES: Cn1c(NC(=O)CN)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and tert-butyl 2-amino-2-oxoethyl carbamate were coupled in a similar fashion as described in Procedure 8A. The product was purified by flash chromatography (DCM/MeOH=20/1) to give tert-butyl 2-((8-(2-aminoacetamido)-3,7-dimethyl-2,6-dioxo-2,3,6,7-tetrahydro-1H-purin-1-yl)methyl)-4-chloro-1H-indole-1-carboxylate (40 mg); ESI: m/z 616.2 (M+H)$^+$. This product (0.08 mmol, 40 mg) in DCM (2 mL) was added TFA (2 mL). The reaction mixture was stirred at 30° C. for 3 h. The reaction mixture was concentrated and purified by Prep-HPLC using Method B. $^1$H NMR (400 MHz, DMSO-d$_6$) δ 11.31 (br s, 1H), 7.33-7.31 (m, 1H), 7.02-7.00 (m, 1H), 6.27 (s, 1H), 5.20 (s, 2H), 3.65 (s, 3H), 3.45-3.41 (m, 5H); ESI: m/z 461.1 (M+H)$^+$.

Example 380

1-((4-chloro-1H-indol-2-yl)methyl)-8-(6-methoxypyridin-3-ylamino)-3,7-dimethyl-1H-purine-2,6(3H,7H)-dione

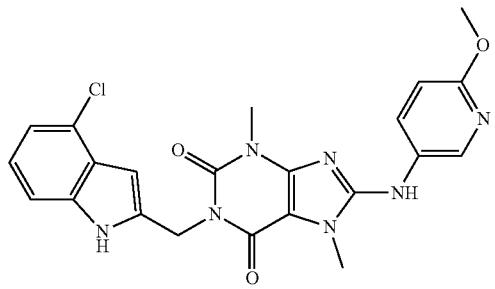 [SMILES: COc1ccc(Nc2nc3c(c(=O)n(Cc4cc5c(Cl)cccc5[nH]4)c(=O)n3C)n2C)cn1]

tert-Butyl 2-((8-bromo-3,7-dimethyl-2,6-dioxo-2,3,6,7-tetrahydro-1H-purin-1-yl)methyl)-4-chloro-1H-indole-1-carboxylate and 6-methoxypyridin-3-amine were coupled in a similar fashion as described in Procedure 8A. The residue was purified by column chromatography (MeOH:DCM=0:100 to 10:90); ESI: m/z 566.2 (M+H−100)$^+$. This product was treated with TFA in DCM as described in Procedure 6. The product was purified by Prep-HPLC using a Method D. $^1$H NMR (400 MHz, DMSO-d$_6$) δ 11.29 (s, 1H), 9.21 (s, 1H), 8.47-8.48 (d, J=2.4 Hz, 1H), 7.99-8.02 (dd, J=2.8 Hz, 2.8 Hz, 1H), 7.32-7.34 (m, 1H), 6.99-7.04 (m, 2H), 6.82- 6.84 (d, J=8.8 Hz, 1H), 6.25 (s, 1H), 5.19 (s, 2H), 3.83 (s, 3H), 3.79 (s, 3H), 3.41 (s, 3H); ESI: m/z 466.1 (M+H)$^+$.

Example 381

1-((4-chloro-1H-indol-2-yl)methyl)-8-(6-chloropyridin-3-ylamino)-3,7-dimethyl-1H-purine-2,6(3H,7H)-dione

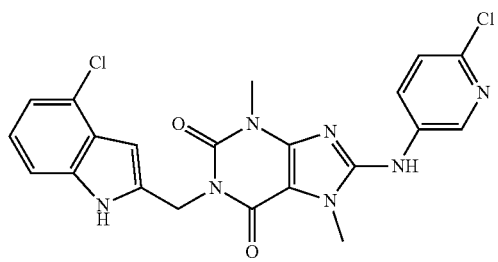 [SMILES: Cn1c(Nc2ccc(Cl)nc2)nc2c1c(=O)n(Cc1cc3c(Cl)cccc3[nH]1)c(=O)n2C]

The title compound was synthesized in a similar fashion as described in Procedure 8A using of tert-butyl 2-((8-bromo-3,7-dimethyl-2,6-dioxo-2,3,6,7-tetrahydro-1H-purin-1-yl)methyl)-4-chloro-1H-indole-1-carboxylate and 6-chloropyridin-3-amine. The product was purified by prep-HPLC using Method D. $^1$H NMR (400 MHz, DMSO-d$_6$) δ 11.30 (s, 1H), 9.60 (s, 1H), 8.72 (d, J=2.6 Hz, 1H), 8.23 (dd, J=8.8, 2.9 Hz, 1H), 7.48 (d, J=8.9 Hz, 1H), 7.34 (d, J=8.9 Hz, 1H), 7.08-6.94 (m, 2H), 6.26 (s, 1H), 5.20 (s, 2H), 3.83 (s, 3H), 3.45 (s, 3H); ESI: m/z 470.0 (M+H)$^+$.

Example 382

1-((4-chloro-1H-indol-2-yl)methyl)-3,7-dimethyl-8-(6-(trifluoromethyl)pyridin-3-ylamino)-1H-purine-2,6(3H,7H)-dione

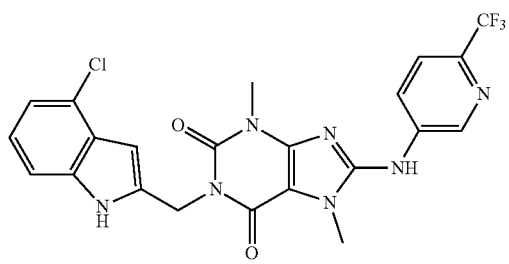 [SMILES: Cn1c(Nc2ccc(C(F)(F)F)nc2)nc2c1c(=O)n(Cc1cc3c(Cl)cccc3[nH]1)c(=O)n2C]

The title compound was synthesized in a similar fashion as Procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and 6-(trifluoromethyl)pyridin-3-amine. The product was purified by column chromatography (DCM/MeOH=10/1) and by Prep-HPLC using Method B (30-65% ACN). $^1$H NMR (400 MHz, DMSO-d$_6$) δ 11.30 (s, 1H), 9.89 (s, 1H), 9.01 (d, J=6.4 Hz, 1H), 8.40 (dd, J=8.8, 2.4 Hz, 1H), 7.86 (d, J=8.8 Hz, 1H), 7.34-7.32 (m, 1H), 7.04-6.99 (m, 2H), 6.26 (d, J=1.2 Hz, 1H), 5.21 (s, 2H), 3.86 (s, 3H), 3.47 (s, 3H); ESI: m/z 504.1 (M+H)$^+$.

Example 383

1-((4-chloro-1H-indol-2-yl)methyl)-3,7-dimethyl-8-(6-methylpyridin-3-ylamino)-1H-purine-2,6(3H,7H)-dione

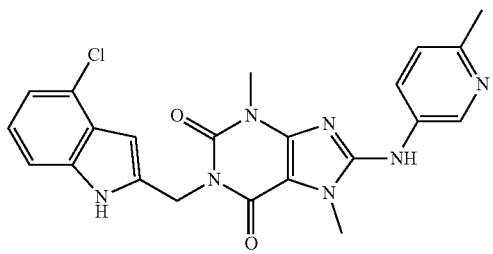 [SMILES: Cc1ccc(Nc2nc3c(c(=O)n(Cc4cc5c(Cl)cccc5[nH]4)c(=O)n3C)n2C)cn1]

tert-Butyl 2-((8-bromo-3,7-dimethyl-2,6-dioxo-2,3,6,7-tetrahydro-1H-purin-1-yl)methyl)-4-chloro-1H-indole-1-carboxylate and 6-methylpyridin-3-amine were coupled according to Procedure 8A. The product was purified by flash chromatography (silica gel, DCM/MeOH=10/1) to give tert-butyl 4-chloro-2-((3,7-dimethyl-8-(6-methylpyridin-3-ylamino)-2,6-dioxo-2,3,6,7-tetrahydro-1H-purin-1-yl)methyl)-1H-indole-1-carboxylate; ESI: m/z 550.2 (M+H)$^+$. The boc protecting group was removed from this product according to Procedure 6. The product was purified by prep-HPLC using Method D (33-61% ACN). $^1$H NMR (400 MHz, DMSO-d$_6$) δ 11.28 (s, 1H), 9.30 (b, 1H), 8.71 (d, J=2.4 Hz, 1H), 8.02 (dd, J=8.4, 2.8 Hz, 1H), 7.34 (m, 1H), 7.20 (d, J=8.4 Hz, 1H), 7.04-6.99 (m, 2H), 6.25 (m, 1H), 5.19 (s, 2H), 3.80 (s, 3H), 3.43 (s, 3H), 2.41 (s, 3H); ESI: m/z 450.2 (M+H)$^+$.

Example 384

1-((4-chloro-1H-indol-2-yl)methyl)-8-(6-fluoropyridin-3-ylamino)-3,7-dimethyl-1H-purine-2,6(3H,7H)-dione

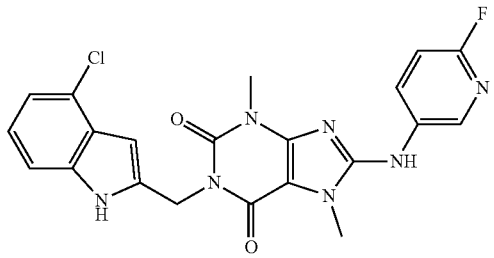 [SMILES: Cn1c(Nc2ccc(F)nc2)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and 6-fluoropyridin-3-amine were coupled according to Procedure 8A. The product was purified by column chromatography (MeOH:DCM=0:100 to 10:90) to give tert-butyl 4-chloro-2-((8-(6-fluoropyridin-3-ylamino)-3,7-dimethyl-2,6-dioxo-2,3,6,7-tetrahydro-1H-purin-1-yl)methyl)-1H-indole-1-carboxylate. The Boc protecting group was removed from this product according to Procedure 6. The product was purified by Prep-HPLC using a Method D. $^1$H NMR (400 MHz, DMSO-d$_6$) δ 11.29 (s, 1H), 9.51 (s, 1H), 8.52 (s, 1H), 8.27-8.32 (m, 1H), 7.32-7.35 (m, 1H), 7.16-7.19 (m, 1H), 6.09-7.04 (m, 2H), 6.25-6.26 (d, J=1.2 Hz, 1H), 5.19 (s, 2H), 3.81 (s, 3H), 3.44 (s, 3H); ESI: m/z 454.1 (M+H)$^+$.

Example 386

8-(2-aminoethyl)-1-((4-chloro-1H-indol-2-yl)methyl)-3,7-dimethyl-1H-purine-2,6(3H,7H)-dione

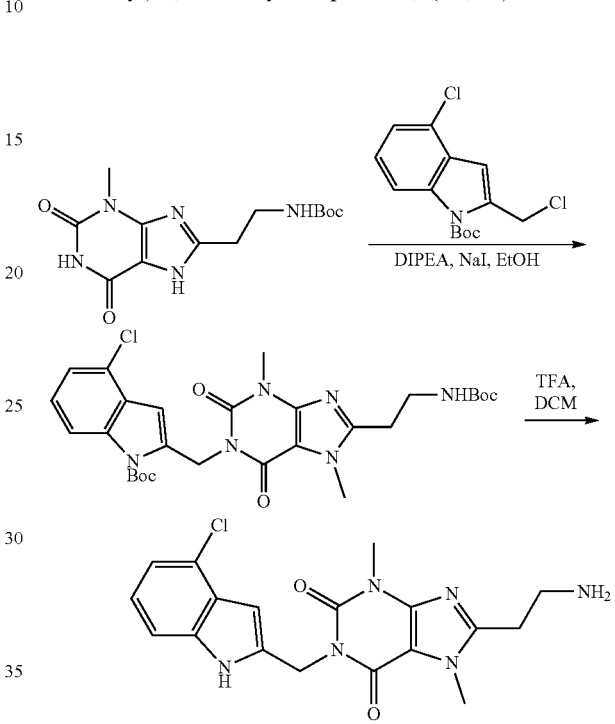

tert-Butyl 2-(3-methyl-2,6-dioxo-2,3,6,7-tetrahydro-1H-purin-8-yl)ethylcarbamate

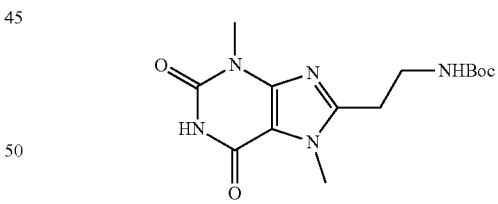

A mixture of 5,6-diamino-1-methylpyrimidine-2,4(1H,3H)-dione (1.56 g, 10.0 mmol), 3-(tert-butoxycarbonylamino)propanoic acid (3.78 g, 20.0 mmol), EDCI (3.83 g, 20.0 mmol) and DMAP (2.44 g, 20.0 mmol) in DMSO (40 mL) was stirred for 16 h at 28° C. The reaction mixture was poured into water (250 mL) and the precipitate was collected. The above crude product and NaOH aqueous (10 mL, 3M) in MeOH (30 mL) was heated to reflux and stirred for 6 h. The reaction mixture was cooled to 28° C. and mixture was concentrated. The aqueous residue was neutralized with citric acid to PH=6~7. The precipitate was collected and dried in vacuo to afford the title compound; ESI: 310.1 (M+H)$^+$.

343 tert-Butyl 2-((8-(2-(tert-butoxycarbonylamino)ethyl)-3,7-dimethyl-2,6-dioxo-2,3,6,7-tetrahydro-1H-purin-1-yl)methyl)-4-chloro-1H-indole-1-carboxylate

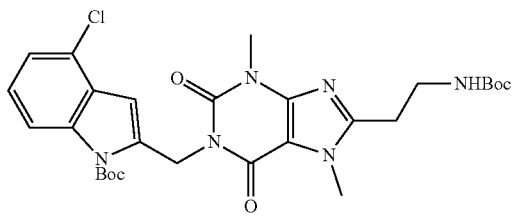 [SMILES: Cn1c(CCNC(=O)OC(C)(C)C)nc2c1c(=O)n(Cc1cc3c(Cl)cccc3n1C(=O)OC(C)(C)C)c(=O)n2C]

A mixture of tert-butyl 2-(3-methyl-2,6-dioxo-2,3,6,7-tetrahydro-1H-purin-8-yl)ethylcarbamate (155 mg, 0.50 mmol) and $K_2CO_3$ (83 mg, 0.60 mmol) in DMSO (5 mL) was stirred for 30 min at 25° C. and MeI (71 mg, 0.50 mmol) was added. The resulting mixture was stirred for 16 h at 25° C. Then tert-butyl 4-chloro-2-(chloromethyl)-1H-indole-1-carboxylate (150 mg, 0.50 mmol) and $K_2CO_3$ (83 mg, 0.60 mmol) was added. The mixture was heated to 50° C. and stirred for 2 h. The reaction mixture was poured into water (50 mL) and extracted with EA (2*30 mL). The combined organic fractions were washed with water (3*50 mL) and brine (1*50 mL), dried over $Na_2SO_4$ and concentrated. The product purified by flash chromatography (30~70% EA/PE); ESI: m/z 587.2 (M+H)$^+$.

8-(2-aminoethyl)-1-((4-chloro-1H-indol-2-yl)methyl)-3,7-dimethyl-1H-purine-2,6(3H,7H)-dione

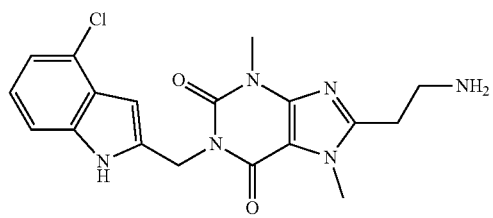 [SMILES: Cn1c(CCN)nc2c1c(=O)n(Cc1cc3c(Cl)cccc3[nH]1)c(=O)n2C]

A mixture of tert-butyl 2-((8-(2-(tert-butoxycarbonylamino)ethyl)-3,7-dimethyl-2,6-dioxo-2,3,6,7-tetrahydro-1H-purin-1-yl)methyl)-4-chloro-1H-indole-1-carboxylate (100 mg, 0.17 mmol) in TFA (0.7 mL) and DCM (3 mL) was stirred for 2 h at 25° C. The reaction mixture was concentrated and the residue was diluted with $NaHCO_3$(aq) to pH=8-9 at 0° C. The mixture was extracted with EA (3*30 mL). The combined organic fractions were concentrated and purified by prep-HPLC using Method F (25-55% ACN). $^1$H NMR (400 MHz, DMSO-d$_6$) δ 11.30 (s, 1H), 7.35-7.30 (m, 1H), 7.05-6.98 (m, 2H), 6.26 (s, 1H), 5.20 (s, 2H), 3.87 (s, 3H), 3.44 (s, 3H), 2.90 (t, J=6.8 Hz, 2H), 2.82 (t, J=6.2 Hz, 2H); ESI: m/z 387.1 (M+H)$^+$.

344

Example 387

1-((4-ethyl-1H-indol-2-yl)methyl)-3,7-dimethyl-8-(pyridin-4-ylamino)-1H-purine-2,6(3H,7H)-dione

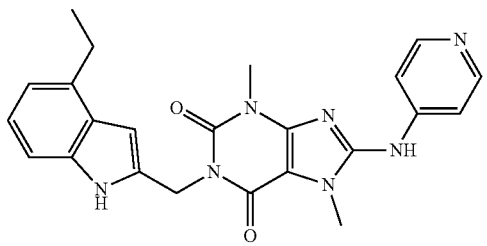

To a 1-((4-chloro-1H-indol-2-yl)methyl)-3,7-dimethyl-8-(pyridin-4-ylamino)-1H-purine-2,6(3H,7H)-dione (0.05 mmol, 20 mg) in DMF/H$_2$O (2 mL/0.5 mL) was added ethylboronic acid (0.92 mmol, 68 mg), Pd(OAc)$_2$ (0.05 mmol, 11 mg), Xantphos (0.10 mmol, 36 mg), and Cs$_2$CO$_3$ (0.14 mmol, 40 mg). The reaction mixture was stirred under N$_2$ at 110° C. for 2 h in a microwave apparatus. The solution was concentrated. The product was purified by prep-HPLC using Method B. $^1$H NMR (400 MHz, CD$_3$OD) δ 8.23 (m, 2H), 7.61 (m, 2H), 7.05 (d, J=8.4 Hz, 1H), 6.85 (m, 1H), 6.17 (d, J=3.2 Hz, 1H), 6.35 (s, 1H), 5.21 (s, 2H), 3.81 (s, 3H), 3.49 (s, 3H), 2.71 (q, J=7.6 Hz, 2H). 1.16 (t, J=7.6 Hz, 3H). ESI 430.2 (M+H)$^+$.

Example 388

1-((4-chloro-1H-indol-2-yl)methyl)-8-(hydroxy(phenyl)methyl)-3,7-dimethyl-1H-purine-2,6(3H,7H)-dione

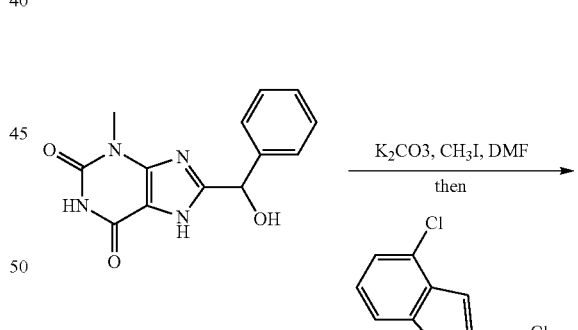

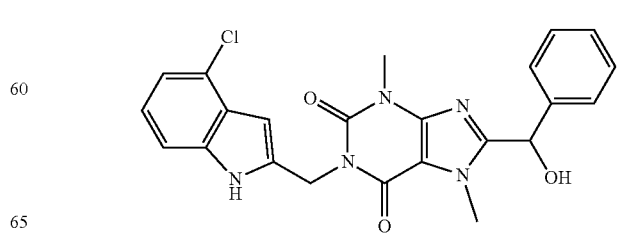

8-(hydroxy(phenyl)methyl)-3-methyl-1H-purine-2,6(3H,7H)-dione

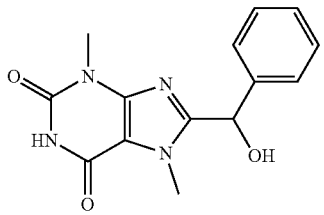 [SMILES: Cn1c(C(O)c2ccccc2)nc2c1c(=O)[nH]c(=O)n2C]

A mixture of 5,6-diamino-1-methylpyrimidine-2,4(1H,3H)-dione (4.0 g, 25.6 mmol) and 2-hydroxy-2-phenylacetic acid (7.8 g, 51.2 mmol) in H₂O (100 mL) was heated to reflux and stirred for 16 h. Then NaOH (2.0 g, 51.2 mmol) was added and the mixture was stirred for 18 h at reflux. The reaction mixture was cooled to 0° C. and neutralized with AcOH to PH=7~8. The precipitate was collected, dried in vacuo and purified by flash chromatography (10% MeOH/DCM) to afford the title compound. ESI: m/z 273.1 (M+H)⁺.

1-((4-chloro-1H-indol-2-yl)methyl)-8-(hydroxy(phenyl)methyl)-3,7-dimethyl-1H-purine-2,6(3H,7H)-dione

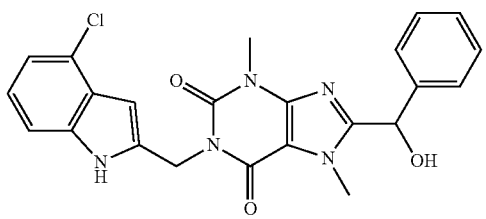 [SMILES: Cn1c(C(O)c2ccccc2)nc2c1c(=O)n(Cc1cc3c(Cl)cccc3[nH]1)c(=O)n2C]

A mixture of 8-(hydroxy(phenyl)methyl)-3-methyl-1H-purine-2,6(3H,7H)-dione (1.3 g, 4.77 mmol) and K₂CO₃ (791 mg, 5.72 mmol) in DMF (20 mL) was stirred for 30 min at 25° C. Then MeI (677 mg, 4.77 mmol) was added and the resulting mixture was stirred for 16 h at 25° C. tert-Butyl 4-chloro-2-(chloromethyl)-1H-indole-1-carboxylate (199 mg, 0.664 mmol) and K₂CO₃ (138 mg, 0.996 mmol) was added and the mixture was heated to 50° C. and stirred for 5 h. The reaction mixture was poured into water (60 mL) and extracted with EA (2*50 mL). The combined organic fractions were washed with water (3*80 mL) and brine (1*80 mL), dried over Na₂SO₄, concentrated and purified by flash chromatography (30~50% EA/PE) to obtain tert-butyl 4-chloro-2-((8-(hydroxy(phenyl)methyl)-3,7-dimethyl-2,6-dioxo-2,3,6,7-tetrahydro-1H-purin-1-yl)methyl)-1H-indole-1-carboxylate as the major product; ESI: m/z 550.2 (M+H)⁺ and the title compound; ¹H NMR (400 MHz, DMSO-d₆) δ 11.27 (br s, 1H), 7.43-7.28 (m, 6H), 7.03-7.00 (m, 2H), 6.58 (d, J=4.8 Hz, 1H), 6.27 (d, J=1.2 Hz, 1H), 6.03 (d, J=4.8 Hz, 1H), 5.19 (s, 2H), 3.86 (s, 3H), 3.44 (s, 3H); ESI: m/z 450.1 (M+H)⁺.

Example 389

8-(1-aminoethyl)-1-[(4-chloro-1H-indol-2-yl)methyl]-3,7-dimethyl-purine-2,6-dione

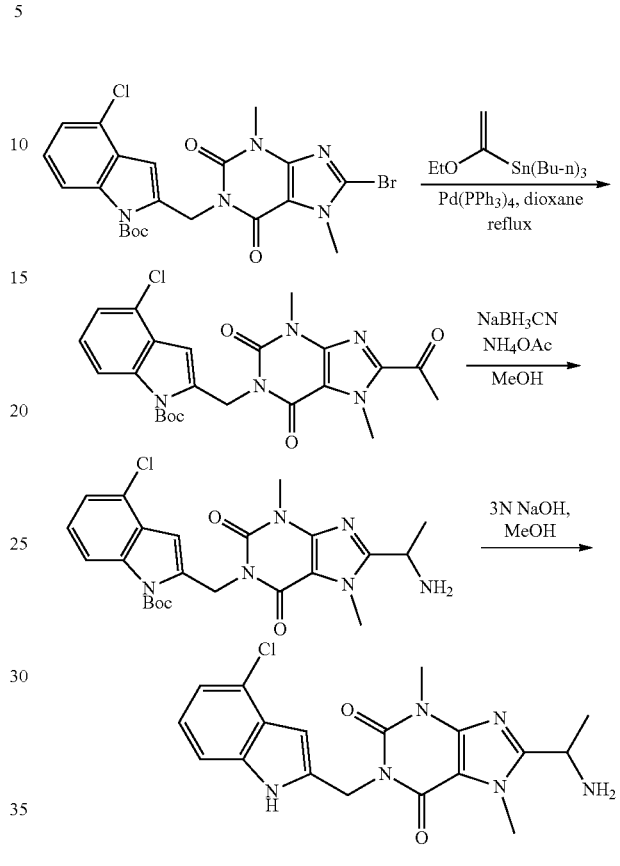

tert-Butyl 2-[(8-acetyl-3,7-dimethyl-2,6-dioxo-purin-1-yl)methyl]-4-chloro-indole-1-carboxylate

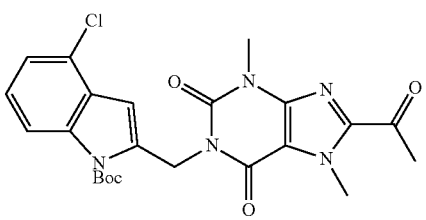 [SMILES: CC(=O)c1nc2c(c(=O)n(Cc3cc4c(Cl)cccc4n3C(=O)OC(C)(C)C)c(=O)n2C)n1C]

To a mixture of tert-butyl 2-[(8-bromo-3,7-dimethyl-2,6-dioxo-purin-1-yl)methyl]-4-chloro-indole-1-carboxylate (100.00 mg, 191.29 umol), tributyl(1-ethoxyvinyl)stannane (138.17 mg, 382.58 umol, 129.13 uL) in 1,4-dioxane (5.00 mL) was added Pd(PPh₃)₄ (22.10 mg, 19.13 umol) at 25° C. under N₂. The mixture was warmed to 110° C. and stirred for 3 hr. The mixture was poured into ice-water (2 mL) and the aqueous phase was extracted with ethyl acetate (5 mL*3). The combined organic fractions were washed with brine (2 mL), dried with anhydrous Na₂SO₄, filtered and concentrated in vacuum to afford tert-butyl 4-chloro-2-[[8-(1-ethoxyvinyl)-3,7-dimethyl-2,6-dioxo-purin-1-yl]methyl]indole-1-carboxylate. To a mixture of tert-butyl 4-chloro-2-[[8-(1-ethoxyvinyl)-3,7-dimethyl-2,6-dioxo-purin-1-yl]

methyl]indole-1-carboxylate (100.00 mg, 194.56 umol) in MeOH (3.00 mL) was added 1N HCl (1.00 mL) at 0° C. The mixture was stirred at 25° C. for 15 h. The mixture was poured into NaHCO$_3$ (5 mL). The aqueous phase was extracted with ethyl acetate (10 mL*3). The combined organic fractions were washed with brine (5 mL), dried with anhydrous Na$_2$SO$_4$, filtered and concentrated. The residue was purified by Prep-TLC (PE/EA=5/1) to afford the title compound. $^1$H NMR (400 MHz CDCl$_3$) δ 8.11-7.93 (m, 1H), 7.21-7.11 (m, 2H), 6.17 (s, 1H), 5.60 (s, 2H), 4.36 (s, 3H), 3.68 (s, 3H), 2.76 (s, 3H), 1.73 (s, 9H).

tert-Butyl 2-[[8-(1-aminoethyl)-3,7-dimethyl-2,6-dioxo-purin-1-yl]methyl]-4-chloro-indole-1-carboxylate

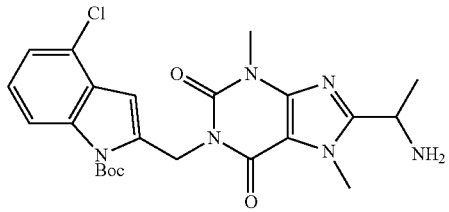 [SMILES: CC(N)c1nc2c(c(=O)n(Cc3cc4c(Cl)cccc4n3C(=O)OC(C)(C)C)c(=O)n2C)n1C]

To a solution of tert-butyl 2-[(8-acetyl-3,7-dimethyl-2,6-dioxo-purin-1-yl)methyl]-4-chloro-indole-1-carboxylate (90.00 mg, 185.22 umol) in MeOH (2.00 mL) and MeCN (2.00 mL) was added NH$_4$OAc (142.76 mg, 1.85 mmol), NaBH$_3$CN (29.10 mg, 463.05 umol). The reaction mixture was heated to 70° C. and stirred for 15 h. The reaction was quenched with H$_2$O (4 mL) at 25° C. The mixture was extracted with EA (2 mL*3). The combined organic fractions were washed with brine (1 mL), dried over Na$_2$SO$_4$ and concentrated; ESI: m/z 487.2/489.2 (M+H)$^+$.

8-(1-Aminoethyl)-1-[(4-chloro-1H-indol-2-yl)methyl]-3,7-dimethyl-purine-2,6-dione

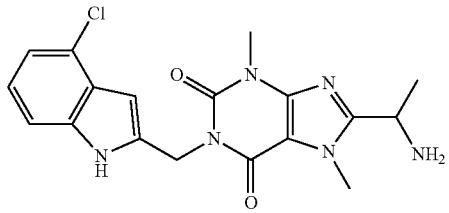

To a solution of tert-butyl 2-[[8-(1-aminoethyl)-3,7-dimethyl-2,6-dioxo-purin-1-yl]methyl]-4-chloro-indole-1-carboxylate (100.00 mg, 205.36 umol) in MeOH (1.00 mL) was added 3N NaOH (1.00 mL). The reaction mixture was stirred at 25° C. for 1 h. The mixture was poured into H$_2$O (2 mL) and extracted with EA (2 mL*3). The combined organic fractions were washed with brine (1 mL), dried over Na$_2$SO$_4$, concentrated. The crude product was purified by Prep-HPLC using Method C (12-42% ACN). $^1$H NMR (400 MHz, DMSO-d$_6$) δ 11.30 (br. s., 1H), 8.55 (br. s., 3H), 7.27-7.33 (m, 1H), 6.95-7.02 (m, 2H), 6.19-6.24 (m, 1H), 5.14-5.23 (m, 2H), 4.73-4.82 (m, 1H), 3.90-3.98 (m, 3H), 3.44-3.50 (m, 3H), 1.46-1.53 (m, 3H); ESI: m/z 387.2 (M+H)$^+$.

Examples 435 and 436

(S)-8-(1-aminoethyl)-1-((4-chloro-1H-indol-2-yl)methyl)-3,7-dimethyl-1H-purine-2,6(3H,7H)-dione and (R)-8-(1-aminoethyl)-1-((4-chloro-1H-indol-2-yl)methyl)-3,7-dimethyl-1H-purine-2,6(3H,7H)-dione

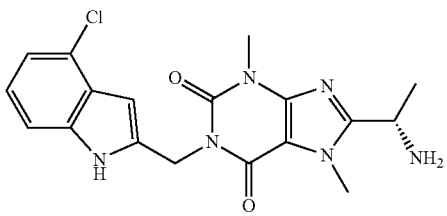 [SMILES: CC(N)c1nc2c(c(=O)n(Cc3cc4c(Cl)cccc4[nH]3)c(=O)n2C)n1C]

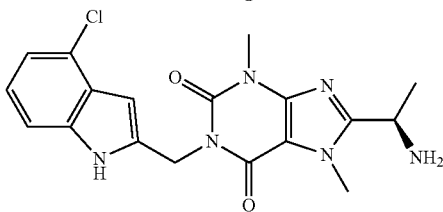

8-(1-Aminoethyl)-1-[(4-chloro-1H-indol-2-yl)methyl]-3,7-dimethyl-purine-2,6-dione was separated into individual enantiomers by chiral SFC using, a CHIRALPAK® AD-H/SFC (250*30 mm i.d., 5 u) column eluting with 45% IPA (0.1% NH$_4$OH) in CO$_2$.

Example 435: (S)-8-(1-aminoethyl)-1-((4-chloro-1H-indol-2-yl)methyl)-3,7-dimethyl-1H-purine-2,6(3H,7H)-dione or (R)-8-(1-aminoethyl)-1-((4-chloro-1H-indol-2-yl)methyl)-3,7-dimethyl-1H-purine-2,6(3H,7H)-dione: (retention time 6.2 min, ee %: 99.44%); $^1$H NMR (400 MHz, CD$_3$OD) δ 7.31-7.24 (m, 1H), 7.05-6.94 (m, 2H), 6.43 (s, 1H), 5.32 (s, 2H), 4.27 (q, J=6.9 Hz, 1H), 4.00 (s, 3H), 3.58 (s, 3H), 1.48 (d, J=6.6 Hz, 3H); ESI: m/z 387.1 (M+H)$^+$ Example 436: (R)-8-(1-aminoethyl)-14(4-chloro-1H-indol-2-yl)methyl)-3,7-dimethyl-1H-purine-2,6(3H,7H)-dione or (S)-8-(1-aminoethyl)-1-((4-chloro-1H-indol-2-yl)methyl)-3,7-dimethyl-1H-purine-2,6(3H,7H)-dione; (retention time 10.3 min, ee %: 92.3%); $^1$H NMR (400 MHz, CD$_3$OD) δ 7.29-7.24 (m, 1H), 7.03-6.93 (m, 2H), 6.42 (d, J=0.9 Hz, 1H), 5.31 (s, 2H), 4.76 (d, J=6.6 Hz, 1H), 4.02 (s, 3H), 3.62-3.52 (m, 3H), 1.63 (d, J=6.6 Hz, 3H); ESI: m/z 387.1 (M+H)$^+$.

Example 456

8-(1-aminoethyl)-1-[(3,4-dichloro-1H-indol-2-yl)methyl]-3,7-dimethyl-purine-2,6-dione

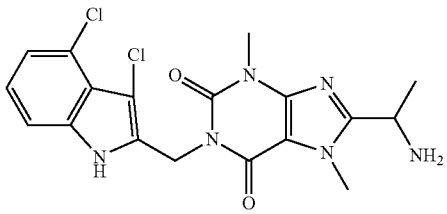 [SMILES: CC(N)c1nc2c(c(=O)n(Cc3[nH]c4cccc(Cl)c4c3Cl)c(=O)n2C)n1C]

To a solution of 8-(1-aminoethyl)-1-[(4-chloro-1H-indol-2-yl)methyl]-3,7-dimethyl-purine-2,6-dione (50.00 mg, 129.26 umol, 1.00 eq) in ACN (200.00 uL) was added NCS (20.71 mg, 155.11 umol, 1.20 eq) at 0° C. The reaction mixture was stirred at 25° C. for 1 h. The crude product was purified by Prep-HPLC using Method C (25-45% ACN) to provide the title compound. $^1$H NMR (400 MHz, DMSO-d$_6$) δ 1.49-1.63 (m, 3H) 3.51 (s, 3H) 3.99 (s, 3H) 4.75-4.90 (m, 1H) 5.19-5.32 (m, 2H) 7.02-7.14 (m, 2H) 7.26-7.40 (m, 1H) 8.59-8.84 (m, 3H) 11.44-11.58 (m, 1H); ESI: m/z 421 (M+1)$^+$.

Example 457

1-[(4-chloro-1H-indol-2-yl)methyl]-8-[1-(dimethylamino)ethyl]-3,7-dimethyl-purine-2,6-dione

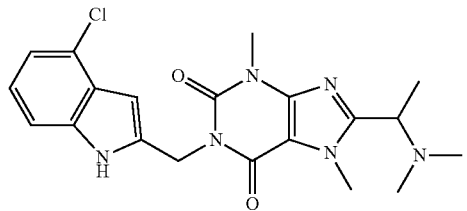 [SMILES: CC(c1nc2c(c(=O)n(Cc3cc4c(Cl)cccc4[nH]3)c(=O)n2C)n1C)N(C)C]

To a solution of 8-(1-aminoethyl)-1-[(4-chloro-1H-indol-2-yl)methyl]-3,7-dimethyl-purine-2,6-dione (15.00 mg, 38.78 umol) in MeOH (200.00 uL) was added HCHO (11.64 mg, 387.77 umol, 10.68 uL) and the reaction mixture was stirred at 25° C. for 10 mins. NaBH$_3$CN (6.09 mg, 96.94 umol) was added and the reaction mixture was stirred at 25° C. for another 1 h. The reaction was quenched with 3N HCl (0.5 mL). The crude product was purified by Prep-HPLC using Method C (25-45% ACN) to give the title compound. $^1$H NMR (400 MHz, DMSO-d$_6$) δ 11.31-11.39 (m, 1H) 10.89-10.98 (m, 1H) 7.32-7.38 (m, 1H) 6.98-7.07 (m, 2H) 6.24-6.32 (m, 1H) 5.21-5.28 (m, 2H) 4.91-5.01 (m, 1H) 4.02-4.09 (m, 3H) 3.50 (s, 3H) 2.81 (br. s., 6H) 1.60-1.69 (m, 3H); ESI: m/z 415 (M+1)$^+$.

Example 390

N-((4-((1-(((4-chloro-1H-indol-2-yl)methyl)-3,7-dimethyl-2,6-dioxo-2,3,6,7-tetrahydro-1H-purin-8-yl)amino)phenyl)sulfonyl)acetamide

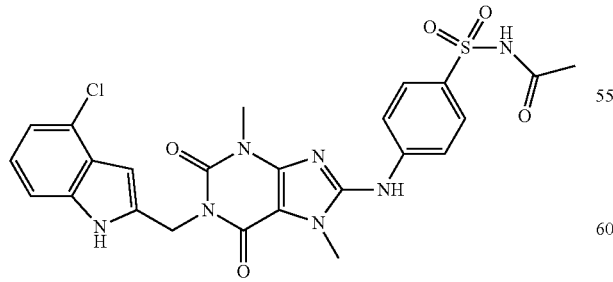

The title compound was synthesized in a similar fashion as Procedure 8B using tert-butyl 2-[(8-bromo-3,7-dimethyl-2,6-dioxo-purin-1-yl)methyl]-4-chloro-indole-1-carboxylate and N-(4-aminophenyl)sulfonylacetamide. The product was purified by prep-HPLC using Method A (15-50% ACN). $^1$H NMR (400 MHz, DMSO-d$_6$) δ 11.29 (s, 1H), 9.71 (s, 1H), 7.85 (s, 4H), 7.37-7.29 (m, 1H), 7.09-6.94 (m, 2H), 6.28 (s, 1H), 5.22 (s, 2H), 3.85 (s, 3H), 3.49 (s, 3H), 1.89 (s, 3H); ESI: m/z 556.2 (M+H)$^+$.

Example 391

1-[(4-chloro-1H-indol-2-yl)methyl]-3,7-dimethyl-8-(3-piperidyl)purine-2,6-dione

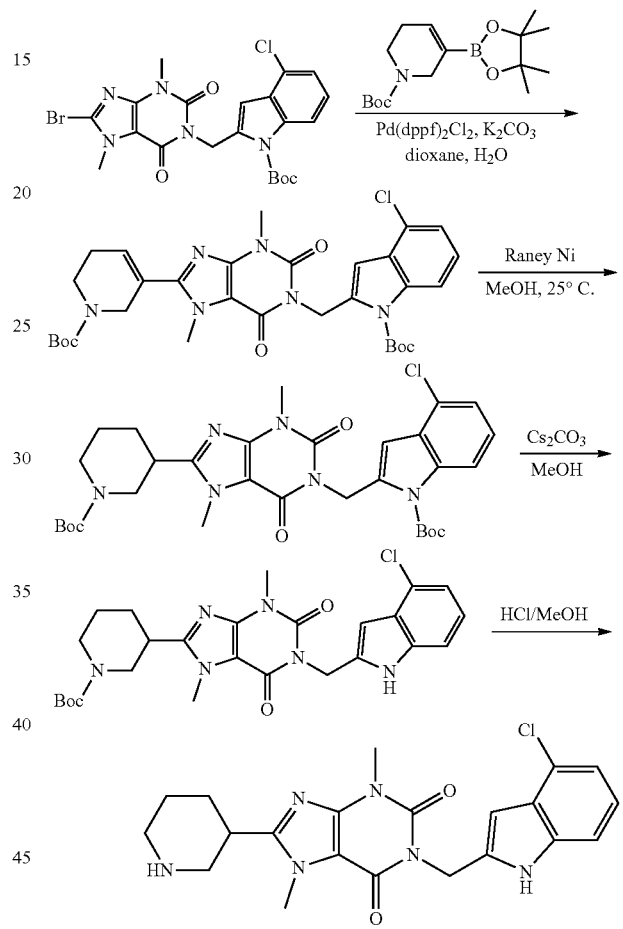

tert-Butyl 2-[[8-(1-tert-butoxycarbonyl-3,6-dihydro-2H-pyridin-5-yl)-3,7-dimethyl-2,6-dioxo-purin-1-yl]methyl]-4-chloro-indole-1-carboxylate

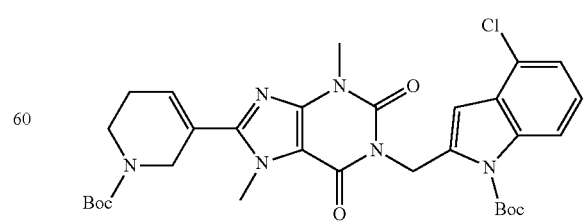

To a mixture of tert-butyl 2-[(8-bromo-3,7-dimethyl-2,6-dioxo-purin-1-yl)methyl]-4-chloro-indole-1-carboxylate (150.00 mg, 286.93 umol), tert-butyl 5-(4,4,5,5-tetramethyl-1,3,2-dioxaborolan-2-yl)-3,6-dihydro-2H-pyridine-1-carboxylate (133.08 mg, 430.40 umol) and $K_2CO_3$ (118.97 mg, 860.79 umol) in dioxane (4.00 mL) and $H_2O$ (1.00 mL) was added Pd(dppf)Cl$_2$ (10.50 mg, 14.35 umol) at 25° C. under $N_2$. The mixture was warmed to 90° C. and stirred for 3 hr. The mixture was poured into ice-water (2 mL) and the aqueous phase was extracted with ethyl acetate (5 mL*3). The combined organic fractions were washed with brine (2 mL), dried with anhydrous $Na_2SO_4$, filtered and concentrated. The product was purified by column chromatography (PE/EA from 10/1 to 1/1) to obtain tert-butyl 2-[[8-(1-tert-butoxycarbonyl-3,6-dihydro-2H-pyridin-5-yl)-3,7-dimethyl-2,6-dioxo-purin-1-yl]methyl]-4-chloro-indole-1-carboxylate: $^1$H NMR (400 MHz, CDCl$_3$) δ 8.03 (dd, J=3.5, 5.7 Hz, 1H), 7.20-7.10 (m, 2H), 6.39 (br. s., 1H), 6.19 (s, 1H), 5.59 (s, 2H), 4.37 (br. s., 2H), 4.06 (s, 3H), 3.65 (s, 3H), 2.44 (br. s., 2H), 2.05 (s, 3H), 1.72 (s, 10H), 1.52 (s, 9H); ESI: m/z 625.3 (M+H)$^+$.

tert-Butyl 2-[[8-(1-tert-butoxycarbonyl-3-piperidyl)-3,7-dimethyl-2,6-dioxo-purin-1-yl]methyl]-4-chloro-indole-1-carboxylate

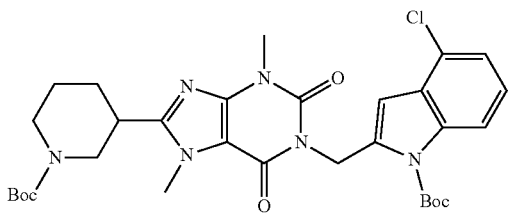 [SMILES: Cn1c(C2CCCN(C(=O)OC(C)(C)C)C2)nc2c1c(=O)n(Cc1cc3c(Cl)cccc3n1C(=O)OC(C)(C)C)c(=O)n2C]

To a solution of tert-butyl 2-[[8-(1-tert-butoxycarbonyl-3,6-dihydro-2H-pyridin-5-yl)-3,7-dimethyl-2,6-dioxo-purin-1-yl]methyl]-4-chloro-indole-1-carboxylate (160.00 mg, 255.95 umol) in MeOH (5.00 mL) was added Raney-Ni (1.00 g, 3.51 mmol) under $N_2$. The suspension was degassed under vacuum and purged with $H_2$ several times. The mixture was stirred under $H_2$ (15 psi) at 25° C. for 0.5 h. The reaction mixture was filtered and the filtrate was concentrated to give crude tert-butyl 2-[[8-(1-tert-butoxycarbonyl-3-piperidyl)-3,7-dimethyl-2,6-dioxo-purin-1-yl]methyl]-4-chloro-indole-1-carboxylate: ESI: m/z 627.4 (M+H)$^+$.

tert-Butyl 3-(1-((4-chloro-1H-indol-2-yl)methyl)-3,7-dimethyl-2,6-dioxo-2,3,6,7-tetrahydro-1H-purin-8-yl)piperidine-1-carboxylate

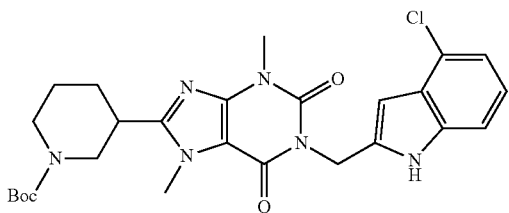 [SMILES: Cn1c(C2CCCN(C(=O)OC(C)(C)C)C2)nc2c1c(=O)n(Cc1cc3c(Cl)cccc3[nH]1)c(=O)n2C]

To a mixture of tert-butyl 2-[[8-(1-tert-butoxycarbonyl-3-piperidyl)-3,7-dimethyl-2,6-dioxo-purin-1-yl]methyl]-4-chloro-indole-1-carboxylate (120.00 mg, 191.35 umol) in MeOH (5.00 mL) was added Cs$_2$CO$_3$ (623.46 mg, 1.91 mmol). The mixture was stirred at 25° C. for 15 h. The mixture was poured into ice-water (2 mL) and the aqueous phase was extracted with ethyl acetate (5 mL*3). The combined organic fractions were washed with brine (2 mL), dried with anhydrous Na$_2$SO$_4$, filtered and concentrated to provide the title compound: ESI: m/z 527.2 (M+H)$^+$.

1-[(4-Chloro-1H-indol-2-yl)methyl]-3,7-dimethyl-8-(3-piperidyl)purine-2,6-dione

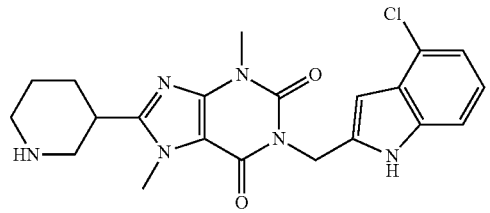 [SMILES: Cn1c(C2CCCNC2)nc2c1c(=O)n(Cc1cc3c(Cl)cccc3[nH]1)c(=O)n2C]

To a mixture of tert-butyl 3-[1-[(4-chloro-1H-indol-2-yl)methyl]-3,7-dimethyl-2,6-dioxo-purin-8-yl]piperidine-1-carboxylate (90.00 mg, 170.77 umol) in MeOH (1.00 mL) was added HCl/MeOH (4M, 3.00 mL) dropwise at 0° C. The mixture was stirred at 25° C. for 2 h. The mixture was concentrated. The residue was purified by prep-HPLC using Method C (12-42% ACN). $^1$H NMR (400 MHz, DMSO-d$_6$) δ 11.32 (br. s., 1H), 8.91-8.75 (m, 2H), 7.32 (d, J=7.1 Hz, 1H), 7.05-6.94 (m, 2H), 6.24 (s, 1H), 5.21 (s, 2H), 3.92 (s, 3H), 3.46 (s, 3H), 3.30-2.93 (m, 6H), 2.07-1.74 (m, 4H); ESI: m/z 427.2 (M+H)$^+$.

Example 392

1-[(4-chloro-1H-indol-2-yl)methyl]-3,7-dimethyl-8-[(5-piperazin-1-yl-2-pyridyl)amino]purine-2,6-dione

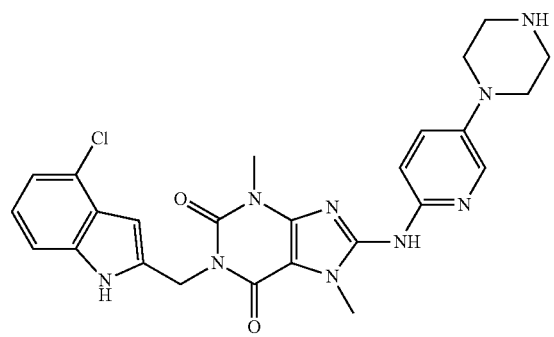 [SMILES: Cn1c(Nc2ccc(N3CCNCC3)cn2)nc2c1c(=O)n(Cc1cc3c(Cl)cccc3[nH]1)c(=O)n2C]

tert-Butyl 2-[(8-bromo-3,7-dimethyl-2,6-dioxo-purin-1-yl)methyl]-4-chloro-indole-1-carboxylate and tert-butyl 4-(6-amino-3-pyridyl)piperazine-1-carboxylate were coupled in a similar fashion as described in Procedure 8B. The product was purified by prep-TLC (EA) to obtain tert-butyl 2-[[8-[[5-(4-tert-butoxycarbonylpiperazin-1-yl)-2-pyridyl]amino]-3,7-dimethyl-2,6-dioxo-purin-1-yl]methyl]-4-chloro-indole-1-carboxylate: ESI: m/z 720.3 (M+H)$^+$. This product was dissolved in MeOH (5.00 mL) and treated with HCl/MeOH (4M, 3.00 mL). The mixture was stirred at 25° C. for 1 h. The reaction mixture was concentrated to give crude tert-butyl 4-chloro-2-[[3,7-dimethyl-2,6-dioxo-8-[(5-piperazin-1-yl-2-pyridyl) amino]purin-1-yl]methyl]indole-1-carboxylate. To a solution of this product in THF (2.00 mL) was added MeOH (2.00 mL) and 1N NaOH (1.00 mL). The mixture was stirred at 25° C. for 16 h. The mixture was concentrated to give crude product which was purified by prep-HPLC using Method A (15-45% ACN). $^1$H NMR (400 MHz, DMSO-d$_6$) δ 11.30 (s, 1H) 8.86 (br. s., 2H) 8.00-8.10 (m, 1H) 7.75-7.85 (m, 1H) 7.51-7.59 (m, 1H) 7.31-7.41 (m, 1H) 6.97-7.07 (m, 2H) 6.27 (s, 1H) 5.21 (s, 2H) 3.80 (s, 3H) 3.46 (s, 3H) 3.10-3.40 (m, 8H)); ESI: m/z 520.3 (M+H)$^+$.

Example 393

1-((1H-pyrrolo[2,3-c]pyridin-2-yl)methyl)-3,7-dimethyl-8-(pyridin-4-ylamino)-1H-purine-2,6(3H,7H)-dione

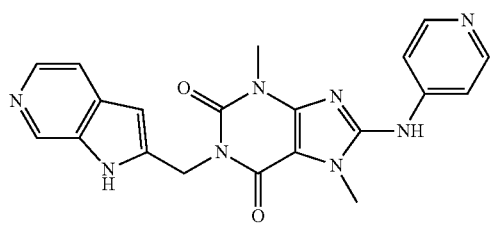 [SMILES: Cn1c(Nc2ccncc2)nc2c1c(=O)n(Cc1cc3ccncc3[nH]1)c(=O)n2C]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-1H-pyrrolo[2,3-c]pyridine-1-carboxylate and pyridin-4-amine hydrochloride. The product was purified by Prep-HPLC using Method D. $^1$H NMR (400 MHz, DMSO-d$_6$) δ 11.43 (s, 1H), 9.76 (s, 1H), 8.66 (s, 1H), 8.37 (s, 1H), 8.01-8.03 (d, J=5.2 Hz, 1H), 7.65-7.66 (m, 2H), 7.39-7.40 (d, J=5.2 Hz, 1H), 6.30 (s, 1H), 5.24 (s, 2H), 4.07 (s, 3H), 3.83 (s, 3H); ESI: m/z 403.1 (M+H)$^+$.

Example 394

8-(2-aminoethyl)-1,3,7-trimethyl-1H-purine-2,6(3H,7H)-dione tert-Butyl 2-(3-methyl-2,6-dioxo-2,3,6,7-tetrahydro-1H-purin-8-yl)ethylcarbamate

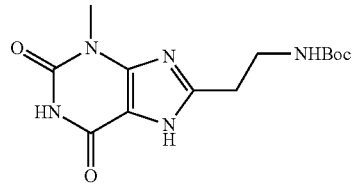 [SMILES: Cn1c(=O)[nH]c(=O)c2[nH]c(CCNC(=O)OC(C)(C)C)nc21]

A mixture of 5,6-diamino-1-methylpyrimidine-2,4(1H,3H)-dione (1.56 g, 10.0 mmol), 3-(tert-butoxycarbonylamino)propanoic acid (3.78 g, 20.0 mmol), EDCI (3.83 g, 20.0 mmol) and DMAP (2.44 g, 20.0 mmol) in DMSO (40 mL) was stirred for 16 h at 28° C. The reaction mixture was poured into water (250 mL) and the precipitate was collected. The solid and 3N NaOH aqueous (10 mL) in MeOH (30 mL) was heated to reflux and stirred for 6 h. The reaction mixture was cooled to 28° C. and mixture was concentrated. The aqueous residue was neutralized with citric acid to pH=6-7. The precipitate was collected and dried in vacuo to afford the product; ESI: m/z 310.1 (M+H)$^+$.

tert-Butyl 2-((8-(2-(tert-butoxycarbonylamino)ethyl)-3,7-dimethyl-2,6-dioxo-2,3,6,7-tetrahydro-1H-purin-1-yl)methyl)-4-chloro-1H-indole-1-carboxylate and tert-butyl 2-(1,3,7-trimethyl-2,6-dioxo-2,3,6,7-tetrahydro-1H-purin-8-yl)ethylcarbamate

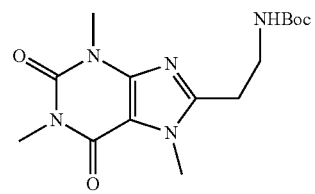

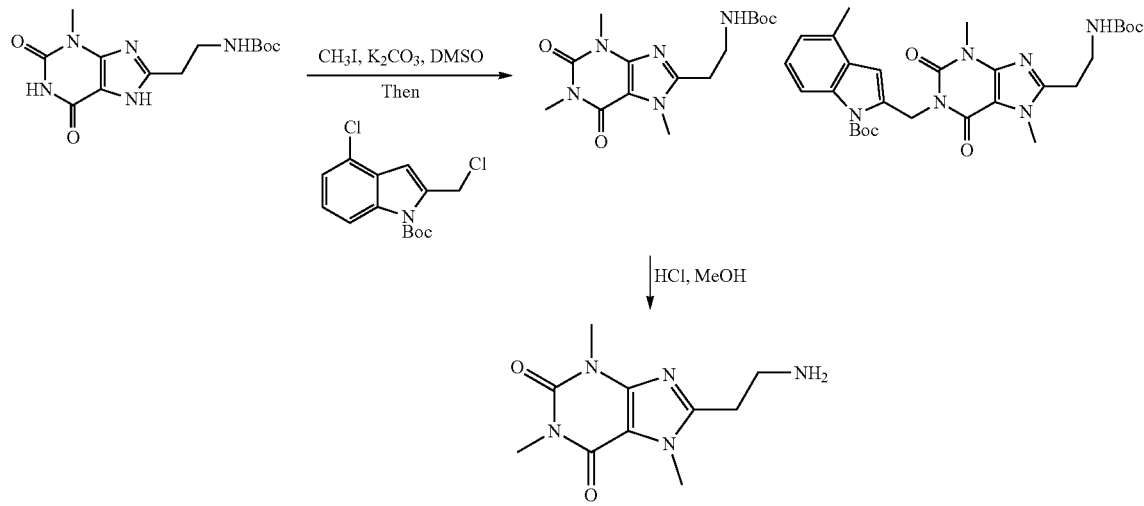

355
-continued

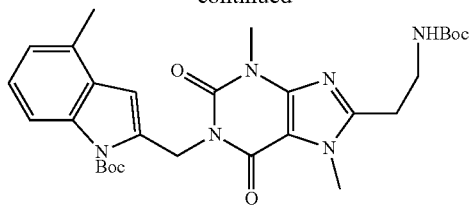

A mixture of tert-butyl 2-(3-methyl-2,6-dioxo-2,3,6,7-tetrahydro-1H-purin-8-yl)ethylcarbamate (155 mg, 0.50 mmol) and K₂CO₃ (83 mg, 0.60 mmol) in DMSO (5 mL) was stirred for 30 min at 25° C. and MeI (71 mg, 0.50 mmol) was added. The resulting mixture was stirred for 16 h at 25° C. Then tert-butyl 4-chloro-2-(chloromethyl)-1H-indole-1-carboxylate (150 mg, 0.50 mmol) and K₂CO₃ (83 mg, 0.60 mmol) was added. The mixture was heated to 50° C. and stirred for 2 h. The reaction mixture was poured into water (50 mL) and extracted with EA (2*30 mL). The combined organic fractions were washed with water (3*50 mL) and brine (1*50 mL), dried over Na₂SO₄, concentrated and purified by flash chromatography (30~70% EA/PE) to obtain tert-butyl 2-((8-(2-(tert-butoxycarbonylamino)ethyl)-3,7-dimethyl-2,6-dioxo-2,3,6,7-tetrahydro-1H-purin-1-yl)methyl)-4-chloro-1H-indole-1-carboxylate; ESI: m/z 587.2 (M+H)⁺ and tert-butyl 2-(1,3,7-trimethyl-2,6-dioxo-2,3,6,7-tetrahydro-1H-purin-8-yl)ethylcarbamate; ESI: m/z 338.2 (M+H)⁺.

8-(2-Aminoethyl)-1,3,7-trimethyl-1H-purine-2,6(3H,7H)-dione

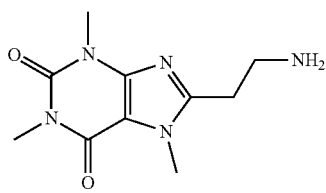 [SMILES: Cn1c(=O)c2c(nc(CCN)n2C)n(C)c1=O]

A mixture of tert-butyl 2-(1,3,7-trimethyl-2,6-dioxo-2,3,6,7-tetrahydro-1H-purin-8-yl)ethylcarbamate (80 mg, 0.237 mmol) in HCl/MeOH (3 mL, 3M) was stirred for 2 h at 25° C. The pH of the reaction mixture was made basic with NaHCO₃ (aq) to pH=8-9 at 0° C., and concentrated and dried in vacuo. The residue was dissolved in DCM/MeOH (10:1 v/v, 50 mL) and filtered. The filtrate was concentrated and the residue was purified by prep-HPLC using Method F (25-55% ACN). ¹H NMR (400 MHz, CDCl₃) δ 3.94 (s, 3H), 3.57 (s, 3H), 3.40 (s, 3H), 3.18 (t, J=6.4 Hz, 2H), 2.86 (t, J=6.4 Hz, 2H); ESI: m/z 238.2 (M+H)⁺.

Example 395

8-((1R,2S)-2-aminocyclopentylamino)-1-((4-chloro-1H-indol-2-yl)methyl)-3,7-dimethyl-1H-purine-2,6(3H,7H)-dione

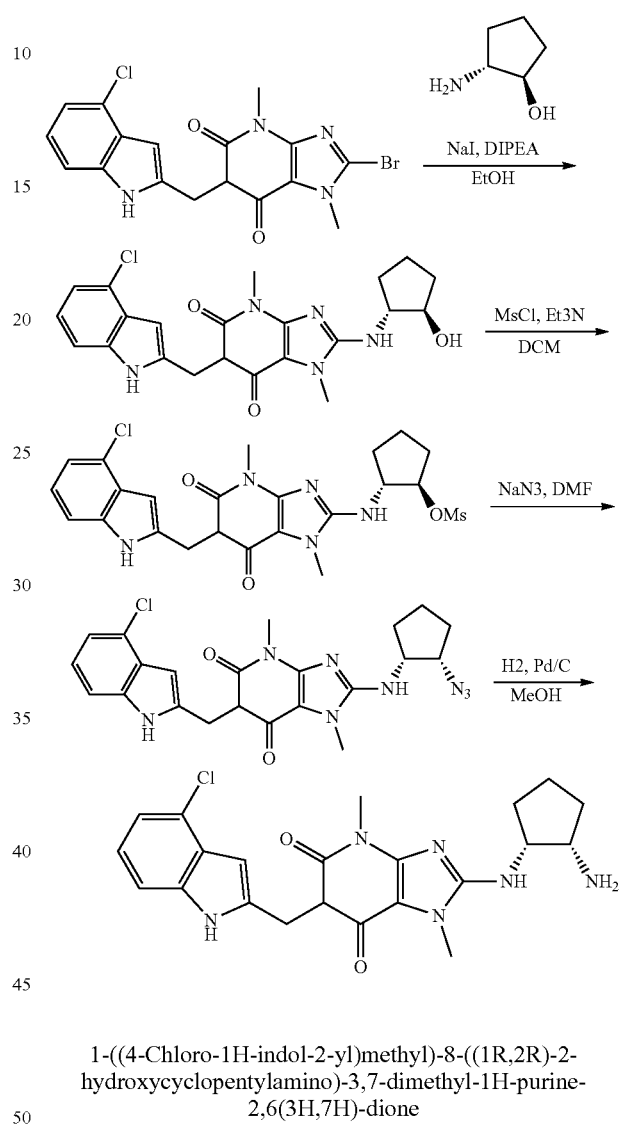

1-((4-Chloro-1H-indol-2-yl)methyl)-8-((1R,2R)-2-hydroxycyclopentylamino)-3,7-dimethyl-1H-purine-2,6(3H,7H)-dione

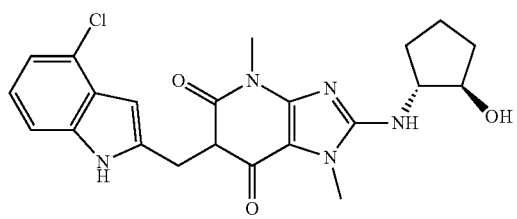 [SMILES: CN1C(=O)C(Cc2cc3c(Cl)cccc3[nH]2)C(=O)c2c1nc(N[C@@H]1CCC[C@H]1O)n2C]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and (1R,2R)-2-aminocyclopentanol. The product was purified by flash chromatography (silica gel, PE/EA=2/1) to give the title compound; ESI: m/z 443.2 (M+H)⁺.

(1R,2R)-2-(1-((4-chloro-1H-indol-2-yl)methyl)-3,7-dimethyl-2,6-dioxo-2,3,6,7-tetrahydro-1H-purin-8-ylamino)cyclopentyl methanesulfonate

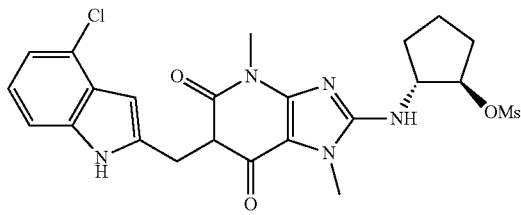 [SMILES: CN1C(=O)C(Cc2cc3c(Cl)cccc3[nH]2)C(=O)c2c1nc(N[C@@H]1CCC[C@H]1OS(C)(=O)=O)n2C]

To a solution of 1-((4-chloro-1H-indol-2-yl)methyl)-8-((1R,2R)-2-hydroxycyclopentylamino)-3,7-dimethyl-1H-purine-2,6(3H,7H)-dione (80 mg, 0.18 mmol) in DCM (2 mL) was added MsCl (31 mg, 0.27 mmol) and Et₃N (36 mg, 0.36 mmol). The mixture was stirred at rt for 4 h. The mixture was concentrated to give the title compound. ESI: m/z 521.1 (M+H)⁺.

1-((4-chloro-1H-indol-2-yl)methyl)-3,7-dimethyl-8-((1R,2S)-2-(triaz-2enyl)cyclopentylamino)-1H-purine-2,6(3H,7H)-dione

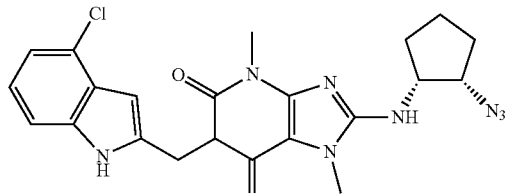

To a solution of (1R,2R)-2-(1-((4-chloro-1H-indol-2-yl)methyl)-3,7-dimethyl-2,6-dioxo-2,3,6,7-tetrahydro-1H-purin-8-ylamino)cyclopentyl methanesulfonate (60 mg, 0.115 mmol) in DMF (2 mL) was added NaN₃ (22 mg, 0.346 mmol). The mixture was stirred at 65° C. for 15 h. The reaction was quenched with H₂O (3 mL) and extracted with EA (3*5 mL). The combined organic fractions were dried with Na₂SO₄, filtered and concentrated. The product was purified by prep-HPLC using method D (64=70% ACN); ESI: m/z 468.1 (M+H)⁺.

8-((1R,2S)-2-aminocyclopentylamino)-1-((4-chloro-1H-indol-2-yl)methyl)-3,7-dimethyl-1H-purine-2,6 (3H,7H)-dione

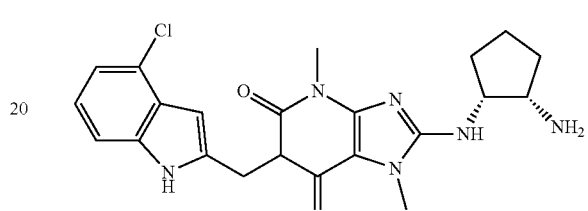

To a solution of 1-((4-chloro-1H-indol-2-yl)methyl)-3,7-dimethyl-8-((1R,2S)-2-(triaz-2 enyl)cyclopentylamino)-1H-purine-2,6(3H,7H)-dione (20 mg, 0.044 mmol) in MeOH (5 mL), was added Pd/C (5 mg). The mixture was stirred at room temperature for 3 h under H₂ atmosphere. The mixture was filtered and concentrated. The product was purified by prep-HPLC using Method D. ¹H NMR (400 MHz, DMSO-d₆) δ 11.24 (s, 1H), 7.33 (dd, J=6.4, 2.3 Hz, 1H), 7.04-6.97 (m, 2H), 6.22 (s, 1H), 5.16 (s, 2H), 4.06-3.93 (m, 1H), 3.61 (m, 7H), 1.97-1.62 (m, 6H); ESI; m/z 442.1 (M+H)⁺.

Example 396

3-(3-chloro-6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid

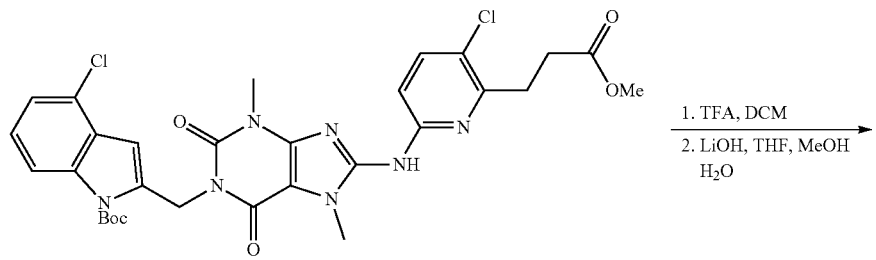

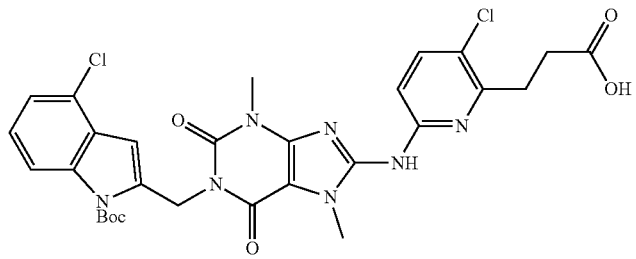

tert-Butyl 4-chloro-2-((8-(5-chloro-6-(3-methoxy-3-oxopropyl)pyridin-2-ylamino)-3,7-dimethyl-2,6-dioxo-2,3,6,7-tetrahydro-1H-purin-1-yl)methyl)-1H-indole-1-carboxylate

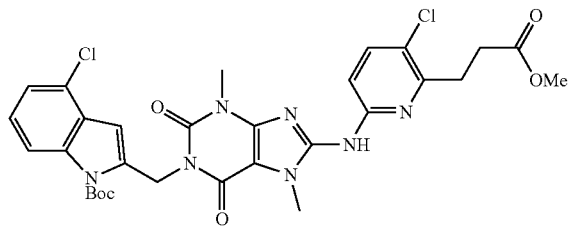 [SMILES: COC(=O)CCc1nc(Nc2nc3c(c(=O)n(Cc4cc5c(Cl)cccc5n4C(=O)OC(C)(C)C)c(=O)n3C)n2C)ccc1Cl]

The title compound was synthesized in a similar fashion as described in Procedure 8A using methyl 3-(6-amino-3-chloropyridin-2-yl)propanoate and tert-butyl 2-((8-bromo-3,7-dimethyl-2,6-dioxo-2,3,6,7-tetrahydro-1H-purin-1-yl)methyl)-4-chloro-1H-indole-1-carboxylate. The product was purified by column chromatography (EA/PE=70%); ESI: m/z 558.2 (M+H−100+2)⁺.

3-(3-Chloro-6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid

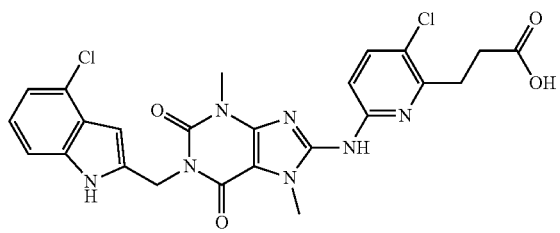

A mixture of tert-butyl 4-chloro-2-((8-(5-chloro-6-(3-methoxy-3-oxopropyl)pyridin-2-ylamino)-3,7-dimethyl-2,6-dioxo-2,3,6,7-tetrahydro-1H-purin-1-yl)methyl)-1H-indole-1-carboxylate (60 mg, 0.09 mmol) in TFA (5 mL) and DCM (5 mL) was stirred at R.T. for 3 h. The mixture was concentrated and the product was directly used in the next-step. A solution of this product and LiOH-H₂O (0.9 mmol, 34 mg) in MeOH (4 mL) and H₂O (1 mL) was stirred at rt. for 3 h. The mixture was concentrated and the residue was purified by prep-HPLC using Method B. ¹H NMR (400 MHz, DMSO-d₆) δ 12.19 (s, 1H), 11.27 (s, 1H), 9.99 (s, 1H), 7.72 (dd, J=58.9, 8.8 Hz, 2H), 7.34 (dd, J=6.5, 2.4 Hz, 1H), 7.10-6.94 (m, 2H), 6.28 (s, 1H), 5.21 (s, 2H), 3.80 (s, 3H), 3.45 (s, 3H), 3.01 (t, J=7.5 Hz, 2H), 2.69 (t, J=7.5 Hz, 2H); ESI: m/z 542.2 (M+H)⁺.

Example 397

8-((4-(1H-tetrazol-5-yl)phenyl)amino)-1-((4-chloro-1H-indol-2-yl)methyl)-3,7-dimethyl-1H-purine-2,6(3H,7H)-dione

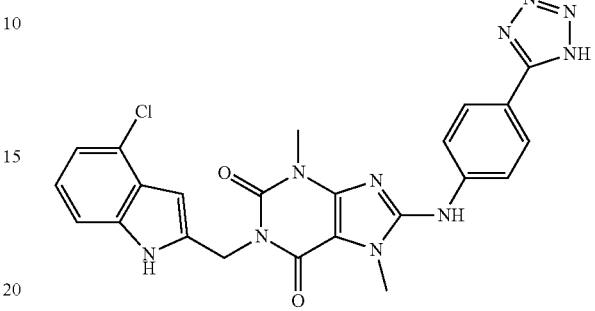

tert-Butyl 2-[(8-bromo-3,7-dimethyl-2,6-dioxo-purin-1-yl)methyl]-4-chloro-indole-1-carboxylate and 4-(1H-tetrazol-5-yl)aniline were coupled in a similar fashion as described in procedure 8B. The product was purified by prep-TLC (DCM/MeOH=10/1) to afford a mixture of tert-butyl 2-((8-((4-(1H-tetrazol-5-yl)phenyl)amino)-3,7-dimethyl-2,6-dioxo-2,3,6,7-tetrahydro-1H-purin-1-yl)methyl)-4-chloro-1H-indole-1-carboxylate and 8-((4-(1H-tetrazol-5-yl)phenyl)amino)-1-((4-chloro-1H-indol-2-yl)methyl)-3,7-dimethyl-1H-purine-2,6(3H,7H)-dione. This mixture of products was dissolved in MeOH (2.00 mL) and treated with Cs₂CO₃ (378.21 mg, 1.16 mmol). The mixture was stirred at 25° C. for 16 h. The mixture was concentrated and the crude product was purified by prep-HPLC using Method A (25-55% ACN). ¹H NMR (400 MHz, CD₃OD) δ 8.01 (d, J=9.0 Hz, 2H), 7.76 (d, J=9.0 Hz, 2H), 7.30 (d, J=7.5 Hz, 1H), 7.05-6.96 (m, 2H), 6.48 (s, 1H), 5.35 (s, 2H), 3.90 (s, 3H), 3.61 (s, 3H); ESI: m/z 503.2 (M+H)⁺.

Example 399

1-[(4-chloro-1H-indol-2-yl)methyl]-3,7-dimethyl-8-[(6-phenyl-2-pyridyl)amino]purine-2,6-dione

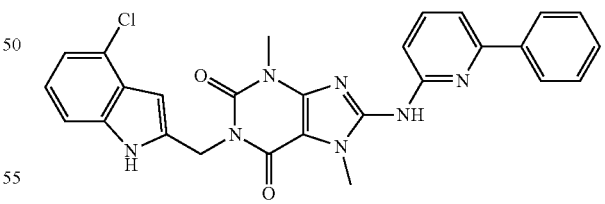

tert-Butyl 2-[(8-bromo-3,7-dimethyl-2,6-dioxo-purin-1-yl)methyl]-4-chloro-indole-1-carboxylate and 6-phenylpyridin-2-amine were coupled as described in procedure 8B. The product was purified by prep-TLC (PE/EA=2/1) to provide tert-butyl 4-chloro-2-[[3,7-dimethyl-2,6-dioxo-8-[(6-phenyl-2-pyridyl)amino]purin-1-yl]methyl]indole-1-carboxylate (95.00 mg). This product was dissolved in THF (5.00 mL), MeOH (5.00 mL) and 1N NaOH (2.00 mL). The mixture was stirred at 25° C. for 16 hr. The mixture was concentrated to give crude product which was purified by prep-HPLC using Method A (35-65% ACN). $^{1}$H NMR (400 MHz, DMSO-$d_6$) δ 11.29 (br. s., 1H), 8.08 (d, J=7.0 Hz, 2H), 7.92-7.81 (m, 1H), 7.64-7.74 (m, 1H), 7.61-7.28 (m, 5H), 7.08-6.97 (m, 2H), 6.30 (s, 1H), 5.24 (s, 2H), 3.86 (s, 3H), 3.49 (s, 3H); ESI: m/z 512.2 (M+H)$^{+}$.

Example 400

1-[(4-chloro-1H-indol-2-yl)methyl]-3,7-dimethyl-8-[(5-phenyl-2-pyridyl)amino]purine-2,6-dione

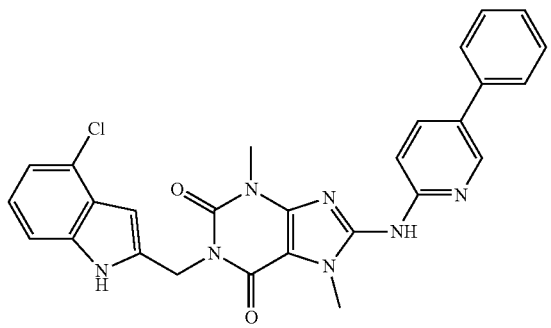 [SMILES: Cn1c(Nc2ccc(-c3ccccc3)cn2)nc2c1c(=O)n(Cc1cc3c(Cl)cccc3[nH]1)c(=O)n2C]

tert-Butyl 2-[(8-bromo-3,7-dimethyl-2,6-dioxo-purin-1-yl)methyl]-4-chloro-indole-1-carboxylate and 5-phenylpyridin-2-amine were coupled in a similar fashion as described in Procedure 8B to afford tert-butyl 4-chloro-2-[[3,7-dimethyl-2,6-dioxo-8-[(5-phenyl-2-pyridyl)amino]purin-1-yl]methyl]indole-1-carboxylate: ESI: m/z 612.3 (M+H)$^{+}$. The Boc group was removed as described in Example 399. The product was purified by prep-HPLC using Method C (35-65% ACN). $^{1}$H NMR (400 MHz, DMSO-$d_6$) δ 11.29 (s, 1H), 8.61 (s, 1H), 8.13 (dd, J=2.5, 8.5 Hz, 1H), 7.91 (d, J=8.5 Hz, 1H), 7.75-7.66 (m, 2H), 7.49 (t, J=7.8 Hz, 2H), 7.41-7.33 (m, 2H), 7.09-6.96 (m, 2H), 6.30 (s, 1H), 5.23 (s, 2H), 3.85 (s, 3H), 3.50 (s, 3H); ESI: m/z 512.2 (M+H)$^{+}$.

Example 401

1-((4-cyclopropyl-1H-indol-2-yl)methyl)-3,7-dimethyl-8-(pyridin-4-ylamino)-1H-purine-2,6(3H,7H)-dione

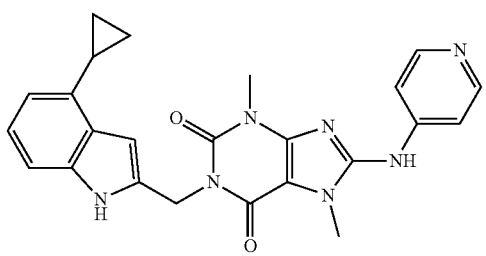 [SMILES: Cn1c(Nc2ccncc2)nc2c1c(=O)n(Cc1cc3c(C4CC4)cccc3[nH]1)c(=O)n2C]

To a solution of 1-((4-chloro-1H-indol-2-yl)methyl)-3,7-dimethyl-8-(pyridin-4-ylamino)-1H-purine-2,6(3H,7H)-dione (0.05 mmol, 20 mg) in DMF/H$_2$O (2 mL/0.5 mL) was added cyclopropylboronic acid (0.92 mmol, 0.10 mg), Pd(OAc)$_2$ (0.05 mmol, 11 mg), Xantphos (0.10 mmol, 36 mg), and Cs$_2$CO$_3$ (0.14 mmol, 45 mg). The reaction mixture was stirred under N$_2$ at 110° C. for 2 h in a microwave apparatus. The solution was concentrated. The residue was purified by prep-HPLC using Method B: $^{1}$H NMR (400 MHz, CD$_3$OD) δ 8.21 (d, J=6.4 Hz, 2H), 7.61 (d, J=6.4 Hz, 2H), 7.01 (d, J=4.0 Hz, 1H), 6.82 (t, J=8.0 Hz, 1H), 6.44 (m, 2H), 5.21 (s, 2H), 3.80 (s, 3H), 3.48 (s, 3H), 2.04 (m, 1H), 0.83 (m, 2H), 0.61 (m, 2H); ESI: m/z 442.2 (M+H)$^{+}$.

Example 402

1-((5-chloronaphthalen-2-yl)methyl)-3,7-dimethyl-8-(pyridin-4-ylamino)-1H-purine-2,6(3H,7H)-dione

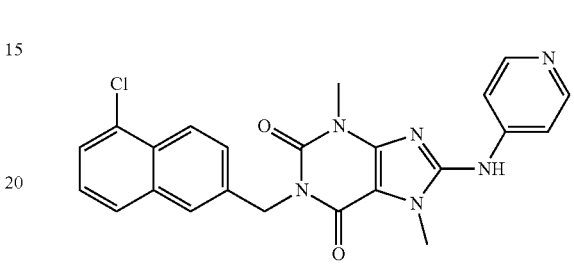

The title compound was synthesized in a similar fashion as described in procedure 8A using 8-bromo-1-((5-chloronaphthalen-2-yl)methyl)-3,7-dimethyl-1H-purine-2,6(3H,7H)-dione and pyridin-4-amine hydrochloride. The product was purified by prep-HPLC using Method B. $^{1}$H NMR (400 MHz, DMSO-$d_6$) δ 9.69 (s, 1H), 8.40 (s, 2H), 8.11 (d, J=8.4 Hz, 1H), 7.87 (m, 2H), 7.65 (m, 4H), 7.46 (t, J=8.0 Hz, 1H), 5.25 (s, 2H), 3.83 (s, 3H), 3.47 (s, 3H), 2.56 (s, 3H); ESI: m/z 446.7 (M+H)$^{+}$.

Example 403

1-((4-chloro-1H-indol-2-yl)methyl)-8-((1S,2S)-2-hydroxycyclopentylamino)-3,7-dimethyl-1H-purine-2,6(3H,7H)-dione

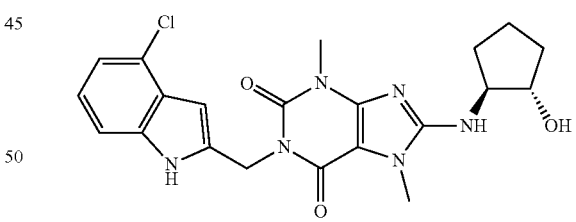

The title compound was synthesized in a similar fashion as described in procedure 7A using of 8-bromo-1-((4-chloro-1H-indol-2-yl)methyl)-3,7-dimethyl-1H-purine-2,6(3H,7H)-dione and (1S,2S)-2-aminocyclopentanol hydrochloride. The product was purified by flash chromatography (DCM/MeOH=20/1) and by Prep-HPLC using Method D (40-70% ACN). $^{1}$H NMR (400 MHz, CD$_3$OD) δ 7.27-7.25 (d, J=8.0 Hz, 1H), 6.99-6.96 (m, 2H), 6.42 (s, 1H), 5.27 (s, 2H), 4.11-4.06 (m, 1H), 4.02-3.97 (m, 1H), 3.66 (s, 3H), 3.50 (s, 3H), 2.26-2.17 (m, 1H), 2.05-1.99 (m, 1H), 1.83-1.76 (m, 2H), 1.69-1.60 (m, 2H); ESI: m/z 443.1 (M+H)$^{+}$.

Example 404

3,7-dimethyl-8-(pyridin-4-ylamino)-1-((4-(trifluoromethyl)-1H-indol-2-yl)methyl)-1H-purine-2,6(3H,7H)-dione

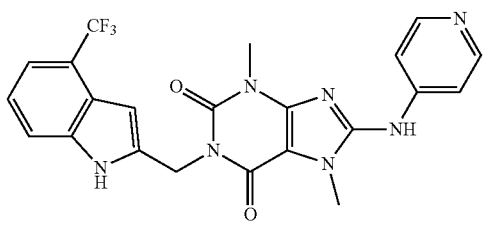 [SMILES: Cn1c(Nc2ccncc2)nc2c1c(=O)n(Cc1cc3c(C(F)(F)F)cccc3[nH]1)c(=O)n2C]

The title compound was synthesized in a similar fashion as described in procedure 8A using 2-((8-bromo-3,7-dimethyl-2,6-dioxo-2,3,6,7-tetrahydro-1H-purin-1-yl)methyl)-4-(trifluoromethyl)-1H-indole-1-carboxylate and pyridin-4-amine hydrochloride. The product was purified by column chromatography (EA/PE=100%). ¹H NMR (400 MHz, DMSO-$d_6$) δ 11.47 (s, 1H), 9.71 (s, 1H), 8.37 (s, 2H), 7.66 (d, J=8.0 Hz, 3H), 7.32 (d, J=7.4 Hz, 1H), 7.19 (t, J=7.8 Hz, 1H), 6.37 (s, 1H), 5.24 (s, 2H), 3.83 (s, 3H), 3.48 (s, 3H); ESI: m/z 470.2 (M+H)⁺.

Example 405

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-dimethylpropanamide

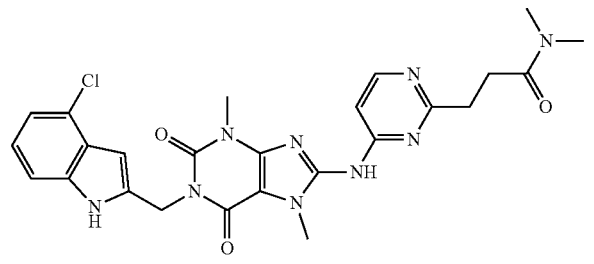 [SMILES: CN(C)C(=O)CCc1nccc(Nc2nc3c(c(=O)n(Cc4cc5c(Cl)cccc5[nH]4)c(=O)n3C)n2C)n1]

To a solution of 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid (0.03 mmol, 15 mg), HATU (0.06 mmol, 22 mg), TEA (0.09 mmol, 10 mg) in DMF (3 mL) was added dimethylamine hydrochloride (0.06 mmol, 5.0 mg). The reaction mixture was stirred at 25° C. for 4 h. The mixture was purified by Prep-HPLC using Method D (45-75% ACN). ¹H NMR (400 MHz, DMSO-$d_6$) δ 11.30 (s, 1H), 8.47 (br s, 1H), 7.49 (br s, 1H), 7.31 (s, 1H), 7.02-7.01 (m, 2H), 6.28 (s, 1H), 5.21 (s, 2H), 3.78 (s, 3H), 3.46 (s, 3H), 2.95-2.94 (m, 5H), 2.78-2.75 (m, 5H); ESI: m/z 536.2 (M+H)⁺.

Example 406

1-((4-chloro-1H-indol-2-yl)methyl)-3,7-dimethyl-8-(2-(3-oxo-3-(piperidin-1-yl)propyl)pyrimidin-4-ylamino)-1H-purine-2,6(3H,7H)-dione

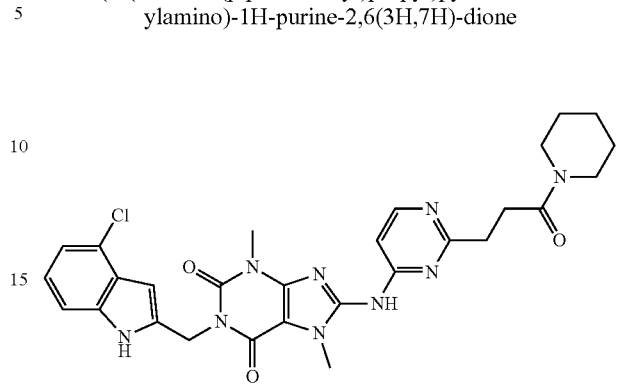

To a solution of 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid (0.03 mmol, 15 mg), HATU (0.06 mmol, 22 mg), TEA (0.09 mmol, 10 mg) in DMF (3 mL) was added piperidine (0.06 mmol, 5.0 mg). The reaction mixture was stirred at 25° C. for 4 h. The mixture was purified by Prep-HPLC using Method D. ¹H NMR (400 MHz, DMSO-$d_6$) δ 11.31 (s, 1H), 8.44 (br s, 1H), 7.51 (s, 1H), 7.29 (s, 2H), 7.02-7.01 (m, 2H), 6.28 (s, 1H), 5.21 (s, 1H), 3.78 (s, 3H), 3.46 (s, 3H), 3.38-3.35 (m, 4H), 2.97-2.93 (t, J=8.0 Hz, 2H), 2.78-2.75 (t, J=4.0 Hz, 2H), 1.54-1.78 (m, 2H), 1.44-1.39 (m, 2H), 1.34-1.30 (m, 2H); ESI: m/z 576.2 (M+H)⁺.

Example 407

1-((4-chloro-1H-indol-2-yl)methyl)-8-(6-(hydroxymethyl)pyridin-3-ylamino)-3,7-dimethyl-1H-purine-2,6(3H,7H)-dione

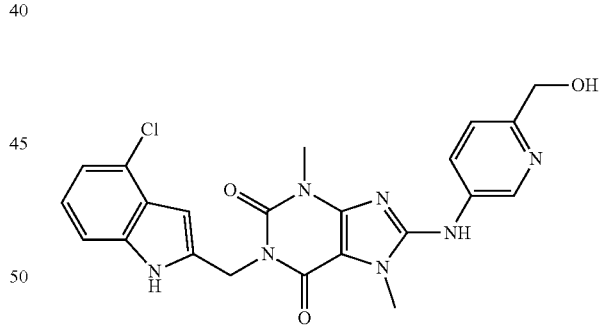

tert-Butyl 2-((8-bromo-3,7-dimethyl-2,6-dioxo-2,3,6,7-tetrahydro-1H-purin-1-yl)methyl)-4-chloro-1H-indole-1-carboxylate and (5-aminopyridin-2-yl)methanol were coupled in a similar fashion as described in procedure 8A. The product was purified by flash chromatography (DCM/MeOH=10/1) to give tert-butyl 2-((8-bromo-3,7-dimethyl-2,6-dioxo-2,3,6,7-tetrahydro-1H-purin-1-yl)methyl)-4-chloro-1H-indole-1-carboxylate; ESI: m/z 566.2 (M+H)⁺. This product was treated with TFA as described in Procedure 6. The product was purified by prep-HPLC using Method B (33-61% ACN). ¹H NMR (400 MHz, DMSO-$d_6$) δ 11.29 (s, 1H), 9.34 (b, 1H), 8.76 (d, J=2.8 Hz, 1H), 8.11 (dd, J=8.8, 2.8 Hz, 1H), 7.42 (d, J=8.4 Hz, 1H), 7.33 (dd, J=6.4, 2.0 Hz, 1H), 7.02-6.99 (m, 2H), 6.24 (m, 1H), 5.32 (t, J=5.6 Hz, 1H), 5.20 (s, 2H), 4.50 (d, J=5.6 Hz, 2H), 3.80 (s, 3H), 3.44 (s, 3H); ESI; m/z 466.1 (M+H)+.

Example 408

Methyl 5-(1-((4-chloro-1H-indol-2-yl)methyl)-3,7-dimethyl-2,6-dioxo-2,3,6,7-tetrahydro-1H-purin-8-ylamino)picolinate

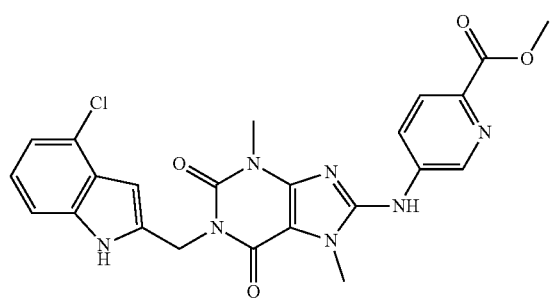 [SMILES: COC(=O)c1ccc(Nc2nc3c(c(=O)n(Cc4cc5c(Cl)cccc5[nH]4)c(=O)n3C)n2C)cn1]

tert-Butyl 2-((8-bromo-3,7-dimethyl-2,6-dioxo-2,3,6,7-tetrahydro-1H-purin-1-yl)methyl)-4-chloro-1H-indole-1-carboxylate and methyl 5-aminopicolinate were coupled in a similar fashion as described in Procedure 8A. The product was purified by column chromatography (DCM/MeOH from 50/1 to 5/1) to give the crude product. The product was further purified by Prep-HPLC using Method B (30-65% ACN) $^1$H NMR (400 MHz, DMSO-$d_6$) δ 11.30 (s, 1H), 9.87 (s, 1H), 8.97 (d, J=2.4 Hz, 1H), 8.34 (dd, J=8.8, 2.4 Hz, 1H), 8.05 (d, J=8.8 Hz, 1H), 7.34-7.32 (m, 1H), 7.02-6.99 (m, 2H), 6.26 (s, 1H), 5.21 (s, 2H), 3.86 (s, 3H), 3.85 (s, 3H), 3.48 (s, 3H).); ESI: m/z 494.1 (M+H)+.

Example 409

5-(1-((4-chloro-1H-indol-2-yl)methyl)-3,7-dimethyl-2,6-dioxo-2,3,6,7-tetrahydro-1H-purin-8-ylamino)picolinamide

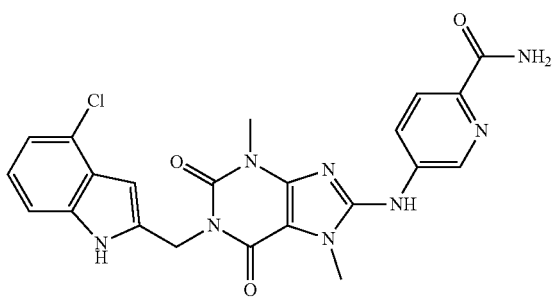

A solution of 5-(1-((4-chloro-1H-indol-2-yl)methyl)-3,7-dimethyl-2,6-dioxo-2,3,6,7-tetrahydro-1H-purin-8-ylamino)picolinonitrile (30 mg, 0.065 mmol) in $H_2SO_4$ was stirred at room temperature for 0.5 h. The mixture was neutralized with sat. $Cs_2CO_3$ and extracted with DCM (3*20 mL). The combined organic fractions were dried with $Na_2SO_4$ and concentrated. The residue was purified by preparative HPLC using Method B (33-60% ACN). $^1$H NMR (400 MHz, DMSO-$d_6$) δ 11.30 (s, 1H), 9.75 (b, 1H), 8.94 (d, J=2.8 Hz, 1H), 8.27 (dd, J=8.8, 2.8 Hz, 1H), 8.01-7.99 (m, 2H), 7.46 (m, 1H), 7.34 (dd, J=6.8, 2.4 Hz, 1H), 7.04-6.99 (m, 2H), 6.26 (m, 1H), 5.21 (s, 2H), 3.85 (s, 3H), 3.47 (s, 3H); ESI: m/z 479.1 (M+H)+.

Example 410

3,7-dimethyl-1-((5-methylnaphthalen-2-yl)methyl)-8-(pyridin-4-ylamino)-1H-purine-2,6(3H,7H)-dione

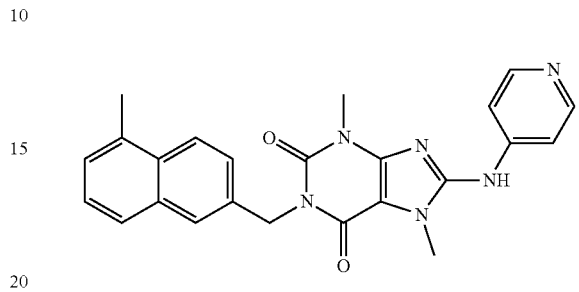

To a solution of 1-((5-chloronaphthalen-2-yl)methyl)-3,7-dimethyl-8-(pyridin-4-ylamino)-1H-purine-2,6(3H,7H)-dione (0.08 mmol, 35 mg) in DMF/$H_2O$ (3 mL/0.5 mL) was added methylboronic acid (1.6 mmol, 96 mg), Pd(OAc)$_2$ (0.01 mmol, 2.2 mg), Xantphos (0.02 mmol, 7.2 mg), and $Cs_2CO_3$ (0.24 mmol, 78 mg). The reaction mixture was stirred under $N_2$ at 110° C. for 2 h in a microwave apparatus. The solution was concentrated. The product was purified by prep-HPLC using Method B. $^1$H NMR (400 MHz, DMSO-$d_6$) δ 9.75 (br s, 1H), 8.34 (d, J=5.2 Hz, 2H), 7.94 (d, J=8.4 Hz, 1H), 7.65 (m, 4H), 7.52 (m, 1H), 7.30 (m, 2H), 5.23 (m, 2H), 3.82 (s, 3H), 3.47 (s, 3H), 2.62 (s, 3H); ESI: m/z 427.2 (M+H)+.

Example 411

8-(amino(phenyl)methyl)-1-((4-chloro-1H-indol-2-yl)methyl)-3,7-dimethyl-1H-purine-2,6(3H,7H)-dione

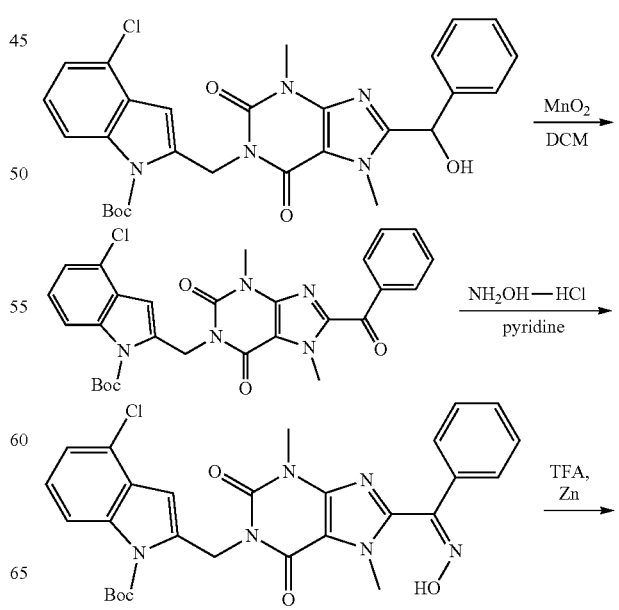

367

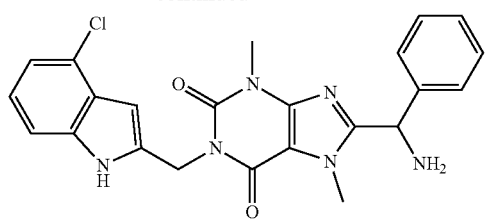

tert-Butyl 2-((8-benzoyl-3,7-dimethyl-2,6-dioxo-2,3,6,7-tetrahydro-1H-purin-1-yl)methyl)-4-chloro-1H-indole-1-carboxylate

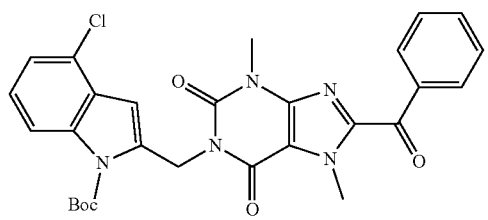 [SMILES: Cn1c(C(=O)c2ccccc2)nc2c1c(=O)n(Cc1cc3c(Cl)cccc3n1C(=O)OC(C)(C)C)c(=O)n2C]

To a solution of tert-butyl 4-chloro-2-((8-(hydroxy(phenyl)methyl)-3,7-dimethyl-2,6-dioxo-2,3,6,7-tetrahydro-1H-purin-1-yl)methyl)-1H-indole-1-carboxylate (60 mg, 0.109 mmol) in DCM (5 mL) was added MnO₂ (190 mg, 2.18 mmol). The mixture was stirred for 3 h at 28° C. The reaction mixture was diluted with DCM (10 mL) and filtered. The filtrate was concentrated to provide the title compound; ESI: m/z 548.2 (M+H)⁺.

tert-Butyl 4-chloro-2-((8-((hydroxyimino)(phenyl)methyl)-3,7-dimethyl-2,6-dioxo-2,3,6,7-tetrahydro-1H-purin-1-yl)methyl)-1H-indole-1-carboxylate

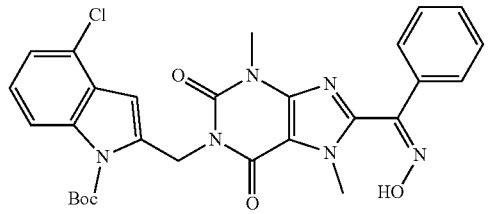 [SMILES: Cn1c(/C(=N\O)c2ccccc2)nc2c1c(=O)n(Cc1cc3c(Cl)cccc3n1C(=O)OC(C)(C)C)c(=O)n2C]

A mixture of tert-butyl 2-((8-benzoyl-3,7-dimethyl-2,6-dioxo-2,3,6,7-tetrahydro-1H-purin-1-yl)methyl)-4-chloro-1H-indole-1-carboxylate (45 mg, 0.082 mmol) and hydroxylamine hydrochloride (114 mg, 1.64 mmol) in pyridine (2 mL) was heated to 50° C. and stirred for 16 h. The reaction mixture was poured into water (30 mL) and extracted with EA (2*20 mL). The combined organic fractions were washed with water (3*30 mL) and brine (1*30 mL), dried over Na₂SO₄, concentrated; ESI: m/z 563.1 (M+H)⁺.

368

8-(Amino(phenyl)methyl)-1-((4-chloro-1H-indol-2-yl)methyl)-3,7-dimethyl-1H-purine-2,6(3H,7H)-dione

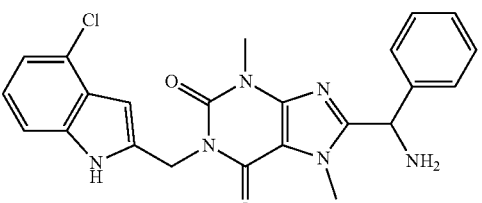

A mixture of tert-butyl 4-chloro-2-((8-((hydroxyimino)(phenyl)methyl)-3,7-dimethyl-2,6-dioxo-2,3,6,7-tetrahydro-1H-purin-1-yl)methyl)-1H-indole-1-carboxylate (30 mg, 0.053 mmol) in TFA (1 mL) was stirred for 1 h. Then Zn dust (172 mg, 2.65 mmol) was added and stirred for another 10 min. The reaction mixture was diluted in EA (20 mL) and filtered. The filtrate was poured into water (20 mL) and the pH was made basic with NaHCO₃(aq) to pH=8~9 at 0° C. The mixture was extracted with EA (2*15 mL). The combined organic fractions were washed with brine (1*30 mL), dried over Na₂SO₄, concentrated and purified by flash chromatography (100% EA/PE) and prep-HPLC using Method B (40-70% ACN). ¹H NMR (400 MHz, CDCl₃) δ 9.16 (br s, 1H), 7.37-7.18 (m, 6H), 7.06-7.03 (m, 2H), 6.70 (d, J=1.6 Hz, 1H), 5.31 (d, J=2.4 Hz, 2H), 5.19 (s, 1H), 3.74 (s, 3H), 3.65 (s, 3H); ESI; m/z 449.1 (M+H)⁺.

Example 412

3-(4-(3,7-dimethyl-1-((4-methyl-1H-indol-2-yl)methyl)-2,6-dioxo-2,3,6,7-tetrahydro-1H-purin-8-ylamino)pyrimidin-2-yl)propanoic acid

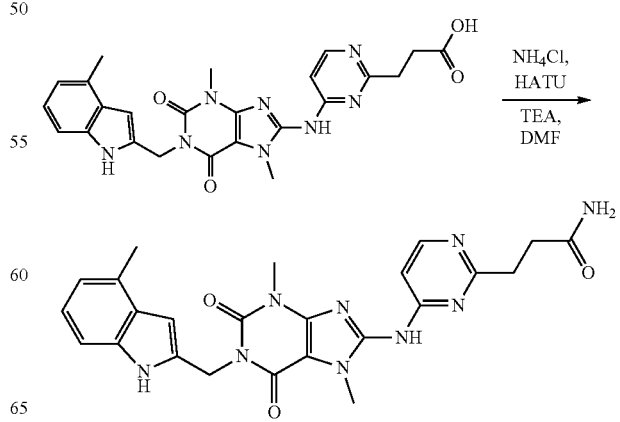

3-(4-((3,7-Dimethyl-1-((4-methyl-1H-indol-2-yl)methyl)-2,6-dioxo-2,3,6,7-tetrahydro-1H-purin-8-yl)amino)pyrimidin-2-yl)propanoic acid

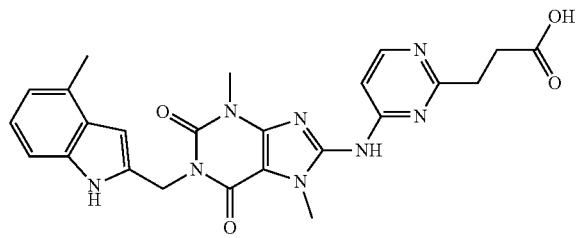 [SMILES: Cc1cccc2[nH]c(Cn3c(=O)c4c(nc(Nc5ccnc(CCC(=O)O)n5)n4C)n(C)c3=O)cc12]

tert-Butyl 2-((8-bromo-3,7-dimethyl-2,6-dioxo-2,3,6,7-tetrahydro-1H-purin-1-yl)methyl)-4-methyl-1H-indole-1-carboxylate and ethyl 3-(4-aminopyrimidin-2-yl)propanoate were coupled in a similar fashion as described in Procedure 8A. The solid product was purified by column chromatography (EA/PE=85%) to give tert-butyl 2-((8-(2-(3-ethoxy-3-oxopropyl)pyrimidin-4-ylamino)-3,7-dimethyl-2,6-dioxo-2,3,6,7-tetrahydro-1H-purin-1-yl)methyl)-4-methyl-1H-indole-1-carboxylate (120 mg); ESI: m/z 603.2 (M+H)+. This product was treated with LiOH (1.9 mmol, 72 mg) in MeOH (4 mL) and H$_2$O (1 mL). The mixture was stirred at rt. overnight. The mixture was concentrated and the pH of the aqueous residue was adjusted to pH 6 with saturated 1N HCl. The solid was collected by filtration and dried under high vacuum to provide the title compound; ESI: m/z 489 (M+H)+.

3-(4-(3,7-Dimethyl-1-((4-methyl-1H-indol-2-yl)methyl)-2,6-dioxo-2,3,6,7-tetrahydro-1H-purin-8-ylamino)pyrimidin-2-yl)propanoic acid

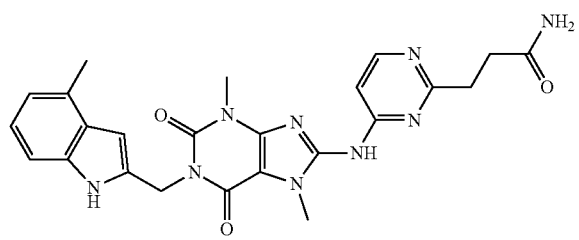 [SMILES: Cc1cccc2[nH]c(Cn3c(=O)c4c(nc(Nc5ccnc(CCC(N)=O)n5)n4C)n(C)c3=O)cc12]

A mixture of 3-(4-(3,7-dimethyl-1-((4-methyl-1H-indol-2-yl)methyl)-2,6-dioxo-2,3,6,7-tetrahydro-1H-purin-8-ylamino)pyrimidin-2-yl)propanoic acid (30 mg, 0.06 mmol), NH$_4$Cl (33 mg, 0.6 mmol), HATU (29 mg, 0.09 mmol), TEA (29 mg, 0.18 mmol) in DMF (2 mL) was stirred at rt. for 3 h. The reaction mixture was diluted with water (40 mL) and extracted with DCM (3*50 mL). The combined organic fractions were dried with Na$_2$SO$_4$, filtered and concentrated. The residue was purified by prep-HPLC using Method B. $^1$H NMR (400 MHz, DMSO-d$_6$) δ 10.81 (s, 1H), 10.48 (s, 1H), 8.43 (s, 1H), 7.55 (s, 1H), 7.33 (s, 1H), 7.17 (d, J=8.1 Hz, 1H), 6.96-6.85 (m, 1H), 6.74 (t, J=8.2 Hz, 2H), 6.26 (s, 1H), 5.20 (s, 2H), 3.81 (s, 3H), 3.46 (s, 3H), 2.94 (t, J=7.6 Hz, 2H), 2.55 (t, J=7.6 Hz, 2H), 2.39 (s, 3H); ESI: m/z 488.2 (M+H)+.

Example 413

8-(2-(3-(azetidin-1-yl)-3-oxopropyl)pyrimidin-4-ylamino)-1-((4-chloro-1H-indol-2-yl)methyl)-3,7-dimethyl-1H-purine-2,6(3H,7H)-dione

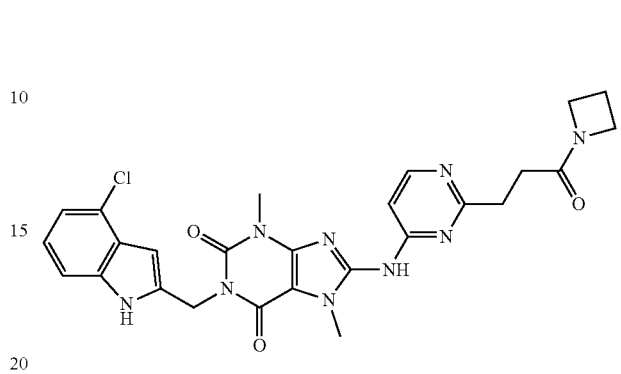

A mixture of 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid (0.04 mmol, 20 mg), azetidine (0.20 mmol, 11 mg), HATU (0.08 mmol, 31 mg) and Et$_3$N (0.12 mmol, 12 mg) in DMF (2 mL) was stirred at 30° C. for 12 h. The product was purified by prep-HPLC Method B. $^1$H NMR (400 MHz, DMSO-d$_6$) δ 11.28 (s, 1H), 8.33 (d, J=6.0 Hz, 1H), 7.51 (d, J=6.0 Hz, 1H), 7.32 (m, 1H), 7.01 (m, 2H), 6.28 (s, 1H), 5.21 (s, 2H), 4.08 (t, J=8.0 Hz, 2H), 3.76 (m, 5H), 3.60 (m, 1H), 3.46 (s, 3H), 2.86 (m, 3H), 2.51 (m, 2H), 2.11 (m, 2H); ESI: m/z 548.2 (M+H)+.

Example 414

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N-cyclopropyl-N-methyl-propanamide

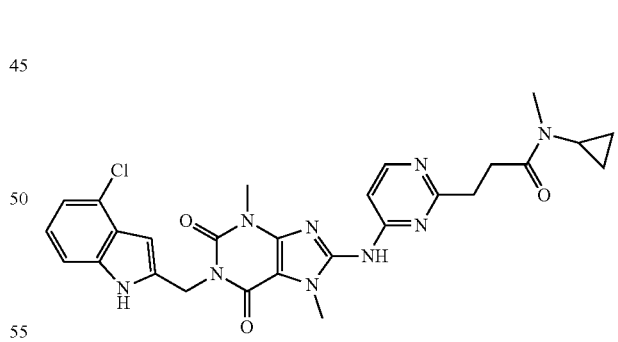

The title compound was synthesized in a similar fashion as Example 413 using 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid and N-methylcyclopropanamine. The product was purified by prep-HPLC using Method B. $^1$H NMR (400 MHz, DMSO-d$_6$) δ 11.29 (s, 1H), 8.38 (d, J=4.0 Hz, 1H), 7.44 (s, 1H), 7.33 (m, 1H), 7.01 (m, 2H), 6.28 (s, 1H), 5.22 (s, 2H), 3.77 (s, 3H), 3.47 (s, 3H), 2.94 (m, 4H), 2.74 (s, 3H), 2.67 (m, 1H), 0.73 (m, 2H), 0.66 (m, 2H); ESI: m/z 562.2 (M+H)+.

Example 415

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N-methylpropanamide

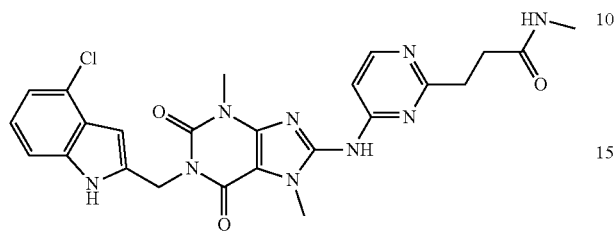

The title compound was synthesized in a similar fashion as Example 413 using 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid and methanamine (40% aqueous). The product was purified by prep-HPLC using Method B. $^1$H NMR (400 MHz, DMSO-$d_6$) δ 11.29 (s, 1H), 10.51 (s, 1H), 8.43 (m, 1H), 7.78 (m, 1H), 7.54 (m, 1H), 7.33 (m, 1H), 7.01 (m, 2H), 6.28 (s, 1H), 5.21 (s, 2H), 3.81 (s, 3H), 3.47 (s, 3H), 2.93 (m, 2H), 2.53 (m, 5H); ESI: m/z 522.2 (M+H)$^+$.

Example 416

1-((4-chloro-1H-indol-2-yl)methyl)-3,7-dimethyl-8-((2-(3-morpholino-3-oxopropyl)pyrimidin-4-yl)amino)-3,7-dihydro-1H-purine-2,6-dione

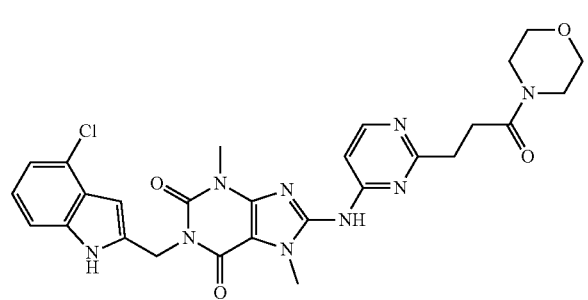 [SMILES: Cn1c(Nc2ccnc(CCC(=O)N3CCOCC3)n2)nc2c1c(=O)n(Cc1cc3c(Cl)cccc3[nH]1)c(=O)n2C]

The title compound was synthesized in a similar fashion as Example 413 using 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid and morpholine. The product was purified by prep-HPLC using Method B. $^1$H NMR (400 MHz, DMSO-$d_6$) δ 11.29 (s, 1H), 8.41 (m, 1H), 7.51 (m, 1H), 7.32 (m, 1H), 7.01 (m, 2H), 6.28 (s, 1H), 5.22 (s, 2H), 3.80 (s, 3H), 3.51 (m, 4H), 3.46 (m, 3H), 3.39 (m, 2H), 2.96 (m, 2H), 2.78 (m, 2H); ESI: m/z 578.2 (M+H)$^+$.

Example 417

1-((4-chloro-1H-indol-2-yl)methyl)-3,7-dimethyl-8-(2-(3-oxo-3-(pyrrolidin-1-yl)propyl)pyrimidin-4-ylamino)-1H-purine-2,6(3H,7H)-dione

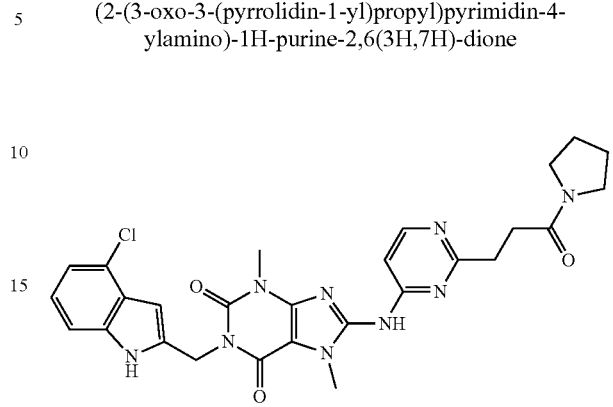

The title compound was synthesized in a similar fashion as Example 413 using 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid and pyrrolidine. The product was purified by prep-HPLC using Method B. $^1$H NMR (400 MHz, DMSO-$d_6$) δ 11.30 (s, 1H), 8.39 (m, 1H), 7.47 (m, 1H), 7.32 (m, 1H), 7.01 (m, 2H), 6.28 (s, 1H), 5.21 (s, 2H), 3.78 (s, 3H), 3.46 (m, 3H), 3.36 (m, 2H), 3.22 (m, 2H), 2.95 (t, J=7.2 Hz, 2H), 2.70 (t, J=7.2 Hz, 2H), 1.80 (m, 2H), 1.74 (m, 2H); ESI: m/z 562.2 (M+H)$^+$.

Example 418

3-(7-(2-aminoethyl)-1-((4-chloro-1H-indol-2-yl)methyl)-3-methyl-2,6-dioxo-2,3,6,7-tetrahydro-1H-purin-8-ylamino)cyclohexanecarboxylic acid

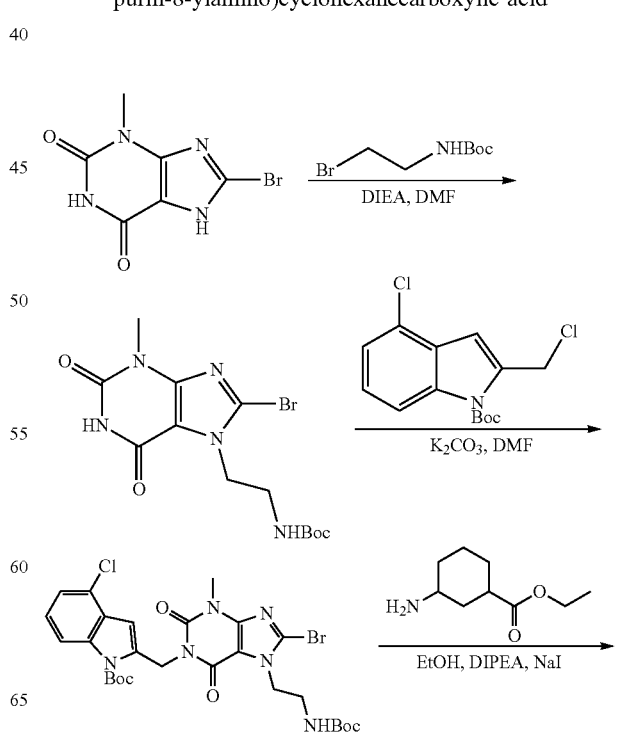

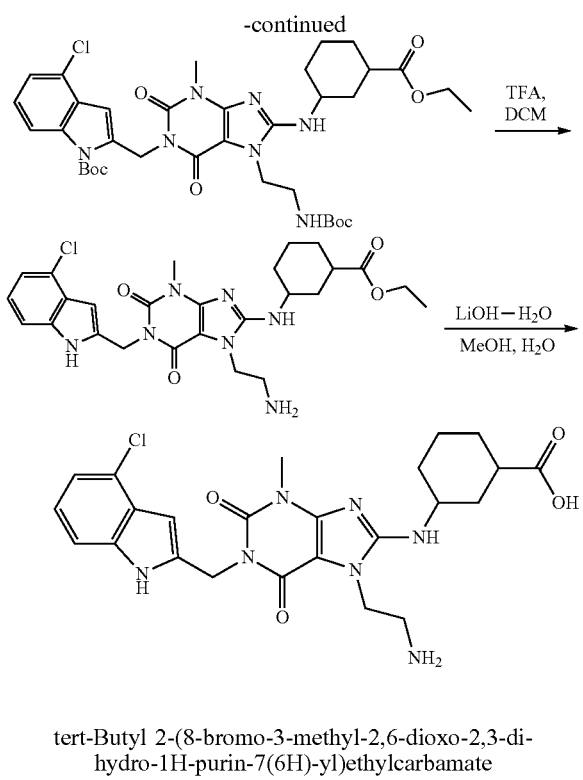

tert-Butyl 2-(8-bromo-3-methyl-2,6-dioxo-2,3-di-hydro-1H-purin-7(6H)-yl)ethylcarbamate

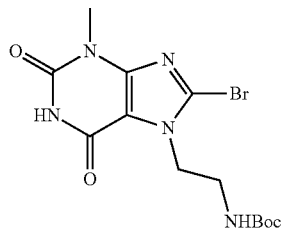 [SMILES: Cn1c(=O)[nH]c(=O)c2c1nc(Br)n2CCNC(=O)OC(C)(C)C]

A solution of 8-bromo-3-methyl-1H-purine-2,6(3H,7H)-dione (1.5 g, 6.15 mmol), tert-butyl 2-bromoethylcarbamate (2.7 g, 12.30 mmol), and DIEA (2.4 g, 18.45 mmol) in DMF (20 mL) was stirred and heated to 80° C. for 18 h. The mixture was concentrated and the residue was purified by column chromatography (MeOH:DCM=0:100 to 10:90) to provide the title compound; ESI: m/z 388.0 (M+H)⁺.

tert-Butyl 2-((8-bromo-7-(2-(tert-butoxycarbo-nylamino)ethyl)-3-methyl-2,6-dioxo-2,3,6,7-tetra-hydro-1H-purin-1-yl)methyl)-4-chloro-1H-indole-1-carboxylate

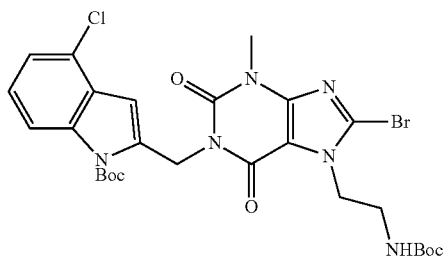 [SMILES: Cn1c(=O)n(Cc2cc3c(Cl)cccc3n2C(=O)OC(C)(C)C)c(=O)c2c1nc(Br)n2CCNC(=O)OC(C)(C)C]

A solution of tert-butyl 2-(8-bromo-3-methyl-2,6-dioxo-2,3-dihydro-1H-purin-7(6H)-yl)ethylcarbamate (1.5 g, 2.09 mmol), tert-butyl 4-chloro-2-(chloromethyl)-1H-indole-1-carboxylate (500 mg, 1.67 mmol), and K₂CO₃ (864 mg, 6.26 mmol) in DMF (20 mL) was stirred and heated to 80° C. for 2 h. The mixture was concentrated and the residue was purified by column chromatography (EA:PE=0:100 to 30:70); ESI: m/z 651.0 (M+H)⁺.

tert-Butyl 2-((7-(2-(tert-butoxycarbonylamino) ethyl)-8-(3-(ethoxycarbonyl)cyclohexyl amino)-3-methyl-2,6-dioxo-2,3,6,7-tetrahydro-1H-purin-1-yl) methyl)-4-chloro-1H-indole-1-carboxylate

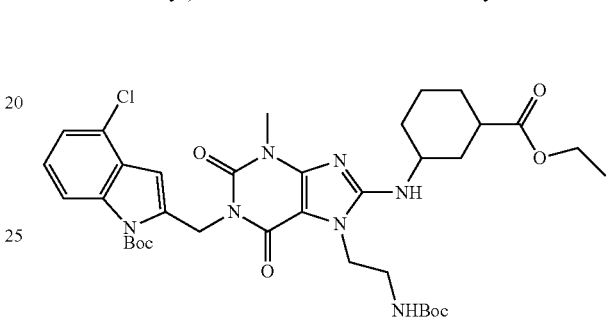

The title compound was synthesized in a similar fashion as described in Procedure 7A using tert-butyl 2-((8-bromo-7-(2-(tert-butoxycarbonylamino)ethyl)-3-methyl-2,6-dioxo-2,3,6,7-tetrahydro-1H-purin-1-yl)methyl)-4-chloro-1H-indole-1-carboxylate and ethyl 3-aminocyclohexanecarboxylate. The product was purified by Prep-HPLC using Method D; ESI: m/z 742.2 (M+H)⁺.

Ethyl 3-(7-(2-aminoethyl)-1-((4-chloro-1H-indol-2-yl)methyl)-3-methyl-2,6-dioxo-2,3,6,7-tetrahydro-1H-purin-8-ylamino)cyclohexanecarboxylate

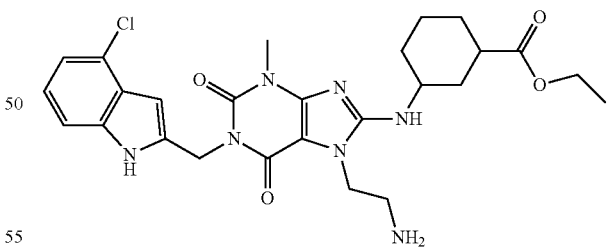

A solution of tert-butyl 2-((7-(2-(tert-butoxycarbo-nylamino)ethyl)-8-(3-(ethoxycarbonyl)cyclohexylamino)-3-methyl-2,6-dioxo-2,3,6,7-tetrahydro-1H-purin-1-yl) methyl)-4-chloro-1H-indole-1-carboxylate (30.2 mg, 0.041 mmol) in DCM (4 mL) was treated with TFA (2 mL). The mixture was stirred at 25° C. for 1 h. The mixture was concentrated and the residue was used directly in next step without further purification.

3-(7-(2-Aminoethyl)-1-((4-chloro-1H-indol-2-yl)methyl)-3-methyl-2,6-dioxo-2,3,6,7-tetrahydro-1H-purin-8-ylamino)cyclohexanecarboxylic acid

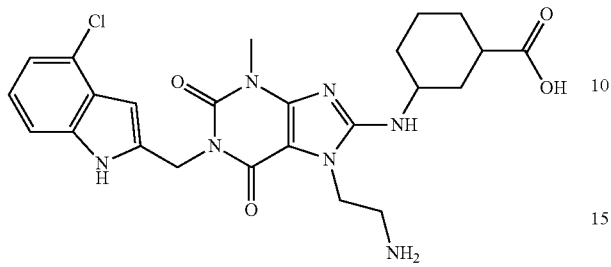

To a solution of ethyl 3-(7-(2-aminoethyl)-1-((4-chloro-1H-indol-2-yl)methyl)-3-methyl-2,6-dioxo-2,3,6,7-tetrahydro-1H-purin-8-ylamino)cyclohexanecarboxylate (25.5 mg, 0.047 mmol), LiOH·H$_2$O (5.9 mg, 0.141 mmol) in MeOH (1 mL) was stirred and heated to 50° C. for 1 h. The mixture was filtered and the filtrate was purified by Prep-HPLC using Method D. $^1$H NMR (400 MHz, DMSO-d$_6$) δ 11.25 (s, 1H), 7.29-7.34 (m, 2H), 6.99-7.03 (m, 2H), 6.68 (s, 1H), 6.23 (s, 1H), 5.16 (s, 1H), 3.99-4.04 (m, 2H), 3.75 (s, 1H), 2.83 (s, 2H), 2.13 (s, 1H), 1.88-1.91 (s, 1H), 1.25-1.76 (m, 10H); ESI: m/z 514.1 (M+H)$^+$.

Example 419

1-((3,4-dimethyl-1H-indol-2-yl)methyl)-3,7-dimethyl-8-(pyridin-4-ylamino)-1H-purine-2,6(3H,7H)-dione

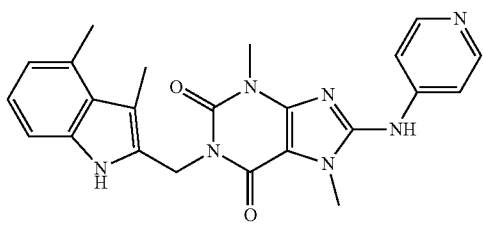 [SMILES: Cc1cccc2[nH]c(Cn3c(=O)c4c(nc(Nc5ccncc5)n4C)n(C)c3=O)c(C)c12]

tert-Butyl 2-((8-bromo-3,7-dimethyl-2,6-dioxo-2,3,6,7-tetrahydro-1H-purin-1-yl)methyl)-3,4-dimethyl-1H-indole-1-carboxylate and pyridin-4-amine hydrochloride were coupled in a similar fashion as described in Procedure 8A. The product was purified by flash chromatography (DCM/MeOH=6/1) to give tert-butyl 2-((3,7-dimethyl-2,6-dioxo-8-(pyridin-4-ylamino)-2,3,6,7-tetrahydro-1H-purin-1-yl)methyl)-3,4-dimethyl-1H-indole-1-carboxylate; ESI: m/z 530.2 (M+H)$^+$. This product was dissolved in DCM (4 mL) and treated with TFA (2 mL). The mixture was stirred at 25° C. for 2 h. The mixture was purified by Prep-HPLC using method D. $^1$H NMR (400 MHz, DMSO-d$_6$) δ 8.94 (s, 1H), 8.47 (d, J=4.8 Hz, 2H), 7.42 (d, J=7.2 Hz, 2H), 7.11 (d, J=8.0 Hz, 1H), 6.99 (t, J=7.2 Hz, 1H), 6.84-6.74 (m, 2H), 5.03 (s, 2H), 3.89 (s, 3H), 3.60 (s, 3H), 2.71 (s, 3H), 2.68 (s, 3H); ESI: m/z 430.1 (M+H)$^+$.

Example 420

4-[[1-[(4-chloro-1H-indol-2-yl)methyl]-3,7-dimethyl-2,6-dioxo-purin-8-yl]amino]benzamide

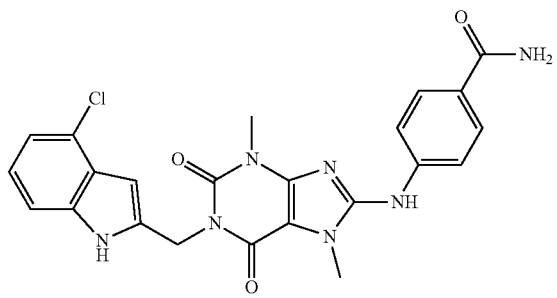 [SMILES: Cn1c(Nc2ccc(C(N)=O)cc2)nc2c1c(=O)n(Cc1cc3c(Cl)cccc3[nH]1)c(=O)n2C]

tert-Butyl 2-[(8-bromo-3,7-dimethyl-2,6-dioxo-purin-1-yl)methyl]-4-chloro-indole-1-carboxylate and 4-aminobenzamide were coupled in a similar fashion as described in Procedure 8B. The product was purified by prep-TLC (EA) to obtain tert-butyl 2-[[8-(4-carbamoylanilino)-3,7-dimethyl-2,6-dioxo-purin-1-yl]methyl]-4-chloro-indole-1-carboxylate: ESI: m/z 578.3 (M+H)$^+$. This product was dissolved in MeOH (4.00 mL), THF (4.00 mL) and 1N NaOH (2.00 mL). The mixture was stirred at 25° C. rt for 16 hr. The mixture was concentrated and the residue was purified by prep-HPLC using Method C (30-60% ACN). $^1$H NMR (400 MHz, DMSO-d$_6$) δ 11.29 (s, 1H), 9.46 (s, 1H), 7.86 (d, J=8.5 Hz, 2H), 7.81 (br. s., 1H), 7.77-7.72 (d, J=8.5 Hz, 2H), 7.35 (dd, J=2.3, 6.8 Hz, 1H), 7.25-7.15 (m, 1H), 7.07-6.97 (m, 2H), 6.28 (s, 1H), 5.22 (s, 2H), 3.84 (s, 3H), 3.48 (s, 3H); ESI: m/z 478.2 (M+H)$^+$.

Example 421

1-[(7-chloro-1H-indol-2-yl)methyl]-8-methoxy-3,7-dimethyl-purine-2,6-dione

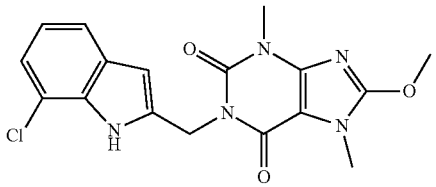 [SMILES: COc1nc2c(c(=O)n(Cc3cc4cccc(Cl)c4[nH]3)c(=O)n2C)n1C]

To a solution of tert-butyl 2-[(8-bromo-3,7-dimethyl-2,6-dioxo-purin-1-yl)methyl]-7-chloro-indole-1-carboxylate (180.00 mg, 344.31 umol) in THF (5.00 mL) was added MeOH (5.00 mL) and 1N NaOH (2.00 mL). The mixture was stirred at 25° C. for 16 h. The reaction mixture was concentrated to dryness. The residue was purified by prep-HPLC using Method A (40-65% ACN). $^1$H NMR: (400 MHz CDCl$_3$) δ 9.23 (br. s., 1H), 7.45 (d, J=8.0 Hz, 1H), 7.20-7.09 (m, 1H), 7.03-6.94 (m, 1H), 6.64 (d, J=2.0 Hz, 1H), 5.32 (s, 2H), 4.13 (s, 3H), 3.71 (s, 3H), 3.55 (s, 3H); ESI: m/z 374.2 (M+H)$^+$.

Example 422

N-[1-[(4-chloro-1H-indol-2-yl)methyl]-3,7-dimethyl-2,6-dioxo-purin-8-yl]-2,2,2-trifluoro-acetamide

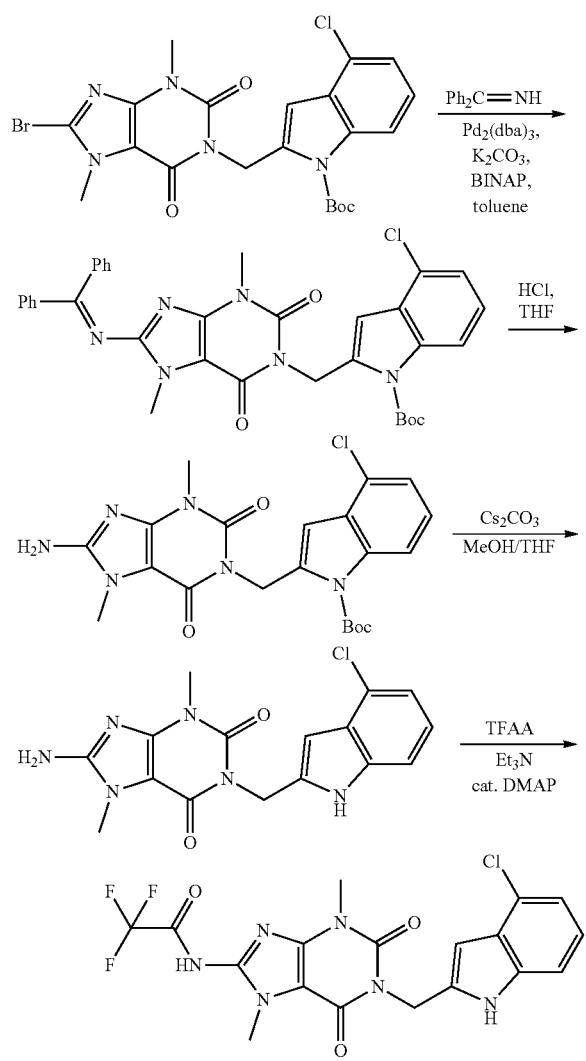

tert-Butyl 2-[[8-(benzhydrylideneamino)-3,7-dimethyl-2,6-dioxo-purin-1-yl]methyl]-4-chloro-indole-1-carboxylate

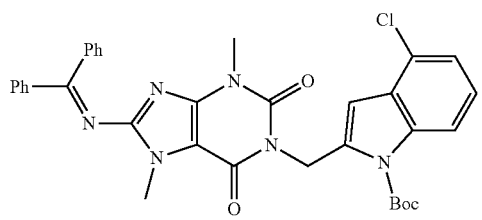 [SMILES: Cn1c(N=C(c2ccccc2)c2ccccc2)nc2c1c(=O)n(Cc1cc3c(Cl)cccc3n1C(=O)OC(C)(C)C)c(=O)n2C]

In a sealed vial a mixture of tert-butyl 2-[(8-bromo-3,7-dimethyl-2,6-dioxo-purin-1-yl)methyl]-4-chloro-indole-1-carboxylate (500.00 mg, 956.43 umol,), diphenylmethanimine (208.00 mg, 1.15 mmol, 192.59 uL), $K_2CO_3$ (396.56 mg, 2.87 mmol,) and BINAP (59.55 mg, 95.64 umol, 0.10 eq) in toluene (5.00 mL) was added $Pd(OAc)_2$ (12.88 mg, 57.39 umol, 0.06 eq). The mixture was bubbled with $N_2$ for 1 min and stirred at 110° C. for 12 hr. The mixture was cooled to room temperature (25° C.) and filtered. The filtrate was concentrated. The crude product was purified by column chromatography (PE/EA from 100/1 to 3/1) to afford the title compound: ESI: m/z 524.1 $(M+H)^+$.

tert-Butyl 2-[(8-amino-3,7-dimethyl-2,6-dioxo-purin-1-yl)methyl]-4-chloro-indole-1-carboxylate

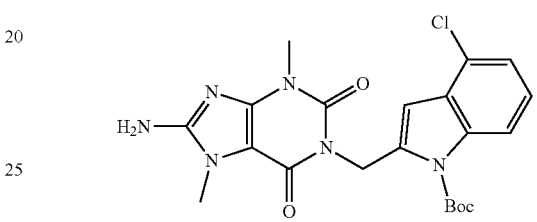

To a solution of tert-butyl 2-[[8-(benzhydrylideneamino)-3,7-dimethyl-2,6-dioxo-purin-1-yl]methyl]-4-chloro-indole-1-carboxylate (320.00 mg, 513.56 umol) in THF (10.00 mL) was added 3M HCl (4.00 mL). The solution was stirred at 25° C. for 12 hr. The solution was made basic with sat.$Na_2CO_3$ to pH=8~9 and extracted with EA (30 mL*3). The organic fractions were washed with brine (5 mL), dried over $Na_2SO_4$ and concentrated. The crude product was washed with MTBE (~10 mL) and filtered to afford the tile compound.

8-Amino-1-[(4-chloro-1H-indol-2-yl)methyl]-3,7-dimethyl-purine-2,6-dione

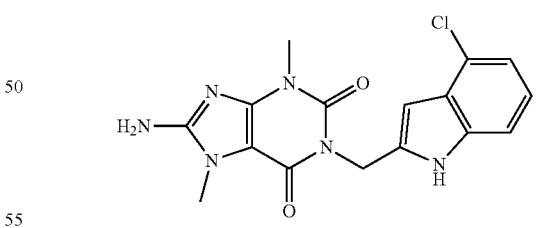

To a solution of tert-butyl 2-[(8-amino-3,7-dimethyl-2,6-dioxo-purin-1-yl)methyl]-4-chloro-indole-1-carboxylate (50.00 mg, 108.96 umol) in MeOH (2.00 mL) and THF (2.00 mL) was added $Cs_2CO_3$ (355.00 mg, 1.09 mmol). The mixture was stirred at 25° C. for 3 hr. The mixture was concentrated and the residue was diluted with $H_2O$ (2 mL) and extracted with EA (5 mL*3). The organic fractions were dried over $Na_2SO_4$ and concentrated to afford the title compound: ESI m/z 359.1 $(M+H)^+$.

379

N-[1-[(4-Chloro-1H-indol-2-yl)methyl]-3,7-dimethyl-2,6-dioxo-purin-8-yl]-2,2,2-trifluoro-acetamide

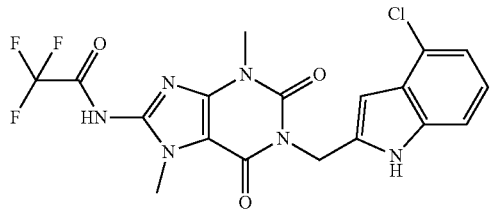 [SMILES: Cn1c(NC(=O)C(F)(F)F)nc2c1c(=O)n(Cc1cc3c(Cl)cccc3[nH]1)c(=O)n2C]

To a solution of 8-amino-1-[(4-chloro-1H-indol-2-yl)methyl]-3,7-dimethyl-purine-2,6-dione (100.00 mg, 278.72 umol), Et₃N (70.51 mg, 696.80 umol, 96.59 uL) and DMAP (3.41 mg, 27.87 umol) in DCM (3.00 mL) at 0° C. was added TFAA (87.81 mg, 418.08 umol, 58.15 uL). The solution was stirred at 25° C. for 20 min. The mixture was diluted with ice-water (1 mL) and extracted with DCM (3 mL*5). The organic fractions were dried over Na₂SO₄ and concentrated. The crude product was purified by prep-HPLC using Method C (30-60% ACN). ¹H NMR (400 MHz, DMSO-d₆) δ 11.23 (m, 1H), 7.35-7.33 (m, 1H), 7.02-7.01 (m, 2H), 6.26 (m, 1H), 5.19 (s, 2H), 3.54 (s, 3H), 3.40 (s, 3H); ESI m/z 455.1 (M+H)⁺.

Example 423

1-((3,4-dichloro-1H-indol-2-yl)methyl)-3,7-dimethyl-8-(pyrrolidin-3-yl)-1H-purine-2,6(3H,7H)-dione

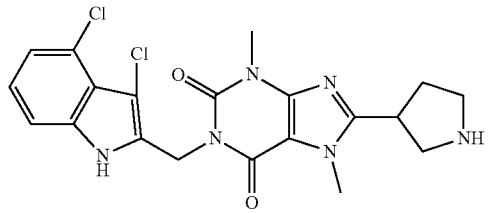 [SMILES: Cn1c(C2CCNC2)nc2c1c(=O)n(Cc1[nH]c3cccc(Cl)c3c1Cl)c(=O)n2C]

To a mixture of tert-butyl 3-[1-[(4-chloro-1H-indol-2-yl)methyl]-3,7-dimethyl-2,6-dioxo-purin-8-yl]pyrrolidine-1-carboxylate (100.00 mg, 194.94 umol) in MeOH (1.00 mL) was added HCl/MeOH (4M, 2.00 mL) dropwise at 0° C. The mixture was stirred at 25° C. for 2 hr. The mixture was dried in vacuo. The residue was purified by prep-HPLC using Method C (17-47% ACN). ¹H NMR (400 MHz, DMSO-d₆) δ 11.42 (s, 1H), 7.32 (dd, 6.6 Hz, 1H), 7.09-7.04 (m, 2H), 5.24 (s, 2H), 3.91 (s, 3H), 3.81-3.89 (m, 1H), 3.51-3.71 (m, 1H), 3.46 (s, 3H), 3.30-3.26 (m, 2H), 2.46-2.39 (m, 2H), 2.10-2.02 (m, 1H); ESI: m/z 447.1 (M+H)⁺.

Example 425

1-[(4-chloro-1H-indol-2-yl)methyl]-3,7-dimethyl-8-pyrrolidin-3-yl-purine-2,6-dione

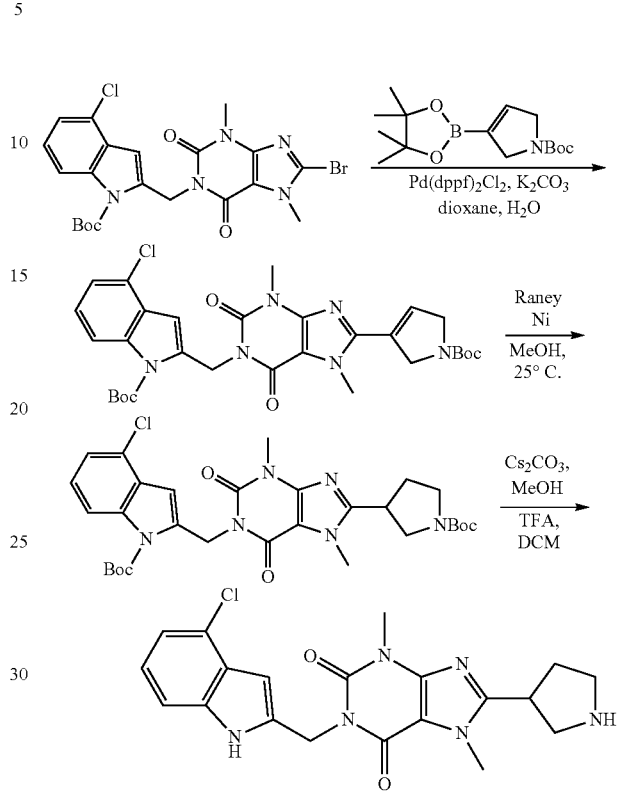

tert-Butyl 2-((8-(1-(tert-butoxycarbonyl)-2,5-dihydro-1H-pyrrol-3-yl)-3,7-dimethyl-2, 6-dioxo-2,3, 6,7-tetrahydro-1H-purin-1-yl)methyl)-4-chloro-1H-indole-1-carboxylate

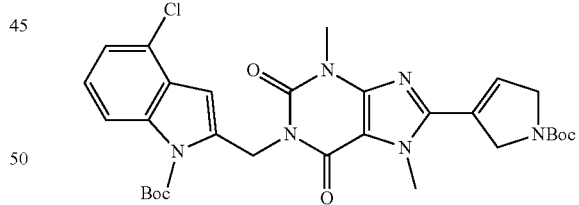

To a mixture of tert-butyl 2-[(8-bromo-3,7-dimethyl-2,6-dioxo-purin-1-yl)methyl]-4-chloro-indole-1-carboxylate (150.00 mg, 286.93 umol), tert-butyl 3-(4,4,5,5-tetramethyl-1,3,2-dioxaborolan-2-yl)-2,5-dihydropyrrole-1-carboxylate (127.04 mg, 430.40 umol) and K₂CO₃ (118.97 mg, 860.79 umol) in dioxane (4.00 mL) and H₂O (1.00 mL) was added Pd(dppf)Cl₂ (10.50 mg, 14.35 umol). The mixture was heated to 90° C. for 12 h. The mixture was cooled to 25° C. and then poured into ice-water (5 mL). The aqueous phase was extracted with EA (10 mL*3). The combined organic fractions were washed with brine (5 mL), dried with anhydrous Na₂SO₄, filtered and concentrated. The product was purified by column chromatography (PE/EA, 5/1 to 1/1) to afford tert-butyl 2-((8-(1-(tert-butoxycarbonyl)-2,5-dihydro- 1H-pyrrol-3-yl)-3,7-dimethyl-2,6-dioxo-2,3,6,7-tetrahydro-1H-purin-1-yl)methyl)-4-chloro-1H-indole-1-carboxylate and tert-butyl 3-(1-((4-chloro-1H-indol-2-yl)methyl)-3,7-dimethyl-2,6-dioxo-2,3,6,7-tetrahydro-1H-purin-8-yl)-2,5-dihydro-1H-pyrrole-1-carboxylate: ESI: m/z 511.3 (M+H−Boc)$^+$, m/z 611.2 (M+H)$^+$.

tert-Butyl 2-((8-(1-(tert-butoxycarbonyl)pyrrolidin-3-yl)-3,7-dimethyl-2,6-dioxo-2,3,6,7-tetrahydro-1H-purin-1-yl)methyl)-4-chloro-1H-indole-1-carboxylate

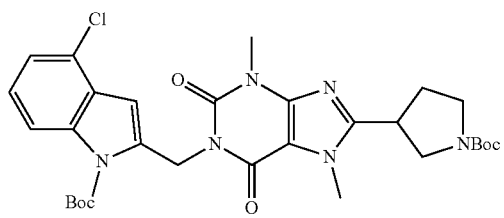 [SMILES: Cn1c(C2CCN(C(=O)OC(C)(C)C)C2)nc2c1c(=O)n(Cc1cc3c(Cl)cccc3n1C(=O)OC(C)(C)C)c(=O)n2C]

To a mixture of tert-butyl 2-((8-(1-(tert-butoxycarbonyl)-2,5-dihydro-1H-pyrrol-3-yl)-3,7-dimethyl-2,6-dioxo-2,3,6,7-tetrahydro-1H-purin-1-yl)methyl)-4-chloro-1H-indole-1-carboxylate (20.00 mg) and tert-butyl 3-(1-((4-chloro-1H-indol-2-yl)methyl)-3,7-dimethyl-2,6-dioxo-2,3,6,7-tetrahydro-1H-purin-8-yl)-2,5-dihydro-1H-pyrrole-1-carboxylate (100.00 mg) in MeOH (1.00 mL) and THF (1.00 mL) was added Ni (1.00 g, 17.04 mmol, 520.58 eq) under N$_2$. The suspension was degassed under vacuum and purged with H$_2$ several times. The mixture was stirred under H$_2$ (15 psi) at 25° C. for 0.5 hr. The reaction mixture was filtered and the filtrate was concentrated to give crude a mixture of tert-butyl 2-((8-(1-(tert-butoxycarbonyl)pyrrolidin-3-yl)-3,7-dimethyl-2,6-dioxo-2,3,6,7-tetrahydro-1H-purin-1-yl)methyl)-4-chloro-1H-indole-1-carboxylate and tert-butyl 3-(1-((4-chloro-1H-indol-2-yl)methyl)-3,7-dimethyl-2,6-dioxo-2,3,6,7-tetrahydro-1H-purin-8-yl)pyrrolidine-1-carboxylate: ESI: m/z 511.3 (M+H−Boc)$^+$.

1-[(4-chloro-1H-indol-2-yl)methyl]-3,7-dimethyl-8-pyrrolidin-3-yl-purine-2,6-dione

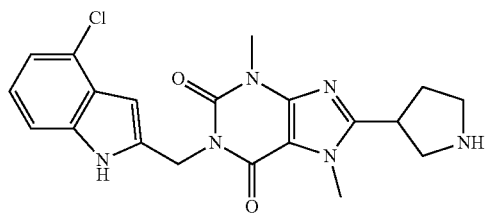 [SMILES: Cn1c(C2CCNC2)nc2c1c(=O)n(Cc1cc3c(Cl)cccc3[nH]1)c(=O)n2C]

To a mixture of tert-butyl 2-((8-(1-(tert-butoxycarbonyl)pyrrolidin-3-yl)-3,7-dimethyl-2,6-dioxo-2,3,6,7-tetrahydro-1H-purin-1-yl)methyl)-4-chloro-1H-indole-1-carboxylate and tert-butyl 3-(1-((4-chloro-1H-indol-2-yl)methyl)-3,7-dimethyl-2,6-dioxo-2,3,6,7-tetrahydro-1H-purin-8-yl)pyrrolidine-1-carboxylate (100.00 mg, 163.11 umol) in MeOH (2.50 mL) and THF (2.50 mL) was added Cs$_2$CO$_3$ (531.45 mg, 1.63 mmol). The mixture was stirred at 25° C. for 15 hr. The mixture was poured into water (2 mL) and the aqueous phase was extracted with ethyl acetate (5 mL*3). The combined organic fractions were washed with brine (2 mL), dried with anhydrous Na$_2$SO$_4$, filtered and concentrated to afford tert-butyl 3-[1-[(4-chloro-1H-indol-2-yl)methyl]-3,7-dimethyl-2,6-dioxo-purin-8-yl]pyrrolidine-1-carboxylate: ESI: m/z 513.3 (M+H)$^+$. To this product in DCM (2.00 mL) was added TFA/DCM (20%, 2.00 mL) dropwise at 0° C. The mixture was stirred at 25° C. for 1 hr. The mixture was concentrated. The residue was dissolved in 1 mL MeOH and the pH was made neutral with triethylamine. The product was purified by prep-HPLC using Method C (20-45% ACN). $^1$H NMR (400 MHz, DMSO-d$_6$) δ 11.32 (br. s., 1H), 9.33-9.12 (m, 3H), 7.32 (d, J=7.9 Hz, 1H), 7.06-6.96 (m, 2H), 6.23 (s, 1H), 5.21 (s, 2H), 3.91 (s, 3H), 3.87-3.80 (m, 1H), 3.60 (br. s., 2H), 3.46 (s, 3H), 3.29 (br. s., 2H), 2.38 (dd, J=6.0, 13.0 Hz, 2H), 2.07 (dd, J=7.5, 12.8 Hz, 1H); ESI: m/z 413.2 (M+H)$^+$.

Example 426

3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-diethylpropanamide

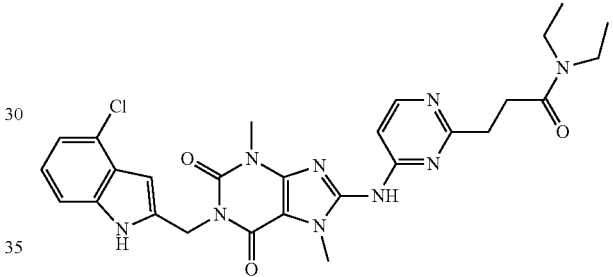

The title compound was synthesized in a similar fashion as example 413 using diethylamine. The product was purified by prep-HPLC using Method B. $^1$H NMR (400 MHz, DMSO-d$_6$) δ 11.30 (s, 1H), 8.38 (m, 1H), 7.45 (m, 1H), 7.33 (m, 1H), 7.00 (m, 2H), 6.28 (s, 1H), 5.22 (s, 2H), 3.78 (s, 3H), 3.46 (s, 3H), 3.27 (m, 2H), 3.17 (m, 2H), 2.95 (m, 2H), 2.73 (m, 2H), 1.03 (t, J=7.2 Hz, 3H), 0.93 (t, J=7.2 Hz, 3H); ESI: m/z 564.2 (M+H)$^+$.

Example 427

5-(1-((4-chloro-1H-indol-2-yl)methyl)-3,7-dimethyl-2,6-dioxo-2,3,6,7-tetrahydro-1H-purin-8-ylamino)picolinonitrile

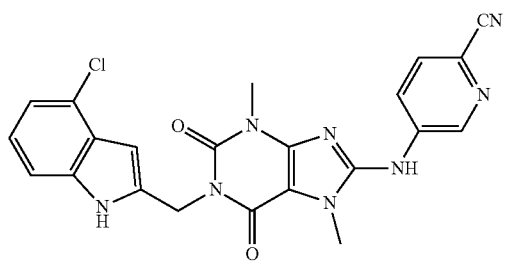 [SMILES: Cn1c(Nc2ccc(C#N)nc2)nc2c1c(=O)n(Cc1cc3c(Cl)cccc3[nH]1)c(=O)n2C]

The title compound was synthesized in a similar fashion as described in Procedure 8A using tert-butyl 2-((8-bromo- 3,7-dimethyl-2,6-dioxo-2,3,6,7-tetrahydro-1H-purin-1-yl)methyl)-4-chloro-1H-indole-1-carboxylate (100 mg, 0.19 mmol) and 5-aminopicolinonitrile. The product was purified by column chromatography (DCM/MeOH from 50/1 to 5/1) followed by Prep-HPLC using Method E. $^1$H NMR (400 MHz, DMSO-$d_6$) δ 11.30 (s, 1H), 10.01 (s, 1H), 8.96 (d, J=2.8 Hz, 1H), 8.38 (dd, J=8.8, 2.4 Hz, 1H), 7.96 (d, J=4.4 Hz, 1H), 7.34 (dd, J=6.8, 1.6 Hz, 1H), 7.04-6.99 (m, 2H), 6.26 (m, 1H), 5.20 (s, 2H), 3.86 (s, 3H), 3.47 (s, 3H); ESI: m/z 461.0 (M+H)$^+$.

Example 428

1-((4-chloro-1H-indol-2-yl)methyl)-3,7-dimethyl-8-(2-(3-oxo-3-(piperazin-1-yl)propyl)pyrimidin-4-ylamino)-1H-purine-2,6(3H,7H)-dione

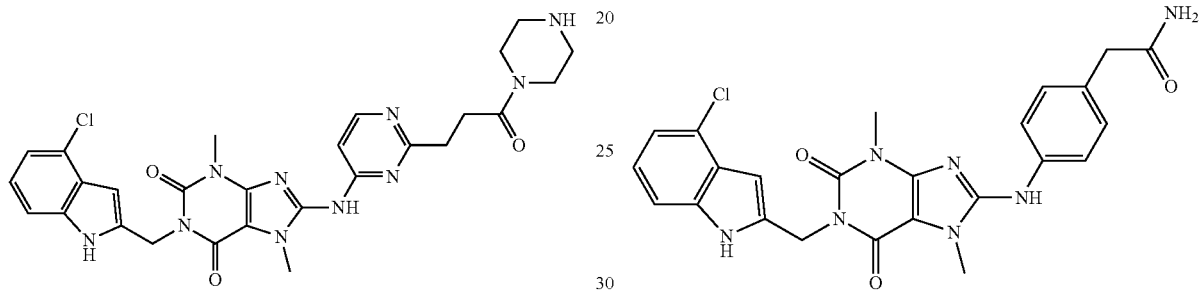

The title compound was synthesized in a similar fashion as Example 413 using 3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid and tert-butyl piperazine-1-carboxylate. The product was purified by prep-HPLC using Method B. $^1$H NMR (400 MHz, DMSO-$d_6$) δ 11.29 (s, 1H), 8.39 (m, 1H), 7.50 (m, 1H), 7.33 (m, 1H), 7.00 (m, 2H), 6.29 (s, 1H), 5.22 (s, 2H), 3.80 (s, 3H), 3.47 (s, 3H), 3.34 (m, 4H), 2.93 (m, 2H), 2.76 (m, 2H), 2.60 (m, 4H); ESI: m/z 577.3 (M+H)$^+$.

Example 429

8-(6-(aminomethyl)pyridin-3-ylamino)-1-((4-chloro-1H-indol-2-yl)methyl)-3,7-dimethyl-1H-purine-2,6(3H,7H)-dione

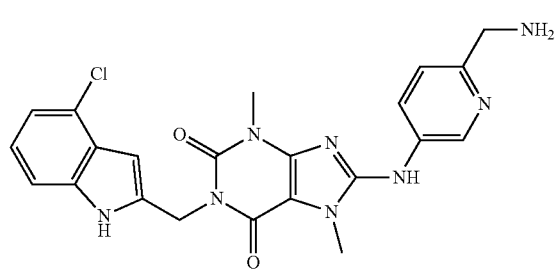 [SMILES: Cn1c(Nc2ccc(CN)nc2)nc2c1c(=O)n(Cc1cc3c(Cl)cccc3[nH]1)c(=O)n2C]

tert-Butyl 2-((8-bromo-3,7-dimethyl-2,6-dioxo-2,3,6,7-tetrahydro-1H-purin-1-yl)methyl)-4-chloro-1H-indole-1-carboxylate and tert-butyl (5-aminopyridin-2-yl)methylcarbamate were synthesized in a similar fashion as described in Procedure 8A. The product was purified by flash chromatography (DCM/MeOH, 20/1) to give tert-butyl 2-((8-(6-((tert-butoxycarbonylamino)methyl)pyridin-3-ylamino)-3,7-dimethyl-2,6-dioxo-2,3,6,7-tetrahydro-1H-purin-1-yl)methyl)-4-chloro-1H-indole-1-carboxylate. ESI: m/z 565.2 (M+H−100)$^+$. To a solution of this product (0.18 g) in DCM (2 mL) was added TFA (2 mL). The mixture was stirred 2 h at room temperature. The reaction mixture was concentrated and the residue was purified by Prep-HPLC using Method D (40-70% ACN). $^1$H NMR (400 MHz, $d_6$-DMSO) δ 11.28 (br s, 1H), 8.81-8.79 (d, J=8.0 Hz, 1H), 8.10-8.07 (m, 1H), 7.40-7.31 (m, 2H), 7.04-7.00 (m, 2H), 6.25 (s, 1H), 5.2 (s, 1H), 3.82-3.73 (m, 5H), 3.45-3.37 (m, 5H); ESI: m/z 465.1 (M+H)$^+$.

Example 431

2-[4-[[1-[(4-chloro-1H-indol-2-yl)methyl]-3,7-dimethyl-2,6-dioxo-purin-8-yl]amino]phenyl]acetamide

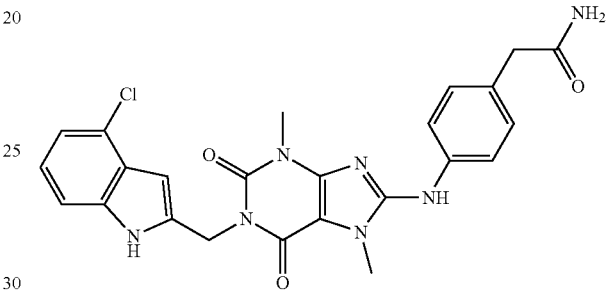

tert-Butyl 2-[(8-bromo-3,7-dimethyl-2,6-dioxo-purin-1-yl)methyl]-4-chloro-indole-1-carboxylate and 2-(4-aminophenyl)acetamide were coupled in a similar fashion as described in Procedure 8B. The product was purified by prep-TLC (PE/EA=0/1) to provide tert-butyl 2-[[8-[4-(2-amino-2-oxo-ethyl)anilino]-3,7-dimethyl-2,6-dioxo-purin-1-yl]methyl]-4-chloro-indole-1-carboxylate: ESI: m/z 592.2 (M+H)$^+$. This product was dissolved in THF (5.00 mL), MeOH (5.00 mL) and 1N NaOH (2.00 mL). The mixture was stirred at 25° C. for 16 hr. The mixture was concentrated to give crude product which was purified by prep-HPLC using Method C (35-55% ACN). $^1$H NMR (400 MHz DMSO-$d_6$) δ 11.26 (s, 1H), 9.14 (s, 1H), 7.58 (d, J=8.5 Hz, 2H), 7.40 (br. s., 1H), 7.35-7.31 (m, 1H), 7.20 (d, J=8.5 Hz, 2H), 7.04-6.98 (m, 2H), 6.83 (br. s., 1H), 6.26 (s, 1H), 5.20 (s, 2H), 3.79 (s, 3H), 3.44 (s, 3H); ESI: m/z 492.2 (M+H)$^+$.

Example 432

1-((4-chloro-1H-indol-2-yl)methyl)-8-(4-(hydroxymethyl)phenylamino)-3,7-dimethyl-1H-purine-2,6(3H,7H)-dione

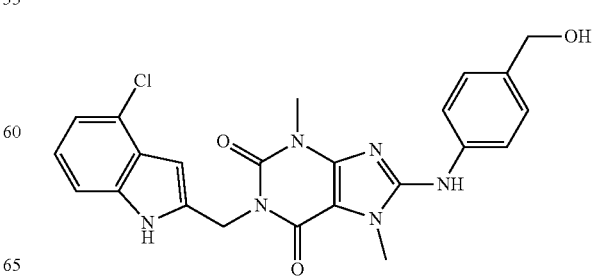

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4-chloro-1H-indole-1-carboxylate and (4-aminophenyl)methanol. The product was purified by column chromatography (DCM/MeOH 50/1 to 5/1) to give the crude product. The product was further purified by Prep-HPLC using Method F (33-65% ACN). $^1$H NMR (400 MHz, DMSO) δ 11.28 (s, 1H), 9.15 (s, 1H), 7.64-7.60 (m, 2H), 7.34-7.32 (m, 1H), 7.27-7.23 (m, 2H), 7.02-6.99 (m, 2H), 6.25 (m, 1H), 5.19-5.06 (m, 3H), 4.44 (d, J=5.6 Hz, 2H), 3.79 (s, 3H), 3.44 (s, 3H); ESI: m/z 465.1 (M+H)$^+$.

Example 433

1-[(7-chloro-1-methyl-indol-2-yl)methyl]-8-methoxy-3,7-dimethyl-purine-2,6-dione

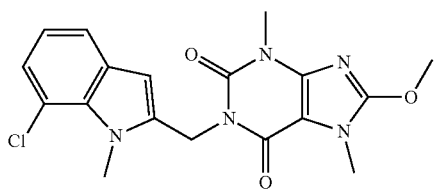 [SMILES: COc1nc2c(c(=O)n(Cc3cc4cccc(Cl)c4n3C)c(=O)n2C)n1C]

To a solution of 1-[(7-chloro-1H-indol-2-yl)methyl]-8-methoxy-3,7-dimethyl-purine-2,6-dione (17.00 mg, 45.48 umol) in DMF (1.00 mL) was added Cs$_2$CO$_3$ (29.64 mg, 90.96 umol) and CH$_3$I (8.39 mg, 59.12 umol) at 25° C. The mixture was stirred at 25° C. for 2 h. The mixture was diluted with H$_2$O (4 mL) and extracted with EA (15 mL*3). The combined organic fractions were washed with brine (5 mL), dried over Na$_2$SO$_4$ and concentrated to give crude product which was purified by prep-HPLC using Method E (33-63% ACN). $^1$H NMR (400 MHz, CDCl$_3$) δ 7.36 (d, J=7.9 Hz, 1H), 7.08 (d, J=6.6 Hz, 1H), 6.95-6.82 (m, 1H), 6.45 (s, 1H), 5.38-5.28 (m, 2H), 4.27 (s, 3H), 4.15 (s, 3H), 3.71 (s, 3H), 3.54 (s, 3H); ESI: m/z 388.1 (M+H)$^+$.

The following examples were synthesized according to the general synthetic scheme shown below.

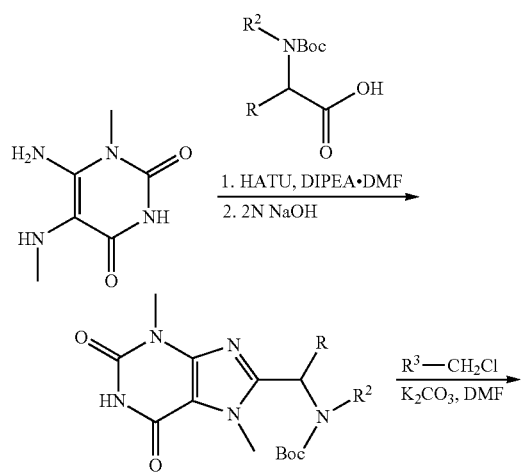

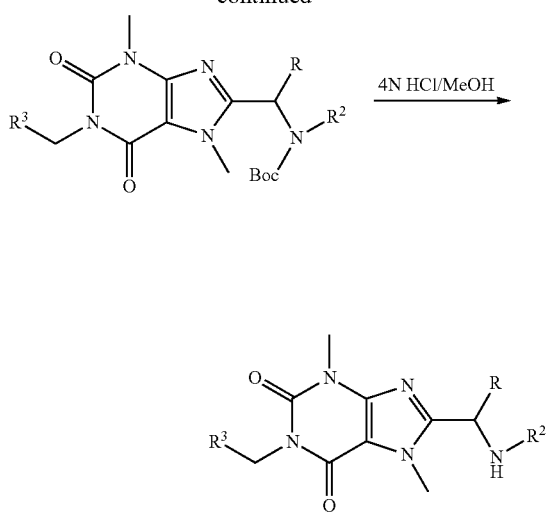

Procedure 9

Illustrative example: tert-butyl 2-(3,7-dimethyl-2,6-dioxo-purin-8-yl)pyrrolidine-1-carboxylate

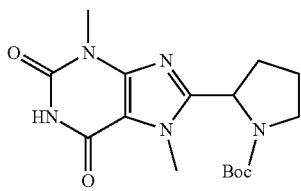 [SMILES: Cn1c(C2CCCN2C(=O)OC(C)(C)C)nc2c1c(=O)[nH]c(=O)n2C]

To a solution of 6-amino-1-methyl-5-(methylamino)pyrimidine-2,4-dione (400.00 mg, 2.35 mmol) and 1-tert-butoxycarbonylpyrrolidine-2-carboxylic acid (607.16 mg, 2.82 mmol) in DMF (10.00 mL) was added HATU (1.07 g, 2.82 mmol) and DIEA (607.58 mg, 4.70 mmol, 821.05 uL). The mixture was stirred at 25° C. for 16 hr. The mixture was diluted with H$_2$O (5 mL) and extracted with DCM/MeOH (20 mL*8). The organic fraction was washed with brine (5 mL), dried over Na$_2$SO$_4$ and concentrated. The product was purified by column chromatography (DCM/MeOH from 30/1 to 20/1) to afford a regioisomeric pair of acylated products. This mixture (598.00 mg, 1.63 mmol) was dissolved in NaOH (2 M, 8.15 mL) and stirred at 110° C. for 2 hr. The mixture was extracted with (DCM/MeOH=10/1) (20 mL*6). The combined organic fractions were washed with brine (10 mL), dried over Na$_2$SO$_4$ and concentrated to provide the title compound: ESI: m/z 350.2 (M+H)$^+$. The compounds in the table below were made according to Procedure 9

| Structure | Mass Spec (ESI: m/z) or ¹H NMR | Compound Name |
|---|---|---|
| | 364.3 (M + H)⁺ | tert-butyl 2-(3,7-dimethyl-2,6-dioxo-2,3,6,7-tetrahydro-1H-purin-8-yl)piperidine-1-carboxylate |
| | 352.3 (M + H)⁺ | tert-butyl (1-(3,7-dimethyl-2,6-dioxo-2,3,6,7-tetrahydro-1H-purin-8-yl)-2-methylpropyl)carbamate |
| | 364.2 (M + H)⁺ | tert-butyl (2-cyclopropyl-1-(3,7-dimethyl-2,6-dioxo-2,3,6,7-tetrahydro-1H-purin-8-yl)ethyl)carbamate |
| | 387.2 (M + H)⁺ | tert-butyl ((3,7-dimethyl-2,6-dioxo-2,3,6,7-tetrahydro-1H-purin-8-yl)(pyridin-3-yl)methyl)carbamate |
| | 366.2 (M + H)⁺ | tert-butyl 3-(3,7-dimethyl-2,6-dioxo-2,3,6,7-tetrahydro-1H-purin-8-yl)morpholine-4-carboxylate |
| | 364.3 (M + H)⁺ | tert-butyl (cyclobutyl(3,7-dimethyl-2,6-dioxo-2,3,6,7-tetrahydro-1H-purin-8-yl)methyl)carbamate |
| | (400 MHz, DMSO-d₆) δ 8.02 (br. s., 1H), 5.19-5.17 (m, 1H), 4.65-4.62 (m, 1H), 4.01 (s, 3H), 3.54 (s, 3H), 1.70-1.99 (m, 5H), 1.62 (s, 9H), 1.02-1.37 (m, 6H) | tert-butyl (cyclohexyl(3,7-dimethyl-2,6-dioxo-2,3,6,7-tetrahydro-1H-purin-8-yl)methyl)carbamate |

-continued

| Structure | Mass Spec (ESI: m/z) or ¹H NMR | Compound Name |
|---|---|---|
| | 338.2 (M + H)⁺ | tert-butyl (1-(3,7-dimethyl-2,6-dioxo-2,3,6,7-tetrahydro-1H-purin-8-yl)propyl)carbamate |
| | 350.2. (M + H)⁺ | tert-butyl (cyclopropyl(3,7-dimethyl-2,6-dioxo-2,3,6,7-tetrahydro-1H-purin-8-yl)methyl)carbamate |
| | (400 MHz DMSO-d₆) 8.07 (br, 1H), 5.18-5.16 (d, J = 8.0 Hz, 1H), 4.73-4.69 (m, 1H), 4.08-3.94 (m, 5H), 3.53 (s, 3H), 2.14-2.11 (m, 1H), 1.86-1.83 (m, 1H), 1.48-1.51 (m 1H), 1.39-1.32 (m, 2H) | tert-butyl ((3,7-dimethyl-2,6-dioxo-2,3,6,7-tetrahydro-1H-purin-8-yl)(tetrahydro-2H-pyran-4-yl)methyl)carbamate |
| | 378.2 (M + H)⁺ | tert-butyl N-[cyclopentyl-(3,7-dimethyl-2,6-dioxo-purin-8-yl)methyl]carbamate |
| | 366.2 (M + H)⁺ | tert-butyl ((3,7-dimethyl-2,6-dioxo-2,3,6,7-tetrahydro-1H-purin-8-yl)(oxetan-3-yl)methyl)carbamate |

The compounds in the table below were synthesized according to Procedure 4.

| Structure | Mass Spec (ESI: m/z) or ¹H NMR | Compound Name |
|---|---|---|
| | 613.3 (M + H)⁺ | tert-butyl 2-((8-(1-(tert-butoxycarbonyl)pyrrolidin-2-yl)-3,7-dimethyl-2,6-dioxo-2,3,6,7-tetrahydro-1H-purin-1-yl)methyl)-4-chloro-1H-indole-1-carboxylate |

| Structure | Mass Spec (ESI: m/z) or $^1$H NMR | Compound Name |
|---|---|---|
| 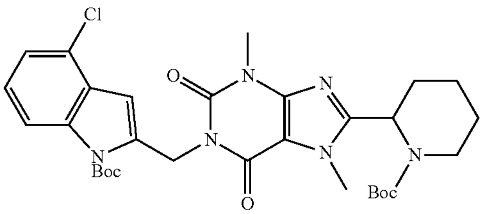 | (400 MHz, CDCl$_3$) δ 8.12-7.98 (m, 1 H) 7.21-7.11 (m, 2 H) 6.26-6.16 (m, 1 H) 5.59 (s, 2 H) 5.55-5.47 (m, 1 H) 4.09-3.95 (m, 4 H) 3.66 (s, 3 H) 3.24-3.11 (m, 2 H) 2.29-2.12 (m, 3 H) 2.01-1.87 (m, 2 H) 1.74 (s, 9 H) 1.58 (s, 9 H) | tert-butyl 2-((8-(1-(tert-butoxycarbonyl)piperidin-2-yl)-3,7-dimethyl-2,6-dioxo-2,3,6,7-tetrahydro-1H-purin-1-yl)methyl)-4-chloro-1H-indole-1-carboxylate |
| 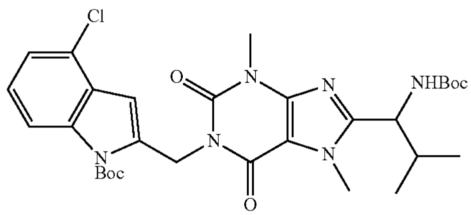 [SMILES: CC(C)C(NC(=O)OC(C)(C)C)c1nc2c(c(=O)n(Cc3cc4c(Cl)cccc4n3C(=O)OC(C)(C)C)c(=O)n2C)n1C] | 615.3 (M + H)$^+$ | tert-butyl 2-((8-(1-((tert-butoxycarbonyl)amino)-2-methylpropyl)-3,7-dimethyl-2,6-dioxo-2,3,6,7-tetrahydro-1H-purin-1-yl)methyl)-4-chloro-1H-indole-1-carboxylate |
| 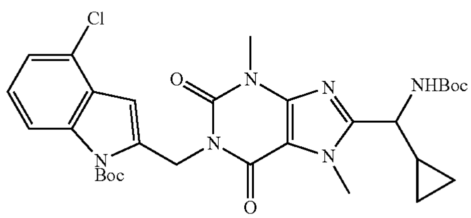 [SMILES: Cn1c(C(NC(=O)OC(C)(C)C)C2CC2)nc2c1c(=O)n(Cc1cc3c(Cl)cccc3n1C(=O)OC(C)(C)C)c(=O)n2C] | 613.3. (M + H)$^+$ | tert-butyl 2-((8-(((tert-butoxycarbonyl)amino)(cyclopropyl)methyl)-3,7-dimethyl-2,6-dioxo-2,3,6,7-tetrahydro-1H-purin-1-yl)methyl)-4-chloro-1H-indole-1-carboxylate |
| 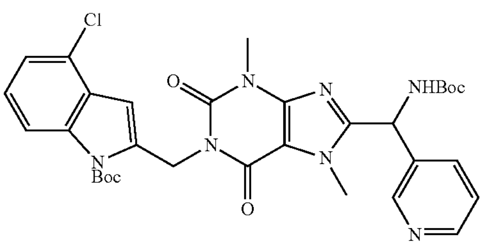 [SMILES: Cn1c(C(NC(=O)OC(C)(C)C)c2cccnc2)nc2c1c(=O)n(Cc1cc3c(Cl)cccc3n1C(=O)OC(C)(C)C)c(=O)n2C] | (400 MHz, CDCl$_3$) δ 8.66-8.60 (m, 1 H) 8.08-7.97 (m, 1 H) 7.77-7.70 (m, 1 H) 7.40-7.32 (m, 1 H) 7.22-7.12 (m, 2 H) 6.20 (s, 1 H) 6.07 (s, 2 H) 5.58 (s, 2 H) 3.93 (s, 3 H) 3.69 (s, 3 H) 1.73 (s, 9 H) 1.49 (s, 9 H) | tert-butyl 2-((8-(((tert-butoxycarbonyl)amino)(pyridin-3-yl)methyl)-3,7-dimethyl-2,6-dioxo-2,3,6,7-tetrahydro-1H-purin-1-yl)methyl)-4-chloro-1H-indole-1-carboxylate |
| 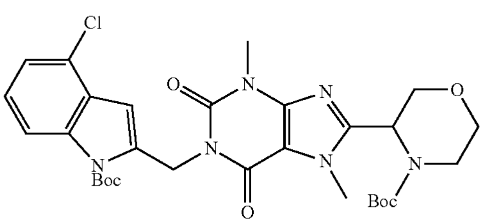 [SMILES: Cn1c(C2COCCN2C(=O)OC(C)(C)C)nc2c1c(=O)n(Cc1cc3c(Cl)cccc3n1C(=O)OC(C)(C)C)c(=O)n2C] | 629.3 (M + H)$^+$ | tert-butyl 3-(1-((1-(tert-butoxycarbonyl)-4-chloro-1H-indol-2-yl)methyl)-3,7-dimethyl-2,6-dioxo-2,3,6,7-tetrahydro-1H-purin-8-yl)morpholine-4-carboxylate |
| 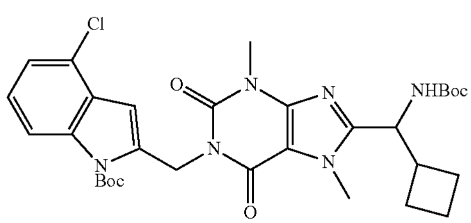 [SMILES: Cn1c(C(NC(=O)OC(C)(C)C)C2CCC2)nc2c1c(=O)n(Cc1cc3c(Cl)cccc3n1C(=O)OC(C)(C)C)c(=O)n2C] | 627.3 (M + H)$^+$ | tert-butyl 2-((8-(((tert-butoxycarbonyl)amino)(cyclobutyl)methyl)-3,7-dimethyl-2,6-dioxo-2,3,6,7-tetrahydro-1H-purin-1-yl)methyl)-4-chloro-1H-indole-1-carboxylate |
| 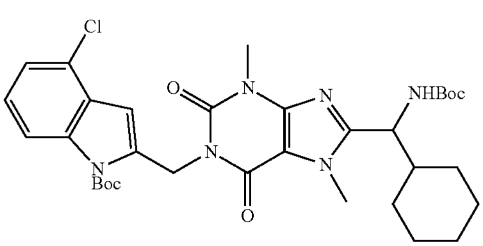 [SMILES: Cn1c(C(NC(=O)OC(C)(C)C)C2CCCCC2)nc2c1c(=O)n(Cc1cc3c(Cl)cccc3n1C(=O)OC(C)(C)C)c(=O)n2C] | (400 MHz, CDCl$_3$) δ 8.10-7.94 (m, 1H), 7.20-7.11 (m, 2H), 6.23 (s, 1H), 5.58 (s, 2H), 5.26 (d, J = 9.0 Hz, 1H), 4.69 (t, J = 8.8 Hz, 1H), 4.05 (s, 3H), 1.73 (s, 9H), 1.46 (s, 9H), 091-2.10 (m, 11H | tert-butyl 2-((8-(((tert-butoxycarbonyl)amino)(cyclohexyl)methyl)-3,7-dimethyl-2,6-dioxo-2,3,6,7-tetrahydro-1H-purin-1-yl)methyl)-4-chloro-1H-indole-1-carboxylate |

-continued

| Structure | Mass Spec (ESI: m/z) or ¹H NMR | Compound Name |
|---|---|---|
| 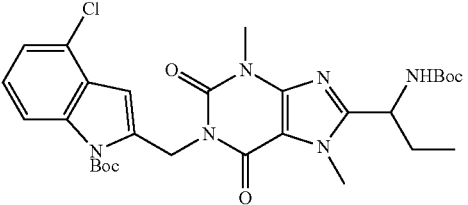 [SMILES: CCC(NC(=O)OC(C)(C)C)c1nc2c(c(=O)n(Cc3cc4c(Cl)cccc4n3C(=O)OC(C)(C)C)c(=O)n2C)n1C] | (400 MHz CDCl₃) δ 8.03-7.94 (m, 1 H) 7.15-7.08 (m, 2 H) 6.6 (s, 1 H) 5.54 (s, 2 H) 5.24-5.12 (m, 1H) 4.88-4.78 (m, 1 H) 4.01 (s, 3 H) 3.60 (s, 3 H) 2.00-1.83 (m, 2 H) 1.69 (s, 9 H) 1.43 (s, 9 H) 1.00-0.91 (t, 3 H) | tert-butyl 2-((8-(1-((tert-butoxycarbonyl)amino)propyl)-3,7-dimethyl-2,6-dioxo-2,3,6,7-tetrahydro-1H-purin-1-yl)methyl)-4-chloro-1H-indole-1-carboxylate |
| 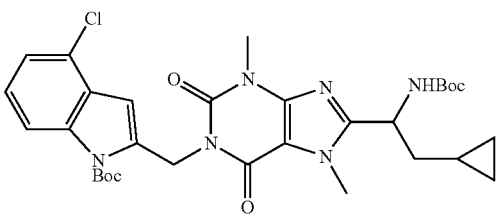 [SMILES: Cn1c(C(CC2CC2)NC(=O)OC(C)(C)C)nc2c1c(=O)n(Cc1cc3c(Cl)cccc3n1C(=O)OC(C)(C)C)c(=O)n2C] | (400 MHz, CDCl₃) δ 7.93-7.97 (m, 1 H) 7.05-7.09 (m, 2 H) 6.12 (s, 1 H) 5.49 (s, 2 H) 5.16-5.22 (m, 1 H) 4.89-4.95 (m, 1 H) 4.00 (s, 2 H) 3.55 (s, 2 H) 1.79-1.92 (m, 2 H) 1.67-1.76 (m, 2 H) 1.64 (s, 7 H) 1.49 (s, 8 H) 0.52-0.61 (m, 1 H) 0.35-0.45 (m, 1 H) 0.07-0.18 (m, 1 H) −0.09-0.02 (m, 1 H) | tert-butyl 2-((8-(1-((tert-butoxycarbonyl)amino)-2-cyclopropylethyl)-3,7-dimethyl-2,6-dioxo-2,3,6,7-tetrahydro-1H-purin-1-yl)methyl)-4-chloro-1H-indole-1-carboxylate |
| 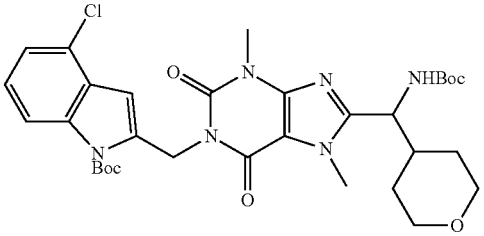 [SMILES: Cn1c(C(NC(=O)OC(C)(C)C)C2CCOCC2)nc2c1c(=O)n(Cc1cc3c(Cl)cccc3n1C(=O)OC(C)(C)C)c(=O)n2C] | 657.3 (M + H)⁺ | tert-butyl 2-((8-(((tert-butoxycarbonyl)amino)(tetrahydro-2H-pyran-4-yl)methyl)-3,7-dimethyl-2,6-dioxo-2,3,6,7-tetrahydro-1H-purin-1-yl)methyl)-4-chloro-1H-indole-1-carboxylate |
| 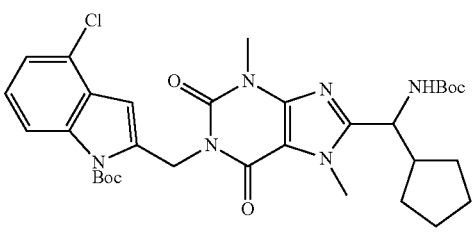 [SMILES: Cn1c(C(NC(=O)OC(C)(C)C)C2CCCC2)nc2c1c(=O)n(Cc1cc3c(Cl)cccc3n1C(=O)OC(C)(C)C)c(=O)n2C] | 641.3 (M + H)⁺ | tert-butyl 2-[[8-[(tert-butoxycarbonylamino)-cyclopentyl-methyl]-3,7-dimethyl-2,6-dioxo-purin-1-yl]methyl]-4-chloro-indole-1-carboxylate |
| 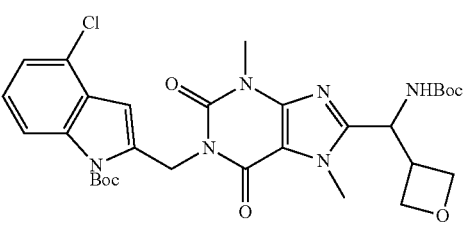 [SMILES: Cn1c(C(NC(=O)OC(C)(C)C)C2COC2)nc2c1c(=O)n(Cc1cc3c(Cl)cccc3n1C(=O)OC(C)(C)C)c(=O)n2C] | 629.3 (M + H)⁺ | tert-butyl 2-((8-(((tert-butoxycarbonyl)amino)(oxetan-3-yl)methyl)-3,7-dimethyl-2,6-dioxo-2,3,6,7-tetrahydro-1H-purin-1-yl)methyl)-4-chloro-1H-indole-1-carboxylate |

Example 424

1-[(4-chloro-1H-indol-2-yl)methyl]-3,7-dimethyl-8-pyrrolidin-2-yl-purine-2,6-dione

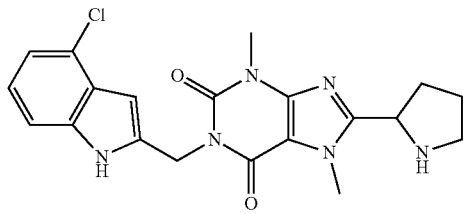 [SMILES: Cn1c(C2CCCN2)nc2c1c(=O)n(Cc1cc3c(Cl)cccc3[nH]1)c(=O)n2C]

To a solution of tert-butyl 2-[[8-(1-tert-butoxycarbonylpyrrolidin-2-yl)-3,7-dimethyl-2,6-dioxo-purin-1-yl]methyl]-4-chloro-indole-1-carboxylate (111.00 mg, 181.05 umol) in MeOH (5.00 mL) was added 4N HCl/MeOH (10.00 mL). The mixture was stirred at 25° C. for 16 hr. The reaction mixture was concentrated to dryness. The product was purified by prep-HPLC using Method C (20-50% ACN). $^1$H NMR (400 MHz, CD$_3$OD) δ 7.29 (d, J=7.5 Hz, 1H), 7.07-6.91 (m, 2H), 6.44 (s, 1H), 5.33 (s, 2H), 5.08 (t, J=7.0 Hz, 1H), 4.05 (s, 3H), 3.68-3.61 (m, 1H), 3.59 (s, 3H), 3.53-3.44 (m, 1H), 2.63-2.54 (m, 1H), 2.36-2.19 (m, 3H); ESI: m/z 413.2 (M+H)$^+$.

Example 430

1-((4-chloro-1H-indol-2-yl)methyl)-3,7-dimethyl-8-(piperidin-2-yl)-3,7-dihydro-1H-purine-2,6-dione

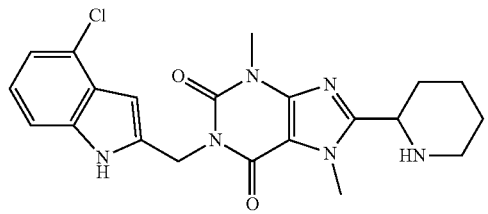 [SMILES: Cn1c(C2CCCCN2)nc2c1c(=O)n(Cc1cc3c(Cl)cccc3[nH]1)c(=O)n2C]

The title compound was synthesized in a similar fashion as described in Example 424 using tert-butyl 2-((8-(1-(tert-butoxycarbonyl)piperidin-2-yl)-3,7-dimethyl-2,6-dioxo-2,3,6,7-tetrahydro-1H-purin-1-yl)methyl)-4-chloro-1H-indole-1-carboxylate. The product was purified by prep-HPLC using Method C 25-60% ACN). $^1$H NMR (400 MHz, CDCl$_3$) δ 9.18 (br. s., 1H), 7.24-7.18 (m, 1H), 7.11-7.00 (m, 2H), 6.72 (s, 1H), 5.33 (s, 2H), 4.04 (s, 3H), 3.89 (dd, J=2.9, 11.2 Hz, 1H), 3.59 (s, 3H), 3.22 (d, J=13.7 Hz, 1H), 2.85-2.68 (m, 1H), 2.05-1.57 (m, 6H); ESI: m/z 427.2 (M+H)$^+$.

Example 434

8-(1-aminopropyl)-1-[(4-chloro-1H-indol-2-yl)methyl]-3,7-dimethyl-purine-2,6-dione

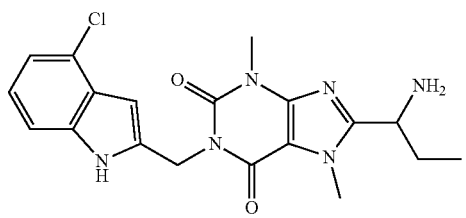 [SMILES: CCC(N)c1nc2c(c(=O)n(Cc3cc4c(Cl)cccc4[nH]3)c(=O)n2C)n1C]

The title compound was synthesized in a similar fashion as Example 424 using tert-butyl 2-((8-(1-((tert-butoxycarbonyl)amino)propyl)-3,7-dimethyl-2,6-dioxo-2,3,6,7-tetrahydro-1H-purin-1-yl)methyl)-4-chloro-1H-indole-1-carboxylate. The mixture was concentrated to provide the title compound. $^1$H NMR (400 MHz DMSO-d$_6$) δ 11.34 (br. s., 1H), 8.71 (br. s., 3H), 7.34 (d, J=7.0 Hz, 1H), 7.12-6.92 (m, 2H), 6.27 (s, 1H), 5.30-5.13 (m, 2H), 4.64 (br. s., 1H), 4.00 (s, 3H), 3.50 (s, 3H), 2.10-1.87 (m, 2H), 0.86 (m, 3H); ESI: m/z 401.1 (M+H)$^+$.

Example 437

8-(1-amino-2-methyl-propyl)-1-[(4-chloro-1H-indol-2-yl)methyl]-3,7-dimethyl-purine-2,6-dione

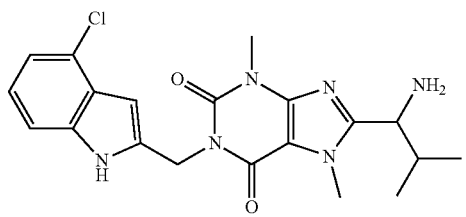 [SMILES: CC(C)C(N)c1nc2c(c(=O)n(Cc3cc4c(Cl)cccc4[nH]3)c(=O)n2C)n1C]

The title compound was synthesized in a similar fashion as described in Example 424 using tert-butyl 2-((8-(1-((tert-butoxycarbonyl)amino)-2-methylpropyl)-3,7-dimethyl-2,6-dioxo-2,3,6,7-tetrahydro-1H-purin-1-yl)methyl)-4-chloro-1H-indole-1-carboxylate. The product was purified by prep-HPLC using Method C (20-80% ACN). $^1$H NMR (400 MHz, DMSO-d$_6$) δ 11.34 (s, 1H), 8.69 (br. s., 3H), 7.34 (dd, J=1.5, 7.0 Hz, 1H), 7.12-6.93 (m, 2H), 6.27 (d, J=1.5 Hz, 1H), 5.32-5.10 (m, 2H), 4.47 (d, J=8.0 Hz, 1H), 3.99 (s, 3H), 3.49 (s, 3H), 2.39-2.19 (m, 1H), 1.04 (d, J=7.0 Hz, 3H), 0.85 (d, J=7.0 Hz, 3H); ESI: m/z 415.2 (M+H)$^+$.

Example 442

8-(1-amino-2-cyclopropyl-ethyl)-1-[(4-chloro-1H-indol-2-yl)methyl-3,7-dimethyl-purine-2,6-dione

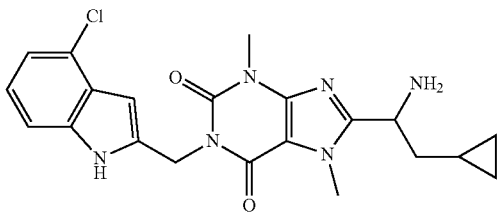 [SMILES: Cn1c(C(N)CC2CC2)nc2c1c(=O)n(Cc1cc3c(Cl)cccc3[nH]1)c(=O)n2C]

The title compound was synthesized in a similar fashion as described in Example 424 using tert-butyl 2-((8-(1-(((tert-butoxycarbonyl)amino)-2-cyclopropylethyl)-3,7-dimethyl-2,6-dioxo-2,3,6,7-tetrahydro-1H-purin-1-yl)methyl)-4-chloro-1H-indole-1-carboxylate. The product was purified by prep-HPLC using Method C (15-55% ACN). $^1$H NMR (400 MHz, DMSO-$d_6$) δ 11.24-11.48 (m, 1H) 8.54-8.78 (m, 3H) 7.25-7.46 (m, 1H) 6.98-7.11 (m, 2H) 6.20-6.34 (m, 1H) 5.18-5.32 (m, 2H) 4.65-4.84 (m, 1H) 4.03 (s, 3H) 3.51 (s, 3H) 1.73-1.97 (m, 2H) 0.60-0.73 (m, 1H) 0.28-0.51 (m, 2H) 0.08-0.21 (m, 1H) −0.16-0.04 (m, 1H); ESI: m/z 427/429 (M+H)$^+$.

Example 443

8-[amino(cyclobutyl)methyl]-1-[(4-chloro-1H-indol-2-yl)methyl]-3,7-dimethyl-purine-2,6-dione

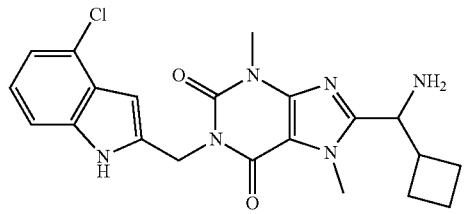 [SMILES: Cn1c(C(N)C2CCC2)nc2c1c(=O)n(Cc1cc3c(Cl)cccc3[nH]1)c(=O)n2C]

The title compound was synthesized in a similar fashion as described in Example 424 using tert-butyl 2-((8-(((tert-butoxycarbonyl)amino)(cyclobutyl)methyl)-3,7-dimethyl-2,6-dioxo-2,3,6,7-tetrahydro-1H-purin-1-yl)methyl)-4-chloro-1H-indole-1-carboxylate. The product was purified by prep-HPLC using Method C (20-50% ACN) to provide the title compound. $^1$H NMR (400 MHz, CD$_3$OD) δ 7.27 (d, J=7.8 Hz, 1H), 7.06-6.90 (m, 2H), 6.43 (s, 1H), 5.31 (s, 2H), 4.72 (d, J=9.0 Hz, 1H), 4.06 (s, 3H), 3.57 (s, 3H), 3.05-2.94 (m, 1H), 2.24-1.78 (m, 6H); ESI: m/z 427.1 (M+H)$^+$.

Example 444

8-[amino(cyclopropyl)methyl]-1-[(4-chloro-1H-indol-2-yl)methyl]-3,7-dimethyl-purine-2,6-dione

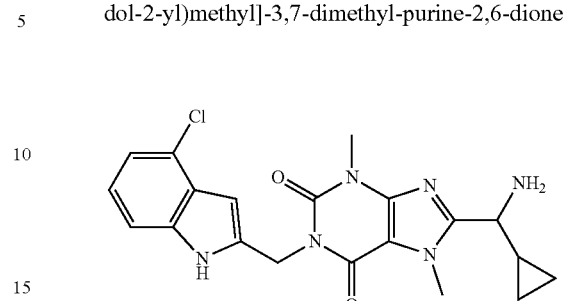

The title compound was synthesized in a similar fashion as described in Example 424 using tert-butyl 2-((8-(((tert-butoxycarbonyl)amino)(cyclopropyl)methyl)-3,7-dimethyl-2,6-dioxo-2,3,6,7-tetrahydro-1H-purin-1-yl)methyl)-4-chloro-1H-indole-1-carboxylate. $^1$H NMR (400 MHz, DMSO-$d_6$) δ 11.33 (s, 1H), 8.77 (br. s., 3H), 7.39-7.26 (m, 1H), 7.10-6.96 (m, 2H), 6.27 (s, 1H), 5.29-5.13 (m, 2H), 4.21 (m, 1H), 3.96 (s, 3H), 3.50 (s, 3H), 1.39 (m, 1H), 0.75-0.47 (m, 4H). ESI: m/z 396.1 (M+H)$^+$.

Example 445

8-[amino(3-pyridyl)methyl]-1-[(4-chloro-1H-indol-2-yl)methyl]-3,7-dimethyl-purine-2,6-dione

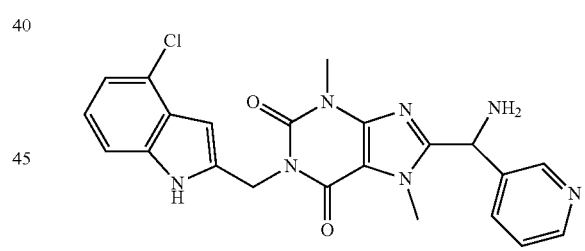

The title compound was synthesized in a similar fashion as described in Example 424 using tert-butyl 2-((8-(((tert-butoxycarbonyl)amino)(pyridin-3-yl)methyl)-3,7-dimethyl-2,6-dioxo-2,3,6,7-tetrahydro-1H-purin-1-yl)methyl)-4-chloro-1H-indole-1-carboxylate. $^1$H NMR (400 MHz, DMSO-$d_6$) δ 11.33 (s, 1H), 9.41 (br. s., 2H), 8.88 (s, 1H), 8.72 (d, J=5.0 Hz, 1H), 8.10 (d, J=8.5 Hz, 1H), 7.66-7.59 (m, 1H), 7.37-7.29 (m, 1H), 7.08-6.96 (m, 2H), 6.34-6.19 (m, 2H), 5.28-5.09 (m, 2H), 3.86 (s, 3H), 3.55 (s, 3H); ESI: m/z 450.1 (M+H)$^+$.

Example 446

8-[amino(cyclohexyl)methyl]-1-[(4-chloro-1H-indol-2-yl)methyl]-3,7-dimethyl-purine-2,6-dione

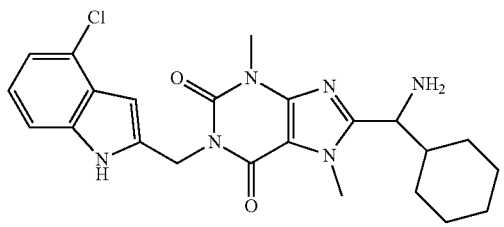 [SMILES: Cn1c(C(N)C2CCCCC2)nc2c1c(=O)n(Cc1cc3c(Cl)cccc3[nH]1)c(=O)n2C]

The title compound was synthesized in a similar fashion as described in Example 424 using tert-butyl 2-((8-(((tert-butoxycarbonyl)amino)(cyclohexyl)methyl)-3,7-dimethyl-2,6-dioxo-2,3,6,7-tetrahydro-1H-purin-1-yl)methyl)-4-chloro-1H-indole-1-carboxylate. After removal of the Boc-protecting groups the reaction mixture was concentrated. The residue was suspended in methanol (3 mL) and the solid was collected by filtration to provide the title compound. $^1$H NMR (400 MHz, DMSO-$d_6$) δ 8.57 (br. s., 2H), 7.35 (d, J=7.0 Hz, 1H), 7.14-6.92 (m, 2H), 6.28 (s, 1H), 5.33-5.09 (m, 2H), 4.48 (d, J=8.0 Hz, 1H), 3.98 (s, 3H), 3.50 (s, 3H), 1.91 (d, J=12.5 Hz, 2H), 1.83-1.55 (m, 3H), 1.32 (d, J=8.0 Hz, 1H), 1.27-0.98 (m, 5H); ESI: m/z 455.2 (M+H)$^+$.

Example 453

1-[(4-chloro-1H-indol-2-yl)methyl]-3,7-dimethyl-8-morpholin-2-yl-purine-2,6-dione

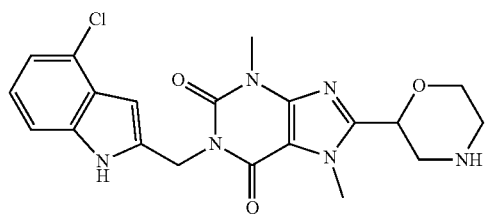 [SMILES: Cn1c(C2CNCCO2)nc2c1c(=O)n(Cc1cc3c(Cl)cccc3[nH]1)c(=O)n2C]

The title compound was synthesized in a similar fashion as described in Example 424 using tert-butyl 3-(1-((1-(tert-butoxycarbonyl)-4-chloro-1H-indol-2-yl)methyl)-3,7-dimethyl-2,6-dioxo-2,3,6,7-tetrahydro-1H-purin-8-yl)morpholine-4-carboxylate. The product was purified by prep-HPLC using Method C (15-45% ACN). $^1$H NMR (400 MHz, CD$_3$OD) δ 7.30-7.23 (m, 1H), 7.04-6.94 (m, 2H), 6.44 (m, 1H), 5.32 (s, 2H), 5.19-5.13 (m, 1H), 4.05 (s, 3H), 4.03-3.98 (m, 2H), 3.82-3.74 (m, 1H), 3.71-3.65 (m, 1H), 3.57 (s, 3H), 3.42-3.35 (m, 1H), 3.29-3.23 (m, 1H); ESI: m/z 429.1 (M+H)$^+$.

Example 464

8-(amino(cyclopentyl)methyl)-1-((4-chloro-1H-indol-2-yl)methyl)-3,7-dimethyl-3,7-dihydro-1H-purine-2,6-dione

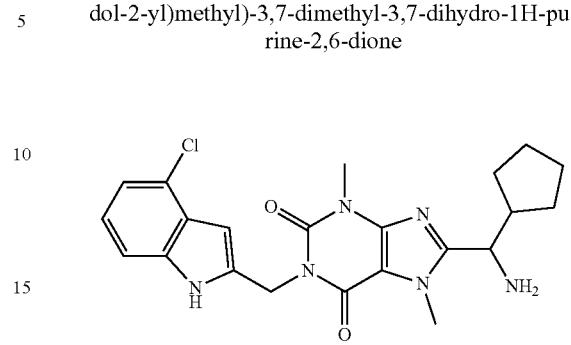

The title compound was synthesized in a similar fashion as described in Example 424 using tert-butyl 2-[[8-[(tert-butoxycarbonylamino)-cyclopentyl-methyl]-3,7-dimethyl-2,6-dioxo-purin-1-yl]methyl]-4-chloro-indole-1-carboxylate. $^1$H NMR (400 MHz, CD$_3$OD) δ 7.27 (d, J=7.9 Hz, 1H), 7.06-6.92 (m, 2H), 6.43 (s, 1H), 5.38-5.26 (m, 2H), 4.64-4.51 (m, 1H), 4.05 (s, 3H), 3.57 (s, 3H), 2.72-2.47 (m, 1H), 1.99 (dd, J=4.2, 11.7 Hz, 1H), 1.82-1.52 (m, 5H), 1.52-1.40 (m, 1H), 1.39-1.25 (m, 1H); ESI: m/z 441.2 (M+H)$^+$.

Example 438

1-[(4-chloro-1H-indol-2-yl)methyl]-3,7-dimethyl-8-[1-(methylamino)ethyl]purine-2,6-dione

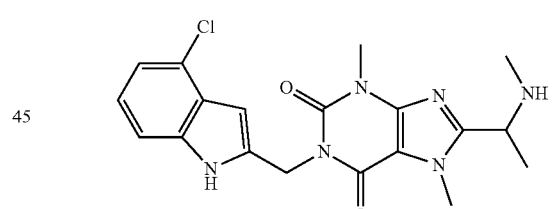

To a solution of tert-butyl 2-[(8-acetyl-3,7-dimethyl-2,6-dioxo-purin-1-yl)methyl]-4-chloro-indole-1-carboxylate (60.00 mg, 123.48 umol) in MeOH (5.00 mL) was added NaBH$_3$CN (19.40 mg, 308.70 umol), methanamine (2 M, 617.40 uL). The reaction mixture was heated to 70° C. and stirred for 2 h and to 80° C. and for 12 h. The mixture was dried in vacuo to afford crude product which was purified by prep-HPLC using Method C (20-60% ACN). $^1$H NMR (400 MHz, CD$_3$OD) δ 7.28 (d, J=8.0 Hz, 1H), 7.05-6.95 (m, 2H), 6.44 (s, 1H), 5.33 (s, 2H), 4.09-4.00 (m, 3H), 3.59 (s, 3H), 2.76 (s, 3H), 1.67 (d, J=7.0 Hz, 3H); ESI: m/z 401.2 (M+H)$^+$.

Examples 454 and 455

8-[amino(tetrahydropyran-4-yl)methyl]-1-[(4-chloro-1H-indol-2-yl)methyl]-3,7-dimethyl-purine-2,6-dione (Example 454) and 8-[amino(tetrahydropyran-4-yl)methyl]-1-[(3,4-dichloro-1H-indol-2-yl)methyl]-3,7-dimethyl-purine-2,6-dione (Example 455)

Example 454

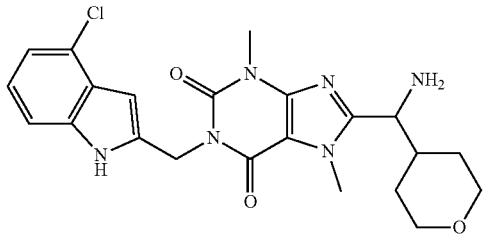

Example 455

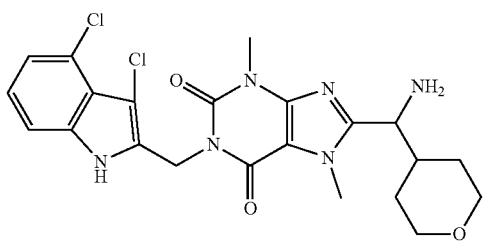

The title compounds were synthesized in a similar fashion as described in Example 424 using 2-(tert-butoxycarbonylamino)-2-tetrahydropyran-4-yl-acetic acid. The products were purified by prep-HPLC using Method C (15-55% ACN).

Example 454: $^1$H NMR (400 MHz, DMSO-$d_6$) δ 11.35 (s, 1H), 8.63 (br. s., 2H), 7.35 (d, J=7.0 Hz, 1H), 7.14-6.94 (m, 2H), 6.28 (s, 1H), 5.38-5.08 (m, 2H), 4.56 (d, J=8.5 Hz, 1H), 4.00 (s, 3H), 3.93 (d, J=8.5 Hz, 1H), 3.81 (d, J=8.5 Hz, 1H), 3.51 (s, 3H), 3.29-3.15 (m, 2H), 2.24 (d, J=8.5 Hz, 1H), 1.78 (d, J=12.0 Hz, 1H), 1.49-1.32 (m, 2H), 1.18 (d, J=13.6 Hz, 1H); ESI: m/z 457.2 (M+H)$^+$.

Example 455: $^1$H NMR (400 MHz, DMSO-$d_6$) δ 11.48 (s, 1H), 8.67 (br. s., 2H), 7.44-7.29 (m, 1H), 7.18-7.01 (m, 2H), 5.26 (d, J=3.0 Hz, 2H), 4.59 (d, J=8.5 Hz, 1H), 4.00 (s, 3H), 3.96-3.89 (m, 1H), 3.83 (d, J=11.5 Hz, 1H), 3.51 (s, 3H), 3.29-3.16 (m, 2H), 2.26 (br. s., 1H), 1.79 (d, J=14.1 Hz, 1H), 1.53-1.30 (m, 2H), 1.18 (d, J=13.6 Hz, 1H); ESI: m/z 491.1 (M+H)$^+$.

Example 467

8-[amino(oxetan-3-yl)methyl]-1-[(4-chloro-1H-indol-2-yl)methyl]-3,7-dimethyl-purine-2,6-dione

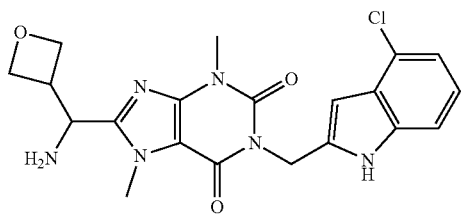 [SMILES: Cn1c(C(N)C2COC2)nc2c1c(=O)n(Cc1cc3c(Cl)cccc3[nH]1)c(=O)n2C]

A solution of tert-butyl 2-[[8-[(tert-butoxycarbonylamino)-(oxetan-3-yl)methyl]-3,7-dimethyl-2,6-dioxo-purin-1-yl]methyl]-4-chloro-indole-1-carboxylate (36.00 mg, 57.22 umol, 1.00 eq) in 4N HCl/MeOH (10.00 mL) was stirred at 25° C. for 16 h. The mixture was concentrated. The residue was purified by prep-HPLC using Method C (15-35% ACN). $^1$H NMR (400 MHz, DMSO-$d_6$) δ 3.63 (d, J=4.85 Hz, 3H) 3.65-3.72 (m, 1H) 3.78-3.85 (m, 1H) 4.19 (s, 3H) 4.50-4.57 (m, 1H) 4.63-4.72 (m, 1H) 4.76-4.86 (m, 1H) 4.90-4.99 (m, 1H) 5.16-5.26 (m, 3H) 6.27 (br. s., 1H) 7.01 (s, 2H) 7.31-7.35 (m, 1H) 11.46 (br. s., 1H); ESI: m/z 429.0 (M+H)$^+$.

Example 458

8-(1-amino-2-hydroxy-ethyl)-1-[(4-chloro-1H-indol-2-yl)methyl]-3,7-dimethyl-purine-2,6-dione

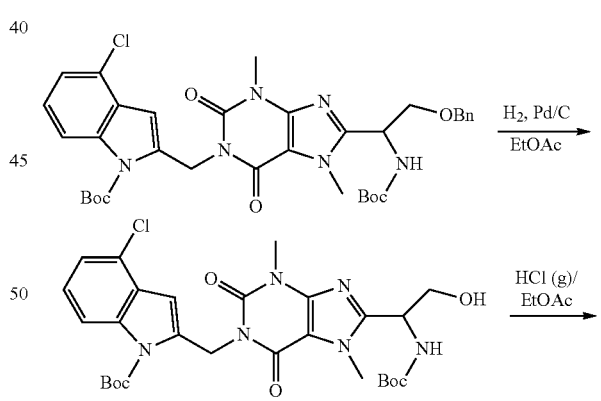

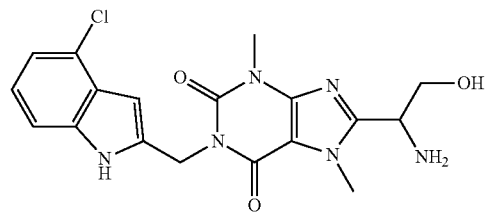

tert-Butyl 2-[[8-[2-benzyloxy-1-(tert-butoxycarbo-
nylamino)ethyl]-3,7-dimethyl-2,6-dioxo-purin-1-yl]
methyl]-4-chloro-indole-1-carboxylate

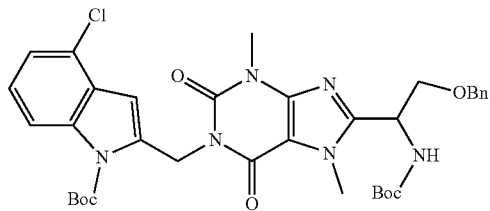 [SMILES: Cn1c(C(COCc2ccccc2)NC(=O)OC(C)(C)C)nc2c1c(=O)n(Cc1cc3c(Cl)cccc3n1C(=O)OC(C)(C)C)c(=O)n2C]

The title compound was synthesized in a similar fashion as described in the preparation of Example 424 using 3-benzyloxy-2-(tert-butoxycarbonylamino) propanoic acid. $^{1}$H NMR (400 MHz, CDCl$_3$) δ 7.29-7.14 (m, 5H), 5.04 (t, J=6.6 Hz, 1H), 4.57-4.41 (m, 2H), 3.92 (s, 3H), 3.88-3.73 (m, 2H), 3.42 (s, 3H), 1.40 (s, 9H); ESI: m/z 430.3 (M+H)$^+$.

tert-Butyl 2-[[8-[1-(tert-butoxycarbonylamino)-2-
hydroxy-ethyl]-3,7-dimethyl-2,6-dioxo-purin1-yl]
methyl]-4-chloro-indole-1-carboxylate

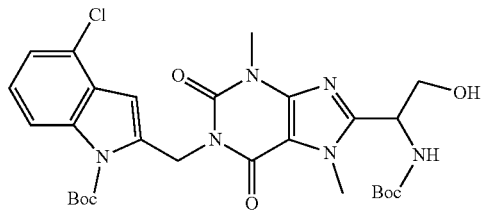 [SMILES: Cn1c(C(CO)NC(=O)OC(C)(C)C)nc2c1c(=O)n(Cc1cc3c(Cl)cccc3n1C(=O)OC(C)(C)C)c(=O)n2C]

A solution of tert-butyl 2-[[8-[2-benzyloxy-1-(tert-butoxycarbonylamino)ethyl]-3,7-dimethyl-2,6-dioxo-purin-1-yl]methyl]-4-chloro-indole-1-carboxylate (100.00 mg, 144.26 umol) and Pd/C (500.00 mg), degassed with H$_2$, then stirred at 25° C. under H$_2$ atmosphere (balloon) for 1 h. The mixture was filtered through celite and concentrated to give crude tert-butyl 2-[[8-[1-(tert-butoxycarbonylamino)-2-hydroxy-ethyl]-3,7-dimethyl-2,6-dioxo-purin-1-yl]methyl]-4-chloro-indole-1-carboxylate: ESI: m/z 693.3 (M+H)$^+$.

8-(1-Amino-2-hydroxy-ethyl)-1-[(4-chloro-1H-in-
dol-2-yl)methyl]-3,7-dimethyl-purine-2,6-dione

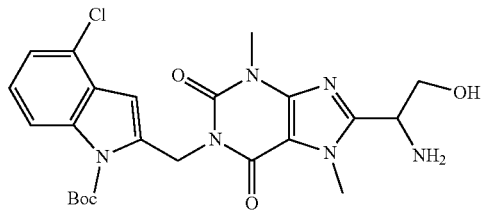 [SMILES: Cn1c(C(N)CO)nc2c1c(=O)n(Cc1cc3c(Cl)cccc3n1C(=O)OC(C)(C)C)c(=O)n2C]

A solution of tert-butyl 2-[[8-[1-(tert-butoxycarbo-nylamino)-2-hydroxy-ethyl]-3,7-dimethyl-2,6-dioxo-purin-1-yl]methyl]-4-chloro-indole-1-carboxylate (100.00 mg, 165.82 umol) in HCl/EA (20.00 mL) was stirred for 22 h. The mixture was concentrated to give a crude product which was purified by prep-HPLC using Method C (15-45% ACN) to give the title compound. $^{1}$H NMR (400 MHz, DMSO-d$_6$) δ 11.35 (s, 1H), 8.69 (br. s., 3H), 7.33 (dd, J=1.3, 6.6 Hz, 1H), 7.10-6.92 (m, 2H), 6.25 (s, 1H), 5.33-5.11 (m, 2H), 4.71 (br. s., 1H), 3.98 (s, 3H), 3.91-3.73 (m, 2H), 3.50 (s, 3H); ESI: m/z 403.2 (M+H)$^+$.

Example 439

8-((1S,2R)-2-aminocyclopentylamino)-1-((4-chloro-
1H-indol-2-yl)methyl)-3,7-dimethyl-1H-purine-2,6
(3H,7H)-dione

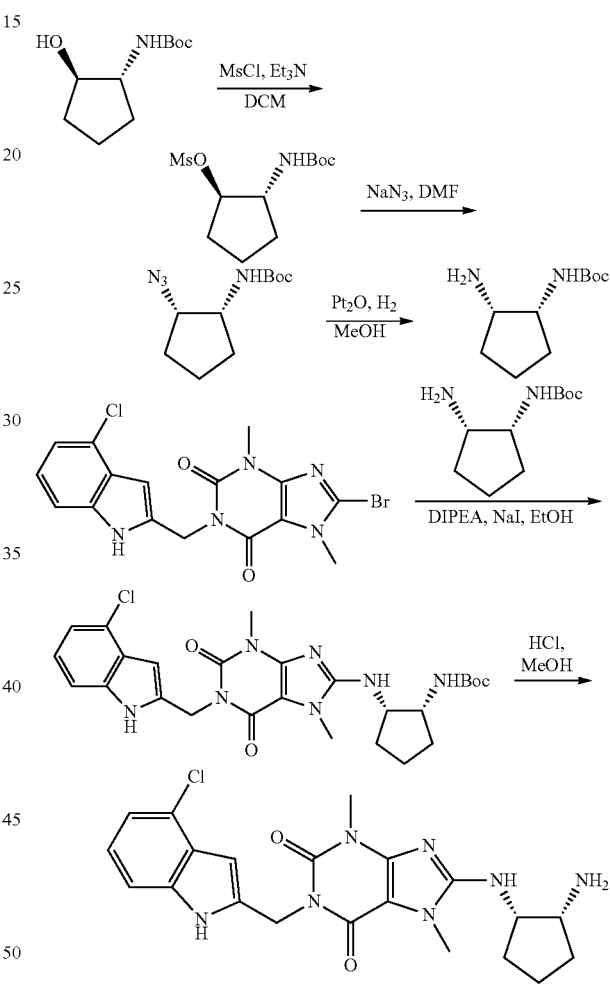

tert-Butyl (1S,2S)-2-hydroxycyclopentylcarbamate

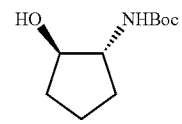

To a solution of (1S,2S)-2-aminocyclopentanol hydrochloride (36.5 mmol, 5 g) in THF (20 mL) and water (10 mL) was added K$_2$CO$_3$ (73.0 mmol, 10 g). The reaction mixture was stirred at 25° C. for 4 h. The reaction was treated with water (50 mL) and extracted with EA (2*100 mL). The organic fractions were washed with water (1*50 mL). The organic fraction was dried over Na₂SO₄, filtered, concentrated to give the product. ¹H NMR (400 MHz, DMSO-d₆) δ 6.70 (br s, 1H), 4.60 (s, 1H), 3.78-3.75 (m, 1H), 3.49 (br s, 1H), 1.89-1.84 (m, 1H), 1.75-1.74 (m, 1H), 1.57-1.53 (m, 2H), 1.40 (s, 9H), 1.38-1.29 (m, 2H).

(1S,2S)-2-(tert-Butoxycarbonylamino)cyclopentyl methanesulfonate

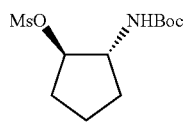

To a solution of tert-butyl (1S,2S)-2-hydroxycyclopentylcarbamate (10 mmol, 2.0 g), triethylamine (12 mmol, 1.2 g) in DCM (10 mL) was added MsCl (11 mmol, 1.1 g). The mixture was stirred at 0° C. for 3 h. The reaction mixture was diluted with water (20 mL) and extracted with EA (3*50 mL). The combined organic fractions were washed with water (1*100 mL). The organic layer was concentrated to give the product, which was used in the next step without further purification.

tert-Butyl (1S, 2R)-2-azidocyclopentylcarbamate

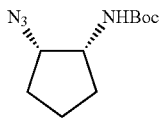

To a solution of (1S,2S)-2-(tert-butoxycarbonylamino) cyclopentyl methanesulfonate (5.4 mmol, 1.5 g) in DMF (10 mL) was added NaN₃ (26.9 mmol, 1.7 g). The reaction mixture was stirred at 80° C. for 16 h. The reaction mixture was diluted with water (30 mL). The mixture was filtered and the filter cake was dried to give the product as a white solid. ¹H NMR (400 MHz, CDCl₃) δ 4.78 (br s, 1H), 7.00-3.95 (m, 2H), 1.95-1.85 (m, 4H), 1.63 (m, 1H), 1.45 (s, 9H).

tert-Butyl (1S,2R)-2-aminocyclopentylcarbamate

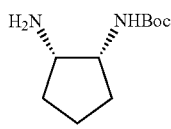

To a solution of tert-butyl (1S,2R)-2-azidocyclopentylcarbamate (2.2 mmol, 0.5 g) in methanol (5 mL) was added PtO₂ (0.04 g). The reaction mixture was stirred at 25° C. for 2 h under H₂ (1 atm). The mixture was filtered and the filtrate was concentrated to give the product; ESI: m/z 201.2 (M+H)⁺.

tert-Butyl (1R,2S)-2-(1-((4-chloro-1H-indol-2-yl) methyl)-3,7-dimethyl-2,6-dioxo-2,3,6,7-tetra hydro-1H-purin-8-ylamino)cyclopentylcarbamate

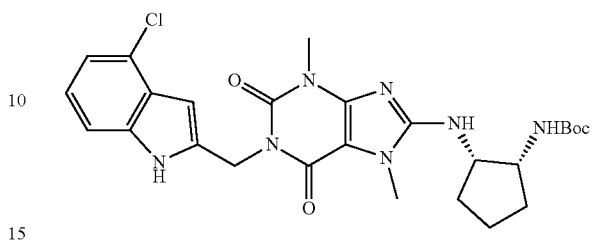

To a solution of 8-bromo-1-((4-chloro-1H-indol-2-yl) methyl)-3,7-dimethyl-1H-purine-2,6(3H,7H)-dione (0.75 mmol, 0.39 g), tert-butyl (1S,2R)-2-aminocyclopentylcarbamate (1.50 mmol, 0.30 g), DIEA (2.25 mmol, 0.29 g) in ethanol (10 mL) was added NaI (0.07 mmol, 0.01 g). The reaction mixture was stirred at 125° C. for 5 h in a microwave reactor. The mixture was concentrated and purified by flash chromatography with EA to give the title compound; ESI: m/z 542.2 (M+H)⁺.

8-((1S,2R)-2-Aminocyclopentylamino)-1-((4-chloro-1H-indol-2-yl)methyl)-3,7-dimethyl-1H-purine-2,6 (3H-7H)-dione

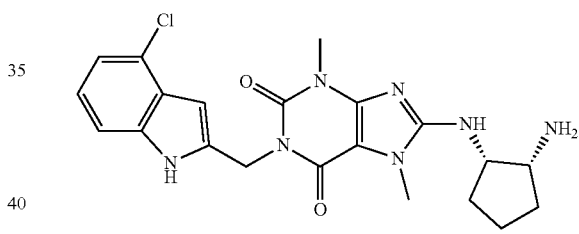

To a solution of tert-butyl (1R,2S)-2-(1-((4-chloro-1H-indol-2-yl)methyl)-3,7-dimethyl-2,6-dioxo-2,3,6,7-tetrahydro-1H-purin-8-ylamino)cyclopentylcarbamate (0.02 g) was added HCl in methanol (2 mL, 3N). The reaction mixture was stirred at 25° C. for 2 h. The mixture was concentrated and purified by Prep-HPLC using Method D (30-70% ACN) to give the product. ¹H NMR (400 MHz, CD₃OD) δ 7.29-7.27 (d, J=7.6 Hz, 1H), 7.01-6.98 (m, 2H), 6.42 (s, 1H), 5.29 (s, 2H), 4.24-4.19 (m, 1H), 3.72 (s, 1H), 3.52-3.50 (m, 4H), 2.12-2.01 (m, 2H), 1.88-1.75 (m, 2H), 1.65-1.52 (m, 2H); ESI: m/z 442.2 (M+H)⁺.

Example 440

2-amino-N-((4-(1((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide

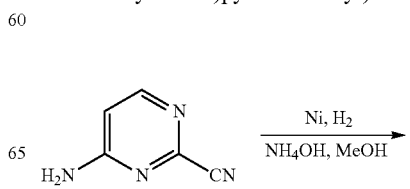

407
-continued tert-Butyl 2-((4-aminopyrimidin-2-yl)methylamino)-2-oxoethylcarbamate

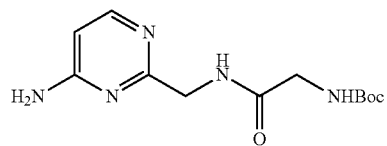 [SMILES: CC(C)(C)OC(=O)NCC(=O)NCc1nccc(N)n1]

A mixture of 2-(aminomethyl)pyrimidin-4-amine (150 mg, 1.21 mmol), 2-(tert-butoxycarbonyl amino) acetic acid (233 mg, 1.33 mmol), HATU (690 mg, 1.81 mmol), DIEA (468 mg, 3.63 mmol) and DMF (5 mL) was stirred at rt. for 3 h. The mixture was diluted with EA (60 mL), washed with brine (20 mL*3). The organic fraction was dried over $Na_2SO_4$ and concentrated to dryness. The residue was purified by flash column chromatography (MeOH/DCM=0-5%) to give the desired product; ESI: m/z 282.2 $(M+H)^+$.

tert-Butyl 2-((8-(2-((2-tert-butoxycarbonylamino) acetamido)methyl)pyrimidin-4-ylamino)-3,7-dimethyl-2,6-dioxo-2,3,6,7-tetrahydro-1H-purin-1-yl) methyl)-4-chloro-1H-indole-1-carboxylate

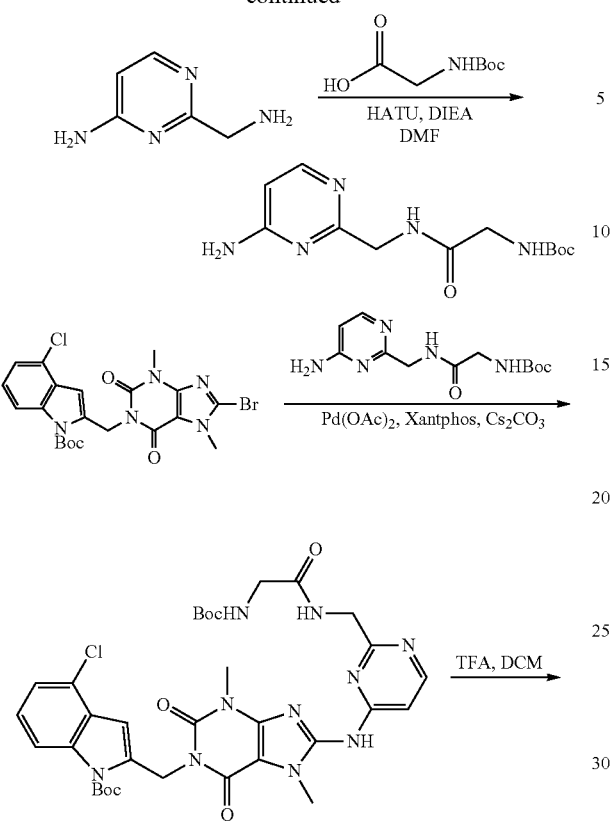

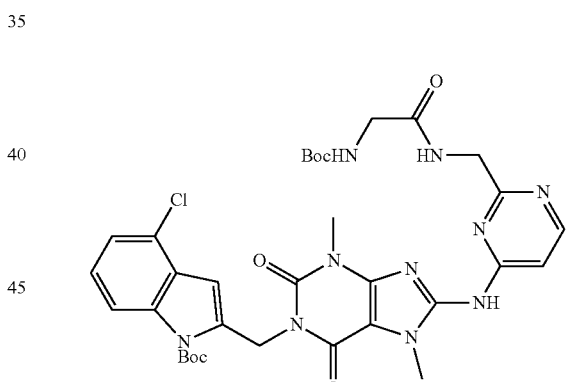

2-(Aminomethyl) pyrimidin-4-amine

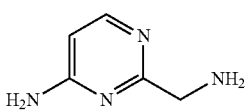

A mixture of 4-aminopyrimidine-2-carbonitrile (1.1 g, 9.17 mmol), Ni (200 mg) and MeOH (20 mL), $NH_4OH$ (5 mL) was stirred at rt. under $H_2$ overnight. The mixture was filtered; the filtrate was concentrated to dryness. The residue was purified by flash column chromatography (MeOH/DCM=0-10%) to give the desired product; ESI: m/z 125.2 $(M+H)^+$.

A mixture of tert-butyl 2-((4-aminopyrimidin-2-yl)methylamino)-2-oxoethylcarbamate (30 mg, 0.107 mmol), 8-bromo-1-((4-chloro-1H-indol-2-yl)methyl-3,7-dimethyl-1H-purine-2,6(3H,7H)-indone (56 mg, 0.107 mmol), $Pd(AcO)_2$ (3 mg, 0.010 mmol), Xantphos (13 mg, 0.021 mmol), $Cs_2CO_3$ (70 mg, 0.214 mmol) and DMF (2 mL) were degassed with Ar and heated by microwave at 100° C. for 3 h. The mixture was poured into water (10 ml) and filtered. The filter cake was purified by prep-HPLC using Method D (30-60% ACN); ESI: m/z 723.2 $(M+H)^+$.

2-Amino-N-((4-(1((4-chloro-1H-indol-2-yl)methyl)-3,7-dimethyl-2,6-dioxo-2,3,6,7-tetrahydro-1H-purin-8-ylamino) pyrimidin-2-yl)methyl)acetamide

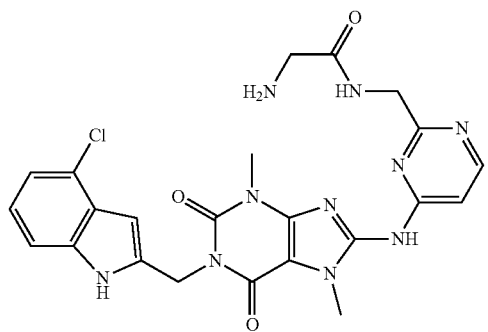 [SMILES: Cn1c(Nc2ccnc(CNC(=O)CN)n2)nc2c1c(=O)n(Cc1cc3c(Cl)cccc3[nH]1)c(=O)n2C]

A mixture of tert-butyl 2-((8-(2-((2-tert-butoxycarbonylamino)acetamido)methyl)pyrimidin-4-ylamino)-3,7-dimethyl-2,6-dioxo-2,3,6,7-tetrahydro-1H-purin-1-yl)methyl)-4-chloro-1H-indole-1-carboxylate (20 mg, 0.028 mmol), TFA (1 mL) and DCM (3 mL) was stirred at rt. for 3 h. The mixture was concentrated to dryness. The residue was neutralized with aq. NaHCO₃ to pH~7 and concentrated to dryness. The residue was purified by prep-HPLC using Method D (40-70% ACN) to give the title compound. ¹H NMR (400 MHz, CD₃OD) δ 8.44 (d, J=5.9 Hz, 1H), 7.61 (s, 1H), 7.28 (dt, J=7.9, 1.0 Hz, 1H), 7.10-6.90 (m, 2H), 6.47 (d, J=0.9 Hz, 1H), 5.33 (s, 2H), 4.51 (s, 2H), 3.87 (s, 2H), 3.58 (s, 2H), 3.34 (d, J=4.7 Hz, 2H); ESI: m/z 523.2 (M+H)⁺.

Example 441

8-(1-aminoethyl)-1-((4-chloro-1H-indol-2-yl)methyl)-3-ethyl-7-methyl-1H-purine-2,6(3H,7H)-dione

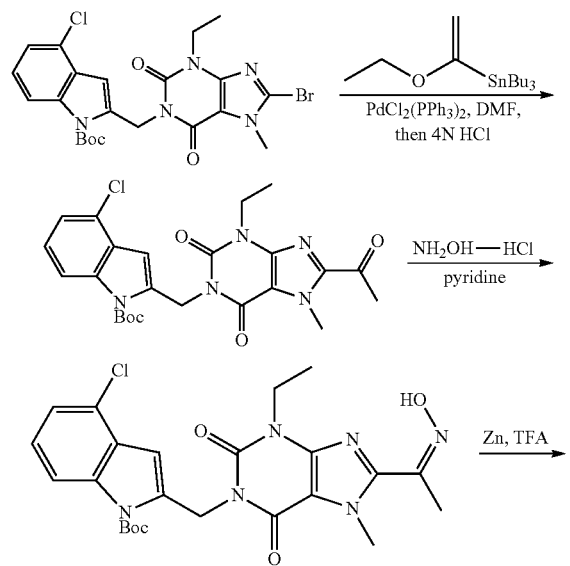

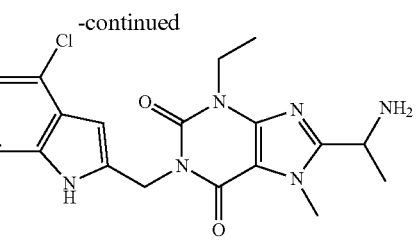

tert-Butyl 2-((8-acetyl-3-ethyl-7-methyl-2,6-dioxo-2,3,6,7-tetrahydro-1H-purin-1-yl)methyl)-4-chloro-1H-indole-1-carboxylate

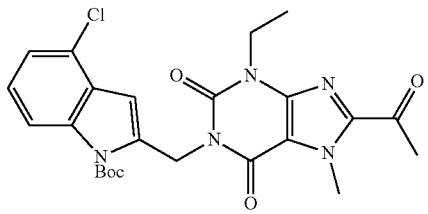 [SMILES: CCn1c(=O)n(Cc2cc3c(Cl)cccc3n2C(=O)OC(C)(C)C)c(=O)c2c1nc(C(C)=O)n2C]

To a solution of tert-butyl 2-((8-bromo-3-ethyl-7-methyl-2,6-dioxo-2,3,6,7-tetrahydro-1H-purin-1-yl)methyl)-4-chloro-1H-indole-1-carboxylate (0.24 mmol, 130 mg), in DMF (4 mL) was added tributyl(1-ethoxyvinyl)stannane (0.36 mmol, 96 mg) and PdCl₂(PPh₃)₂ (0.02 mmol, 14 mg). The reaction mixture was stirred at 75° C. for 5 h, then 4N HCl (2 mL) was added. The mixture was stirred at 75° C. for 1 h. After cooling to rt the mixture was diluted with sat. NaHCO₃ (20 mL). The solution was extracted with EA (30 mL*3) and the organic fractions were combined, washed with brine (30 mL), dried with Na₂SO₄ and concentrated to get the crude product, which was purified by flash chromatography (EA/PE=30%) to give the product; ESI: m/z 400.1 (M+H-100)⁺.

tert-Butyl 4-chloro-2-((3-ethyl-8-(1-(hydroxyimino)ethyl)-7-methyl-2,6-dioxo-2,3,6,7-tetrahydro-1H-purin-1-yl)methyl)-1H-indole-1-carboxylate

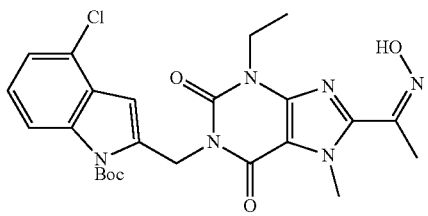 [SMILES: CCn1c(=O)n(Cc2cc3c(Cl)cccc3n2C(=O)OC(C)(C)C)c(=O)c2c1nc(/C(C)=N\O)n2C]

A solution of tert-butyl 2-((8-acetyl-3-ethyl-7-methyl-2,6-dioxo-2,3,6,7-tetrahydro-1H-purin-1-yl)methyl)-4-chloro-1H-indole-1-carboxylate (0.16 mmol, 80 mg) and NH₂OH·HCl (1.6 mmol, 110 mg) in pyridine (4 mL) was stirred at 50° C. for 12 h, then concentrated. The mixture was treated with water (20 mL) and extracted with EA (2*50 mL). The combined organic fractions were dried with Na₂SO₄, filtered and concentrated to give the crude product; ESI: m/z 415.2 (M+H-100)⁺.

411

8-(1-Aminoethyl)-1-((4-chloro-1H-indol-2-yl)methyl)-3-ethyl-7-methyl-1H-purine-2,6(3H,7H)-dione

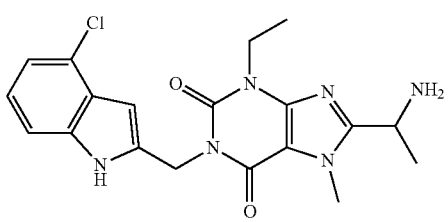 [SMILES: CCn1c(=O)n(Cc2cc3c(Cl)cccc3[nH]2)c(=O)c2c1nc(C(C)N)n2C]

To a solution of tert-butyl 4-chloro-2-((3-ethyl-8-(1-(hydroxyimino)ethyl)-7-methyl-2,6-dioxo-2,3,6,7-tetrahydro-1H-purin-1-yl)methyl)-1H-indole-1-carboxylate (0.078 mmol, 40 mg) in TFA (6 mL) was added zinc powder (1.56 mmol, 101 mg). The reaction mixture was stirred at 100° C. for 2 h, then filtered and the filtrate was purified by preparative HPLC using Method B. $^1$H NMR (400 MHz, MeOD): δ 7.17 (d, J=7.9 Hz, 1H), 6.95-6.77 (m, 2H), 6.31 (s, 1H), 5.20 (s, 2H), 4.47-4.43 (m, 1H), 4.08 (q, J=7.1 Hz, 2H), 3.89 (d, J=7.1 Hz, 3H), 1.46 (d, J=6.7 Hz, 3H), 1.22 (t, J=7.0 Hz, 3H); ESI: m/z 401.2 (M+H)$^+$.

Example 447

(R)-8-(1-amino-2-(pyridin-4-yl)ethyl)-1-((4-chloro-1H-indol-2-yl)methyl)-3,7-dimethyl-1H-purine-2,6(3H,7H)-dione

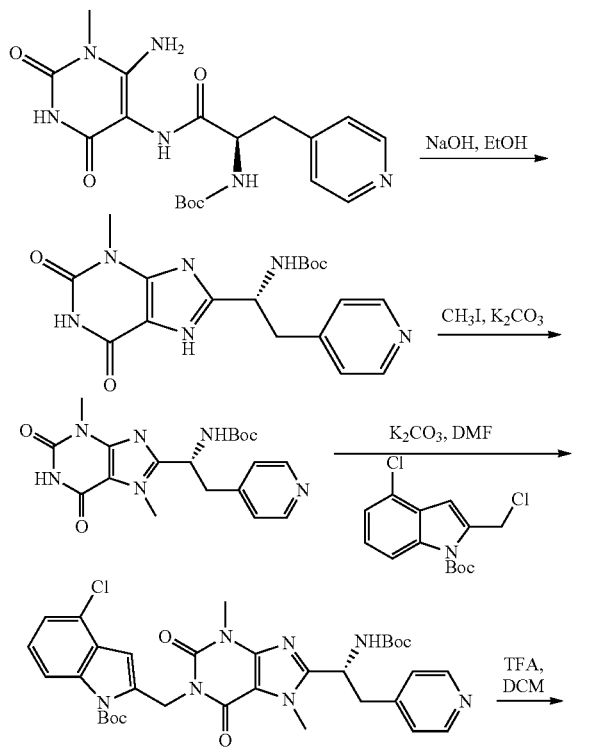

412

-continued

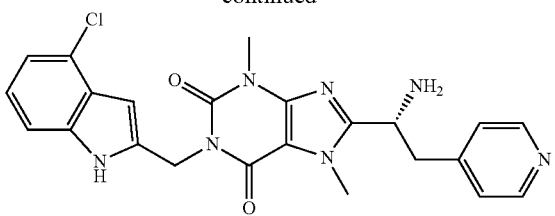

(R)-tert-Butyl 1-(6-amino-1-methyl-2,4-dioxo-1,2,3,4-tetrahydropyrimidin-5-ylamino)-1-oxo-3-(pyridin-4-yl)propan-2-ylcarbamate

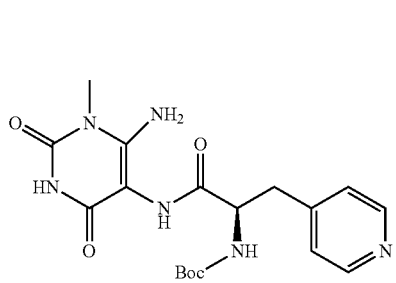 [SMILES: Cn1c(N)c(NC(=O)[C@@H](Cc2ccncc2)NC(=O)OC(C)(C)C)c(=O)[nH]c1=O]

To a mixture of (R)-2-(tert-butoxycarbonylamino)-3-(pyridin-4-yl)propanoic acid (2.0 mmol, 0.533 g) and 5,6-diamino-1-methylpyrimidine-2,4(1H,3H)-dione (2.0 mmol, 0.312 g) in DMF (15 mL) was added DCC (8.0 mmol, 1.70 g). The reaction mixture was stirred at 26° C. for 18 h under N$_2$ atmosphere. The reaction was concentrated and purified by flash chromatography (MeOH/EA=1/3) to give the product; ESI: m/z 405.2 (M+H)$^+$.

(R)-tert-Butyl 1-(3-methyl-2,6-dioxo-2,3,6,7-tetrahydro-1H-purin-8-yl)-2-(pyridin-4-yl)ethylcarbamate

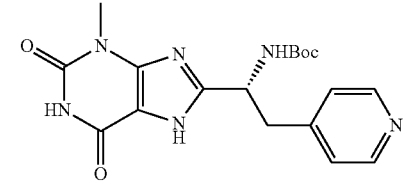 [SMILES: Cn1c(=O)[nH]c(=O)c2[nH]c([C@@H](Cc3ccncc3)NC(=O)OC(C)(C)C)nc21]

To a solution of (R)-tert-butyl 1-(6-amino-1-methyl-2,4-dioxo-1,2,3,4-tetrahydropyrimidin-5-ylamino)-1-oxo-3-(pyridin-4-yl)propan-2-ylcarbamate (2.5 mmol, 1.0 g) in EtOH (100 mL) was added NaOH (1.0 mol/L, 10.0 mmol, 10 mL). The mixture was heated to 50° C. and held for 16 h. The reaction mixture was concentrated to give the crude product, which was used directly in next step without further purification; ESI: m/z 387.2 (M+H)$^+$.

R)-tert-Butyl 1-(3,7-dimethyl-2,6-dioxo-2,3,6,7-tetrahydro-1H-purin-8-yl)-2-(pyridin-4-yl)ethylcarbamate

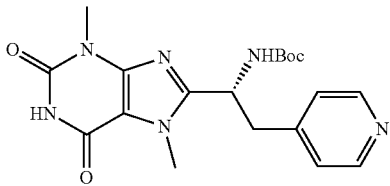 [SMILES: Cn1c([C@@H](Cc2ccncc2)NC(=O)OC(C)(C)C)nc2c1c(=O)[nH]c(=O)n2C]

To a solution of (R)-tert-butyl 1-(3-methyl-2, 6-dioxo-2, 3, 6, 7-tetrahydro-1H-purin-8-yl)-2-(pyridin-4-yl) ethylcarbamate (2.1 mmol, 0.80 g) in DMF (15 mL) was added $K_2CO_3$ (2.7 mmol, 0.37 g). After aging for 10 min, MeI (2.3 mmol, 0.32 g) was added dropwise. The reaction mixture was stirred at 26° C. for 1 h under $H_2$ atmosphere. The reaction mixture was filtered and the filtrate was concentrated and purified by flash chromatography (MeOH/EA=1/3) to give the product; ESI: m/z 401.2 $(M+H)^+$.

(R)-tert-Butyl 2-((8-(1-(tert-butoxycarbonylamino)-2-(pyridin-4-yl)ethyl)-3,7-dimethyl-2,6-dioxo-2,3-dihydro-6H-purin-1(7H)-yl)methyl)-4-chloro-1H-indole-1-carboxylate

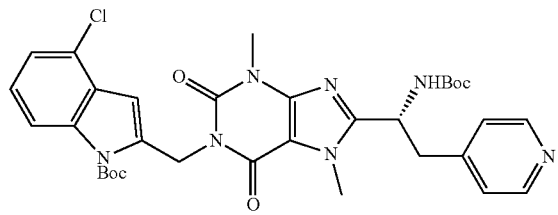 [SMILES: Cn1c([C@@H](Cc2ccncc2)NC(=O)OC(C)(C)C)nc2c1c(=O)n(Cc1cc3c(Cl)cccc3n1C(=O)OC(C)(C)C)c(=O)n2C]

To a solution of (R)-tert-butyl 1-(3,7-dimethyl-2,6-dioxo-2,3,6,7-tetrahydro-1H-purin-8-yl)-2-(pyridin-4-yl)ethylcarbamate (0.2 mmol, 80 mg), tert-butyl 4-chloro-2-(chloromethyl)-1H-indole-1-carboxylate (0.2 mmol, 60 mg) in DMF (5 mL) was added $K_2CO_3$ (0.3 mmol, 42 mg). The reaction mixture was heated to 50° C. and held for 5 h. The mixture was concentrated to give the crude product, which was used in next step without further purification; ESI: m/z 664.2 $(M+H)^+$.

(R)-8-(1-Amino-2-(pyridin-4-yl)ethyl)-1-((4-chloro-1H-indol-2-yl)methyl)-3,7-dimethyl-1H-purine-2,6(3H,7H)-dione

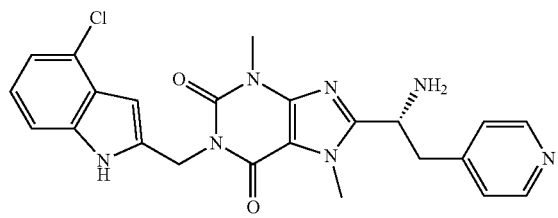 [SMILES: Cn1c([C@H](N)Cc2ccncc2)nc2c1c(=O)n(Cc1cc3c(Cl)cccc3[nH]1)c(=O)n2C]

(R)-tert-butyl 2-((8-(1-(tert-butoxycarbonylamino)-2-(pyridin-4-yl)ethyl)-3,7-dimethyl-2,6-dioxo-2,3-dihydro-6H-purin-1(7H)-yl)methyl)-4-chloro-1H-indole-1-carboxylate (0.2 mmol, 0.13 g) in DCM (5 mL) was added TFA (1 mL). The reaction mixture was stirred at 25° C. and held for 2 h. The reaction mixture was concentrated and purified by reversed phase column chromatography (C18, ACN/water ($NH_4HCO_3$)=40%) to give the title compound. $^1$H NMR (400 MHz, $CDCl_3$) δ 9.22 (s, 1H), 8.49-8.50 (m, 2H), 7.19-7.22 (m, 1H), 7.03-7.06 (m, 4H), 6.70 (s, 1H), 5.30 (s, 2H), 4.19-4.23 (t, J=7.2 Hz, 1H), 3.75 (s, 3H), 3.59 (s, 3H), 3.15-3.20 (dd, J=13.2 Hz, 7.2 Hz, 1H), 3.05-3.09 (dd, J=13.2 Hz, 7.2 Hz, 1H); ESI: m/z 464.2 $(M+H)^+$.

Example 448

8-(1-aminoethyl)-3,7-dimethyl-1-((5-methylnaphthalen-2-yl)methyl)-1H-purine-2,6(3H,7H)-dione

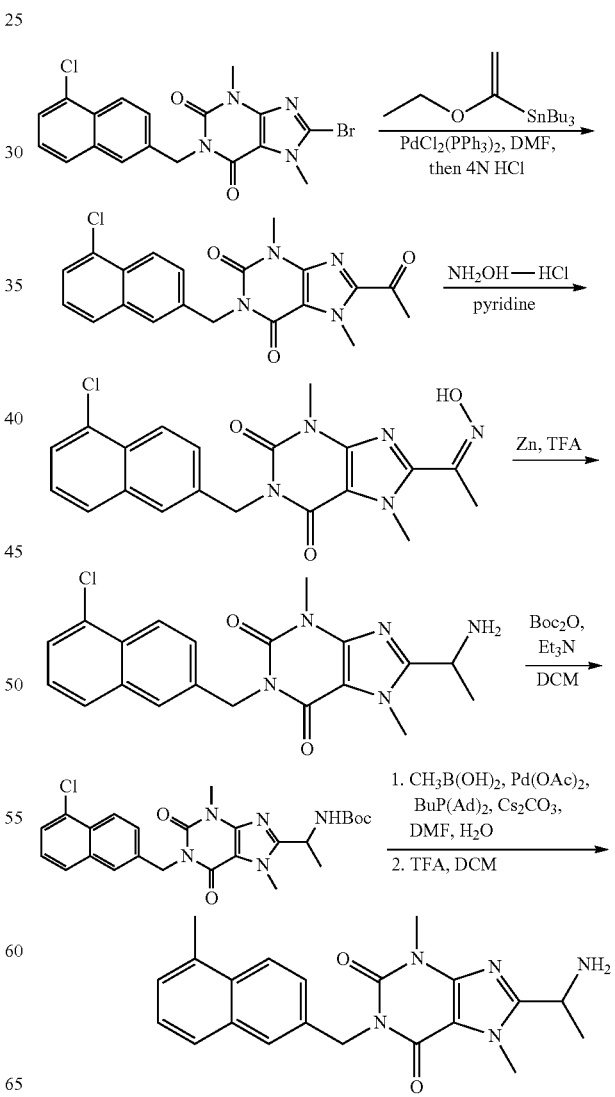

8-Acetyl-1-((5-chloronaphthalen-2-yl)methyl)-3,7-dimethyl-1H-purine-2,6(3H,7H)-dione

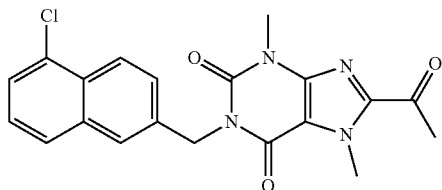 [SMILES: CC(=O)c1nc2c(c(=O)n(Cc3ccc4c(Cl)cccc4c3)c(=O)n2C)n1C]

To a solution of 8-bromo-1-((5-chloronaphthalen-2-yl)methyl)-3,7-dimethyl-1H-purine-2,6(3H,7H)-dione (0.92 mmol, 400 mg), in DMF (10 mL) was added tributyl(1-ethoxyvinyl)stannane (1.25 mmol, 452 mg) and PdCl$_2$(dppf) (0.01 mmol, 7 mg). The reaction mixture was stirred at 75° C. for 5 h. Then 4 N of HCl (2 mL) was added. It was stirred at 75° C. for 1 h. The mixture was diluted with sat. NaHCO$_3$ (20 mL). The solution was extracted with EA (30 mL*3). The organic fractions were combined, washed with brine (30 mL), dried with Na$_2$SO$_4$ and concentrated to get the crude product. It was purified by flash chromatography (PE/EA=1/1) to give the product; ESI: m/z 397.1 (M+H)$^+$.

1-((5-Chloronaphthalen-2-yl)methyl)-8-(1-(hydroxyimino)ethyl)-3,7-dimethyl-1H-purine-2,6(3H,7H)-dione

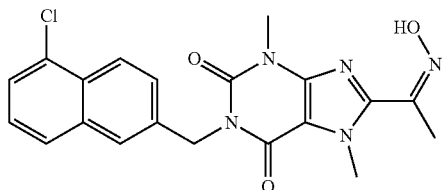 [SMILES: C/C(=N/O)c1nc2c(c(=O)n(Cc3ccc4c(Cl)cccc4c3)c(=O)n2C)n1C]

The solution of 8-acetyl-1-((5-chloronaphthalen-2-yl)methyl)-3,7-dimethyl-1H-purine-2,6(3H,7H)-dione (0.6 mmol, 240 mg) and NH$_2$OH·HCl (12 mmol, 840 mg) in pyridine (6 mL) was stirred at 50° C. for 12 h. The solution was diluted with water (30 mL). The solid was collected by filtration to get the crude product which was used for next step without further purification.

8-(1-Aminoethyl)-1-((5-chloronaphthalen-2-yl)methyl)-3,7-dimethyl-1H-purine-2,6(3H,7H)-dione

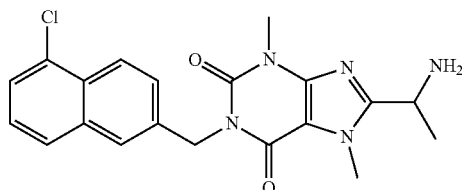

To a solution of 1-((5-chloronaphthalen-2-yl)methyl)-8-(1-(hydroxyimino)ethyl)-3,7-dimethyl-1H-purine-2,6(3H,7H)-dione (0.6 mmol, 247 mg) in TFA (6 mL) was added Zinc powder (12 mmol, 768 mg). The reaction mixture was stirred at 100° C. for 2 h. The reaction was concentrated. The residue wan diluted with EA (30 mL) and filtered. The organic layer was washed with sat. NaHCO$_3$ (15 mL), brine (15 mL), dried with Na$_2$SO$_4$ and concentrated to get the product; ESI: m/z 398.1 (M+H)$^+$.

tert-Butyl 1-(1-((5-chloronaphthalen-2-yl)methyl)-3,7-dimethyl-2,6-dioxo-2,3,6,7-tetrahydro-1H-purin-8-yl)ethylcarbamate

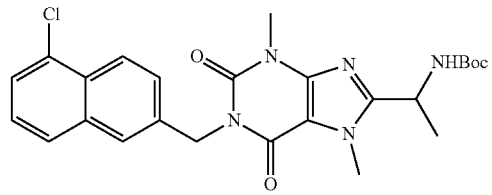 [SMILES: CC(NC(=O)OC(C)(C)C)c1nc2c(c(=O)n(Cc3ccc4c(Cl)cccc4c3)c(=O)n2C)n1C]

To a solution of 8-(1-aminoethyl)-1-((5-chloronaphthalen-2-yl)methyl)-3,7-dimethyl-1H-purine-2,6(3H,7H)-dione (0.52 mmol, 210 mg) and Et$_3$N (1.0 mmol, 101 mg) in DCM (20 mL) was added (Boc)$_2$O (0.75 mmol, 170 mg). The reaction mixture was stirred at 30° C. for 12 h. The reaction was concentrated and the crude product was purified by flash chromatography (PE/EA=1/1) to give the product; ESI: m/z 498.2 (M+H)$^+$.

8-(1-Aminoethyl)-3,7-dimethyl-1-((5-methylnaphthalen-2-yl)methyl)-1H-purine-2,6(3H,7H)-dione

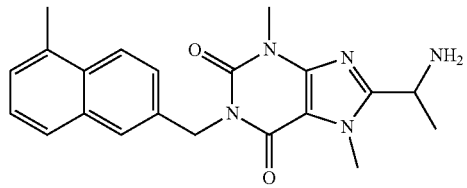 [SMILES: Cc1cccc2cc(Cn3c(=O)c4c(nc(C(C)N)n4C)n(C)c3=O)ccc12]

To a solution of tert-butyl 1-(1-((5-chloronaphthalen-2-yl)methyl)-3,7-dimethyl-2,6-dioxo-2,3,6,7-tetrahydro-1H-purin-8-yl)ethylcarbamate (0.06 mmol, 30 mg) in DMF/H$_2$O (3 mL/0.5 mL) was added methylboronic acid (1.2 mmol, 72 mg), Pd(OAc)$_2$ (0.006 mmol, 2.2 mg), n-BuP(Ad)$_2$ (0.012 mmol, 7.2 mg), and Cs$_2$CO$_3$ (0.18 mmol, 60 mg). The reaction mixture was stirred under N$_2$ at 100° C. for 12 h. Water (10 mL) was added and the solution was extracted with EA (10 mL*3). The organic layers were combined, washed with brine (30 mL), dried with Na$_2$SO$_4$ and concentrated to get tert-butyl 1-(3,7-dimethyl-1-((5-methylnaphthalen-2-yl)methyl)-2,6-dioxo-2,3,6,7-tetrahydro-1H-purin-8-yl)ethylcarbamate, which was used in the next step without further purification.

A solution of the product from above (0.06 mmol, 28 mg) in DCM/TFA (1 mL/1 mL) was stirred at 30° C. for 1 h. The solution was concentrated and the residue was purified by prep-HPLC using Method B. $^1$H NMR (400 MHz, CDCl$_3$) δ 7.85 (m, 2H), 7.60 (m, 2H), 7.24 (m, 1H), 7.19 (s, 1H), 5.29 (s, 2H), 4.13 (br s, 1H), 3.92 (s, 3H), 3.50 (s, 3H), 2.56 (s, 3H), 1.41 (d, J=6.8 Hz, 3H); ESI: m/z 378.2 (M+H)$^+$.

Example 449

(S)-8-(1-amino-2-(pyridin-4-yl)ethyl)-1-((4-chloro-1H-indol-2-yl)methyl)-3,7-dimethyl-1H-purine-2,6(3H,7H)-dione

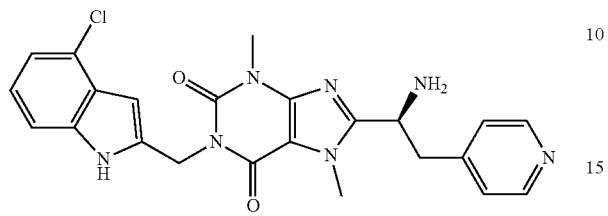

The title compound was synthesized according to the synthetic scheme and experimental conditions described for Example 447 using (S)-2-(tert-butoxycarbonylamino)-3-(pyridin-4-yl)propanoic acid. $^1$H NMR (400 MHz, CDCl$_3$): δ 9.15 (s, 1H), 8.51-8.50 (m, 2H), 7.24-7.20 (m, 1H), 7.08-7.03 (m, 4H), 6.71 (d, J=1.2 Hz, 1H), 5.33 (s, 2H), 4.21 (t, J=6.0 Hz, 1H), 3.17 (s, 3H), 3.60 (s, 3H), 3.21-3.05 (m, 2H); ESI: m/z 464.2 (M+H)$^+$.

Example 450

8-(1-amino-2-phenylethyl)-1-((4-chloro-1H-indol-2-yl)methyl)-3,7-dimethyl-1H-purine-2,6(3H,7H)-dione

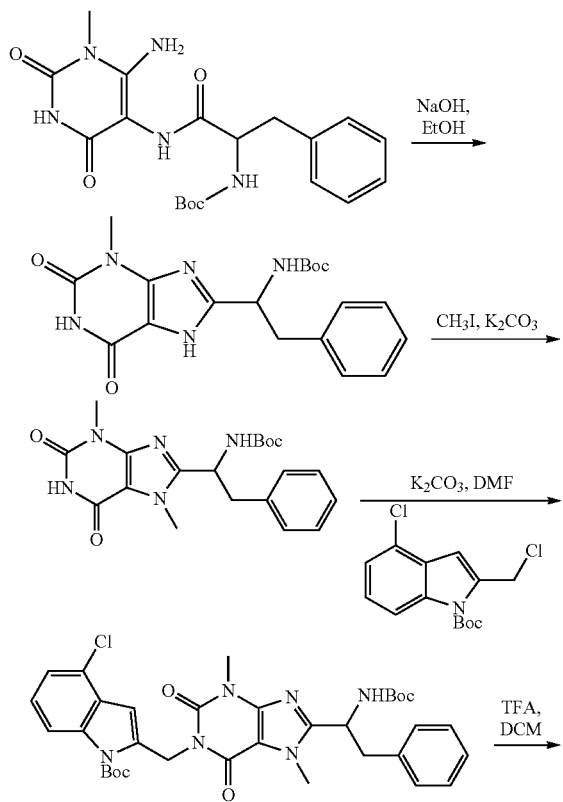

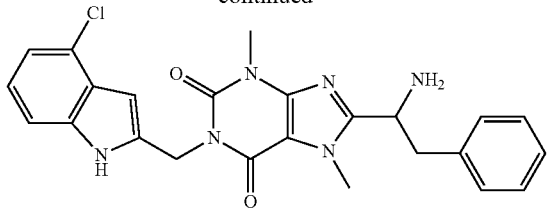

tert-Butyl 1-(5-amino-3-methyl-2,6-dioxo-1,2,3,6-tetrahydropyrimidin-4-ylamino)-1-oxo-3-phenylpropan-2-ylcarbamate The title compound was synthesized in a similar fashion as described in Example 447 using 2-(tert-butoxycarbonylamino)-3-phenylpropanoic acid; ESI: m/z 404.2 (M+H)$^+$.

tert-Butyl 1-(3-methyl-2,6-dioxo-2,3,6,7-tetrahydro-1H-purin-8-yl)-2-phenylethylcarbamate

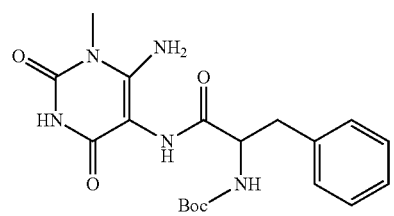 [SMILES: Cn1c(N)c(NC(=O)C(Cc2ccccc2)NC(=O)OC(C)(C)C)c(=O)[nH]c1=O]

The title compound was synthesized in a similar fashion as described in Example 447 step 1 using tert-butyl 1-(5-amino-3-methyl-2,6-dioxo-1,2,3,6-tetrahydropyrimidin-4-ylamino)-1-oxo-3-phenylpropan-2-ylcarbamate; ESI: m/z 386.0 (M+H)$^+$.

tert-Butyl 1-(3,7-dimethyl-2,6-dioxo-2,3,6,7-tetrahydro-1H-purin-8-yl)-2-phenylethylcarbamate

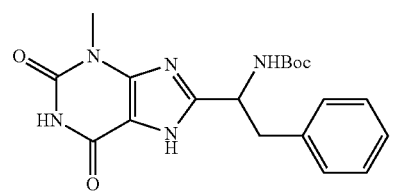

The title compound was synthesized in a similar fashiona as described in Example 447 step 2 using tert-butyl 1-(3-methyl-2,6-dioxo-2,3,6,7-tetrahydro-1H-purin-8-yl)-2-phenylethylcarbamate; ESI: m/z 400.2 (M+H)$^+$.

tert-Butyl 2-((8-(1-(tert-butoxycarbonylamino)-2-phenylethyl)-3,7-dimethyl-2,6-dioxo-2,3,6,7-tetrahydro-1H-purin-1-yl)methyl)-4-chloro-1H-indole-1-carboxylate

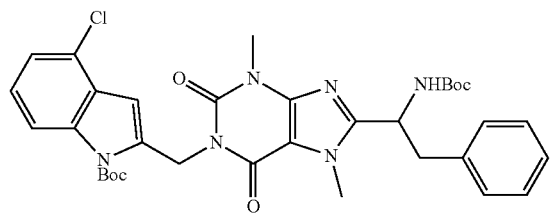 [SMILES: Cn1c(C(Cc2ccccc2)NC(=O)OC(C)(C)C)nc2c1c(=O)n(Cc1cc3c(Cl)cccc3n1C(=O)OC(C)(C)C)c(=O)n2C]

The title compound was synthesized in a similar fashion as described in Example 447 step 3 using tert-butyl 1-(3,7-dimethyl-2,6-dioxo-2,3,6,7-tetrahydro-1H-purin-8-yl)-2-phenylethylcarbamate.

8-(1-Amino-2-phenylethyl)-1-((4-chloro-1H-indol-2-yl)methyl)-3,7-dimethyl-1H-purine-2,6(3H,7H)-dione

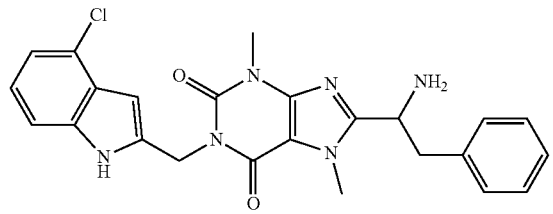 [SMILES: Cn1c(C(N)Cc2ccccc2)nc2c1c(=O)n(Cc1cc3c(Cl)cccc3[nH]1)c(=O)n2C]

The title compound was synthesized in a similar fashiona as described in Example 447 step 4 using tert-butyl 2-((8-(1-(tert-butoxycarbonylamino)-2-phenylethyl)-3,7-dimethyl-2,6-dioxo-2,3,6,7-tetrahydro-1H-purin-1-yl)methyl)-4-chloro-1H-indole-1-carboxylate. The product was purified by prep-HPLC using Method D. $^1$H NMR (400 MHz, CD$_3$OD) δ 7.20-7.29 (m, 4H), 6.42 (s, 1H), 5.29 (s, 2H), 3.62 (s, 3H), 3.44 (s, 3H), 3.19-3.24 (m, 1H), 3.05-3.11 (m, 1H); ESI: m/z 463.1 (M+H)$^+$.

Example 469

8-(2-(aminomethyl)pyrimidin-4-ylamino)-1-((4-chloro-1H-indol-2-yl)methyl)-3,7-dimethyl-1H-purine-2,6(3H,7H)-dione

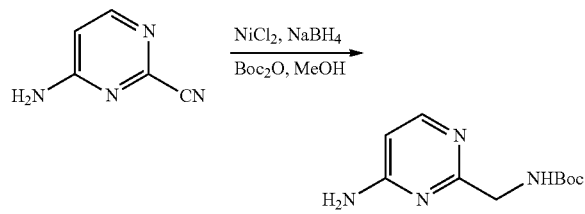

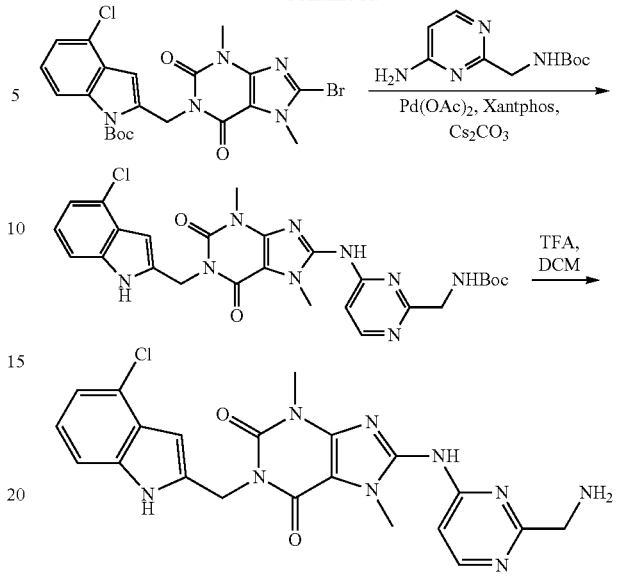

tert-Butyl (4-aminopyrimidin-2-yl)methylcarbamate

To a solution of 4-aminopyrimidine-2-carbonitrile (7.3 mmol, 0.88 g), NiCl$_2$ (1.5 mmol, 0.19 g), and (Boc)$_2$O (9 mmol, 2 g) in MeOH (5 mL) was added NaBH$_4$ (84 mmol, 3.2 g) at 0° C. This solution was stirred at 0° C. for 4 h. The solution was diluted with EA 200 mL and washed with water (3*100 mL). The organic fraction was dried with Na$_2$SO$_4$ and evaporated to dryness. The crude product was purified by flash chromatography (PE/EA=2/1) to give the product; ESI: m/z 225.2 (M+H)$^+$.

tert-butyl (4-(1-((4-chloro-1H-indol-2-yl)methyl)-3,7-dimethyl-2,6-dioxo-2,3,6,7-tetrahydro-1H-purin-8-ylamino)pyrimidin-2-yl)methylcarbamate

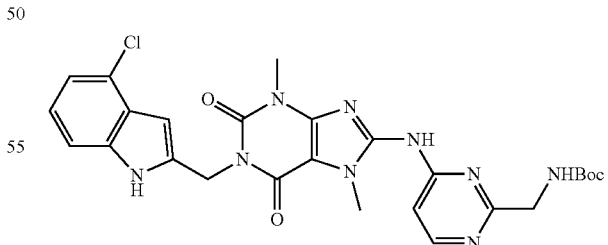

The title compound was synthesized in a similar fashion as described in Procedure 8a using tert-butyl (4-aminopyrimidin-2-yl)methylcarbamate and tert-butyl 2-((8-bromo-3,7-dimethyl-2,6-dioxo-2,3-dihydro-6H-purin-1(7H)-yl)methyl)-4-chloro-1H-indole-1-carboxylate. The crude product was purified by flash chromatography (DCM/MeOH=30/1); ESI: m/z 566.2 (M+H)$^+$.

421

8-(2-(Aminomethyl)pyrimidin-4-ylamino)-1-((4-chloro-1H-indol-2-yl)methyl)-3,7-dimethyl-1H-purine-2,6(3H,7H)-dione

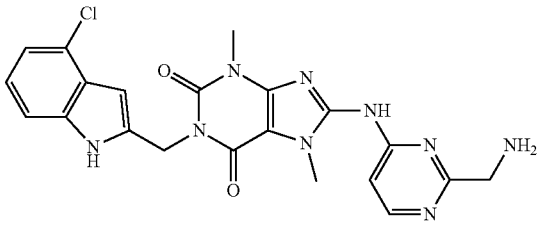 [SMILES: Cn1c(Nc2ccnc(CN)n2)nc2c1c(=O)n(Cc1cc3c(Cl)cccc3[nH]1)c(=O)n2C]

To a solution of tert-butyl (4-(1-((4-chloro-1H-indol-2-yl)methyl)-3,7-dimethyl-2,6-dioxo-2,3,6,7-tetrahydro-1H-purin-8-ylamino)pyrimidin-2-yl)methylcarbamate (0.09 mmol, 0.050 g), TFA (1 mL) in DMF (2 mL). The reaction mixture was stirred at room temperature for 2 h and concentrated to dryness. The crude product was purified by Prep-HPLC using Method D. $^1$H NMR (400 MHz, d$_6$-DMSO) δ 11.28 (s, 1H), 7.32-7.34 (m, 2H), 7.02-7.00 (m, 3H), 6.27 (s, 1H), 5.20 (s, 2H), 3.74-3.83 (m, 5H), 3.49 (s, 3H); ESI: m/z 466.1 (M+H)$^+$.

Example 451

N-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide

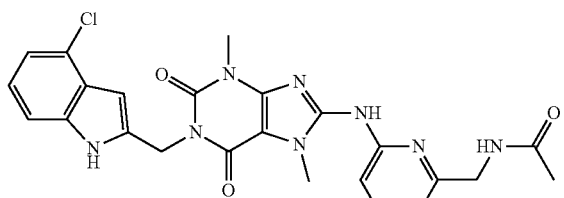

A solution of 8-(2-(aminomethyl)pyrimidin-4-ylamino)-1-((4-chloro-1H-indol-2-yl)methyl)-3,7-dimethyl-1H-purine-2,6(3H,7H)-dione (0.04 mmol, 0.020 g), Et$_3$N (0.01 mmol, 0.0013 g), and Ac$_2$O (0.04 mmol, 0.0044 g), in DCM (2 mL) was stirred at 0° C. for 2 h. The solution was evaporated to dryness and purified by Prep-HPLC using Method D. $^1$H NMR (400 MHz, CD$_3$OD) δ 8.44-8.43 (m, 1H), 7.64-7.62 (m, 1H), 7.28 (d, J=7.8 Hz, 1H), 7.04-6.96 (m, 2H), 6.46 (s, 1H), 5.36 (s, 2H), 4.45 (s, 2H), 3.88 (s, 3H), 3.59 (s, 3H), 2.00 (s, 3H); ESI: m/z 508.1 (M+H)$^+$.

Example 452

8-(1-aminoethyl)-1-((5-cyclopropylnaphthalen-2-yl)methyl)-3,7-dimethyl-1H-purine-2,6(3H,7H)-dione

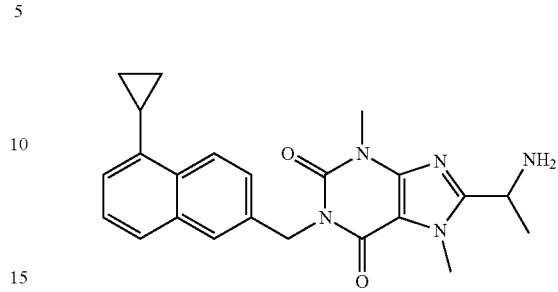

To a solution of tert-butyl 1-(1-((5-chloronaphthalen-2-yl)methyl)-3,7-dimethyl-2,6-dioxo-2,3,6,7-tetrahydro-1H-purin-8-yl)ethylcarbamate (0.06 mmol, 30 mg) in DMF/H$_2$O (3 mL/0.5 mL) was added cyclopropylboronic acid (1.2 mmol, 103 mg), Pd(OAc)$_2$ (0.006 mmol, 2.2 mg), n-BuP(Ad)$_2$ (0.012 mmol, 7.2 mg), and Cs$_2$CO$_3$ (0.18 mmol, 60 mg). The reaction mixture was stirred under N$_2$ at 100° C. for 12 h. Water (10 mL) was added and the solution was extracted with EA (10 mL*3). The organic fractions were combined, washed with brine (30 mL), dried with Na$_2$SO$_4$ and concentrated to get the crude tert-butyl 1-(1-((5-cyclopropylnaphthalen-2-yl)methyl)-3,7-dimethyl-2,6-dioxo-2,3,6,7-tetrahydro-1H-purin-8-yl)ethylcarbamate, which was used for next step without further purification. A solution of this product (0.06 mmol, 30 mg) in DCM/TFA (1 mL/1 mL) was stirred at 30° C. for 1 h. The solution was concentrated. The residue was purified by prep-HPLC using Method B to give the title compound: $^1$H NMR (400 MHz, CDCl$_3$) δ 8.26 (d, J=7.2 Hz, 1H). 7.85 (s, 1H), 7.59 (m, 2H), 7.24 (t, J=8.0 Hz 1H), 7.12 (m, 1H), 5.29 (s, 2H), 4.12 (m, 1H), 3.92 (s, 3H), 3.50 (s, 3H), 2.21 (m, 1H), 1.41 (d, J=6.8 Hz, 3H), 0.94 (m, 2H), 0.64 (m, 2H); ESI: m/z 404.2 (M+H)$^+$.

Example 459

8-(1-aminoethyl)-3-ethyl-7-methyl-1-((5-methylnaphthalen-2-yl)methyl)-1H-purine-2,6(3H,7H)-dione

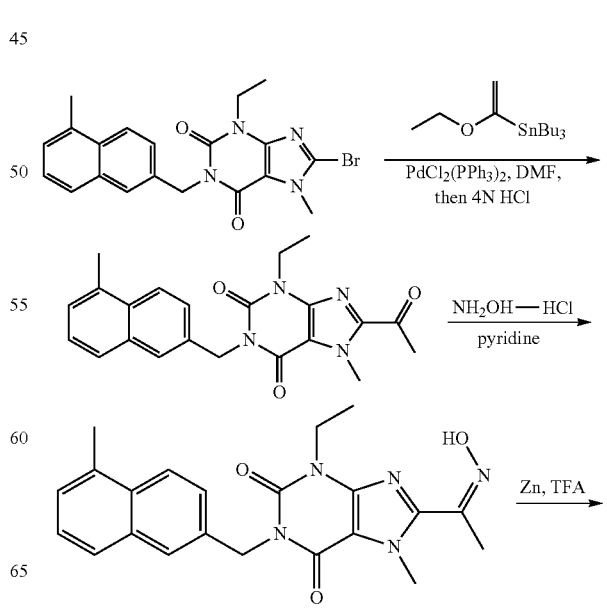

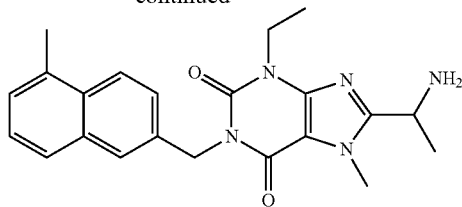

8-Acetyl-3-ethyl-7-methyl-1-((5-methylnaphthalen-2-yl)methyl)-1H-purine-2,6(3H,7H)-dione

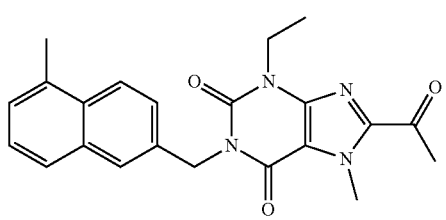 [SMILES: CCn1c(=O)n(Cc2ccc3c(C)cccc3c2)c(=O)c2c1nc(C(C)=O)n2C]

The title compound was synthesized in a similar fashion as described in Example 441 step 1 using 8-bromo-3-ethyl-7-methyl-1-((5-methylnaphthalen-2-yl)methyl)-1H-purine-2,6(3H,7H)-dione. The product was purified by flash chromatography (EA/PE=35%) to give the title compound; ESI: m/z 391.2 (M+H)⁺.

3-Ethyl-8-(1-(hydroxyimino)ethyl)-7-methyl-1-((5-methylnaphthalen-2-yl)methyl)-1H-purine-2,6(3H,7H)-dione

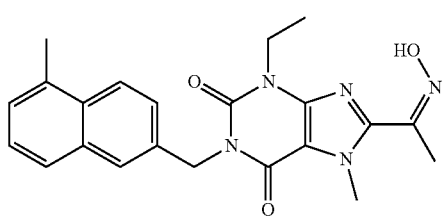 [SMILES: CCn1c(=O)n(Cc2ccc3c(C)cccc3c2)c(=O)c2c1nc(/C(C)=N\O)n2C]

The title compound was synthesized in a similar fashion as described in Example 441 step 2 using 8-acetyl-3-ethyl-7-methyl-1-((5-methylnaphthalen-2-yl)methyl)-1H-purine-2,6(3H,7H)-dione; ESI: m/z 406 (M+H)⁺.

8-(1-Aminoethyl)-3-ethyl-7-methyl-1-((5-methylnaphthalen-2-yl)methyl)-1H-purine-2,6(3H,7H)-dione

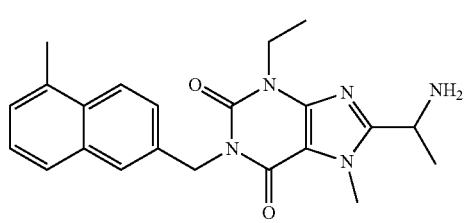 [SMILES: CCn1c(=O)n(Cc2ccc3c(C)cccc3c2)c(=O)c2c1nc(C(C)N)n2C]

The title compound was synthesized in a similar fashion as described in Example 441 step 3 using 3-ethyl-8-(1-(hydroxyimino)ethyl)-7-methyl-1-((5-methylnaphthalen-2-yl)methyl)-1H-purine-2,6(3H,7H)-dione. The product was purified by prep-HPLC using Method B: ¹H NMR (400 MHz, CD₃OD): δ 7.96 (d, J=8.7 Hz, 1H), 7.79 (s, 1H), 7.64 (d, J=8.1 Hz, 1H), 7.56 (dd, J=8.7, 1.8 Hz, 1H), 7.32 (dt, J=14.7, 7.0 Hz, 2H), 5.35 (d, J=8.9 Hz, 2H), 4.32 (d, J=6.7 Hz, 1H), 4.19 (q, J=7.1 Hz, 2H), 2.66 (s, 3H), 1.51 (d, J=6.7 Hz, 3H), 1.33 (t, J=7.1 Hz, 3H); ESI: m/z 392.2 (M+H)⁺.

Example 460

1-((1H-pyrrolo[3,2-c]pyridin-2-yl)methyl)-3,7-dimethyl-8-(pyridin-4-ylamino)-1H-purine-2,6(3H,7H)-dione

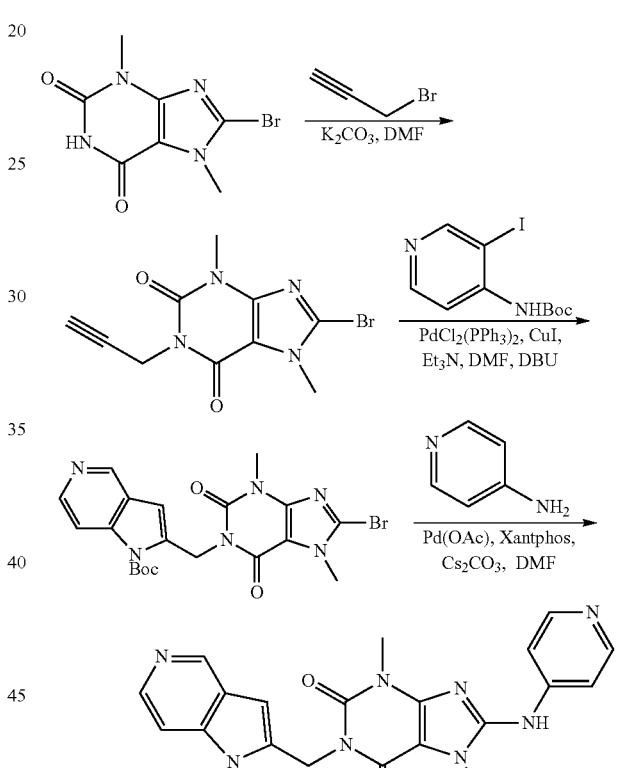

8-Bromo-3,7-dimethyl-1-(prop-2-ynyl)-1H-purine-2,6(3H,7H)-dione

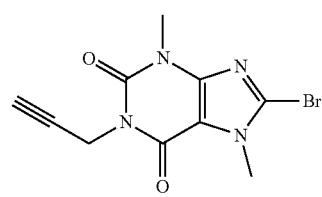 [SMILES: C#CCn1c(=O)c2c(nc(Br)n2C)n(C)c1=O]

A solution of 8-bromo-3,7-dimethyl-1H-purine-2,6(3H,7H)-dione (1.0 g, 3.87 mmol), propargyl chloride (288 mg, 3.87 mmol) and K₂CO₃ (1.60 g, 11.61 mmol) in DMSO (15 mL) was stirred at rt for 2 h. The solid was collected by filtration. The solid was washed with water and dried to give the product; ESI: m/z 299.0 (M+H)⁺.

tert-Butyl 2-((8-bromo-3,7-dimethyl-2,6-dioxo-2,3, 6,7-tetrahydro-1H-purin-1-yl)methyl)-1H-pyrrolo[3, 2-c]pyridine-1-carboxylate

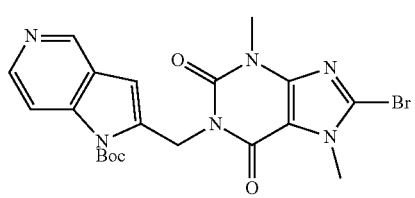 [SMILES: Cn1c(Br)nc2c1c(=O)n(Cc1cc3cnccc3n1C(=O)OC(C)(C)C)c(=O)n2C]

To a solution of tert-butyl 3-iodopyridin-4-ylcarbamate (800 mg, 2.5 mmol) in DMF (3 mL) was added 8-bromo-3,7-dimethyl-1-(prop-2-ynyl)-1H-purine-2,6(3H,7H)-dione (962 mg, 3.25 mmol), Et₃N (760 mg, 7.5 mmol), PdCl₂ (PPh₃)₂ (35 mg, 0.05 mmol), and CuI (24 mg, 0.125 mmol). The mixture was stirred at 55° C. for 3 h. Then DBU (500 mg, 3.28 mmol) was added and the mixture was stirred at 55° C. for 2 h. The mixture was cooled, quenched with water (20 mL) and extracted with EA (3*15 mL). The combined organic fractions were dried with Na₂SO₄, filtered and purified by flash chromatography (DCM/MeOH=5/1) to give the product; ESI: m/z 489.1 (M+H)⁺.

1-((1H-Pyrrolo[3,2-c]pyridin-2-yl)methyl)-3,7-dimethyl-8-(pyridin-4-ylamino)-1H-purine-2,6(3H,7H)-dione

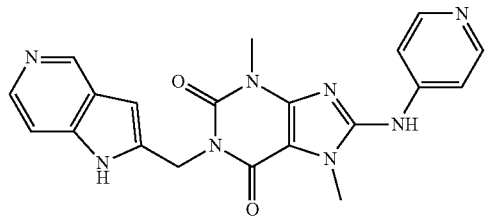 [SMILES: Cn1c(Nc2ccncc2)nc2c1c(=O)n(Cc1cc3cnccc3[nH]1)c(=O)n2C]

The title compound was synthesized in a similar fashion as described in Procedure 8A using tert-butyl 2-((8-bromo-3,7-dimethyl-2,6-dioxo-2,3,6,7-tetrahydro-1H-purin-1-yl) methyl)-1H-pyrrolo[3,2-c]pyridine-1-carboxylate and pyridin-4-amine hydrochloride. The product was purified by preparative HPLC using method D: ¹H NMR (400 MHz, CD₃OD) δ 8.58 (s, 1H), 8.23 (d, J=5.8 Hz, 2H), 7.98 (d, J=5.9 Hz, 1H), 7.63 (s, 2H), 7.28 (d, J=5.9 Hz, 1H), 6.47 (s, 1H), 5.24 (s, 2H), 4.49 (s, 2H), 3.80 (s, 3H), 3.49 (s, 3H); ESI: m/z 403.1 (M+H)⁺.

Example 461

8-(amino(pyridin-4-yl)methyl)-1-((4-chloro-1H-indol-2-yl)methyl)-3,7-dimethyl-1H-purine-2,6(3H, 7H)-dione

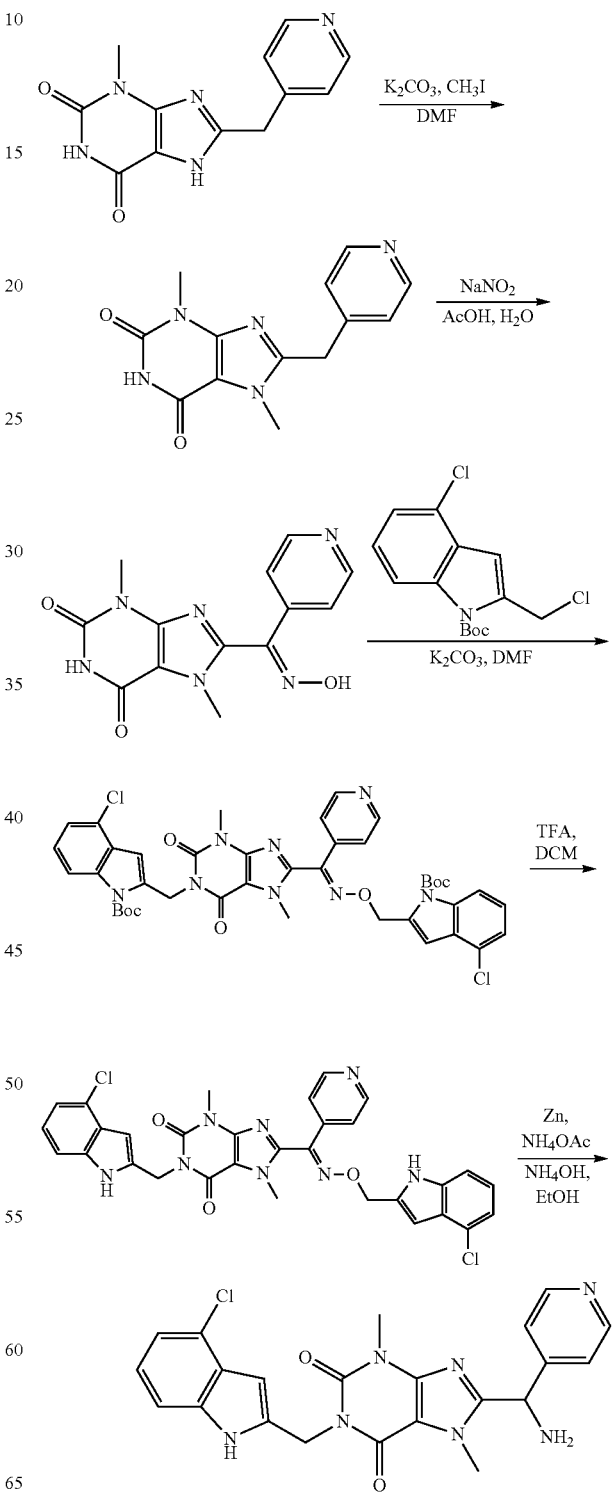

427

3,7-Dimethyl-8-(pyridin-4-ylmethyl)-1H-purine-2,6(3H,7H)-dione

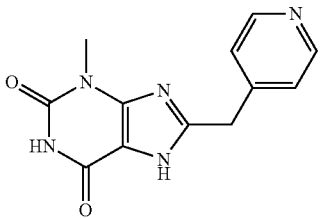 [SMILES: Cn1c(=O)[nH]c(=O)c2[nH]c(Cc3ccncc3)nc21]

A mixture of 2-(pyridin-4-yl)acetic acid (2.33 g, 13.45 mmol), HATU (5.11 g, 13.45 mmol) and DIEA (4.97 g, 38.43 mmol) in DMF (40 mL) was stirred for 20 min at 25° C. Then 5,6-diamino-1-methylpyrimidine-2,4(1H,3H)-dione (2.0 g, 12.81 mmol) was added and stirred for 16 h. The precipitate was collected. The residue and NaOH aqueous (30 mL, 3M) in EtOH (100 mL) was heated to reflux and stirred for 3 h. The reaction mixture was cooled to 28° C. and concentrated. The pH of the mixture was neutralized with concentrated HCl to PH=8~9. The precipitate was collected and dried in vacuo to afford the product; ESI: m/z 258.1 (M+H)$^+$.

3,7-Dimethyl-8-(pyridin-4-ylmethyl)-1H-purine-2,6(3H,7H)-dione

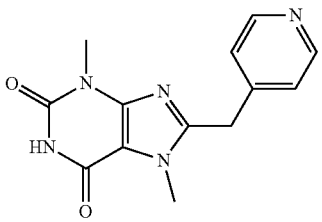 [SMILES: Cn1c(Cc2ccncc2)nc2c1c(=O)[nH]c(=O)n2C]

A mixture of 3-methyl-8-(pyridin-4-ylmethyl)-1H-purine-2,6(3H,7H)-dione (1.0 g, 3.89 mmol) and K$_2$CO$_3$ (806 mg, 5.84 mmol) in DMF (20 mL) was stirred for 20 min at 25° C. and MeI (552 mg, 3.89 mmol) was added. The resulting mixture was stirred for 16 h at 25° C. The reaction mixture was purified by reverse flash chromatography (C18, 0~40% MeOH in H$_2$O (10 mM NH$_4$HCO$_3$) to obtain the product. ESI: m/z 272.1 (M+H)$^+$.

8-((Hydroxyimino)(pyridin-4-yl)methyl)-3,7-dimethyl-1H-purine-2,6(3H,7H)-dione

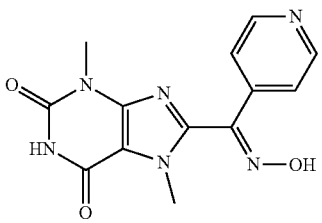 [SMILES: Cn1c(/C(=N/O)c2ccncc2)nc2c1c(=O)[nH]c(=O)n2C]

428

To a suspension of 3,7-dimethyl-8-(pyridin-4-ylmethyl)-1H-purine-2,6(3H,7H)-dione (330 mg, 1.22 mmol) in AcOH (6 mL) was added dropwise a solution of NaNO$_2$ (252 mg, 3.66 mmol) in H$_2$O (1 mL) at 5° C. The mixture was stirred for 4 h at 25° C. The reaction mixture was concentrated and the pH was adjusted with NaHCO$_3$ aq. to pH=8~9 at 0° C. The precipitate was collected and dried in vacuo to afford the product as a light brown solid, which was purified by preparative HPLC using Method E (20-80% ACN); ESI: m/z 301.1 (M+H)$^+$.

tert-Butyl 2-((8-(((1-(tert-butoxycarbonyl)-4-chloro-1H-indol-2-yl)methoxyimino)(pyridin-4-yl)methyl)-3,7-dimethyl-2,6-dioxo-2,3,6,7-tetrahydro-1H-purin-1-yl)methyl)-4-chloro-1H-indole-1-carboxylate

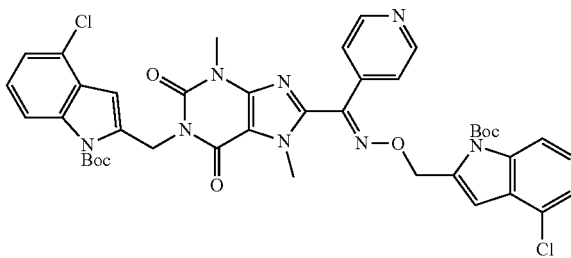

A mixture of 8-((hydroxyimino)(pyridin-4-yl)methyl)-3,7-dimethyl-1H-purine-2,6(3H,7H)-dione (54 mg, 0.18 mmol), tert-butyl 4-chloro-2-(chloromethyl)-1H-indole-1-carboxylate (54 mg, 0.18 mmol) and K$_2$CO$_3$ (62 mg, 0.45 mmol) in DMF (2 mL) was heated to 50° C. and stirred for 1 h. The reaction mixture was poured into water (30 mL) and extracted with EtOAc (2*30 mL). The combined organic fractions were washed with water (3*50 mL) and brine (1*50 mL), dried over Na$_2$SO$_4$, concentrated and concentrated in vacuo to afford the product; ESI: m/z 827.2 (M+H)$^+$.

8-(((4-Chloro-1H-indol-2-yl)methoxyimino)(pyridin-4-yl)methyl)-1-((4-chloro-1H-indol-2-yl)methyl)-3,7-dimethyl-1H-purine-2,6(3H,7H)-dione

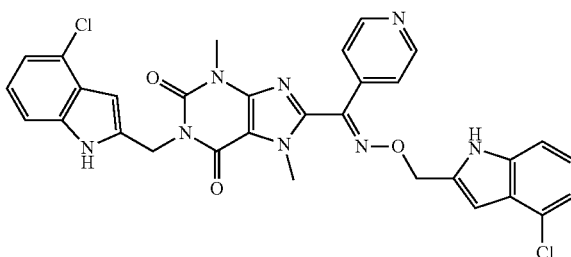

A mixture of tert-butyl 2-((8-(((1-(tert-butoxycarbonyl)-4-chloro-1H-indol-2-yl)methoxyimino)(pyridin-4-yl)methyl)-3,7-dimethyl-2,6-dioxo-2,3,6,7-tetrahydro-1H-purin-1-yl)methyl)-4-chloro-1H-indole-1-carboxylate (85 mg, 0.103 mmol) in TFA (0.7 mL) and DCM (2 mL) was stirred for 2 h at 25° C. The reaction mixture was concentrated, the pH was adjusted with NaHCO$_3$ aq. to PH=8~9 at 0° C. The mixture was extracted with EtOAc (2*20 mL). The com- 8-(Amino(pyridin-4-yl)methyl)-1-((4-chloro-1H-indol-2-yl)methyl)-3,7-dimethyl-1H-purine-2,6(3H,7H)-dione

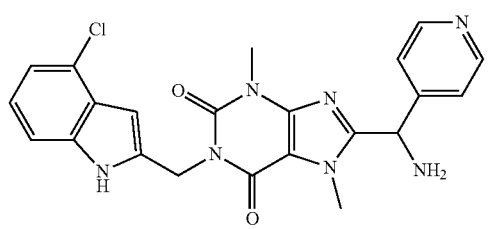 [SMILES: Cn1c(C(N)c2ccncc2)nc2c1c(=O)n(Cc1cc3c(Cl)cccc3[nH]1)c(=O)n2C]

A mixture of 8-((((4-chloro-1H-indol-2-yl)methoxyimino)(pyridin-4-yl)methyl)-1-((4-chloro-1H-indol-2-yl)methyl)-3,7-dimethyl-1H-purine-2,6(3H,7H)-dione (65 mg, 0.103 mmol), Zn dust (268 mg, 4.12 mmol), NH₄OAc (238 mg, 3.09 mmol), NH₄OH (1 mL, 25%) in EtOH (4 mL) was heated to reflux and stirred for 1 h. The reaction mixture was diluted in EtOAc (20 mL) and filtered. The filtrate was poured into water (30 mL) and extracted with EtOAc (2*20 mL). The combined organic fractions were washed with brine (1*50 mL), dried over $Na_2SO_4$, concentrated and purified by flash chromatography (10% MeOH/DCM) to give the title compound. ¹H NMR (400 MHz, CDCl₃) δ 9.14 (s, 1H), 8.62-8.58 (m, 2H), 7.26-7.18 (m, 3H), 7.06-7.04 (m, 2H), 6.70 (d, J=1.6 Hz, 1H), 5.31 (s, 2H), 5.22 (s, 1H), 3.84 (s, 3H), 3.62 (s, 3H), 1.60 (s, 2H); ESI: m/z 450.2 (M+H)⁺.

Example 462

1-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)urea

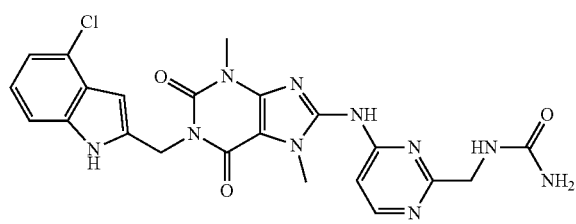 [SMILES: Cn1c(Nc2ccnc(CNC(N)=O)n2)nc2c1c(=O)n(Cc1cc3c(Cl)cccc3[nH]1)c(=O)n2C]

A solution of 8-(2-(aminomethyl)pyrimidin-4-ylamino)-1-((4-chloro-1H-indol-2-yl)methyl)-3,7-dimethyl-1H-purine-2,6(3H,7H)-dione (0.1 mmol, 0.05 g) and KCNO (0.5 mmol, 0.044 g) in CH₃COOH (0.1 mmol) and H₂O (5 mL) was stirred at 80° C. for 2 h. The reaction mixture was filtered. The filter cake was purified by Prep-HPLC using Method D. ¹H NMR (400 MHz, DMSO-d₆) δ 10.59 (s, 1H), 8.49 (s, 1H), 7.59 (s, 1H), 7.08-6.94 (m, 2H), 6.38 (s, 1H), 6.28 (s, 1H), 5.66 (s, 2H), 5.22 (s, 2H), 4.26 (d, J=5.5 Hz, 2H), 3.81 (s, 3H), 3.46 (s, 3H). ESI: m/z 509.1 (M+H)⁺.

Example 463

8-(1-aminoethyl)-1-((5-ethylnaphthalen-2-yl)methyl)-3,7-dimethyl-1H-purine-2,6(3H,7H)-dione

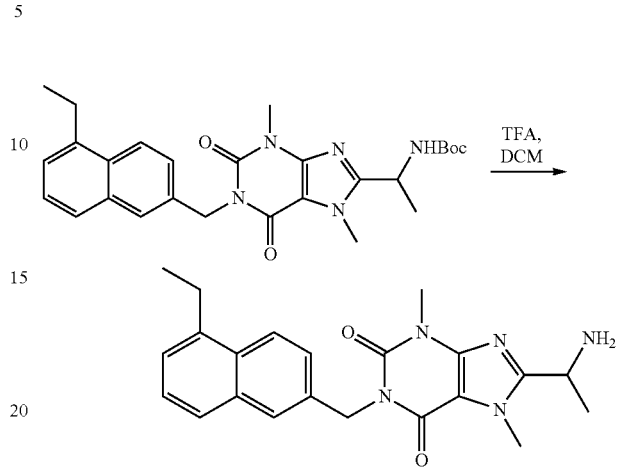

tert-Butyl 1-(1-((5-ethylnaphthalen-2-yl)methyl)-3,7-dimethyl-2,6-dioxo-2,3,6,7-tetrahydro-1H-purin-8-yl)ethylcarbamate

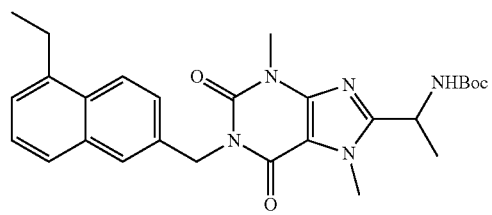 [SMILES: CCc1cccc2cc(Cn3c(=O)c4c(nc(C(C)NC(=O)OC(C)(C)C)n4C)n(C)c3=O)ccc12]

To a solution of tert-butyl 1-(1-((5-chloronaphthalen-2-yl)methyl)-3,7-dimethyl-2,6-dioxo-2,3,6,7-tetrahydro-1H-purin-8-yl)ethylcarbamate (0.06 mmol, 30 mg) in DMF/H₂O (3 mL/0.5 mL) was added ethylboronic acid (1.2 mmol, 89 mg), Pd(OAc)₂ (0.006 mmol, 2.2 mg), n-BuP(Ad)₂ (0.012 mmol, 7.2 mg), and Cs₂CO₃ (0.18 mmol, 60 mg). The reaction mixture was stirred under N₂ at 100° C. for 12 h. Water (10 mL) was added and the solution was extracted with EA (10 mL*3). The organic fractions were combined, washed with brine (30 mL), dried with Na₂SO₄ and concentrated to get the crude product, which was used for next step without further purification.

8-(1-Aminoethyl)-1-((5-ethylnaphthalen-2-yl)methyl)-3,7-dimethyl-1H-purine-2,6(3H,7H)-dione

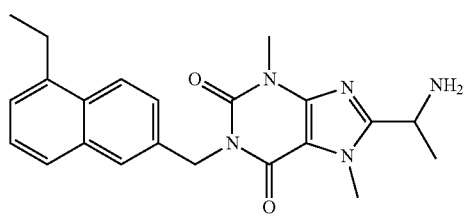 [SMILES: CCc1cccc2cc(Cn3c(=O)c4c(nc(C(C)N)n4C)n(C)c3=O)ccc12]

A solution of tert-butyl 1-(1-((5-ethylnaphthalen-2-yl)methyl)-3,7-dimethyl-2,6-dioxo-2,3,6,7-tetrahydro-1H-purin-8-yl)ethylcarbamate (0.06 mmol, 29 mg) in DCM/TFA (1 mL/1 mL) was stirred at 30° C. for 1 h. The solution was concentrated. The residue was purified by prep-HPLC using Method B. $^1$H NMR (400 MHz, CDCl$_3$) δ 7.90 (d, J=8.8 Hz, 1H). 7.85 (s, 1H), 7.56 (m, 2H), 7.27 (m, 1H), 7.20 (m, 1H), 5.28 (s, 2H), 4.13 (s, 1H), 3.98 (s, 3H), 3.50 (s, 3H), 2.97 (q, J=7.6 Hz, 1H), 1.41 (d, J=6.8 Hz, 3H), 1.25 (t, J=7.6 Hz, 3H); ESI: m/z 392.2 (M+H)$^+$.

Example 465

8-[1-amino-3-hydroxy-2-(hydroxymethyl)propyl]-1-[(4-chloro-1H-indol-2-yl)methyl]-3,7-dimethyl-purine-2,6-dione

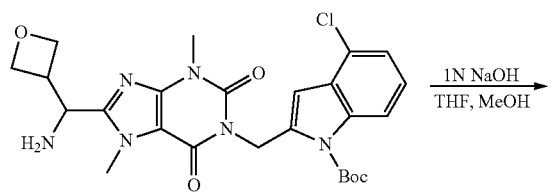

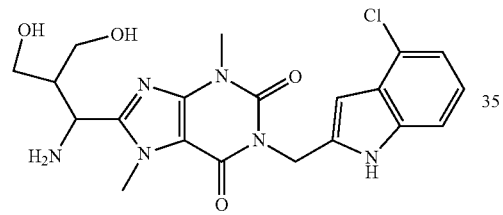

tert-butyl 2-[[8-[amino(oxetan-3-yl)methyl]-3,7-dimethyl-2,6-dioxo-purin-1-yl]methyl]-4-chloro-indole-1-carboxylate

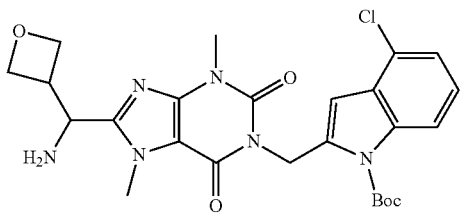 [SMILES: Cn1c(C(N)C2COC2)nc2c1c(=O)n(Cc1cc3c(Cl)cccc3n1C(=O)OC(C)(C)C)c(=O)n2C]

To a solution of tert-butyl 2-[[8-[(tert-butoxycarbonylamino)-(oxetan-3-yl)methyl]-3,7-dimethyl-2,6-dioxo-purin-1-yl]methyl]-4-chloro-indole-1-carboxylate (100.00 mg, 158.96 umol) in 4N HCl/MeOH (2.00 mL). The mixture was stirred at 25° C. for 3 h. The mixture was concentrated to give crude tert-butyl 2-[[8-[amino(oxetan-3-yl)methyl]-3,7-dimethyl-2,6-dioxo-purin-1-yl]methyl]-4-chloro-indole-1-carboxylate, which was used in next step without further purification.

8-[1-amino-3-hydroxy-2-(hydroxymethyl)propyl]-1-[(4-chloro-1H-indol-2-yl)methyl]-3,7-dimethyl-purine-2,6-dione

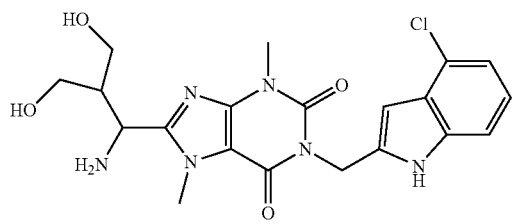 [SMILES: Cn1c(C(N)C(CO)CO)nc2c1c(=O)n(Cc1cc3c(Cl)cccc3[nH]1)c(=O)n2C]

To a solution of tert-butyl 2-[[8-[amino(oxetan-3-yl)methyl]-3,7-dimethyl-2,6-dioxo-purin-1-yl]methyl]-4-chloro-indole-1-carboxylate (94.00 mg, 177.70 umol) in MeOH (4.00 mL) was added THF (4.00 mL) and 1N NaOH (2.00 mL). The mixture was stirred at 25° C. for 16 h. The mixture was concentrated. The residue was purified by prep-HPLC using Method A (15-40% ACN). $^1$H NMR (400 MHz, DMSO-d$_6$) δ 2.94-3.04 (m, 3H) 3.16 (d, J=15.06 Hz, 1H) 3.37 (s, 3H) 3.46-3.54 (m, 1H) 3.61 (d, J=10.54 Hz, 1H) 3.78 (dd, J=10.54, 4.52 Hz, 1H) 3.93 (s, 1H) 4.15 (dd, J=16.56, 7.03 Hz, 1H) 5.05-5.14 (m, 2H) 6.29 (s, 1H) 6.96-7.06 (m, 3H) 7.36 (dd, J=6.27, 2.26 Hz, 1H) 11.20 (br. s., 1H); ESI: m/z 447.2 (M+H)$^+$.

Example 466

1-[(4-chloro-1H-indol-2-yl)methyl]-3-cyclopropyl-7-methyl-8-(4-pyridylamino)purine-2,6-dione

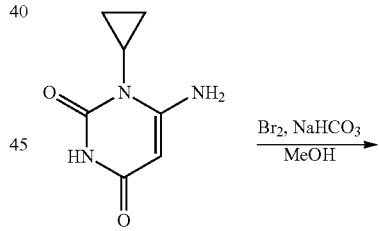

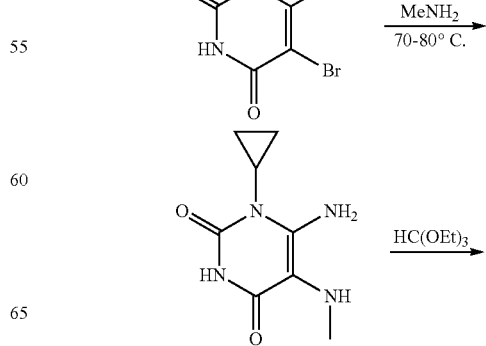

433
-continued

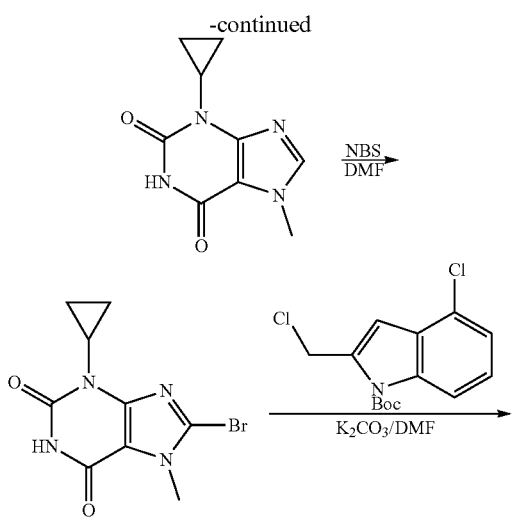

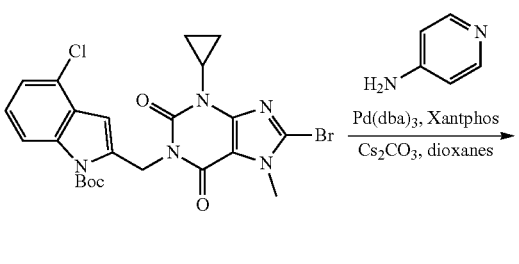

6-Amino-5-bromo-1-cyclopropyl-pyrimidine-2,4-dione

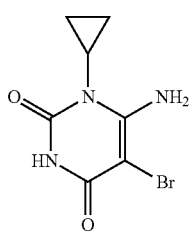 [SMILES: Nc1c(Br)c(=O)[nH]c(=O)n1C1CC1]

To a solution of 6-amino-1-cyclopropyl-pyrimidine-2,4-dione (2.00 g, 11.96 mmol) and NaHCO₃ (1.00 g, 11.96 mmol, 465.17 uL) in MeOH (12.00 mL) was added dropwise Br₂ (1.91 g, 11.96 mmol, 616.13 uL) at 0° C. for 20 min. The mixture was stirred at 0° C. for 40 min. The mixture was cooled to 4° C. and the solid was collected by filtration and used without further purification. ¹H NMR (400 MHz, DMSO-d₆) δ 10.75 (s, 1H) 7.04-6.88 (m, 2H) 1.22-1.00 (m, 2H) 0.85-0.65 (m, 2H)

434

6-Amino-1-cyclopropyl-5-(methylamino)pyrimidine-2,4-dione

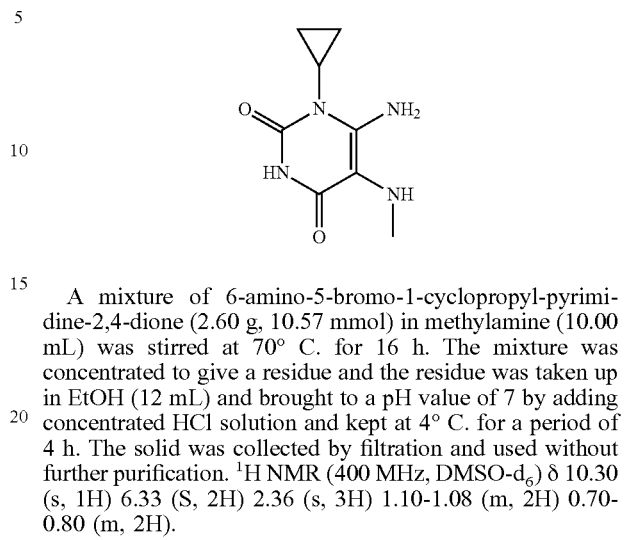

A mixture of 6-amino-5-bromo-1-cyclopropyl-pyrimidine-2,4-dione (2.60 g, 10.57 mmol) in methylamine (10.00 mL) was stirred at 70° C. for 16 h. The mixture was concentrated to give a residue and the residue was taken up in EtOH (12 mL) and brought to a pH value of 7 by adding concentrated HCl solution and kept at 4° C. for a period of 4 h. The solid was collected by filtration and used without further purification. ¹H NMR (400 MHz, DMSO-d₆) δ 10.30 (s, 1H) 6.33 (S, 2H) 2.36 (s, 3H) 1.10-1.08 (m, 2H) 0.70-0.80 (m, 2H).

3-Cyclopropyl-7-methyl-purine-2,6-dione

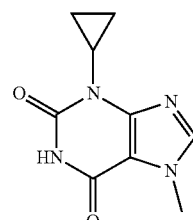

A mixture of 6-amino-1-cyclopropyl-5-(methylamino)pyrimidine-2,4-dione (1.67 g, 8.51 mmol) in HCOOH (30.00 mL) was stirred at 100° C. for 3 hours. The mixture was concentrated to give a crude formylated product. This product was dissolved in 2N NaOH (12.77 mL) and stirred at 100° C. for 2 hours. LC-MS showed most of the starting material still remained. The mixture was cooled to 25° C. and additional 2N NaOH (12.77 mL) was added to the above solution. The mixture was stirred at 100° C. for 3 hours. The mixture was acidified with HOAc until pH=5. The mixture was filtered. The solid was washed with H₂O (10 mL*3) to afford the title compound. ¹H NMR (400 MHz, DMSO-d₆) δ 10.98 (br. s., 1H) 7.91 (s, 1H) 3.81 (s, 3H) 0.62-1.08 (m, 4H).

8-Bromo-3-cyclopropyl-7-methyl-purine-2,6-dione

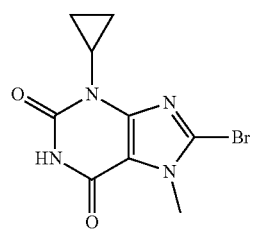 [SMILES: Cn1c(Br)nc2c1c(=O)[nH]c(=O)n2C1CC1]

To a solution of 3-cyclopropyl-7-methyl-purine-2,6-dione (150.00 mg, 727.45 umol) in DMF (3.00 mL) was added NBS (258.94 mg, 1.45 mmol). The reaction mixture was stirred at 25° C. for 15 h. The reaction was quenched with sat. NaHCO₃ (5 mL), and then extracted with EtOAc (10 mL*3). The combined organic fractions were washed with Na₂SO₃ aq (3 mL), brine (2 mL), dried over Na₂SO₄, and concentrated in vacuum. The crude product was purified by Prep-TLC (DCM/MeOH=10/1) to obtain the title compound; ESI: m/z 285.0, 287.0 (M+H)⁺.

tert-Butyl 2-[(8-bromo-3-cyclopropyl-7-methyl-2,6-dioxo-purin-1-yl)methyl]-4-chloro-indole-1-carboxylate

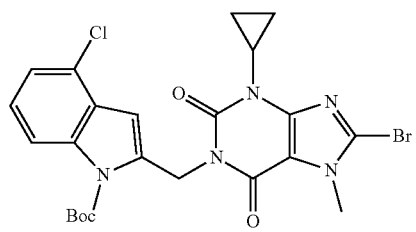 [SMILES: Cn1c(Br)nc2c1c(=O)n(Cc1cc3c(Cl)cccc3n1C(=O)OC(C)(C)C)c(=O)n2C1CC1]

The title compound was synthesized in a similar fashion as described in Procedure using 8-bromo-3-cyclopropyl-7-methyl-purine-2,6-dione and tert-butyl 4-chloro-2-(chloromethyl)indole-1-carboxylate. The product was purified by Prep-TLC (PE/EtOAc=2/1): ¹H NMR (400 MHz. CDCl₃) δ 8.06-8.02 (m, 1H), 7.18 (s, 2H), 6.18-6.14 (m, 1H), 5.63-5.54 (m, 2H), 4.00 (s, 3H), 3.11-3.04 (m, 1H), 1.77-1.73 (d, 9H), 1.27-1.20 (m, 2H), 1.14-1.08 (m, 2H).

1-[(4-Chloro-1H-indol-2-yl)methyl]-3-cyclopropyl-7-methyl-8-(4-pyridylamino)purine-2,6-dione

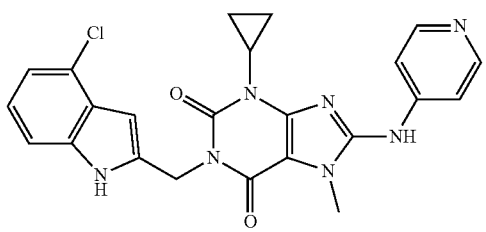 [SMILES: Cn1c(Nc2ccncc2)nc2c1c(=O)n(Cc1cc3c(Cl)cccc3[nH]1)c(=O)n2C1CC1]

The title compound was synthesized in a similar fashion as described in procedure 8B using tert-butyl 2-[(8-bromo-3-cyclopropyl-7-methyl-2,6-dioxo-purin-1-yl)methyl]-4-chloro-indole-1-carboxylate and pyridin-4-amine. The crude product was purified by Prep-TLC (DCM/MeOH=10/1) and then by Prep-HPLC using Method C (20-55% ACN). ¹H NMR (400 MHz, DMSO-d₆) δ 1.39-11.24 (m, 1H), 8.66-8.51 (m, 2H), 8.01-8.19 (m, 2H), 7.36 (dd, J=1.7, 7.1 Hz, 1H), 7.11-6.94 (m, 2H), 6.29 (s, 1H), 5.21 (s, 2H), 3.94 (s, 3H), 3.10-2.93 (m, 1H), 1.22-0.91 (m, 4H); ESI: m/z 462.2 (M+H)⁺.

Example 468 and 471

(E)-1-((4-chloro-1H-indol-2-yl)methyl)-8-((hydroxyimino)(pyridin-4-yl)methyl)-3,7-dimethyl-1H-purine-2,6(3H,7H)-dione and (Z)-1-((4-chloro-1H-indol-2-yl)methyl)-8-((hydroxyimino)(pyridin-4-yl)methyl)-3,7-dimethyl-1H-purine-2,6(3H,7H)-dione

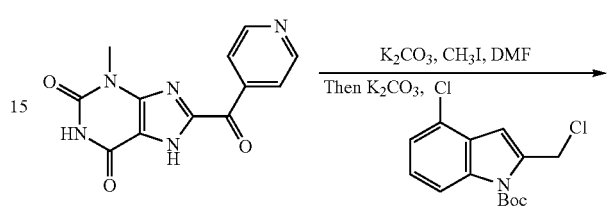

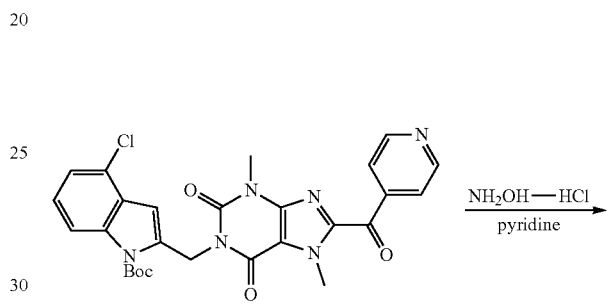

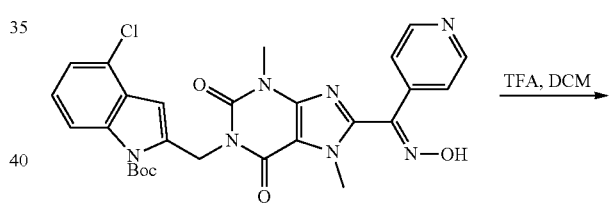

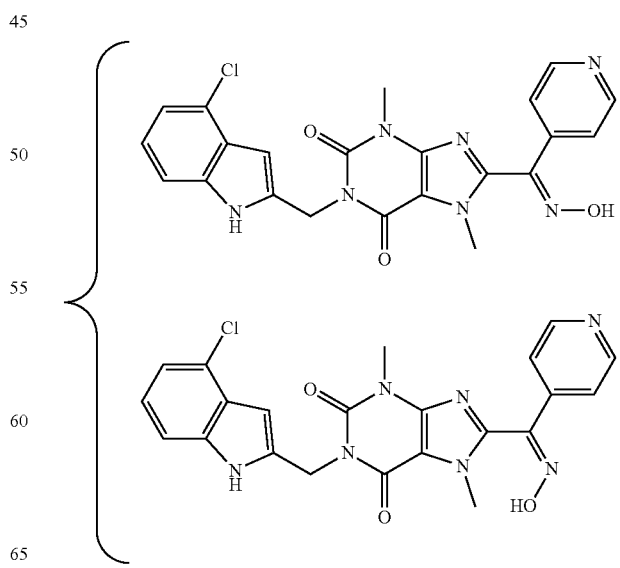

8-Isonicotinoyl-3-methyl-1H-purine-2,6(3H,7H)-dione

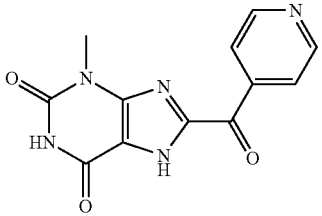 [SMILES: Cn1c(=O)[nH]c(=O)c2[nH]c(C(=O)c3ccncc3)nc21]

A mixture of 3-methyl-8-(pyridin-4-ylmethyl)-1H-purine-2,6(3H,7H)-dione (1.2 g, 4.66 mmol) and SeO$_2$ (1.55 g, 14.0 mmol) in AcOH (30 mL) was heated to reflux and stirred for 5 h. The reaction mixture was filtered and the residue was washed with NaHCO$_3$ aqueous (1*50 mL), dried in vacuo to afford the product; ESI: m/z 272.1 (M+H)$^+$.

tert-Butyl 4-chloro-2-((8-isonicotinoyl-3,7-dimethyl-2,6-dioxo-2,3,6,7-tetrahydro-1H-purin-1-yl)methyl)-1H-indole-1-carboxylate

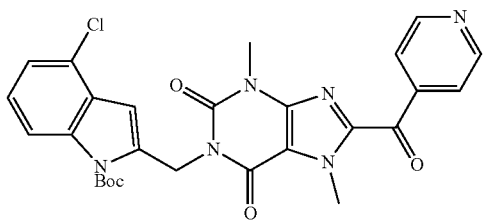 [SMILES: Cn1c(C(=O)c2ccncc2)nc2c1c(=O)n(Cc1cc3c(Cl)cccc3n1C(=O)OC(C)(C)C)c(=O)n2C]

A mixture of 8-isonicotinoyl-3-methyl-1H-purine-2,6(3H,7H)-dione (200 mg, 0.74 mmol) and K$_2$CO$_3$ (153 mg, 1.11 mmol) in DMF (6 mL) was stirred for 20 min at 25° C. then MeI (105 mg, 0.74 mmol) was added. The resulting mixture was stirred for 16 h at 25° C. Then tert-butyl 4-chloro-2-(chloromethyl)-1H-indole-1-carboxylate (115 mg, 0.38 mmol) and K$_2$CO$_3$ (79 mg, 0.57 mmol) were added. The mixture was heated to 50° C. and stirred for 2 h. The reaction mixture was poured into water (40 mL) and extracted with EA (2*30 mL). The combined organic fractions were washed with water (3*50 mL) and brine (1*50 mL), dried over Na$_2$SO$_4$, concentrated and purified by flash chromatography (30~50% EA/PE) to obtain the title compound; ESI: m/z 549.2 (M+H)$^+$.

tert-Butyl 4-chloro-2-((8-((hydroxyimino)(pyridin-4-yl)methyl)-3,7-dimethyl-2,6-dioxo-2,3,6,7-tetrahydro-1H-purin-1-yl)methyl)-1H-indole-1-carboxylate

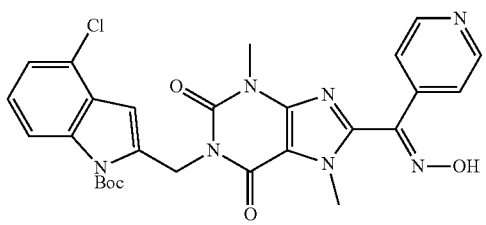 [SMILES: Cn1c(/C(=N/O)c2ccncc2)nc2c1c(=O)n(Cc1cc3c(Cl)cccc3n1C(=O)OC(C)(C)C)c(=O)n2C]

A mixture of tert-butyl 4-chloro-2-((8-isonicotinoyl-3,7-dimethyl-2,6-dioxo-2,3,6,7-tetrahydro-1H-purin-1-yl)methyl)-1H-indole-1-carboxylate (100 mg, 0.18 mmol) and hydroxylamine hydrochloride (253 mg, 3.64 mmol) in pyridine (4 mL) was heated to 50° C. and stirred for 16 h. The reaction mixture was poured into water (30 mL) and extracted with EA (2*20 mL). The combined organic fractions were washed with water (3*30 mL) and brine (1*30 mL), dried over Na$_2$SO$_4$, concentrated and dried in vacuo to afford the product; ESI: m/z 564.2 (M+H)$^+$.

(E)-1-((4-chloro-1H-indol-2-yl)methyl)-8-((hydroxyimino)(pyridin-4-yl)methyl)-3,7-dimethyl-1H-purine-2,6(3H,7H)-dione and (Z)-1-((4-chloro-1H-indol-2-yl)methyl)-8-((hydroxyimino)(pyridin-4-yl)methyl)-3,7-dimethyl-1H-purine-2,6(3H,7H)-dione

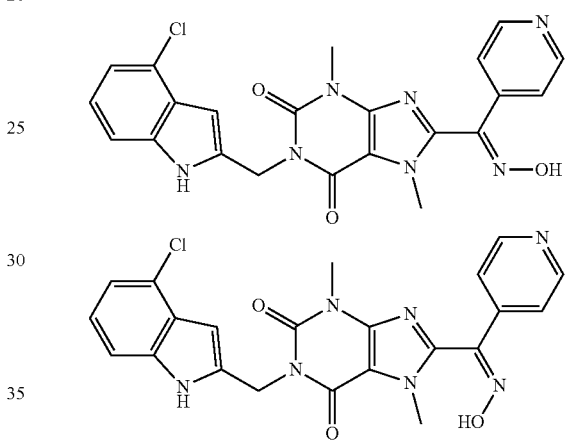

A solution of tert-butyl 4-chloro-2-((8-((hydroxyimino)(pyridin-4-yl)methyl)-3,7-dimethyl-2,6-dioxo-2,3,6,7-tetrahydro-1H-purin-1-yl)methyl)-1H-indole-1-carboxylate (103 mg, 0.18 mmol) in TFA (1 mL) and DCM (3 mL) was stirred for 2 h at 25° C. The reaction mixture was concentrated. The residue was dissolved in EA (20 mL), washed with NaHCO$_3$ aq. (1*15 mL) and brine (1*15 mL), dried over Na$_2$SO$_4$, concentrated and purified by preparative HPLC using Method B (25-75% ACN) to give:

Example 468: (E)-1-((4-chloro-1H-indol-2-yl)methyl)-8-((hydroxyimino)(pyridin-4-yl)methyl)-3,7-dimethyl-1H-purine-2,6(3H,7H)-dione or (Z)-1-((4-chloro-1H-indol-2-yl)methyl)-8-((hydroxyimino)(pyridin-4-yl)methyl)-3,7-dimethyl-1H-purine-2,6(3H,7H)-dione: $^1$H NMR (400 MHz, DMSO-d$_6$) δ 13.11 (br s, 1H), 11.32 (s, 1H), 8.63-8.61 (m, 2H), 7.50-7.47 (m, 2H), 7.36-7.33 (m, 1H), 7.06-7.00 (m, 2H), 6.34 (s, 1H), 5.25 (s, 2H), 3.79 (s, 3H), 3.46 (s, 3H); ESI: m/z 464.1 (M+H)$^+$.

Example 471: (E)-1-((4-chloro-1H-indol-2-yl)methyl)-8-((hydroxyimino)(pyridin-4-yl)methyl)-3,7-dimethyl-1H-purine-2,6(3H,7H)-dione or (Z)-1-((4-chloro-1H-indol-2-yl)methyl)-8-((hydroxyimino)(pyridin-4-yl)methyl)-3,7-dimethyl-1H-purine-2,6(3H,7H)-dione: $^1$H NMR (400 MHz, DMSO-d$_6$) δ 12.74 (br s, 1H), 11.31 (s, 1H), 8.70-8.67 (m, 2H), 7.50-7.47 (m, 2H), 7.34-7.32 (m, 1H), 7.06-7.00 (m, 2H), 6.29 (s, 1H), 5.23 (s, 2H), 4.13 (s, 3H), 3.33 (s, 3H); ESI: m/z 464.1 (M+H)$^+$.

Example 470

(R)-8-(1-amino-2-(pyridin-3-yl)ethyl)-1-((4-chloro-1H-indol-2-yl)methyl)-3,7-dimethyl-1H-purine-2,6(3H,7H)-dione

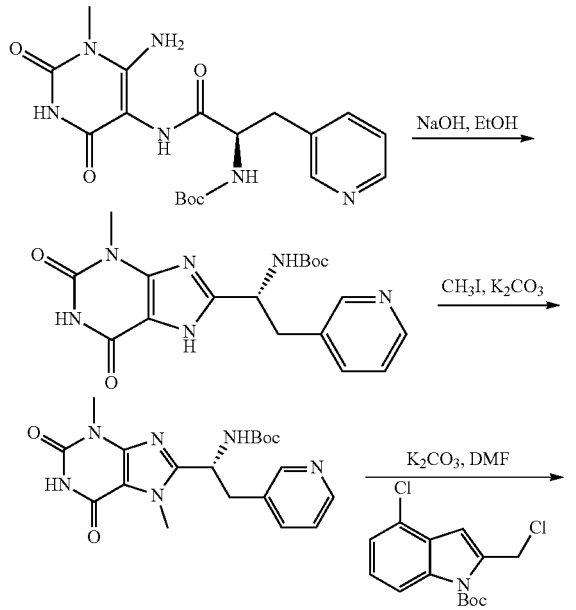

(R)-tert-Butyl 1-(6-amino-1-methyl-2,4-dioxo-1,2,3,4-tetrahydropyrimidin-5-ylamino)-1-oxo-3-(pyridin-3-yl)propan-2-ylcarbamate

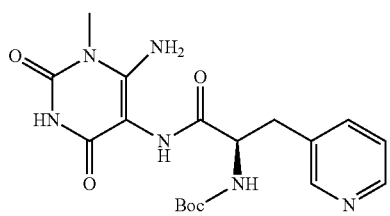 [SMILES: Cn1c(N)c(NC(=O)[C@@H](Cc2cccnc2)NC(=O)OC(C)(C)C)c(=O)[nH]c1=O]

The title compound was synthesized in a similar fashion as described in Example 447 step 1 using (R)-2-(tert-butoxycarbonylamino)-3-(pyridin-3-yl)propanoic acid and 5,6-diamino-1-methylpyrimidine-2,4(1H,3H)-dione; ESI: m/z 405.2 (M+H)+.

(R)-tert-butyl 1-(3-methyl-2,6-dioxo-2,3,6,7-tetrahydro-1H-purin-8-yl)-2-(pyridin-3-yl)ethylcarbamate

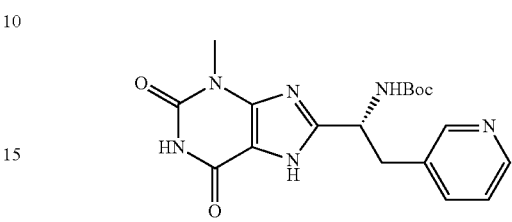

The title compound was synthesized in a similar fashion as described in Example 447 step 2 using (R)-tert-butyl 1-(6-amino-1-methyl-2,4-dioxo-1,2,3,4-tetrahydropyrimidin-5-ylamino)-1-oxo-3-(pyridin-3-yl)propan-2-ylcarbamate; ESI: m/z 387.2 (M+H)+.

(R)-tert-butyl 1-(3,7-dimethyl-2,6-dioxo-2,3,6,7-tetrahydro-1H-purin-8-yl)-2-(pyridin-3-yl)ethylcarbamate

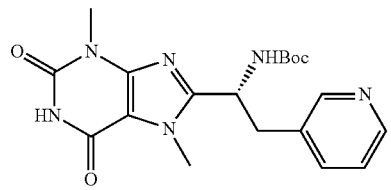 [SMILES: Cn1c([C@@H](Cc2cccnc2)NC(=O)OC(C)(C)C)nc2c1c(=O)[nH]c(=O)n2C]

The title compound was synthesized in a similar fashion as described in Example 447 step 3 using (R)-tert-butyl 1-(3-methyl-2,6-dioxo-2,3,6,7-tetrahydro-1H-purin-8-yl)-2-(pyridin-3-yl)ethylcarbamate and MeI; ESI: m/z 401.2 (M+H)+.

(R)-tert-butyl 2-((8-(1-(tert-butoxycarbonylamino)-2-(pyridin-3-yl)ethyl)-3,7-dimethyl-2,6-dioxo-2,3,6,7-tetrahydro-1H-purin-1-yl)methyl)-4-chloro-1H-indole-1-carboxylate

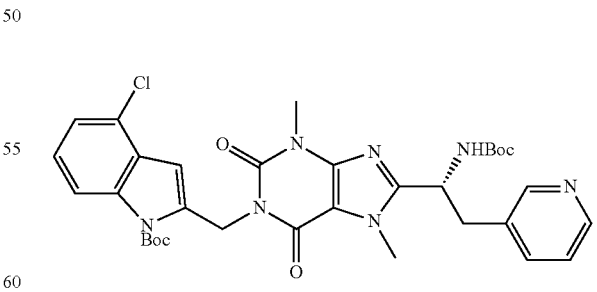

The title compound was synthesized in a similar fashion as described in Example 447 step 4 using (R)-tert-butyl 1-(3,7-dimethyl-2,6-dioxo-2,3,6,7-tetrahydro-1H-purin-8-yl)-2-(pyridin-3-yl)ethylcarbamate and tert-butyl 4-chloro-2-(chloromethyl)-1H-indole-1-carboxylate; ESI: m/z 664.4 (M+H)+.

441

(R)-8-(1-amino-2-(pyridin-3-yl)ethyl)-1-((4-chloro-1H-indol-2-yl)methyl)-3,7-dimethyl-1H-purine-2,6(3H,7H)-dione

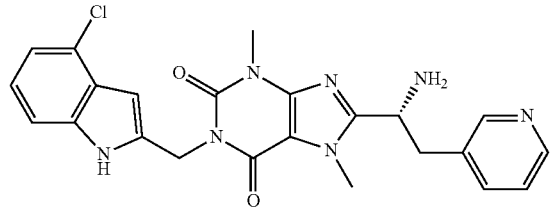 [SMILES: Cn1c([C@H](N)Cc2cccnc2)nc2c1c(=O)n(Cc1cc3c(Cl)cccc3[nH]1)c(=O)n2C]

The title compound was synthesized in a similar fashion as described in Example 447 step 5 using (R)-tert-butyl 2-((8-(1-(tert-butoxycarbonylamino)-2-(pyridin-3-yl)ethyl)-3,7-dimethyl-2,6-dioxo-2,3,6,7-tetrahydro-1H-purin-1-yl)methyl)-4-chloro-1H-indole-1-carboxylate. The product was purified by reverse phase column chromatography (C18, ACN/water (NH$_4$HCO$_3$)=40%) to provide the title compound: $^1$H NMR (400 MHz, CD$_3$OD) δ 8.49 (d, J=3.8 Hz, 1H), 8.29 (s, 1H), 7.65 (d, J=8.0 Hz, 1H), 7.41 (dd, J=7.8, 4.9 Hz, 1H), 7.29 (d, J=7.9 Hz, 1H), 7.06-6.94 (m, 2H), 6.45 (s, 1H), 5.30 (s, 2H), 5.02 (m, 1H), 3.62 (s, 3H), 3.61 (s, 3H), 3.50-3.37 (m, 2H); ESI: m/z 464.2 (M+H)$^+$.

Example 472

(R)-8-(1-amino-2-(pyridin-2-yl)ethyl)-1-((4-chloro-1H-indol-2-yl)methyl)-3,7-dimethyl-1H-purine-2,6(3H,7H)-dione

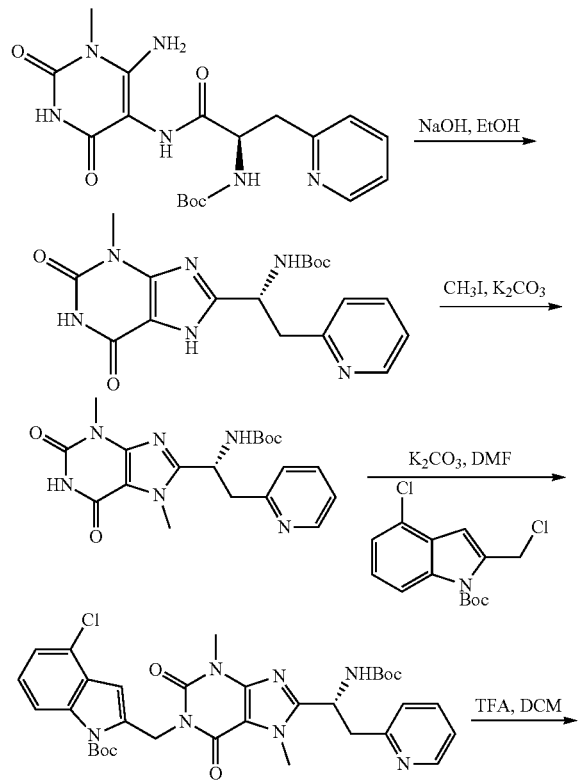

442

-continued

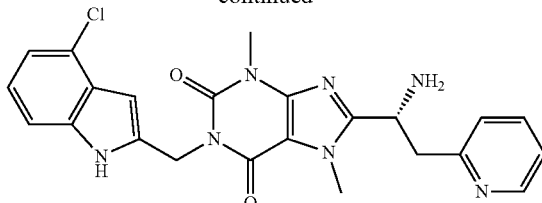

(R)-tert-Butyl 1-(6-amino-1-methyl-2,4-dioxo-1,2,3,4-tetrahydropyrimidin-5-ylamino)-1-oxo-3-(pyridin-2-yl)propan-2-ylcarbamate

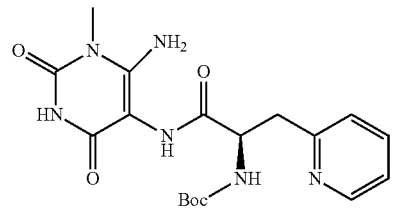 [SMILES: Cn1c(N)c(NC(=O)[C@@H](Cc2ccccn2)NC(=O)OC(C)(C)C)c(=O)[nH]c1=O]

The title compound was synthesized in a similar fashion as described in Example 447 step 1 using (R)-2-(tert-butoxycarbonylamino)-3-(pyridin-2-yl)propanoic acid and 5,6-diamino-1-methylpyrimidine-2,4(1H,3H)-dione; ESI: m/z 405.1 (M+H)$^+$.

(R)-tert-Butyl 1-(3-methyl-2,6-dioxo-2,3,6,7-tetrahydro-1H-purin-8-yl)-2-(pyridin-2-yl)ethylcarbamate

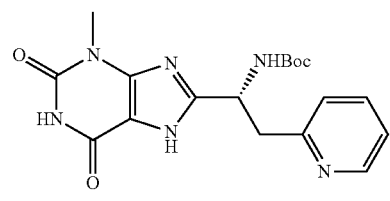 [SMILES: Cn1c(=O)[nH]c(=O)c2[nH]c([C@@H](Cc3ccccn3)NC(=O)OC(C)(C)C)nc21]

The title compound was synthesized in a similar fashion as described in Example 447 step 2 using (R)-tert-butyl 1-(6-amino-1-methyl-2,4-dioxo-1,2,3,4-tetrahydropyrimidin-5-ylamino)-1-oxo-3-(pyridin-2-yl)propan-2-ylcarbamate; ESI: m/z 387.2 (M+H)$^+$.

(R)-tert-butyl 1-(3,7-dimethyl-2,6-dioxo-2,3,6,7-tetrahydro-1H-purin-8-yl)-2-(pyridin-2-yl)ethylcarbamate

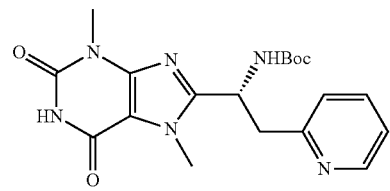 [SMILES: Cn1c([C@@H](Cc2ccccn2)NC(=O)OC(C)(C)C)nc2c1c(=O)[nH]c(=O)n2C]

The title compound was synthesized in a similar fashion as described in Example 447 step 3 using (R)-tert-butyl 1-(3-methyl-2,6-dioxo-2,3,6,7-tetrahydro-1H-purin-8-yl)-2-(pyridin-2-yl)ethylcarbamate and MeI. ESI: m/z 401.2 (M+H)⁺.

(R)-tert-butyl 2-((8-(1-(tert-butoxycarbonylamino)-2-(pyridin-2-yl)ethyl)-3,7-dimethyl-2,6-dioxo-2,3,6,7-tetrahydro-1H-purin-1-yl)methyl)-4-chloro-1H-indole-1-carboxylate

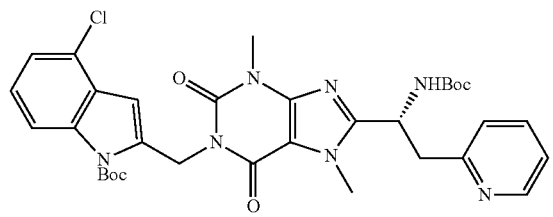 [SMILES: Cn1c([C@@H](Cc2ccccn2)NC(=O)OC(C)(C)C)nc2c1c(=O)n(Cc1cc3c(Cl)cccc3n1C(=O)OC(C)(C)C)c(=O)n2C]

The title compound was synthesized in a similar fashion as described in Example 447 step 4 using (R)-tert-butyl 1-(3,7-dimethyl-2,6-dioxo-2,3,6,7-tetrahydro-1H-purin-8-yl)-2-(pyridin-2-yl)ethylcarbamate and tert-butyl 4-chloro-2-(chloromethyl)-1H-indole-1-carboxylate; ESI: m/z 664.2 (M+H)⁺.

(R)-8-(1-amino-2-(pyridin-2-yl)ethyl)-1-((4-chloro-1H-indol-2-yl)methyl)-3,7-dimethyl-1H-purine-2,6(3H,7H)-dione

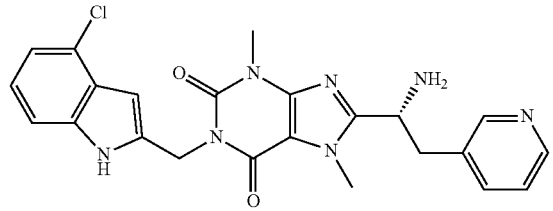 [SMILES: Cn1c([C@H](N)Cc2cccnc2)nc2c1c(=O)n(Cc1cc3c(Cl)cccc3[nH]1)c(=O)n2C]

The title compound was synthesized in a similar fashion as described in Example 447 step 5 using (R)-tert-butyl 2-((8-(1-(tert-butoxycarbonylamino)-2-(pyridin-3-yl)ethyl)-3,7-dimethyl-2,6-dioxo-2,3,6,7-tetrahydro-1H-purin-1-yl)methyl)-4-chloro-1H-indole-1-carboxylate. The product was purified by reverse phase column chromatography (C18, ACN/water (NH₄HCO₃)=40%) to provide the title compound; ¹H NMR (400 MHz, CD₃OD) δ 8.54 (d, J=4.3 Hz, 1H), 7.83-7.66 (m, 1H), 7.42-7.17 (m, 3H), 7.05-6.82 (m, 2H), 6.41 (s, 1H), 5.32-5.18 (m, 3H), 3.85 (s, 3H), 3.62-3.45 (m, 5H); ESI: m/z 464.2 (M+H)⁺.

Example 473

8-(amino(pyridin-2-yl)methyl)-1-((4-chloro-1H-indol-2-yl)methyl)-3,7-dimethyl-1H-purine-2,6(3H,7H)-dione

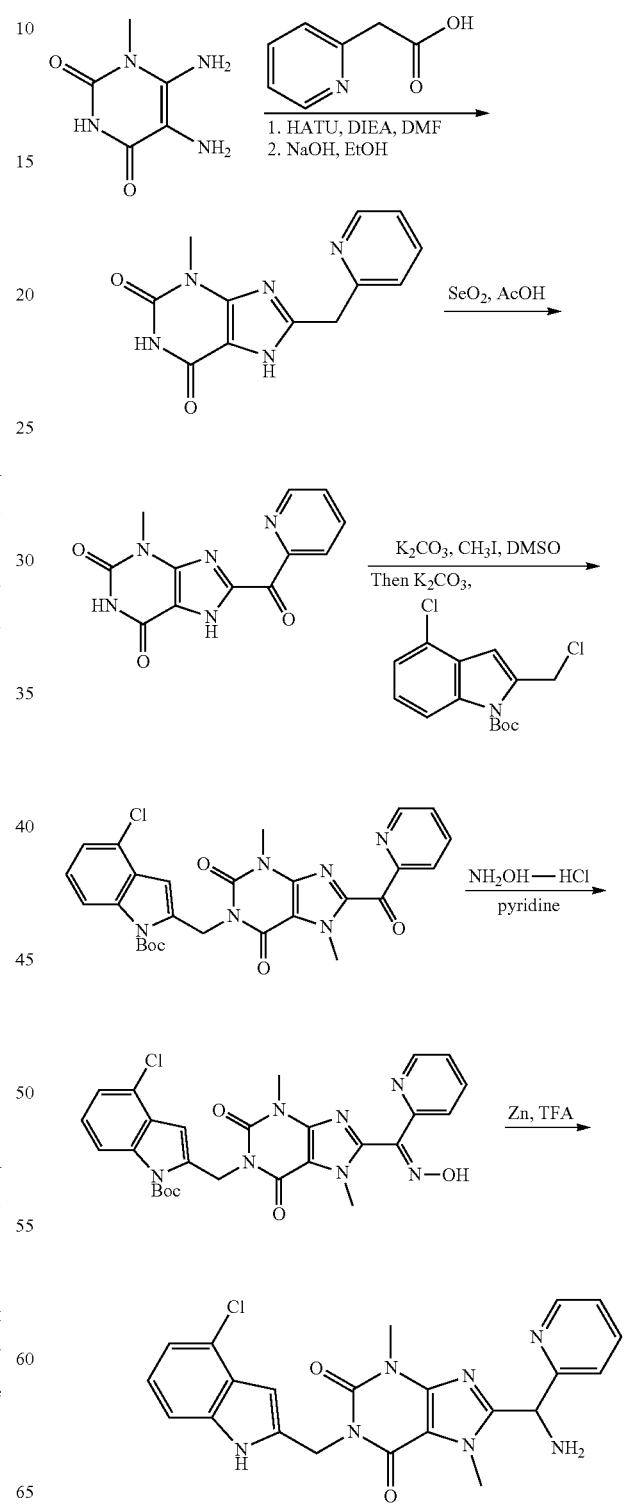

3-Methyl-8-(pyridin-2-ylmethyl)-1H-purine-2,6(3H,7H)-dione

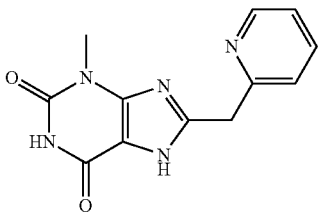 [SMILES: Cn1c(=O)[nH]c(=O)c2[nH]c(Cc3ccccn3)nc21]

To the suspension of 5,6-diamino-1-methylpyrimidine-2,4(1H,3H)-dione (1.0 g, 6.40 mmol), 2-(pyridin-2-yl)acetic acid (1.17 g, 6.72 mmol) and DIEA (2.48 g, 19.2 mmol) in DMF (20 mL) was added HATU (2.56 g, 6.72 mmol) and the mixture was stirred for 16 h at 25° C. The precipitate was collected. The solid and NaOH aq. (10 mL, 3M) in EtOH (20 mL) were heated to reflux for 3 h. The reaction mixture was cooled to 28° C. and organic solvent was removed. The mixture was neutralized with concentrated HCl to pH=8-9. The precipitate was collected and dried in vacuo to afford the product; ESI: m/z 258.1 (M+H)+.

3-Methyl-8-picolinoyl-1H-purine-2,6(3H,7H)-dione

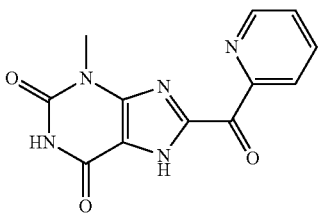 [SMILES: Cn1c(=O)[nH]c(=O)c2[nH]c(C(=O)c3ccccn3)nc21]

A mixture of 3-methyl-8-(pyridin-2-ylmethyl)-1H-purine-2,6(3H,7H)-dione (1.0 g, 3.89 mmol) and SeO2 (1.30 g, 11.7 mmol) in AcOH (20 mL) was heated to reflux and stirred for 2 h. The reaction mixture was filtered, concentrated and the residue was washed with NaHCO3 aq. (1*30 mL) and water (1*20 mL), and dried in vacuo; ESI: m/z 272.1 (M+H)+.

tert-Butyl 4-chloro-2-((3,7-dimethyl-2,6-dioxo-8-picolinoyl-2,3,6,7-tetrahydro-1H-purin-1-yl)methyl)-1H-indole-1-carboxylate

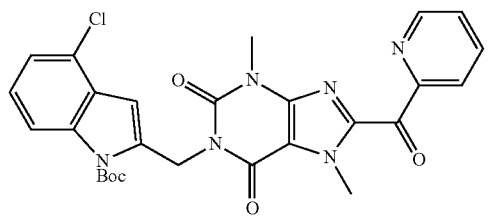 [SMILES: Cn1c(C(=O)c2ccccn2)nc2c1c(=O)n(Cc1cc3c(Cl)cccc3n1C(=O)OC(C)(C)C)c(=O)n2C]

A mixture of 3-methyl-8-picolinoyl-1H-purine-2,6(3H,7H)-dione (136 mg, 0.50 mmol) and K2CO3 (83 mg, 0.60 mmol) in DMSO (4 mL) was stirred for 20 min at 25° C. then MeI (71 mg, 0.50 mmol) was added. The resulting mixture was stirred for 5 h at 25° C. Then tert-butyl 4-chloro-2-(chloromethyl)-1H-indole-1-carboxylate (88 mg, 0.29 mmol) and K2CO3 (41 mg, 0.29 mmol) was added. The mixture was heated to 50° C. and stirred for 2 h. The reaction mixture was poured into water (30 mL) and extracted with EA (2*20 mL). The combined organic fractions were washed with water (3*40 mL) and brine (1*40 mL), dried over Na2SO4, concentrated and purified by flash chromatography (3050% EA/PE); ESI: m/z 549.2 (M+H)+.

tert-Butyl 4-chloro-2-((8-((hydroxyimino)(pyridin-2-yl)methyl)-3,7-dimethyl-2,6-dioxo-2,3,6,7-tetrahydro-1H-purin-1-yl)methyl)-1H-indole-1-carboxylate

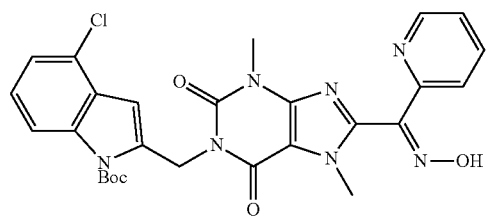 [SMILES: Cn1c(/C(=N/O)c2ccccn2)nc2c1c(=O)n(Cc1cc3c(Cl)cccc3n1C(=O)OC(C)(C)C)c(=O)n2C]

A mixture of tert-butyl 4-chloro-2-((3,7-dimethyl-2,6-dioxo-8-picolinoyl-2,3,6,7-tetrahydro-1H-purin-1-yl)methyl)-1H-indole-1-carboxylate (65 mg, 0.12 mmol) and hydroxylamine hydrochloride (165 mg, 2.37 mmol) in pyridine (3 mL) was heated to 50° C. and stirred for 3 h. The reaction mixture was poured into water (30 mL) and extracted with EA (2*20 mL). The combined organic fractions were washed with water (3*30 mL) and brine (1*30 mL), dried over Na2SO4, and concentrated; ESI: m/z 564.2 (M+H)+.

8-(Amino(pyridin-2-yl)methyl)-1-((4-chloro-1H-indol-2-yl)methyl)-3,7-dimethyl-1H-purine-2,6(3H,7H)-dione

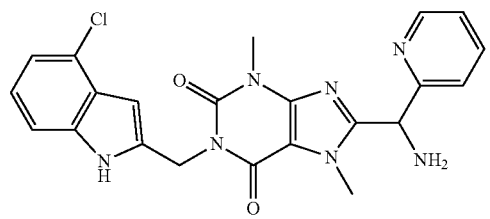 [SMILES: Cn1c(C(N)c2ccccn2)nc2c1c(=O)n(Cc1cc3c(Cl)cccc3[nH]1)c(=O)n2C]

The mixture of tert-butyl 4-chloro-2-((8-((hydroxyimino)(pyridin-2-yl)methyl)-3,7-dimethyl-2,6-dioxo-2,3,6,7-tetrahydro-1H-purin-1-yl)methyl)-1H-indole-1-carboxylate (50 mg, 0.089 mmol) in TFA (2 mL) was stirred for 1 h at 25° C. Then Zn dust (174 mg, 2.67 mmol) was added and the mixture was stirred for another 1 h. The reaction mixture was filtered and the filtrate was concentrated. The residue was dissolved in EA (20 mL) and washed by NaHCO3 aq. (1*20 mL) and brine (1*20 mL), dried over Na2SO4, concentrated and purified by flash chromatography (EA/PE, 1:1) and preparative HPLC using Method B. 1H NMR (400 MHz, DMSO-d6) δ 11.27 (br s, 1H), 8.46-8.45 (m, 1H), 7.86-7.80 (m, 1H), 7.67 (d, J=8.0 Hz, 1H), 7.33-7.26 (m, 2H), 7.03-7.00 (m, 2H), 6.26 (s, 1H), 5.42 (s, 1H), 5.20 (s, 2H), 3.94 (s, 3H), 3.40 (s, 3H), 2.65 (s, 2H); ESI: m/z 450.1 (M+H)+.

Example 474

1-((4-chloro-7-fluoro-1H-indol-2-yl)methyl)-3,7-dimethyl-8-(pyridin-4-ylamino)-1H-purine-2,6(3H,7H)-dione

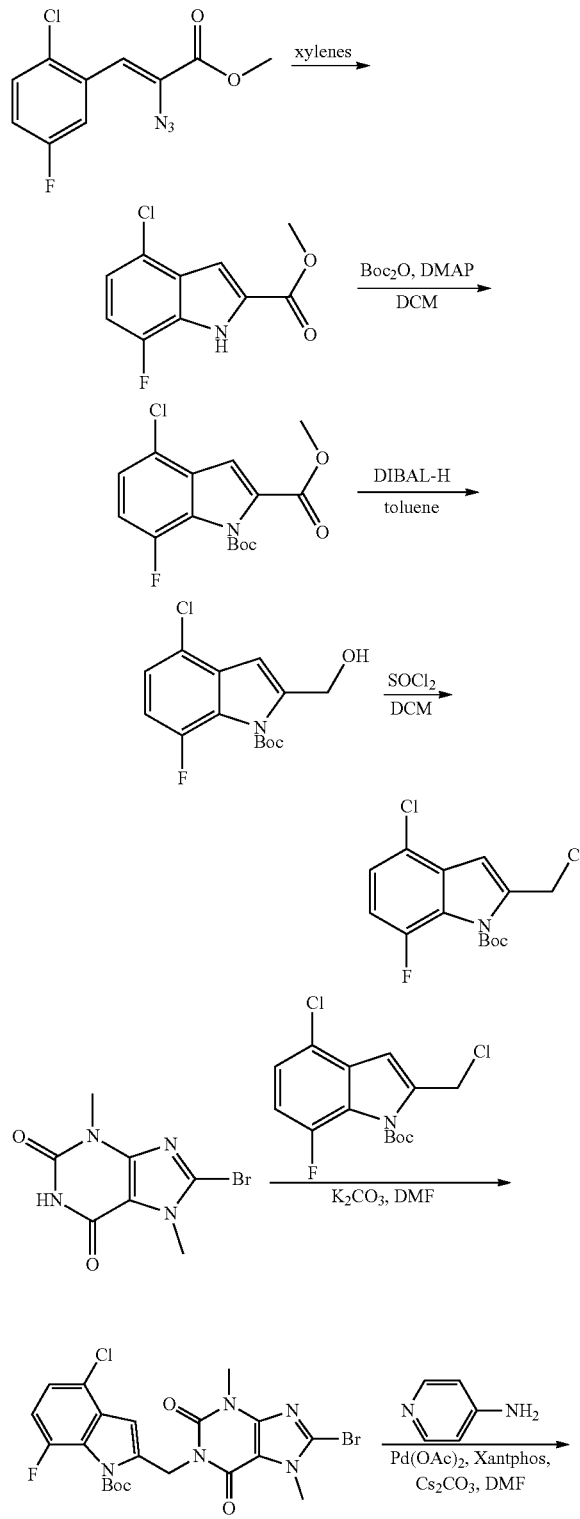

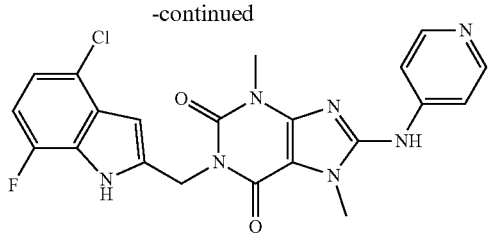

(Z)-methyl 2-azido-3-(2-chloro-5-fluorophenyl)acrylate

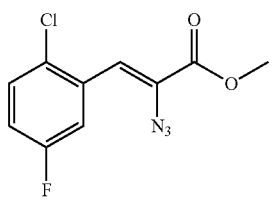

A solution of CH$_3$ONa (209 mmol, 11.3 g) in methanol (150 mL) was cooled at −10° C. Then a mixture of 2-chloro-5-fluorobenzaldehyde (52 mmol, 8.3 g) and ethyl 2-azido-acetate (209 mol, 27 g) in methanol (30 mL) was added dropwise over 1.5 h. The mixture was stirred at −10° C. for an additional 16 h, poured into ice-water (400 mL), and extracted with PE (3*300 mL). The combined extracts were washed with brine (100 mL), dried over MgSO$_4$, filtered and concentrated to give the title compound. $^1$H NMR (400 MHz, CDCl$_3$) δ 7.99 (dd, J=10.2, 3.0 Hz, 1H), 7.52-7.32 (m, 1H), 7.22 (s, 1H), 7.08-6.85 (m, 1H), 3.94 (s, 3H).

Methyl 4-chloro-7-fluoro-M-indole-2-carboxylate

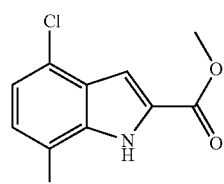

(Z)-methyl 2-azido-3-(2-chloro-5-fluorophenyl)acrylate (31 mmol, 7.8 g) dissolved in xylene (50 mL) was added dropwise to refluxing xylene (200 mL). The solution was refluxed for 2 h, then the mixture was evaporated under reduced pressure. The product was recrystalized from PE and DCM; $^1$H NMR (400 MHz, CDCl$_3$) δ 9.47 (s, 1H), 7.31 (s, 1H), 7.05 (dd, J=8.3, 3.8 Hz, 1H), 6.95 (dd, J=10.3, 8.3 Hz, 1H), 3.99 (s, 3H).

1-tert-Butyl 2-methyl 4-chloro-7-fluoro-1H-indole-1,2-dicarboxylate

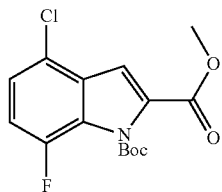

To a solution of methyl 4-chloro-7-fluoro-1H-indole-2-carboxylate (9.7 mmol, 2.2 g), Boc$_2$O (14.5 mmol, 3.2 g) and DMAP (1.5 mmol, 180 mg) in DCM (100 mL) was stirred at rt. over 1 h. The mixture was purified by flash chromatography (PE/EA=10/1) to give the product. $^1$H NMR (400 MHz, CDCl$_3$) δ 7.29 (s, 1H), 7.13 (dd, J=8.4, 3.5 Hz, 1H), 7.02 (dd, J=11.4, 8.4 Hz, 1H), 3.94 (s, 3H), 1.65 (s, 9H).

tert-butyl 4-chloro-7-fluoro-2-(hydroxymethyl)-1H-indole-1-carboxylate

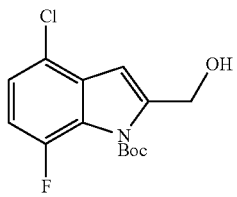 [SMILES: CC(C)(C)OC(=O)n1c(CO)cc2c(Cl)ccc(F)c21]

To a solution of 1-tert-butyl 2-methyl 4-chloro-7-fluoro-1H-indole-1,2-dicarboxylate (8.0 mmol, 2.6 g) in toluene (30 mL) was added dropwise DIBAL-H (24 mmol, 24 mL (1 M)) at −78° C., The mixture was allowed to stir for an additional 3 h, 5 mL of MeOH was added, then 150 mL of potassium sodium tartrate (aq.) was added, and the mixture was extracted with EA (2*50 mL). The combined organic fractions were washed with brine, dried over MgSO$_4$, filtered and concentrated. The mixture was purified by flash chromatography (PE/EA=6/1) to give the product; $^1$H NMR (400 MHz, CDCl$_3$) δ 7.14 (dd, J=8.5, 3.4 Hz, 1H), 6.94 (dd, J=12.0, 8.5 Hz, 1H), 6.70 (s, 1H), 4.77 (d, J=6.8 Hz, 2H), 3.66-3.50 (m, 1H), 1.66 (s, 9H).

tert-Butyl 4-chloro-2-(chloromethyl)-7-fluoro-1H-indole-1-carboxylate

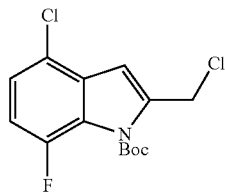

To a solution of tert-butyl 4-chloro-7-fluoro-2-(hydroxymethyl)-1H-indole-1-carboxylate (3.0 mmol, 900 mg) in DCM (30 mL) was added dropwise SOCl$_2$ (13 mmol, 1.43 g) at 0° C. After the addition was complete the mixture was allowed to stir for an additional 3 h. The mixture was concentrated under reduced pressure to give the product which was used without further purification. $^1$H NMR (400 MHz, CDCl$_3$) δ 7.17-7.10 (m, 1H), 7.02-6.85 (m, 1H), 6.80 (s, 1H), 4.95 (s, 2H), 1.66 (s, 9H).

tert-Butyl 2-((8-bromo-3,7-dimethyl-2,6-dioxo-2,3,6,7-tetrahydro-1H-purin-1-yl)methyl)-4-chloro-7-fluoro-1H-indole-1-carboxylate

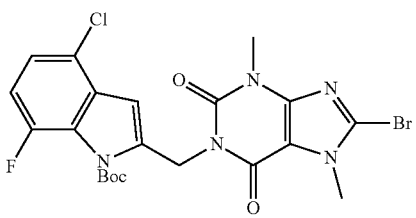 [SMILES: Cn1c(Br)nc2c1c(=O)n(Cc1cc3c(Cl)ccc(F)c3n1C(=O)OC(C)(C)C)c(=O)n2C]

A solution of tert-butyl 4-chloro-2-(chloromethyl)-7-fluoro-1H-indole-1-carboxylate (1.9 mmol, 600 mg), 8-bromo-3,7-dimethyl-1H-purine-2,6(3H,7H)-dione (1.7 mmol, 440 mg) and K$_2$CO$_3$ (5.2 mmol, 710 mg) in DMF (30 mL) was stirred and heated to 50° C. overnight. The mixture was poured into water and extracted with EA (2*50 mL). The combined organic fractions were dried with Na$_2$SO$_4$, filtered and concentrated. The residue was purified by flash chromatography (DCM/MeOH=10/1) to give the product; ESI: m/z 442.0 (M+H)$^+$.

1-((4-chloro-7-fluoro-1H-indol-2-yl)methyl)-3,7-dimethyl-8-(pyridin-4-ylamino)-1H-purine-2,6(3H,7H)-dione

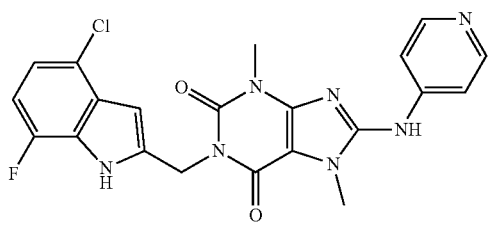 [SMILES: Cn1c(Nc2ccncc2)nc2c1c(=O)n(Cc1cc3c(Cl)ccc(F)c3[nH]1)c(=O)n2C]

The title compound was synthesized in a similar fashion as described in Procedure 8a using tert-butyl 2-((8-bromo-3,7-dimethyl-2,6-dioxo-2,3,6,7-tetrahydro-1H-purin-1-yl)methyl)-4-chloro-7-fluoro-1H-indole-1-carboxylate and pyridin-4-amine hydrochloride. The product was purified by flash chromatography (DCM/MeOH=6/1) to provide the title compound: $^1$H NMR (400 MHz, DMSO-d$_6$) δ 11.93 (s, 1H), 9.68 (s, 1H), 8.39 (s, 2H), 7.68 (s, 2H), 7.03-6.83 (m, 2H), 6.25 (s, 1H), 5.23 (s, 2H), 3.83 (s, 3H), 3.48 (s, 3H); ESI: m/z 454.1 (M+H)$^+$.

Example 475

3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanamide

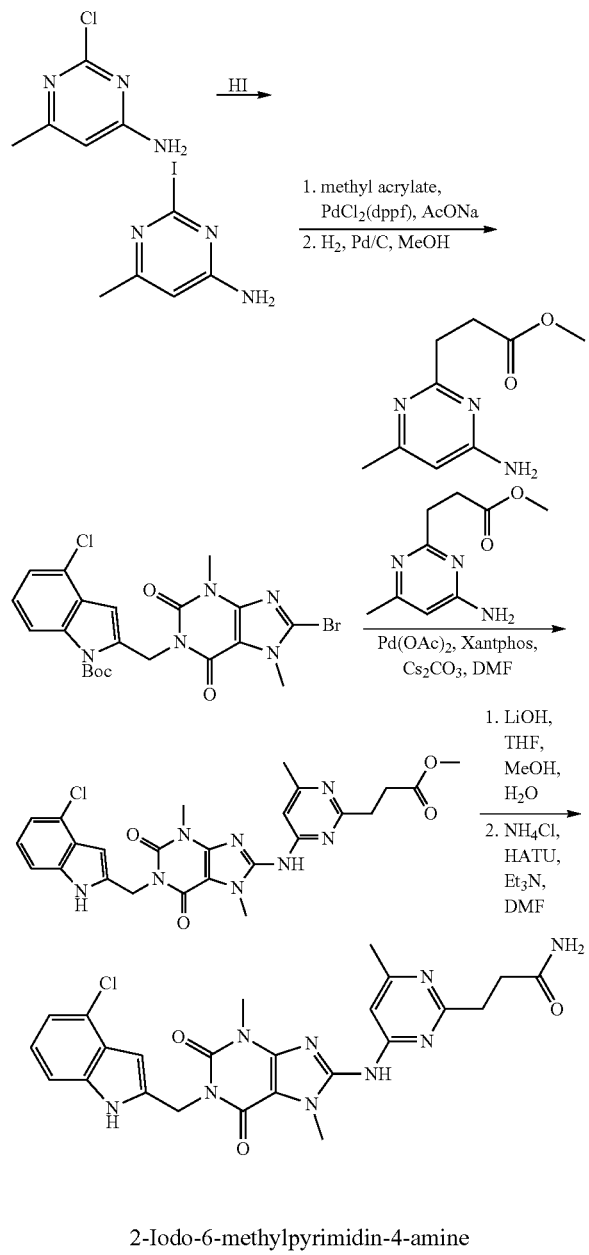

2-Iodo-6-methylpyrimidin-4-amine

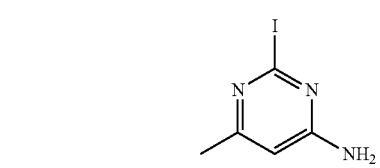

A solution of 2-chloro-6-methylpyrimidin-4-amine (3.5 mmol, 5.0 g) in HI (57%) (50 mL) was stirred at −5~0° C. for 20 h. The mixture was diluted with was with NaHCO$_3$ (50 g) and extracted with EA (100 mL*3). The combined organic fractions were concentrated to get a crude product that was triturated with PE/EA (1:1) to get the title compound. ESI; m/z 236.0 (M+H)$^+$.

Methyl 3-(4-amino-6-methylpyrimidin-2-yl)propanoate

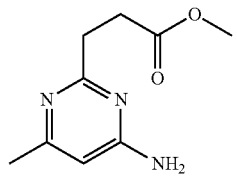

To a solution of 2-iodo-6-methylpyrimidin-4-amine (5.06 mmol, 1.20 g), methyl acrylate (25.0 mmol, 2.20 g), PdCl$_2$(dppf) (0.5 mmol, 0.35 g) and AcONa (12.5 mmol, 1.03 g) in DMA (10 mL) was heated to 130° C. in a microwave for 1 h. The mixture was poured into water (50 mL) and extracted with EA (2*150 mL). The combined organic fractions were dried with Na$_2$SO$_4$, filtered and concentrated. The residue was purified by flash chromatography (DCM/MeOH=10%) to give the product as a brown solid. The solid was dissolved in MeOH (15 mL) and Pd/C (250 mg) was added. The solution was stirred under H$_2$ balloon for 2 h. The mixture was filtered. The filtrate was concentrated to provide the title compound. ESI: m/z 196.2 (M+H)$^+$.

Methyl 3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanoate

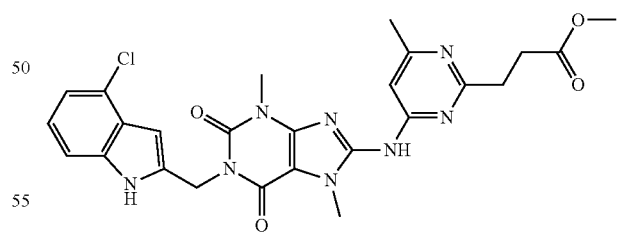

The title compound was synthesized in a similar fashion as described in Procedure 8A using methyl 3-(4-amino-6-methylpyrimidin-2-yl)propanoate and tert-butyl 2-((8-bromo-3,7-dimethyl-2,6-dioxo-2,3,6,7-tetrahydro-1H-purin-1-yl)methyl)-4-chloro-1H-indole-1-carboxylate. The product was purified by column chromatography (EA/PE=70%): ESI: m/z 537.2 (M+H−100+2)$^+$.

3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanamide

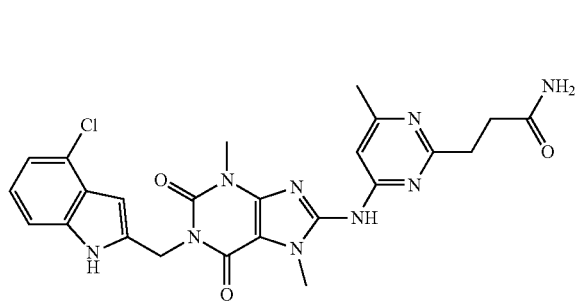 [SMILES: Cc1cc(Nc2nc3c(c(=O)n(Cc4cc5c(Cl)cccc5[nH]4)c(=O)n3C)n2C)nc(CCC(N)=O)n1]

A solution of methyl 3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanoate (0.37 mmol, 200 mg) and LiOH (1.85 mmol, 74 mg) in MeOH/THF/H$_2$O (2 mL/2 mL/2 mL) was stirred at 30° C. for 5 h. The mixture was diluted with H$_2$O (10 mL). The pH was adjusted to pH=1.0 with 1M HCl. The solid was collected by filtration and dried under high vacuum to provide the carboxylic acid: ESI: m/z 523.2 (M+H)$^+$. A solution of the solid (0.2 mmol, 100 mg), NH$_4$Cl (4.0 mmol, 200 mg), HATU (0.4 mmol, 160 mg) and Et$_3$N (0.6 mmol, 60 mg) in DMF (2 mL) was stirred at 30° C. for 12 h. The mixture was purified by prep-HPLC using Method B to provide the title compound: $^1$H NMR (400 MHz, DMSO-d$_6$) δ 11.28 (s, 1H), 10.33 (s, 1H), 7.31 (m, 3H), 7.01 (m, 2H), 6.74 (s, 1H), 6.28 (s, 1H), 5.21 (s, 2H), 3.78 (s, 3H), 3.48 (s, 3H), 2.88 (m, 2H), 2.53 (m, 2H), 2.35 (s, 3H); ESI: m/z 522.2 (M+H)$^+$.

Example 476

3-((4-chloro-1H-indol-2-yl)methyl)-1-methyl-6,7,8,9-tetrahydropyrazino[1,2-f]purine-2,4(1H,3H)-dione

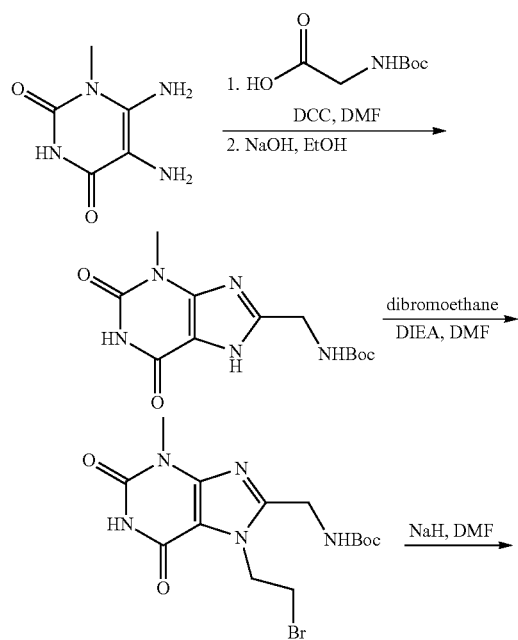

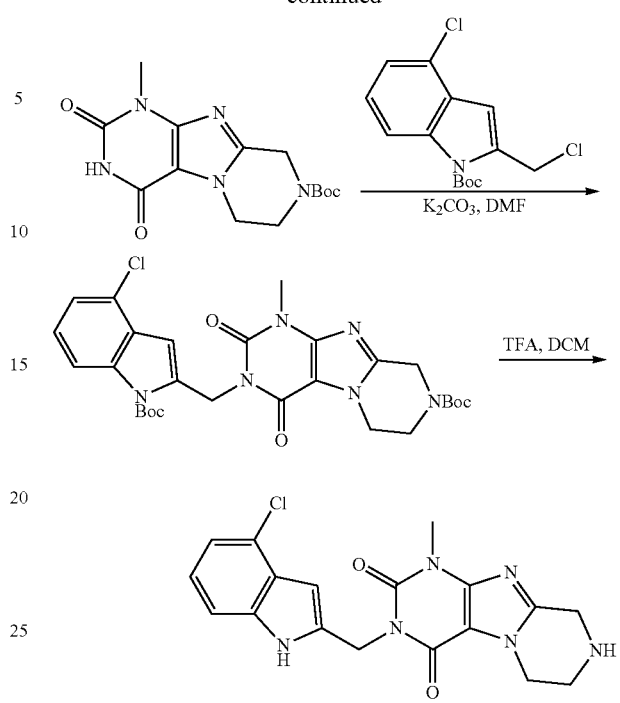

tert-Butyl (3-methyl-2,6-dioxo-2,3,6,7-tetrahydro-1H-purin-8-yl)methylcarbamate

A mixture of 2-(tert-butoxycarbonylamino) acetic acid (1.75 g, 10 mmol), 5,6-diamino-1-methylpyrimidine-2,4(1H,3H)-dione (1.56 g, 10 mmol), DCC (8.25 g, 40 mmol) in DMF (40 mL) was stirred at rt overnight. The mixture was diluted with H$_2$O (300 mL) and stirred for 30 min, then filtered. The filtrate was concentrated in vacuo to give crude product which was purified by flash column chromatography (MeOH/DCM 10%~30%) to give tert-butyl 2-(6-amino-1-methyl-2,4-dioxo-1,2,3,4-tetrahydropyrimidin-5-ylamino)-2-oxoethylcarbamate; ESI: m/z 314.2 (M+H)$^+$. This product (700 mg, 2.23 mmol) and NaOH (1 N aqueous, 9 mL, 9.00 mmol) in EtOH (90 mL) was heated to 50° C. overnight. The solvent was concentrated in vacuo and the residue was diluted with H$_2$O (100 mL). The pH was adjusted to 7.0 with 1N HCl. The precipitate was collected by filtration and dried under vacuum. ESI 296.7 (M+H)$^+$.

tert-Butyl (7-(2-bromoethyl)-3-methyl-2,6-dioxo-2,3,6,7-tetrahydro-1H-purin-8-yl)methylcarbamate

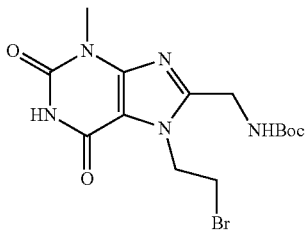 [SMILES: Cn1c(=O)[nH]c(=O)c2c1nc(CNC(=O)OC(C)(C)C)n2CCBr]

A mixture of tert-butyl (3-methyl-2,6-dioxo-2,3,6,7-tetrahydro-1H-purin-8-yl)methylcarbamate (350 mg, 1.2 mmol), 1,2-dibromoethane (223 mg, 1.2 mmol), DIEA (155 mg, 1.2 mmol) in DMF (1.7 mL) was stirred at rt overnight. The mixture was diluted with EA (50 mL) and washed with H$_2$O (20 mL). The aqueous phase was extracted with EA (20 mL*2), the combined organic fractions were washed with brine (30 mL*3), dried over Na$_2$SO$_4$, filtered and concentrated. The residue was purified by flash column chromatography (MeOH/DCM 1%~5%): ESI: m/z 402.1 (M+H)$^+$.

tert-Butyl 1-methyl-2,4-dioxo-1,2,3,4,6,7-hexahydropyrazino[1,2-f]purine-8(9H)-carboxylate

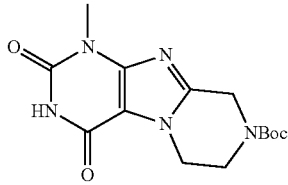 [SMILES: Cn1c(=O)[nH]c(=O)c2c1nc1n2CCN(C(=O)OC(C)(C)C)C1]

A mixture of tert-butyl (7-(2-bromoethyl)-3-methyl-2,6-dioxo-2,3,6,7-tetrahydro-1H-purin-8-yl)methylcarbamate (188 mg, 0.46 mmol), NaH (93 mg, 2.34 mmol) in DMF (15 mL) was stirred at for 2 h. The reaction was quenched with H$_2$O (10 mL) and diluted with EA (30 mL). The aqueous phase was extracted with EA (15 mL*3) and the combined organic fractions were washed with brine (15 mL), dried over Na$_2$SO$_4$, and concentrated. ESI: m/z 322.2 (M+H)$^+$.

tert-butyl 3-((1-(tert-butoxycarbonyl)-4-chloro-1H-indol-2-yl)methyl)-1-methyl-2,4-dioxo-1,2,3,4,6,7-hexahydropyrazino[1,2-f]purine-8(9H)-carboxylate

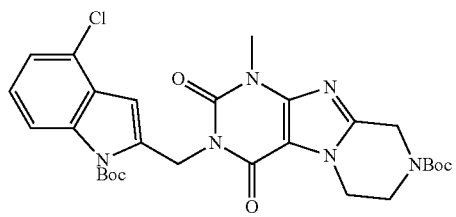 [SMILES: Cn1c(=O)n(Cc2cc3c(Cl)cccc3n2C(=O)OC(C)(C)C)c(=O)c2c1nc1n2CCN(C(=O)OC(C)(C)C)C1]

A mixture of tert-butyl 1-methyl-2,4-dioxo-1,2,3,4,6,7-hexahydropyrazino[1,2-f]purine-8(9H)-carboxylate (140 mg, 0.43 mmol), tert-butyl 4-chloro-2-(chloromethyl)-1H-indole-1-carboxylate (182 mg, 0.63 mmol), potassium bicarbonate (170 mg, 1.14 mmol) in DMF (4 mL) was heated to 50° C. and stirred overnight. The mixture was diluted with EA (60 mL), H$_2$O (30 mL) and partitioned. The aqueous fraction was extracted with EA (30 mL*3). The combined organic fractions were washed with brine (30 mL*2), dried over Na$_2$SO$_4$, concentrated. The residue was purified by flash column chromatography (EA/PE 50%). ESI: m/z 585.2 (M+H)$^+$.

3-((4-Chloro-1H-indol-2-yl)methyl)-1-methyl-6,7,8,9-tetrahydropyrazino[1,2-f]purine-2,4(1H,3H)-dione

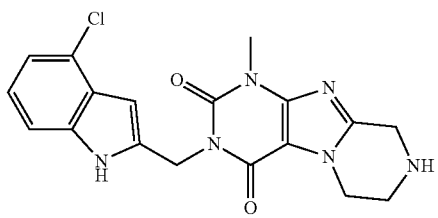 [SMILES: Cn1c(=O)n(Cc2cc3c(Cl)cccc3[nH]2)c(=O)c2c1nc1n2CCNC1]

A mixture of tert-butyl 3-((1-(tert-butoxycarbonyl)-4-chloro-1H-indol-2-yl)methyl)-1-methyl-2,4-dioxo-1,2,3,4,6,7-hexahydropyrazino[1,2-f]purine-8(9H)-carboxylate (200 mg, 0.34 mmol), TFA (195 mg, 1.71 mmol) in DCM (3.4 mL) was stirred at rt for 2 h. The mixture was concentrated and the residue was purified by prep-HPLC using Method B (50-68% ACN); $^1$H NMR (400 MHz, DMSO-d$_6$) δ 11.28 (s, 1H), 7.42-7.26 (m, 1H), 7.09-6.93 (m, 2H), 6.25 (s, 1H), 5.20 (s, 2H), 4.14 (t, J=5.1 Hz, 2H), 3.96 (s, 2H), 3.44 (s, 3H), 3.10 (t, J=5.1 Hz, 2H), 2.82 (s, 1H); ESI: m/z 385.1 (M+H)$^+$.

Example 477

1-((4,7-dichloro-1H-indol-2-yl)methyl)-3,7-dimethyl-8-(pyridin-4-ylamino)-1H-purine-2,6(3H,7H)-dione

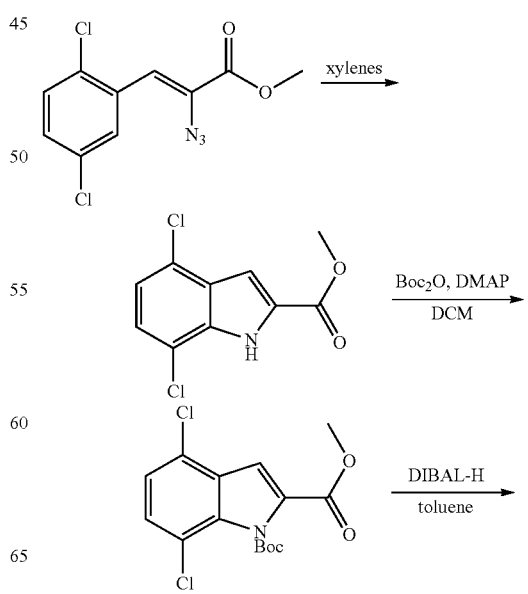

458

Methyl 4,7-dichloro-1H-indole-2-carboxylate

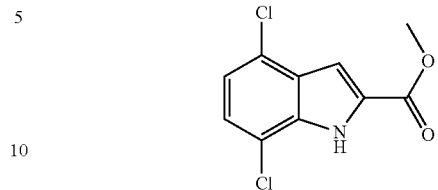

(Z)-methyl 2-azido-3-(2,5-dichlorophenyl)acrylate (11 mmol, 3 g) dissolved in xylene (150 mL) was added dropwise to refluxing xylene (100 mL). The solution was refluxed for 2 h, after that the solvent was evaporated under reduced pressure. The product was recrystallized from PE and DCM. $^1$H NMR (400 MHz, d$_6$-DMSO) δ 12.64 (s, 1H), 7.37 (d, J=8.1 Hz, 1H), 7.21-7.19 (m, 2H), 3.93 (s, 3H).

1-tert-Butyl 2-methyl 4,7-dichloro-1H-indole-1,2-dicarboxylate

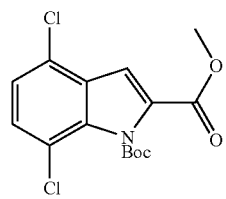

To a solution of methyl 4,7-dichloro-1H-indole-2-carboxylate (3.9 mmol, 0.95 g), DMAP (0.8 mmol, 95 mg) in DCM (20 mL) was added Boc$_2$O (5.9 mmol, 1.28 g). The mixture was stirred at 20° C. for 4 h. The mixture was concentrated and purified by flash chromatography (PE/EA=10/1) to give the product. $^1$H NMR (400 MHz, DMSO-d$_6$) δ 7.52 (d, J=8.1 Hz, 1H), 7.28-7.36 (m, 2H), 3.93 (s, 3H), 1.62 (s, 9H).

tert-Butyl 4,7-dichloro-2-(hydroxymethyl)-1H-indole-1-carboxylate

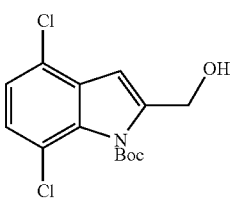

To a solution of 1-tert-butyl 2-methyl 4,7-dichloro-1H-indole-1,2-dicarboxylate (3.6 mmol, 1.25 g) in toluene (10 mL) was added dropwise DIBAL-H (10.9 mmol, 10.9 mL (1 M)) at −78° C., The mixture was allowed to stir for an additional 3 h. The reaction was quenched with 5 mL of MeOH, then 100 mL of potassium sodium tartrate (aq.) was added, and the mixture was extracted with EA (2*100 mL). The combined extracts were washed with brine, dried over MgSO$_4$, filtered and concentrated. The mixture was purified by flash chromatography (PE/EA=5/1) to give the product. ESI: m/z 242.0 (M+H−74)$^+$.

457

-continued

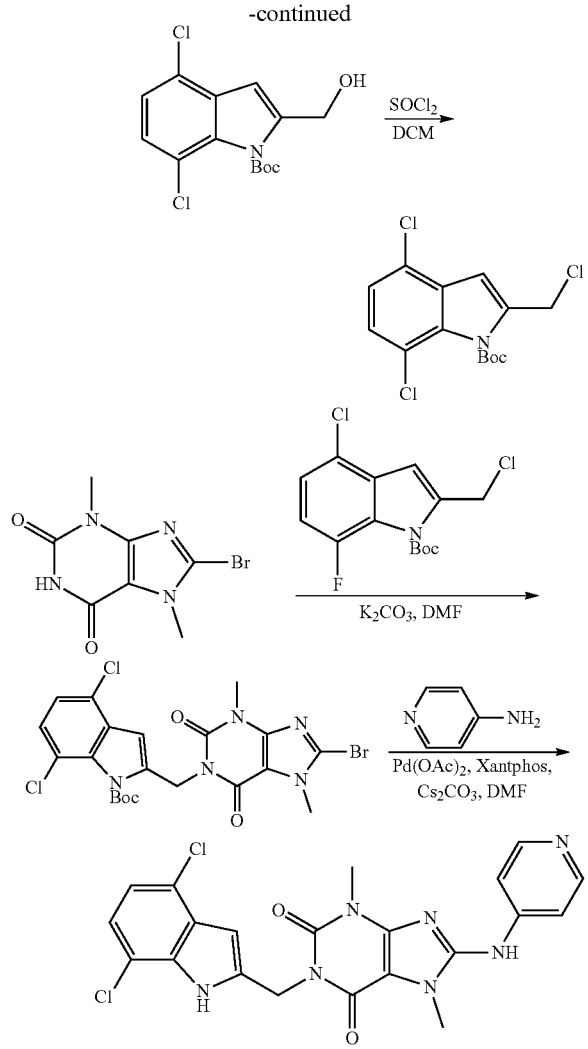

(Z)-Methyl 2-azido-3-(2,5-dichlorophenyl)acrylate

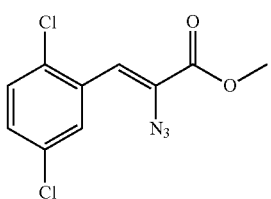 [SMILES: COC(=O)/C(=C/c1cc(Cl)ccc1Cl)N=[N+]=[N-]]

A solution of CH$_3$ONa (230 mmol, 12.4 g) in methanol (150 mL) was cooled at −10° C. Then a mixture of 2,5-dichlorobenzaldehyde (57.5 mmol, 10 g) and ethyl 2-azido-acetate (201 mol, 26 g) in methanol (50 mL) was added dropwise to it over 2 h. The mixture was stirred at −10° C. for an additional 3 h. The mixture was concentrated and the residue was suspended in PE (100 mL). The mixture was filtered and the filter cake was dried to give the title compound. $^1$H NMR (400 MHz, CDCl$_3$): δ 8.20 (d, J=2.4 Hz, 1H), 7.34-7.32 (d, J=8.4 Hz, 1H), 7.24-7.21 (dd, J=8.4 Hz, 2.4 Hz, 1H), 3.94 (s, 3H).

tert-Butyl 4,7-dichloro-2-(chloromethyl)-1H-indole-1-carboxylate

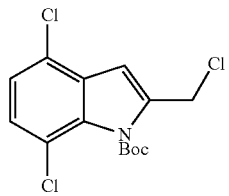

To a cooled solution (0° C.) of tert-butyl 4,7-dichloro-2-(hydroxymethyl)-1H-indole-1-carboxylate (2.2 mmol, 0.70 g) in DCM (10 mL) was added SOCl₂ (6.67 mmol, 1.9 g). The reaction mixture was stirred at 0° C. for 4 h. The mixture was concentrated and the pH was adjusted to 8 by addition of NaHCO₃ aq. solution. The mixture was extracted with DCM (2*100 mL). The combined organic fractions were concentrated and purified by flash chromatography (PE/EA=10/1).

tert-Butyl 2-((8-bromo-3,7-dimethyl-2,6-dioxo-2,3,6,7-tetrahydro-1H-purin-1-yl)methyl)-4,7-dichloro-1H-indole-1-carboxylate

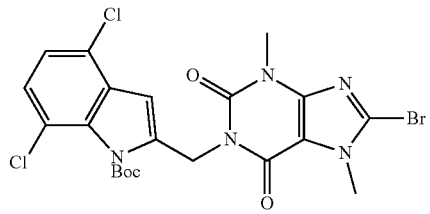 [SMILES: Cn1c(Br)nc2c1c(=O)n(Cc1cc3c(Cl)ccc(Cl)c3n1C(=O)OC(C)(C)C)c(=O)n2C]

The title compound was synthesized in a similar fashion as described in Procedure 4 using tert-butyl 4,7-dichloro-2-(chloromethyl)-1H-indole-1-carboxylate and 8-bromo-3,7-dimethyl-1H-purine-2,6(3H,7H)-dione. The product was purified by flash chromatography (PE/EA=1/2) to give the product. ESI: m/z 456.0 (M+H−100)⁺.

1-((4,7-Dichloro-1H-indol-2-yl)methyl)-3,7-dimethyl-8-(pyridin-4-ylamino)-1H-purine-2,6(3H,7H)-dione

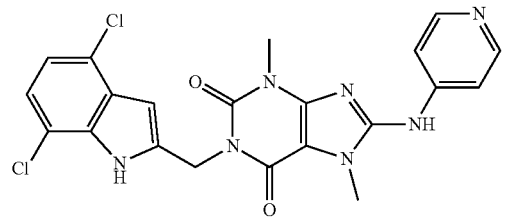 [SMILES: Cn1c(Nc2ccncc2)nc2c1c(=O)n(Cc1cc3c(Cl)ccc(Cl)c3[nH]1)c(=O)n2C]

The title compound was synthesized in a similar fashion as described in Procedure 8A using tert-butyl 2-((8-bromo-3,7-dimethyl-2,6-dioxo-2,3,6,7-tetrahydro-1H-purin-1-yl)methyl)-4,7-dichloro-1H-indole-1-carboxylate and pyridin-4-amine hydrochloride. The product was purified by Prep-HPLC using Method D. 1H NMR (400 MHz, DMSO-d₆) δ 11.79 (s, 1H), 9.95-9.52 (br s, 1H), 8.37 (s, 2H), 7.66 (s, 2H), 7.14 (d, J=8.1 Hz, 1H), 7.05 (d, J=8.1 Hz, 1H), 6.22 (s, 1H), 5.25 (s, 2H), 3.83 (s, 3H), 3.49 (s, 3H); ESI: m/z 470.0 (M+H)⁺.

Example 478 and 481

(E)-1-((4-chloro-1H-indol-2-yl)methyl)-8-(1-(hydroxyimino)ethyl)-3,7-dimethyl-1H-purine-2,6(3H,7H)-dione and (Z)-1-((4-chloro-1H-indol-2-yl)methyl)-8-(1-(hydroxyimino)ethyl)-3,7-dimethyl-1H-purine-2,6(3H,7H)-dione

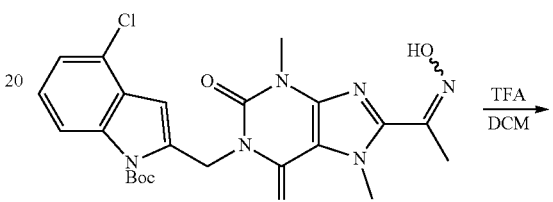

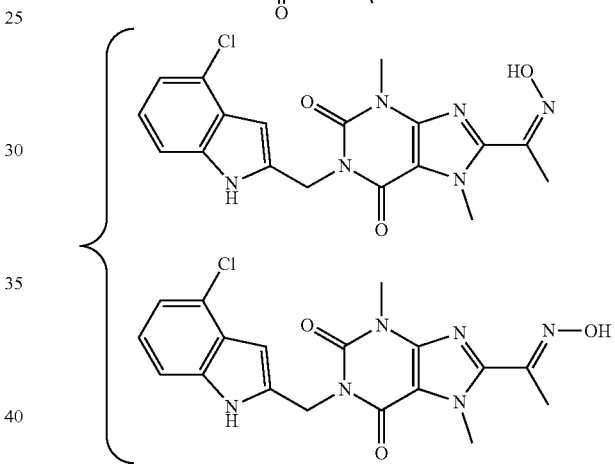

tert-Butyl 4-chloro-2-((8-(1-(hydroxyimino)ethyl)-3,7-dimethyl-2,6-dioxo-2,3,6,7-tetrahydro-1H-purin-1-yl)methyl)-1H-indole-1-carboxylate

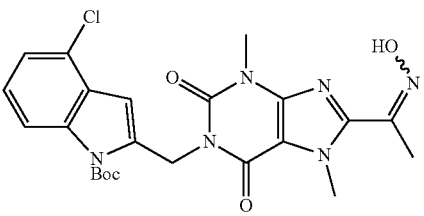 [SMILES: CC(=NO)c1nc2c(c(=O)n(Cc3cc4c(Cl)cccc4n3C(=O)OC(C)(C)C)c(=O)n2C)n1C]

To a solution of tert-butyl 2-((8-acetyl-3,7-dimethyl-2,6-dioxo-2,3,6,7-tetrahydro-1H-purin-1-yl)methyl)-4-chloro-1H-indole-1-carboxylate (0.57 mmol, 280 mg) in pyridine (4 mL) was added NH₂OH·HCl (11.4 mmol, 0.78 g). The mixture was stirred at 50° C. for 2 h. The reaction mixture was diluted with water (20 mL) and extracted with EA (2*100 mL). The combined organic fractions were concentrated and purified by flash chromatography (PE/EA=1/1) to give the title compound. ESI: m/z 501.1 (M+H)⁺.

(E)-1-((4-chloro-1H-indol-2-yl)methyl)-8-(1-(hydroxyimino)ethyl)-3,7-dimethyl-1H-purine-2,6(3H,7H)-dione and (Z)-1-((4-chloro-1H-indol-2-yl)methyl)-8-(1-(hydroxyimino)ethyl)-3,7-dimethyl-1H-purine-2,6(3H,7H)-dione

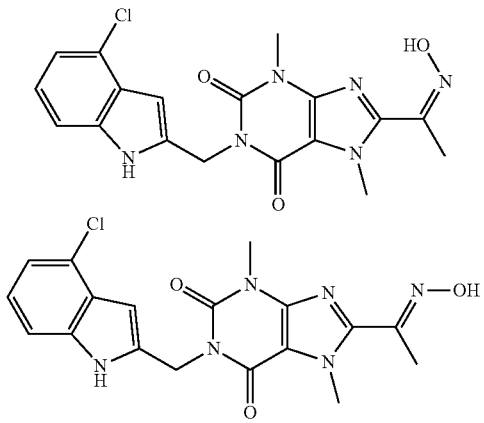

To a solution of tert-butyl 4-chloro-2-((8-(1-(hydroxyimino)ethyl)-3,7-dimethyl-2,6-dioxo-2,3,6,7-tetrahydro-1H-purin-1-yl)methyl)-1H-indole-1-carboxylate (1.8 mmol, 900 mg) in DCM (4 mL) was added TFA (4 mL). The mixture was stirred at 20° C. for 4 h. The pH of the reaction mixture was adjusted to 8 with NaHCO₃ aq. solution. The mixture was extracted with EA (2*50 mL). The combined organic fractions were concentrated and purified by prep-HPLC using method D to give two isomers.

Example 478: (E)-1-((4-chloro-1H-indol-2-yl)methyl)-8-(1-(hydroxyimino)ethyl)-3,7-dimethyl-1H-purine-2,6(3H,7H)-dione or (Z)-1-((4-chloro-1H-indol-2-yl)methyl)-8-(1-(hydroxyimino)ethyl)-3,7-dimethyl-1H-purine-2,6(3H,7H)-dione (retention time 2.051 min): ¹H NMR (400 MHz, DMSO-d₆) δ 12.11 (s, 1H), 11.29 (s, 1H), 7.32 (d, J=7.8 Hz, 1H), 7.11-6.90 (m, 2H), 6.29 (s, 1H), 5.22 (s, 2H), 4.11 (s, 3H), 3.48 (s, 3H), 2.26 (s, 3H); ESI: m/z 401.1 (M+H)⁺.

Example 481: (Z)-1-((4-chloro-1H-indol-2-yl)methyl)-8-(1-(hydroxyimino)ethyl)-3,7-dimethyl-1H-purine-2,6(3H,7H)-dione or (E)-1-((4-chloro-1H-indol-2-yl)methyl)-8-(1-(hydroxyimino)ethyl)-3,7-dimethyl-1H-purine-2,6(3H,7H)-dione (retention time 1.944 min): ¹H NMR (400 MHz, CD₃OD) δ 7.27 (d, J=7.8 Hz, 1H), 7.09-6.85 (m, 2H), 6.46 (s, 1H), 5.33 (s, 2H), 3.89 (s, 3H), 3.57 (s, 3H), 2.23 (s, 3H); ESI: m/z 401.1 (M+H)⁺.

Example 479

Methyl 2-(1-((4-chloro-1H-indol-2-yl)methyl)-3,7-dimethyl-2,6-dioxo-2,3,6,7-tetrahydro-1H-purin-8-yl)-2-methylpropanoate

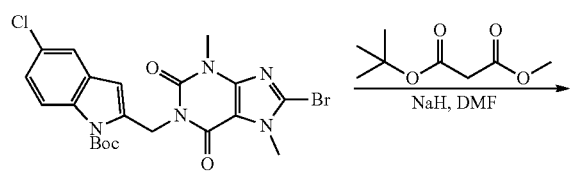

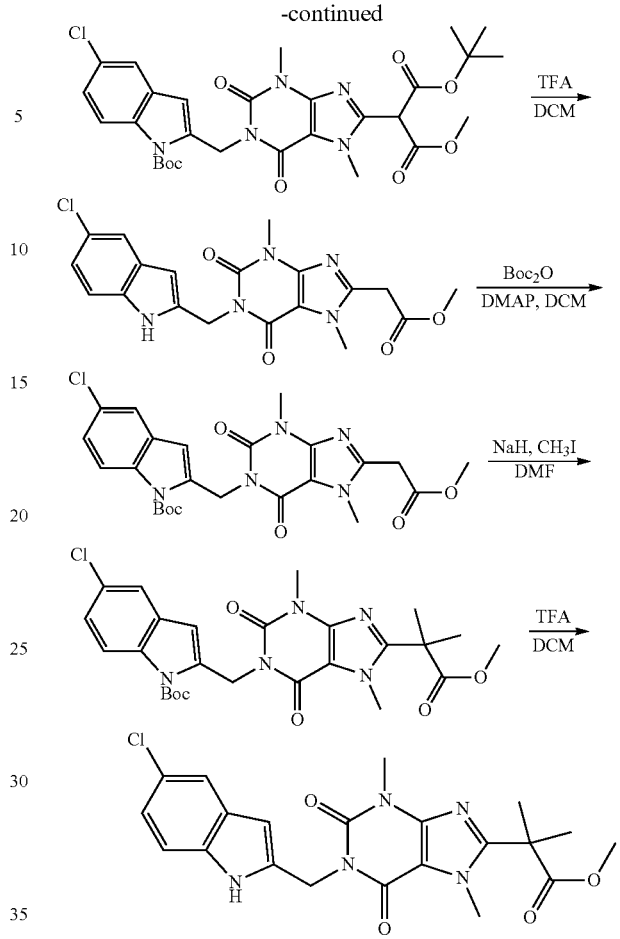

1-tert-butyl 3-methyl 2-(1-((4-chloro-1H-indol-2-yl)methyl)-3,7-dimethyl-2,6-dioxo-2,3,6,7-tetrahydro-1H-purin-8-yl)malonate

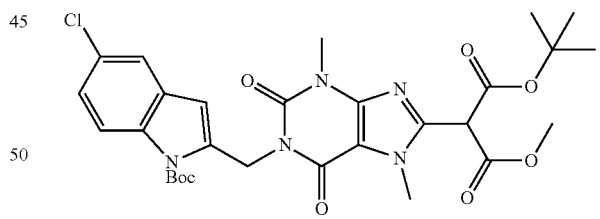

To a suspension of NaH (69 mg, 1.72 mmol) in DMF (3 mL) was added dropwise a solution of tert-butyl methyl malonate (300 mg, 1.72 mmol) in DMF (2 mL) at 0° C. The mixture was stirred for 15 min. Then a suspension of tert-butyl 2-((8-bromo-3,7-dimethyl-2,6-dioxo-2,3,6,7-tetrahydro-1H-purin-1-yl)methyl)-4-chloro-1H-indole-1-carboxylate (600 mg, 1.15 mmol) in DMF (5 mL) was added slowly at 0° C. The resulting mixture was stirred at 80° C. for 6 h. The reaction mixture was poured into water (50 mL) and extracted with EA (3*40 mL). The combined organic fractions were dried over Na₂SO₄, filtered, concentrated and purified by flash chromatography (30~50% EA/PE) to obtain the desired product. ESI: m/z 516 (M+H)⁺.

Methyl 2-(1-((4-chloro-1H-indol-2-yl)methyl)-3,7-dimethyl-2,6-dioxo-2,3,6,7-tetrahydro-1H-purin-8-yl)acetate

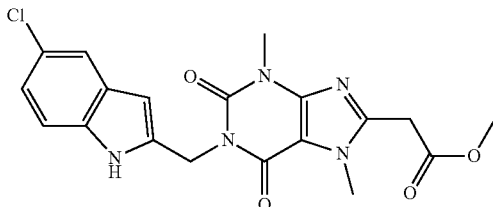

To a solution of 1-tert-butyl 3-methyl 2-(1-((4-chloro-1H-indol-2-yl)methyl)-3,7-dimethyl-2,6-dioxo-2,3,6,7-tetrahydro-1H-purin-8-yl)malonate (600 mg, 1.16 mmol) in DCM (5 mL) was added TFA (5 mL). The reaction was stirred at rt for 2 h. The solvent was removed in vacuo. The residue was purified by flash chromatography (0~5% MeOH/DCM); ESI: m/z 416 (M+H)⁺.

tert-Butyl 4-chloro-2-((8-(2-methoxy-2-oxoethyl)-3,7-dimethyl-2,6-dioxo-2,3-dihydro-6H-purin-1(7H)-yl)methyl)-1H-indole-1-carboxylate

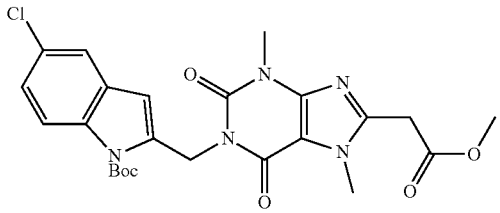 [SMILES: COC(=O)Cc1nc2c(c(=O)n(Cc3cc4cc(Cl)ccc4n3C(=O)OC(C)(C)C)c(=O)n2C)n1C]

A mixture of methyl 2-(1-((4-chloro-1H-indol-2-yl)methyl)-3,7-dimethyl-2,6-dioxo-2,3,6,7-tetrahydro-1H-purin-8-yl)acetate (290 mg, 0.70 mmol), Boc₂O (228 mg, 1.05 mmol) and DMAP (43 mg, 0.35 mmol) in DCM (10 mL) was stirred at rt for 4 h. The mixture was concentrated in vacuo. The residue was purified by flash chromatography (30~50% EA/PE) to obtain the product. ESI: m/z 516 (M+H)⁺.

tert-Butyl 4-chloro-2-((8-(1-methoxy-2-methyl-1-oxopropan-2-yl)-3,7-dimethyl-2,6-dioxo-2,3-dihydro-6H-purin-1(7H)-yl)methyl)-1H-indole-1-carboxylate

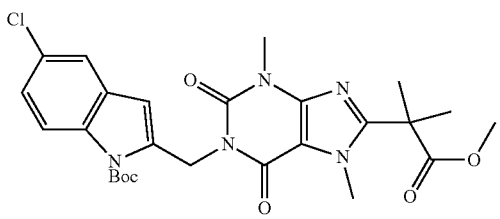 [SMILES: COC(=O)C(C)(C)c1nc2c(c(=O)n(Cc3cc4cc(Cl)ccc4n3C(=O)OC(C)(C)C)c(=O)n2C)n1C]

To a solution of tert-butyl 4-chloro-2-((8-(2-methoxy-2-oxoethyl)-3,7-dimethyl-2,6-dioxo-2,3-dihydro-6H-purin-1(7H)-yl)methyl)-1H-indole-1-carboxylate (120 mg, 0.23 mmol) in DMF (5 mL) was added NaH (28 mg, 0.70 mmol) at 0° C. The mixture was stirred at 0° C. for 30 min, and then MeI (99 mg, 0.70 mmol) was added. The reaction was stirred at rt for 1 h and then quenched with saturated aq. NH₄Cl (5 mL), and extracted with EA (3*20 mL). The combined organic fractions were dried over Na₂SO₄, filtered, concentrated and purified by flash chromatography (3050% EA/PE) to obtain the title compound. ESI: m/z 544 (M+H)⁺.

Methyl 2-(1-((4-chloro-1H-indol-2-yl)methyl)-3,7-dimethyl-2,6-dioxo-2,3,6,7-tetrahydro-1H-purin-8-yl)-2-methylpropanoate

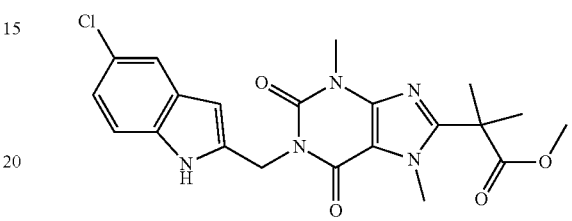

A solution of tert-butyl 4-chloro-2-((8-(1-methoxy-2-methyl-1-oxopropan-2-yl)-3,7-dimethyl-2,6-dioxo-2,3-dihydro-6H-purin-1(7H)-yl)methyl)-1H-indole-1-carboxylate (10 mg, 0.018 mmol) in TFA (0.5 mL) and DCM (2 mL) was stirred at 25° C. for 1 h. The reaction mixture was concentrated in vacuo. The residue was purified by prep-HPLC using Method B (25-75% ACN) to provide the title compound. ¹H NMR (400 MHz, CD₃OD) δ 7.27 (d, J=8.0 Hz, 1H), 7.02-6.98 (m, 2H), 6.45 (s, 1H), 5.32 (s, 2H), 3.85 (s, 3H), 3.77 (s, 3H), 3.58 (s, 3H), 1.68 (s, 6H); ESI: m/z 444.1 (M+H)⁺.

Example 480

2-(1-((4-chloro-1H-indol-2-yl)methyl)-3,7-dimethyl-2,6-dioxo-2,3,6,7-tetrahydro-1H-purin-8-yl)-2-(pyridin-4-yl)acetamide

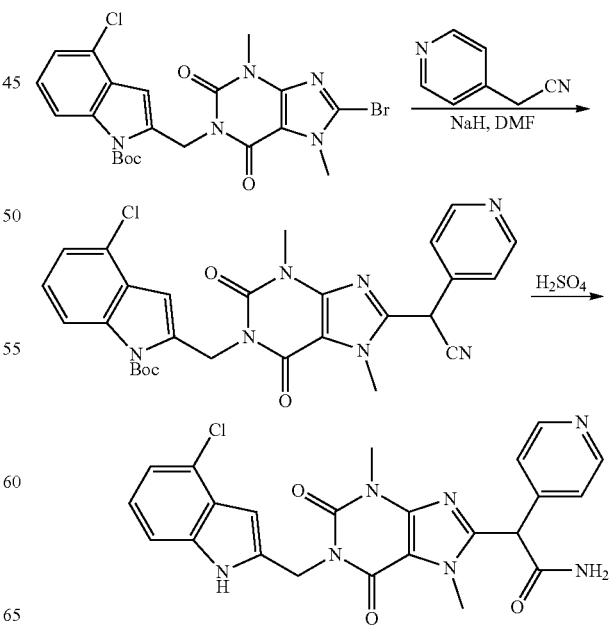

465 tert-Butyl 4-chloro-2-((8-(cyano(pyridin-4-yl)methyl)-3,7-dimethyl-2,6-dioxo-2,3,6,7-tetrahydro-1H-purin-1-yl)methyl)-1H-indole-1-carboxylate

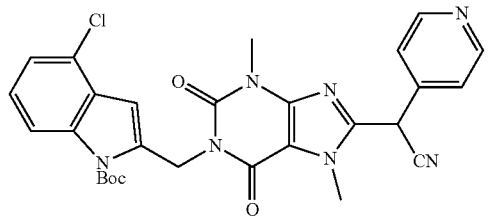 [SMILES: Cn1c(C(C#N)c2ccncc2)nc2c1c(=O)n(Cc1cc3c(Cl)cccc3n1C(=O)OC(C)(C)C)c(=O)n2C]

To a suspension of NaH (46 mg, 1.14 mmol) in DMF (3 mL) was added dropwise a solution of 2-(pyridin-4-yl)acetonitrile (102 mg, 0.86 mmol) in DMF (2 mL) at 0° C. The mixture was stirred for 15 min. then a suspension of tert-butyl 2-((8-bromo-3,7-dimethyl-2,6-dioxo-2,3,6,7-tetrahydro-1H-purin-1-yl)methyl)-4-chloro-1H-indole-1-carboxylate (300 mg, 0.57 mmol) in DMF (5 mL) was added slowly at 0° C. The resulting mixture was stirred for 2 h at 25° C. The reaction mixture was poured into water (50 mL) and extracted with EA (2*40 mL). The combined organic fractions were washed with water (3*50 mL) and brine (1*50 mL), dried over $Na_2SO_4$, concentrated and purified by flash chromatography (30~100% EA/PE) to obtain the product. ESI: m/z 560.2 $(M+H)^+$.

2-(1-((4-Chloro-1H-indol-2-yl)methyl)-3,7-dimethyl-2,6-dioxo-2,3,6,7-tetrahydro-1H-purin-8-yl)-2-(pyridin-4-yl)acetamide

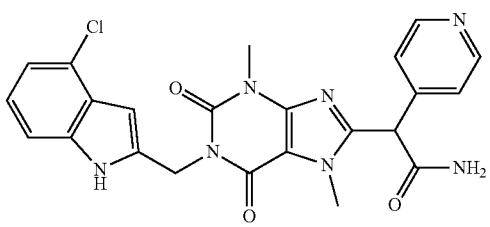 [SMILES: Cn1c(C(C(N)=O)c2ccncc2)nc2c1c(=O)n(Cc1cc3c(Cl)cccc3[nH]1)c(=O)n2C]

A solution of tert-butyl 4-chloro-2-((8-(cyano(pyridin-4-yl)methyl)-3,7-dimethyl-2,6-dioxo-2,3,6,7-tetrahydro-1H-purin-1-yl)methyl)-1H-indole-1-carboxylate (45 mg, 0.081 mmol) in conc. $H_2SO_4$ (1 mL) was stirred for 1 h at 25° C. The reaction mixture was poured into water (20 mL) and the pH was adjusted to pH=9~10 with aq $NaHCO_3$. The mixture was extracted with EA (2*20 mL). The combined organic fractions were washed with brine (1*30 mL), dried over $Na_2SO_4$, filtered and concentrated. The residue was purified by prep-HPLC using Method B (25-75% ACN) to provide the title compound. $^1$H NMR (400 MHz, DMSO-$d_6$) δ 11.28 (s, 1H), 8.55 (d, J=6.0 Hz, 2H), 7.70 (s, 1H), 7.47-7.31 (m, 4H), 7.03-7.00 (m, 2H), 6.26 (s, 1H), 5.37 (s, 1H), 5.21 (s, 2H), 3.85 (s, 3H), 3.41 (s, 3H); ESI 478.1 $(M+H)^+$.

466

Example 483

1-((4-chloro-1-methyl-1H-indol-5-yl)methyl)-3,7-dimethyl-8-(pyridin-4-ylamino)-1H-purine-2,6(3H,7H)-dione

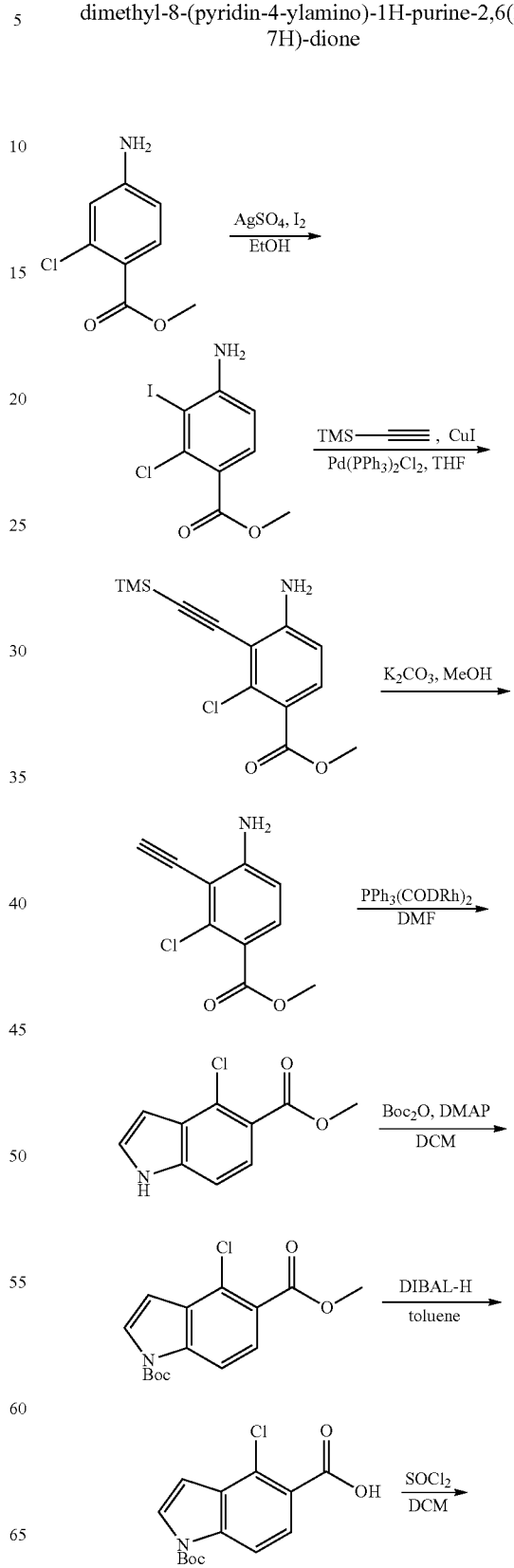

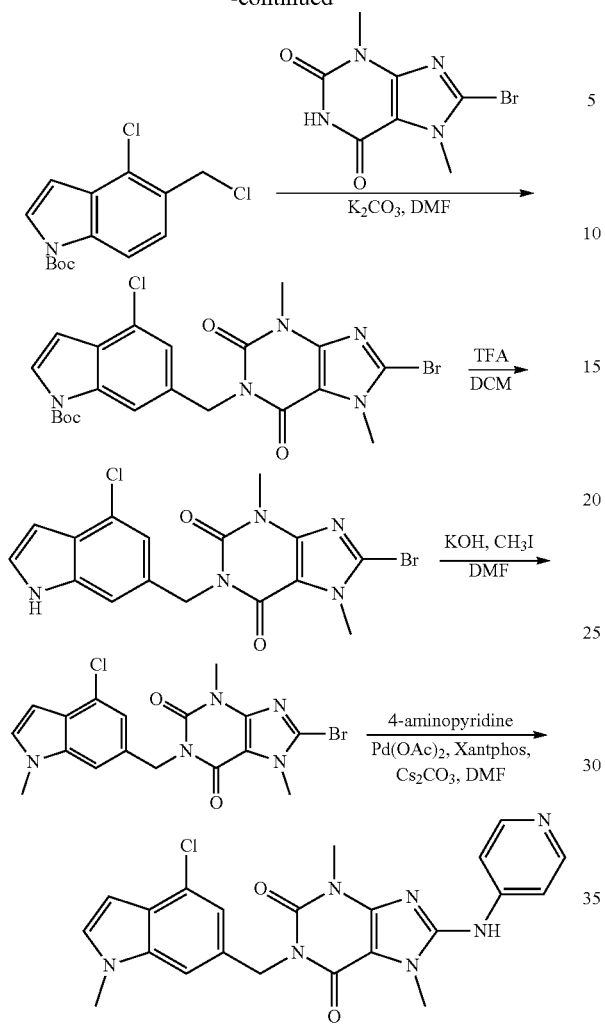

Methyl 4-amino-2-chlorobenzoate

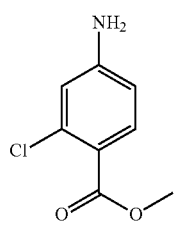

To a solution of 4-amino-2-chlorobenzoic acid (116 mmol, 20 g) in MeOH (200 mL) was added SOCl$_2$ (234 mmol, 27 g) at 0° C. The ice-water bath was removed after the addition and the mixture was heated to reflux until the starting material had disappeared, as indicated by LC-MS. The reaction was cooled to rt and the solvent and excess of SOCl$_2$ were evaporated under reduced pressure. The residue was suspended in 10 percent aqueous Na$_2$CO$_3$ solution. The precipitate that formed was filtered and washed with water until the washes became neutral. The filter cake was then re-dissolved in 500 mL of ethyl acetate. The mixture was washed with water, brine, and dried over anhydrous Na$_2$SO$_4$. The ethyl acetate was evaporated under reduced pressure to give the product. ESI: m/z 186.1 (M+H)$^+$.

Methyl 4-amino-2-chloro-3-iodobenzoate

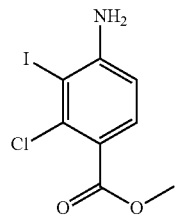

To a solution of methyl 4-amino-2-chlorobenzoate (40 mmol, 7.4 mg) in EtOH (350 mL) was added Ag$_2$SO$_4$ (40 mmol, 145 12.5 g) and I$_2$ (42 mmol, 10.8 mg). The mixture was allowed to stir for an additional 3 h. The mixture was concentrated under reduced pressure. The residue was dissolved in 200 mL of ethyl acetate and the mixture was washed with water, brine, and dried over anhydrous Na$_2$SO$_4$. The mixture was concentrated under reduced pressure to give the product. ESI: m/z 312.0 (M+H)$^+$.

Methyl 4-amino-2-chloro-3-((trimethylsilyl)ethynyl)benzoate

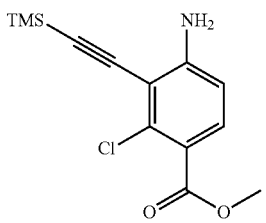 [SMILES: COC(=O)c1ccc(N)c(C#C[Si](C)(C)C)c1Cl]

To a solution of methyl 4-amino-2-chloro-3-iodobenzoate (18 mmol, 6 g) in THF (60 mL) was added CuI (2 mmol, 360 mg), Pd(PPh$_3$)$_2$Cl$_2$ (2 mmol, 1350 mg) and ethynyltrimethylsilane (30 mmol, 3 g). The mixture was allowed to stir for 1 h. The mixture was poured into water and extracted with EA (2*100 mL). The combined organic fractions were dried with Na$_2$SO$_4$, filtered and concentrated. The residue was purified by flash chromatography (PE/EA=5/1) to give the product. ESI: m/z 282.1 (M+H)$^+$.

Methyl 4-amino-2-chloro-3-ethynylbenzoate

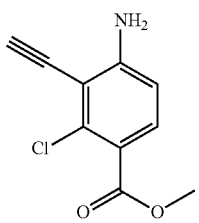

To a solution of methyl 4-amino-2-chloro-3-((trimethylsilyl)ethynyl)benzoate (6.0 mmol, 1.7 g) in MeOH (30 mL) was added K$_2$CO$_3$ (6.6 mmol, 0.9 g). The mixture was allowed to stir for 1 h, and then poured into water and extracted with EA (2*60 mL). The combined organic fractions were dried with Na₂SO₄, filtered and concentrated. The residue was purified by flash chromatography (PE/EA=4/1) to give the title compound. ESI: m/z 210.1 (M+H)⁺.

Methyl 4-chloro-1H-indole-5-carboxylate

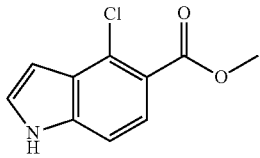

To a solution of methyl 4-amino-2-chloro-3-ethynylbenzoate (4.8 mmol, 1.0 g) in DMF (30 mL) was added PPh₃ (3.8 mmol, 1.0 mg) and (CODRhCl)₂ (0.24 mmol, 110 mg). The mixture was allowed to stir for 1 h at 80° C. The mixture was poured into water and extracted with EA (2*50 mL). The combined organic fractions were dried with Na₂SO₄, filtered and concentrated. The residue was purified by flash chromatography (PE/EA=3/1) to give the product. ESI: m/z 210.1 (M+H)⁺.

1-tert-Butyl 5-methyl 4-chloro-1H-indole-1,5-dicarboxylate

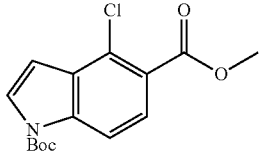 [SMILES: COC(=O)c1ccc2c(ccn2C(=O)OC(C)(C)C)c1Cl]

To a solution of methyl 4-chloro-1H-indole-5-carboxylate (3.8 mmol, 800 mg), Boc₂O (5.7 mmol, 1250 mg) and DMAP (0.6 mmol, 74 mg) in DCM (3 mL) was stirred at rt for 1 h. The mixture was purified by flash chromatography (PE/EA=10/1) to give the product. ESI: m/z 310.1 (M+H)⁺.

tert-Butyl 4-chloro-5-(hydroxymethyl)-1H-indole-1-carboxylate

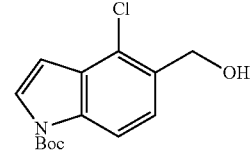 [SMILES: CC(C)(C)OC(=O)n1ccc2c(Cl)c(CO)ccc21]

To a solution of 1-tert-butyl 5-methyl 4-chloro-1H-indole-1,5-dicarboxylate (2.9 mmol, 900 g) in toluene (20 mL) was added dropwise DIBAL-H (8.7 mmol, 8.7 mL (1 M)) at −78° C. After the addition was complete the mixture was allowed to stir for an additional 3 h. The reaction was quenched with 2 mL of MeOH, and diluted with 150 mL of potassium sodium tartrate (aq.). The mixture was extracted with EA (2*40 mL). The combined organic fractions were washed with brine, dried over MgSO₄, filtered and concentrated. The mixture was purified by flash chromatography (PE/EA=6/1) to give the product. ESI: m/z 304.1 (M+Na)⁺.

tert-Butyl 4-chloro-5-(chloromethyl)-1H-indole-1-carboxylate

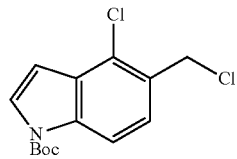 [SMILES: CC(C)(C)OC(=O)n1ccc2c(Cl)c(CCl)ccc21]

To a solution of tert-butyl 4-chloro-5-(hydroxymethyl)-1H-indole-1-carboxylate (1.6 mmol, 450 mg) in DCM (20 mL) was added dropwise SOCl₂ (6.4 mmol, 760 mg) at 0° C. The mixture was allowed to stir for 3 h. The mixture was concentrated under reduced pressure to give the product, which was used directly in next step without further purification.

tert-Butyl 5-((8-bromo-3,7-dimethyl-2,6-dioxo-2,3,6,7-tetrahydro-1H-purin-1-yl)methyl)-4-chloro-1H-indole-1-carboxylate

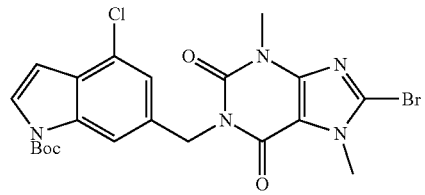 [SMILES: Cn1c(Br)nc2c1c(=O)n(Cc1cc(Cl)c3ccn(C(=O)OC(C)(C)C)c3c1)c(=O)n2C]

A solution of tert-butyl 4-chloro-5-(chloromethyl)-1H-indole-1-carboxylate (1.4 mmol, 430 mg), 8-bromo-3,7-dimethyl-1H-purine-2,6(3H,7H)-dione (1.4 mmol, 360 mg) and K₂CO₃ (4.2 mmol, 580 mg) in DMF (30 mL) was stirred and heated to 50° C. overnight. The mixture was poured into water and extracted with EA (2*50 mL). The combined organic fractions were dried with Na₂SO₄, filtered and concentrated. The residue was purified by flash chromatography (DCM/MeOH=10/1) to give the title compound. ESI: m/z 522.0 (M+H)⁺.

8-Bromo-1-((4-chloro-1-methyl-1H-indol-5-yl)methyl)-3,7-dimethyl-1H-purine-2,6(3H,7H)-dione

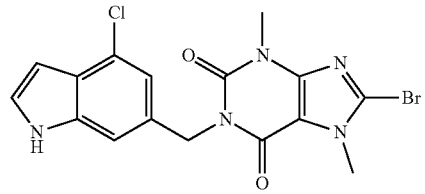 [SMILES: Cn1c(Br)nc2c1c(=O)n(Cc1cc(Cl)c3cc[nH]c3c1)c(=O)n2C]

To a solution of 8-bromo-1-((4-chloro-1H-indol-5-yl)methyl)-3,7-dimethyl-1H-purine-2,6(3H,7H)-dione (0.24 mmol, 100 mg) in DMF (10 mL) was added KOH (0.48 mmol, 27 mg) and CH₃I (0.48 mmol, 68 mg). The mixture was stirred and heated to 50° C. for 5 h. The mixture was poured into water and extracted with EA (2*50 mL). The combined organic fractions were dried with Na₂SO₄, filtered and concentrated. The residue was purified by flash chromatography (DCM/MeOH=6/1) to give the product. ESI: m/z 436.0 (M+H)⁺.

1-((4-Chloro-1-methyl-1H-indol-5-yl)methyl)-3,7-dimethyl-8-(pyridin-4-ylamino)-1H-purine-2,6(3H,7H)-dione

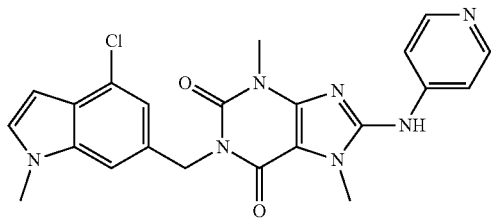 [SMILES: Cn1ccc2c(Cl)cc(Cn3c(=O)c4c(nc(Nc5ccncc5)n4C)n(C)c3=O)cc21]

To a solution of 8-bromo-1-((4-chloro-1-methyl-1H-indol-5-yl)methyl)-3,7-dimethyl-1H-purine-2,6(3H,7H)-dione (0.14 mmol, 60 mg) in DMF (5 mL) was added pyridin-4-amine hydrochloride (0.28 mmol, 37 mg), Pd(OAc)₂ (0.015 mmol, 4 mg), Xantphos (0.03 mmol, 16 mg) and Cs₂CO₃ (0.42 mmol, 130 mg). The mixture was placed in microware reactor (100° C., 2 h). The mixture was poured into water and extracted with EA (2*50 mL). The combined organic fractions were dried with Na₂SO₄, filtered and concentrated. The residue was purified by flash chromatography (DCM/MeOH=6/1) to give the title compound: ¹H NMR (400 MHz, CDCl₃) δ 8.49 (s, 1H), 7.45 (s, 1H), 7.12 (d, J=8.5 Hz, 1H), 7.03 (dd, J=8.1, 5.9 Hz, 1H), 6.57 (s, 1H), 5.48 (s, 1H), 5.35 (br s, 1H), 3.86 (s, 2H), 3.74 (s, 2H), 3.61 (s, 2H); ESI: m/z 450.2 (M+H)⁺.

Example 484

1-((4-chloro-1H-indol-5-yl)methyl)-3,7-dimethyl-8-(pyridin-4-ylamino)-1H-purine-2,6(3H,7H)-dione

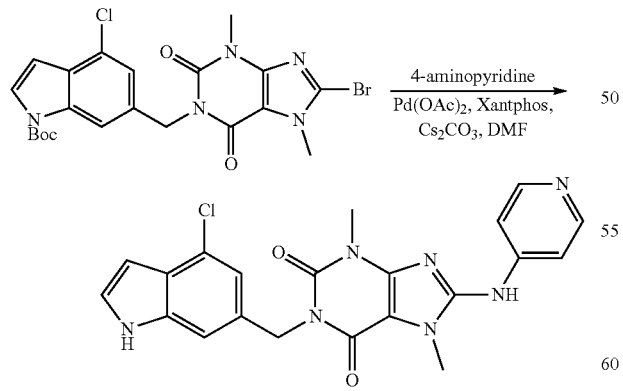

The title compound was synthesized in a similar fashion as described in Procedure 8a using tert-butyl 5-((8-bromo-3,7-dimethyl-2,6-dioxo-2,3,6,7-tetrahydro-1H-purin-1-yl)methyl)-4-chloro-1H-indole-1-carboxylate and pyridin-4-amine hydrochloride. The product was purified by flash chromatography (DCM/MeOH=6/1) to give the title compound. ¹H NMR (400 MHz, DMSO-d₆) δ 11.35 (s, 1H), 9.70 (s, 1H), 8.40 (s, 2H), 7.70 (s, 2H), 7.43 (s, 1H), 7.27 (d, J=8.4 Hz, 1H), 6.72 (d, J=8.5 Hz, 1H), 6.47 (s, 1H), 5.23 (s, 2H), 3.83 (s, 3H), 3.47 (s, 3H); ESI: m/z 436.1 (M+H)⁺.

Example 485

8-(1-aminopropan-2-yl)-1-((4-chloro-1H-indol-2-yl)methyl)-3,7-dimethyl-1H-purine-2,6(3H,7H)-dione

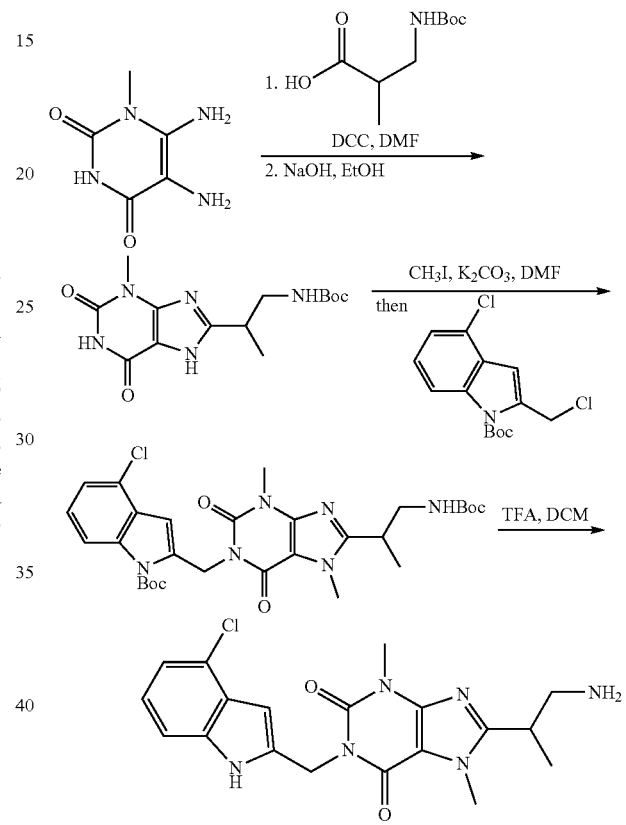

tert-Butyl 2-(3-methyl-2,6-dioxo-2,3,6,7-tetrahydro-1H-purin-8-yl)propylcarbamate

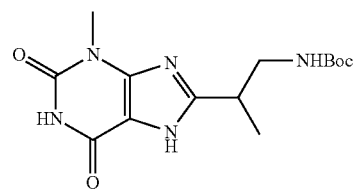 [SMILES: CC(CNC(=O)OC(C)(C)C)c1nc2c([nH]1)c(=O)[nH]c(=O)n2C]

To a mixture of 3-(tert-butoxycarbonylamino)-2-methylpropanoic acid (3.50 g, 17.2 mmol) and 5,6-diamino-1-methylpyrimidine-2,4(1H,3H)-dione (2.69 g, 17.2 mmol) in DMF (20 mL) was added DCC (10.66 g, 51.7 mmol). The reaction mixture was stirred at 50° C. for 15 h under N₂ atmosphere. Water (50 mL) was added and the solid was removed by filtration. The filtrate was concentrated in vacuo. The residue was purified by flash chromatography (MeOH/DCM=1/10) to give tert-butyl 3-(6-amino-1-methyl-2,4-dioxo-1,2,3,4-tetrahydropyrimidin-5-ylamino)-2-methyl-3-oxopropylcarbamate: ESI: m/z 342.0 (M+H)+.

To a solution of tert-butyl 3-(6-amino-1-methyl-2,4-dioxo-1,2,3,4-tetrahydropyrimidin-5-ylamino)-2-methyl-3-oxopropylcarbamate (200 mg, 0.59 mmol) in EtOH (29 mL) was added aqueous NaOH (1N, 2.9 mL, 2.9 mmol). The mixture was heated to 50° C. and held at this temperature for 16 h. Aqueous HCl (1N) was added to pH~5. The organic solvent was evaporated in vacuo and the aqueous residue was extracted with EA (20 mL*3). The combined organic fractions were concentrated. The residue was purified by flash column chromatography (DCM:MeOH=30:1) to give the title compound. ESI: 324.0 m/z (M+H)+.

tert-Butyl 2-((8-(1-(tert-butoxycarbonylamino)propan-2-yl)-3,7-dimethyl-2,6-dioxo-2,3-dihydro-6H-purin-1(7H)-yl)methyl)-4-chloro-1H-indole-1-carboxylate

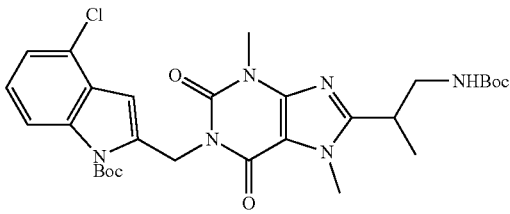 [SMILES: CC(CNC(=O)OC(C)(C)C)c1nc2c(c(=O)n(Cc3cc4c(Cl)cccc4n3C(=O)OC(C)(C)C)c(=O)n2C)n1C]

To a solution of tert-butyl 2-(3-methyl-2,6-dioxo-2,3,6,7-tetrahydro-1H-purin-8-yl)propylcarbamate (80 mg, 0.25 mmol) in DMF (4 mL) was added $K_2CO_3$ (103 mg, 0.74 mmol) and MeI (35 mg, 0.25 mmol). The reaction mixture was stirred at 25° C. for 2 h, then tert-butyl 4-chloro-2-(chloromethyl)-1H-indole-1-carboxylate (75 mg, 0.25 mmol) was added and the mixture was stirred at 50° C. for 16 h. The mixture was diluted with $H_2O$ (20 mL). The solid was collected by filtration and purified by flash chromatography (MeOH/DCM=1/20) to give the product. ESI: 601.0 (M+H)+.

8-(1-Aminopropan-2-yl)-1-((4-chloro-1H-indol-2-yl)methyl)-3,7-dimethyl-1H-purine-2,6(3H,7H)-dione

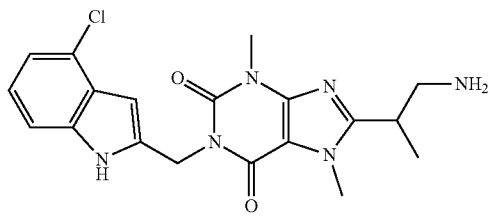 [SMILES: CC(CN)c1nc2c(c(=O)n(Cc3cc4c(Cl)cccc4[nH]3)c(=O)n2C)n1C]

A solution of tert-butyl 2-((8-(1-(tert-butoxycarbonylamino)propan-2-yl)-3,7-dimethyl-2,6-dioxo-2,3-dihydro-6H-purin-1(7H)-yl)methyl)-4-chloro-1H-indole-1-carboxylate (50 mg, 0.083 mmol) in DCM (5 mL) was treated with TFA (1 mL). The reaction mixture was stirred at 25° C. for 2 h. The reaction mixture was concentrated and purified by preparative HPLC using Method F (25-45% ACN) to provide the title compound: $^1$H NMR (400 MHz, $CD_3OD$) δ 7.20 (d, J=7.6 Hz, 1H), 6.94-6.87 (m, 2H), 6.29 (s, 1H), 5.20 (s, 2H), 3.87 (s, 3H), 3.45 (s, 3H), 3.05-2.85 (m, 3H), 1.19 (d, J=6.8 Hz, 3H); ESI: m/z 401.1 (M+H)+.

MTHFD2 Activity Assay

Human MTHFD2 (residues 36-350 in Uniport ID P13995) was expressed as an N-terminal $His_6$ tagged protein and purified in *E. coli* using nickel capture followed by size-exclusion chromatography.

MTHFD2 dehydrogenase activity oxidizes methylene tetrahyrofolate to methenyl-tetrahydrofolate with the concomitant reduction of NAD to NADH. MTHFD2 dehydrogenase activity was followed by coupling the generation of NADH to diaphorase catalyzed oxidation of resazurin to fluorescent resorufin. Briefly, control (DMSO) or compound was incubated with 0.2 nM MTHFD2 for 15 minutes in 10.5 µl assay buffer containing 100 mM Hepes, pH 8.0, 5 mM $MgCl_2$, 5 mM $KH_2PO_4$, 0.05% BSA, 0.01% Tween-20 in a 384 well Griener, low volume, black plate. 10 µl of substrate buffer containing 70 µM $CH_2$-THF, 1 mM $NAD^+$, 100 µM Resazurin and 0.42 mg/ml diaphorase was then added to initiate the reaction and the reaction plate was incubated for 30 minutes. 5 µl of 250 mM EDTA was then added to each well to stop the reaction and MTHFD2 activity was quantified by measuring resorufin fluorescence emission at 598 nm following excitation at 525 nm. Activity in positive control wells containing the complete reaction mixture and DMSO alone was set to 100% while activity in negative control wells with the complete reaction mix without MTHFD2 was set to 0%. 11 concentrations of each compound were tested and the fluorescent data at each concentration was normalized to the positive and negative controls and represented as % inhibition. Median inhibitory concentration ($IC_{50}$) was calculated by fitting % inhibition at each concentration to a 4 parameter logistic fit equation using Graphpad Prizm.

Table 5 shows the inhibitory activity ($IC_{50}$ and/or binding constant) of selected compounds of this invention. The compound numbers correspond to the compound numbers in Table A (i.e., the example numbers). Compounds having an activity designated as "A" provided inhibitory activity ($IC_{50}$ and/or binding constant) of 0.01-1 µM; compounds designated as "B" provided inhibitory activity ($IC_{50}$ and/or binding constant) of 1-5 µM; compounds designated as "C" provided inhibitory activity ($IC_{50}$ and/or binding constant) of 5-10 µM and compounds designated as "D" provided inhibitory activity ($IC_{50}$ and/or binding constant)>10 µM.

TABLE 5

| MTHFD2 Activity of Exemplary Compounds | |
| --- | --- |
| Compound # | Average MTHFD2 Activity |
| 1 | B |
| 2 | D |
| 3 | D |
| 4 | D |
| 5 | D |
| 6 | D |
| 7 | D |
| 8 | A |
| 9 | A |
| 10 | D |
| 11 | D |
| 12 | D |
| 13 | A |
| 14 | A |
| 15 | C |
| 16 | D |
| 17 | C |
| 18 | C |

TABLE 5-continued

MTHFD2 Activity of Exemplary Compounds

| Compound # | Average MTHFD2 Activity |
|---|---|
| 19 | D |
| 20 | C |
| 21 | B |
| 22 | A |
| 23 | B |
| 24 | C |
| 25 | B |
| 26 | B |
| 27 | A |
| 28 | A |
| 29 | D |
| 30 | D |
| 31 | B |
| 32 | A |
| 33 | A |
| 34 | D |
| 35 | B |
| 36 | C |
| 37 | A |
| 38 | B |
| 39 | B |
| 40 | B |
| 41 | A |
| 42 | B |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | C |
| 57 | C |
| 58 | B |
| 59 | B |
| 60 | B |
| 61 | B |
| 62 | D |
| 63 | A |
| 64 | A |
| 65 | B |
| 66 | A |
| 67 | A |
| 68 | B |
| 69 | A |
| 70 | A |
| 71 | A |
| 72 | D |
| 73 | B |
| 74 | A |
| 75 | A |
| 76 | B |
| 77 | B |
| 78 | A |
| 79 | A |
| 80 | A |
| 81 | A |
| 82 | A |
| 83 | A |
| 84 | B |
| 85 | B |
| 86 | A |
| 87 | A |
| 88 | A |
| 89 | A |
| 90 | B |
| 91 | A |
| 92 | A |
| 93 | A |
| 94 | A |
| 95 | B |
| 96 | B |
| 97 | B |
| 98 | C |
| 99 | B |
| 100 | B |
| 101 | C |
| 102 | C |
| 103 | B |
| 104 | B |
| 105 | D |
| 106 | B |
| 107 | D |
| 108 | B |
| 109 | A |
| 110 | B |
| 111 | A |
| 112 | B |
| 113 | D |
| 114 | A |
| 115 | B |
| 116 | B |
| 117 | B |
| 118 | B |
| 119 | A |
| 120 | D |
| 121 | A |
| 122 | A |
| 123 | C |
| 124 | A |
| 125 | A |
| 126 | A |
| 127 | B |
| 128 | D |
| 129 | B |
| 130 | B |
| 131 | B |
| 132 | A |
| 133 | B |
| 134 | B |
| 135 | B |
| 136 | A |
| 137 | C |
| 138 | A |
| 139 | B |
| 140 | A |
| 141 | B |
| 142 | B |
| 143 | B |
| 144 | B |
| 145 | D |
| 146 | A |
| 147 | A |
| 148 | A |
| 149 | D |
| 150 | A |
| 151 | D |
| 152 | B |
| 153 | C |
| 154 | B |
| 155 | A |
| 156 | B |
| 157 | B |
| 158 | A |
| 159 | A |
| 160 | B |
| 161 | B |
| 162 | C |
| 163 | B |
| 164 | A |
| 165 | B |
| 166 | D |
| 167 | D |
| 168 | D |
| 169 | A |
| 170 | B |

TABLE 5-continued

MTHFD2 Activity of Exemplary Compounds

| Compound # | Average MTHFD2 Activity |
|---|---|
| 171 | B |
| 172 | A |
| 173 | A |
| 174 | A |
| 175 | A |
| 176 | A |
| 177 | A |
| 178 | A |
| 179 | A |
| 180 | D |
| 181 | A |
| 182 | A |
| 183 | A |
| 184 | A |
| 185 | A |
| 186 | A |
| 187 | A |
| 188 | B |
| 189 | A |
| 190 | A |
| 191 | A |
| 192 | B |
| 193 | A |
| 194 | B |
| 195 | B |
| 196 | A |
| 197 | A |
| 198 | A |
| 199 | B |
| 200 | B |
| 201 | A |
| 202 | B |
| 203 | C |
| 204 | A |
| 205 | A |
| 206 | A |
| 207 | B |
| 208 | A |
| 209 | A |
| 210 | B |
| 211 | A |
| 212 | B |
| 213 | A |
| 214 | A |
| 215 | A |
| 216 | A |
| 217 | A |
| 218 | A |
| 219 | A |
| 220 | A |
| 221 | B |
| 222 | A |
| 223 | B |
| 224 | A |
| 225 | A |
| 226 | A |
| 227 | B |
| 228 | B |
| 229 | A |
| 230 | A |
| 231 | C |
| 232 | D |
| 233 | C |
| 234 | B |
| 235 | B |
| 236 | B |
| 237 | B |
| 238 | D |
| 239 | B |
| 240 | B |
| 241 | C |
| 242 | B |
| 243 | D |
| 244 | B |
| 245 | A |
| 246 | D |
| 247 | B |
| 248 | C |
| 249 | D |
| 250 | C |
| 251 | D |
| 252 | D |
| 253 | D |
| 254 | A |
| 255 | A |
| 256 | B |
| 257 | B |
| 258 | A |
| 259 | A |
| 260 | A |
| 261 | A |
| 262 | D |
| 263 | C |
| 264 | A |
| 265 | A |
| 266 | A |
| 267 | B |
| 268 | A |
| 269 | A |
| 270 | B |
| 271 | A |
| 272 | A |
| 273 | B |
| 274 | B |
| 275 | A |
| 276 | A |
| 277 | A |
| 278 | A |
| 279 | A |
| 281 | B |
| 282 | A |
| 283 | A |
| 284 | A |
| 285 | A |
| 286 | A |
| 287 | A |
| 288 | A |
| 289 | A |
| 290 | C |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | B |
| 304 | A |
| 305 | A |
| 306 | A |
| 307 | B |
| 308 | A |
| 309 | A |
| 310 | A |
| 311 | A |
| 312 | A |
| 313 | A |
| 314 | A |
| 315 | A |
| 316 | A |
| 317 | A |
| 318 | A |
| 319 | A |
| 320 | A |
| 321 | A |
| 322 | A |
| 323 | B |

TABLE 5-continued

MTHFD2 Activity of Exemplary Compounds

| Compound # | Average MTHFD2 Activity |
|---|---|
| 324 | B |
| 325 | A |
| 326 | A |
| 327 | A |
| 328 | A |
| 329 | A |
| 330 | A |
| 331 | A |
| 332 | A |
| 333 | A |
| 334 | B |
| 335 | B |
| 336 | A |
| 337 | B |
| 338 | C |
| 339 | A |
| 340 | A |
| 341 | C |
| 342 | A |
| 343 | A |
| 344 | B |
| 345 | A |
| 346 | A |
| 347 | A |
| 348 | C |
| 349 | A |
| 350 | C |
| 351 | A |
| 352 | B |
| 353 | B |
| 354 | A |
| 355 | A |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | A |
| 369 | A |
| 370 | A |
| 371 | A |
| 372 | A |
| 373 | A |
| 374 | D |
| 375 | A |
| 376 | A |
| 377 | A |
| 378 | A |
| 379 | B |
| 380 | A |
| 381 | A |
| 382 | A |
| 383 | A |
| 384 | A |
| 386 | A |
| 387 | A |
| 388 | A |
| 389 | A |
| 390 | A |
| 391 | A |
| 392 | A |
| 393 | C |
| 394 | C |
| 395 | B |
| 396 | A |
| 397 | A |
| 398 | A |
| 399 | B |
| 400 | B |
| 401 | A |
| 402 | A |
| 403 | A |
| 404 | A |
| 405 | A |
| 406 | A |
| 407 | A |
| 408 | A |
| 409 | A |
| 410 | A |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | A |
| 430 | A |
| 431 | A |
| 432 | A |
| 433 | A |
| 434 | A |
| 435 | A |
| 436 | A |
| 437 | A |
| 438 | A |
| 439 | A |
| 440 | A |
| 441 | A |
| 442 | A |
| 443 | A |
| 444 | A |
| 445 | A |
| 446 | A |
| 447 | A |
| 448 | A |
| 449 | A |
| 450 | A |
| 451 | A |
| 452 | A |
| 453 | A |
| 454 | A |
| 455 | A |
| 456 | A |
| 457 | A |
| 458 | A |
| 459 | A |
| 460 | A |
| 461 | A |
| 462 | A |
| 463 | A |
| 464 | A |
| 465 | A |
| 466 | A |
| 467 | C |
| 468 | A |
| 469 | A |
| 470 | A |
| 471 | A |
| 472 | A |
| 473 | A |
| 474 | A |
| 475 | A |
| 476 | A |

TABLE 5-continued

MTHFD2 Activity of Exemplary Compounds

| Compound # | Average MTHFD2 Activity |
|---|---|
| 477 | A |
| 478 | A |
| 479 | B |
| 480 | A |
| 481 | A |
| 483 | A |
| 484 | B |
| 485 | A |

We claim:
1. A compound of formula I:

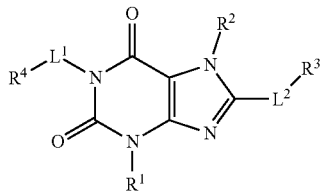

or a pharmaceutically acceptable salt thereof, wherein:
$R^1$ is hydrogen or methyl;
$R^2$ is methyl;
$L^1$ is a covalent bond or a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—;
each R is independently hydrogen, or an optionally substituted group selected from $C_{1-6}$ aliphatic, phenyl, a 4-7 membered saturated or partially unsaturated monocyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur; or:
two R groups on the same nitrogen are taken together with their intervening atoms to form a 4-7 membered monocyclic saturated, partially unsaturated, or heteroaryl ring having 0-3 heteroatoms, in addition to the nitrogen, independently selected from nitrogen, oxygen, or sulfur;
$L^2$ is a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R)SO$_2$—, —SO$_2$N(R)—, —C(O)—, —OC(O)—, —C(O)O—, —O—, —S—, —SO—, or —SO$_2$—, or:
$R^2$ and $L^2$ are taken together with their intervening atoms to form a 5-7 membered partially unsaturated heterocyclic ring having 1-2 nitrogens;
$R^3$ is an optionally substituted $C_{1-6}$ aliphatic or Ring B optionally substituted with 0-4 independently selected $R^y$ groups;

each $R^y$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH) R;
$R^4$ is Ring A optionally substituted with 0-4 independently selected $R^x$ groups;
each $R^x$ is independently halogen, R, —OR, —SR, —N(R)$_2$, —C(O)R, —C(O)OR, —C(O)N(R)$_2$, —N(R)C(O)R, —N(R)C(O)N(R)$_2$, —N(R)C(NR)N(R)$_2$, —NO$_2$, —CN, —SO$_2$N(R)$_2$, —N(R)SO$_2$R, —SO$_2$N(R)C(O)R, —SO$_2$N(R)C(O)N(R)$_2$, —SO$_2$N(R)C(NR)N(R)$_2$, —C(O)N(R)C(O)R or —CR$^1$(OH) R;
Ring A is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur, or an 8-11 membered bicyclic saturated, partially saturated or aromatic ring having 0-3 heteroatoms independently selected from nitrogen, oxygen, or sulfur; and
Ring B is a 4-7 membered monocyclic saturated or partially unsaturated carbocyclic ring, a 4-7 membered monocyclic saturated or partially unsaturated heterocyclic ring having 1-2 heteroatoms independently selected from nitrogen, oxygen, or sulfur, phenyl, or a 5-6 membered heteroaryl ring having 1-3 heteroatoms independently selected from nitrogen, oxygen, or sulfur.

2. The compound according to claim 1, wherein $L^1$ is a bivalent $C_{1-4}$ saturated or unsaturated, straight or branched, hydrocarbon chain.

3. The compound according to claim 1, wherein $L^1$ is —CH$_2$—.

4. The compound according to claim 1, wherein $L^2$ is a bivalent $C_{1-4}$ saturated or unsaturated, straight or branched, hydrocarbon chain, wherein one or two methylene units of the chain are optionally and independently replaced by —C(O)NR—, —N(R)C(O)—, —N(R)C(O)NR—, —NR—, —N(R) SO$_2$—, —SO$_2$N(R)—, —C(O)—, —OC(O)—, —C(O)O—, —O—, —S—, —SO—, or —SO$_2$—.

5. The compound according to claim 1, wherein $L^2$ is —NR—.

6. The compound according to claim 1, wherein $R^3$ is Ring B optionally substituted with 0-4 independently selected $R^y$ groups.

7. The compound according to claim 1, wherein Ring B is a 4-7 membered monocyclic saturated or partially unsaturated heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur.

8. The compound according to claim 1, wherein Ring B is cyclobutyl, cyclopentyl, cyclohexyl, piperidonyl, morpholinyl, pyrrolidinonyl, piperinyl, tetrahydropyranyl, pyridinyl, 2-pyrimidonyl, pyrimidinyl, or pyrazinyl.

9. The compound according to claim 1, wherein $R^y$ is —OR or —C(O)OR.

10. The compound according to claim 1, wherein Ring A is an 8-11 membered bicyclic saturated, partially saturated or aromatic ring having 0-3 heteroatoms independently selected from nitrogen, oxygen, or sulfur.

11. The compound according to claim 1, wherein Ring A is phenyl, dichlorophenyl, naphthyl, indolyl, benzothiophenyl, or benzimidazolyl.

12. The compound according to claim 1, wherein $R^x$ is halogen, R, OR or —C(O)N(R)$_2$.

13. The compound according to claim 1, wherein $R^x$ is fluoro, chloro, methyl, ethyl, —CF$_3$, cyclopropyl, —CH$_2$OH, —CH$_2$NH$_2$, —CH$_2$NHC(O)CH$_3$, —OCH$_3$, —OCHF$_2$, or —C(O)NH$_2$.

14. The compound according to claim 1, wherein said compound is selected from:

3,7-dimethyl-1-[(7-methyl-1H-indol-2-yl)methyl]-8-(4-pyridylamino) purine-2,6-dione, 1-(1-benzothiophen-5-ylmethyl)-8-{[(2S)-4-hydroxybutan-2-yl]amino}-3,7-dimethyl-2,3,6,7-tetrahydro-1H-purine-2,6-dione, 1-(1-benzothiophen-5-ylmethyl)-8-[(3-hydroxypropyl)amino]-3,7-dimethyl-2,3,6,7-tetrahydro-1H-purine-2,6-dione, (±)-1-(1-benzothiophen-5-ylmethyl)-8-{[(cis)-3-hydroxycyclopentyl]amino}-3,7-dimethyl-2,3,6,7-tetrahydro-1H-purine-2,6-dione, (±)-1-(1-benzothiophen-5-ylmethyl)-8-{[(trans)-3-hydroxycyclopentyl]amino}-3,7-dimethyl-2,3,6,7-tetrahydro-1H-purine-2,6-dione, (1R,3S)-3-{[1-(1-benzothiophen-5-ylmethyl)-3,7-dimethyl-2,6-dioxo-2,3,6,7-tetrahydro-1H-purin-8-yl]amino}cyclopentane-1-carboxylic acid, 1-((1H-benzo[d]imidazol-2-yl)methyl)-8-((1S,3R)-3-hydroxycyclopentylamino)-3,7-dimethyl-1H-purine-2,6(3H,7H)-dione, (±)-1-((1H-indol-2-yl)methyl)-8-((cis)-3-hydroxycyclopentylamino)-3,7-dimethyl-1H-purine-2,6(3H,7H)-dione, (±)-1-((1H-indol-6-yl)methyl)-8-((cis)-3-hydroxycyclopentylamino)-3,7-dimethyl-1H-purine-2,6(3H,7H)-dione, 1-((1H-indol-2-yl)methyl)-3,7-dimethyl-8-(pyridin-4-ylamino)-1H-purine-2,6(3H,7H)-dione, (±)-1-((5-chloro-1H-indol-2-yl)methyl)-8-((cis)-3-hydroxycyclopentylamino)-3,7-dimethyl-1H-purine-2,6(3H,7H)-dione, 1-((5-chloro-1H-indol-2-yl)methyl)-3,7-dimethyl-8-(pyridin-4-ylamino)-1H-purine-2,6(3H,7H)-dione, (±)-8-((cis)-3-hydroxycyclopentylamino)-3,7-dimethyl-1-((5-methyl-1H-indol-2-yl)methyl)-1H-purine-2,6(3H,7H)-dione, (±)-1-((5-chloro-1-methyl-1H-indol-2-yl)methyl)-8-((cis)-3-hydroxycyclopentylamino)-3,7-dimethyl-1H-purine-2,6(3H,7H)-dione, (±)-8-((cis)-3-hydroxycyclopentylamino)-3,7-dimethyl-1-((1-methyl-1H-indol-2-yl)methyl)-1H-purine-2,6(3H,7H)-dione, (±)-8-((cis)-3-hydroxycyclopentylamino)-3,7-dimethyl-1-((3-phenyl-1H-pyrazol-5-yl)methyl)-1H-purine-2,6(3H,7H)-dione, 3,7-dimethyl-1-((5-methyl-1H-indol-2-yl)methyl)-8-(pyridin-4-ylamino)-1H-purine-2,6(3H,7H)-dione, (±)-8-((cis)-3-hydroxycyclopentylamino)-1-((5-methoxy-1H-indol-2-yl)methyl)-3,7-dimethyl-1H-purine-2,6(3H,7H)-dione, 1-((5-methoxy-1H-indol-2-yl)methyl)-3,7-dimethyl-8-(pyridin-4-ylamino)-1H-purine-2,6(3H,7H)-dione, 1-((1,5-dimethyl-1H-indol-2-yl)methyl)-8-((1S,3R)-3-hydroxycyclopentylamino)-3,7-dimethyl-1H-purine-2,6(3H,7H)-dione, (±)-8-((cis)-3-hydroxycyclopentylamino)-1-((5-methoxy-1-methyl-1H-indol-2-yl)methyl)-3,7-dimethyl-1H-purine-2,6(3H,7H)-dione, 1-((1H-indol-2-yl)methyl)-3,7-dimethyl-8-(2-oxo-1,2-dihydropyrimidin-4-ylamino)-1H-purine-2,6(3H,7H)-dione, 3,7-dimethyl-1-((5-methyl-1H-indol-2-yl)methyl)-8-(2-oxo-1,2-dihydropyrimidin-4-ylamino)-1H-purine-2,6(3H,7H)-dione, 1-((1H-indol-2-yl)methyl)-8-(2H-1,2,4-triazol-3-ylamino)-3,7-dimethyl-1H-purine-2,6(3H,7H)-dione, 1-((5-chloro-1H-indol-2-yl)methyl)-3,7-dimethyl-8-(pyridazin-3-ylamino)-1H-purine-2,6(3H,7H)-dione, 1-((1H-indol-2-yl)methyl)-3,7-dimethyl-8-(pyridazin-3-ylamino)-1H-purine-2,6(3H,7H)-dione, 8-(1H-1,2,4-triazol-5-ylamino)-3,7-dimethyl-1-((5-methyl-1H-indol-2-yl)methyl)-1H-purine-2,6(3H,7H)-dione, 1-((5-chloro-1-methyl-1H-indol-2-yl)methyl)-3,7-dimethyl-8-(pyridazin-3-ylamino)-1H-purine-2,6(3H,7H)-dione, 1-((5-chloro-1-methyl-1H-indol-2-yl)methyl)-3,7-dimethyl-8-(pyrimidin-4-ylamino)-1H-purine-2,6(3H,7H)-dione, 3,7-dimethyl-1-((5-methyl-1H-indol-2-yl)methyl)-8-(pyrimidin-4-ylamino)-1H-purine-2,6(3H,7H)-dione, 1-((5-chloro-1H-indol-2-yl)methyl)-3,7-dimethyl-8-(2-oxo-1,2-dihydropyrimidin-4-ylamino)-1H-purine-2,6(3H,7H)-dione, 8-(1H-1,2,4-triazol-5-ylamino)-1-((5-chloro-1H-indol-2-yl)methyl)-3,7-dimethyl-1H-purine-2,6(3H,7H)-dione, 1-((5-chloro-1H-indol-2-yl)methyl)-3,7-dimethyl-8-(pyrimidin-4-ylamino)-1H-purine-2,6(3H,7H)-dione, 8-(2-hydroxyethyl)-3,7-dimethyl-1-((5-methyl-1H-indol-2-yl)methyl)-1H-purine-2,6(3H,7H)-dione, 1-((1H-indol-2-yl)methyl)-8-(2-hydroxyethyl)-3,7-dimethyl-1H-purine-2,6(3H,7H)-dione, (S)-1-((1H-indol-2-yl)methyl)-3,7-dimethyl-8-(2-oxopiperidin-3-ylamino)-1H-purine-2,6(3H,7H)-dione, (±)-1-((1H-indol-2-yl)methyl)-3,7-dimethyl-8-(5-oxopyrrolidin-3-ylamino)-1H-purine-2,6(3H,7H)-dione, (±)-1-((1H-indol-2-yl)methyl)-3,7-dimethyl-8-(2-oxopiperidin-4-ylamino)-1H-purine-2,6(3H,7H)-dione, 1-((1H-indol-2-yl)methyl)-3,7-dimethyl-8-(pyrimidin-4-ylamino)-1H-purine-2,6(3H,7H)-dione, (R)-1-((1H-indol-2-yl)methyl)-3,7-dimethyl-8-(2-oxopiperidin-3-ylamino)-1H-purine-2,6(3H,7H)-dione, 1-((1H-indol-2-yl)methyl)-3,7-dimethyl-8-(2-oxopyrrolidin-3-ylamino)-1H-purine-2,6(3H,7H)-dione, 1-((5-chloro-1H-indol-2-yl)methyl)-8-(2-hydroxyethyl)-3,7-dimethyl-1H-purine-2,6(3H,7H)-dione, 1-((5-chloro-1-methyl-1H-indol-2-yl)methyl)-3,7-dimethyl-8-(2-oxo-1,2-dihydropyrimidin-4-ylamino)-1H-purine-2,6(3H,7H)-dione, 1-((5-chloro-1-methyl-1H-indol-2-yl)methyl)-3,7-dimethyl-8-(2-morpholinoethyl)-1H-purine-2,6(3H,7H)-dione, 1-((1H-indol-2-yl)methyl)-3,7-dimethyl-8-(2-morpholinoethyl)-1H-purine-2,6(3H,7H)-dione, 3,7-dimethyl-1-((5-methyl-1H-indol-2-yl)methyl)-8-(2-morpholinoethyl)-1H-purine-2,6(3H,7H)-dione, (S)-1-((1H-indol-2-yl)methyl)-3,7-dimethyl-8-(6-oxopiperidin-3-ylamino)-1H-purine-2,6(3H,7H)-dione or (R)-1-((1H-indol-2-yl)methyl)-3,7-dimethyl-8-(6-oxopiperidin-3-ylamino)-1H-purine-2,6(3H,7H)-dione, 1-((5-chloro-1H-indol-2-yl)methyl)-3,7-dimethyl-8-(2-morpholinoethyl)-1H-purine-2,6(3H,7H)-dione, 1-((1H-indol-2-yl)methyl)-8-amino-3,7-dimethyl-1H-purine-2,6(3H,7H)-dione,
8-amino-3,7-dimethyl-1-((5-methyl-1H-indol-2-yl)methyl)-1H-purine-2,6(3H,7H)-dione,
8-amino-1-((5-chloro-1-methyl-1H-indol-2-yl)methyl)-3,7-dimethyl-1H-purine-2,6(3H,7H)-dione,
8-amino-1-((5-chloro-1H-indol-2-yl)methyl)-3,7-dimethyl-1H-purine-2,6(3H,7H)-dione,
8-amino-1-((5-methoxy-1H-indol-2-yl)methyl)-3,7-dimethyl-1H-purine-2,6(3H,7H)-dione,
(±)-2-chloro-4-((8-((trans)-3-hydroxycyclopentylamino)-3,7-dimethyl-2,6-dioxo-2,3,6,7-tetrahydro-1H-purin-1-yl)methyl)benzonitrile,
3-(1-((1H-indol-6-yl)methyl)-3,7-dimethyl-2,6-dioxo-2,3,6,7-tetrahydro-1H-purin-8-ylamino)cyclohexanecarboxylic acid,
1-((4-chloro-1H-indol-2-yl)methyl)-3,7-dimethyl-8-(pyridin-4-ylamino)-1H-purine-2,6(3H,7H)-dione,
(1R,3R)-3-(1-((1H-indol-2-yl)methyl)-3,7-dimethyl-2,6-dioxo-2,3,6,7-tetrahydro-1H-purin-8-ylamino)cyclobutanecarboxylic acid,
3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid,
1-((1H-indol-2-yl)methyl)-8-((1R,3R)-3-(hydroxymethyl)cyclobutylamino)-3,7-dimethyl-1H-purine-2,6(3H,7H)-dione,
4-[[1-(1H-indol-2-ylmethyl)-3,7-dimethyl-2,6-dioxo-purin-8-yl]amino]benzoic acid,
1-(3,4-dichlorobenzyl)-8-((4-(hydroxymethyl)phenyl)amino)-3,7-dimethyl-3,7-dihydro-1H-purine-2,6-dione,
1-((4-chloro-1H-indol-2-yl)methyl)-3,7-dimethyl-8-(pyridin-2-ylamino)-1H-purine-2,6(3H,7H)-dione,
3-(6-(1-((4-chloro-1H-indol-2-yl)methyl)-3,7-dimethyl-2,6-dioxo-2,3,6,7-tetrahydro-1H-purin-8-ylamino)pyridin-2-yl)propanamide,
1-((4-chloro-1H-indol-2-yl)methyl)-8-((1r,3r)-3-(hydroxymethyl)cyclobutylamino)-3,7-dimethyl-1H-purine-2,6(3H,7H)-dione,
3-(1-((4-chloro-1H-indol-2-yl)methyl)-3,7-dimethyl-2,6-dioxo-2,3,6,7-tetrahydro-1H-purin-8-ylamino)cyclohexanecarboxylic acid,
1-((4-fluoro-1H-indol-2-yl)methyl)-3,7-dimethyl-8-(pyridin-4-ylamino)-1H-purine-2,6(3H,7H)-dione,
1-((3-chloro-1H-indol-2-yl)methyl)-3,7-dimethyl-8-(pyridin-4-ylamino)-1H-purine-2,6(3H,7H)-dione,
1-((6-chloro-1H-indol-2-yl)methyl)-3,7-dimethyl-8-(pyridin-4-ylamino)-1H-purine-2,6(3H,7H)-dione,
(±)-trans-2-[6-[[1-[(4-chloro-1H-indol-2-yl)methyl]-3,7-dimethyl-2,6-dioxo-purin-8-yl] amino]-2-pyridyl]cyclopropanecarboxylic acid,
(1R,2R)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid,
(1S,2S)-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid,
1-((1H-indol-2-yl)methyl)-8-((1S,3R)-3-(hydroxymethyl)cyclopentylamino)-3,7-dimethyl-1H-purine-2,6(3H,7H)-dione,
(±)-trans-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid,
(1R,2R)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic, (1S,2S)-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid,
3,7-dimethyl-1-((6-methyl-1H-indol-2-yl)methyl)-8-(pyridin-4-ylamino)-1H-purine-2,6(3H,7H)-dione,
8-((1R,3R)-3-(hydroxymethyl)cyclobutylamino)-3,7-dimethyl-1-((4-methyl-1H-indol-2-yl)methyl)-1H-purine-2,6(3H,7H)-dione,
1-((4-methyl-1H-indol-2-yl)methyl)-3,7-dimethyl-8-(pyridin-4-ylamino)-1H-purine-2,6(3H,7H)-dione,
3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N,N-dimethylpropanamide,
3-(6-(1-((4-chloro-1H-indol-2-yl)methyl)-3,7-dimethyl-2,6-dioxo-2,3,6,7-tetrahydro-1H-purin-8-ylamino)pyridin-2-yl)-N-methylpropanamide,
4-[[1-[(4-chloro-1H-indol-2-yl)methyl]-3,7-dimethyl-2,6-dioxo-purin-8-yl]amino]benzoic acid,
1-[(4-chloro-1H-indol-2-yl)methyl]-8-[(2-methoxy-4-pyridyl)amino]-3,7-dimethyl-purine-2,6-dione,
1-[(4-chloro-1H-indol-2-yl)methyl]-8-[(2-trifluoromethyl-4-pyridyl)amino]-3,7-dimethyl-purine-2,6-dione,
(±)-trans-1-((4-chloro-1H-indol-2-yl)methyl)-8-((6-(-2-(hydroxymethyl)cyclopropyl)pyridin-2-yl)amino)-3,7-dimethyl-1H-purine-2,6(3H,7H)-dione,
N-[1-[(4-chloro-1H-indol-2-yl)methyl]-3,7-dimethyl-2,6-dioxo-purin-8-yl]methanesulfonamide,
2-(3-((1-((4-chloro-1H-indol-2-yl)methyl)-3,7-dimethyl-2,6-dioxo-2,3,6,7-tetrahydro-1H-purin-8-yl)amino)phenyl)acetic acid,
3,7-dimethyl-1-((3-methyl-1H-indol-2-yl)methyl)-8-(pyridin-4-ylamino)-1H-purine-2,6(3H,7H)-dione,
3-(3,7-dimethyl-1-((4-methyl-1H-indol-2-yl)methyl)-2,6-dioxo-2,3,6,7-tetrahydro-1H-purin-8-ylamino)cyclohexanecarboxylic acid,
1-((4-chloro-1H-indol-2-yl)methyl)-3,7-dimethyl-8-(pyridin-3-ylamino)-1H-purine-2,6(3H,7H)-dione,
2-[4-[[1-[(4-chloro-1H-indol-2-yl)methyl]-3,7-dimethyl-2,6-dioxo-purin-8-yl]amino]phenyl]acetic acid,
3-[[1-[(4-chloro-1H-indol-2-yl)methyl]-3,7-dimethyl-2,6-dioxo-purin-8-yl]amino]benzoic acid,
1-((4-chloro-1H-indol-2-yl)methyl)-8-((1S,2R)-2-hydroxycyclopentylamino)-3,7-dimethyl-1H-purine-2,6(3H,7H)-dione,
1-((4-bromo-1H-indol-2-yl)methyl)-3,7-dimethyl-8-(pyridin-4-ylamino)-1H-purine-2,6(3H,7H)-dione,
3,7-dimethyl-1-(naphthalen-2-ylmethyl)-8-(pyridin-4-ylamino)-1H-purine-2,6(3H,7H)-dione,
2-((3,7-dimethyl-2,6-dioxo-8-(pyridin-4-ylamino)-2,3,6,7-tetrahydro-1H-purin-1-yl)methyl)-1H-indole-4-carbonitrile,
1-((4-chloro-1H-indol-2-yl)methyl)-8-(6-(3-hydroxycyclopentyl) pyridin-2-ylamino)-3,7-dimethyl-1H-purine 2,6(3H,7H)-dione,
8-(2-amino-1H-benzo[d]imidazol-1-yl)-1-((4-chloro-1H-indol-2-yl)methyl)-3,7-dimethyl-1H-purine-2,6(3H,7H)-dione,
1-((4-chloro-1H-indol-2-yl)methyl)-3,7-dimethyl-8-(pyrazin-2-ylamino)-1H-purine-2,6(3H,7H)-dione,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanoic acid,
1-[(4-chloro-1H-indol-2-yl)methyl]-8-(1H-imidazol-2-ylamino)-3,7-dimethyl-purine-2,6-dione,
8-(aminomethyl)-1-[(4-chloro-1H-indol-2-yl)methyl]-3,7-dimethyl-purine-2,6-dione, 4-chloro-2-((8-(((1R,2S)-2-hydroxycyclopentyl)amino)-3,7-dimethyl-2,6-dioxo-2,3,6,7-tetrahydro-1H-purin-1-yl)methyl)-1H-indole-1-carboxylic acid,
2-(1-((4-chloro-1H-indol-2-yl)methyl)-3,7-dimethyl-2,6-dioxo-2,3,6,7-tetrahydro-1H-purin-8-ylamino)acetamide,
1-((4-chloro-1H-indol-2-yl)methyl)-3,7-dimethyl-8-(pyrimidin-4-ylamino)-3,7-dihydro-1H-purine-2,6-dione,
(±)-trans-2-(6-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxamide,
1-[(7-fluoro-1H-indol-2-yl)methyl]-3,7-dimethyl-8-(4-pyridylamino) purine-2,6-dione,
1-[(4-chloro-1H-indol-2-yl)methyl]-3,7-dimethyl-8-(4-methylsulfonylanilino) purine-2,6-dione,
(±)-cis-2-(4-((1-((4-chloro-1H-indol-2-yl)methyl)-3,7-dimethyl-2,6-dioxo-2,3,6,7-tetrahydro-1H-purin-8-yl)amino)pyridin-2-yl)cyclopropanecarboxylic acid,
3-(7-(2-aminoethyl)-1-(3,4-dichlorobenzyl)-3-methyl-2,6-dioxo-2,3,6,7-tetrahydro-1H-1-((4-methoxy-1H-indol-2-yl)methyl)-3,7-dimethyl-8-(pyridin-4-ylamino)-1H-purine-2,6(3H,7H)-dione,
8-(3-aminopiperidin-1-yl)-1-((4-chloro-1H-indol-2-yl)methyl)-3,7-dimethyl-1H-purine-2,6(3H,7H)-dione,
(±)-cis-2-(6-((1-((4-chloro-1H-indol-2-yl)methyl)-3,7-dimethyl-2,3,6,7-tetrahydro-1H-purin-8-yl)amino)pyridin-2-yl) cyclopropane-1-carboxylic acid,
1-[(7-chloro-1H-indol-2-yl)methyl]-3,7-dimethyl-8-(4-pyridylamino) purine-2,6-dione,
3,7-dimethyl-1-((4-phenyl-1H-indol-2-yl)methyl)-8-(pyridin-4-ylamino)-1H-purine-2,6(3H,7H)-dione,
1-((1-chloronaphthalen-2-yl)methyl)-3,7-dimethyl-8-(pyridin-4-ylamino)-1H-purine-2,6(3H,7H)-dione,
3-(6-(1-((4-chloro-1H-indol-2-yl)methyl)-3,7-dimethyl-2,6-dioxo-2,3,6,7-tetrahydro-1H-purin-8-ylamino)-3-methylpyridin-2-yl)propanoic acid,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)propanamide,
2-((8-(2-aminoacetamido)-3,7-dimethyl-2,6-dioxo-2,3,6,7-tetrahydro-1H-purin-1-yl)methyl)-4-chloro-1H-indole-1-carboxylic acid,
1-((4-chloro-1H-indol-2-yl)methyl)-8-(6-methoxypyridin-3-ylamino)-3,7-dimethyl-1H-purine-2,6(3H,7H)-dione,
1-((4-chloro-1H-indol-2-yl)methyl)-8-(6-chloropyridin-3-ylamino)-3,7-dimethyl-1H-purine-2,6(3H,7H)-dione,
1-((4-chloro-1H-indol-2-yl)methyl)-3,7-dimethyl-8-(6-(trifluoromethyl) pyridin-3-ylamino)-1H-purine-2,6(3H,7H)-dione,
1-((4-chloro-1H-indol-2-yl)methyl)-3,7-dimethyl-8-(6-methylpyridin-3-ylamino)-1H-purine-2,6(3H,7H)-dione,
1-((4-chloro-1H-indol-2-yl)methyl)-8-(6-fluoropyridin-3-ylamino)-3,7-dimethyl-1H-purine-2,6(3H,7H)-dione,
8-(2-aminoethyl)-1-((4-chloro-1H-indol-2-yl)methyl)-3,7-dimethyl-1H-purine-2,6(3H,7H)-dione,
1-((4-ethyl-1H-indol-2-yl)methyl)-3,7-dimethyl-8-(pyridin-4-ylamino)-1H-purine-2,6(3H,7H)-dione,
1-((4-chloro-1H-indol-2-yl)methyl)-8-(hydroxy (phenyl)methyl)-3,7-dimethyl-1H-purine-2,6(3H,7H)-dione,
8-(1-aminoethyl)-1-[(4-chloro-1H-indol-2-yl)methyl]-3,7-dimethyl-purine-2,6-dione,
(S)-8-(1-aminoethyl)-1-((4-chloro-1H-indol-2-yl)methyl)-3,7-dimethyl-1H-purine-2,6(3H,7H)-dione,
(R)-8-(1-aminoethyl)-1-((4-chloro-1H-indol-2-yl)methyl)-3,7-dimethyl-1H-purine-2,6(3H,7H)-dione,
8-(1-aminoethyl)-1-[(3,4-dichloro-1H-indol-2-yl)methyl]-3,7-dimethyl-purine-2,6-dione,
1-[(4-chloro-1H-indol-2-yl)methyl]-8-[1-(dimethylamino)ethyl]-3,7-dimethyl-purine-2,6-dione,
N-((4-((1-((4-chloro-1H-indol-2-yl)methyl)-3,7-dimethyl-2,6-dioxo-2,3,6,7-tetrahydro-1H-purin-8-yl)amino)phenyl)sulfonyl)acetamide,
1-[(4-chloro-1H-indol-2-yl)methyl]-3,7-dimethyl-8-[(5-piperazin-1-yl-2-pyridyl)amino]purine-2,6-dione,
1-((1H-pyrrolo[2,3-c]pyridin-2-yl)methyl)-3,7-dimethyl-8-(pyridin-4-ylamino)-1H-purine-2,6(3H,7H)-dione,
8-((1R,2S)-2-aminocyclopentylamino)-1-((4-chloro-1H-indol-2-yl)methyl)-3,7-dimethyl-1H-purine-2,6(3H,7H)-dione,
3-(3-chloro-6-(1-((4-chloro-1H-indol-2-yl)methyl)-3,7-dimethyl-2,6-dioxo-2,3,6,7-tetrahydro-1H-purin-8-ylamino)pyridin-2-yl)propanoic acid,
8-((4-(1H-tetrazol-5-yl)phenyl)amino)-1-((4-chloro-1H-indol-2-yl)methyl)-3,7-dimethyl-1H-purine-2,6(3H,7H)-dione,
1-[(4-chloro-1H-indol-2-yl)methyl]-3,7-dimethyl-8-[(6-phenyl-2-pyridyl)amino]purine-2,6-dione,
1-[(4-chloro-1H-indol-2-yl)methyl]-3,7-dimethyl-8-[(5-phenyl-2-pyridyl)amino]purine-2,6-dione,
1-((4-cyclopropyl-1H-indol-2-yl)methyl)-3,7-dimethyl-8-(pyridin-4-ylamino)-1H-purine-2,6(3H,7H)-dione,
1-((5-chloronaphthalen-2-yl)methyl)-3,7-dimethyl-8-(pyridin-4-ylamino)-1H-purine-2,6(3H,7H)-dione,
1-((4-chloro-1H-indol-2-yl)methyl)-8-((1S,2S)-2-hydroxycyclopentylamino)-3,7-dimethyl-1H-purine-2,6(3H,7H)-dione,
3,7-dimethyl-8-(pyridin-4-ylamino)-1-((4-(trifluoromethyl)-1H-indol-2-yl)methyl)-1H-purine-2,6(3H,7H)-dione,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-dimethylpropanamide,
1-((4-chloro-1H-indol-2-yl)methyl)-3,7-dimethyl-8-(2-(3-oxo-3-(piperidin-1-yl)propyl)pyrimidin-4-ylamino)-1H-purine-2,6(3H,7H)-dione,
1-((4-chloro-1H-indol-2-yl)methyl)-8-(6-(hydroxymethyl)pyridin-3-ylamino)-3,7-dimethyl-1H-purine-2,6(3H,7H)-dione,
Methyl-5-(1-((4-chloro-1H-indol-2-yl)methyl)-3,7-dimethyl-2,6-dioxo-2,3,6,7-tetrahydro-1H-purin-8-ylamino)picolinate,
5-(1-((4-chloro-1H-indol-2-yl)methyl)-3,7-dimethyl-2,6-dioxo-2,3,6,7-tetrahydro-1H-purin-8-ylamino)picolinamide,
3,7-dimethyl-1-((5-methylnaphthalen-2-yl)methyl)-8-(pyridin-4-ylamino)-1H-purine-2,6(3H,7H)-dione,
8-(amino(phenyl)methyl)-1-((4-chloro-1H-indol-2-yl)methyl)-3,7-dimethyl-1H-purine-2,6(3H,7H)-dione,
3-(4-(3,7-dimethyl-1-((4-methyl-1H-indol-2-yl)methyl)-2,6-dioxo-2,3,6,7-tetrahydro-1H-purin-8-ylamino)pyrimidin-2-yl)propanoic acid,
8-(2-(3-(azetidin-1-yl)-3-oxopropyl)pyrimidin-4-ylamino)-1-((4-chloro-1H-indol-2-yl)methyl)-3,7-dimethyl-1H-purine-2,6(3H,7H)-dione,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N-cyclopropyl-N-methylpropanamide,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N-methylpropanamide, 1-((4-chloro-1H-indol-2-yl)methyl)-3,7-dimethyl-8-((2-(3-morpholino-3-oxopropyl)pyrimidin-4-yl)amino)-3,7-dihydro-1H-purine-2,6-dione,
1-((4-chloro-1H-indol-2-yl)methyl)-3,7-dimethyl-8-(2-(3-oxo-3-(pyrrolidin-1-yl)propyl)pyrimidin-4-ylamino)-1H-purine-2,6(3H,7H)-dione,
1-((3,4-dimethyl-1H-indol-2-yl)methyl)-3,7-dimethyl-8-(pyridin-4-ylamino)-1H-purine-2,6(3H,7H)-dione,
4-[[1-[(4-chloro-1H-indol-2-yl)methyl]-3,7-dimethyl-2,6-dioxo-purin-8-yl]amino]benzamide,
1-[(7-chloro-1H-indol-2-yl)methyl]-8-methoxy-3,7-dimethyl-purine-2,6-dione,
N-[1-[(4-chloro-1H-indol-2-yl)methyl]-3,7-dimethyl-2,6-dioxo-purin-8-yl]-2,2,2-trifluoro-acetamide,
3-(4-(1-((4-chloro-1H-indol-2-yl)methyl)-3,7-dimethyl-2,6-dioxo-2,3,6,7-tetrahydro-1H-purin-8-ylamino)pyrimidin-2-yl)-N,N-diethylpropanamide,
5-(1-((4-chloro-1H-indol-2-yl)methyl)-3,7-dimethyl-2,6-dioxo-2,3,6,7-tetrahydro-1H-purin-8-ylamino)picolinonitrile,
1-((4-chloro-1H-indol-2-yl)methyl)-3,7-dimethyl-8-(2-(3-oxo-3-(piperazin-1-yl)propyl)pyrimidin-4-ylamino)-1H-purine-2,6(3H,7H)-dione,
8-(6-(aminomethyl) pyridin-3-ylamino)-1-((4-chloro-1H-indol-2-yl)methyl)-3,7-dimethyl-1H-purine-2,6(3H,7H)-dione,
2-[4-[[1-[(4-chloro-1H-indol-2-yl)methyl]-3,7-dimethyl-2,6-dioxo-purin-8-yl]amino]phenyl]acetamide,
1-((4-chloro-1H-indol-2-yl)methyl)-8-(4-(hydroxymethyl)phenylamino)-3,7-dimethyl-1H-purine-2,6(3H,7H)-dione,
1-[(7-chloro-1-methyl-indol-2-yl)methyl]-8-methoxy-3,7-dimethyl-purine-2,6-dione,
8-(1-aminopropyl)-1-[(4-chloro-1H-indol-2-yl)methyl]-3,7-dimethyl-purine-2,6-dione,
8-(1-amino-2-methyl-propyl)-1-[(4-chloro-1H-indol-2-yl)methyl]-3,7-dimethyl-purine-2,6-dione,
8-(1-amino-2-cyclopropyl-ethyl)-1-[(4-chloro-1H-indol-2-yl)methyl-3,7-dimethyl-purine-2,6-dione,
8-[amino(cyclobutyl)methyl]-1-[(4-chloro-1H-indol-2-yl)methyl]-3,7-dimethyl-purine-2,6-dione,
8-[amino(cyclopropyl)methyl]-1-[(4-chloro-1H-indol-2-yl)methyl]-3,7-dimethyl-purine-2,6-dione,
8-[amino(3-pyridyl)methyl]-1-[(4-chloro-1H-indol-2-yl)methyl]-3,7-dimethyl-purine-2,6-dione,
8-[amino(cyclohexyl)methyl]-1-[(4-chloro-1H-indol-2-yl)methyl]-3,7-dimethyl-purine-2,6-dione,
8-(amino(cyclopentyl)methyl)-1-((4-chloro-1H-indol-2-yl)methyl)-3,7-dimethyl-3,7-dihydro-1H-purine-2,6-dione,
1-[(4-chloro-1H-indol-2-yl)methyl]-3,7-dimethyl-8-[1-(methylamino)ethyl]purine-2,6-dione,
8-[amino(tetrahydropyran-4-yl)methyl]-1-[(4-chloro-1H-indol-2-yl)methyl]-3,7-dimethyl-purine-2,6-dione,
8-[amino(tetrahydropyran-4-yl)methyl]-1-[(3,4-dichloro-1H-indol-2-yl)methyl]-3,7-dimethyl-purine-2,6-dione,
8-[amino(oxetan-3-yl)methyl]-1-[(4-chloro-1H-indol-2-yl)methyl]-3,7-dimethyl-purine-2,6-dione,
8-(1-amino-2-hydroxy-ethyl)-1-[(4-chloro-1H-indol-2-yl)methyl]-3,7-dimethyl-purine-2,6-dione,
8-((1S,2R)-2-aminocyclopentylamino)-1-((4-chloro-1H-indol-2-yl)methyl)-3,7-dimethyl-1H-purine-2,6(3H,7H)-dione,
2-amino-N-((4-(1((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide,
(R)-8-(1-amino-2-(pyridin-4-yl)ethyl)-1-((4-chloro-1H-indol-2-yl)methyl)-3,7-dimethyl-1H-purine-2,6(3H,7H)-dione,
8-(1-aminoethyl)-3,7-dimethyl-1-((5-methylnaphthalen-2-yl)methyl)-1H-purine-2,6(3H,7H)-dione,
(S)-8-(1-amino-2-(pyridin-4-yl)ethyl)-1-((4-chloro-1H-indol-2-yl)methyl)-3,7-dimethyl-1H-purine-2,6(3H,7H)-dione,
8-(1-amino-2-phenylethyl)-1-((4-chloro-1H-indol-2-yl)methyl)-3,7-dimethyl-1H-purine-2,6(3H,7H)-dione,
8-(2-(aminomethyl)pyrimidin-4-ylamino)-1-((4-chloro-1H-indol-2-yl)methyl)-3,7-dimethyl-1H-purine-2,6(3H,7H)-dione,
N-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)acetamide,
8-(1-aminoethyl)-1-((5-cyclopropylnaphthalen-2-yl)methyl)-3,7-dimethyl-1H-purine-2,6(3H,7H)-dione,
1-((1H-pyrrolo[3,2-c]pyridin-2-yl)methyl)-3,7-dimethyl-8-(pyridin-4-ylamino)-1H-purine-2,6(3H,7H)-dione,
8-(amino(pyridin-4-yl)methyl)-1-((4-chloro-1H-indol-2-yl)methyl)-3,7-dimethyl-1H-purine-2,6(3H,7H)-dione,
1-((4-(1-((4-chloro-1H-indol-2-yl)methyl)-3,7-dimethyl-2,6-dioxo-2,3,6,7-tetrahydro-1H-purin-8-ylamino)pyrimidin-2-yl)methyl)urea,
8-(1-aminoethyl)-1-((5-ethylnaphthalen-2-yl)methyl)-3,7-dimethyl-1H-purine-2,6(3H,7H)-dione,
8-[1-amino-3-hydroxy-2-(hydroxymethyl)propyl]-1-[(4-chloro-1H-indol-2-yl)methyl]-3,7-dimethyl-purine-2,6-dione,
(E)-1-((4-chloro-1H-indol-2-yl)methyl)-8-((hydroxyimino)(pyridin-4-yl)methyl)-3,7-dimethyl-1H-purine-2,6(3H,7H)-dione,
(Z)-1-((4-chloro-1H-indol-2-yl)methyl)-8-((hydroxyimino)(pyridin-4-yl)methyl)-3,7-dimethyl-1H-purine-2,6(3H,7H)-dione,
(R)-8-(1-amino-2-(pyridin-3-yl)ethyl)-1-((4-chloro-1H-indol-2-yl)methyl)-3,7-dimethyl-1H-purine-2,6(3H,7H)-dione,
(R)-8-(1-amino-2-(pyridin-2-yl)ethyl)-1-((4-chloro-1H-indol-2-yl)methyl)-3,7-dimethyl-1H-purine-2,6(3H,7H)-dione,
8-(amino(pyridin-2-yl)methyl)-1-((4-chloro-1H-indol-2-yl)methyl)-3,7-dimethyl-1H-purine-2,6(3H,7H)-dione,
1-((4-chloro-7-fluoro-1H-indol-2-yl)methyl)-3,7-dimethyl-8-(pyridin-4-ylamino)-1H-purine-2,6(3H,7H)-dione,
3-(4-(1-((4-chloro-1H-indol-2-yl)methyl)-3,7-dimethyl-2,6-dioxo-2,3,6,7-tetrahydro-1H-purin-8-ylamino)-6-methylpyrimidin-2-yl)propanamide,
3-((4-chloro-1H-indol-2-yl)methyl)-1-methyl-6,7,8,9-tetrahydropyrazino[1,2-f]purine-2,4(1H,3H)-dione,
1-((4,7-dichloro-1H-indol-2-yl)methyl)-3,7-dimethyl-8-(pyridin-4-ylamino)-1H-purine-2,6(3H,7H)-dione,
(E)-1-((4-chloro-1H-indol-2-yl)methyl)-8-(1-(hydroxyimino)ethyl)-3,7-dimethyl-1H-purine-2,6(3H,7H)-dione,
(Z)-1-((4-chloro-1H-indol-2-yl)methyl)-8-(1-(hydroxyimino)ethyl)-3,7-dimethyl-1H-purine-2,6(3H,7H)-dione,
Methyl-2-(1-((4-chloro-1H-indol-2-yl)methyl)-3,7-dimethyl-2,6-dioxo-2,3,6,7-tetrahydro-1H-purin-8-yl)-2-methylpropanoate,
1-((4-chloro-1-methyl-1H-indol-5-yl)methyl)-3,7-dimethyl-8-(pyridin-4-ylamino)-1H-purine-2,6(3H,7H)-dione, 1-((4-chloro-1H-indol-5-yl)methyl)-3,7-dimethyl-8-(pyridin-4-ylamino)-1H-purine-2,6(3H,7H)-dione, 2-(1-((4-chloro-1H-indol-2-yl)methyl)-3,7-dimethyl-2,6-dioxo-2,3,6,7-tetrahydro-1H-purin-8-yl)-2-(pyridin-4-yl) acetamide, 8-(1-aminopropan-2-yl)-1-((4-chloro-1H-indol-2-yl)methyl)-3,7-dimethyl-1H-purine-2,6(3H,7H)-dione, or a pharmaceutically acceptable salt thereof.

15. A pharmaceutical composition comprising the compound according to claim 1 and a pharmaceutically acceptable carrier, adjuvant or vehicle.

16. The composition according to claim 15, wherein said composition is administered in combination with an additional therapeutic agent.

* * * * *